US011370830B2

(12) United States Patent
Robbiani et al.

(10) Patent No.: US 11,370,830 B2
(45) Date of Patent: Jun. 28, 2022

(54) NEUTRALIZING ANTIBODIES THAT BIND TO THE ZIKA VIRUS DOMAIN III ENVELOPE REGION

(71) Applicant: The Rockefeller University, New York, NY (US)

(72) Inventors: Davide Robbiani, Brooklyn, NY (US); Michel Nussenzweig, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 16/603,341

(22) PCT Filed: Apr. 9, 2018

(86) PCT No.: PCT/US2018/026676
§ 371 (c)(1),
(2) Date: Oct. 7, 2019

(87) PCT Pub. No.: WO2018/187799
PCT Pub. Date: Oct. 11, 2018

(65) Prior Publication Data

US 2020/0147199 A1 May 14, 2020

Related U.S. Application Data

(60) Provisional application No. 62/483,001, filed on Apr. 7, 2017.

(51) Int. Cl.
*C07K 16/10* (2006.01)
*A61K 39/12* (2006.01)
*A61K 39/42* (2006.01)
*C12N 15/86* (2006.01)
*A61K 39/00* (2006.01)

(52) U.S. Cl.
CPC .......... *C07K 16/1081* (2013.01); *A61K 39/12* (2013.01); *A61K 39/42* (2013.01); *C12N 15/86* (2013.01); *A61K 2039/505* (2013.01); *C07K 2317/21* (2013.01); *C07K 2317/33* (2013.01); *C07K 2317/34* (2013.01); *C07K 2317/55* (2013.01); *C07K 2317/76* (2013.01); *C12N 2770/24022* (2013.01); *C12N 2770/24134* (2013.01)

(58) Field of Classification Search
CPC ................................................ C07K 16/1081
See application file for complete search history.

(56) References Cited

U.S. PATENT DOCUMENTS 9,212,217 B2 12/2015 Robinson et al.
2015/0284448 A1 10/2015 Weiner et al.

FOREIGN PATENT DOCUMENTS

WO 2016/070178 A1 5/2016

OTHER PUBLICATIONS

Sela-Culang, I., et al., Oct. 2013, The structural basis of antibody-antigen recognition, Front. Immunol. 4(302):1-13.*
Klein, F., et al., Mar. 2013, Somatic mutations of the immunoglobulin framework are generally required for broad and potent HIV-1 neutralization, Cell 153:126-138.*
Yuan, W., and C. R. Parrish, 2000, Comparison of two single-chain antibodies that neutralize canine parvovirus: analysis of an antibody-combining site and mechanisms of neutralization, Virol. 269:471-480.*
Sirin, S., et al., 2016, AB-Bind: antibody binding mutational database for computational affinity predictions, Prot. Sci. 25:393-409.*
Hasan, S.S., et al., A human antibody against Zika virus crosslinks the E protein to prevent infection, Nature Communications, Mar. 16, 2017, vol. 8, No. 14722, pp. 1-6.
Zhang, S., et al., Neutralization mechanism of a highly potent antibody against Zika virus, Nature Communications, Nov. 24, 2016, vol. 7, No. 13679, pp. 1-7.
Robbiani, D.F., et al., Recurrent Potent Human Neutralizing Antibodies to Zika Virus in Brazil and Mexico, Cell, May 4, 2017, vol. 169, No. 4, pp. 597-609.
Sapparapu, G. et al., Neutralizing human antibodies prevent Zika virus replication and fetal disease in mice, Nature, Nov. 2016, vol. 540, No. 7633, pp. 443-447.
Stettler, K. et al., Specificity, cross-reactivity, and function of antibodies elicited by Zika virus infection, Science, Aug. 19, 2016, vol. 353, No. 6301, pp. 823-826.
Wang, Q. et al., Molecular determinants of human neutralizing antibodies isolated from a patient infected with Zika virus, Science Translational Medicine, Dec. 14, 2016, vol. 8, pp. 1-10.
Zhao, H. et al.,, Structural Basis of Zika Virus-Specific Antibody Protection, Cell, Aug. 11, 2016, vol. 166, No. 4, pp. 1016-1027.
Block, O., A tetravalent recombinant dengue doamin III protein vaccine stimulates neutralizing and enhancing antibodies in mice, Vaccine, Oct. 16, 2010, vol. 28, No. 51, pp. 8085-8094.
Emmerich, P. et al., Detection of Serotype-Specific Antibodies to the Four Dengue Viruses Using an Immune Complex Binding (ICB) ELISA, PLOS Neglected Tropical Diseases, Dec. 26, 2013, vol. 7, No. 12. e2580, 12 pages.
Wu, Y. et al., Neutralization of Zika virus by germline-like human monoclonal antobodies targeting cryptic epitopes on envelope domain III, Emerging Microbes and Infections, Oct. 11, 2017, vol. 6, No. 10, pp. 1-11.

(Continued)

*Primary Examiner* — Jeffrey S Parkin
(74) *Attorney, Agent, or Firm* — Hodgson Russ LLP

(57) ABSTRACT

Antibodies to Zika virus (ZIKV) and dengue 1 virus (DENV1) are provided. The amino acid sequences of the antibodies may be modified. Methods for prophylaxis and/or therapy by administering the antibodies and combinations thereof are provided. Immunological detection methods using the antibodies are provided. Also provided are vaccine compositions which comprise peptides derived from ZIKV and DENV1.

7 Claims, 37 Drawing Sheets

Specification includes a Sequence Listing.

(56) References Cited

OTHER PUBLICATIONS

Robbiani, D.F., et al., 5vic, Crystal structure of anti-Zika antibody Z004 bound to DENV-1 Envelope protein DIII, Protein Data Bank in Europe, May 3, 2017, pp. 1-3. https://www.ebi.ac.uk/pdbe/entry/pdb/5vic.
Protein Data Bank in Europe, 5vic Fab heavy chain, May 3, 2017, pp. 1-2. https://www.ebi.ac.uk/pdbe/entry/pdb/5vic/protein/1.
Protein Data Bank in Europe, 5vic Fab light chain, May 3, 2017, pp. 1-2. https://www.ebi.ac.uk/pdbe/entry/pdb/5vic/protein/2.

* cited by examiner

C

| | HEAVY CHAIN | | | LIGHT CHAIN | |
|---|---|---|---|---|---|
| DONOR ID | V GENE | D GENE | J GENE | V GENE | J GENE |
| **MEX 84** | IGHV3-23*01 | IGHD3-10*01 | IGHJ5*01 | IGKV1-5*03 | IGKJ1*01 |
| **MEX 18** | IGHV3-23*01 | IGHD3-10*01 | IGHJ4*02 | IGKV1-5*03 | IGKJ1*01 |
| **MEX 105** | IGHV3-23*03 | IGHD6-19*01 | IGHJ4*02 | IGKV1-5*03 | IGKJ1*01 |
| **BRA 112** | IGHV3-23*01 | IGHD3-10*01 | IGHJ4*02 | IGKV1-5*03 | IGKJ1*01 |
| **BRA 12** | IGHV3-23*01 | IGHD6-19*01 | IGHJ4*02 | IGKV1-5*03 | IGKJ1*01 |

387
```
IVIGVGEKKITHHW  ZIKV(KJ776791)
IVIGVGDKKITHHW  ZIKV African(MR766)
IVVGAGEKALKLSW  DENV1(NC_001477)
IIIGVEPGQLKLNW  DENV2(NC_001474)
IVIGIGDNALKINW  DENV3(NC_001475)
IVIGVGNSALTLHW  DENV4(NC_002640)
IIVGRGDSRLTYQW  YFV 17D(KF769015)
IIVGRGDSRLTYQW  YFV Asibi(KF769016)
IVVGRGEQQKNHHW  WNV(NC_009942)
```

H

I

E

| Mouse ID | Treatment | day 4 | day 5 | day 6 | day 7 |
|---|---|---|---|---|---|
| PO32-1 | 10-1074 | | wt | | |
| PO32-B1 | 10-1074 | | wt | | |
| PO32-B2 | 10-1074 | | wt | | |
| PO32-B3 | 10-1074 | | wt | | |
| PO38-A | 10-1074 | wt | | | wt |
| PO38-B | 10-1074 | wt | | | wt |
| PO38-C | 10-1074 | wt | | | wt |
| PO32-6 | Z004 | | wt | | |
| PO32-7 | Z004 | | wt | | |
| PO32-8 | Z004 | | wt | | |
| PO38-D | Z004 | wt | | | |
| PO38-E | Z004 | wt | | | |
| PO38-F | Z004 | wt | | | |
| PO38-G | Z004 | K394R | | | |
| PO38-H | Z004 | wt | | | |

b

FcγR and FcRn Affinity of Z004 Human IgG1 Fc domain variants

| | | Human IgG1 variants | | | |
|---|---|---|---|---|---|
| | | Wild Type | LS | GRLR | GRLR/LS |
| Human | FcγRIIa[H131] | $2.51x10^{-6}$ | $2.09x10^{-6}$ | n.d.b. | n.d.b |
| | FcγRIIb | $8.02x10^{-8}$ | $6.38x10^{-6}$ | n.d.b. | n.d.b. |
| | FcγRIIIa[V158] | $2.43x10^{-7}$ | $2.33x10^{-7}$ | n.d.b. | n.d.b. |
| | FcRn | $4.85x10^{-8}$ | $4.76x10^{-9}$ | $2.24x10^{-8}$ | $5.20x10^{-9}$ |
| NHP | FcγRIIa | $8.52x10^{-8}$ | $7.97x10^{-8}$ | n.d.b. | n.d.b. |
| | FcγRIIb | $1.42x10^{-6}$ | $2.69x10^{-8}$ | n.d.b. | n.d.b. |
| | FcγRIII | $5.81x10^{-7}$ | $4.24x10^{-7}$ | n.d.b. | n.d.b. |

Values represent KD (M) determined by SPR using soluble FcR ectodomains;
n.d.b.: no detectable binding c

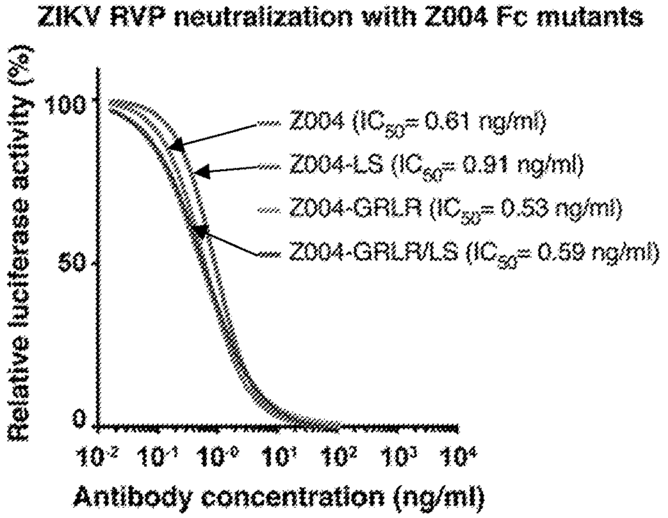

SEQUENCE LISTING

```
<160> NUMBER OF SEQ ID NOS: 1070

<210> SEQ ID NO 1
<211> LENGTH: 8
<212> TYPE: PRT
<213> ORGANISM: Homo sapiens

<400> SEQUENCE: 1

Gly Phe Thr Phe Arg Asp Tyr Ala
1               5


<210> SEQ ID NO 2
<211> LENGTH: 8
<212> TYPE: PRT
<213> ORGANISM: Homo sapiens

<400> SEQUENCE: 2

Tyr Ser Gly Ile Asp Asp Ser Thr
1               5


<210> SEQ ID NO 3
<211> LENGTH: 15
<212> TYPE: PRT
<213> ORGANISM: Homo sapiens

<400> SEQUENCE: 3

Ala Lys Asp Arg Gly Pro Arg Gly Val Gly Glu Leu Phe Asp Ser
1               5                   10                  15


<210> SEQ ID NO 4
<211> LENGTH: 6
<212> TYPE: PRT
<213> ORGANISM: Homo sapiens

<400> SEQUENCE: 4

Gln Ser Ile Ser Lys Trp
1               5


<210> SEQ ID NO 5
<211> LENGTH: 9
<212> TYPE: PRT
<213> ORGANISM: Homo sapiens

<400> SEQUENCE: 5

Gln His Phe Tyr Ser Val Pro Trp Thr
1               5


<210> SEQ ID NO 6
<211> LENGTH: 8
<212> TYPE: PRT
<213> ORGANISM: Homo sapiens

<400> SEQUENCE: 6

Gly Gly Ser Ile Asp Thr Tyr Tyr
1               5
```

-continued

<210> SEQ ID NO 7
<211> LENGTH: 7
<212> TYPE: PRT
<213> ORGANISM: Homo sapiens

<400> SEQUENCE: 7

```
Phe Tyr Tyr Ser Val Asp Asn
1               5
```

<210> SEQ ID NO 8
<211> LENGTH: 12
<212> TYPE: PRT
<213> ORGANISM: Homo sapiens

<400> SEQUENCE: 8

```
Ala Arg Asn Gln Pro Gly Gly Arg Ala Phe Asp Tyr
1               5                   10
```

<210> SEQ ID NO 9
<211> LENGTH: 6
<212> TYPE: PRT
<213> ORGANISM: Homo sapiens

<400> SEQUENCE: 9

```
Gln Ser Val Ser Asn Tyr
1               5
```

<210> SEQ ID NO 10
<211> LENGTH: 11
<212> TYPE: PRT
<213> ORGANISM: Homo sapiens

<400> SEQUENCE: 10

```
Gln Glu Arg Asn Asn Trp Pro Leu Thr Trp Thr
1               5                   10
```

<210> SEQ ID NO 11
<211> LENGTH: 122
<212> TYPE: PRT
<213> ORGANISM: Homo sapiens

<400> SEQUENCE: 11

```
Glu Val Gln Leu Leu Glu Ser Gly Gly Gly Leu Val Gln Pro Gly Gly
1               5                   10                  15

Ser Leu Arg Leu Thr Cys Ala Thr Ser Gly Phe Thr Phe Arg Asp Tyr
            20                  25                  30

Ala Met Ser Trp Val Arg Gln Ala Pro Gly Lys Gly Leu Glu Trp Val
        35                  40                  45

Ser Ser Tyr Ser Gly Ile Asp Asp Ser Thr Tyr Tyr Ala Asp Ser Val
    50                  55                  60

Lys Gly Arg Phe Thr Ile Ser Arg Asp Asn Ser Lys Ser Thr Leu Ser
65                  70                  75                  80

Leu His Met Asn Ser Leu Arg Ala Glu Asp Ser Ala Leu Tyr Phe Cys
                85                  90                  95

Ala Lys Asp Arg Gly Pro Arg Gly Val Gly Glu Leu Phe Asp Ser Trp
            100                 105                 110

Gly Gln Gly Thr Leu Val Thr Val Ser Ser
        115                 120
```

<210> SEQ ID NO 12
<211> LENGTH: 107

<212> TYPE: PRT
<213> ORGANISM: Homo sapiens

<400> SEQUENCE: 12

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Lys Trp
20 25 30

Leu Ala Trp Tyr Gln Gln Lys Pro Gly Lys Ala Pro Lys Leu Leu Ile
35 40 45

Tyr Thr Thr Ser Thr Leu Lys Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Phe Tyr Ser Val Pro Trp
85 90 95

Thr Phe Gly Gln Gly Thr Lys Val Glu Ile Lys
100 105

<210> SEQ ID NO 13
<211> LENGTH: 118
<212> TYPE: PRT
<213> ORGANISM: Homo sapiens

<400> SEQUENCE: 13

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Asp Thr Tyr
20 25 30

Tyr Trp Ser Trp Ile Arg Gln Thr Pro Gly Lys Gly Leu Glu Trp Ile
35 40 45

Gly Cys Phe Tyr Tyr Ser Val Asp Asn His Phe Asn Pro Ser Leu Glu
50 55 60

Ser Arg Val Thr Ile Ser Val Asp Thr Ser Lys Asn Gln Phe Ser Leu
65 70 75 80

Lys Met Thr Ser Met Thr Ala Ser Asp Thr Ala Val Tyr Tyr Cys Ala
85 90 95

Arg Asn Gln Pro Gly Gly Arg Ala Phe Asp Tyr Trp Gly Pro Gly Thr
100 105 110

Leu Val Thr Val Ser Ser
115

<210> SEQ ID NO 14
<211> LENGTH: 109
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
1 5 10 15

Gln Arg Ala Thr Leu Ser Cys Arg Ala Ser Gln Ser Val Ser Asn Tyr
20 25 30

Phe Ala Trp Tyr Gln Gln Lys Pro Gly Gln Ala Pro Arg Leu Leu Ile
35 40 45

Tyr Asp Thr Ser Lys Arg Ala Thr Gly Thr Pro Ala Arg Phe Ser Gly
50 55 60

Ser Gly Ser Gly Thr Asp Phe Thr Leu Thr Ile Ser Ser Leu Glu Pro 65 70 75 80

Glu Asp Phe Ala Val Tyr Tyr Cys Gln Glu Arg Asn Asn Trp Pro Leu
85 90 95

Thr Trp Thr Phe Gly Leu Gly Thr Lys Val Glu Ile Lys
100 105

<210> SEQ ID NO 15
<211> LENGTH: 451
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 15

Glu Val Gln Leu Leu Glu Ser Gly Gly Gly Leu Val Gln Pro Gly Gly
1 5 10 15

Ser Leu Arg Leu Thr Cys Ala Thr Ser Gly Phe Thr Phe Arg Asp Tyr
20 25 30

Ala Met Ser Trp Val Arg Gln Ala Pro Gly Lys Gly Leu Glu Trp Val
35 40 45

Ser Ser Tyr Ser Gly Ile Asp Asp Ser Thr Tyr Tyr Ala Asp Ser Val
50 55 60

Lys Gly Arg Phe Thr Ile Ser Arg Asp Asn Ser Lys Ser Thr Leu Ser
65 70 75 80

Leu His Met Asn Ser Leu Arg Ala Glu Asp Ser Ala Leu Tyr Phe Cys
85 90 95

Ala Lys Asp Arg Gly Pro Arg Gly Val Gly Glu Leu Phe Asp Ser Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Arg Val Glu Pro Lys Ser
210 215 220

Cys Asp Lys Thr His Thr Cys Pro Pro Cys Pro Ala Pro Glu Leu Leu
225 230 235 240

Arg Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Asn Ser Thr
290 295 300

Tyr Arg Val Val Ser Val Leu Thr Val Leu His Gln Asp Trp Leu Asn
305 310 315 320

```
Gly Lys Glu Tyr Lys Cys Lys Val Ser Asn Lys Ala Arg Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Leu His Glu Ala Leu His Ser His Tyr Thr Gln Lys Ser Leu Ser Leu
        435                 440                 445

Ser Pro Gly
    450


<210> SEQ ID NO 16
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Lys Trp
            20                  25                  30

Leu Ala Trp Tyr Gln Gln Lys Pro Gly Lys Ala Pro Lys Leu Leu Ile
        35                  40                  45

Tyr Thr Thr Ser Thr Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Phe Tyr Ser Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 17
<211> LENGTH: 447
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 17

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asp Thr Tyr
            20                  25                  30

Tyr Trp Ser Trp Ile Arg Gln Thr Pro Gly Lys Gly Leu Glu Trp Ile
        35                  40                  45

Gly Cys Phe Tyr Tyr Ser Val Asp Asn His Phe Asn Pro Ser Leu Glu
    50                  55                  60

Ser Arg Val Thr Ile Ser Val Asp Thr Ser Lys Asn Gln Phe Ser Leu
65                  70                  75                  80

Lys Met Thr Ser Met Thr Ala Ser Asp Thr Ala Val Tyr Tyr Cys Ala
                85                  90                  95

Arg Asn Gln Pro Gly Gly Arg Ala Phe Asp Tyr Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Arg Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
```

```
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ser His Tyr Thr Gln Lys Ser Leu Ser Leu Ser Pro Gly
        435                 440                 445


<210> SEQ ID NO 18
<211> LENGTH: 216
<212> TYPE: PRT
<213> ORGANISM: Homo sapiens

<400> SEQUENCE: 18

Glu Ile Val Leu Thr Gln Ser Pro Ala Thr Leu Ser Leu Ser Pro Gly
1               5                   10                  15

Gln Arg Ala Thr Leu Ser Cys Arg Ala Ser Gln Ser Val Ser Asn Tyr
            20                  25                  30

Phe Ala Trp Tyr Gln Gln Lys Pro Gly Gln Ala Pro Arg Leu Leu Ile
        35                  40                  45

Tyr Asp Thr Ser Lys Arg Ala Thr Gly Thr Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Glu Arg Asn Asn Trp Pro Leu
                85                  90                  95

Thr Trp Thr Phe Gly Leu Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 19
<211> LENGTH: 122
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Arg Arg Leu Ser Cys Ala Thr Ser Gly Phe Ser Phe Asp Thr Tyr
```

```
            20                  25                  30

Ala Met Ser Trp Leu Arg Gln Ala Pro Gly Lys Gly Leu Glu Trp Val
        35                  40                  45

Ser Ser Phe Ser Gly Leu Asp Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Asp Arg Gly Pro Arg Gly Ile Gly Glu Leu Phe Asp Phe Trp
            100                 105                 110

Gly Gln Gly Thr Leu Val Thr Val Ser Ser
        115                 120


<210> SEQ ID NO 20
<211> LENGTH: 107
<212> TYPE: PRT
<213> ORGANISM: Homo sapiens

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Lys Thr Ser Thr Leu Lys Ser Glu Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Phe His Ser Val Pro Trp
                85                  90                  95

Thr Phe Gly Gln Gly Thr Lys Val Glu Ile Lys
            100                 105


<210> SEQ ID NO 21
<211> LENGTH: 120
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asn Tyr
            20                  25                  30

Ala Met Ala Trp Val Arg Gln Ala Pro Gly Lys Gly Leu Glu Trp Val
        35                  40                  45

Ser Leu Leu Tyr Asn Ser Glu Glu Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Arg Leu Arg Val Glu Asp Thr Ala Val Tyr Phe Cys
                85                  90                  95

Val Arg Asp Arg Ser Asn Gly Trp Ser Ser Ile Asn Leu Trp Gly Arg
            100                 105                 110

Gly Thr Leu Val Thr Val Ser Ser
```

115 120

<210> SEQ ID NO 22
<211> LENGTH: 106
<212> TYPE: PRT
<213> ORGANISM: Homo sapiens

<400> SEQUENCE: 22

Asp Ile Gln Met Thr Gln Ser Pro Ser Thr Leu Ser Ala Ser Val Gly
1 5 10 15

Asp Arg Val Thr Met Thr Cys Arg Ala Ser Gln Thr Ile Ser Gly Trp
20 25 30

Leu Ala Trp Tyr Gln Gln Lys Pro Gly Lys Ala Pro Lys Leu Leu Ile
35 40 45

Tyr Gln Ala Ser Arg Leu Glu Ser Gly Ile Pro Ser Arg Phe Ser Gly
50 55 60

Ser Gly Ser Gly Thr Glu Phe Thr Leu Thr Ile Ser Ser Leu Gln Pro
65 70 75 80

Asp Asp Val Ala Thr Tyr Tyr Cys Gln Gln Tyr Ser Thr Phe Trp Thr
85 90 95

Phe Gly Leu Gly Thr Lys Val Glu Ile Lys
100 105

<210> SEQ ID NO 23
<211> LENGTH: 120
<212> TYPE: PRT
<213> ORGANISM: Homo sapiens

<400> SEQUENCE: 23

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Ala Trp Val Arg Gln Ala Pro Gly Lys Gly Leu Glu Trp Val
35 40 45

Ser Leu Ile Tyr Ser Gly Asp Asp Ser Thr Tyr Tyr Ala Asp Phe Val
50 55 60

Lys Gly Arg Phe Thr Ile Ser Arg His Asn Ser Lys Asn Thr Leu Ser
65 70 75 80

Leu Gln Met Asn Ser Leu Arg Ala Glu Asp Thr Ala Ile Tyr Tyr Cys
85 90 95

Val Lys Asp Arg Gly Thr Gly Trp Ser Ser Ile Val His Trp Gly Gln
100 105 110

Gly Thr Leu Val Thr Val Ser Ser
115 120

<210> SEQ ID NO 24
<211> LENGTH: 106
<212> TYPE: PRT
<213> ORGANISM: Homo sapiens

<400> SEQUENCE: 24

Asp Ile Gln Met Thr Gln Ser Pro Ser Thr Leu Ser Ala Ser Val Gly
1 5 10 15

Asp Arg Val Thr Ile Thr Cys Arg Ala Ser Gln Thr Ile Ser Asn Trp
20 25 30

Leu Ala Trp Tyr Gln Gln Lys Pro Gly Lys Ala Pro Lys Leu Leu Ile
35 40 45

Tyr Gln Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Thr Tyr Trp Thr
                85                  90                  95

Phe Gly Gln Gly Thr Lys Val Glu Ile Lys
            100                 105

<210> SEQ ID NO 25
<211> LENGTH: 128
<212> TYPE: PRT
<213> ORGANISM: Homo sapiens

<400> SEQUENCE: 25

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Thr Asn
            20                  25                  30

Tyr Ile His Trp Val Arg Gln Ala Pro Gly Gln Gly Pro Glu Trp Met
        35                  40                  45

Gly Ile Ile Asn Pro Arg Gly Gly Ser Thr Thr Tyr Ala Gln Lys Phe
    50                  55                  60

Gln Gly Arg Val Leu Met Thr Ser Asp Thr Ser Thr Ser Thr Val Tyr
65                  70                  75                  80

Met Glu Leu Ser Ser Leu Arg Ser Glu Asp Arg Ala Val Tyr Tyr Cys
                85                  90                  95

Ala Arg Gly Lys Asn His Gln Thr Thr Val Ala Val Leu Ser Trp Tyr
            100                 105                 110

Tyr Gly Met Asp Val Trp Gly Gln Gly Thr Thr Val Thr Val Ser Ser
        115                 120                 125

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Glu Asp Phe Ala Thr Tyr Phe Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 27
<211> LENGTH: 122
<212> TYPE: PRT
<213> ORGANISM: Homo sapiens

<400> SEQUENCE: 27

Glu Val Gln Leu Leu Glu Ser Gly Gly Asp Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Gly Lys Gly Leu Glu Trp Val
35 40 45

Ser Ser Ile Ser Gly Phe Asp Pro Ser Thr Tyr Tyr Ala Asp Ser Val
50 55 60

Arg Gly Arg Phe Thr Ile Ala Arg Asp Asn Ser Lys Asn Thr Leu Tyr
65 70 75 80

Leu Gln Met Lys Ser Leu Arg Val Glu Asp Thr Ala Ile Tyr Tyr Cys
85 90 95

Ala Lys Asp Arg Leu Val Arg Gly Phe Gly Glu Val Leu Asp Ser Trp
100 105 110

Gly Gln Gly Thr Leu Val Thr Val Ser Ser
115 120

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Tyr Gln Gln Lys Pro Arg Glu Val Pro Lys Leu Leu Ile
35 40 45

Tyr Ala Ala Ser Thr Leu His Ser Gly Val Pro Ser Arg Phe Ser Gly
50 55 60

Ser Gly Ser Gly Thr Asp Phe Thr Leu Thr Ile Ser Gly Leu Gln Pro
65 70 75 80

Glu Asp Val Ala Thr Tyr Tyr Cys Gln Lys Tyr Asn Ser Val Pro Trp
85 90 95

Thr Phe Gly Gln Gly Thr Lys Val Glu Ile Lys
100 105

<210> SEQ ID NO 29
<211> LENGTH: 124
<212> TYPE: PRT
<213> ORGANISM: Homo sapiens

<400> SEQUENCE: 29

Gln Val Gln Leu Val Gln Ser Gly Ala Glu Val Lys Lys Pro Gly Ala
1 5 10 15

Ser Val Lys Leu Ser Cys Lys Ser Ser Gly Tyr Ser Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Val Phe Thr Ser Tyr Ala Gln Arg Phe
50 55 60

Gln Gly Arg Val Thr Met Thr Ser Asp Thr Ala Thr Ser Thr Val Tyr
65 70 75 80

-continued

```
Met Glu Leu Ser Ser Leu Arg Ser Gly Asp Thr Ala Val Tyr Tyr Cys
                85                  90                  95

Thr Arg Ser Leu Val Thr Pro Ala Ala Gln Ser Val Gln Tyr Phe Asp
            100                 105                 110

Ser Trp Gly Gln Gly Thr Leu Val Thr Val Ser Ser
        115                 120


<210> SEQ ID NO 30
<211> LENGTH: 108
<212> TYPE: PRT
<213> ORGANISM: Homo sapiens

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Leu Ser
            20                  25                  30

Phe Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Gly Asp Phe Ala Val Tyr Tyr Cys Gln Gln Tyr Gly Ser Ser Pro
                85                  90                  95

Leu Thr Phe Gly Pro Gly Thr Lys Val Asp Ile Lys
            100                 105


<210> SEQ ID NO 31
<211> LENGTH: 121
<212> TYPE: PRT
<213> ORGANISM: Homo sapiens

<400> SEQUENCE: 31

Gln Val Gln Leu Val Gln Ser Gly Pro Gly Val Lys Lys Pro Gly Ala
1               5                   10                  15

Ser Val Lys Val Ser Cys Lys Ala Ser Gly Tyr Ile Phe Ser Asp Tyr
            20                  25                  30

Tyr Ile Leu Trp Val Arg Gln Ala Pro Gly Gln Gly Leu Glu Tyr Met
        35                  40                  45

Gly Trp Met Asn Pro Ile Ser Gly Phe Thr His Tyr Ala Gln Asn Phe
    50                  55                  60

Gln Gly Arg Val Thr Met Thr Arg Asp Thr Ser Ile Ser Thr Ala Tyr
65                  70                  75                  80

Met Glu Leu Thr Arg Leu Ala Ser Asp Asp Thr Ala Val Tyr Tyr Cys
                85                  90                  95

Ala Arg Gly Gly Arg Ile Asn Ser Pro Leu Gly Phe Asp Pro Trp Gly
            100                 105                 110

Gln Gly Thr Leu Val Thr Val Ser Ser
        115                 120


<210> SEQ ID NO 32
<211> LENGTH: 108
<212> TYPE: PRT
<213> ORGANISM: Homo sapiens

<400> SEQUENCE: 32

Glu Ile Val Leu Thr Gln Ser Pro Ala Thr Leu Ser Leu Ser Pro Gly
```

-continued

```
1               5                   10                  15

Glu Arg Ala Thr Leu Ser Cys Arg Ala Ser Gln Ser Ile Ser Thr Phe
            20                  25                  30

Ser Leu Ala Trp Tyr Gln Gln Lys Phe Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Ser Ser Pro
                85                  90                  95

Leu Thr Phe Gly Gly Gly Thr Lys Val Glu Ile Lys
            100                 105


<210> SEQ ID NO 33
<211> LENGTH: 128
<212> TYPE: PRT
<213> ORGANISM: Homo sapiens

<400> SEQUENCE: 33

Glu Val Gln Leu Val Gln Ser Gly Ala Glu Val Arg Lys Pro Gly Glu
1               5                   10                  15

Ser Leu Arg Ile Ser Cys Lys Thr Ser Gly Tyr Thr Phe Thr Ser His
            20                  25                  30

Trp Val Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Ile Ser Ile Ser Ala Asp Lys Ser Ile Asn Thr Ala Tyr
65                  70                  75                  80

Leu Gln Trp Ser Ser Leu Lys Ala Ser Asp Thr Gly Ile Tyr Tyr Cys
                85                  90                  95

Ala Arg His Asp Gly Arg Gly Tyr Cys Ser Pro Thr Arg Cys Phe Phe
            100                 105                 110

Ser Gly Met Asp Val Trp Gly Gln Gly Thr Thr Val Thr Val Ser Ser
        115                 120                 125


<210> SEQ ID NO 34
<211> LENGTH: 107
<212> TYPE: PRT
<213> ORGANISM: Homo sapiens

<400> SEQUENCE: 34

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Tyr Ala Ile Tyr Tyr Cys Gln Gln Thr Asp Arg Thr Pro Leu
                85                  90                  95

Thr Phe Gly Gln Gly Thr Lys Val Glu Ile Lys
```

100 105

<210> SEQ ID NO 35
<211> LENGTH: 122
<212> TYPE: PRT
<213> ORGANISM: Homo sapiens

<400> SEQUENCE: 35

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ala Tyr
20 25 30

Ala Met Ser Trp Val Arg Gln Ala Pro Gly Lys Gly Leu Glu Trp Val
35 40 45

Ser Ser Ile Asn Gly His Ser Asp Ser Thr Tyr Phe Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Leu Tyr Tyr Cys
85 90 95

Ala Lys Asp Arg Leu Arg Glu Gly Ile Gly Glu Leu Phe His Ser Trp
100 105 110

Gly Gln Gly Thr Leu Val Thr Val Ser Ser
115 120

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Thr Leu Ser Ala Ser Ile Gly
1 5 10 15

Asp Arg Val Thr Ile Thr Cys Arg Ala Ser Gln Ser Ile Thr Pro Trp
20 25 30

Leu Ala Trp Tyr Gln Gln Lys Pro Gly Lys Ala Pro Lys Phe Leu Ile
35 40 45

Tyr Gln Thr Ser Ile Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Tyr His Ser Tyr Pro Trp
85 90 95

Thr Phe Gly Gln Gly Thr Lys Val Glu Ile Lys
100 105

<210> SEQ ID NO 37
<211> LENGTH: 122
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
1 5 10 15

Ser Leu Arg Leu Ser Cys Val Ala Ser Gly Phe Thr Phe Gly Ser Tyr
20 25 30

Gly Met Ala Trp Val Arg Gln Ala Pro Gly Lys Gly Leu Glu Trp Ile
35 40 45

Ser Ser Ile Ser Ser Ile Asp Pro Ser Thr Tyr Tyr Ala Asp Ser Val
    50                  55                  60

Lys Gly Arg Phe Thr Val Ser Arg Asp Asn Ser Glu Asn Thr Leu Tyr
65                  70                  75                  80

Leu His Met Ser Ser Leu Lys Val Glu Asp Thr Ala Val Tyr Phe Cys
                85                  90                  95

Ala Lys Asp Arg Leu Asn Gly Gly Phe Gly Glu Leu Phe Ala Ser Trp
            100                 105                 110

Gly Gln Gly Thr Leu Val Thr Val Ser Ser
        115                 120

<210> SEQ ID NO 38
<211> LENGTH: 107
<212> TYPE: PRT
<213> ORGANISM: Homo sapiens

<400> SEQUENCE: 38

Asp Ile Gln Met Thr Gln Ser Pro Ser Thr Leu Ser Ala Ser Val Gly
1               5                   10                  15

Asp Ser Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

His Lys Ala Ser Ser Leu Glu Ser Gly Ile Pro Ser Arg Phe Ser Gly
    50                  55                  60

Ser Gly Ser Gly Thr Glu Phe Thr Leu Thr Ile Asn Asn Leu Gln Pro
65                  70                  75                  80

Asp Asp Phe Ala Thr Tyr Tyr Cys Gln His Tyr His Ser Tyr Pro Trp
                85                  90                  95

Thr Phe Gly Gln Gly Thr Lys Val Glu Ile Lys
            100                 105

<210> SEQ ID NO 39
<211> LENGTH: 128
<212> TYPE: PRT
<213> ORGANISM: Homo sapiens

<400> SEQUENCE: 39

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ala Ser Asp Asn Gly Ala Ser Arg
    50                  55                  60

Tyr Tyr Ala Asp Ser Val Lys Gly Arg Phe Ser Ile Ser Arg Asp Asn
65                  70                  75                  80

Ser Lys Asn Thr Val Tyr Leu Gln Met Asn Ser Leu Arg Ala Glu Asp
                85                  90                  95

Thr Ala Val Tyr Tyr Cys Ala Lys Asp Arg Leu Ser Gly Gly Phe Gly
            100                 105                 110

Glu Leu Phe Gln Lys Trp Gly Gln Gly Thr Leu Val Thr Val Ser Ser
        115                 120                 125

<210> SEQ ID NO 40

<211> LENGTH: 107
<212> TYPE: PRT
<213> ORGANISM: Homo sapiens

<400> SEQUENCE: 40

Asp Ile Gln Met Thr Gln Ser Pro Ser Thr Leu Ala Ala Ser Val Gly
1 5 10 15

Asp Arg Val Thr Ile Thr Cys Arg Ala Ser Gln Asn Ile Asn Ser Trp
20 25 30

Leu Ala Trp Tyr Gln Gln Lys Pro Gly Lys Ala Pro Lys Phe Leu Ile
35 40 45

Tyr Lys Ala Ser Thr Leu Glu Ser Gly Ala Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Tyr Tyr Ser Tyr Pro Tyr
85 90 95

Thr Phe Gly Gln Gly Thr Lys Val Glu Ile Lys
100 105

<210> SEQ ID NO 41
<211> LENGTH: 130
<212> TYPE: PRT
<213> ORGANISM: Homo sapiens

<400> SEQUENCE: 41

Gln Val Gln Leu Gln Glu Ser Gly Pro Gly Leu Val Lys Pro Ser Glu
1 5 10 15

Thr Leu Ser Leu Thr Cys Ser Val Ser Gly Tyr Phe Ile Ser Ser Gly
20 25 30

His Tyr Trp Gly Trp Ile Arg Gln Ser Pro Gly Lys Gly Leu Glu Trp
35 40 45

Ile Ala Ser Ile Tyr Gln Ser Gly Ser Lys Phe Gln Thr Gly Asn Thr
50 55 60

Tyr Tyr Asn Pro Ser Leu Glu Ser Arg Val Thr Ile Ser Met Asp Thr
65 70 75 80

Ser Lys Asn Gln Phe Ser Leu Lys Leu Ser Ser Val Thr Ala Ala Asp
85 90 95

Thr Ala Val Tyr Phe Cys Ala Arg Asp Ala Arg Ser Arg Ser Trp Asp
100 105 110

Arg Thr Gly Phe Phe Gly Pro Trp Gly Gln Gly Ile Leu Val Thr Val
115 120 125

Ser Ser
130

<210> SEQ ID NO 42
<211> LENGTH: 108
<212> TYPE: PRT
<213> ORGANISM: Homo sapiens

<400> SEQUENCE: 42

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Leu Ser Ser Ser
20 25 30

Phe Leu Ala Trp Tyr Gln Gln Lys Pro Gly Gln Ser Pro Arg Leu Leu
35 40 45

Ile Tyr Gly Thr Ser Ser Arg Asp Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Ser Ala Val Tyr Tyr Cys Gln Gln Tyr Gly Ser Ser Trp
85 90 95

Gly Thr Phe Gly Gln Gly Thr Lys Leu Glu Ile Lys
100 105

<210> SEQ ID NO 43
<211> LENGTH: 127
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
1 5 10 15

Ser Leu Arg Leu Ser Cys Glu Ala Ser Gly Phe Thr Phe Ser Asn Tyr
20 25 30

Ala Met Asn Trp Val Arg Gln Ala Pro Gly Lys Gly Leu Glu Trp Val
35 40 45

Ser Thr Leu Gly Ala Thr Asp Asn Ser Gly Asp Ser Thr Tyr Tyr Val
50 55 60

Glu Ser Ala Lys Gly Arg Phe Thr Ile Ser Arg Asp Asn Ser Lys Asn
65 70 75 80

Thr Leu Tyr Leu Gln Met Asn Ser Leu Arg Val Glu Asp Thr Ala Val
85 90 95

Tyr Phe Cys Ala Lys Asp Arg Thr Gly Asn Ile Gly Ala Gly Thr Gly
100 105 110

Tyr Phe Asp Lys Trp Gly Gln Gly Thr Leu Val Thr Val Ser Ser
115 120 125

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Thr Leu Ser Ala Ser Val Gly
1 5 10 15

Asp Arg Val Thr Ile Thr Cys Arg Ala Ser His Arg Ile Ser Gly Trp
20 25 30

Leu Ala Trp Tyr Gln Gln Lys Pro Gly Lys Ala Pro Lys Leu Leu Ile
35 40 45

Tyr Gln Ala Ser Gly Leu Glu Ser Gly Val Pro Ser Arg Phe Ser Gly
50 55 60

Ser Gly Tyr Gly Thr Glu Phe Thr Leu Thr Ile Ser Ser Leu Gln Ala
65 70 75 80

Asp Asp Phe Ala Thr Tyr Tyr Cys Gln Gln Tyr Asn Asn Tyr Pro Trp
85 90 95

Thr Phe Gly Gln Gly Thr Lys Val Glu Ile Lys
100 105

<210> SEQ ID NO 45
<211> LENGTH: 122
<212> TYPE: PRT
<213> ORGANISM: Homo sapiens

```
<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Ile Phe Asp Asn Tyr
            20                  25                  30

Ala Met Ser Trp Val Arg Gln Ala Pro Gly Lys Gly Leu Glu Trp Val
        35                  40                  45

Ser Tyr Ile Asn Gly Gly Gly Tyr Gly Thr Asp Tyr Ala Asp Ser Val
    50                  55                  60

Lys Gly Arg Phe Thr Ile Ser Arg Asp Asn Ser Lys Arg Ile Leu Tyr
65                  70                  75                  80

Leu Gln Met Asn Ser Leu Arg Val Gly Asp Thr Ala Val Tyr Tyr Cys
                85                  90                  95

Ala Lys Ser Pro Tyr Val Gly Gly Tyr Gly Leu Pro Gly Asp Ser Trp
            100                 105                 110

Gly Gln Gly Thr Leu Val Thr Val Ser Ser
        115                 120


<210> SEQ ID NO 46
<211> LENGTH: 108
<212> TYPE: PRT
<213> ORGANISM: Homo sapiens

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Ile Phe Phe Asn
            20                  25                  30

Tyr Leu Ala Trp Tyr Gln Lys Lys Pro Gly Gln Ala Pro Arg Leu Leu
        35                  40                  45

Val His Gly Ala Ser Thr Arg Ala Thr Gly Ile Pro Asp Arg Phe Ser
    50                  55                  60

Gly Ser Gly Ser Gly Thr Asp Phe Thr Leu Thr Ile Asn Ser Leu Asp
65                  70                  75                  80

Pro Glu Asp Phe Ala Val Tyr Tyr Cys Gln Gln Tyr Gly Asp Ser Pro
                85                  90                  95

Pro Thr Phe Gly Gly Gly Thr Lys Val Glu Ile Lys
            100                 105


<210> SEQ ID NO 47
<211> LENGTH: 122
<212> TYPE: PRT
<213> ORGANISM: Homo sapiens

<400> SEQUENCE: 47

Gln Val Gln Leu Val Gln Ser Gly Ala Glu Val Lys Lys Pro Gly Ser
1               5                   10                  15

Ser Val Arg Leu Ser Cys Lys Ala Ser Gly Gly Ser Tyr Ser Thr Tyr
            20                  25                  30

Ala Ile Ser Trp Val Arg Gln Ala Pro Gly Gln Gly Leu Glu Trp Met
        35                  40                  45

Gly Arg Ile Ile Pro Ser Leu Gly Lys Thr His Leu Ala Gln Lys Phe
    50                  55                  60

Gln Gly Arg Val Thr Phe Thr Ala Asp Glu Ser Thr Thr Thr Val Tyr
65                  70                  75                  80

Met Ile Leu Ser Ser Leu Lys Ser Glu Asp Thr Ala Leu Tyr Tyr Cys
```

```
                85                  90                  95

Ala Thr Pro Asp Trp Gln Tyr Ser Ser Ala Tyr Ser Leu Asp His Trp
            100                 105                 110

Gly Gln Gly Thr Leu Val Thr Val Ser Ser
        115                 120


<210> SEQ ID NO 48
<211> LENGTH: 112
<212> TYPE: PRT
<213> ORGANISM: Homo sapiens

<400> SEQUENCE: 48

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Thr Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110


<210> SEQ ID NO 49
<211> LENGTH: 114
<212> TYPE: PRT
<213> ORGANISM: Homo sapiens

<400> SEQUENCE: 49

Gln Val Gln Leu Gln Glu Ser Gly Pro Gly Leu Val Lys Pro Ser Glu
1               5                   10                  15

Thr Leu Ser Leu Ser Cys Thr Val Ser Ser Gly Ser Ile Ser Asn Tyr
            20                  25                  30

Tyr Trp Asn Trp Ile Arg Gln Pro Pro Gly Lys Gly Leu Glu Trp Ile
        35                  40                  45

Gly Tyr Ile Tyr Tyr Ser Gly Ser Ile Ser Tyr Asn Pro Ser Leu Lys
    50                  55                  60

Ser Arg Val Thr Ile Ser Val Asp Thr Ser Lys Asn Gln Leu Ser Leu
65                  70                  75                  80

Lys Leu Asn Ser Val Thr Ala Ala Asp Thr Ala Val Tyr Tyr Cys Ala
                85                  90                  95

Arg Gly Pro Asp Asn Arg Tyr Trp Gly Gln Gly Thr Leu Val Thr Val
            100                 105                 110

Ser Ser


<210> SEQ ID NO 50
<211> LENGTH: 109
<212> TYPE: PRT
<213> ORGANISM: Homo sapiens

<400> SEQUENCE: 50

Glu Ile Val Met Thr Gln Ser Pro Ala Thr Leu Ser Val Ser Pro Gly
1               5                   10                  15
```

```
Glu Arg Val Thr Leu Ser Cys Arg Ala Ser Gln Ser Val Ser Tyr Asn
            20                  25                  30

Leu Ala Trp His Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Asn Met Gln Ser
65                  70                  75                  80

Glu Asp Phe Ala Val Tyr Tyr Cys Gln Gln Tyr Asn Asn Trp Pro Pro
                85                  90                  95

Val Phe Thr Phe Gly Pro Gly Thr Lys Val Asp Ile Lys
            100                 105


<210> SEQ ID NO 51
<211> LENGTH: 123
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ser Tyr
            20                  25                  30

Tyr Met Asn Trp Val Arg Gln Ala Pro Gly Gln Gly Leu Glu Trp Met
        35                  40                  45

Gly Ile Ile Lys Pro Ser Asp Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Arg Ser Leu Arg Ser Glu Asp Thr Ala Val Tyr Tyr Cys
                85                  90                  95

Gly Arg Asp Ser Lys Gly Trp Leu Gln Leu Arg Gly Asp Ile Asp Tyr
            100                 105                 110

Trp Gly Gln Gly Thr Leu Val Thr Val Ser Ser
        115                 120


<210> SEQ ID NO 52
<211> LENGTH: 110
<212> TYPE: PRT
<213> ORGANISM: Homo sapiens

<400> SEQUENCE: 52

Gln Ser Ala Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Asn Tyr
            20                  25                  30

Asn Leu Val Ser Trp Tyr Gln Gln His Pro Gly Lys Ala Pro Lys Leu
        35                  40                  45

Leu Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Tyr Val Phe Gly Thr Gly Thr Glu Val Thr Val Leu
            100                 105                 110
```

<210> SEQ ID NO 53
<211> LENGTH: 122
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
1 5 10 15

Ser Leu Arg Leu Ser Cys Ala Thr Ser Gly Phe Thr Phe Ser Thr Tyr
20 25 30

Ala Met Ser Trp Val Arg Gln Ala Pro Gly Lys Gly Leu Glu Trp Val
35 40 45

Ser Ser Phe Ser Gly Val Asp Asp Ser Thr Tyr Tyr Ala Glu Ser Val
50 55 60

Lys Gly Arg Phe Thr Ile Ser Arg Asp Asn Ser Lys Asn Thr Val Tyr
65 70 75 80

Leu Gln Met Thr Arg Leu Arg Ala Glu Asp Thr Ala Val Tyr Tyr Cys
85 90 95

Ala Lys Asp Arg Gly Pro Arg Gly Val Gly Glu Leu Phe Asp Ser Trp
100 105 110

Gly Gln Gly Thr Leu Val Thr Val Ser Ser
115 120

<210> SEQ ID NO 54
<211> LENGTH: 107
<212> TYPE: PRT
<213> ORGANISM: Homo sapiens

<400> SEQUENCE: 54

Asp Ile Gln Met Thr Gln Ser Pro Ser Thr Leu Ser Ala Ser Val Gly
1 5 10 15

Asp Arg Val Thr Met Thr Cys Arg Ala Ser Gln Ser Ile Asn Arg Trp
20 25 30

Leu Ala Trp Tyr Gln Gln Lys Pro Gly Lys Ala Pro Lys Leu Leu Ile
35 40 45

Tyr Thr Thr Ser Thr Leu Lys Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Phe His Ser Val Pro Trp
85 90 95

Thr Phe Gly Gln Gly Thr Lys Val Glu Ile Lys
100 105

<210> SEQ ID NO 55
<211> LENGTH: 122
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
1 5 10 15

Ser Leu Arg Leu Ser Cys Ala Thr Ser Gly Phe Thr Phe Thr Thr Phe
20 25 30

Ala Met Ser Trp Val Arg Gln Ala Pro Gly Lys Gly Leu Glu Trp Val
35 40 45

Ser Ser Ile Ser Gly Ala Asp Asp Ser Thr Tyr Tyr Ala Ala Ser Val

```
    50                  55                  60

Lys Gly Arg Phe Thr Ile Ser Arg Asp Asn Ser Arg Ser Thr Leu Phe
65                  70                  75                  80

Leu Gln Met Asn Ser Leu Arg Ala Glu Asp Thr Ala Val Tyr Tyr Cys
                85                  90                  95

Ala Lys Asp Arg Gly Pro Arg Gly Val Gly Glu Leu Phe Asp Ser Trp
            100                 105                 110

Gly Gln Gly Thr Leu Val Thr Val Ser Ser
        115                 120


<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Lys Trp
            20                  25                  30

Leu Ala Trp Tyr Gln Gln Lys Pro Gly Lys Ala Pro Arg Leu Leu Ile
        35                  40                  45

Tyr Thr Thr Ser Thr Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Phe Phe Ser Val Pro Trp
                85                  90                  95

Thr Phe Gly Gln Gly Thr Lys Val Glu Ile Lys
            100                 105


<210> SEQ ID NO 57
<211> LENGTH: 122
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Phe Ser Gly Ile Asp Asp Ser Thr Trp Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Val Arg Gly Phe Ala Glu Val Leu Asp Tyr Trp
            100                 105                 110

Gly Arg Gly Thr Leu Val Thr Val Ser Ser
        115                 120


<210> SEQ ID NO 58
<211> LENGTH: 107
<212> TYPE: PRT
```

<213> ORGANISM: Homo sapiens

<400> SEQUENCE: 58

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Lys Tyr
20 25 30

Leu Ala Trp Tyr Gln Gln Arg Pro Gly Lys Val Pro Asn Leu Leu Ile
35 40 45

Tyr Thr Ala Ser Thr Leu Gln Ser Gly Val Pro Ser Arg Phe Ser Gly
50 55 60

Ser Gly Ser Gly Thr His Phe Thr Leu Thr Ile Ser Ser Leu Gln Pro
65 70 75 80

Glu Asp Val Ala Thr Tyr Tyr Cys Gln Lys Tyr Asn Ser Val Pro Trp
85 90 95

Thr Phe Gly Gln Gly Thr Lys Val Glu Ile Lys
100 105

<210> SEQ ID NO 59
<211> LENGTH: 120
<212> TYPE: PRT
<213> ORGANISM: Homo sapiens

<400> SEQUENCE: 59

Glu Val Gln Leu Leu Glu Ser Gly Gly Gly Leu Val Arg Pro Gly Gly
1 5 10 15

Ser Leu Arg Leu Ser Cys Thr Ala Ser Gly Phe Thr Phe Arg Arg Tyr
20 25 30

Ala Met Ala Trp Val Arg Gln Ala Pro Gly Lys Gly Leu Glu Trp Val
35 40 45

Ser Leu Ile Tyr Asp Gly Asp Asp Ser Thr Tyr Tyr Ala Lys Ser Val
50 55 60

Lys Gly Arg Phe Ala Ile Ser Arg Asp Asn Ser Lys Asn Thr Leu Ser
65 70 75 80

Leu Gln Met Asn Ser Leu Arg Ala Glu Asp Thr Ala Val Tyr Tyr Cys
85 90 95

Val Lys Asp Arg Asp Asn Gly Trp Ser Ser Ile Val Asp Trp Gly Gln
100 105 110

Gly Thr Leu Val Thr Val Ser Ser
115 120

<210> SEQ ID NO 60
<211> LENGTH: 106
<212> TYPE: PRT
<213> ORGANISM: Homo sapiens

<400> SEQUENCE: 60

Asp Ile Gln Met Thr Gln Ser Pro Ser Thr Leu Ser Ala Ser Val Gly
1 5 10 15

Asp Arg Val Thr Ile Thr Cys Arg Ala Ser His Ser Ile Ser Gly Trp
20 25 30

Leu Ala Trp Tyr Gln Gln Lys Pro Gly Lys Ala Pro Lys Leu Leu Ile
35 40 45

Tyr Gln Ala Ser Ile Leu Glu Ser Gly Val Pro Ser Arg Phe Ser Gly
50 55 60

Ser Gly Ser Gly Thr Glu Phe Thr Leu Thr Ile Gly Ser Leu Gln Pro
65 70 75 80

```
Glu Asp Phe Ala Thr Tyr Phe Cys Gln Gln Tyr Ser Thr Phe Trp Thr
                85                  90                  95

Phe Gly Gln Gly Thr Lys Val Glu Ile Lys
            100                 105


<210> SEQ ID NO 61
<211> LENGTH: 120
<212> TYPE: PRT
<213> ORGANISM: Homo sapiens

<400> SEQUENCE: 61

Glu Val Gln Leu Leu Glu Ser Gly Gly Gly Leu Val Arg Pro Gly Gly
1               5                   10                  15

Ser Leu Arg Leu Ser Cys Thr Ala Ser Gly Phe Thr Phe Arg Arg Phe
            20                  25                  30

Ala Met Ala Trp Val Arg Gln Ala Pro Gly Lys Gly Leu Glu Trp Val
        35                  40                  45

Ser Leu Ile Trp Asn Gly Asp Asp Ser Thr Tyr Tyr Ala Glu Ser Val
    50                  55                  60

Arg Gly Arg Phe Thr Ile Ser Arg Asp Asn Ser His Asn Thr Leu Ser
65                  70                  75                  80

Leu Gln Met Arg Ser Leu Arg Ala Glu Asp Thr Ala Ile Tyr Tyr Cys
                85                  90                  95

Val Lys Asp Arg Asp Asn Gly Trp Ser Ser Ile Val Asp Trp Gly Gln
            100                 105                 110

Gly Thr Leu Val Thr Val Ser Ser
        115                 120


<210> SEQ ID NO 62
<211> LENGTH: 106
<212> TYPE: PRT
<213> ORGANISM: Homo sapiens

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Gly Asn Trp
            20                  25                  30

Leu Ala Trp Tyr Gln Gln Lys Pro Gly Lys Ala Pro Lys Leu Leu Ile
        35                  40                  45

Tyr Gln Ala Ser Val Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Tyr Ser Thr Phe Trp Thr
                85                  90                  95

Phe Gly Gln Gly Thr Lys Val Glu Ile Lys
            100                 105


<210> SEQ ID NO 63
<211> LENGTH: 120
<212> TYPE: PRT
<213> ORGANISM: Homo sapiens

<400> SEQUENCE: 63

Glu Val Gln Leu Leu Glu Ser Gly Gly Gly Leu Val Arg Pro Gly Gly
1               5                   10                  15
```

-continued

```
Ser Leu Arg Leu Ser Cys Thr Ala Ser Gly Phe Thr Phe Arg Arg Tyr
            20                  25                  30

Ala Met Ala Trp Val Arg Gln Ala Pro Gly Lys Gly Leu Glu Trp Val
        35                  40                  45

Ser Leu Ile Tyr Asn Gly Asp Asp Ser Thr Tyr Tyr Ala Glu Ser Val
    50                  55                  60

Lys Gly Arg Phe Thr Val Ser Arg Asp Asn Ser Gln Asn Thr Leu Ser
65                  70                  75                  80

Leu Gln Met Asn Ser Leu Arg Ala Glu Asp Thr Ala Ile Tyr Tyr Cys
                85                  90                  95

Val Arg Asp Arg Asp Asn Gly Trp Ser Ser Ile Val Asp Trp Gly Gln
            100                 105                 110

Gly Thr Leu Val Thr Val Ser Ser
        115                 120


<210> SEQ ID NO 64
<211> LENGTH: 106
<212> TYPE: PRT
<213> ORGANISM: Homo sapiens

<400> SEQUENCE: 64

Asp Ile Gln Met Thr Gln Ser Pro Ser Thr Leu Ser Ala Ser Val Gly
1               5                   10                  15

Asp Arg Val Thr Ile Thr Cys Arg Ala Ser Arg Thr Ile Gly Ser Trp
            20                  25                  30

Leu Ala Trp Tyr Gln Gln Lys Pro Gly Lys Ala Pro Lys Leu Leu Ile
        35                  40                  45

Tyr Gln Ala Ser Ile Leu Glu Gly Gly Val Pro Ser Arg Phe Ser Gly
    50                  55                  60

Ser Val Ser Gly Thr Glu Phe Thr Leu Thr Ile Arg Ser Leu Gln Pro
65                  70                  75                  80

Glu Asp Phe Ala Thr Tyr Phe Cys Gln Gln Tyr Ser Thr Phe Trp Thr
                85                  90                  95

Phe Gly Gln Gly Thr Lys Val Glu Ile Lys
            100                 105


<210> SEQ ID NO 65
<211> LENGTH: 122
<212> TYPE: PRT
<213> ORGANISM: Homo sapiens

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Thr Tyr
            20                  25                  30

Ala Met Ser Trp Val Arg Gln Pro Pro Gly Lys Gly Leu Glu Trp Val
        35                  40                  45

Ser Ser Ile Ser Ala Arg Glu Asp Ser Thr Tyr Phe Ala Ala Ser Val
    50                  55                  60

Arg Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Leu Tyr Tyr Cys
                85                  90                  95

Ala Lys Asp Arg Leu Gln Leu Gly Val Gly Glu Leu Tyr Glu Ser Trp
            100                 105                 110
```

Gly Gln Gly Thr Leu Val Thr Val Ser Ser
        115                 120

<210> SEQ ID NO 66
<211> LENGTH: 107
<212> TYPE: PRT
<213> ORGANISM: Homo sapiens

<400> SEQUENCE: 66

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Ser Trp
            20                  25                  30

Leu Ala Trp Tyr Gln Gln Lys Pro Gly Lys Ala Pro Lys Leu Leu Ile
        35                  40                  45

Tyr Met Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Asp Asp Phe Ala Thr Tyr Tyr Cys Gln His Tyr His Ser Tyr Pro Trp
                85                  90                  95

Thr Phe Gly Gln Gly Thr Lys Val Glu Ile Lys
            100                 105

<210> SEQ ID NO 67
<211> LENGTH: 124
<212> TYPE: PRT
<213> ORGANISM: Homo sapiens

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Asn Trp Val Arg Gln Ala Pro Gly Lys Gly Leu Glu Trp Val
        35                  40                  45

Ser Gly Ile Gly Gly Arg Gly Ala Ile Ala Gly Asp Gly Ser Ile Tyr
    50                  55                  60

Tyr Ala Asp Ser Val Lys Gly Arg Phe Thr Ile Ser Arg Asp Asn Ser
65                  70                  75                  80

Lys Asn Ile Val Tyr Leu Gln Met Asn Gly Leu Arg Val Glu Asp Thr
                85                  90                  95

Ala Val Tyr Tyr Cys Ala Lys Asp Arg Val Ala Phe Asp Gly Phe His
            100                 105                 110

Val Trp Gly Gln Gly Thr Leu Val Thr Val Ser Ser
        115                 120

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Pro Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile

```
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Gln Gln Tyr Asn Ser Tyr Pro Trp
                85                  90                  95

Thr Phe Gly Gln Gly Thr Lys Val Glu Ile Lys
            100                 105


<210> SEQ ID NO 69
<211> LENGTH: 124
<212> TYPE: PRT
<213> ORGANISM: Homo sapiens

<400> SEQUENCE: 69

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ser Tyr
            20                  25                  30

Tyr Val His Trp Val Arg Gln Ala Pro Gly Gln Gly Leu Glu Trp Met
        35                  40                  45

Gly Ile Ile Asn Pro Gly Asn Asn Phe Val Ser Phe Ala Gln Asn Phe
    50                  55                  60

Tyr Asp Arg Ala Thr Met Thr Arg Asp Thr Ser Thr Asn Thr Val Tyr
65                  70                  75                  80

Met Glu Leu Thr Asn Leu Gln Ser Glu Asp Thr Ala Val Tyr Tyr Cys
                85                  90                  95

Ala Arg Thr Leu Val Ala Pro Ser Ala Gln Ser Met Tyr Tyr Phe Asp
            100                 105                 110

Phe Trp Gly Gln Gly Thr Leu Val Thr Val Ser Ser
        115                 120


<210> SEQ ID NO 70
<211> LENGTH: 108
<212> TYPE: PRT
<213> ORGANISM: Homo sapiens

<400> SEQUENCE: 70

Glu Ile Val Leu Thr Gln Ser Pro Gly Thr Leu Ser Leu Ser Pro Gly
1               5                   10                  15

Glu Arg Gly Thr Leu Ser Cys Arg Ala Ser Gln Tyr Ile Thr Thr Gly
            20                  25                  30

His Phe Ala Trp Tyr Gln Gln Lys Pro Gly Arg Ala Pro Arg Leu Leu
        35                  40                  45

Ile Tyr Gly Ala Ser Val Arg Ala Thr Gly Val Pro Asp Arg Phe Ser
    50                  55                  60

Gly Ser Gly Ala Glu Thr Asp Phe Thr Leu Thr Ile Ser Arg Leu Asp
65                  70                  75                  80

Pro Glu Asp Val Gly Val Tyr Tyr Cys Gln Gln Tyr Gly Ser Ser Pro
                85                  90                  95

Val Thr Phe Gly Pro Gly Thr Lys Val Asp Ile Lys
            100                 105


<210> SEQ ID NO 71
<211> LENGTH: 121
<212> TYPE: PRT
```

<213> ORGANISM: Homo sapiens

<400> SEQUENCE: 71

Gln Val Gln Leu Val Gln Ser Gly Ala Gly Met Arg Lys Pro Gly Ala
1 5 10 15

Ser Val Lys Val Ser Cys Lys Ala Ser Gly Tyr Ser Phe Asn Asp Tyr
20 25 30

Tyr Ile His Trp Val Arg Gln Ala Pro Gly Gln Gly Leu Glu Trp Met
35 40 45

Gly Trp Ile Asn Pro Lys Ser Gly Phe Thr Asn Tyr Ala Gln Arg Phe
50 55 60

Gln Gly Arg Val Thr Met Thr Gly Asp Thr Ser Asn Ser Val Ala Tyr
65 70 75 80

Met Glu Leu Thr Arg Leu Thr Ser Asp Asp Thr Ala Val Tyr Tyr Cys
85 90 95

Ala Arg Gly Gly Arg Ile Asn Ala Pro Leu Gly Phe Asp Pro Trp Gly
100 105 110

Gln Gly Thr Leu Val Thr Val Ser Ser
115 120

<210> SEQ ID NO 72
<211> LENGTH: 108
<212> TYPE: PRT
<213> ORGANISM: Homo sapiens

<400> SEQUENCE: 72

Glu Ile Val Leu Thr Gln Ser Pro Asp Thr Leu Ser Leu Ser Pro Gly
1 5 10 15

Glu Thr Ala Thr Leu Ser Cys Arg Ala Ser Gln Ser Ile Gly Ser Ile
20 25 30

Ser Leu Gly Trp Tyr Gln Gln Lys Phe Gly Gln Ala Pro Arg Leu Leu
35 40 45

Ile Tyr Gly Ala Ser Thr Arg Ala Thr Gly Thr Pro Asp Arg Phe Ser
50 55 60

Gly Ser Gly Ser Glu Thr Asp Phe Thr Leu Thr Ile Ser Arg Leu Glu
65 70 75 80

Pro Glu Asp Ser Ala Val Tyr Tyr Cys Gln Gln Tyr Val Ser Ser Pro
85 90 95

Leu Arg Phe Gly Gly Gly Thr Lys Val Glu Ile Lys
100 105

<210> SEQ ID NO 73
<211> LENGTH: 124
<212> TYPE: PRT
<213> ORGANISM: Homo sapiens

<400> SEQUENCE: 73

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Thr Tyr
20 25 30

Phe Ile His Trp Val Arg Gln Ala Pro Gly Gln Gly Leu Glu Trp Met
35 40 45

Gly Ile Ile Asn Pro Asn Ser Gly Ser Thr Asn Tyr Ala Gln Lys Ile
50 55 60

Gln Gly Arg Val Thr Met Thr Thr Asp Thr Ser Ala Ser Thr Val Tyr
65 70 75 80

```
Met Glu Leu Ser Gly Leu Arg Ser Glu Asp Thr Ala Val Tyr Tyr Cys
                85                  90                  95

Ala Arg Gly Gly Ser Tyr Pro Val Ala Ile Arg Gly Val Thr Phe Gly
            100                 105                 110

Ile Trp Gly Gln Gly Thr Met Val Thr Val Ser Ser
        115                 120
```

<210> SEQ ID NO 74
<211> LENGTH: 107
<212> TYPE: PRT
<213> ORGANISM: Homo sapiens

<400> SEQUENCE: 74

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Asn Leu Leu Ile
        35                  40                  45

Phe Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Leu
                85                  90                  95

Thr Phe Gly Gly Gly Thr Lys Val Glu Ile Lys
            100                 105
```

<210> SEQ ID NO 75
<211> LENGTH: 130
<212> TYPE: PRT
<213> ORGANISM: Homo sapiens

<400> SEQUENCE: 75

```
Gln Val Gln Leu Gln Gln Trp Gly Ala Arg Pro Leu Lys Pro Ser Glu
1               5                   10                  15

Thr Leu Ser Leu Thr Cys Gly Val Asn Gly Gly Ser Phe Ser Gly Tyr
            20                  25                  30

His Trp Ser Trp Ile Arg Gln Pro Pro Gly Lys Gly Leu Glu Trp Ile
        35                  40                  45

Gly Glu Ile Asp His Asn Gly Arg Ile Asn Tyr Asn Pro Ser Leu Lys
    50                  55                  60

Ser Arg Val Thr Ile Ser Ile Asp Thr Phe Lys Ser Gln Phe Ser Leu
65                  70                  75                  80

Arg Leu Thr Ser Ile Ile Ala Ala Asp Thr Ala Val Tyr Tyr Cys Ala
                85                  90                  95

Arg Asp Val Val Thr Met Val Glu Gly Leu Arg Phe His Tyr Tyr Tyr
            100                 105                 110

Asn Tyr Tyr Gly Met Asp Val Trp Gly Gln Gly Thr Thr Val Thr Val
        115                 120                 125

Ser Ser
    130
```

<210> SEQ ID NO 76
<211> LENGTH: 108
<212> TYPE: PRT
<213> ORGANISM: Homo sapiens

<400> SEQUENCE: 76

Glu Ile Val Leu Thr Gln Ser Pro Gly Thr Leu Ser Leu Ser Pro Gly
1               5                   10                  15

Asp Arg Ala Thr Leu Ser Cys Gly Ala Ser Gln Ser Val Ser Ser Asn
            20                  25                  30

Tyr Leu Ala Trp Tyr Gln Gln Lys Leu Gly Gln Ala Pro Arg Leu Leu
        35                  40                  45

Ile Tyr Ala Ala Ser Thr Arg Ala Thr Gly Ile Pro Asp Arg Phe Ser
    50                  55                  60

Gly Gly Gly Ser Gly Thr Asp Phe Thr Leu Thr Ile Asn Lys Leu Glu
65                  70                  75                  80

Ala Glu Asp Phe Ala Met Tyr Tyr Cys Gln Ile Tyr Asp Ser Ser Val
                85                  90                  95

Arg Thr Phe Gly Gln Gly Thr Lys Val Glu Ile Lys
            100                 105

<210> SEQ ID NO 77
<211> LENGTH: 122
<212> TYPE: PRT
<213> ORGANISM: Homo sapiens

<400> SEQUENCE: 77

Glu Val Gln Leu Leu Glu Ser Gly Gly Arg Leu Val Gln Pro Gly Gly
1               5                   10                  15

Ser Leu Thr Leu Ser Cys Ala Ala Ser Gly Phe Pro Phe Ser Thr Tyr
            20                  25                  30

Ala Met Ser Trp Leu Arg Gln Ala Pro Gly Lys Gly Leu Glu Trp Val
        35                  40                  45

Ser Gly Ile Thr Gly Asp Ser Gly Ser Thr Tyr Tyr Ala Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Asp Asp Thr Ala Val Tyr Tyr Cys
                85                  90                  95

Ala Lys Asp Arg Leu His Ser Gly Leu Gly Glu Leu Phe Ser Tyr Trp
            100                 105                 110

Gly Gln Gly Thr Leu Val Thr Val Ser Ser
        115                 120

<210> SEQ ID NO 78
<211> LENGTH: 107
<212> TYPE: PRT
<213> ORGANISM: Homo sapiens

<400> SEQUENCE: 78

Asp Ile Gln Met Thr Gln Ser Pro Ser Thr Leu Ser Ala Ser Val Gly
1               5                   10                  15

Asp Arg Val Asn Ile Thr Cys Arg Ala Ser Gln Ser Ile Asn Gln Trp
            20                  25                  30

Leu Ala Trp Tyr Gln Gln Lys Pro Gly Lys Ala Pro Lys Phe Leu Met
        35                  40                  45

Tyr Lys Ala Ser Thr Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Phe Ser Tyr Pro Trp
85 90 95

Thr Phe Gly Gln Gly Thr Lys Val Glu Ile Lys
100 105

<210> SEQ ID NO 79
<211> LENGTH: 122
<212> TYPE: PRT
<213> ORGANISM: Homo sapiens

<400> SEQUENCE: 79

Glu Val Gln Leu Leu Glu Ser Gly Gly Gly Leu Ala Gln Pro Gly Gly
1 5 10 15

Ser Leu Arg Leu Ser Cys Glu Thr Ser Gly Phe Thr Phe Arg Ser Tyr
20 25 30

Gly Met Gly Trp Val Arg Gln Ala Pro Gly Lys Gly Leu Glu Trp Val
35 40 45

Ser Ser Ile Tyr Ile Ser Gly Asp Ser Thr Tyr Tyr Ala Ala Ser Val
50 55 60

Lys Gly Arg Phe Thr Ile Ser Arg Asp Asn Ser Lys Ser Thr Leu Tyr
65 70 75 80

Leu Gln Met Asp Arg Leu Thr Ala Glu Asp Thr Ala Val Tyr Tyr Cys
85 90 95

Val Arg Asp Arg Ile Gln Gly Gly Phe Gly Glu Leu Tyr Arg Tyr Trp
100 105 110

Gly Gln Gly Thr Leu Val Thr Val Ser Ser
115 120

<210> SEQ ID NO 80
<211> LENGTH: 107
<212> TYPE: PRT
<213> ORGANISM: Homo sapiens

<400> SEQUENCE: 80

Asp Ile Gln Met Thr Gln Ser Pro Ser Thr Leu Ser Ala Ser Val Gly
1 5 10 15

Asp Arg Val Thr Met Thr Cys Arg Ala Ser Gln Ser Val Asn Lys Trp
20 25 30

Leu Ala Trp Tyr Gln Gln Lys Pro Gly Lys Ala Pro Lys Leu Leu Ile
35 40 45

Tyr Glu Thr Ser Ile Leu Glu Ser Gly Val Ser Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln His Tyr His Gly Tyr Pro Trp
85 90 95

Thr Phe Gly Gln Gly Thr Lys Val Glu Ile Lys
100 105

<210> SEQ ID NO 81
<211> LENGTH: 122
<212> TYPE: PRT
<213> ORGANISM: Homo sapiens

<400> SEQUENCE: 81

Glu Val Gln Leu Leu Glu Ser Gly Gly Asp Leu Val Gln Pro Gly Gly
1 5 10 15

Ser Leu Arg Leu Ser Cys Ala Ala Ser Gly Phe Thr Phe Ser Thr Tyr

```
            20                  25                  30

Gly Met Ala Trp Val Arg Gln Ala Pro Gly Lys Gly Leu Glu Trp Leu
        35                  40                  45

Ser Ser Ile Ser Ser Val Asp Asp Ser Lys Tyr Tyr Ala Ala Ser Val
    50                  55                  60

Lys Gly Arg Phe Thr Ile Ser Arg Asp Asn Ser Arg Asn Thr Leu Tyr
65                  70                  75                  80

Leu His Met Asn Ser Leu Arg Val Asp Asp Thr Ala Val Tyr Tyr Cys
                85                  90                  95

Ala Lys Asp Arg Ile Pro His Gly Leu Gly Glu Leu Tyr Ala Asn Trp
            100                 105                 110

Gly Gln Gly Thr Leu Val Thr Val Ser Ser
        115                 120


<210> SEQ ID NO 82
<211> LENGTH: 107
<212> TYPE: PRT
<213> ORGANISM: Homo sapiens

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Gly Trp
            20                  25                  30

Leu Ala Trp Tyr Gln Gln Lys Pro Gly Lys Ala Pro Arg Leu Leu Met
        35                  40                  45

His Lys Ala Ser Asn Leu Tyr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr His Ser Tyr Pro Tyr
                85                  90                  95

Thr Phe Gly Gln Gly Thr Lys Val Glu Ile Lys
            100                 105


<210> SEQ ID NO 83
<211> LENGTH: 127
<212> TYPE: PRT
<213> ORGANISM: Homo sapiens

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Val Tyr Tyr Cys
                85                  90                  95

Ala Lys Ser Ser Gly Gly His Asn Trp Asn Tyr Val Asp Tyr Tyr Tyr
            100                 105                 110

Gly Met Asp Val Trp Gly Gln Gly Thr Thr Val Thr Val Ser Ser
```

115 120 125

<210> SEQ ID NO 84
<211> LENGTH: 107
<212> TYPE: PRT
<213> ORGANISM: Homo sapiens

<400> SEQUENCE: 84

Asp Ile Gln Leu Thr Gln Ser Pro Ser Phe Leu Ser Ala Ser Val Gly
1 5 10 15

Asp Arg Val Thr Ile Thr Cys Arg Ala Ser Gln Gly Ile Ser Ser Tyr
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Leu Asn Ser Tyr Pro Val
85 90 95

Thr Phe Gly Pro Gly Thr Lys Val Asp Ile Lys
100 105

<210> SEQ ID NO 85
<211> LENGTH: 125
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Thr
20 25 30

Tyr Ile His Trp Val Arg Gln Ala Pro Gly Gln Gly Leu Glu Trp Met
35 40 45

Gly Ile Ile Asn Pro Ser Ser Ser Asn Thr Asn Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Phe Gly Gly Tyr Ser Ser Ser Ser Val Ser Asp Ala Phe
100 105 110

Asp Ile Trp Gly Gln Gly Thr Met Val Thr Val Ser Ser
115 120 125

<210> SEQ ID NO 86
<211> LENGTH: 110
<212> TYPE: PRT
<213> ORGANISM: Homo sapiens

<400> SEQUENCE: 86

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Phe
20 25 30

Asn Leu Val Ser Trp Tyr Gln Gln His Pro Gly Lys Ala Pro Lys Leu
35 40 45

```
Ile Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Val His Tyr Tyr Cys Cys Ser Tyr Ala Gly Ser
                85                  90                  95

Ser Arg Phe Val Phe Gly Thr Gly Thr Lys Val Thr Val Leu
            100                 105                 110


<210> SEQ ID NO 87
<211> LENGTH: 119
<212> TYPE: PRT
<213> ORGANISM: Homo sapiens

<400> SEQUENCE: 87

Glu Val Gln Leu Leu Glu Ser Gly Gly Ala Leu Val Gln Pro Gly Gly
1               5                   10                  15

Ser Leu Arg Leu Ser Cys Ala Ala Ser Gly Phe Thr Phe Asn Tyr Tyr
            20                  25                  30

Ala Met Thr Trp Val Arg Gln Ala Pro Gly Arg Gly Leu Glu Trp Val
        35                  40                  45

Ser Thr Ile Thr Asp Asn Gly Gly Thr Thr Tyr Leu Ala Asp Ser Val
    50                  55                  60

Lys Gly Arg Phe Thr Ile Ser Arg Asp Asn Ser Gln Asn Thr Gln Ser
65                  70                  75                  80

Leu Gln Met Asn Asn Leu Arg Ala Asp Asp Thr Ala Val Tyr Phe Cys
                85                  90                  95

Val Lys His Leu Arg Gly Trp Tyr Thr Phe Glu Ile Trp Gly Gln Gly
            100                 105                 110

Thr Leu Val Thr Val Ser Ser
        115


<210> SEQ ID NO 88
<211> LENGTH: 109
<212> TYPE: PRT
<213> ORGANISM: Homo sapiens

<400> SEQUENCE: 88

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Arg Tyr Thr Phe Gly Gln Gly Thr Lys Leu Glu Ile Lys
            100                 105


<210> SEQ ID NO 89
<211> LENGTH: 120
<212> TYPE: PRT
<213> ORGANISM: Homo sapiens
```

<400> SEQUENCE: 89

Glu Val Gln Leu Leu Glu Ser Gly Gly Gly Leu Val Lys Pro Gly Gly
1               5                   10                  15

Ser Leu Arg Leu Ser Cys Ala Ala Ser Gly Leu Thr Phe Ser Thr Tyr
            20                  25                  30

Ala Met Ser Trp Val Arg Gln Ala Pro Gly Lys Gly Leu Glu Trp Val
        35                  40                  45

Ser Ala Ile Ser Pro Gly Ser Gly Asp Asn Ile Tyr Tyr Gly Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Val Asn Gly Gly Phe Ser Gly Tyr Tyr Ser Asp Tyr Trp Gly Gln
            100                 105                 110

Gly Thr Leu Val Thr Val Ser Ser
        115                 120

<210> SEQ ID NO 90
<211> LENGTH: 106
<212> TYPE: PRT
<213> ORGANISM: Homo sapiens

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Met Ala Pro Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Leu Thr
                85                  90                  95

Phe Gly Gly Gly Thr Lys Val Asp Ile Lys
            100                 105

<210> SEQ ID NO 91
<211> LENGTH: 129
<212> TYPE: PRT
<213> ORGANISM: Homo sapiens

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Pro Gly Gly Thr Phe Ser Arg Tyr
            20                  25                  30

Ser Ile Ala Trp Val Arg Gln Ala Pro Gly Gln Gly Leu Glu Trp Met
        35                  40                  45

Gly Gly Ile Asn Pro Thr Phe Thr Thr Pro Asn Tyr Ala Gln Lys Phe
    50                  55                  60

Gln Gly Arg Val Thr Ile Thr Ala Asp Glu Ser Thr Asn Thr Ala Tyr
65                  70                  75                  80

```
Leu Asp Leu Ser Ser Leu Arg Ser Glu Asp Thr Ala Val Tyr Tyr Cys
                85                  90                  95

Ala Arg Phe Arg Tyr Tyr Tyr Glu Ser Gly Gly Tyr Ser Asp Ala Ser
            100                 105                 110

Pro Tyr Tyr Leu Asp Tyr Trp Gly Gln Gly Thr Leu Val Thr Val Ser
        115                 120                 125

Ser


<210> SEQ ID NO 92
<211> LENGTH: 107
<212> TYPE: PRT
<213> ORGANISM: Homo sapiens

<400> SEQUENCE: 92

Glu Ile Val Leu Thr Gln Ser Pro Ala Thr Leu Ser Leu Ser Pro Gly
1               5                   10                  15

Glu Arg Val Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Thr Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105


<210> SEQ ID NO 93
<211> LENGTH: 123
<212> TYPE: PRT
<213> ORGANISM: Homo sapiens

<400> SEQUENCE: 93

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Tyr Ser Trp Phe Arg Gln Leu Pro Gly Lys Gly Leu Glu
        35                  40                  45

Trp Ile Gly His Ile Tyr Tyr Thr Gly Asn Thr His Tyr Asn Pro Ser
    50                  55                  60

Leu Arg Ser Arg Leu Thr Ile Ser Val Asp Thr Ser Lys Asn Gln Phe
65                  70                  75                  80

Ser Leu Lys Leu Ser Ser Val Thr Ala Ala Asp Thr Ala Arg Tyr Tyr
                85                  90                  95

Cys Ala Arg Ala Trp Cys Glu Tyr Ala Ala Tyr Cys Trp Phe Asp Pro
            100                 105                 110

Trp Gly Arg Gly Thr Leu Val Thr Val Ser Ser
        115                 120


<210> SEQ ID NO 94
<211> LENGTH: 108
<212> TYPE: PRT
<213> ORGANISM: Homo sapiens

<400> SEQUENCE: 94
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln His Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Trp Cys Gln Gln Tyr Gly Arg Ser Pro
                85                  90                  95

Phe Thr Phe Gly Gln Gly Thr Lys Leu Glu Ile Lys
            100                 105


<210> SEQ ID NO 95
<211> LENGTH: 124
<212> TYPE: PRT
<213> ORGANISM: Homo sapiens

<400> SEQUENCE: 95

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Gly Gly
            20                  25                  30

Val Tyr Tyr Trp Asn Trp Ile Arg His His Pro Gly Lys Gly Leu Glu
        35                  40                  45

Trp Ile Gly Tyr Met Phe Tyr Ser Gly Asp Thr Asp Tyr Asn Pro Ser
    50                  55                  60

Leu Arg Ser Arg Val Thr Ile Ser Gly Asp Thr Ser Lys Asn Lys Phe
65                  70                  75                  80

Ser Leu Asn Leu Asn Ser Val Thr Ala Ala Asp Thr Ala Val Tyr Tyr
                85                  90                  95

Cys Ala Arg Ala Gly Phe Asp Tyr Gly Ser Pro Val Ser Ala Phe Asp
            100                 105                 110

Ile Trp Gly Gln Gly Thr Leu Val Thr Val Ser Ser
        115                 120


<210> SEQ ID NO 96
<211> LENGTH: 110
<212> TYPE: PRT
<213> ORGANISM: Homo sapiens

<400> SEQUENCE: 96

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Val Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Tyr Ala His Ser Pro
                85                  90                  95
```

Arg Gly Tyr Thr Phe Gly Gln Gly Thr Lys Leu Glu Ile Lys
100 105 110

<210> SEQ ID NO 97
<211> LENGTH: 123
<212> TYPE: PRT
<213> ORGANISM: Homo sapiens

<400> SEQUENCE: 97

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Asn Tyr Tyr Trp Gly Trp Ile Arg Gln Pro Pro Gly Lys Gly Leu Glu
35 40 45

Phe Ile Gly Ser Ile Tyr Tyr Thr Gly Ser Thr Tyr Tyr Asn Pro Ser
50 55 60

Leu Arg Ser Arg Val Thr Ile Ser Val Asp Thr Ser Lys Asn Gln Phe
65 70 75 80

Ser Leu Lys Leu Thr Ser Val Thr Ala Ala Asp Thr Ala Val Tyr Tyr
85 90 95

Cys Ala Arg His Gly Pro Gly Met Gly His Asn Trp Tyr Phe Asp Leu
100 105 110

Trp Gly Arg Gly Thr Leu Val Thr Val Ser Ser
115 120

<210> SEQ ID NO 98
<211> LENGTH: 106
<212> TYPE: PRT
<213> ORGANISM: Homo sapiens

<400> SEQUENCE: 98

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Ile Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Pro Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Thr Trp Leu Thr
85 90 95

Phe Gly Gly Gly Thr Lys Val Glu Ile Lys
100 105

<210> SEQ ID NO 99
<211> LENGTH: 125
<212> TYPE: PRT
<213> ORGANISM: Homo sapiens

<400> SEQUENCE: 99

Gln Leu Gln Leu Gln Glu Ser Gly Pro Arg Leu Val Lys Pro Ser Glu
1 5 10 15

Thr Leu Phe Leu Thr Cys Thr Val Ser Gly Asp Ser Ile Ser Ser Ser
20 25 30

Ser Tyr Phe Trp Gly Trp Ile Arg Gln Pro Pro Gly Lys Gly Leu Glu
35 40 45

Trp Ile Gly Ser Ile Ser Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Val Val Tyr Tyr
85 90 95

Cys Ala Lys His Leu Tyr Ser Ser Ser Trp Asn Ile Gly Ser Ser Phe
100 105 110

Asp Ser Trp Gly Pro Gly Thr Leu Val Thr Val Ser Ser
115 120 125

<210> SEQ ID NO 100
<211> LENGTH: 108
<212> TYPE: PRT
<213> ORGANISM: Homo sapiens

<400> SEQUENCE: 100

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ile Tyr
20 25 30

Leu Ala Trp Tyr Gln Gln Lys Pro Gly Gln Ala Pro Arg Leu Leu Ile
35 40 45

Tyr Asp Ala Ser Ser Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Val
85 90 95

Tyr Thr Phe Gly Gln Gly Thr Lys Val Glu Ile Lys
100 105

<210> SEQ ID NO 101
<211> LENGTH: 124
<212> TYPE: PRT
<213> ORGANISM: Homo sapiens

<400> SEQUENCE: 101

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ser Gly Tyr
20 25 30

Tyr Ile His Trp Leu Arg Gln Ala Pro Gly Gln Gly Leu Glu Trp Met
35 40 45

Gly Trp Ile Asn Ser Asn Ser Gly Gly Ala Asp Ser Gly Pro Arg Phe
50 55 60

His Gly Arg Val Thr Met Thr Arg Asp Thr Ser Ile Asn Thr Ala Tyr
65 70 75 80

Leu Glu Leu Thr Asn Leu Arg Ser Asp Asp Thr Ala Val Tyr Tyr Cys
85 90 95

Ala Arg Arg Thr Tyr Tyr Asp Thr Arg Phe Pro Tyr Trp Tyr Phe Asp
100 105 110

Leu Trp Gly Arg Gly Thr Leu Val Thr Val Ser Ser
115 120

<210> SEQ ID NO 102
<211> LENGTH: 107
<212> TYPE: PRT
<213> ORGANISM: Homo sapiens

<400> SEQUENCE: 102

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Tyr
            20                  25                  30

Leu Asn Trp Tyr Gln Gln Lys Pro Gly Lys Ala Pro Asn Val Leu Ile
        35                  40                  45

Ser Ala Ala Ser Thr Leu Gln Ser Gly Val Pro Ser Arg Ile Ser Gly
    50                  55                  60

Ile Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Ser Ala Pro Tyr
                85                  90                  95

Thr Phe Gly Gln Gly Thr Lys Leu Glu Ile Lys
            100                 105

<210> SEQ ID NO 103
<211> LENGTH: 121
<212> TYPE: PRT
<213> ORGANISM: Homo sapiens

<400> SEQUENCE: 103

Glu Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Met Gly Tyr
            20                  25                  30

Tyr Phe His Trp Val Arg Gln Ala Pro Gly Gln Gly Leu Glu Trp Met
        35                  40                  45

Gly Trp Ile Asn Pro Asn Ser Gly His Ala Asn Ile Ala Gln Thr Phe
    50                  55                  60

Gln Gly Arg Val Thr Met Thr Arg Asp Pro Ser Ile Thr Thr Ala Tyr
65                  70                  75                  80

Met Glu Leu Ser Arg Leu Arg Ser Asp Asp Thr Ala Val Phe Tyr Cys
                85                  90                  95

Ala Arg Gly Gly Met Leu Gly Gln Leu Trp Ala Leu Asp Asn Trp Gly
            100                 105                 110

Gln Gly Thr Leu Val Thr Val Ser Ser
        115                 120

<210> SEQ ID NO 104
<211> LENGTH: 107
<212> TYPE: PRT
<213> ORGANISM: Homo sapiens

<400> SEQUENCE: 104

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser His Trp
            20                  25                  30

Leu Ala Trp Tyr Gln Gln Arg Pro Gly Glu Ala Pro Lys Leu Leu Ile
        35                  40                  45

Tyr Gln Ala Ser Thr Leu Glu Ser Gly Val Pro Ser Arg Phe Ser Gly

```
    50                  55                  60

Ser Gly Ser Gly Thr Glu Phe Thr Leu Ser Ile Ser Ser Leu Gln Pro
65                  70                  75                  80

Asp Asp Phe Ala Thr Tyr Tyr Cys Gln Gln Tyr Gln Ser Ser Pro Tyr
                85                  90                  95

Thr Phe Gly Gln Gly Thr Lys Leu Glu Ile Lys
            100                 105


<210> SEQ ID NO 105
<211> LENGTH: 121
<212> TYPE: PRT
<213> ORGANISM: Homo sapiens

<400> SEQUENCE: 105

Glu Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Ala Asp Tyr
            20                  25                  30

Tyr Ile His Trp Val Arg Gln Ala Pro Gly Leu Gly Leu Glu Trp Met
        35                  40                  45

Gly Trp Ile Asn Pro Lys Thr Gly Phe Ser His Tyr Glu Gln Thr Phe
    50                  55                  60

Gln Gly Arg Val Thr Met Ala Arg Asp Thr Ser Ile Pro Ala Ala Tyr
65                  70                  75                  80

Met Glu Leu Ser Ser Leu Lys Ser Asp Asp Thr Ala Ile Tyr Tyr Cys
                85                  90                  95

Ala Arg Gly Gly Arg Ile Asn Val Ala Glu Ala Leu Arg Tyr Trp Gly
            100                 105                 110

Gln Gly Ser Leu Val Thr Val Ser Ser
        115                 120


<210> SEQ ID NO 106
<211> LENGTH: 107
<212> TYPE: PRT
<213> ORGANISM: Homo sapiens

<400> SEQUENCE: 106

Asp Ile Gln Met Thr Gln Ser Pro Ser Thr Leu Ser Thr Phe Val Gly
1               5                   10                  15

Asp Arg Val Thr Ile Thr Cys Arg Ala Ser Gln Thr Ile Gly Asp Trp
            20                  25                  30

Leu Ala Trp Tyr Gln Gln Lys Pro Gly Lys Ala Pro Lys Leu Leu Ile
        35                  40                  45

Ser Lys Ala Thr Arg Leu Glu Ser Gly Val Pro Ser Arg Phe Ser Gly
    50                  55                  60

Ser Gly Ser Glu Thr Glu Phe Ser Leu Thr Ile Asn Ser Leu Gln Pro
65                  70                  75                  80

Asp Asp Val Ala Ala Tyr Tyr Cys Gln Gln Tyr Met Ser Tyr Pro Trp
                85                  90                  95

Thr Phe Gly Gln Gly Thr Lys Leu Glu Ile Lys
            100                 105


<210> SEQ ID NO 107
<211> LENGTH: 122
<212> TYPE: PRT
<213> ORGANISM: Homo sapiens

<400> SEQUENCE: 107
```

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ile Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Lys Phe
    50                  55                  60

Arg Gly Arg Val Thr Ile Ala Thr Asp Ala Ser Lys Ser Ala Ala Tyr
65                  70                  75                  80

Met Asp Leu Ser Ser Leu Lys Ser Glu Asp Thr Ala Ile Tyr Tyr Cys
                85                  90                  95

Ala Arg Ser Trp Gly Thr Ala Ala Thr Gly Gly Ser Phe Val Gln Trp
            100                 105                 110

Gly Gln Gly Thr Leu Val Thr Val Ser Ser
        115                 120


<210> SEQ ID NO 108
<211> LENGTH: 109
<212> TYPE: PRT
<213> ORGANISM: Homo sapiens

<400> SEQUENCE: 108

Glu Ile Val Met Thr Gln Ser Pro Ala Thr Leu Ser Val Ser Pro Gly
1               5                   10                  15

Glu Arg Ala Thr Leu Ser Cys Arg Ala Ser His Ser Val Thr Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Ser Ala Val Tyr Tyr Cys Gln Tyr Tyr Thr Asn Trp Pro Pro
                85                  90                  95

His Val Ala Phe Gly Gln Gly Thr Lys Leu Glu Ile Lys
            100                 105


<210> SEQ ID NO 109
<211> LENGTH: 120
<212> TYPE: PRT
<213> ORGANISM: Homo sapiens

<400> SEQUENCE: 109

Glu Val Gln Leu Val Gln Ser Gly Ala Glu Val Lys Thr Pro Gly Ser
1               5                   10                  15

Ser Val Lys Val Ser Cys Lys Thr Ser Gly Gly Thr Phe Ser Asn Phe
            20                  25                  30

Ala Ile Thr Trp Val Arg Gln Ala Pro Gly Gln Gly Leu Glu Trp Met
        35                  40                  45

Gly Gly Ile Ile Pro Leu Phe Gly Ile Thr Asn Tyr Thr Gln Lys Phe
    50                  55                  60

Gln Gly Arg Val Thr Ile Thr Thr Asp Glu Ser Lys Thr Thr Ala Tyr
65                  70                  75                  80

Met Asp Leu Ser Gly Leu Arg Ser Glu Asp Thr Ala Val Tyr Phe Cys
                85                  90                  95
```

```
Ala Arg Gly Arg Asp Ser Ser Gly Arg Leu Leu Asp His Trp Gly Gln
            100                 105                 110

Gly Thr Leu Val Thr Val Ser Ser
        115                 120


<210> SEQ ID NO 110
<211> LENGTH: 108
<212> TYPE: PRT
<213> ORGANISM: Homo sapiens

<400> SEQUENCE: 110

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Asn Arg Asn
            20                  25                  30

Leu Ala Trp Tyr Gln Gln Lys Pro Gly Gln Ala Pro Arg Leu Leu Ile
        35                  40                  45

Tyr Ala Ala Ser Ala Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Val Val Tyr Tyr Cys Gln Gln Tyr Asn Asn Trp Pro Pro
                85                  90                  95

Leu Thr Phe Gly Gly Gly Thr Lys Leu Glu Ile Lys
            100                 105


<210> SEQ ID NO 111
<211> LENGTH: 124
<212> TYPE: PRT
<213> ORGANISM: Homo sapiens

<400> SEQUENCE: 111

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Phe Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asp Tyr Tyr Tyr Asp Ser Ser Gly Tyr Leu Tyr Tyr Phe Asp
            100                 105                 110

Tyr Trp Gly Gln Gly Thr Leu Val Thr Val Ser Ser
        115                 120


<210> SEQ ID NO 112
<211> LENGTH: 107
<212> TYPE: PRT
<213> ORGANISM: Homo sapiens

<400> SEQUENCE: 112

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Val
                85                  90                  95

Thr Phe Gly Gly Gly Thr Lys Val Glu Ile Lys
            100                 105


<210> SEQ ID NO 113
<211> LENGTH: 117
<212> TYPE: PRT
<213> ORGANISM: Homo sapiens

<400> SEQUENCE: 113

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ile Ser
            20                  25                  30

Thr Ile His Trp Val Arg Gln Ala Pro Gly Lys Gly Leu Glu Tyr Val
        35                  40                  45

Val Val Ile Ser His Asp Gly Asn Thr Lys Tyr Tyr Ala Asp Ser Val
    50                  55                  60

Lys Gly Arg Phe Ile Ile Ser Arg Asp Asn Ser Lys Asn Thr Val Phe
65                  70                  75                  80

Leu Gln Met Asn Ser Leu Arg Pro Val Asp Thr Ala Val Tyr Tyr Cys
                85                  90                  95

Ala Arg Gly Glu Val Gly Tyr Phe Asp Leu Trp Gly Arg Gly Thr Leu
            100                 105                 110

Val Thr Val Ser Ser
        115


<210> SEQ ID NO 114
<211> LENGTH: 108
<212> TYPE: PRT
<213> ORGANISM: Homo sapiens

<400> SEQUENCE: 114

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Pro Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ile Thr Phe Gly Gln Gly Thr Arg Leu Glu Ile Lys
            100                 105
```

<210> SEQ ID NO 115
<211> LENGTH: 120
<212> TYPE: PRT
<213> ORGANISM: Homo sapiens

<400> SEQUENCE: 115

Glu Val Gln Leu Val Glu Ser Gly Gly Gly Val Val Gln Pro Gly Arg
1 5 10 15

Ser Leu Arg Leu Ser Cys Ala Ala Ser Gly Phe Ser Phe Ser Ser His
20 25 30

Ala Met Tyr Trp Val Arg Gln Ala Pro Gly Lys Gly Leu Glu Trp Val
35 40 45

Ala Ile Val Ser Tyr Asp Gly Ser Thr Lys Asn Tyr Ala Asp Ser Val
50 55 60

Lys Gly Arg Phe Thr Ile Ser Arg Asp Asn Ser Lys Asn Thr Ile Tyr
65 70 75 80

Leu His Leu Asn Ser Leu Arg Ala Glu Asp Thr Ala Val Tyr Phe Cys
85 90 95

Ala Arg Glu Val Asp Gly Ile Tyr Gly Tyr Leu His Tyr Trp Gly Gln
100 105 110

Gly Thr Leu Val Thr Val Ser Ser
115 120

<210> SEQ ID NO 116
<211> LENGTH: 106
<212> TYPE: PRT
<213> ORGANISM: Homo sapiens

<400> SEQUENCE: 116

Glu Ile Val Leu Thr Gln Ser Pro Ala Thr Leu Ser Leu Ser Pro Gly
1 5 10 15

Glu Arg Ala Thr Leu Ser Cys Arg Ala Arg Gln Asn Val Arg Asn Phe
20 25 30

Leu Ala Trp Tyr Gln Gln Lys Pro Gly Gln Ala Pro Arg Leu Leu Ile
35 40 45

Tyr Asp Ala Ser Asn Arg Ala Thr Asp Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Tyr Ser Ile Thr
85 90 95

Phe Gly Gln Gly Thr Arg Leu Glu Ile Lys
100 105

<210> SEQ ID NO 117
<211> LENGTH: 101
<212> TYPE: PRT
<213> ORGANISM: Zika virus

<400> SEQUENCE: 117

Val Ser Tyr Ser Leu Cys Thr Ala Ala Phe Thr Phe Thr Lys Ile Pro
1 5 10 15

Ala Glu Thr Leu His Gly Thr Val Thr Val Glu Val Gln Tyr Ala Gly
20 25 30

Thr Asp Gly Pro Cys Lys Val Pro Ala Gln Met Ala Val Asp Met Gln
35 40 45

Thr Leu Thr Pro Val Gly Arg Leu Ile Thr Ala Asn Pro Val Ile Thr

```
    50                  55                  60

Glu Ser Thr Glu Asn Ser Lys Met Met Leu Glu Leu Asp Pro Pro Phe
65                  70                  75                  80

Gly Asp Ser Tyr Ile Val Ile Gly Val Gly Glu Lys Lys Ile Thr His
                85                  90                  95

His Trp His Arg Ser
            100


<210> SEQ ID NO 118
<211> LENGTH: 98
<212> TYPE: PRT
<213> ORGANISM: Dengue virus 1

<400> SEQUENCE: 118

Met Ser Tyr Val Met Cys Thr Gly Ser Phe Lys Leu Glu Lys Glu Val
1               5                   10                  15

Ala Glu Thr Gln His Gly Thr Val Leu Val Gln Val Lys Tyr Glu Gly
            20                  25                  30

Thr Asp Ala Pro Cys Lys Ile Pro Phe Ser Ser Gln Asp Glu Lys Gly
        35                  40                  45

Val Thr Gln Asn Gly Arg Leu Ile Thr Ala Asn Pro Ile Val Thr Asp
    50                  55                  60

Lys Glu Lys Pro Val Asn Ile Glu Ala Glu Pro Pro Phe Gly Glu Ser
65                  70                  75                  80

Tyr Ile Val Val Gly Ala Gly Glu Lys Ala Leu Lys Leu Ser Trp Phe
                85                  90                  95

Lys Lys


<210> SEQ ID NO 119
<211> LENGTH: 24
<212> TYPE: PRT
<213> ORGANISM: Homo sapiens

<400> SEQUENCE: 119

Met Pro Met Gly Ser Leu Gln Pro Leu Ala Thr Leu Tyr Leu Leu Gly
1               5                   10                  15

Met Leu Val Ala Ser Cys Leu Gly
            20


<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

His His His His His His Gly Leu Asn Asp Ile Phe Glu Ala Gln Lys
1               5                   10                  15

Ile Glu Trp His Glu
            20


<210> SEQ ID NO 121
<211> LENGTH: 303
<212> TYPE: DNA
<213> ORGANISM: Zika virus

<400> SEQUENCE: 121

gtgtcatact ccttgtgtac cgcagcgttc acattcacca agatcccggc tgaaacactg     60
```

cacgggacag tcacagtgga ggtacagtac gcagggacag atggaccttg caaggttcca 120
gctcagatgg cggtggacat gcaaactctg accccagttg ggaggttgat aaccgctaac 180
cccgtaatca ctgaaagcac tgagaactct aagatgatgc tggaacttga tccaccattt 240
ggggactctt acattgtcat aggagtcggg gagaagaaga tcacccacca ctggcacagg 300
agt 303

<210> SEQ ID NO 122
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atgtcatatg tgatgtgtac ggggtccttt aaacttgaaa aggaggtggc agaaacacag 60
cacggaacag tacttgtgca ggttaaatat gagggaaccg atgctccttg taaaataccg 120
ttttcaagcc aggacgaaaa gggtgtaaca caaaatggtc gcctgattac agccaaccca 180
atagtcactg ataaggagaa acctgtgaat atcgaggcag agccaccatt cggcgaaagt 240
tatatcgtag ttggtgctgg agaaaaggcc ctgaaactct cttggtttaa gaag 294

<210> SEQ ID NO 123
<211> LENGTH: 294
<212> TYPE: DNA
<213> ORGANISM: Dengue virus 2

<400> SEQUENCE: 123
atgtcatact ctatgtgcac aggaaagttt aaagttgtga aggaaatagc agaaacacaa 60
catggaacaa tagttatcag agtgcaatat gaaggggacg gctctccatg caagatccct 120
tttgagataa tggatttgga aaaaagacat gtcttaggtc gcctgattac agtcaaccca 180
attgtgacag aaaaagatag cccagtcaac atagaagcag aacctccatt cggagacagc 240
tacatcatca taggagtaga gccgggacaa ctgaagctca actggtttaa gaaa 294

<210> SEQ ID NO 124
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
atgtcatacg caatgtgtac gaacacattc gttcttaaaa aagaggtaag tgaaacccaa 60
catggtacta tccttataaa agttgagtac aagggcgagg acgctccctg caaaataccg 120
ttttccacag aggacgggca aggtaaggca cacaatggga gacttataac cgccaatcca 180
gtagtgacca agaaagagga accagtcaac attgaagcgg agcccccttt cggagaatcc 240
aacatagtga taggcattgg ggacaacgct ctgaagatca actggtataa gaag 294

<210> SEQ ID NO 125
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
atgtcatata caatgtgtag cggtaaattc agcattgata aagaaatggc cgagacacag 60
cacggcacca ccgtggtaaa agtgaaatac gaaggagcgg gagccccgtg caaggtcccc 120
atcgaaatca gggatgtaaa caaagagaag gtcgttggta gaataatttc ttctacacca 180
ctggccgaga acactaattc agttacgaat atagaacttg agcccccctt tggtgacagc 240
tatatagtta ttggcgtggg aaattctgca ctgactctgc attggttccg aaaa 294

<210> SEQ ID NO 126
<211> LENGTH: 294
<212> TYPE: DNA
<213> ORGANISM: Yellow fever virus

<400> SEQUENCE: 126
acatcctaca aaatgtgcac tgacaaaatg tcttttgtca agaacccaac tgacactggc 60
catggcactg ttgtgatgca ggtgaaagtg ccaaaaggag ccccctgcaa gattccagtg 120
atagtagctg atgatcttac agcggcaatc aataaaggca ttttggttac agttaacccc 180
atcgcctcaa ccaatgatga tgaagtgctg attgaggtga acccaccttt tggagacagc 240
tacattatcg ttgggacagg agattcacgt ctcacttacc agtggcacaa agag 294

<210> SEQ ID NO 127
<211> LENGTH: 294
<212> TYPE: DNA
<213> ORGANISM: Yellow fever virus

<400> SEQUENCE: 127
acatcctaca aaatatgcac tgacaaaatg ttttttgtca agaacccaac tgacactggc 60
catggcactg ttgtgatgca ggtgaaagtg tcaaaaggag ccccctgcag gattccagtg 120
atagtagctg atgatcttac agcggcaatc aataaaggca ttttggttac agttaacccc 180
atcgcctcaa ccaatgatga tgaagtgctg attgaggtga acccaccttt tggagacagc 240
tacattatcg ttgggagagg agattcacgt ctcacttacc agtggcacaa agag 294

<210> SEQ ID NO 128
<211> LENGTH: 303
<212> TYPE: DNA
<213> ORGANISM: West Nile virus

<400> SEQUENCE: 128
acaacctatg gcgtctgttc aaaggctttc aagtttcttg ggactcccgc agacacaggt 60
cacggcactg tggtgttgga attgcagtac actggcacgg atggaccttg caaagttcct 120
atctcgtcag tggcttcatt gaacgaccta acgccagtgg gcagattggt cactgtcaac 180
ccttttgttt cagtggccac ggccaacgct aaggtcctga ttgaattgga accacccttt 240
ggagactcat acatagtggt gggcagagga gaacaacaga tcaatcacca ctggcacaag 300
tct 303

<210> SEQ ID NO 129
<211> LENGTH: 367
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 129
gaggtgcagc tgttggagtc tgggggaggt cttgttcagc cgggtggatc attgagactt 60
tcttgtgctg caagtggatt tactttctct tcctacgcca tgtcttgggt tcgacaagct 120
ccagggaaag gactcgaatg ggttagtgcg atatctgggt ctggaggatc tacttactac 180
gcagattcag taaaagggcg cttcacaata tcacgcgata attccaagaa tacgctctac 240
cttcagatga acagtcttcg ggcagaggac acagcggttt attattgtgc gaaagatcgc 300
ggtcccagag gcgtgggcga actgttcgac tattggggac aaggcaccct ggtcaccgtc 360
tcctcag 367

<210> SEQ ID NO 130
<211> LENGTH: 322
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130
gacatccaga tgacccagtc accgtctacc ttgtcagcgt cagttggtga ccgggtaacc 60
attacttgcc gcgctagtca gagtatttcc tcctggctcg cctggtatca acaaaaacca 120
ggtaaagccc ccaaattgct gatctataag gcaagtagct tggaatcagg agttcccagc 180
cgcttctctg gctcagggtc cggtactgaa tttacattga ccatctcttc tctccagcca 240
gatgacttcg ccacgtacta ttgtcaacag tataactcat atccctggac ttttggacag 300
gggaccaagg tggaaatcaa ac 322

<210> SEQ ID NO 131
<211> LENGTH: 115
<212> TYPE: PRT
<213> ORGANISM: Homo sapiens

<400> SEQUENCE: 131

Gly Gly Gly Leu Ile Gln Pro Gly Gly Thr Leu Arg Leu Ser Cys Ala
1 5 10 15

Ala Ser Gly Phe Ser Phe Thr Asn Tyr Ala Met Ser Trp Val Arg Gln
20 25 30

Ala Pro Gly Lys Gly Leu Glu Trp Val Ser Ala Ile Thr Gly Asp Gly
35 40 45

Glu Ser Thr Tyr Tyr Ser Asp Ser Val Lys Gly Arg Phe Thr Ile Ser
50 55 60

Arg Asp Asn Ser Lys Asn Thr Leu Tyr Leu Gln Met Asn Ser Leu Thr
65 70 75 80

Ala Asp Asp Thr Ala Leu Tyr Tyr Cys Ala Lys Asp Arg Pro Arg Gln
85 90 95

Gly Val Gly Glu Leu Tyr Asp Ser Trp Gly Gln Gly Thr Leu Val Thr
100 105 110

Val Ser Ser
115

<210> SEQ ID NO 132
<211> LENGTH: 115
<212> TYPE: PRT
<213> ORGANISM: Homo sapiens

<400> SEQUENCE: 132

Gly Gly Gly Leu Val Gln Pro Gly Gly Ser Leu Arg Leu Ser Cys Ala

-continued

```
1               5                   10                  15

Ala Ser Gly Phe Thr Phe Ser Ala Tyr Ala Met Ser Trp Val Arg Gln
            20                  25                  30

Ala Pro Gly Lys Gly Leu Glu Trp Val Ser Ser Ile Ser Val Gln Ser
        35                  40                  45

Asp Ser Thr Tyr Phe Ala Asp Ser Val Lys Gly Arg Phe Thr Ile Ser
    50                  55                  60

Arg Asp Asn Ser Lys Asn Thr Leu Tyr Leu Gln Met Asn Ser Leu Arg
65                  70                  75                  80

Ala Glu Asp Thr Ala Leu Tyr Tyr Cys Ala Lys Asp Arg Leu Glu Lys
                85                  90                  95

Gly Ile Gly Glu Leu Phe His Ser Trp Gly Gln Gly Thr Leu Val Thr
            100                 105                 110

Val Ser Ser
        115
```

<210> SEQ ID NO 133
<211> LENGTH: 115
<212> TYPE: PRT
<213> ORGANISM: Homo sapiens

<400> SEQUENCE: 133

```
Gly Gly Gly Leu Val Gln Pro Gly Gly Ser Leu Arg Leu Ser Cys Ala
1               5                   10                  15

Ala Ser Gly Phe Thr Phe Ser Ala Tyr Ala Met Ser Trp Val Arg Gln
            20                  25                  30

Ala Pro Gly Lys Gly Leu Glu Trp Val Ser Gly Ile Ser Val Gln Ser
        35                  40                  45

Asp Ser Thr Tyr Leu Ala Asp Ser Val Lys Gly Arg Phe Thr Thr Ser
    50                  55                  60

Arg Asp Asn Ser Lys Asn Thr Leu Tyr Leu Gln Met Asn Ser Leu Arg
65                  70                  75                  80

Val Glu Asp Thr Ala Leu Tyr Tyr Cys Ala Lys Asp Arg Leu Arg Gln
                85                  90                  95

Gly Val Gly Glu Leu Phe His Ser Trp Gly Gln Gly Thr Leu Val Thr
            100                 105                 110

Val Ser Ser
        115
```

<210> SEQ ID NO 134
<211> LENGTH: 115
<212> TYPE: PRT
<213> ORGANISM: Homo sapiens

<400> SEQUENCE: 134

```
Gly Gly Gly Leu Val Gln Pro Gly Gly Ser Leu Arg Leu Ser Cys Ala
1               5                   10                  15

Ala Ser Gly Phe Thr Phe Gly Ala Tyr Ala Met Ser Trp Val Arg Gln
            20                  25                  30

Ala Pro Gly Lys Gly Leu Glu Trp Val Ser Ser Ile Ser Val His Ser
        35                  40                  45

Asp Ser Thr Tyr Tyr Ala Asp Ser Val Arg Gly Arg Phe Thr Ile Ser
    50                  55                  60

Arg Asp Asn Ser Lys Asn Thr Leu Tyr Leu Gln Met Asn Ser Leu Arg
65                  70                  75                  80

Ala Glu Asp Thr Ala Leu Tyr Tyr Cys Ala Lys Asp Arg Leu Arg Glu
```

```
                85                  90                  95

Gly Val Gly Glu Leu Tyr Gln Tyr Trp Gly His Gly Thr Leu Val Thr
            100                 105                 110

Val Ser Ser
        115


<210> SEQ ID NO 135
<211> LENGTH: 115
<212> TYPE: PRT
<213> ORGANISM: Homo sapiens

<400> SEQUENCE: 135

Gly Gly Gly Leu Val Gln Pro Gly Gly Ser Leu Arg Leu Ser Cys Ala
1               5                   10                  15

Ala Ser Gly Phe Thr Phe Ser Ala Tyr Ala Met Ser Trp Val Arg Gln
            20                  25                  30

Ala Pro Gly Lys Gly Leu Glu Trp Val Ser Ser Ile Asn Gly His Ser
        35                  40                  45

Asp Ser Thr Tyr Phe Ala Asp Ser Val Lys Gly Arg Phe Thr Ile Ser
    50                  55                  60

Arg Asp Asn Ser Lys Asn Thr Leu Tyr Leu Gln Met Asn Ser Leu Arg
65                  70                  75                  80

Ala Glu Asp Thr Ala Leu Tyr Tyr Cys Ala Lys Asp Arg Leu Arg Glu
                85                  90                  95

Gly Ile Gly Glu Leu Phe His Ser Trp Gly Gln Gly Thr Leu Val Thr
            100                 105                 110

Val Ser Ser
        115


<210> SEQ ID NO 136
<211> LENGTH: 112
<212> TYPE: PRT
<213> ORGANISM: Homo sapiens

<400> SEQUENCE: 136

Gly Gly Gly Leu Val Gln Pro Gly Gly Ser Leu Arg Leu Ser Cys Ala
1               5                   10                  15

Gly Ser Gly Phe Thr Phe Ser Ser Phe Ala Met Ser Trp Val Arg Gln
            20                  25                  30

Ala Pro Gly Lys Gly Leu Glu Trp Val Ser Thr Ile Thr Gly Ile Gly
        35                  40                  45

Gly Asp Thr Tyr Tyr Thr Asp Ser Val Lys Gly Arg Phe Thr Val Ser
    50                  55                  60

Arg Asp Asn Ser Lys Lys Thr Val Phe Leu His Met Asn Ser Leu Arg
65                  70                  75                  80

Ala Glu Asp Thr Ala Val Tyr Tyr Cys Ala Lys Asp Arg Asp His Phe
                85                  90                  95

Asp Gly His Asp Val Trp Gly Gln Gly Thr Met Val Thr Val Ser Ser
            100                 105                 110


<210> SEQ ID NO 137
<211> LENGTH: 114
<212> TYPE: PRT
<213> ORGANISM: Homo sapiens

<400> SEQUENCE: 137

Gly Ala Gly Val Lys Lys Pro Gly Ala Ser Val Lys Val Ser Cys Lys
1               5                   10                  15
```

Ala Ser Gly Tyr Ile Phe Ser Asp Tyr Tyr Met Gln Trp Val Arg Gln
20 25 30

Ala Pro Gly Gln Gly Leu Gln Trp Met Gly Trp Ile Asn Pro Lys Ser
35 40 45

Gly Phe Thr Asn Tyr Ala Gln Lys Phe Gln Gly Arg Val Thr Met Thr
50 55 60

Arg Asp Thr Ser Ile Ser Thr Ala Tyr Met Glu Leu Thr Gly Leu Thr
65 70 75 80

Ser Asp Asp Thr Ala Ile Tyr Tyr Cys Ala Arg Gly Gly Pro Val Asn
85 90 95

Ala Pro Arg Gly Phe Asp Pro Trp Gly Gln Gly Thr Leu Val Thr Val
100 105 110

Ser Ser

<210> SEQ ID NO 138
<211> LENGTH: 114
<212> TYPE: PRT
<213> ORGANISM: Homo sapiens

<400> SEQUENCE: 138

Gly Ala Gly Val Lys Ile Pro Gly Ala Ser Val Lys Val Ser Cys Lys
1 5 10 15

Ala Ser Gly Tyr Ile Phe Ser Asp Tyr Tyr Met Gln Trp Val Arg Gln
20 25 30

Ala Pro Gly Gln Gly Leu Glu Trp Met Gly Trp Ile Asn Pro Lys Ser
35 40 45

Gly Phe Ser Asp Tyr Ala Gln Lys Phe Gln Gly Arg Val Ser Met Thr
50 55 60

Arg Asp Thr Ala Ile Ser Thr Ala Tyr Met Glu Leu Thr Arg Leu Thr
65 70 75 80

Ser Asp Asp Thr Ala Val Tyr Tyr Cys Ala Arg Gly Gly Pro Val Asn
85 90 95

Ser Pro Leu Gly Phe Asp Pro Trp Gly Gln Gly Thr Leu Val Thr Val
100 105 110

Ser Ser

<210> SEQ ID NO 139
<211> LENGTH: 114
<212> TYPE: PRT
<213> ORGANISM: Homo sapiens

<400> SEQUENCE: 139

Gly Pro Gly Val Lys Lys Pro Gly Ala Ser Val Lys Val Ser Cys Lys
1 5 10 15

Ala Ser Gly Tyr Ile Phe Ser Asp Tyr Tyr Ile Leu Trp Val Arg Gln
20 25 30

Ala Pro Gly Gln Gly Leu Glu Tyr Met Gly Trp Met Asn Pro Ile Ser
35 40 45

Gly Phe Thr His Tyr Ala Gln Asn Phe Gln Gly Arg Val Thr Met Thr
50 55 60

Arg Asp Thr Ser Ile Ser Thr Ala Tyr Met Glu Leu Thr Arg Leu Ala
65 70 75 80

Ser Asp Asp Thr Ala Val Tyr Tyr Cys Ala Arg Gly Gly Arg Ile Asn
85 90 95

Ser Pro Leu Gly Phe Asp Pro Trp Gly Gln Gly Thr Leu Val Thr Val 100 105 110

Ser Ser

<210> SEQ ID NO 140
<211> LENGTH: 114
<212> TYPE: PRT
<213> ORGANISM: Homo sapiens

<400> SEQUENCE: 140

Gly Ala Glu Val Lys Lys Pro Gly Ala Ser Val Lys Val Ser Cys Lys
1 5 10 15

Val Ser Gly Tyr Thr Phe Thr Gly Tyr Tyr Met Gln Trp Val Arg Gln
20 25 30

Ala Pro Gly Gln Gly Leu Glu Trp Met Gly Trp Ile Asn Pro Lys Thr
35 40 45

Gly His Thr Asn Phe Ala Gln Lys Phe Gln Gly Arg Val Thr Met Thr
50 55 60

Arg Asp Thr Ser Ile Ser Thr Ala Tyr Met Glu Leu Ala Arg Leu Thr
65 70 75 80

Ser Asp Asp Thr Ala Val Tyr Phe Cys Ala Arg Gly Gly Gln Ile Ser
85 90 95

Ala Pro His Gly Phe Asp Pro Trp Gly Gln Gly Thr Leu Val Thr Val
100 105 110

Ser Ser

<210> SEQ ID NO 141
<211> LENGTH: 114
<212> TYPE: PRT
<213> ORGANISM: Homo sapiens

<400> SEQUENCE: 141

Gly Ala Gly Met Arg Lys Pro Gly Ala Ser Val Lys Val Ser Cys Lys
1 5 10 15

Ala Ser Gly Tyr Ser Phe Asn Asp Tyr Tyr Ile His Trp Val Arg Gln
20 25 30

Ala Pro Gly Gln Gly Leu Glu Trp Met Gly Trp Ile Asn Pro Lys Ser
35 40 45

Gly Phe Thr Asn Tyr Ala Gln Arg Phe Gln Gly Arg Val Thr Met Thr
50 55 60

Gly Asp Thr Ser Asn Ser Val Ala Tyr Met Glu Leu Thr Arg Leu Thr
65 70 75 80

Ser Asp Asp Thr Ala Val Tyr Tyr Cys Ala Arg Gly Gly Arg Ile Asn
85 90 95

Ala Pro Leu Gly Phe Asp Pro Trp Gly Gln Gly Thr Leu Val Thr Val
100 105 110

Ser Ser

<210> SEQ ID NO 142
<211> LENGTH: 114
<212> TYPE: PRT
<213> ORGANISM: Homo sapiens

<400> SEQUENCE: 142

Gly Ala Glu Val Lys Lys Pro Gly Ala Ser Val Lys Val Ser Cys Lys
1 5 10 15

Val Ser Gly Tyr Thr Phe Ser Asp Tyr Tyr Met Gln Trp Val Arg Gln
20 25 30

```
Ala Pro Gly Gln Gly Leu Glu Trp Met Gly Trp Ile Asn Pro Lys Thr
        35                  40                  45

Gly His Thr Asn Phe Ala Gln Lys Phe Gln Gly Arg Val Thr Val Thr
    50                  55                  60

Arg Asp Thr Ser Ile Thr Thr Ala Tyr Met Glu Leu Arg Thr Leu Thr
65                  70                  75                  80

Ser Asp Asp Thr Ala Val Tyr Phe Cys Ala Arg Gly Gly Pro Ile Ser
                85                  90                  95

Ala Pro Leu Gly Phe Asp Pro Trp Gly Gln Gly Thr Leu Val Thr Val
            100                 105                 110

Ser Ser


<210> SEQ ID NO 143
<211> LENGTH: 120
<212> TYPE: PRT
<213> ORGANISM: Homo sapiens

<400> SEQUENCE: 143

Gly Ala Glu Val Lys Lys Pro Gly Ala Ser Val Lys Val Ser Cys Lys
1               5                   10                  15

Ala Ser Ala Tyr Ser Phe Thr Asp Tyr Tyr Ile His Trp Val Arg Gln
            20                  25                  30

Ala Pro Gly Gln Gly Leu Gln Trp Met Gly Trp Ile Asn Pro Asp Ser
        35                  40                  45

Gly Glu Val Asn Tyr Val Gln Lys Phe Gln Asp Arg Val Thr Met Thr
    50                  55                  60

Arg Gly Thr Ser Ile Ser Thr Ala Tyr Met Glu Leu Arg Arg Leu Arg
65                  70                  75                  80

Ser Asp Asp Thr Ala Val Tyr Tyr Cys Ala Arg Ala Ala Met Asn Arg
                85                  90                  95

Ile Ser Gly Val Val Pro Pro Gly Asp Ala Phe Asp Leu Trp Gly Gln
            100                 105                 110

Gly Thr Leu Val Thr Val Ser Ser
        115                 120


<210> SEQ ID NO 144
<211> LENGTH: 117
<212> TYPE: PRT
<213> ORGANISM: Homo sapiens

<400> SEQUENCE: 144

Gly Ala Glu Val Lys Lys Pro Gly Ala Ser Val Lys Leu Ser Cys Lys
1               5                   10                  15

Ser Ser Gly Tyr Ser Phe Thr Ser Tyr Tyr Met His Trp Val Arg Gln
            20                  25                  30

Ala Pro Gly Gln Gly Leu Glu Trp Met Gly Ile Ile Asn Pro Ser Gly
        35                  40                  45

Val Phe Thr Ser Tyr Ala Gln Arg Phe Gln Gly Arg Val Thr Met Thr
    50                  55                  60

Ser Asp Thr Ala Thr Ser Thr Val Tyr Met Glu Leu Ser Ser Leu Arg
65                  70                  75                  80

Ser Gly Asp Thr Ala Val Tyr Tyr Cys Thr Arg Ser Leu Val Thr Pro
                85                  90                  95

Ala Ala Gln Ser Val Gln Tyr Phe Asp Ser Trp Gly Gln Gly Thr Leu
            100                 105                 110
```

Ile Thr Val Ser Ser
115

<210> SEQ ID NO 145
<211> LENGTH: 117
<212> TYPE: PRT
<213> ORGANISM: Homo sapiens

<400> SEQUENCE: 145

Gly Ala Glu Val Lys Lys Pro Gly Ala Ser Val Lys Leu Ser Cys Lys
1 5 10 15

Ala Ser Gly Tyr Thr Phe Thr Ser Tyr Tyr Val His Trp Val Arg Gln
20 25 30

Ala Pro Gly Gln Gly Leu Glu Trp Met Gly Ile Ile Asn Pro Gly Asn
35 40 45

Asn Phe Val Ser Phe Ala Gln Asn Phe Tyr Asp Arg Ala Thr Met Thr
50 55 60

Arg Asp Thr Ser Thr Asn Thr Val Tyr Met Glu Leu Thr Asn Leu Gln
65 70 75 80

Ser Glu Asp Thr Ala Val Tyr Tyr Cys Ala Arg Thr Leu Val Ala Pro
85 90 95

Ser Ala Gln Ser Met Tyr Tyr Phe Asp Phe Trp Gly Gln Gly Thr Leu
100 105 110

Val Thr Val Ser Ser
115

<210> SEQ ID NO 146
<211> LENGTH: 117
<212> TYPE: PRT
<213> ORGANISM: Homo sapiens

<400> SEQUENCE: 146

Gly Ser Glu Val Lys Lys Pro Gly Ala Ser Val Lys Leu Ser Cys Lys
1 5 10 15

Ala Ser Gly Tyr Thr Phe Thr Ser Tyr Tyr Ile His Trp Val Arg Gln
20 25 30

Ala Pro Gly Gln Gly Leu Glu Trp Val Gly Val Ile Asn Pro Gly Asn
35 40 45

Val Phe Thr Ser Tyr Ala Gln Arg Phe His Asp Arg Val Thr Met Thr
50 55 60

Arg Asp Thr Ser Thr Ser Thr Val Tyr Met Glu Met Ser Ser Leu Arg
65 70 75 80

Ser Glu Asp Thr Ala Val Tyr Tyr Cys Thr Arg Thr Gln Val Val Pro
85 90 95

Ser Ala Gln Ser Val Tyr Tyr Phe Asp Phe Trp Gly Gln Gly Thr Leu
100 105 110

Val Thr Val Ser Ser
115

<210> SEQ ID NO 147
<211> LENGTH: 117
<212> TYPE: PRT
<213> ORGANISM: Homo sapiens

<400> SEQUENCE: 147

Gly Ala Glu Val Lys Lys Pro Gly Thr Ser Val Lys Val Ser Cys Lys
1 5 10 15

Ala Ser Gly Tyr Thr Phe Thr Ser Tyr Tyr Ile His Trp Val Arg Glu

```
            20                  25                  30

Ala Pro Gly Gln Gly Leu Glu Trp Val Gly Ile Ile Asn Pro Gly Asn
        35                  40                  45

Thr Phe Thr Ser Tyr Ala Pro Arg Phe His Gly Arg Val Ser Met Thr
    50                  55                  60

Arg Asp Thr Ser Thr Ser Thr Val Tyr Met Glu Leu Ser Ser Leu Arg
65                  70                  75                  80

Ser Glu Asp Thr Ala Val Tyr Tyr Cys Thr Arg Thr Arg Val Val Pro
                85                  90                  95

Ser Ala Gln Ser Val Tyr Tyr Phe Asp Phe Trp Gly Gln Gly Thr Leu
            100                 105                 110

Val Thr Val Ser Ser
        115


<210> SEQ ID NO 148
<211> LENGTH: 117
<212> TYPE: PRT
<213> ORGANISM: Homo sapiens

<400> SEQUENCE: 148

Gly Ala Glu Val Lys Lys Pro Gly Ala Ser Val Lys Val Ser Cys Lys
1               5                   10                  15

Thr Ser Gly Phe Thr Phe Thr Ser Tyr Tyr Ile His Trp Val Arg Gln
            20                  25                  30

Ala Pro Gly Gln Gly Leu Glu Trp Met Gly Phe Ile Asn Pro Thr Ser
        35                  40                  45

Gly Phe Thr Ser Tyr Thr Gln Asn Leu His Gly Arg Val Thr Met Thr
    50                  55                  60

Arg Asp Thr Ser Thr Arg Thr Val Phe Met Glu Leu Arg Ser Leu Ala
65                  70                  75                  80

Ser Gly Asp Thr Ala Val Tyr Tyr Cys Thr Arg Thr Gln Ile Ile Pro
                85                  90                  95

Ala Ala Gln Ser Val Tyr Phe Phe Asp Tyr Trp Gly Pro Gly Thr Leu
            100                 105                 110

Val Thr Val Ser Ser
        115


<210> SEQ ID NO 149
<211> LENGTH: 117
<212> TYPE: PRT
<213> ORGANISM: Homo sapiens

<400> SEQUENCE: 149

Gly Ala Glu Val Ala Lys Pro Gly Thr Ser Val Lys Val Ser Cys Lys
1               5                   10                  15

Ala Ser Gly Tyr Thr Phe Thr Ser Tyr Tyr Ile His Trp Val Arg Gln
            20                  25                  30

Ala Pro Gly Gln Gly Leu Glu Trp Val Gly Ile Ile Asn Pro Gly Gly
        35                  40                  45

Ala Phe Thr Ser Tyr Ala Gln Arg Phe His Gly Arg Val Arg Met Thr
    50                  55                  60

Arg Asp Thr Ser Ala Ser Thr Val Tyr Val Glu Leu Ser Ser Leu Arg
65                  70                  75                  80

Ser Asp Asp Thr Ala Val Tyr Tyr Cys Thr Arg Thr Arg Ile Ile Ala
                85                  90                  95

Ala Ala Gln Ser Val Tyr His Tyr Asp Leu Trp Gly Gln Gly Thr Leu
```

```
            100                 105                 110

Val Thr Val Ser Ser
        115


<210> SEQ ID NO 150
<211> LENGTH: 117
<212> TYPE: PRT
<213> ORGANISM: Homo sapiens

<400> SEQUENCE: 150

Gly Ala Glu Val Lys Lys Pro Gly Ala Ser Val Lys Val Ser Cys Lys
1               5                   10                  15

Ala Ser Gly Tyr Thr Phe Ser Ser Tyr Tyr Ile His Trp Val Arg Gln
            20                  25                  30

Ala Pro Gly Gln Gly Leu Glu Trp Met Gly Ile Ile Lys Pro Ser Ser
        35                  40                  45

Gly Ser Thr Asn Tyr Ala His Lys Phe Gln Asp Arg Val Thr Met Thr
    50                  55                  60

Thr Asp Thr Ser Thr Ser Thr Val Tyr Met Glu Leu Ser Ser Leu Arg
65                  70                  75                  80

Tyr Gln Asp Thr Ala Val Tyr Tyr Cys Ala Arg Ala Gln Asp Pro Ala
                85                  90                  95

Thr Ala Ile Arg Gly Leu Arg Trp Glu Tyr Trp Gly Gln Gly Ser Leu
            100                 105                 110

Val Thr Val Ser Ser
        115


<210> SEQ ID NO 151
<211> LENGTH: 117
<212> TYPE: PRT
<213> ORGANISM: Homo sapiens

<400> SEQUENCE: 151

Gly Ala Glu Val Lys Lys Pro Gly Ala Ser Val Lys Val Ser Cys Lys
1               5                   10                  15

Ala Ser Gly Tyr Thr Phe Thr Thr Tyr Phe Ile His Trp Val Arg Gln
            20                  25                  30

Ala Pro Gly Gln Gly Leu Glu Trp Met Gly Ile Ile Asn Pro Asn Ser
        35                  40                  45

Gly Ser Thr Asn Tyr Ala Gln Lys Ile Gln Gly Arg Val Thr Met Thr
    50                  55                  60

Thr Asp Thr Ser Ala Ser Thr Val Tyr Met Glu Leu Ser Gly Leu Arg
65                  70                  75                  80

Ser Glu Asp Thr Ala Val Tyr Tyr Cys Ala Arg Gly Gly Ser Tyr Pro
                85                  90                  95

Val Ala Ile Arg Gly Val Thr Phe Gly Ile Trp Gly Gln Gly Thr Met
            100                 105                 110

Val Thr Val Ser Ser
        115


<210> SEQ ID NO 152
<211> LENGTH: 117
<212> TYPE: PRT
<213> ORGANISM: Homo sapiens

<400> SEQUENCE: 152

Gly Ala Glu Val Lys Lys Pro Gly Ala Ser Val Arg Val Ser Cys Lys
1               5                   10                  15
```

```
Ala Ser Gly Tyr Thr Phe Thr Ser Tyr Tyr Met His Trp Val Arg Gln
            20                  25                  30

Ala Pro Gly Gln Gly Leu Glu Trp Met Gly Ile Ile Asn Pro Ser Ser
        35                  40                  45

Gly Ser Thr Ser Tyr Ala Gln Lys Leu His Asp Arg Val Thr Met Thr
    50                  55                  60

Arg Asp Thr Ser Thr Ser Thr Val Tyr Met Glu Met Ser Ser Leu Arg
65                  70                  75                  80

Ser Glu Asp Thr Ala Val Tyr Tyr Cys Ala Arg Gly Ala Ala Tyr Pro
                85                  90                  95

Thr Ala Ile Arg Gly Val Ile Tyr Gly Phe Trp Gly Gln Gly Thr Met
            100                 105                 110

Val Thr Val Ser Ser
        115


<210> SEQ ID NO 153
<211> LENGTH: 118
<212> TYPE: PRT
<213> ORGANISM: Homo sapiens

<400> SEQUENCE: 153

Gly Ala Glu Val Lys Lys Pro Gly Ala Ser Val Lys Ile Ser Cys Lys
1               5                   10                  15

Ala Ser Ala Asp Thr Phe Thr Lys Asn Tyr Val His Trp Val Arg Gln
            20                  25                  30

Ala Pro Gly Gln Gly Leu Glu Trp Met Gly Ile Ile Asn Pro Ser Ser
        35                  40                  45

Gly Trp Thr Ser Asn Pro Gln Lys Phe Gln Gly Arg Val Thr Met Thr
    50                  55                  60

Arg Asp Thr Ser Thr Ser Thr Val Tyr Met Glu Leu Ser Ser Leu Arg
65                  70                  75                  80

Ser Asp Asp Thr Ala Leu Tyr Tyr Cys Ala Thr Ser Pro Ala Ala Ala
                85                  90                  95

Gly Ser Gly His Pro Ser Gly Trp Phe Asp Pro Trp Gly Pro Gly Thr
            100                 105                 110

Leu Val Thr Val Ser Ser
        115


<210> SEQ ID NO 154
<211> LENGTH: 114
<212> TYPE: PRT
<213> ORGANISM: Homo sapiens

<400> SEQUENCE: 154

Gly Ala Glu Met Lys Lys Pro Gly Ala Ser Val Lys Val Ser Cys Gln
1               5                   10                  15

Ala Ser Gly Tyr Ser Phe Thr Asn His Phe Ile His Trp Val Arg Gln
            20                  25                  30

Ala Pro Gly Gln Gly Leu Glu Trp Met Gly Thr Ile Asn Pro Ser Gly
        35                  40                  45

Gly Ser Thr Thr Phe Ala Gln Lys Phe Gln Gly Arg Val Thr Met Thr
    50                  55                  60

Arg Asp Thr Ser Thr Ser Thr Val Tyr Met Glu Leu Ser Ser Leu Arg
65                  70                  75                  80

Ser Glu Asp Thr Ala Val Tyr Tyr Cys Ala Arg Pro Pro Gly Arg Ser
                85                  90                  95
```

```
Phe Leu Asp Gly Met Asp Val Trp Gly Gln Gly Thr Thr Val Thr Val
            100                 105                 110

Ser Ser


<210> SEQ ID NO 155
<211> LENGTH: 115
<212> TYPE: PRT
<213> ORGANISM: Homo sapiens

<400> SEQUENCE: 155

Gly Ala Gly Leu Leu Lys Thr Ser Glu Thr Leu Tyr Leu Thr Cys Thr
1               5                   10                  15

Val Tyr Gly Asp Ser Phe Asn His Tyr Tyr Trp Gly Trp Ile Arg Gln
            20                  25                  30

Pro Pro Gly Lys Gly Leu Glu Trp Leu Gly Glu Ile Asn His Arg Gly
        35                  40                  45

Thr Thr Asn Tyr Asn Pro Ser Leu Lys Ser Arg Val Ser Ile Leu Val
    50                  55                  60

Asp Thr Ser Gln Lys Gln Phe Ser Leu Arg Val Thr Ser Val Thr Ala
65                  70                  75                  80

Ala Asp Thr Ser Val Tyr Tyr Cys Thr Arg Val Arg Trp Asp Gly Ile
                85                  90                  95

Glu Phe Thr Met Phe Phe Asp Ser Trp Gly Gln Gly Ser Leu Val Thr
            100                 105                 110

Val Ser Pro
        115


<210> SEQ ID NO 156
<211> LENGTH: 115
<212> TYPE: PRT
<213> ORGANISM: Homo sapiens

<400> SEQUENCE: 156

Gly Ala Gly Leu Leu Lys Thr Ser Glu Thr Leu Tyr Leu Thr Cys Thr
1               5                   10                  15

Val Tyr Gly Asp Ser Phe Asn His Tyr Tyr Trp Gly Trp Ile Arg Gln
            20                  25                  30

Pro Pro Gly Lys Gly Leu Glu Trp Leu Gly Glu Ile Asn His Arg Gly
        35                  40                  45

Thr Thr Asn Tyr Asn Pro Ser Leu Lys Ser Arg Val Ser Ile Leu Val
    50                  55                  60

Asp Thr Ser His Lys Gln Phe Ser Leu Arg Val Thr Ser Val Thr Ala
65                  70                  75                  80

Ala Asp Thr Ser Val Tyr Tyr Cys Ala Arg Val Arg Trp Asp Gly Ile
                85                  90                  95

Glu Ser Thr Met Phe Phe Asp Ser Trp Gly Gln Gly Ser Leu Val Thr
            100                 105                 110

Val Ser Pro
        115


<210> SEQ ID NO 157
<211> LENGTH: 115
<212> TYPE: PRT
<213> ORGANISM: Homo sapiens

<400> SEQUENCE: 157

Gly Ala Gly Leu Leu Lys Thr Ser Glu Thr Leu Tyr Leu Thr Cys Thr
```

```
1               5                   10                  15

Val Tyr Gly Asp Ser Phe Asn His Tyr Tyr Trp Gly Trp Ile Arg Gln
            20                  25                  30

Pro Pro Gly Lys Gly Leu Glu Trp Leu Gly Glu Ile Asn His Arg Gly
        35                  40                  45

Thr Thr Asn Tyr Asn Pro Ser Leu Lys Ser Arg Val Ser Ile Leu Val
    50                  55                  60

Asp Thr Ser Gln Lys Gln Phe Ser Leu Arg Val Thr Ser Val Thr Ala
65                  70                  75                  80

Ala Asp Thr Ser Val Tyr Tyr Cys Thr Arg Val Arg Trp Asp Gly Ile
                85                  90                  95

Glu Ser Thr Met Phe Phe Asp Ser Trp Gly Gln Gly Ser Leu Val Thr
            100                 105                 110

Val Ser Pro
        115


<210> SEQ ID NO 158
<211> LENGTH: 123
<212> TYPE: PRT
<213> ORGANISM: Homo sapiens

<400> SEQUENCE: 158

Gly Ala Arg Pro Leu Lys Pro Ser Glu Thr Leu Ser Leu Thr Cys Gly
1               5                   10                  15

Val Asn Gly Gly Ser Phe Ser Gly Tyr His Trp Ser Trp Ile Arg Gln
            20                  25                  30

Pro Pro Gly Lys Gly Leu Glu Trp Ile Gly Glu Ile Asp His Asn Gly
        35                  40                  45

Arg Ile Asn Tyr Asn Pro Ser Leu Lys Ser Arg Val Thr Ile Ser Ile
    50                  55                  60

Asp Thr Phe Lys Ser Gln Phe Ser Leu Arg Leu Thr Ser Ile Ile Ala
65                  70                  75                  80

Ala Asp Thr Ala Val Tyr Tyr Cys Ala Arg Asp Val Val Thr Met Val
                85                  90                  95

Glu Gly Leu Arg Phe His Tyr Tyr Tyr Asn Tyr Tyr Gly Met Asp Val
            100                 105                 110

Trp Gly Gln Gly Thr Pro Val Thr Val Ser Ser
        115                 120


<210> SEQ ID NO 159
<211> LENGTH: 123
<212> TYPE: PRT
<213> ORGANISM: Homo sapiens

<400> SEQUENCE: 159

Gly Ala Arg Pro Leu Lys Pro Ser Glu Thr Leu Ser Leu Thr Cys Gly
1               5                   10                  15

Val Asn Gly Gly Ser Phe Ser Gly Tyr His Trp Thr Trp Ile Arg Gln
            20                  25                  30

Pro Pro Gly Lys Gly Leu Glu Trp Ile Gly Glu Ile Asp His Asn Gly
        35                  40                  45

Arg Ile Asn Tyr Asn Pro Ser Leu Lys Ser Arg Val Thr Ile Ser Ile
    50                  55                  60

Asp Thr Phe Lys Ser Gln Phe Ser Leu Arg Leu Thr Ser Ile Thr Ala
65                  70                  75                  80

Ala Asp Thr Ala Ile Tyr Tyr Cys Ala Arg Asp Val Val Thr Met Val
```

```
                85                  90                  95

Glu Gly Leu Arg Phe His Tyr Tyr Tyr Asn Tyr Tyr Gly Met Asp Val
            100                 105                 110

Trp Gly Gln Gly Thr Pro Val Thr Val Ser Ser
        115                 120


<210> SEQ ID NO 160
<211> LENGTH: 123
<212> TYPE: PRT
<213> ORGANISM: Homo sapiens

<400> SEQUENCE: 160

Gly Ala Arg Pro Leu Lys Pro Ser Glu Thr Leu Ser Leu Thr Cys Gly
1               5                   10                  15

Val Asn Gly Gly Ser Phe Ser Gly Tyr His Trp Ser Trp Ile Arg Gln
            20                  25                  30

Pro Pro Gly Lys Gly Leu Glu Trp Ile Gly Glu Ile Asp His Asn Gly
        35                  40                  45

Arg Ile Asn Tyr Asn Pro Ser Leu Lys Ser Arg Val Thr Met Ser Ile
    50                  55                  60

Asp Thr Phe Lys Ser Gln Phe Ser Leu Arg Leu Thr Ser Ile Thr Ala
65                  70                  75                  80

Ala Asp Thr Ala Val Tyr Tyr Cys Ala Arg Asp Val Val Thr Met Val
                85                  90                  95

Glu Gly Leu Arg Phe His Tyr Tyr Tyr Asn Tyr Tyr Gly Met Asp Val
            100                 105                 110

Trp Gly Gln Gly Thr Pro Val Thr Val Ser Ser
        115                 120


<210> SEQ ID NO 161
<211> LENGTH: 111
<212> TYPE: PRT
<213> ORGANISM: Homo sapiens

<400> SEQUENCE: 161

Gly Pro Gly Leu Val Lys Pro Ser Glu Thr Leu Ser Leu Thr Cys Thr
1               5                   10                  15

Val Ser Gly Gly Ser Ile Ser Thr Tyr Tyr Trp Ser Trp Ile Arg Gln
            20                  25                  30

Thr Pro Gly Lys Gly Leu Glu Trp Ile Gly Cys Ile Tyr Tyr Ser Val
        35                  40                  45

Asp Thr His Phe Asn Pro Ser Leu Glu Ser Arg Val Thr Ile Ser Val
    50                  55                  60

Asp Thr Ser Lys Asn Gln Phe Ser Leu Lys Met Thr Ser Met Thr Ala
65                  70                  75                  80

Ala Asp Thr Ala Val Tyr Tyr Cys Ala Arg Asn Gln Pro Gly Gly Arg
                85                  90                  95

Ala Phe Asp Tyr Trp Gly Pro Gly Thr Leu Val Thr Val Ser Ser
            100                 105                 110


<210> SEQ ID NO 162
<211> LENGTH: 111
<212> TYPE: PRT
<213> ORGANISM: Homo sapiens

<400> SEQUENCE: 162

Gly Pro Gly Leu Val Lys Pro Ser Glu Thr Leu Ser Leu Thr Cys Thr
1               5                   10                  15
```

-continued

```
Val Ser Gly Gly Ser Ile Asp Thr Tyr Tyr Trp Ser Trp Ile Arg Gln
            20                  25                  30

Thr Pro Gly Lys Gly Leu Glu Trp Ile Gly Cys Phe Tyr Tyr Ser Val
        35                  40                  45

Asp Asn His Phe Asn Pro Ser Leu Glu Ser Arg Val Thr Ile Ser Val
    50                  55                  60

Asp Thr Ser Lys Asn Gln Phe Ser Leu Lys Met Thr Ser Met Thr Ala
65                  70                  75                  80

Ser Asp Thr Ala Val Tyr Tyr Cys Ala Arg Asn Gln Pro Gly Gly Arg
                85                  90                  95

Ala Phe Asp Tyr Trp Gly Pro Gly Thr Leu Val Thr Val Ser Ser
            100                 105                 110


<210> SEQ ID NO 163
<211> LENGTH: 121
<212> TYPE: PRT
<213> ORGANISM: Homo sapiens

<400> SEQUENCE: 163

Gly Ala Glu Val Lys Lys Pro Gly Glu Ser Leu Arg Ile Ser Cys Lys
1               5                   10                  15

Thr Ser Gly Tyr Thr Phe Thr Ser His Trp Leu Ala Trp Val Arg Gln
            20                  25                  30

Met Pro Gly Lys Gly Leu Glu Trp Met Gly Ile Ile Tyr Pro Gly Asp
        35                  40                  45

Ser Asp Thr Arg Tyr Ser Pro Ser Phe Gln Gly Gln Ile Ser Ile Ser
    50                  55                  60

Ala Asp Lys Ser Ile Asn Thr Ala Tyr Leu Gln Trp Ser Ser Leu Lys
65                  70                  75                  80

Ala Ser Asp Thr Ala Ile Tyr Tyr Cys Ala Arg His Asp Gly Arg Gly
                85                  90                  95

Tyr Cys Ser Pro Thr Arg Cys Phe Phe Ser Gly Met Asp Val Trp Gly
            100                 105                 110

Gln Gly Thr Thr Val Ile Val Ser Pro
        115                 120


<210> SEQ ID NO 164
<211> LENGTH: 121
<212> TYPE: PRT
<213> ORGANISM: Homo sapiens

<400> SEQUENCE: 164

Gly Ala Glu Val Arg Lys Pro Gly Glu Ser Leu Arg Ile Ser Cys Lys
1               5                   10                  15

Thr Ser Gly Tyr Thr Phe Thr Ser His Trp Val Ala Trp Val Arg Gln
            20                  25                  30

Met Pro Gly Lys Gly Leu Glu Trp Met Gly Ile Ile Tyr Pro Gly Asp
        35                  40                  45

Ser Asp Thr Arg Tyr Ser Pro Ser Phe Gln Gly Gln Ile Ser Ile Ser
    50                  55                  60

Ala Asp Lys Ser Ile Asn Thr Ala Tyr Leu Gln Trp Ser Ser Leu Lys
65                  70                  75                  80

Ala Ser Asp Thr Gly Ile Tyr Tyr Cys Ala Arg His Asp Gly Arg Gly
                85                  90                  95

Tyr Cys Ser Pro Thr Arg Cys Phe Phe Ser Gly Met Asp Val Trp Gly
            100                 105                 110
```

Gln Gly Thr Thr Val Ile Val Ser Pro
115 120

<210> SEQ ID NO 165
<211> LENGTH: 117
<212> TYPE: PRT
<213> ORGANISM: Homo sapiens

<400> SEQUENCE: 165

Gly Ala Glu Val Lys Lys Pro Gly Ala Ser Val Arg Val Ser Cys Lys
1 5 10 15

Ala Ser Gly Tyr Thr Phe Ser Asp Tyr Tyr Val His Trp Leu Arg Gln
20 25 30

Ala Pro Gly Gln Arg Leu Glu Trp Met Gly Trp Ile Asn Ala Asn Thr
35 40 45

Gly Gly Ser Asp Ser Gly Pro Lys Phe Tyr Gly Arg Val Thr Leu Thr
50 55 60

Arg Asp Thr Ser Val Asn Thr Ala Tyr Met Glu Leu Ser Arg Leu Arg
65 70 75 80

Ser Asp Asp Thr Ala Val Tyr Phe Cys Ala Arg Arg Thr Tyr Tyr Asp
85 90 95

Asn Arg Phe Pro Tyr Trp Tyr Phe Asp Leu Trp Gly Arg Gly Thr Leu
100 105 110

Val Thr Val Ser Ser
115

<210> SEQ ID NO 166
<211> LENGTH: 117
<212> TYPE: PRT
<213> ORGANISM: Homo sapiens

<400> SEQUENCE: 166

Gly Ala Glu Val Lys Lys Pro Gly Ala Ser Val Lys Val Ser Cys Lys
1 5 10 15

Ala Ser Gly Tyr Thr Phe Ser Gly Tyr Tyr Ile His Trp Leu Arg Gln
20 25 30

Ala Pro Gly Gln Gly Leu Glu Trp Met Gly Trp Ile Asn Ser Asn Ser
35 40 45

Gly Gly Ala Asp Ser Gly Pro Arg Phe His Gly Arg Val Thr Met Thr
50 55 60

Arg Asp Thr Ser Ile Asn Thr Ala Tyr Leu Glu Leu Thr Asn Leu Arg
65 70 75 80

Ser Asp Asp Thr Ala Val Tyr Tyr Cys Ala Arg Arg Thr Tyr Tyr Asp
85 90 95

Thr Arg Phe Pro Tyr Trp Tyr Phe Asp Leu Trp Gly Arg Gly Thr Leu
100 105 110

Val Thr Val Ser Ser
115

<210> SEQ ID NO 167
<211> LENGTH: 115
<212> TYPE: PRT
<213> ORGANISM: Homo sapiens

<400> SEQUENCE: 167

Gly Ala Glu Val Lys Lys Pro Gly Ser Ser Val Lys Val Ser Cys Lys
1 5 10 15

```
Ala Ser Gly Gly Thr Phe Ser Ser Tyr Ala Ile Ile Trp Val Arg Gln
            20                  25                  30

Ala Pro Gly Gln Gly Leu Glu Trp Met Gly Gly Ile Ile Pro Ile Phe
        35                  40                  45

Gly Thr Thr Asn Tyr Ala Gln Lys Phe Arg Gly Arg Val Thr Ile Ala
    50                  55                  60

Thr Asp Ala Ser Lys Ser Ala Ala Tyr Met Asp Leu Ser Ser Leu Lys
65                  70                  75                  80

Ser Glu Asp Thr Ala Ile Tyr Tyr Cys Ala Arg Ser Trp Gly Thr Ala
                85                  90                  95

Ala Thr Gly Gly Ser Phe Val Gln Trp Gly Gln Gly Thr Leu Val Thr
            100                 105                 110

Val Ser Ser
        115
```

<210> SEQ ID NO 168
<211> LENGTH: 113
<212> TYPE: PRT
<213> ORGANISM: Homo sapiens

<400> SEQUENCE: 168

```
Gly Ala Glu Val Lys Thr Pro Gly Ser Ser Val Lys Val Ser Cys Lys
1               5                   10                  15

Thr Ser Gly Gly Thr Phe Ser Asn Phe Ala Ile Thr Trp Val Arg Gln
            20                  25                  30

Ala Pro Gly Gln Gly Leu Glu Trp Met Gly Gly Ile Ile Pro Leu Phe
        35                  40                  45

Gly Ile Thr Asn Tyr Thr Gln Lys Phe Gln Gly Arg Val Thr Ile Thr
    50                  55                  60

Thr Asp Glu Ser Lys Thr Thr Ala Tyr Met Asp Leu Ser Gly Leu Arg
65                  70                  75                  80

Ser Glu Asp Thr Ala Val Tyr Phe Cys Ala Arg Gly Arg Asp Ser Ser
                85                  90                  95

Gly Arg Leu Leu Asp His Trp Gly Gln Gly Thr Leu Val Thr Val Ser
            100                 105                 110

Ser
```

<210> SEQ ID NO 169
<211> LENGTH: 114
<212> TYPE: PRT
<213> ORGANISM: Homo sapiens

<400> SEQUENCE: 169

```
Gly Ala Glu Val Lys Lys Pro Gly Ala Ser Val Lys Val Ser Cys Lys
1               5                   10                  15

Ala Ser Gly Asn Thr Phe Met Gly Tyr Tyr Phe His Trp Val Arg Gln
            20                  25                  30

Ala Pro Gly Gln Gly Leu Glu Trp Met Gly Trp Ile Asn Pro Asn Ser
        35                  40                  45

Gly His Ala Asn Ile Ala Gln Thr Phe Gln Gly Arg Val Thr Met Thr
    50                  55                  60

Arg Asp Pro Ser Ile Thr Thr Ala Tyr Met Glu Leu Ser Arg Leu Arg
65                  70                  75                  80

Ser Asp Asp Thr Ala Val Phe Tyr Cys Ala Arg Gly Gly Met Leu Gly
                85                  90                  95

Gln Leu Trp Ala Leu Asp Asn Trp Gly Gln Gly Thr Leu Val Thr Val
```

100 105 110

Ser Ser

<210> SEQ ID NO 170
<211> LENGTH: 114
<212> TYPE: PRT
<213> ORGANISM: Homo sapiens

<400> SEQUENCE: 170

Gly Ala Glu Val Lys Arg Pro Gly Ala Ser Val Lys Val Ser Cys Lys
1 5 10 15

Ala Ser Gly Tyr Thr Phe Ala Asp Tyr Tyr Ile His Trp Val Arg Gln
20 25 30

Ala Pro Gly Leu Gly Leu Glu Trp Met Gly Trp Ile Asn Pro Lys Thr
35 40 45

Gly Phe Ser His Tyr Glu Gln Thr Phe Gln Gly Arg Val Thr Met Ala
50 55 60

Arg Asp Thr Ser Ile Pro Ala Ala Tyr Met Glu Leu Ser Ser Leu Lys
65 70 75 80

Ser Asp Asp Thr Ala Ile Tyr Tyr Cys Ala Arg Gly Gly Arg Ile Asn
85 90 95

Val Ala Glu Ala Leu Arg Tyr Trp Gly Gln Gly Ser Leu Val Ile Val
100 105 110

Ser Ser

<210> SEQ ID NO 171
<211> LENGTH: 15
<212> TYPE: PRT
<213> ORGANISM: Homo sapiens

<400> SEQUENCE: 171

Ala Lys Asp Arg Pro Arg Gln Gly Val Gly Glu Leu Tyr Asp Ser
1 5 10 15

<210> SEQ ID NO 172
<211> LENGTH: 15
<212> TYPE: PRT
<213> ORGANISM: Homo sapiens

<400> SEQUENCE: 172

Ala Lys Asp Arg Leu Glu Lys Gly Ile Gly Glu Leu Phe His Ser
1 5 10 15

<210> SEQ ID NO 173
<211> LENGTH: 15
<212> TYPE: PRT
<213> ORGANISM: Homo sapiens

<400> SEQUENCE: 173

Ala Lys Asp Arg Leu Arg Gln Gly Val Gly Glu Leu Phe His Ser
1 5 10 15

<210> SEQ ID NO 174
<211> LENGTH: 15
<212> TYPE: PRT
<213> ORGANISM: Homo sapiens

<400> SEQUENCE: 174

Ala Lys Asp Arg Leu Arg Glu Gly Val Gly Glu Leu Tyr Gln Tyr
1 5 10 15

<210> SEQ ID NO 175
<211> LENGTH: 15
<212> TYPE: PRT
<213> ORGANISM: Homo sapiens

<400> SEQUENCE: 175

Ala Lys Asp Arg Leu Arg Glu Gly Ile Gly Glu Leu Phe His Ser
1 5 10 15

<210> SEQ ID NO 176
<211> LENGTH: 12
<212> TYPE: PRT
<213> ORGANISM: Homo sapiens

<400> SEQUENCE: 176

Ala Lys Asp Arg Asp His Phe Asp Gly His Asp Val
1 5 10

<210> SEQ ID NO 177
<211> LENGTH: 14
<212> TYPE: PRT
<213> ORGANISM: Homo sapiens

<400> SEQUENCE: 177

Ala Arg Gly Gly Pro Val Asn Ala Pro Arg Gly Phe Asp Pro
1 5 10

<210> SEQ ID NO 178
<211> LENGTH: 14
<212> TYPE: PRT
<213> ORGANISM: Homo sapiens

<400> SEQUENCE: 178

Ala Arg Gly Gly Pro Val Asn Ser Pro Leu Gly Phe Asp Pro
1 5 10

<210> SEQ ID NO 179
<211> LENGTH: 14
<212> TYPE: PRT
<213> ORGANISM: Homo sapiens

<400> SEQUENCE: 179

Ala Arg Gly Gly Arg Ile Asn Ser Pro Leu Gly Phe Asp Pro
1 5 10

<210> SEQ ID NO 180
<211> LENGTH: 14
<212> TYPE: PRT
<213> ORGANISM: Homo sapiens

<400> SEQUENCE: 180

Ala Arg Gly Gly Gln Ile Ser Ala Pro His Gly Phe Asp Pro
1 5 10

<210> SEQ ID NO 181
<211> LENGTH: 14
<212> TYPE: PRT
<213> ORGANISM: Homo sapiens

<400> SEQUENCE: 181

Ala Arg Gly Gly Arg Ile Asn Ala Pro Leu Gly Phe Asp Pro
1 5 10

<210> SEQ ID NO 182

-continued

<211> LENGTH: 14
<212> TYPE: PRT
<213> ORGANISM: Homo sapiens

<400> SEQUENCE: 182

```
Ala Arg Gly Gly Pro Ile Ser Ala Pro Leu Gly Phe Asp Pro
1               5                   10
```

<210> SEQ ID NO 183
<211> LENGTH: 20
<212> TYPE: PRT
<213> ORGANISM: Homo sapiens

<400> SEQUENCE: 183

```
Ala Arg Ala Ala Met Asn Arg Ile Ser Gly Val Val Pro Pro Gly Asp
1               5                   10                  15

Ala Phe Asp Leu
            20
```

<210> SEQ ID NO 184
<211> LENGTH: 17
<212> TYPE: PRT
<213> ORGANISM: Homo sapiens

<400> SEQUENCE: 184

```
Thr Arg Ser Leu Val Thr Pro Ala Ala Gln Ser Val Gln Tyr Phe Asp
1               5                   10                  15

Ser
```

<210> SEQ ID NO 185
<211> LENGTH: 17
<212> TYPE: PRT
<213> ORGANISM: Homo sapiens

<400> SEQUENCE: 185

```
Ala Arg Thr Leu Val Ala Pro Ser Ala Gln Ser Met Tyr Tyr Phe Asp
1               5                   10                  15

Phe
```

<210> SEQ ID NO 186
<211> LENGTH: 17
<212> TYPE: PRT
<213> ORGANISM: Homo sapiens

<400> SEQUENCE: 186

```
Thr Arg Thr Gln Val Val Pro Ser Ala Gln Ser Val Tyr Tyr Phe Asp
1               5                   10                  15

Phe
```

<210> SEQ ID NO 187
<211> LENGTH: 17
<212> TYPE: PRT
<213> ORGANISM: Homo sapiens

<400> SEQUENCE: 187

```
Thr Arg Thr Arg Val Val Pro Ser Ala Gln Ser Val Tyr Tyr Phe Asp
1               5                   10                  15

Phe
```

<210> SEQ ID NO 188
<211> LENGTH: 17
<212> TYPE: PRT

<213> ORGANISM: Homo sapiens

<400> SEQUENCE: 188

Thr Arg Thr Gln Ile Ile Pro Ala Ala Gln Ser Val Tyr Phe Phe Asp
1               5                   10                  15

Tyr

<210> SEQ ID NO 189
<211> LENGTH: 17
<212> TYPE: PRT
<213> ORGANISM: Homo sapiens

<400> SEQUENCE: 189

Thr Arg Thr Arg Ile Ile Ala Ala Ala Gln Ser Val Tyr His Tyr Asp
1               5                   10                  15

Leu

<210> SEQ ID NO 190
<211> LENGTH: 17
<212> TYPE: PRT
<213> ORGANISM: Homo sapiens

<400> SEQUENCE: 190

Ala Arg Ala Gln Asp Pro Ala Thr Ala Ile Arg Gly Leu Arg Trp Glu
1               5                   10                  15

Tyr

<210> SEQ ID NO 191
<211> LENGTH: 17
<212> TYPE: PRT
<213> ORGANISM: Homo sapiens

<400> SEQUENCE: 191

Ala Arg Gly Gly Ser Tyr Pro Val Ala Ile Arg Gly Val Thr Phe Gly
1               5                   10                  15

Ile

<210> SEQ ID NO 192
<211> LENGTH: 17
<212> TYPE: PRT
<213> ORGANISM: Homo sapiens

<400> SEQUENCE: 192

Ala Arg Gly Ala Ala Tyr Pro Thr Ala Ile Arg Gly Val Ile Tyr Gly
1               5                   10                  15

Phe

<210> SEQ ID NO 193
<211> LENGTH: 18
<212> TYPE: PRT
<213> ORGANISM: Homo sapiens

<400> SEQUENCE: 193

Ala Thr Ser Pro Ala Ala Ala Gly Ser Gly His Pro Ser Gly Trp Phe
1               5                   10                  15

Asp Pro

<210> SEQ ID NO 194
<211> LENGTH: 14
<212> TYPE: PRT
<213> ORGANISM: Homo sapiens

<400> SEQUENCE: 194

Ala Arg Pro Pro Gly Arg Ser Phe Leu Asp Gly Met Asp Val
1 5 10

<210> SEQ ID NO 195
<211> LENGTH: 16
<212> TYPE: PRT
<213> ORGANISM: Homo sapiens

<400> SEQUENCE: 195

Thr Arg Val Arg Trp Asp Gly Ile Glu Phe Thr Met Phe Phe Asp Ser
1 5 10 15

<210> SEQ ID NO 196
<211> LENGTH: 16
<212> TYPE: PRT
<213> ORGANISM: Homo sapiens

<400> SEQUENCE: 196

Ala Arg Val Arg Trp Asp Gly Ile Glu Ser Thr Met Phe Phe Asp Ser
1 5 10 15

<210> SEQ ID NO 197
<211> LENGTH: 16
<212> TYPE: PRT
<213> ORGANISM: Homo sapiens

<400> SEQUENCE: 197

Thr Arg Val Arg Trp Asp Gly Ile Glu Ser Thr Met Phe Phe Asp Ser
1 5 10 15

<210> SEQ ID NO 198
<211> LENGTH: 24
<212> TYPE: PRT
<213> ORGANISM: Homo sapiens

<400> SEQUENCE: 198

Ala Arg Asp Val Val Thr Met Val Glu Gly Leu Arg Phe His Tyr Tyr
1 5 10 15

Tyr Asn Tyr Tyr Gly Met Asp Val
20

<210> SEQ ID NO 199
<211> LENGTH: 24
<212> TYPE: PRT
<213> ORGANISM: Homo sapiens

<400> SEQUENCE: 199

Ala Arg Asp Val Val Thr Met Val Glu Gly Leu Arg Phe His Tyr Tyr
1 5 10 15

Tyr Asn Tyr Tyr Gly Met Asp Val
20

<210> SEQ ID NO 200
<211> LENGTH: 24
<212> TYPE: PRT
<213> ORGANISM: Homo sapiens

<400> SEQUENCE: 200

Ala Arg Asp Val Val Thr Met Val Glu Gly Leu Arg Phe His Tyr Tyr
1 5 10 15

Tyr Asn Tyr Tyr Gly Met Asp Val

20

<210> SEQ ID NO 201
<211> LENGTH: 12
<212> TYPE: PRT
<213> ORGANISM: Homo sapiens

<400> SEQUENCE: 201

Ala Arg Asn Gln Pro Gly Gly Arg Ala Phe Asp Tyr
1 5 10

<210> SEQ ID NO 202
<211> LENGTH: 12
<212> TYPE: PRT
<213> ORGANISM: Homo sapiens

<400> SEQUENCE: 202

Ala Arg Asn Gln Pro Gly Gly Arg Ala Phe Asp Tyr
1 5 10

<210> SEQ ID NO 203
<211> LENGTH: 21
<212> TYPE: PRT
<213> ORGANISM: Homo sapiens

<400> SEQUENCE: 203

Ala Arg His Asp Gly Arg Gly Tyr Cys Ser Pro Thr Arg Cys Phe Phe
1 5 10 15

Ser Gly Met Asp Val
20

<210> SEQ ID NO 204
<211> LENGTH: 21
<212> TYPE: PRT
<213> ORGANISM: Homo sapiens

<400> SEQUENCE: 204

Ala Arg His Asp Gly Arg Gly Tyr Cys Ser Pro Thr Arg Cys Phe Phe
1 5 10 15

Ser Gly Met Asp Val
20

<210> SEQ ID NO 205
<211> LENGTH: 17
<212> TYPE: PRT
<213> ORGANISM: Homo sapiens

<400> SEQUENCE: 205

Ala Arg Arg Thr Tyr Tyr Asp Asn Arg Phe Pro Tyr Trp Tyr Phe Asp
1 5 10 15

Leu

<210> SEQ ID NO 206
<211> LENGTH: 17
<212> TYPE: PRT
<213> ORGANISM: Homo sapiens

<400> SEQUENCE: 206

Ala Arg Arg Thr Tyr Tyr Asp Thr Arg Phe Pro Tyr Trp Tyr Phe Asp
1 5 10 15

Leu

<210> SEQ ID NO 207
<211> LENGTH: 15
<212> TYPE: PRT
<213> ORGANISM: Homo sapiens

<400> SEQUENCE: 207

Ala Arg Ser Trp Gly Thr Ala Ala Thr Gly Gly Ser Phe Val Gln
1 5 10 15

<210> SEQ ID NO 208
<211> LENGTH: 13
<212> TYPE: PRT
<213> ORGANISM: Homo sapiens

<400> SEQUENCE: 208

Ala Arg Gly Arg Asp Ser Ser Gly Arg Leu Leu Asp His
1 5 10

<210> SEQ ID NO 209
<211> LENGTH: 14
<212> TYPE: PRT
<213> ORGANISM: Homo sapiens

<400> SEQUENCE: 209

Ala Arg Gly Gly Met Leu Gly Gln Leu Trp Ala Leu Asp Asn
1 5 10

<210> SEQ ID NO 210
<211> LENGTH: 14
<212> TYPE: PRT
<213> ORGANISM: Homo sapiens

<400> SEQUENCE: 210

Ala Arg Gly Gly Arg Ile Asn Val Ala Glu Ala Leu Arg Tyr
1 5 10

<210> SEQ ID NO 211
<211> LENGTH: 96
<212> TYPE: PRT
<213> ORGANISM: Homo sapiens

<400> SEQUENCE: 211

Ser Ala Ser Val Gly Asp Arg Val Thr Ile Thr Cys Arg Ala Ser Gln
1 5 10 15

Ser Ile Gly Ser Trp Leu Ala Trp Tyr Gln Gln Lys Pro Gly Lys Ala
20 25 30

Pro Lys Leu Leu Ile Tyr Thr Ala Ser Ile Leu Glu Ser Gly Val Pro
35 40 45

Ser Arg Phe Ser Gly Ser Gly Ser Gly Thr Glu Phe Thr Leu Thr Ile
50 55 60

Asn Ser Leu Gln Pro Asp Asp Phe Ala Thr Tyr Tyr Cys Gln Lys Phe
65 70 75 80

Asn Ser Val Pro Trp Thr Phe Gly Pro Gly Thr Lys Val Glu Val Lys
85 90 95

<210> SEQ ID NO 212
<211> LENGTH: 96
<212> TYPE: PRT
<213> ORGANISM: Homo sapiens

<400> SEQUENCE: 212

Ser Ala Ser Leu Gly Asp Arg Val Thr Ile Thr Cys Arg Ala Ser Gln
1 5 10 15

```
Ser Ile Ser Pro Trp Leu Ala Trp Tyr Gln Gln Lys Pro Gly Lys Ala
            20                  25                  30

Pro Lys Phe Leu Ile Tyr Gln Thr Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 213
<211> LENGTH: 96
<212> TYPE: PRT
<213> ORGANISM: Homo sapiens

<400> SEQUENCE: 213

Ser Ala Ser Ile Gly Asp Arg Val Thr Ile Thr Cys Arg Ala Ser Gln
1               5                   10                  15

Ser Ile Ser Pro Trp Leu Ala Trp Tyr Gln Gln Lys Pro Gly Lys Ala
            20                  25                  30

Pro Lys Phe Leu Ile Tyr Gln Thr Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Leu Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 214
<211> LENGTH: 96
<212> TYPE: PRT
<213> ORGANISM: Homo sapiens

<400> SEQUENCE: 214

Ser Ala Ser Val Gly Asp Arg Val Thr Ile Thr Cys Arg Ala Ser Gln
1               5                   10                  15

Asn Ile Ser Pro Trp Leu Ala Trp Tyr Gln Gln Lys Pro Gly Lys Ala
            20                  25                  30

Pro Lys Phe Leu Ile Tyr Gln Thr Ser Ile Leu Glu Ser Gly Val Pro
        35                  40                  45

Ser Arg Phe Ser Gly Ser Gly Ser Gly Thr Asp Phe Thr Leu Thr Ile
    50                  55                  60

Ser Ser Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 215
<211> LENGTH: 96
<212> TYPE: PRT
<213> ORGANISM: Homo sapiens

<400> SEQUENCE: 215

Ser Ala Ser Ile Gly Asp Arg Val Thr Ile Thr Cys Arg Ala Ser Gln
1               5                   10                  15
```

```
Ser Ile Thr Pro Trp Leu Ala Trp Tyr Gln Gln Lys Pro Gly Lys Ala
            20                  25                  30

Pro Lys Phe Leu Ile Tyr Gln Thr Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 216
<211> LENGTH: 96
<212> TYPE: PRT
<213> ORGANISM: Homo sapiens

<400> SEQUENCE: 216

Ser Ala Ser Val Gly Gly Arg Val Thr Ile Thr Cys Arg Ala Ser Gln
1               5                   10                  15

Ser Ile Ser Ser Trp Leu Ala Trp Tyr Gln Gln Lys Pro Gly Lys Ala
            20                  25                  30

Pro Lys Leu Leu Ile Ser Lys Ala Ser Asn Leu Glu Ser Gly Val Pro
        35                  40                  45

Ser Arg Phe Ser Gly Gly Gly Ser Glu Thr Glu Phe Thr Leu Thr Ile
    50                  55                  60

Ser Ser Leu Gln Pro Asp Asp Phe Ala Thr Tyr Tyr Cys Gln Arg Tyr
65                  70                  75                  80

Asp Ser Tyr Pro Phe Thr Phe Gly Pro Gly Thr Lys Val Thr Ile Lys
                85                  90                  95


<210> SEQ ID NO 217
<211> LENGTH: 97
<212> TYPE: PRT
<213> ORGANISM: Homo sapiens

<400> SEQUENCE: 217

Ser Leu Ser Pro Gly Glu Arg Ala Thr Leu Ser Cys Arg Ala Ser Gln
1               5                   10                  15

Glu Ile Gly Ser Phe Ser Leu Gly Trp Tyr Gln Gln Lys Phe Gly Gln
            20                  25                  30

Pro Pro Arg Leu Leu Ile Tyr Gly Ala Ser Ser Arg Ala Thr Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Val Ala Val Tyr Tyr Cys Gln Gln
65                  70                  75                  80

Tyr Val Ser Ser Pro Leu Thr Phe Gly Gly Gly Thr Lys Val Glu Ile
                85                  90                  95

Lys


<210> SEQ ID NO 218
<211> LENGTH: 97
<212> TYPE: PRT
<213> ORGANISM: Homo sapiens

<400> SEQUENCE: 218

Ser Leu Ser Pro Gly Asp Arg Ala Thr Leu Ser Cys Arg Ala Ser Gln
1               5                   10                  15
```

Ser Ile Gly Ser Phe Ser Leu Ala Trp Tyr Gln Gln Lys Phe Gly His
            20                  25                  30

Ala Pro Arg Leu Leu Ile Tyr Gly Ala Ser Ser Arg Ala Thr Gly Ile
        35                  40                  45

Pro Asp Arg Phe Ser Gly Ser Gly Ser Asp Thr Asp Tyr Thr Leu Thr
    50                  55                  60

Ile Ser Arg Leu Glu Pro Glu Asp Phe Ala Val Tyr Tyr Cys Gln Gln
65                  70                  75                  80

Tyr Val Ser Ser Pro Leu Thr Phe Gly Gly Gly Thr Lys Val Glu Ile
                85                  90                  95

Lys

<210> SEQ ID NO 219
<211> LENGTH: 97
<212> TYPE: PRT
<213> ORGANISM: Homo sapiens

<400> SEQUENCE: 219

Ser Leu Ser Pro Gly Glu Arg Ala Thr Leu Ser Cys Arg Ala Ser Gln
1               5                   10                  15

Ser Ile Ser Thr Phe Ser Leu Ala Trp Tyr Gln Gln Lys Phe Gly Gln
            20                  25                  30

Ala Pro Arg Leu Leu Ile Tyr Gly Ala Ser Ser Arg Ala Thr Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Phe Ala Val Tyr Tyr Cys Gln Gln
65                  70                  75                  80

Tyr Val Ser Ser Pro Leu Thr Phe Gly Gly Gly Thr Lys Val Glu Ile
                85                  90                  95

Arg

<210> SEQ ID NO 220
<211> LENGTH: 97
<212> TYPE: PRT
<213> ORGANISM: Homo sapiens

<400> SEQUENCE: 220

Ser Leu Ser Pro Gly Glu Arg Ala Thr Leu Ser Cys Arg Ala Ser Gln
1               5                   10                  15

Ser Val Ser Ser Ile His Leu Gly Trp Tyr Gln Gln Lys Pro Gly Gln
            20                  25                  30

Ala Pro Arg Leu Leu Ile Tyr Gly Ala Ser Ser Arg Ala Thr Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Phe Ala Val Tyr Tyr Cys Gln Gln
65                  70                  75                  80

Tyr Gly Ser Ser Pro Leu Thr Phe Gly Gly Gly Thr Lys Val Glu Ile
                85                  90                  95

Lys

<210> SEQ ID NO 221
<211> LENGTH: 97
<212> TYPE: PRT
<213> ORGANISM: Homo sapiens

<400> SEQUENCE: 221

Ser Leu Ser Pro Gly Glu Thr Ala Thr Leu Ser Cys Arg Ala Ser Gln
1 5 10 15

Ser Ile Gly Ser Ile Ser Leu Gly Trp Tyr Gln Gln Lys Phe Gly Gln
20 25 30

Ala Pro Arg Leu Leu Ile Tyr Gly Ala Ser Thr Arg Ala Thr Gly Thr
35 40 45

Pro Asp Arg Phe Ser Gly Ser Gly Ser Glu Thr Asp Phe Thr Leu Thr
50 55 60

Ile Ser Arg Leu Glu Pro Glu Asp Ser Ala Val Tyr Tyr Cys Gln Gln
65 70 75 80

Tyr Val Ser Ser Pro Leu Arg Phe Gly Gly Gly Thr Lys Val Glu Ile
85 90 95

Lys

<210> SEQ ID NO 222
<211> LENGTH: 97
<212> TYPE: PRT
<213> ORGANISM: Homo sapiens

<400> SEQUENCE: 222

Ser Leu Ser Pro Gly Glu Arg Ala Thr Leu Ser Cys Arg Ala Ser Gln
1 5 10 15

Ser Val Ser Ser Ile His Leu Ala Trp Tyr Gln Gln Arg Pro Gly Gln
20 25 30

Ala Pro Arg Leu Leu Ile Asn Gly Ala Ser Ser Arg Ala Thr Gly Ile
35 40 45

Pro Asp Arg Phe Ser Gly Ser Gly Ser Gly Thr Asp Phe Thr Leu Thr
50 55 60

Ile Ser Arg Leu Glu Pro Glu Asp Phe Ala Val Tyr Tyr Cys Gln Gln
65 70 75 80

Tyr Gly Ser Ser Pro Leu Thr Phe Gly Gly Gly Thr Lys Val Glu Ile
85 90 95

Lys

<210> SEQ ID NO 223
<211> LENGTH: 97
<212> TYPE: PRT
<213> ORGANISM: Homo sapiens

<400> SEQUENCE: 223

Ser Leu Ser Pro Gly Glu Arg Ala Thr Leu Ser Cys Arg Ala Ser Gln
1 5 10 15

Ser Leu Ser Ser Asn Tyr Leu Ala Trp Tyr Gln Gln Lys Pro Gly Gln
20 25 30

Ala Pro Arg Leu Leu Ile Tyr Gly Ala Ser Ser Arg Ala Thr Gly Ile
35 40 45

Pro Asp Arg Phe Ser Gly Ser Gly Ser Gly Thr Asp Phe Thr Leu Thr
50 55 60

Ile Ser Arg Leu Glu Pro Glu Asp Phe Ala Val Tyr Tyr Cys Gln Gln
65 70 75 80

Tyr Gly Ser Ser Arg Gly Thr Phe Gly Gln Gly Thr Lys Val Glu Ile
85 90 95

Lys

<210> SEQ ID NO 224
<211> LENGTH: 97
<212> TYPE: PRT
<213> ORGANISM: Homo sapiens

<400> SEQUENCE: 224

Ser Leu Ser Pro Gly Glu Arg Ala Thr Leu Ser Cys Arg Ala Ser Gln
1 5 10 15

Ser Val Ser Leu Ser Phe Leu Ala Trp Tyr Gln Gln Lys Pro Gly Gln
20 25 30

Ala Pro Arg Leu Leu Ile Tyr Gly Ala Ser Asn Arg Ala Thr Gly Ile
35 40 45

Pro Asp Arg Phe Ser Gly Ser Gly Ser Gly Thr Asp Phe Thr Leu Thr
50 55 60

Ile Ser Arg Leu Glu Pro Gly Asp Phe Ala Val Tyr Tyr Cys Gln Gln
65 70 75 80

Tyr Gly Ser Ser Pro Leu Thr Phe Gly Pro Gly Thr Lys Val Asp Ile
85 90 95

Lys

<210> SEQ ID NO 225
<211> LENGTH: 97
<212> TYPE: PRT
<213> ORGANISM: Homo sapiens

<400> SEQUENCE: 225

Ser Leu Ser Pro Gly Glu Arg Gly Thr Leu Ser Cys Arg Ala Ser Gln
1 5 10 15

Tyr Ile Thr Thr Gly His Phe Ala Trp Tyr Gln Gln Lys Pro Gly Arg
20 25 30

Ala Pro Arg Leu Leu Ile Tyr Gly Ala Ser Val Arg Ala Thr Gly Val
35 40 45

Pro Asp Arg Phe Ser Gly Ser Gly Ala Glu Thr Asp Phe Thr Leu Thr
50 55 60

Ile Ser Arg Leu Asp Pro Glu Asp Val Gly Val Tyr Tyr Cys Gln Gln
65 70 75 80

Tyr Gly Ser Ser Pro Val Thr Phe Gly Pro Gly Thr Lys Val Glu Ile
85 90 95

Lys

<210> SEQ ID NO 226
<211> LENGTH: 97
<212> TYPE: PRT
<213> ORGANISM: Homo sapiens

<400> SEQUENCE: 226

Ser Leu Ser Pro Gly Glu Arg Ala Thr Leu Ser Cys Arg Ala Ser Gln
1 5 10 15

Asn Ile Gly Leu Asp Tyr Phe Ala Trp Tyr Gln Gln Lys Pro Gly Gln
20 25 30

Ala Pro Arg Leu Leu Ile Tyr Gly Ala Ser Ile Arg Ala Thr Gly Ile
35 40 45

Pro Asp Arg Phe Ser Gly Ser Gly Ser Gly Thr Asp Phe Thr Leu Thr
50 55 60

Ile Ser Arg Leu Val Pro Glu Asp Ile Ala Val Tyr Tyr Cys Gln Gln
65 70 75 80

Tyr Gly Ser Ser Pro Val Thr Phe Gly Pro Gly Thr Lys Val Glu Val
85 90 95

Lys

<210> SEQ ID NO 227
<211> LENGTH: 97
<212> TYPE: PRT
<213> ORGANISM: Homo sapiens

<400> SEQUENCE: 227

Ser Leu Ser Pro Gly Glu Arg Ala Thr Leu Ser Cys Arg Ala Ser Gln
1 5 10 15

Ser Val Thr Ser Gly Tyr Phe Ala Trp Tyr Gln His Lys Pro Gly Gln
20 25 30

Ala Pro Arg Leu Leu Ile Tyr Gly Ala Ser Ile Arg Ala Thr Gly Ile
35 40 45

Pro Asp Arg Phe Ser Gly Ser Glu Ser Gly Thr Asp Phe Thr Leu Thr
50 55 60

Ile Ser Arg Leu Glu Pro Glu Asp Val Ala Val Tyr Tyr Cys Gln Gln
65 70 75 80

Tyr Gly Ser Ser Pro Val Thr Phe Gly Pro Gly Thr Lys Val Asp Ile
85 90 95

Lys

<210> SEQ ID NO 228
<211> LENGTH: 97
<212> TYPE: PRT
<213> ORGANISM: Homo sapiens

<400> SEQUENCE: 228

Ser Leu Ser Pro Gly Glu Arg Ala Thr Leu Ser Cys Arg Ala Ser Gln
1 5 10 15

Phe Val Ile Ser Gly His Phe Ala Trp Tyr Gln Gln Lys Pro Gly Gln
20 25 30

Ala Pro Arg Leu Leu Ile Tyr Gly Thr Ser Asn Arg Ala Thr Gly Ile
35 40 45

Pro Asp Arg Phe Ser Gly Ser Glu Ser Gly Ala Asp Phe Thr Leu Thr
50 55 60

Ile Ser Arg Leu Glu Pro Glu Asp Phe Ala Val Tyr Phe Cys Gln Gln
65 70 75 80

Tyr Gly Ser Ser Pro Pro Thr Phe Gly Pro Gly Thr Lys Val Asp Ile
85 90 95

Lys

<210> SEQ ID NO 229
<211> LENGTH: 97
<212> TYPE: PRT
<213> ORGANISM: Homo sapiens

<400> SEQUENCE: 229

Ser Leu Ser Pro Gly Asp Arg Ala Thr Leu Ser Cys Arg Ala Ser Gln
1 5 10 15

His Ile Thr Thr Gly His Phe Ala Trp Tyr Gln Gln Lys Pro Gly Gln
20 25 30

Ala Pro Arg Leu Leu Ile Tyr Gly Ala Ser Ile Arg Ala Ser Gly Ile
35 40 45

Pro Asp Arg Phe Ser Gly Ser Gly Ser Gly Thr Asp Phe Ser Leu Thr

```
    50                  55                  60

Ile Ser Arg Leu Glu Pro Glu Asp Cys Ala Val Tyr Tyr Cys Gln Gln
65                  70                  75                  80

Tyr Gly Ser Ser Pro Val Thr Phe Gly Pro Gly Thr Lys Val Asp Ile
                85                  90                  95

Lys


<210> SEQ ID NO 230
<211> LENGTH: 96
<212> TYPE: PRT
<213> ORGANISM: Homo sapiens

<400> SEQUENCE: 230

Ser Ala Ser Val Gly Asp Arg Val Thr Ile Thr Cys Arg Ala Ser Gln
1               5                   10                  15

Ser Ile Asp Thr Tyr Leu Asn Trp Tyr Gln Gln Lys Pro Gly Lys Val
            20                  25                  30

Pro Ala Ile Leu Ile Tyr Ala Ala Ser Ser Leu Gln Ser Gly Val Pro
        35                  40                  45

Ser Arg Phe Ser Gly Ser Gly Ser Gly Thr Asp Phe Thr Leu Thr Ile
    50                  55                  60

Asn Ser Leu Gln Pro Glu Asp Phe Ala Thr Tyr Tyr Cys Gln Gln Ser
65                  70                  75                  80

Tyr Ile Thr Pro Leu Thr Phe Gly Gly Gly Thr Lys Val Glu Ile Lys
                85                  90                  95


<210> SEQ ID NO 231
<211> LENGTH: 96
<212> TYPE: PRT
<213> ORGANISM: Homo sapiens

<400> SEQUENCE: 231

Ser Ala Ser Val Gly Asp Arg Val Thr Ile Thr Cys Arg Ala Ser Gln
1               5                   10                  15

Ser Ile Ser Asn Tyr Leu Asn Trp Tyr Gln Gln Lys Pro Gly Lys Ala
            20                  25                  30

Pro Asn Leu Leu Ile Phe Ala Thr Ser Ser Leu Gln Ser Gly Val Pro
        35                  40                  45

Ser Arg Phe Ser Gly Ser Gly Ser Gly Thr Asp Phe Thr Leu Thr Ile
    50                  55                  60

Ser Ser Leu Gln Pro Glu Asp Phe Ala Thr Tyr Tyr Cys Gln Gln Ser
65                  70                  75                  80

Phe Ser Thr Pro Leu Thr Phe Gly Gly Gly Thr Lys Val Glu Ile Arg
                85                  90                  95


<210> SEQ ID NO 232
<211> LENGTH: 96
<212> TYPE: PRT
<213> ORGANISM: Homo sapiens

<400> SEQUENCE: 232

Ser Ala Ser Val Gly Asp Arg Val Thr Ile Thr Cys Arg Ala Ser Gln
1               5                   10                  15

Ser Ile Ser Thr Tyr Leu Asn Trp Tyr Gln Gln Lys Pro Gly Lys Ala
            20                  25                  30

Pro Lys Leu Leu Ile Phe Ala Ala Ser Thr Leu Gln Ser Gly Val Pro
        35                  40                  45
```

```
Ser Arg Phe Ser Gly Ser Gly Ser Gly Thr Glu Phe Thr Leu Thr Ile
    50                  55                  60

Thr Ser Leu Gln Pro Ala Asp Phe Ala Ile Tyr Tyr Cys Gln Gln Ser
65                  70                  75                  80

Tyr Ile Ser Pro Leu Thr Phe Gly Gly Gly Thr Lys Val Glu Ile Asn
                85                  90                  95


<210> SEQ ID NO 233
<211> LENGTH: 96
<212> TYPE: PRT
<213> ORGANISM: Homo sapiens

<400> SEQUENCE: 233

Ser Ala Ser Val Gly Asp Arg Val Thr Ile Thr Cys Arg Ala Ser Gln
1               5                   10                  15

Ser Ile Ile Asn Tyr Leu Asn Trp Tyr Gln Gln Lys Pro Gly Lys Ala
            20                  25                  30

Pro Lys Leu Leu Ile Tyr Thr Ala Ser Ser Leu Gln Ser Gly Val Pro
        35                  40                  45

Ser Arg Phe Ser Gly Ser Gly Ser Gly Thr Ser Phe Thr Leu Thr Ile
    50                  55                  60

Ile Ser Leu Gln Pro Glu Asp Phe Ala Ile Tyr Tyr Cys His Gln Ser
65                  70                  75                  80

Phe Ser Ala Pro Tyr Thr Phe Gly Gln Gly Thr Lys Leu Glu Ile Lys
                85                  90                  95


<210> SEQ ID NO 234
<211> LENGTH: 96
<212> TYPE: PRT
<213> ORGANISM: Homo sapiens

<400> SEQUENCE: 234

Ser Ala Ser Val Gly His Arg Val Thr Ile Thr Cys Arg Ala Ser Gln
1               5                   10                  15

Ser Ile Ser Ser Tyr Leu Asn Trp Tyr Gln Gln Lys Pro Gly Lys Ala
            20                  25                  30

Pro Lys Leu Leu Ile Phe Ala Ala Ser Ser Leu Gln Ser Gly Val Pro
        35                  40                  45

Ser Arg Phe Ser Gly Ser Gly Ser Gly Thr Asp Phe Thr Leu Thr Ile
    50                  55                  60

Asn Ser Leu Gln Pro Gly Asp Phe Ala Thr Tyr Tyr Cys Gln Gln Ser
65                  70                  75                  80

Tyr Ser Thr Pro Leu Ser Phe Gly Gln Gly Thr Arg Val Glu Ile Lys
                85                  90                  95


<210> SEQ ID NO 235
<211> LENGTH: 103
<212> TYPE: PRT
<213> ORGANISM: Homo sapiens

<400> SEQUENCE: 235

Pro Ala Ser Val Ser Gly Ser Pro Gly Gln Ser Ile Thr Ile Tyr Cys
1               5                   10                  15

Ser Gly Ser Ser Ser Asp Val Gly Ser Tyr Asn Leu Val Ser Trp Tyr
            20                  25                  30

Gln Gln His Pro Gly Lys Ala Pro Lys Leu Ile Ile Tyr Gly Val Thr
        35                  40                  45

Arg Arg Pro Ser Gly Val Ser Ser Arg Phe Ser Gly Ser Lys Ser Gly
```

```
    50                  55                  60

Asn Thr Ala Ser Leu Thr Phe Ser Gly Leu Gln Val Glu Asp Asp Ala
65                  70                  75                  80

Asp Tyr Tyr Cys Cys Ser Tyr Ala Asn Ser Gly Thr Phe Val Phe Gly
                85                  90                  95

Thr Gly Thr Lys Val Thr Val
            100
```

<210> SEQ ID NO 236
<211> LENGTH: 103
<212> TYPE: PRT
<213> ORGANISM: Homo sapiens

<400> SEQUENCE: 236

```
Pro Ala Ser Val Ser Gly Ser Pro Gly Gln Ser Ile Thr Ile Tyr Cys
1               5                   10                  15

Ser Gly Ser Ser Ser Asp Val Gly Ser Tyr Asn Leu Val Ser Trp Tyr
            20                  25                  30

Gln Gln His Pro Gly Lys Ala Pro Lys Leu Ile Ile Tyr Gly Val Thr
        35                  40                  45

Arg Arg Pro Ser Gly Val Ser Ser Arg Phe Ser Gly Ser Lys Ser Gly
    50                  55                  60

Asn Thr Ala Ser Leu Thr Phe Ser Gly Leu Gln Val Glu Asp Asp Ala
65                  70                  75                  80

Asp Tyr Tyr Cys Cys Ser Tyr Ala Asn Ser Gly Thr Phe Val Phe Gly
                85                  90                  95

Thr Gly Thr Lys Val Thr Val
            100
```

<210> SEQ ID NO 237
<211> LENGTH: 103
<212> TYPE: PRT
<213> ORGANISM: Homo sapiens

<400> SEQUENCE: 237

```
Pro Ala Ser Val Ser Gly Ser Pro Gly Gln Ser Ile Thr Ile Tyr Cys
1               5                   10                  15

Ser Gly Ser Ser Ser Asp Val Gly Ser Tyr Asn Leu Val Ser Trp Tyr
            20                  25                  30

Gln Gln His Pro Gly Lys Ala Pro Lys Leu Ile Ile Tyr Gly Val Thr
        35                  40                  45

Arg Arg Pro Ser Gly Val Ser Ser Arg Phe Ser Gly Ser Lys Ser Gly
    50                  55                  60

Asn Thr Ala Ser Leu Thr Phe Ser Gly Leu Gln Val Glu Asp Asp Ala
65                  70                  75                  80

Asp Tyr Tyr Cys Cys Ser Tyr Ala Asn Ser Gly Thr Phe Val Phe Gly
                85                  90                  95

Thr Gly Thr Lys Val Thr Val
            100
```

<210> SEQ ID NO 238
<211> LENGTH: 97
<212> TYPE: PRT
<213> ORGANISM: Homo sapiens

<400> SEQUENCE: 238

```
Ser Leu Ser Pro Gly Asp Arg Ala Thr Leu Ser Cys Gly Ala Ser Gln
1               5                   10                  15
```

```
Ser Val Ser Ser Asn Tyr Leu Ala Trp Tyr Gln Gln Lys Leu Gly Gln
            20                  25                  30

Ala Pro Arg Leu Leu Ile Tyr Ala Ala Ser Thr Arg Ala Thr Gly Ile
        35                  40                  45

Pro Asp Arg Phe Ser Gly Gly Gly Ser Gly Thr Asp Phe Thr Leu Thr
    50                  55                  60

Ile Asn Lys Leu Glu Ala Glu Asp Phe Ala Met Tyr Tyr Cys Gln Ile
65                  70                  75                  80

Tyr Asp Ser Ser Val Arg Thr Phe Gly Gln Gly Thr Lys Val Glu Ile
                85                  90                  95

Lys
```

<210> SEQ ID NO 239
<211> LENGTH: 97
<212> TYPE: PRT
<213> ORGANISM: Homo sapiens

<400> SEQUENCE: 239

```
Ser Leu Ser Pro Gly Asp Arg Ala Thr Leu Ser Cys Arg Ala Ser Gln
1               5                   10                  15

Ser Val Ser Ser Asn Tyr Leu Ala Trp Tyr Gln Gln Lys Leu Gly Gln
            20                  25                  30

Ala Pro Arg Leu Leu Ile Tyr Gly Ala Ser Thr Arg Ala Thr Gly Ile
        35                  40                  45

Pro Asp Arg Phe Ser Gly Gly Gly Ser Gly Thr Asp Phe Thr Leu Thr
    50                  55                  60

Ile Asn Lys Leu Glu Ala Glu Asp Phe Ala Val Tyr Tyr Cys Gln Ile
65                  70                  75                  80

Tyr Asp Ser Ser Val Arg Thr Phe Gly Gln Gly Thr Lys Val Glu Ile
                85                  90                  95

Lys
```

<210> SEQ ID NO 240
<211> LENGTH: 97
<212> TYPE: PRT
<213> ORGANISM: Homo sapiens

<400> SEQUENCE: 240

```
Ser Leu Ser Pro Gly Asp Arg Ala Thr Leu Ser Cys Gly Ala Ser Gln
1               5                   10                  15

Ser Val Ser Ser Asn Tyr Leu Ala Trp Tyr Gln Gln Lys Leu Gly Gln
            20                  25                  30

Ala Pro Arg Leu Leu Ile Tyr Gly Ala Ser Thr Arg Ala Thr Gly Ile
        35                  40                  45

Pro Asp Arg Phe Ser Gly Gly Gly Ser Gly Thr Asp Phe Thr Leu Thr
    50                  55                  60

Ile Asn Lys Leu Glu Ala Glu Asp Phe Ala Met Tyr Tyr Cys Gln Ile
65                  70                  75                  80

Tyr Asp Ser Ser Leu Arg Thr Phe Gly Gln Gly Thr Lys Val Glu Ile
                85                  90                  95

Lys
```

<210> SEQ ID NO 241
<211> LENGTH: 98
<212> TYPE: PRT
<213> ORGANISM: Homo sapiens

<400> SEQUENCE: 241

Ser Leu Ser Pro Gly Gln Arg Ala Thr Leu Ser Cys Arg Ala Ser Gln
1 5 10 15

Ser Val Ser Asn Tyr Phe Ala Trp Tyr Gln Gln Lys Pro Gly Gln Ala
20 25 30

Pro Arg Leu Leu Ile Tyr Asp Thr Ser Lys Arg Ala Thr Gly Thr Pro
35 40 45

Ala Arg Phe Ser Gly Ser Gly Ser Gly Thr Asp Phe Thr Leu Thr Ile
50 55 60

Ser Ser Leu Glu Pro Glu Asp Phe Ala Val Tyr Tyr Cys Gln Glu Arg
65 70 75 80

Asn Asn Trp Pro Leu Thr Trp Thr Phe Gly Leu Gly Thr Lys Val Glu
85 90 95

Ile Lys

<210> SEQ ID NO 242
<211> LENGTH: 98
<212> TYPE: PRT
<213> ORGANISM: Homo sapiens

<400> SEQUENCE: 242

Ser Leu Ser Pro Gly Gln Arg Ala Thr Leu Ser Cys Arg Ala Ser Gln
1 5 10 15

Ser Val Ser Asn Tyr Phe Ala Trp Tyr Gln Gln Lys Pro Gly Gln Ala
20 25 30

Pro Arg Leu Leu Ile Tyr Asp Thr Ser Lys Arg Ala Thr Gly Thr Pro
35 40 45

Ala Arg Phe Ser Gly Ser Gly Ser Gly Thr Asp Phe Thr Leu Thr Ile
50 55 60

Ser Ser Leu Glu Pro Glu Asp Phe Ala Val Tyr Tyr Cys Gln Glu Arg
65 70 75 80

Asn Asn Trp Pro Leu Thr Trp Thr Phe Gly Leu Gly Thr Lys Val Glu
85 90 95

Ile Lys

<210> SEQ ID NO 243
<211> LENGTH: 96
<212> TYPE: PRT
<213> ORGANISM: Homo sapiens

<400> SEQUENCE: 243

Ser Ala Ser Val Gly Asp Arg Val Thr Ile Thr Cys Arg Ala Ser Gln
1 5 10 15

Ser Ile Ser Asn Tyr Leu Asn Trp Tyr Gln Gln Lys Pro Gly Lys Ala
20 25 30

Pro Asn Leu Leu Ile Tyr Ala Ala Ser Ser Leu Gln Ser Gly Val Pro
35 40 45

Ser Arg Phe Ser Gly Ser Gly Ser Gly Thr Asp Phe Thr Leu Thr Ile
50 55 60

Ser Ser Leu Gln Pro Glu Asp Tyr Ala Ile Tyr Tyr Cys Gln Gln Thr
65 70 75 80

Asp Arg Thr Pro Leu Thr Phe Gly Gln Gly Thr Lys Val Glu Ile Lys
85 90 95

<210> SEQ ID NO 244

<211> LENGTH: 96
<212> TYPE: PRT
<213> ORGANISM: Homo sapiens

<400> SEQUENCE: 244

Ser Ala Ser Val Gly Asp Arg Val Thr Ile Thr Cys Arg Ala Ser Gln
1               5                   10                  15

Ser Ile Ser Asn Tyr Leu Asn Trp Tyr Gln Gln Lys Pro Gly Lys Ala
            20                  25                  30

Pro Asn Leu Leu Ile Tyr Ala Ala Ser Ser Leu Gln Ser Gly Val Pro
        35                  40                  45

Ser Arg Phe Ser Gly Ser Gly Ser Gly Thr Asp Phe Thr Leu Thr Ile
    50                  55                  60

Ser Ser Leu Gln Pro Glu Asp Tyr Ala Ile Tyr Tyr Cys Gln Gln Thr
65                  70                  75                  80

Asp Arg Thr Pro Leu Thr Phe Gly Gln Gly Thr Lys Val Glu Ile Lys
                85                  90                  95

<210> SEQ ID NO 245
<211> LENGTH: 96
<212> TYPE: PRT
<213> ORGANISM: Homo sapiens

<400> SEQUENCE: 245

Ser Ala Ser Val Gly Asp Arg Val Thr Ile Thr Cys Arg Ala Ser Gln
1               5                   10                  15

Ser Ile Gly Lys Tyr Leu Asn Trp Tyr Gln Gln Lys Pro Gly Leu Ala
            20                  25                  30

Pro Glu Val Leu Ile Ser Gly Ala Thr Thr Leu Gln Ser Gly Val Pro
        35                  40                  45

Ser Arg Phe Ser Gly Ser Gly Ser Glu Thr Asp Phe Thr Leu Thr Ile
    50                  55                  60

Asn Ser Leu Gln Pro Glu Asp Leu Ala Thr Tyr Val Cys Gln Gln Ser
65                  70                  75                  80

Ile Ser Ala Pro Tyr Thr Phe Gly Pro Gly Thr Lys Leu Glu Ile Lys
                85                  90                  95

<210> SEQ ID NO 246
<211> LENGTH: 96
<212> TYPE: PRT
<213> ORGANISM: Homo sapiens

<400> SEQUENCE: 246

Ser Ala Ser Val Gly Asp Arg Val Thr Ile Thr Cys Arg Ala Ser Gln
1               5                   10                  15

Asp Ile Gly Ser Tyr Leu Asn Trp Tyr Gln Gln Lys Pro Gly Lys Ala
            20                  25                  30

Pro Asn Val Leu Ile Ser Ala Ala Ser Thr Leu Gln Ser Gly Val Pro
        35                  40                  45

Ser Arg Ile Ser Gly Ile Gly Ser Gly Thr Asp Phe Thr Leu Thr Ile
    50                  55                  60

Ser Ser Leu Gln Pro Glu Asp Phe Ala Thr Tyr Tyr Cys Gln Gln Ser
65                  70                  75                  80

Leu Ser Ala Pro Tyr Thr Phe Gly Gln Gly Thr Lys Leu Glu Ile Lys
                85                  90                  95

<210> SEQ ID NO 247
<211> LENGTH: 98

<212> TYPE: PRT
<213> ORGANISM: Homo sapiens

<400> SEQUENCE: 247

```
Ser Val Ser Pro Gly Glu Arg Ala Thr Leu Ser Cys Arg Ala Ser His
1               5                   10                  15

Ser Val Thr Ser Asn Leu Ala Trp Tyr Gln Gln Lys Pro Gly Gln Ala
            20                  25                  30

Pro Arg Leu Leu Ile Tyr Gly Ala Ser Thr Arg Ala Thr Gly Ile Pro
        35                  40                  45

Ala Arg Phe Ser Gly Ser Gly Ser Gly Thr Glu Phe Thr Leu Thr Ile
    50                  55                  60

Ser Ser Leu Gln Ser Glu Asp Ser Ala Val Tyr Tyr Cys Gln Tyr Tyr
65                  70                  75                  80

Thr Asn Trp Pro Pro His Val Ala Phe Gly Gln Gly Thr Lys Leu Glu
                85                  90                  95

Ile Lys
```

<210> SEQ ID NO 248
<211> LENGTH: 97
<212> TYPE: PRT
<213> ORGANISM: Homo sapiens

<400> SEQUENCE: 248

```
Ser Val Ser Pro Gly Glu Arg Ala Thr Leu Ser Cys Arg Ala Ser Gln
1               5                   10                  15

Thr Val Asn Arg Asn Leu Ala Trp Tyr Gln Gln Lys Pro Gly Gln Ala
            20                  25                  30

Pro Arg Leu Leu Ile Tyr Ala Ala Ser Ala Arg Ala Thr Gly Val Pro
        35                  40                  45

Ala Arg Phe Ser Gly Ser Gly Ser Gly Thr Glu Phe Thr Leu Thr Ile
    50                  55                  60

Ser Ser Leu Gln Ser Glu Asp Phe Ala Val Tyr Tyr Cys Gln Gln Tyr
65                  70                  75                  80

Asn Asn Trp Pro Pro Leu Thr Phe Gly Gly Gly Thr Lys Val Glu Ile
                85                  90                  95

Lys
```

<210> SEQ ID NO 249
<211> LENGTH: 96
<212> TYPE: PRT
<213> ORGANISM: Homo sapiens

<400> SEQUENCE: 249

```
Ser Ala Ser Val Gly Asp Arg Val Thr Ile Thr Cys Arg Ala Ser Gln
1               5                   10                  15

Ser Ile Ser His Trp Leu Ala Trp Tyr Gln Gln Arg Pro Gly Glu Ala
            20                  25                  30

Pro Lys Leu Leu Ile Tyr Gln Ala Ser Thr Leu Glu Ser Gly Val Pro
        35                  40                  45

Ser Arg Phe Ser Gly Ser Gly Ser Gly Thr Glu Phe Thr Leu Ser Ile
    50                  55                  60

Ser Ser Leu Gln Pro Asp Asp Phe Ala Thr Tyr Tyr Cys Gln Gln Tyr
65                  70                  75                  80

Gln Ser Ser Pro Tyr Thr Phe Gly Gln Gly Thr Lys Leu Glu Ile Lys
                85                  90                  95
```

<210> SEQ ID NO 250
<211> LENGTH: 96
<212> TYPE: PRT
<213> ORGANISM: Homo sapiens

<400> SEQUENCE: 250

Ser Thr Phe Val Gly Asp Arg Val Thr Ile Thr Cys Arg Ala Ser Gln
1               5                   10                  15

Thr Ile Gly Asp Trp Leu Ala Trp Tyr Gln Gln Lys Pro Gly Lys Ala
            20                  25                  30

Pro Lys Leu Leu Ile Ser Lys Ala Thr Arg Leu Glu Ser Gly Val Pro
        35                  40                  45

Ser Arg Phe Ser Gly Ser Gly Ser Glu Thr Glu Phe Ser Leu Thr Ile
    50                  55                  60

Asn Ser Leu Gln Pro Asp Asp Val Ala Ala Tyr Tyr Cys Gln Gln Tyr
65                  70                  75                  80

Met Ser Tyr Pro Trp Thr Phe Gly Gln Gly Thr Lys Val Glu Ile Lys
                85                  90                  95

<210> SEQ ID NO 251
<211> LENGTH: 9
<212> TYPE: PRT
<213> ORGANISM: Homo sapiens

<400> SEQUENCE: 251

Gln Lys Phe Asn Ser Val Pro Trp Thr
1               5

<210> SEQ ID NO 252
<211> LENGTH: 9
<212> TYPE: PRT
<213> ORGANISM: Homo sapiens

<400> SEQUENCE: 252

Gln His Tyr His Ser Tyr Pro Trp Thr
1               5

<210> SEQ ID NO 253
<211> LENGTH: 9
<212> TYPE: PRT
<213> ORGANISM: Homo sapiens

<400> SEQUENCE: 253

Gln His Tyr His Ser Tyr Pro Trp Thr
1               5

<210> SEQ ID NO 254
<211> LENGTH: 9
<212> TYPE: PRT
<213> ORGANISM: Homo sapiens

<400> SEQUENCE: 254

Gln His Tyr His Ser Tyr Pro Trp Thr
1               5

<210> SEQ ID NO 255
<211> LENGTH: 9
<212> TYPE: PRT
<213> ORGANISM: Homo sapiens

<400> SEQUENCE: 255

Gln His Tyr His Ser Tyr Pro Trp Thr 1 5

<210> SEQ ID NO 256
<211> LENGTH: 9
<212> TYPE: PRT
<213> ORGANISM: Homo sapiens

<400> SEQUENCE: 256

Gln Arg Tyr Asp Ser Tyr Pro Phe Thr
1 5

<210> SEQ ID NO 257
<211> LENGTH: 9
<212> TYPE: PRT
<213> ORGANISM: Homo sapiens

<400> SEQUENCE: 257

Gln Gln Tyr Val Ser Ser Pro Leu Thr
1 5

<210> SEQ ID NO 258
<211> LENGTH: 9
<212> TYPE: PRT
<213> ORGANISM: Homo sapiens

<400> SEQUENCE: 258

Gln Gln Tyr Val Ser Ser Pro Leu Thr
1 5

<210> SEQ ID NO 259
<211> LENGTH: 9
<212> TYPE: PRT
<213> ORGANISM: Homo sapiens

<400> SEQUENCE: 259

Gln Gln Tyr Val Ser Ser Pro Leu Thr
1 5

<210> SEQ ID NO 260
<211> LENGTH: 9
<212> TYPE: PRT
<213> ORGANISM: Homo sapiens

<400> SEQUENCE: 260

Gln Gln Tyr Gly Ser Ser Pro Leu Thr
1 5

<210> SEQ ID NO 261
<211> LENGTH: 9
<212> TYPE: PRT
<213> ORGANISM: Homo sapiens

<400> SEQUENCE: 261

Gln Gln Tyr Val Ser Ser Pro Leu Arg
1 5

<210> SEQ ID NO 262
<211> LENGTH: 9
<212> TYPE: PRT
<213> ORGANISM: Homo sapiens

<400> SEQUENCE: 262

Gln Gln Tyr Gly Ser Ser Pro Leu Thr
1 5

<210> SEQ ID NO 263
<211> LENGTH: 9
<212> TYPE: PRT
<213> ORGANISM: Homo sapiens

<400> SEQUENCE: 263

Gln Gln Tyr Gly Ser Ser Arg Gly Thr
1               5

<210> SEQ ID NO 264
<211> LENGTH: 9
<212> TYPE: PRT
<213> ORGANISM: Homo sapiens

<400> SEQUENCE: 264

Gln Gln Tyr Gly Ser Ser Pro Leu Thr
1               5

<210> SEQ ID NO 265
<211> LENGTH: 9
<212> TYPE: PRT
<213> ORGANISM: Homo sapiens

<400> SEQUENCE: 265

Gln Gln Tyr Gly Ser Ser Pro Val Thr
1               5

<210> SEQ ID NO 266
<211> LENGTH: 9
<212> TYPE: PRT
<213> ORGANISM: Homo sapiens

<400> SEQUENCE: 266

Gln Gln Tyr Gly Ser Ser Pro Val Thr
1               5

<210> SEQ ID NO 267
<211> LENGTH: 9
<212> TYPE: PRT
<213> ORGANISM: Homo sapiens

<400> SEQUENCE: 267

Gln Gln Tyr Gly Ser Ser Pro Val Thr
1               5

<210> SEQ ID NO 268
<211> LENGTH: 9
<212> TYPE: PRT
<213> ORGANISM: Homo sapiens

<400> SEQUENCE: 268

Gln Gln Tyr Gly Ser Ser Pro Pro Thr
1               5

<210> SEQ ID NO 269
<211> LENGTH: 9
<212> TYPE: PRT
<213> ORGANISM: Homo sapiens

<400> SEQUENCE: 269

Gln Gln Tyr Gly Ser Ser Pro Val Thr
1               5

<210> SEQ ID NO 270

<211> LENGTH: 9
<212> TYPE: PRT
<213> ORGANISM: Homo sapiens

<400> SEQUENCE: 270

Gln Gln Ser Tyr Ile Thr Pro Leu Thr
1 5

<210> SEQ ID NO 271
<211> LENGTH: 9
<212> TYPE: PRT
<213> ORGANISM: Homo sapiens

<400> SEQUENCE: 271

Gln Gln Ser Phe Ser Thr Pro Leu Thr
1 5

<210> SEQ ID NO 272
<211> LENGTH: 9
<212> TYPE: PRT
<213> ORGANISM: Homo sapiens

<400> SEQUENCE: 272

Gln Gln Ser Tyr Ile Ser Pro Leu Thr
1 5

<210> SEQ ID NO 273
<211> LENGTH: 9
<212> TYPE: PRT
<213> ORGANISM: Homo sapiens

<400> SEQUENCE: 273

His Gln Ser Phe Ser Ala Pro Tyr Thr
1 5

<210> SEQ ID NO 274
<211> LENGTH: 9
<212> TYPE: PRT
<213> ORGANISM: Homo sapiens

<400> SEQUENCE: 274

Gln Gln Ser Tyr Ser Thr Pro Leu Ser
1 5

<210> SEQ ID NO 275
<211> LENGTH: 10
<212> TYPE: PRT
<213> ORGANISM: Homo sapiens

<400> SEQUENCE: 275

Cys Ser Tyr Ala Asn Ser Gly Thr Phe Val
1 5 10

<210> SEQ ID NO 276
<211> LENGTH: 10
<212> TYPE: PRT
<213> ORGANISM: Homo sapiens

<400> SEQUENCE: 276

Cys Ser Tyr Ala Asn Ser Gly Thr Phe Val
1 5 10

<210> SEQ ID NO 277
<211> LENGTH: 10
<212> TYPE: PRT

<213> ORGANISM: Homo sapiens

<400> SEQUENCE: 277

Cys Ser Tyr Ala Asn Ser Gly Thr Phe Val
1 5 10

<210> SEQ ID NO 278
<211> LENGTH: 9
<212> TYPE: PRT
<213> ORGANISM: Homo sapiens

<400> SEQUENCE: 278

Gln Ile Tyr Asp Ser Ser Val Arg Thr
1 5

<210> SEQ ID NO 279
<211> LENGTH: 9
<212> TYPE: PRT
<213> ORGANISM: Homo sapiens

<400> SEQUENCE: 279

Gln Ile Tyr Asp Ser Ser Val Arg Thr
1 5

<210> SEQ ID NO 280
<211> LENGTH: 9
<212> TYPE: PRT
<213> ORGANISM: Homo sapiens

<400> SEQUENCE: 280

Gln Ile Tyr Asp Ser Ser Leu Arg Thr
1 5

<210> SEQ ID NO 281
<211> LENGTH: 11
<212> TYPE: PRT
<213> ORGANISM: Homo sapiens

<400> SEQUENCE: 281

Gln Glu Arg Asn Asn Trp Pro Leu Thr Trp Thr
1 5 10

<210> SEQ ID NO 282
<211> LENGTH: 11
<212> TYPE: PRT
<213> ORGANISM: Homo sapiens

<400> SEQUENCE: 282

Gln Glu Arg Asn Asn Trp Pro Leu Thr Trp Thr
1 5 10

<210> SEQ ID NO 283
<211> LENGTH: 9
<212> TYPE: PRT
<213> ORGANISM: Homo sapiens

<400> SEQUENCE: 283

Gln Gln Thr Asp Arg Thr Pro Leu Thr
1 5

<210> SEQ ID NO 284
<211> LENGTH: 9
<212> TYPE: PRT
<213> ORGANISM: Homo sapiens

<400> SEQUENCE: 284

Gln Gln Thr Asp Arg Thr Pro Leu Thr
1 5

<210> SEQ ID NO 285
<211> LENGTH: 9
<212> TYPE: PRT
<213> ORGANISM: Homo sapiens

<400> SEQUENCE: 285

Gln Gln Ser Ile Ser Ala Pro Tyr Thr
1 5

<210> SEQ ID NO 286
<211> LENGTH: 9
<212> TYPE: PRT
<213> ORGANISM: Homo sapiens

<400> SEQUENCE: 286

Gln Gln Ser Leu Ser Ala Pro Tyr Thr
1 5

<210> SEQ ID NO 287
<211> LENGTH: 11
<212> TYPE: PRT
<213> ORGANISM: Homo sapiens

<400> SEQUENCE: 287

Gln Tyr Tyr Thr Asn Trp Pro Pro His Val Ala
1 5 10

<210> SEQ ID NO 288
<211> LENGTH: 10
<212> TYPE: PRT
<213> ORGANISM: Homo sapiens

<400> SEQUENCE: 288

Gln Gln Tyr Asn Asn Trp Pro Pro Leu Thr
1 5 10

<210> SEQ ID NO 289
<211> LENGTH: 9
<212> TYPE: PRT
<213> ORGANISM: Homo sapiens

<400> SEQUENCE: 289

Gln Gln Tyr Gln Ser Ser Pro Tyr Thr
1 5

<210> SEQ ID NO 290
<211> LENGTH: 9
<212> TYPE: PRT
<213> ORGANISM: Homo sapiens

<400> SEQUENCE: 290

Gln Gln Tyr Met Ser Tyr Pro Trp Thr
1 5

<210> SEQ ID NO 291
<211> LENGTH: 117
<212> TYPE: PRT
<213> ORGANISM: Homo sapiens

<400> SEQUENCE: 291

```
Gly Gly Gly Leu Val Gln Pro Gly Gly Ser Leu Arg Leu Ser Cys Ala
1               5                   10                  15

Ala Ser Gly Phe Thr Phe Ser Ser Tyr Ala Met Asn Trp Val Arg Gln
            20                  25                  30

Ala Pro Gly Lys Gly Leu Glu Trp Val Ser Gly Ile Gly Gly Arg Gly
        35                  40                  45

Ala Ile Ala Gly Asp Gly Ser Ile Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Gly Leu Arg Val Glu Asp Thr Ala Val Tyr Tyr Cys Ala Lys
                85                  90                  95

Asp Arg Val Ala Phe Asp Gly Phe His Val Trp Gly Gln Gly Thr Thr
            100                 105                 110

Val Thr Val Ser Ser
        115


<210> SEQ ID NO 292
<211> LENGTH: 115
<212> TYPE: PRT
<213> ORGANISM: Homo sapiens

<400> SEQUENCE: 292

Gly Gly Gly Leu Ile Gln Pro Gly Gly Ser Leu Arg Leu Ser Cys Ser
1               5                   10                  15

Ala Ser Gly Phe Thr Phe Ser Ser Tyr Ala Met Ser Trp Val Arg Gln
            20                  25                  30

Ala Pro Gly Lys Gly Leu Glu Trp Val Ser Gly Ile Ser Pro Leu Asp
        35                  40                  45

Gly Ser Thr Tyr Tyr Ala Ala Ser Val Lys Gly Arg Phe Thr Ile Ser
    50                  55                  60

Arg Asp Asn Ser Lys Asn Thr Leu Phe Leu Gln Met Asn Ser Leu Arg
65                  70                  75                  80

Val Glu Asp Thr Ala Ile Tyr Tyr Cys Ala Lys Asp Arg Leu Thr Met
                85                  90                  95

Gly Val Gly Glu Leu Phe Val Asp Trp Gly Pro Gly Thr Leu Val Ser
            100                 105                 110

Val Ser Ser
        115


<210> SEQ ID NO 293
<211> LENGTH: 115
<212> TYPE: PRT
<213> ORGANISM: Homo sapiens

<400> SEQUENCE: 293

Gly Gly Gly Leu Val Gln Pro Gly Gly Ser Arg Arg Leu Ser Cys Ala
1               5                   10                  15

Thr Ser Gly Phe Ser Phe Asp Thr Tyr Ala Met Ser Trp Leu Arg Gln
            20                  25                  30

Ala Pro Gly Lys Gly Leu Glu Trp Val Ser Ser Phe Ser Gly Leu Asp
        35                  40                  45

Asp Ser Thr Tyr Tyr Ala Asp Ser Val Lys Gly Arg Phe Thr Ile Ser
    50                  55                  60

Arg Asp Asn Ser Lys Asn Thr Leu Tyr Leu Gln Met Asn Ser Leu Arg
65                  70                  75                  80
```

Ala Glu Asp Thr Ala Ile Tyr Tyr Cys Ala Lys Asp Arg Gly Pro Arg
85 90 95

Gly Ile Gly Glu Leu Phe Asp Phe Trp Gly Gln Gly Thr Leu Val Ser
100 105 110

Val Ser Ser
115

<210> SEQ ID NO 294
<211> LENGTH: 115
<212> TYPE: PRT
<213> ORGANISM: Homo sapiens

<400> SEQUENCE: 294

Gly Gly Gly Leu Val Gln Pro Gly Gly Ser Leu Arg Leu Ser Cys Val
1 5 10 15

Thr Ser Gly Phe Ser Phe Asp Thr Tyr Ala Leu Ser Trp Val Arg Gln
20 25 30

Ala Pro Gly Lys Gly Leu Glu Trp Val Ser Ser Phe Ser Gly Ile Asp
35 40 45

Asp Ser Thr Tyr Tyr Thr Glu Ser Val Lys Gly Arg Phe Thr Met Ser
50 55 60

Arg Asp Asn Ser Lys Ser Thr Leu Phe Leu Gln Met Asn Gly Leu Arg
65 70 75 80

Ala Glu Asp Thr Ala Met Tyr Tyr Cys Ser Lys Asp Arg Gly Pro Arg
85 90 95

Gly Val Gly Glu Leu Phe Asp Ser Trp Gly Gln Gly Thr Leu Val Ile
100 105 110

Phe Ser Ser
115

<210> SEQ ID NO 295
<211> LENGTH: 115
<212> TYPE: PRT
<213> ORGANISM: Homo sapiens

<400> SEQUENCE: 295

Gly Gly Gly Leu Val Gln Pro Gly Gly Ser Leu Arg Leu Ser Cys Ala
1 5 10 15

Thr Ser Gly Phe Thr Phe Ser Thr Tyr Ala Met Ser Trp Val Arg Gln
20 25 30

Ala Pro Gly Lys Gly Leu Glu Trp Val Ser Ser Phe Ser Gly Val Asp
35 40 45

Asp Ser Thr Tyr Tyr Ala Glu Ser Val Lys Gly Arg Phe Thr Ile Ser
50 55 60

Arg Asp Asn Ser Lys Asn Thr Val Tyr Leu Gln Met Thr Arg Leu Arg
65 70 75 80

Ala Glu Asp Thr Ala Val Tyr Tyr Cys Ala Lys Asp Arg Gly Pro Arg
85 90 95

Gly Val Gly Glu Leu Phe Asp Ser Trp Gly Gln Gly Thr Leu Val Thr
100 105 110

Val Ser Ser
115

<210> SEQ ID NO 296
<211> LENGTH: 115
<212> TYPE: PRT
<213> ORGANISM: Homo sapiens

<400> SEQUENCE: 296

Gly Gly Gly Leu Val Arg Pro Gly Gly Ser Leu Thr Leu Thr Cys Ala
1 5 10 15

Thr Ser Gly Phe Thr Phe Ser Asp Tyr Ala Met Ser Trp Val Arg Gln
20 25 30

Ala Pro Gly Lys Gly Leu Glu Trp Val Ser Ser Tyr Ser Gly Ile Asp
35 40 45

Asp Ser Thr Tyr Tyr Ala Asp Ser Val Lys Gly Arg Phe Thr Ile Ser
50 55 60

Arg Asp Asn Ser Lys Arg Thr Leu Ser Leu His Met Asn Ser Leu Arg
65 70 75 80

Ala Gly Asp Ser Ala Leu Tyr Tyr Cys Ala Lys Asp Arg Gly Pro Arg
85 90 95

Gly Val Gly Glu Leu Phe Asp Ser Trp Gly Pro Gly Thr Leu Val Thr
100 105 110

Val Ser Ser
115

<210> SEQ ID NO 297
<211> LENGTH: 115
<212> TYPE: PRT
<213> ORGANISM: Homo sapiens

<400> SEQUENCE: 297

Gly Gly Gly Leu Val Gln Pro Gly Gly Ser Leu Arg Leu Ser Cys Ala
1 5 10 15

Ala Ser Gly Phe Thr Phe Ser Asp Tyr Ala Met Gly Trp Val Arg Gln
20 25 30

Ala Pro Gly Lys Gly Leu Glu Trp Leu Ser Ser Met Thr Arg Thr Gly
35 40 45

Asp Asn Leu Tyr Tyr Ala Asp Ser Val Lys Gly Arg Phe Thr Ile Ser
50 55 60

Arg Asp Asn Ser Lys Asn Thr Leu Tyr Leu Gln Met Ser Ser Leu Arg
65 70 75 80

Val Glu Asp Thr Ala Ile Tyr Phe Cys Ala Lys Asp Arg Leu Pro Glu
85 90 95

Gly Phe Gly Lys Leu Phe Asp Tyr Trp Gly Gln Gly Thr Leu Val Thr
100 105 110

Val Ser Thr
115

<210> SEQ ID NO 298
<211> LENGTH: 114
<212> TYPE: PRT
<213> ORGANISM: Homo sapiens

<400> SEQUENCE: 298

Gly Gly Gly Leu Val Gln Pro Gly Gly Ser Leu Arg Leu Ser Cys Ala
1 5 10 15

Ala Ser Gly Phe Ser Phe Ser Asp Phe Ala Met Ser Trp Val Arg Gln
20 25 30

Ala Pro Asn Gln Gly Leu Asp Trp Val Ser Cys Val Ser Gly Gly Gly
35 40 45

Asp Thr Thr Tyr Tyr Ala Asp Ser Val Lys Gly Arg Phe Thr Ile Ser
50 55 60

Arg Asp Asn Ser Lys Asn Thr Val Phe Leu Glu Met Asn Asn Leu Arg 65 70 75 80

Pro Glu Asp Thr Ala Val Tyr Tyr Cys Ala Arg Asp Gln Glu Val Ile
85 90 95

Gly His Tyr Pro Ser Asp His Trp Gly Gln Gly Thr Leu Val Ile Val
100 105 110

Ser Ser

<210> SEQ ID NO 299
<211> LENGTH: 112
<212> TYPE: PRT
<213> ORGANISM: Homo sapiens

<400> SEQUENCE: 299

Gly Gly Gly Leu Val Gln Pro Gly Gly Ser Leu Arg Leu Ser Cys Val
1 5 10 15

Ala Ser Gly Phe Thr Phe Ser Asn Tyr Gly Met Asn Trp Val Arg Gln
20 25 30

Ala Pro Gly Lys Gly Leu Glu Trp Val Ser Gly Ile Thr Gly Ser Gly
35 40 45

Asp Asp Thr Tyr Tyr Ala Asp Ser Val Lys Gly Arg Phe Thr Ile Ser
50 55 60

Arg Asp Asn Ser Arg Asn Thr Leu Tyr Val Gln Met Asn Asn Leu Arg
65 70 75 80

Ala Glu Asp Thr Ala Ile Tyr Tyr Cys Thr Lys Asp Arg Ile Leu Phe
85 90 95

Asp Ala Phe His Val Trp Gly Gln Gly Thr Met Val Thr Val Ser Ser
100 105 110

<210> SEQ ID NO 300
<211> LENGTH: 115
<212> TYPE: PRT
<213> ORGANISM: Homo sapiens

<400> SEQUENCE: 300

Gly Gly Asp Leu Val Gln Pro Gly Gly Ser Leu Arg Leu Ser Cys Val
1 5 10 15

Ala Ser Gly Phe Thr Phe Ser Ala Tyr Gly Met Ser Trp Val Arg Gln
20 25 30

Ala Pro Gly Lys Gly Leu Glu Trp Val Ser Ala Met Thr Gly Ser Gly
35 40 45

Asp Ser Thr Tyr Tyr Ala Asp Ser Val Lys Gly Arg Phe Thr Ile Ser
50 55 60

Arg Asp Asn Ser Lys Asn Thr Leu Tyr Leu Gln Met Asn Ser Leu Arg
65 70 75 80

Val Glu Asp Thr Ala Ile Tyr Tyr Cys Ala Lys Asp Arg Val Ser Gly
85 90 95

Gly Phe Gly Glu Leu Gln Asp Tyr Trp Gly Gln Gly Thr Leu Val Thr
100 105 110

Val Ser Ser
115

<210> SEQ ID NO 301
<211> LENGTH: 115
<212> TYPE: PRT
<213> ORGANISM: Homo sapiens

<400> SEQUENCE: 301

```
Gly Gly Gly Leu Val Gln Pro Gly Gly Ser Leu Arg Leu Ser Cys Ala
1               5                   10                  15

Thr Ser Gly Phe Thr Phe Thr Thr Phe Ala Met Ser Trp Val Arg Gln
            20                  25                  30

Ala Pro Gly Lys Gly Leu Glu Trp Val Ser Ser Ile Ser Gly Ala Asp
        35                  40                  45

Asp Ser Thr Tyr Tyr Ala Ala Ser Val Lys Gly Arg Phe Thr Ile Ser
    50                  55                  60

Arg Asp Asn Ser Arg Ser Thr Leu Phe Leu Gln Met Asn Ser Leu Arg
65                  70                  75                  80

Ala Glu Asp Thr Ala Val Tyr Tyr Cys Ala Lys Asp Arg Gly Pro Arg
                85                  90                  95

Gly Val Gly Glu Leu Phe Asp Ser Trp Gly Gln Gly Thr Val Val Ser
            100                 105                 110

Val Ser Ser
        115


<210> SEQ ID NO 302
<211> LENGTH: 115
<212> TYPE: PRT
<213> ORGANISM: Homo sapiens

<400> SEQUENCE: 302

Gly Gly Gly Leu Val Gln Pro Gly Gly Ser Leu Thr Leu Ser Cys Ala
1               5                   10                  15

Gly Ser Gly Phe Pro Phe Asn Thr Tyr Ala Leu Ile Trp Val Arg Gln
            20                  25                  30

Ala Pro Gly Lys Gly Leu Glu Trp Val Ser Ser Ile Ser Tyr Asp Ser
        35                  40                  45

Ala Ser Thr Tyr Tyr Ala Glu Ser Val Lys Gly Arg Phe Thr Ile Ser
    50                  55                  60

Arg Asp Asn Ser Gln Asn Thr Leu Tyr Leu Glu Met Asn Phe Leu Arg
65                  70                  75                  80

Ala Asp Asp Thr Ala Val Tyr Phe Cys Ala Lys Asp Arg Val Thr Met
                85                  90                  95

Gly Phe Gly Glu Leu Phe Ala His Trp Gly Gln Gly Thr Leu Val Ala
            100                 105                 110

Val Ser Ser
        115


<210> SEQ ID NO 303
<211> LENGTH: 115
<212> TYPE: PRT
<213> ORGANISM: Homo sapiens

<400> SEQUENCE: 303

Gly Gly Gly Leu Lys Gln Pro Gly Gly Ser Leu Arg Leu Ser Cys Ala
1               5                   10                  15

Ala Ser Gly Phe Thr Phe Arg Asn Tyr Gly Met Ser Trp Val Arg Gln
            20                  25                  30

Ala Pro Gly Lys Gly Leu Glu Trp Val Ser Ser Ile Ser Ser Leu Asp
        35                  40                  45

Asp Ser Thr Tyr Tyr Ala Asp Ser Val Lys Gly Arg Ser Ala Ile Ser
    50                  55                  60

Arg Asp Asp Ser Lys Asn Thr Leu Tyr Leu Gln Ile His Ser Leu Arg
65                  70                  75                  80
```

```
Ala Glu Asp Thr Ala Leu Tyr Phe Cys Ala Lys Asp Arg Val Glu Lys
                85                  90                  95

Gly Phe Gly Glu Leu Trp Ala Ser Trp Gly Gln Gly Thr Leu Val Thr
            100                 105                 110

Val Ser Ser
        115


<210> SEQ ID NO 304
<211> LENGTH: 115
<212> TYPE: PRT
<213> ORGANISM: Homo sapiens

<400> SEQUENCE: 304

Gly Gly Gly Leu Val Gln Pro Gly Gly Ser Leu Arg Leu Thr Cys Ala
1               5                   10                  15

Thr Ser Gly Phe Thr Phe Ser Asp Tyr Ala Met Ser Trp Val Arg Gln
            20                  25                  30

Ala Pro Gly Lys Gly Leu Glu Trp Val Ser Ser Tyr Ser Gly Ile Asp
        35                  40                  45

Asp Ser Thr Tyr Tyr Ala Asp Ser Val Lys Gly Arg Phe Ile Ile Ser
    50                  55                  60

Arg Asp Asn Ser Lys Asn Thr Leu Ser Leu His Met Asn Ser Leu Arg
65                  70                  75                  80

Ala Glu Asp Ser Ala Leu Tyr Phe Cys Ala Lys Asp Arg Gly Pro Arg
                85                  90                  95

Gly Val Gly Glu Leu Phe Asp Ser Trp Gly Gln Gly Thr Leu Val Thr
            100                 105                 110

Val Ser Ser
        115


<210> SEQ ID NO 305
<211> LENGTH: 115
<212> TYPE: PRT
<213> ORGANISM: Homo sapiens

<400> SEQUENCE: 305

Gly Gly Gly Leu Val Gln Pro Gly Gly Ser Leu Arg Leu Thr Cys Ala
1               5                   10                  15

Thr Ser Gly Phe Thr Phe Ser Asp Tyr Ala Met Ser Trp Val Arg Gln
            20                  25                  30

Ala Pro Gly Lys Gly Leu Glu Trp Val Ser Ser Tyr Ser Gly Ile Asp
        35                  40                  45

Asp Ser Thr Tyr Tyr Ala Asp Ser Val Lys Gly Arg Phe Thr Ile Ser
    50                  55                  60

Arg Asp Asn Ser Arg Ser Thr Leu Ser Leu His Met Asn Ser Leu Arg
65                  70                  75                  80

Ala Glu Asp Ser Ala Leu Tyr Phe Cys Ala Lys Asp Arg Gly Pro Arg
                85                  90                  95

Gly Val Gly Glu Leu Phe Asp Ser Trp Gly Gln Gly Thr Leu Val Thr
            100                 105                 110

Val Ser Ser
        115


<210> SEQ ID NO 306
<211> LENGTH: 117
<212> TYPE: PRT
<213> ORGANISM: Homo sapiens
```

<400> SEQUENCE: 306

Gly Gly Gly Leu Val Gln Pro Gly Gly Ser Leu Arg Leu Ser Cys Ala
1               5                   10                  15

Ala Ser Gly Phe Thr Phe Thr Ser Tyr Ala Met Asn Trp Val Arg Gln
            20                  25                  30

Ala Pro Gly Lys Gly Leu Glu Trp Val Ser Gly Ile Gly Gly Arg Gly
        35                  40                  45

Ala Ile Ala Gly Asp Gly Ser Ile Tyr Tyr Ala Asp Ser Val Lys Gly
    50                  55                  60

Arg Phe Thr Ile Ser Arg Asp Asn Ser Lys Asn Ile Val Tyr Leu Gln
65                  70                  75                  80

Met Asn Gly Leu Arg Val Glu Asp Thr Ala Val Tyr Tyr Cys Ala Lys
                85                  90                  95

Asp Arg Val Ala Phe Asp Gly Phe His Val Trp Gly Gln Gly Thr Thr
            100                 105                 110

Val Thr Val Ser Ser
        115

<210> SEQ ID NO 307
<211> LENGTH: 115
<212> TYPE: PRT
<213> ORGANISM: Homo sapiens

<400> SEQUENCE: 307

Gly Gly Gly Leu Val Gln Pro Gly Gly Ser Leu Arg Leu Thr Cys Ala
1               5                   10                  15

Thr Ser Gly Phe Thr Phe Ser Asp Tyr Ala Met Ser Trp Val Arg Gln
            20                  25                  30

Ala Pro Gly Lys Gly Leu Glu Trp Val Ser Ser Tyr Ser Gly Ile Asp
        35                  40                  45

Asp Ser Thr Tyr Tyr Ala Asp Ser Val Lys Gly Arg Phe Ile Ile Ser
    50                  55                  60

Arg Asp Asn Ser Lys Ser Thr Leu Ser Leu His Met Asn Ser Leu Arg
65                  70                  75                  80

Ala Glu Asp Ser Ala Leu Tyr Phe Cys Ala Lys Asp Arg Gly Pro Arg
                85                  90                  95

Gly Val Gly Glu Leu Phe Asp Ser Trp Gly Gln Gly Thr Leu Val Thr
            100                 105                 110

Val Ser Ser
        115

<210> SEQ ID NO 308
<211> LENGTH: 115
<212> TYPE: PRT
<213> ORGANISM: Homo sapiens

<400> SEQUENCE: 308

Gly Gly Gly Leu Val Gln Pro Gly Gly Ser Leu Arg Leu Thr Cys Ala
1               5                   10                  15

Thr Ser Gly Phe Thr Phe Arg Asp Tyr Ala Met Ser Trp Val Arg Gln
            20                  25                  30

Ala Pro Gly Lys Gly Leu Glu Trp Val Ser Ser Tyr Ser Gly Ile Asp
        35                  40                  45

Asp Ser Thr Tyr Tyr Ala Asp Ser Val Lys Gly Arg Phe Thr Ile Ser
    50                  55                  60

Arg Asp Asn Ser Lys Ser Thr Leu Ser Leu His Met Asn Ser Leu Arg

```
65                  70                  75                  80

Ala Glu Asp Ser Ala Leu Tyr Phe Cys Ala Lys Asp Arg Gly Pro Arg
                85                  90                  95

Gly Val Gly Glu Leu Phe Asp Ser Trp Gly Gln Gly Thr Leu Val Thr
            100                 105                 110

Val Ser Ser
        115


<210> SEQ ID NO 309
<211> LENGTH: 115
<212> TYPE: PRT
<213> ORGANISM: Homo sapiens

<400> SEQUENCE: 309

Gly Gly Gly Leu Val Gln Pro Gly Gly Ser Leu Arg Leu Thr Cys Ala
1               5                   10                  15

Thr Ser Gly Phe Thr Phe Ser Asp Tyr Ala Met Ser Trp Val Arg Gln
            20                  25                  30

Ala Pro Gly Lys Gly Leu Glu Trp Val Ser Ser Tyr Ser Gly Ile Asp
        35                  40                  45

Asp Ser Thr Tyr Tyr Ala Asp Ser Val Lys Gly Arg Phe Thr Ile Ser
    50                  55                  60

Arg Asp Asn Ser Lys Ser Thr Leu Ser Leu Tyr Met Lys Ser Leu Arg
65                  70                  75                  80

Ala Glu Asp Ser Ala Leu Tyr Tyr Cys Ala Lys Asp Arg Gly Pro Arg
                85                  90                  95

Gly Val Gly Glu Leu Phe Asp Ser Trp Gly Gln Gly Thr Leu Val Thr
            100                 105                 110

Val Ser Ser
        115


<210> SEQ ID NO 310
<211> LENGTH: 115
<212> TYPE: PRT
<213> ORGANISM: Homo sapiens

<400> SEQUENCE: 310

Gly Gly Gly Leu Val Gln Pro Gly Gly Ser Leu Arg Leu Thr Cys Ala
1               5                   10                  15

Thr Ser Gly Phe Thr Phe Ser Asp Tyr Ala Met Ser Trp Val Arg Gln
            20                  25                  30

Ala Pro Gly Lys Gly Leu Glu Trp Val Ser Ser Tyr Ser Gly Ile Asp
        35                  40                  45

Asp Ser Thr Tyr Tyr Ala Asp Ser Val Lys Gly Arg Phe Thr Ile Ser
    50                  55                  60

Arg Asp Asn Ser Lys Ser Thr Leu Ser Leu His Met Asn Ser Leu Arg
65                  70                  75                  80

Ala Glu Asp Ser Ala Leu Tyr Phe Cys Ala Lys Asp Arg Gly Pro Arg
                85                  90                  95

Gly Val Gly Glu Leu Phe Asp Ser Trp Gly Gln Gly Thr Leu Val Thr
            100                 105                 110

Val Ser Ser
        115


<210> SEQ ID NO 311
<211> LENGTH: 115
<212> TYPE: PRT
```

<213> ORGANISM: Homo sapiens

<400> SEQUENCE: 311

Gly Gly Asp Leu Val Gln Pro Gly Gly Ser Leu Arg Leu Ser Cys Ala
1 5 10 15

Ala Ser Gly Phe Thr Phe Ser Ser Tyr Gly Met Ser Trp Val Arg Gln
20 25 30

Ala Pro Gly Lys Gly Leu Glu Trp Val Ser Ser Ile Ser Gly Phe Asp
35 40 45

Pro Ser Thr Tyr Tyr Ala Asp Ser Val Arg Gly Arg Phe Thr Ile Ala
50 55 60

Arg Asp Asn Ser Lys Asn Thr Leu Tyr Leu Gln Met Lys Ser Leu Arg
65 70 75 80

Val Glu Asp Thr Ala Ile Tyr Tyr Cys Ala Lys Asp Arg Leu Val Arg
85 90 95

Gly Phe Gly Glu Val Leu Ala Ser Trp Gly Gln Gly Thr Leu Val Thr
100 105 110

Val Ser Ser
115

<210> SEQ ID NO 312
<211> LENGTH: 115
<212> TYPE: PRT
<213> ORGANISM: Homo sapiens

<400> SEQUENCE: 312

Gly Gly Gly Leu Val Gln Pro Gly Gly Ser Leu Arg Leu Ser Cys Ala
1 5 10 15

Ala Ser Gly Phe Thr Phe Ser Ser Tyr Ala Met Ser Trp Val Arg Gln
20 25 30

Ala Pro Gly Lys Gly Leu Glu Trp Val Ser Ser Phe Ser Gly Ile Asp
35 40 45

Asp Ser Thr Trp Tyr Ala Asp Ser Val Lys Gly Arg Phe Thr Ile Ser
50 55 60

Arg Asp Asn Ser Lys Ser Thr Leu Tyr Leu Gln Met Asn Ser Leu Arg
65 70 75 80

Ala Glu Asp Thr Ala Val Tyr Tyr Cys Ala Lys Asp Arg Leu Val Arg
85 90 95

Gly Phe Ala Glu Val Leu Asp Tyr Trp Gly Arg Gly Thr Leu Val Thr
100 105 110

Val Ser Ser
115

<210> SEQ ID NO 313
<211> LENGTH: 115
<212> TYPE: PRT
<213> ORGANISM: Homo sapiens

<400> SEQUENCE: 313

Gly Gly Gly Leu Val Gln Pro Gly Gly Ser Leu Arg Leu Ser Cys Ala
1 5 10 15

Ala Ser Gly Phe Thr Phe Ser Ser Tyr Ala Met Ser Trp Val Arg Gln
20 25 30

Ala Pro Gly Lys Gly Leu Glu Trp Val Ser Ser Phe Ser Gly Ile Asp
35 40 45

Asp Ser Thr Trp Tyr Ala Asp Ser Val Lys Gly Arg Phe Thr Ile Ser
50 55 60

Arg Asp Asn Ser Lys Ser Thr Leu Phe Leu Gln Met Asn Ser Leu Arg
65 70 75 80

Ala Glu Asp Thr Ala Val Tyr Tyr Cys Ala Lys Asp Arg Leu Val Arg
85 90 95

Gly Phe Ala Glu Val Leu Glu His Trp Gly Arg Gly Thr Leu Val Thr
100 105 110

Val Ser Ser
115

<210> SEQ ID NO 314
<211> LENGTH: 115
<212> TYPE: PRT
<213> ORGANISM: Homo sapiens

<400> SEQUENCE: 314

Gly Gly Asp Leu Val Gln Pro Gly Gly Ser Leu Arg Leu Ser Cys Ala
1 5 10 15

Ala Ser Gly Phe Thr Phe Ser Ser Tyr Gly Met Ser Trp Val Arg Gln
20 25 30

Ala Pro Gly Lys Gly Leu Glu Trp Val Ser Ser Ile Ser Gly Phe Asp
35 40 45

Pro Ser Thr Tyr Tyr Ala Asp Ser Val Arg Gly Arg Phe Thr Ile Ala
50 55 60

Arg Asp Asn Ser Lys Asn Thr Leu Tyr Leu Gln Met Lys Ser Leu Arg
65 70 75 80

Val Glu Asp Thr Ala Ile Tyr Tyr Cys Ala Lys Asp Arg Leu Val Arg
85 90 95

Gly Phe Gly Glu Val Leu Asp Ser Trp Gly Gln Gly Thr Leu Val Thr
100 105 110

Val Ser Ser
115

<210> SEQ ID NO 315
<211> LENGTH: 12
<212> TYPE: PRT
<213> ORGANISM: Homo sapiens

<400> SEQUENCE: 315

Ala Lys Asp Arg Val Ala Phe Asp Gly Phe His Val
1 5 10

<210> SEQ ID NO 316
<211> LENGTH: 15
<212> TYPE: PRT
<213> ORGANISM: Homo sapiens

<400> SEQUENCE: 316

Ala Lys Asp Arg Leu Thr Met Gly Val Gly Glu Leu Phe Val Asp
1 5 10 15

<210> SEQ ID NO 317
<211> LENGTH: 15
<212> TYPE: PRT
<213> ORGANISM: Homo sapiens

<400> SEQUENCE: 317

Ala Lys Asp Arg Gly Pro Arg Gly Ile Gly Glu Leu Phe Asp Phe
1 5 10 15

<210> SEQ ID NO 318
<211> LENGTH: 15
<212> TYPE: PRT
<213> ORGANISM: Homo sapiens

<400> SEQUENCE: 318

Ser Lys Asp Arg Gly Pro Arg Gly Val Gly Glu Leu Phe Asp Ser
1 5 10 15

<210> SEQ ID NO 319
<211> LENGTH: 15
<212> TYPE: PRT
<213> ORGANISM: Homo sapiens

<400> SEQUENCE: 319

Ala Lys Asp Arg Gly Pro Arg Gly Val Gly Glu Leu Phe Asp Ser
1 5 10 15

<210> SEQ ID NO 320
<211> LENGTH: 15
<212> TYPE: PRT
<213> ORGANISM: Homo sapiens

<400> SEQUENCE: 320

Ala Lys Asp Arg Gly Pro Arg Gly Val Gly Glu Leu Phe Asp Ser
1 5 10 15

<210> SEQ ID NO 321
<211> LENGTH: 15
<212> TYPE: PRT
<213> ORGANISM: Homo sapiens

<400> SEQUENCE: 321

Ala Lys Asp Arg Leu Pro Glu Gly Phe Gly Lys Leu Phe Asp Tyr
1 5 10 15

<210> SEQ ID NO 322
<211> LENGTH: 14
<212> TYPE: PRT
<213> ORGANISM: Homo sapiens

<400> SEQUENCE: 322

Ala Arg Asp Gln Glu Val Ile Gly His Tyr Pro Ser Asp His
1 5 10

<210> SEQ ID NO 323
<211> LENGTH: 12
<212> TYPE: PRT
<213> ORGANISM: Homo sapiens

<400> SEQUENCE: 323

Thr Lys Asp Arg Ile Leu Phe Asp Ala Phe His Val
1 5 10

<210> SEQ ID NO 324
<211> LENGTH: 15
<212> TYPE: PRT
<213> ORGANISM: Homo sapiens

<400> SEQUENCE: 324

Ala Lys Asp Arg Val Ser Gly Gly Phe Gly Glu Leu Gln Asp Tyr
1 5 10 15

<210> SEQ ID NO 325
<211> LENGTH: 15

<212> TYPE: PRT
<213> ORGANISM: Homo sapiens

<400> SEQUENCE: 325

Ala Lys Asp Arg Gly Pro Arg Gly Val Gly Glu Leu Phe Asp Ser
1 5 10 15

<210> SEQ ID NO 326
<211> LENGTH: 15
<212> TYPE: PRT
<213> ORGANISM: Homo sapiens

<400> SEQUENCE: 326

Ala Lys Asp Arg Val Thr Met Gly Phe Gly Glu Leu Phe Ala His
1 5 10 15

<210> SEQ ID NO 327
<211> LENGTH: 15
<212> TYPE: PRT
<213> ORGANISM: Homo sapiens

<400> SEQUENCE: 327

Ala Lys Asp Arg Val Glu Lys Gly Phe Gly Glu Leu Trp Ala Ser
1 5 10 15

<210> SEQ ID NO 328
<211> LENGTH: 15
<212> TYPE: PRT
<213> ORGANISM: Homo sapiens

<400> SEQUENCE: 328

Ala Lys Asp Arg Gly Pro Arg Gly Val Gly Glu Leu Phe Asp Ser
1 5 10 15

<210> SEQ ID NO 329
<211> LENGTH: 15
<212> TYPE: PRT
<213> ORGANISM: Homo sapiens

<400> SEQUENCE: 329

Ala Lys Asp Arg Gly Pro Arg Gly Val Gly Glu Leu Phe Asp Ser
1 5 10 15

<210> SEQ ID NO 330
<211> LENGTH: 12
<212> TYPE: PRT
<213> ORGANISM: Homo sapiens

<400> SEQUENCE: 330

Ala Lys Asp Arg Val Ala Phe Asp Gly Phe His Val
1 5 10

<210> SEQ ID NO 331
<211> LENGTH: 15
<212> TYPE: PRT
<213> ORGANISM: Homo sapiens

<400> SEQUENCE: 331

Ala Lys Asp Arg Gly Pro Arg Gly Val Gly Glu Leu Phe Asp Ser
1 5 10 15

<210> SEQ ID NO 332
<211> LENGTH: 15
<212> TYPE: PRT
<213> ORGANISM: Homo sapiens

<400> SEQUENCE: 332

Ala Lys Asp Arg Gly Pro Arg Gly Val Gly Glu Leu Phe Asp Ser
1 5 10 15

<210> SEQ ID NO 333
<211> LENGTH: 15
<212> TYPE: PRT
<213> ORGANISM: Homo sapiens

<400> SEQUENCE: 333

Ala Lys Asp Arg Gly Pro Arg Gly Val Gly Glu Leu Phe Asp Ser
1 5 10 15

<210> SEQ ID NO 334
<211> LENGTH: 15
<212> TYPE: PRT
<213> ORGANISM: Homo sapiens

<400> SEQUENCE: 334

Ala Lys Asp Arg Gly Pro Arg Gly Val Gly Glu Leu Phe Asp Ser
1 5 10 15

<210> SEQ ID NO 335
<211> LENGTH: 15
<212> TYPE: PRT
<213> ORGANISM: Homo sapiens

<400> SEQUENCE: 335

Ala Lys Asp Arg Leu Val Arg Gly Phe Gly Glu Val Leu Ala Ser
1 5 10 15

<210> SEQ ID NO 336
<211> LENGTH: 15
<212> TYPE: PRT
<213> ORGANISM: Homo sapiens

<400> SEQUENCE: 336

Ala Lys Asp Arg Leu Val Arg Gly Phe Ala Glu Val Leu Asp Tyr
1 5 10 15

<210> SEQ ID NO 337
<211> LENGTH: 15
<212> TYPE: PRT
<213> ORGANISM: Homo sapiens

<400> SEQUENCE: 337

Ala Lys Asp Arg Leu Val Arg Gly Phe Ala Glu Val Leu Glu His
1 5 10 15

<210> SEQ ID NO 338
<211> LENGTH: 15
<212> TYPE: PRT
<213> ORGANISM: Homo sapiens

<400> SEQUENCE: 338

Ala Lys Asp Arg Leu Val Arg Gly Phe Gly Glu Val Leu Asp Ser
1 5 10 15

<210> SEQ ID NO 339
<211> LENGTH: 96
<212> TYPE: PRT
<213> ORGANISM: Homo sapiens

<400> SEQUENCE: 339

-continued

```
Ser Ala Ser Val Gly Asp Arg Val Thr Ile Thr Cys Arg Ala Ser Gln
1               5                   10                  15

Ser Ile Ser Ser Trp Leu Ala Trp Tyr Gln Gln Lys Pro Gly Lys Ala
            20                  25                  30

Pro Lys Leu Leu Ile Tyr Lys Ala Ser Ser Leu Glu Ser Gly Val Pro
        35                  40                  45

Ser Arg Phe Ser Gly Ser Gly Ser Gly Thr Glu Phe Ser Leu Thr Ile
    50                  55                  60

Ser Ser Leu Gln Pro Asp Asp Phe Ala Thr Tyr Tyr Cys Gln Gln Tyr
65                  70                  75                  80

Asn Ser Tyr Pro Trp Thr Phe Gly Gln Gly Thr Lys Val Glu Ile Lys
                85                  90                  95
```

<210> SEQ ID NO 340
<211> LENGTH: 96
<212> TYPE: PRT
<213> ORGANISM: Homo sapiens

<400> SEQUENCE: 340

```
Ser Ala Ser Val Gly Asp Arg Val Thr Ile Thr Cys Arg Ala Ser Gln
1               5                   10                  15

Asn Ile Asn Ser Trp Leu Ala Trp Tyr Gln Gln Lys Pro Gly Lys Ala
            20                  25                  30

Pro Lys Phe Leu Ile Tyr Gln Ala Ser Thr Leu Gln Asn Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

Tyr Ser Tyr Pro Trp Thr Phe Gly Gln Gly Thr Lys Val Glu Ile Lys
                85                  90                  95
```

<210> SEQ ID NO 341
<211> LENGTH: 96
<212> TYPE: PRT
<213> ORGANISM: Homo sapiens

<400> SEQUENCE: 341

```
Ser Ala Ser Val Gly Asp Arg Val Thr Ile Thr Cys Arg Ala Ser Gln
1               5                   10                  15

Ser Ile Ser Arg Trp Leu Ala Trp Tyr Gln Gln Lys Pro Gly Lys Ala
            20                  25                  30

Pro Lys Leu Leu Ile Tyr Lys Thr Ser Thr Leu Lys Ser Glu Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

His Ser Val Pro Trp Thr Phe Gly Gln Gly Thr Lys Val Glu Ile Lys
                85                  90                  95
```

<210> SEQ ID NO 342
<211> LENGTH: 96
<212> TYPE: PRT
<213> ORGANISM: Homo sapiens

<400> SEQUENCE: 342

```
Ser Ala Ser Val Gly Asp Arg Val Thr Ile Thr Cys Arg Ala Ser Gln
1               5                   10                  15

Ser Ile Ser Lys Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

Tyr Ser Val Pro Trp Thr Phe Gly Gln Gly Thr Lys Val Glu Ile Lys
                85                  90                  95


<210> SEQ ID NO 343
<211> LENGTH: 96
<212> TYPE: PRT
<213> ORGANISM: Homo sapiens

<400> SEQUENCE: 343

Ser Ala Ser Val Gly Asp Arg Val Thr Met Thr Cys Arg Ala Ser Gln
1               5                   10                  15

Ser Ile Asn Arg Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

His Ser Val Pro Trp Thr Phe Gly Gln Gly Thr Lys Val Glu Ile Lys
                85                  90                  95


<210> SEQ ID NO 344
<211> LENGTH: 96
<212> TYPE: PRT
<213> ORGANISM: Homo sapiens

<400> SEQUENCE: 344

Ser Ala Ser Val Gly Asp Arg Val Thr Ile Thr Cys Arg Ala Ser Gln
1               5                   10                  15

Ser Ile Ser Lys Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

Tyr Ser Val Pro Trp Thr Phe Gly Gln Gly Thr Lys Val Glu Ile Lys
                85                  90                  95


<210> SEQ ID NO 345
<211> LENGTH: 96
<212> TYPE: PRT
<213> ORGANISM: Homo sapiens

<400> SEQUENCE: 345

Ser Ala Ala Ile Gly Asp Arg Val Thr Phe Thr Cys Arg Ala Ser Gln
```

```
1               5                   10                  15

Ser Ile Asn Thr Trp Leu Ala Trp Tyr Gln Gln Lys Pro Gly Lys Ala
            20                  25                  30

Pro Lys Leu Leu Met His Lys Ala Ser Thr Leu His Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

Tyr Ser Tyr Pro Trp Thr Phe Gly Gln Gly Thr Lys Val Glu Ile Lys
                85                  90                  95


<210> SEQ ID NO 346
<211> LENGTH: 95
<212> TYPE: PRT
<213> ORGANISM: Homo sapiens

<400> SEQUENCE: 346

Ser Val Ser Val Gly Asp Arg Val Thr Ile Thr Cys Arg Ala Ser Gln
1               5                   10                  15

Asn Ile Asn Ser Trp Leu Ala Trp Tyr Gln Gln Lys Pro Gly Lys Ala
            20                  25                  30

Pro Lys Leu Leu Ile Tyr Lys Ala Ser Arg Leu Glu Arg Gly Val Pro
        35                  40                  45

Ser Arg Phe Ser Gly Arg Gly Ser Gly Thr Glu Phe Ala Leu Thr Ile
    50                  55                  60

Ser Gly Leu Gln Pro Asp Asp Phe Ala Thr Tyr Tyr Cys Gln Gln Tyr
65                  70                  75                  80

Ser Ser Phe Phe Thr Phe Gly Gly Gly Thr Lys Val Glu Ile Lys
                85                  90                  95


<210> SEQ ID NO 347
<211> LENGTH: 96
<212> TYPE: PRT
<213> ORGANISM: Homo sapiens

<400> SEQUENCE: 347

Ser Ala Ser Val Gly Asp Arg Val Thr Ile Thr Cys Arg Ala Ser Gln
1               5                   10                  15

Ser Ile Ser Ser Trp Leu Ala Trp Tyr Gln Gln Lys Pro Gly Lys Ala
            20                  25                  30

Pro Asn Leu Leu Ile Tyr Lys Ala Ser Thr Leu Glu Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln Gln Tyr
65                  70                  75                  80

Asn Asn Tyr Pro Trp Thr Phe Gly Gln Gly Thr Lys Val Glu Ile Lys
                85                  90                  95


<210> SEQ ID NO 348
<211> LENGTH: 96
<212> TYPE: PRT
<213> ORGANISM: Homo sapiens

<400> SEQUENCE: 348

Ser Ala Ser Val Gly Asp Arg Val Thr Ile Thr Cys Arg Ala Ser Gln
1               5                   10                  15
```

Asn Ile Asn Ser Trp Leu Ala Trp Phe Gln Gln Lys Pro Gly Lys Ala
20 25 30

Pro Glu Leu Leu Ile Tyr Lys Thr Ser Thr Leu His Thr Gly Val Pro
35 40 45

Ser Arg Phe Arg Gly Arg Gly Ser Gly Thr Glu Phe Thr Leu Thr Ile
50 55 60

Ser Ser Leu Gln Pro Asp Asp Phe Ala Thr Tyr Tyr Cys Gln His Tyr
65 70 75 80

Tyr Ser Tyr Pro Trp Thr Phe Gly Gln Gly Thr Lys Val Glu Ile Lys
85 90 95

<210> SEQ ID NO 349
<211> LENGTH: 96
<212> TYPE: PRT
<213> ORGANISM: Homo sapiens

<400> SEQUENCE: 349

Ser Ala Ser Val Gly Asp Arg Val Thr Ile Thr Cys Arg Ala Ser Gln
1 5 10 15

Ser Ile Ser Lys Trp Leu Ala Trp Tyr Gln Gln Lys Pro Gly Lys Ala
20 25 30

Pro Arg Leu Leu Ile Tyr Thr Thr Ser Thr Leu Lys Ser Gly Val Pro
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Tyr Cys Gln His Phe
65 70 75 80

Phe Ser Val Pro Trp Thr Phe Gly Gln Gly Thr Lys Val Glu Ile Lys
85 90 95

<210> SEQ ID NO 350
<211> LENGTH: 96
<212> TYPE: PRT
<213> ORGANISM: Homo sapiens

<400> SEQUENCE: 350

Ser Ala Ser Ile Gly Asp Arg Val Thr Ile Thr Cys Arg Ala Ser Gln
1 5 10 15

Ser Val Ser Gly Trp Leu Ala Trp Tyr Gln Gln Lys Pro Gly Lys Ala
20 25 30

Pro Lys Leu Leu Ile His Lys Ala Ser Thr Leu Gln Ser Gly Val Pro
35 40 45

Ser Arg Phe Ser Gly Ser Gly Ser Gly Thr Glu Phe Thr Leu Thr Ile
50 55 60

Thr Ser Leu Gln Pro Asp Asp Phe Ala Thr Tyr Tyr Cys Gln His Tyr
65 70 75 80

Tyr Ser Tyr Pro Trp Thr Phe Gly Gln Gly Thr Lys Val Glu Val Lys
85 90 95

<210> SEQ ID NO 351
<211> LENGTH: 96
<212> TYPE: PRT
<213> ORGANISM: Homo sapiens

<400> SEQUENCE: 351

Pro Ala Ser Val Gly Asp Arg Val Thr Ile Thr Cys Arg Ala Ser Gln
1 5 10 15

```
Asn Ile Asn Ser Trp Leu Ala Trp Tyr Gln Gln Thr Pro Gly Arg Pro
            20                  25                  30

Pro Lys Leu Leu Ile Tyr Lys Ala Ser Ala Ser Leu Asp Gly Val Pro
        35                  40                  45

Ser Arg Phe Ser Gly Ser Gly Ser Gly Thr Glu Phe Thr Leu Thr Ile
    50                  55                  60

Thr Ser Leu Gln Pro His Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 352
<211> LENGTH: 96
<212> TYPE: PRT
<213> ORGANISM: Homo sapiens

<400> SEQUENCE: 352

Ser Ala Ser Val Gly Asp Arg Val Thr Ile Thr Cys Arg Ala Ser Gln
1               5                   10                  15

Ser Ile Ser Lys Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

His Ser Val Pro Trp Thr Phe Gly Gln Gly Thr Lys Val Glu Ile Lys
                85                  90                  95


<210> SEQ ID NO 353
<211> LENGTH: 96
<212> TYPE: PRT
<213> ORGANISM: Homo sapiens

<400> SEQUENCE: 353

Ser Ala Ser Val Gly Asp Arg Val Thr Ile Thr Cys Arg Ala Ser Gln
1               5                   10                  15

Ser Val Ser Lys Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

His Ser Val Pro Trp Ala Phe Gly Gln Gly Thr Lys Val Glu Ile Lys
                85                  90                  95


<210> SEQ ID NO 354
<211> LENGTH: 96
<212> TYPE: PRT
<213> ORGANISM: Homo sapiens

<400> SEQUENCE: 354

Ser Ala Ser Val Gly Asp Arg Val Thr Ile Thr Cys Arg Ala Ser Gln
1               5                   10                  15

Ser Ile Ser Ser Trp Leu Ala Trp Tyr Gln Gln Lys Pro Gly Lys Ala
```

-continued

```
            20                  25                  30

Pro Lys Leu Leu Ile Tyr Lys Ala Ser Ser Leu Glu Ser Gly Val Pro
        35                  40                  45

Ser Arg Phe Ser Gly Ser Gly Ser Gly Thr Glu Phe Ser Leu Thr Ile
    50                  55                  60

Ser Ser Leu Gln Pro Glu Asp Phe Ala Thr Tyr Tyr Cys Gln Gln Tyr
65                  70                  75                  80

Asn Ser Tyr Pro Trp Thr Phe Gly Gln Gly Thr Lys Val Glu Ile Lys
                85                  90                  95
```

<210> SEQ ID NO 355
<211> LENGTH: 96
<212> TYPE: PRT
<213> ORGANISM: Homo sapiens

<400> SEQUENCE: 355

```
Ser Ala Ser Val Gly Asp Arg Val Thr Ile Thr Cys Arg Ala Ser Gln
1               5                   10                  15

Ser Ile Ser Lys Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

Tyr Ser Val Pro Trp Thr Phe Gly Gln Gly Thr Lys Val Glu Ile Lys
                85                  90                  95
```

<210> SEQ ID NO 356
<211> LENGTH: 96
<212> TYPE: PRT
<213> ORGANISM: Homo sapiens

<400> SEQUENCE: 356

```
Ser Ala Ser Val Gly Asp Arg Val Thr Ile Thr Cys Arg Ala Ser Gln
1               5                   10                  15

Ser Ile Ser Lys Trp Leu Ala Trp Tyr Gln Gln Lys Pro Gly Lys Ala
            20                  25                  30

Pro Lys Leu Leu Ile Tyr Thr Thr Ser Thr Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Phe
65                  70                  75                  80

Tyr Ser Val Pro Trp Thr Phe Gly Gln Gly Thr Lys Val Glu Ile Lys
                85                  90                  95
```

<210> SEQ ID NO 357
<211> LENGTH: 96
<212> TYPE: PRT
<213> ORGANISM: Homo sapiens

<400> SEQUENCE: 357

```
Ser Ala Ser Val Gly Asp Arg Val Thr Ile Thr Cys Arg Ala Ser Gln
1               5                   10                  15

Ser Ile Ser Lys Trp Leu Ala Trp Tyr Gln Gln Lys Pro Gly Lys Ala
            20                  25                  30
```

Pro Lys Leu Leu Ile Tyr Thr Thr Ser Thr Leu Lys Ser Gly Val Pro
35 40 45

Ser Arg Phe Ser Gly Ser Gly Ser Gly Thr Glu Phe Thr Leu Thr Ile
50 55 60

Ser Gly Leu Gln Pro Asp Asp Phe Ala Thr Tyr Tyr Cys Gln His Phe
65 70 75 80

Phe Ser Val Pro Trp Thr Phe Gly Gln Gly Thr Lys Val Glu Ser Lys
85 90 95

<210> SEQ ID NO 358
<211> LENGTH: 96
<212> TYPE: PRT
<213> ORGANISM: Homo sapiens

<400> SEQUENCE: 358

Ser Ala Ser Val Gly Asp Arg Val Thr Ile Thr Cys Arg Ala Ser Gln
1 5 10 15

Ser Ile Ser Lys Trp Leu Ala Trp Tyr Gln Gln Lys Pro Gly Lys Ala
20 25 30

Pro Lys Leu Leu Ile Tyr Thr Thr Ser Thr Leu Lys Thr Gly Val Pro
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Tyr Cys Gln His Phe
65 70 75 80

Tyr Ser Val Pro Trp Thr Phe Gly Gln Gly Thr Lys Val Glu Ile Lys
85 90 95

<210> SEQ ID NO 359
<211> LENGTH: 96
<212> TYPE: PRT
<213> ORGANISM: Homo sapiens

<400> SEQUENCE: 359

Ser Ala Ser Val Gly Asp Arg Val Thr Ile Thr Cys Arg Ala Ser Gln
1 5 10 15

Gly Ile Ser Asn Tyr Leu Ala Trp Tyr Gln Gln Lys Pro Arg Glu Val
20 25 30

Pro Lys Leu Leu Ile Tyr Ala Ala Ser Thr Leu His Ser Gly Val Pro
35 40 45

Ser Arg Phe Ser Gly Ser Gly Ser Gly Thr Asp Phe Thr Leu Thr Ile
50 55 60

Ser Gly Leu Gln Pro Glu Asp Val Ala Thr Tyr Tyr Cys Gln Lys Tyr
65 70 75 80

Asn Ser Val Pro Trp Thr Phe Gly Gln Gly Thr Lys Val Glu Met Lys
85 90 95

<210> SEQ ID NO 360
<211> LENGTH: 96
<212> TYPE: PRT
<213> ORGANISM: Homo sapiens

<400> SEQUENCE: 360

Ser Ala Ser Val Gly Asp Arg Val Thr Ile Thr Cys Arg Ala Ser Gln
1 5 10 15

Asp Ile Ser Lys Tyr Leu Ala Trp Tyr Gln Gln Arg Pro Gly Lys Val
20 25 30

Pro Asn Leu Leu Ile Tyr Thr Ala Ser Thr Leu Gln Ser Gly Val Pro
35 40 45

Ser Arg Phe Ser Gly Ser Gly Ser Gly Thr His Phe Thr Leu Thr Ile
50 55 60

Ser Ser Leu Gln Pro Glu Asp Val Ala Thr Tyr Tyr Cys Gln Lys Tyr
65 70 75 80

Asn Ser Val Pro Trp Thr Phe Gly Gln Gly Thr Lys Val Glu Ile Lys
85 90 95

<210> SEQ ID NO 361
<211> LENGTH: 96
<212> TYPE: PRT
<213> ORGANISM: Homo sapiens

<400> SEQUENCE: 361

Ser Ala Ser Val Gly Asp Arg Val Thr Ile Thr Cys Arg Ala Ser Gln
1 5 10 15

Asp Ile Ser Lys Tyr Leu Ala Trp Tyr Gln Gln Arg Pro Gly Lys Val
20 25 30

Pro Asn Leu Leu Ile Tyr Thr Ala Ser Thr Leu Gln Ser Gly Val Pro
35 40 45

Ser Arg Phe Ser Gly Ser Gly Ser Gly Thr His Phe Thr Leu Thr Ile
50 55 60

Ser Ser Leu Gln Pro Glu Asp Val Ala Thr Tyr Tyr Cys Gln Lys Tyr
65 70 75 80

Asn Ser Val Pro Trp Thr Phe Gly Gln Gly Thr Lys Val Glu Ile Lys
85 90 95

<210> SEQ ID NO 362
<211> LENGTH: 96
<212> TYPE: PRT
<213> ORGANISM: Homo sapiens

<400> SEQUENCE: 362

Ser Ala Ser Val Gly Asp Arg Val Thr Ile Thr Cys Arg Ala Ser Gln
1 5 10 15

Gly Ile Ser Asn Tyr Leu Ala Trp Tyr Gln Gln Lys Pro Arg Glu Val
20 25 30

Pro Lys Leu Leu Ile Tyr Ala Ala Ser Thr Leu His Ser Gly Val Pro
35 40 45

Ser Arg Phe Ser Gly Ser Gly Ser Gly Thr Asp Phe Thr Leu Thr Ile
50 55 60

Ser Gly Leu Gln Pro Glu Asp Val Ala Thr Tyr Tyr Cys Gln Lys Tyr
65 70 75 80

Asn Ser Val Pro Trp Thr Phe Gly Gln Gly Thr Lys Val Glu Met Lys
85 90 95

<210> SEQ ID NO 363
<211> LENGTH: 9
<212> TYPE: PRT
<213> ORGANISM: Homo sapiens

<400> SEQUENCE: 363

Gln Gln Tyr Asn Ser Tyr Pro Trp Thr
1 5

<210> SEQ ID NO 364
<211> LENGTH: 9
<212> TYPE: PRT

<213> ORGANISM: Homo sapiens

<400> SEQUENCE: 364

Gln His Tyr Tyr Ser Tyr Pro Trp Thr
1               5

<210> SEQ ID NO 365
<211> LENGTH: 9
<212> TYPE: PRT
<213> ORGANISM: Homo sapiens

<400> SEQUENCE: 365

Gln His Phe His Ser Val Pro Trp Thr
1               5

<210> SEQ ID NO 366
<211> LENGTH: 9
<212> TYPE: PRT
<213> ORGANISM: Homo sapiens

<400> SEQUENCE: 366

Gln His Phe Tyr Ser Val Pro Trp Thr
1               5

<210> SEQ ID NO 367
<211> LENGTH: 9
<212> TYPE: PRT
<213> ORGANISM: Homo sapiens

<400> SEQUENCE: 367

Gln His Phe His Ser Val Pro Trp Thr
1               5

<210> SEQ ID NO 368
<211> LENGTH: 9
<212> TYPE: PRT
<213> ORGANISM: Homo sapiens

<400> SEQUENCE: 368

Gln His Phe Tyr Ser Val Pro Trp Thr
1               5

<210> SEQ ID NO 369
<211> LENGTH: 9
<212> TYPE: PRT
<213> ORGANISM: Homo sapiens

<400> SEQUENCE: 369

Gln His Tyr Tyr Ser Tyr Pro Trp Thr
1               5

<210> SEQ ID NO 370
<211> LENGTH: 8
<212> TYPE: PRT
<213> ORGANISM: Homo sapiens

<400> SEQUENCE: 370

Gln Gln Tyr Ser Ser Phe Phe Thr
1               5

<210> SEQ ID NO 371
<211> LENGTH: 9
<212> TYPE: PRT
<213> ORGANISM: Homo sapiens

<400> SEQUENCE: 371

Gln Gln Tyr Asn Asn Tyr Pro Trp Thr
1               5

<210> SEQ ID NO 372
<211> LENGTH: 9
<212> TYPE: PRT
<213> ORGANISM: Homo sapiens

<400> SEQUENCE: 372

Gln His Tyr Tyr Ser Tyr Pro Trp Thr
1               5

<210> SEQ ID NO 373
<211> LENGTH: 9
<212> TYPE: PRT
<213> ORGANISM: Homo sapiens

<400> SEQUENCE: 373

Gln His Phe Phe Ser Val Pro Trp Thr
1               5

<210> SEQ ID NO 374
<211> LENGTH: 9
<212> TYPE: PRT
<213> ORGANISM: Homo sapiens

<400> SEQUENCE: 374

Gln His Tyr Tyr Ser Tyr Pro Trp Thr
1               5

<210> SEQ ID NO 375
<211> LENGTH: 9
<212> TYPE: PRT
<213> ORGANISM: Homo sapiens

<400> SEQUENCE: 375

Gln His Tyr His Ser Tyr Pro Trp Thr
1               5

<210> SEQ ID NO 376
<211> LENGTH: 9
<212> TYPE: PRT
<213> ORGANISM: Homo sapiens

<400> SEQUENCE: 376

Gln His Phe His Ser Val Pro Trp Thr
1               5

<210> SEQ ID NO 377
<211> LENGTH: 9
<212> TYPE: PRT
<213> ORGANISM: Homo sapiens

<400> SEQUENCE: 377

Gln His Phe His Ser Val Pro Trp Ala
1               5

<210> SEQ ID NO 378
<211> LENGTH: 9
<212> TYPE: PRT
<213> ORGANISM: Homo sapiens

<400> SEQUENCE: 378

Gln Gln Tyr Asn Ser Tyr Pro Trp Thr
1               5

<210> SEQ ID NO 379
<211> LENGTH: 9
<212> TYPE: PRT
<213> ORGANISM: Homo sapiens

<400> SEQUENCE: 379

Gln His Phe Tyr Ser Val Pro Trp Thr
1               5

<210> SEQ ID NO 380
<211> LENGTH: 9
<212> TYPE: PRT
<213> ORGANISM: Homo sapiens

<400> SEQUENCE: 380

Gln His Phe Tyr Ser Val Pro Trp Thr
1               5

<210> SEQ ID NO 381
<211> LENGTH: 9
<212> TYPE: PRT
<213> ORGANISM: Homo sapiens

<400> SEQUENCE: 381

Gln His Phe Phe Ser Val Pro Trp Thr
1               5

<210> SEQ ID NO 382
<211> LENGTH: 9
<212> TYPE: PRT
<213> ORGANISM: Homo sapiens

<400> SEQUENCE: 382

Gln His Phe Tyr Ser Val Pro Trp Thr
1               5

<210> SEQ ID NO 383
<211> LENGTH: 9
<212> TYPE: PRT
<213> ORGANISM: Homo sapiens

<400> SEQUENCE: 383

Gln Lys Tyr Asn Ser Val Pro Trp Thr
1               5

<210> SEQ ID NO 384
<211> LENGTH: 9
<212> TYPE: PRT
<213> ORGANISM: Homo sapiens

<400> SEQUENCE: 384

Gln Lys Tyr Asn Ser Val Pro Trp Thr
1               5

<210> SEQ ID NO 385
<211> LENGTH: 9
<212> TYPE: PRT
<213> ORGANISM: Homo sapiens

<400> SEQUENCE: 385

Gln Lys Tyr Asn Ser Val Pro Trp Thr
1               5

<210> SEQ ID NO 386
<211> LENGTH: 9
<212> TYPE: PRT
<213> ORGANISM: Homo sapiens

<400> SEQUENCE: 386

Gln Lys Tyr Asn Ser Val Pro Trp Thr
1               5

<210> SEQ ID NO 387
<211> LENGTH: 113
<212> TYPE: PRT
<213> ORGANISM: Homo sapiens

<400> SEQUENCE: 387

Gly Gly Gly Leu Val Arg Pro Gly Gly Ser Leu Arg Leu Ser Cys Lys
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Ile Tyr Asn Gly Asp
        35                  40                  45

Asp Ser Thr Tyr Tyr Ala Lys Ser Val Lys Gly Arg Phe Thr Ile Ser
    50                  55                  60

Arg Asp Asp Ser Gln Ser Thr Leu Ser Leu Gln Met Asn Ser Leu Arg
65                  70                  75                  80

Ala Glu Asp Thr Ala Val Tyr Tyr Cys Val Lys Asp Arg Asp Thr Gly
                85                  90                  95

Trp Ser Ser Ile Val Asp Trp Gly Gln Gly Thr Leu Val Thr Val Ser
            100                 105                 110

Ser

<210> SEQ ID NO 388
<211> LENGTH: 113
<212> TYPE: PRT
<213> ORGANISM: Homo sapiens

<400> SEQUENCE: 388

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Ile Tyr Asn Gly Asp
        35                  40                  45

Asp Ser Thr Tyr Tyr Ser Lys Ser Val Lys Gly Arg Phe Thr Ile Ser
    50                  55                  60

Arg Asp Asn Ser Gln Asn Thr Leu Ser Leu Gln Met Asn Ser Leu Arg
65                  70                  75                  80

Val Glu Asp Thr Ala Val Tyr Tyr Cys Val Lys Asp Arg Asp Asn Gly
                85                  90                  95

Trp Ser Ser Ile Val Asp Trp Gly Gln Gly Thr Leu Val Thr Val Ser
            100                 105                 110

Ser

<210> SEQ ID NO 389
<211> LENGTH: 113
<212> TYPE: PRT
<213> ORGANISM: Homo sapiens

<400> SEQUENCE: 389

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Ile Phe Asn Gly Asp
35 40 45

Asp Ser Thr Tyr Tyr Ala Ala Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Val Tyr Tyr Cys Val Lys Asp Arg Asp Asn Gly
85 90 95

Trp Ser Ser Ile Val Asp Trp Gly Gln Gly Thr Leu Val Thr Val Ser
100 105 110

Ser

<210> SEQ ID NO 390
<211> LENGTH: 113
<212> TYPE: PRT
<213> ORGANISM: Homo sapiens

<400> SEQUENCE: 390

Gly Gly Gly Leu Val Arg Pro Gly Gly Ser Leu Arg Leu Ser Cys Thr
1 5 10 15

Ala Ser Gly Phe Thr Phe Arg Arg Tyr Ala Leu Ala Trp Val Arg Gln
20 25 30

Val Pro Gly Lys Gly Leu Glu Trp Val Ser Leu Ile Tyr Asn Gly Asp
35 40 45

Asp Ser Thr Tyr Tyr Ala Glu Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Val Tyr Tyr Cys Val Lys Asp Arg Asp Asn Gly
85 90 95

Trp Ser Ser Ile Val Asp Trp Gly Gln Gly Thr Leu Val Thr Val Ser
100 105 110

Ser

<210> SEQ ID NO 391
<211> LENGTH: 113
<212> TYPE: PRT
<213> ORGANISM: Homo sapiens

<400> SEQUENCE: 391

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Ile Tyr Asn Gly Asp
35 40 45

Asp Ser Thr Tyr Tyr Ala Glu Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Ile Tyr Tyr Cys Val Lys Asp Arg Asp Thr Gly
85 90 95

Trp Ser Ser Ile Val Asp Trp Gly Gln Gly Thr Leu Val Thr Val Ser
100 105 110

Ser

<210> SEQ ID NO 392
<211> LENGTH: 113
<212> TYPE: PRT
<213> ORGANISM: Homo sapiens

<400> SEQUENCE: 392

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Ile Tyr Asp Gly Glu
35 40 45

Asp Ser Thr Tyr Tyr Ala Ala Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Ile Tyr Tyr Cys Val Lys Asp Arg Asp Asn Gly
85 90 95

Trp Ser Ser Ile Val Asp Trp Gly Gln Gly Thr Leu Val Thr Val Ser
100 105 110

Ser

<210> SEQ ID NO 393
<211> LENGTH: 112
<212> TYPE: PRT
<213> ORGANISM: Homo sapiens

<400> SEQUENCE: 393

Gly Gly Asp Leu Ala Gln Pro Gly Gly Ser Leu Arg Leu Ser Cys Ala
1 5 10 15

Val Ser Gly Leu Ser Ile Gly Arg Tyr Gly Met Asn Trp Ile Arg Gln
20 25 30

Ala Pro Gly Lys Gly Leu Glu Trp Val Ser Gly Ile Ser Asp Asp Gly
35 40 45

Gly Ser Thr Tyr Tyr Ala Ala Ser Val Lys Gly Arg Phe Thr Ile Ser
50 55 60

Arg Asp Asn Ser Lys Asn Ser Val Tyr Leu Gln Met Ser Ser Leu Arg
65 70 75 80

Ala Glu Asp Thr Ala Arg Tyr Tyr Cys Ala Lys Asp Arg Leu Met Phe
85 90 95

Asp Gly Phe His Met Trp Gly Gln Gly Thr Met Val Thr Val Ser Ser
100 105 110

<210> SEQ ID NO 394
<211> LENGTH: 115
<212> TYPE: PRT
<213> ORGANISM: Homo sapiens

<400> SEQUENCE: 394

Gly Gly Gly Leu Val Gln Pro Gly Gly Ser Leu Arg Leu Ser Cys Ala
1 5 10 15

Ala Ser Gly Phe Thr Phe Arg Thr Tyr Ala Met Ser Trp Val Arg Gln
20 25 30

Pro Pro Gly Lys Gly Leu Glu Trp Val Ser Ser Ile Ser Ala Arg Glu
35 40 45

Asp Ser Thr Tyr Phe Ala Ala Ser Val Arg Gly Arg Phe Thr Ile Ser
50 55 60

Arg Asp Asn Ser Lys Asn Thr Leu Tyr Leu Gln Met Asn Asn Leu Arg
65 70 75 80

Ala Glu Asp Thr Ala Leu Tyr Tyr Cys Ala Lys Asp Arg Leu Gln Leu
85 90 95

Gly Val Gly Glu Leu Tyr Glu Ser Trp Gly Gln Gly Thr Leu Val Thr
100 105 110

Val Ser Ser
115

<210> SEQ ID NO 395
<211> LENGTH: 113
<212> TYPE: PRT
<213> ORGANISM: Homo sapiens

<400> SEQUENCE: 395

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Ile Tyr Asn Ala Asp
35 40 45

Asp Ser Thr Tyr Tyr Ala Glu Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Val Tyr Tyr Cys Val Lys Asp Arg Asp Thr Gly
85 90 95

Trp Ser Ser Ile Val Asp Trp Gly Gln Gly Thr Leu Val Thr Val Ser
100 105 110

Ser

<210> SEQ ID NO 396
<211> LENGTH: 113
<212> TYPE: PRT
<213> ORGANISM: Homo sapiens

<400> SEQUENCE: 396

Gly Gly Gly Leu Val Arg Pro Gly Gly Ser Leu Arg Leu Ser Cys Ser
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Leu Tyr Asn Gly Asp
35 40 45

Asp Ser Thr Tyr Tyr Ala Glu Ser Val Lys Gly Arg Phe Ile Ile Ser
50 55 60

Arg Asp Asn Ser Leu Asn Thr Leu Ser Leu Gln Met Asn Ser Leu Arg
65 70 75 80

Ala Glu Asp Thr Ala Val Tyr Tyr Cys Val Lys Asp Arg Asp Thr Gly
85 90 95

Trp Ser Ser Ile Val Asp Trp Gly Arg Gly Thr Leu Val Thr Val Ser
100 105 110

Ser

<210> SEQ ID NO 397
<211> LENGTH: 113
<212> TYPE: PRT
<213> ORGANISM: Homo sapiens

<400> SEQUENCE: 397

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Ile Tyr Asp Gly His
35 40 45

Asp Thr Thr Tyr Tyr Ala Asp Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Val Tyr Tyr Cys Val Lys Asp Arg Asp Asn Gly
85 90 95

Trp Ser Ser Ile Val Asp Trp Gly Gln Gly Thr Leu Val Ala Val Ser
100 105 110

Ser

<210> SEQ ID NO 398
<211> LENGTH: 113
<212> TYPE: PRT
<213> ORGANISM: Homo sapiens

<400> SEQUENCE: 398

Gly Gly Gly Leu Val Arg Pro Gly Gly Ser Leu Arg Leu Ser Cys Thr
1 5 10 15

Ala Ser Gly Phe Asn Phe Arg Arg Tyr Ala Met Ala Trp Val Arg Gln
20 25 30

Ala Pro Gly Lys Gly Leu Glu Trp Val Ser Leu Leu Tyr Asn Gly Asp
35 40 45

Asp Ser Thr Tyr Tyr Ala Lys Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Ala Glu Asp Thr Ala Val Tyr Tyr Cys Val Lys Asp Arg Asp Asn Gly
85 90 95

Trp Ser Ser Ile Val Asp Trp Gly Gln Gly Thr Leu Val Thr Val Ser
100 105 110

Ser

<210> SEQ ID NO 399
<211> LENGTH: 113
<212> TYPE: PRT
<213> ORGANISM: Homo sapiens

<400> SEQUENCE: 399

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln

```
            20                  25                  30

Ala Pro Gly Lys Gly Leu Glu Trp Val Ser Leu Ile Trp Asn Gly Asp
        35                  40                  45

Asp Ser Thr Tyr Tyr Ala Ser Ser Val Lys Gly Arg Phe Thr Ile Ser
    50                  55                  60

Arg Asp Asn Ser Gln Asn Thr Leu Ser Leu Gln Met Asn Ser Leu Arg
65                  70                  75                  80

Ala Glu Asp Thr Ala Val Tyr Tyr Cys Val Lys Asp Arg Asp Asn Gly
                85                  90                  95

Trp Ser Ser Ile Val Asp Trp Gly Gln Gly Thr Leu Val Thr Val Ser
            100                 105                 110

Ala


<210> SEQ ID NO 400
<211> LENGTH: 113
<212> TYPE: PRT
<213> ORGANISM: Homo sapiens

<400> SEQUENCE: 400

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Leu Tyr Asn Gly Asp
        35                  40                  45

Asp Ser Thr Tyr Tyr Ala Glu Ser Val Lys Gly Arg Phe Thr Ile Ser
    50                  55                  60

Arg Asp Asn Ser Gln Asn Thr Leu Ser Leu Gln Met Asn Ser Leu Arg
65                  70                  75                  80

Ala Glu Asp Thr Ala Val Tyr Tyr Cys Val Lys Asp Arg Asp Thr Gly
                85                  90                  95

Arg Ser Ser Ile Val Glu Trp Gly Gln Gly Thr Trp Val Thr Val Ser
            100                 105                 110

Ser


<210> SEQ ID NO 401
<211> LENGTH: 115
<212> TYPE: PRT
<213> ORGANISM: Homo sapiens

<400> SEQUENCE: 401

Gly Gly Gly Leu Val Gln Pro Gly Gly Ser Leu Arg Leu Ser Cys Ala
1               5                   10                  15

Ala Ser Gly Phe Thr Phe Arg Thr Tyr Ala Met Ser Trp Val Arg Gln
            20                  25                  30

Ala Pro Gly Lys Gly Leu Glu Trp Val Ser Ser Ile Ser Ala Ser Asp
        35                  40                  45

Asp Ser Thr Tyr Phe Ala Ala Ser Val Arg Gly Arg Phe Thr Ile Ser
    50                  55                  60

Arg Asp Asn Ser Lys Asn Thr Leu Tyr Leu Gln Met Asn Asn Leu Arg
65                  70                  75                  80

Ala Glu Asp Thr Ala Leu Tyr Tyr Cys Ala Lys Asp Arg Leu Glu Leu
                85                  90                  95

Gly Val Gly Glu Leu Tyr Glu Phe Trp Gly Gln Gly Thr Leu Val Thr
            100                 105                 110
```

```
Val Ser Ser
        115


<210> SEQ ID NO 402
<211> LENGTH: 113
<212> TYPE: PRT
<213> ORGANISM: Homo sapiens

<400> SEQUENCE: 402

Gly Gly Gly Leu Val Gln Pro Gly Gly Ser Leu Arg Leu Ser Cys Ala
1               5                   10                  15

Ala Ser Gly Phe Thr Phe Lys Asn Tyr Ala Met Ala Trp Val Arg Gln
            20                  25                  30

Ala Pro Gly Lys Gly Leu Glu Trp Val Ser Leu Leu Tyr Asn Ser Glu
        35                  40                  45

Glu Ser Thr Tyr Tyr Ala Asp Ser Val Lys Gly Arg Phe Thr Ile Ser
    50                  55                  60

Arg Asp Asn Ser Lys Asn Thr Leu Phe Leu Gln Met Asn Arg Leu Arg
65                  70                  75                  80

Val Glu Asp Thr Ala Val Tyr Phe Cys Val Arg Asp Arg Ser Asn Gly
                85                  90                  95

Trp Ser Ser Ile Asn Leu Trp Gly Arg Gly Thr Leu Val Thr Val Ser
            100                 105                 110

Ser


<210> SEQ ID NO 403
<211> LENGTH: 113
<212> TYPE: PRT
<213> ORGANISM: Homo sapiens

<400> SEQUENCE: 403

Gly Gly Gly Leu Val Arg Pro Gly Gly Ser Leu Arg Leu Ser Cys Thr
1               5                   10                  15

Ala Ser Gly Phe Asn Phe Arg Arg Tyr Ala Met Ala Trp Val Arg Gln
            20                  25                  30

Ala Pro Gly Lys Gly Leu Glu Trp Val Ser Gln Ile Tyr Asn Gly Glu
        35                  40                  45

Asp Ser Thr Tyr Tyr Ala Glu Ser Val Lys Gly Arg Phe Thr Ile Ser
    50                  55                  60

Arg Asp Asn Ser Gln Asn Thr Leu Ser Leu Gln Met Asn Gly Leu Arg
65                  70                  75                  80

Ala Glu Asp Thr Ala Ile Tyr Tyr Cys Val Lys Asp Arg Asp Asn Gly
                85                  90                  95

Trp Ser Ser Ile Val Asp Trp Gly Gln Gly Thr Leu Val Thr Val Ser
            100                 105                 110

Ser


<210> SEQ ID NO 404
<211> LENGTH: 113
<212> TYPE: PRT
<213> ORGANISM: Homo sapiens

<400> SEQUENCE: 404

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30
```

```
Ala Pro Gly Lys Gly Leu Glu Trp Val Ser Leu Ile Tyr Asp Gly Asp
        35                  40                  45

Asp Ser Thr Tyr Tyr Ala Glu Ser Val Lys Gly Arg Phe Thr Ile Ser
    50                  55                  60

Arg Asp Asn Ser Gln Asn Thr Val Ser Leu Gln Met Thr Ser Leu Arg
65                  70                  75                  80

Ala Glu Asp Thr Ala Leu Tyr Tyr Cys Val Lys Asp Arg Asp Asn Gly
                85                  90                  95

Trp Ser Ser Ile Val Asp Trp Gly Gln Gly Thr Leu Val Thr Val Ser
            100                 105                 110

Ser


<210> SEQ ID NO 405
<211> LENGTH: 113
<212> TYPE: PRT
<213> ORGANISM: Homo sapiens

<400> SEQUENCE: 405

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Ile Tyr Asp Gly Asp
        35                  40                  45

Asp Ser Thr Tyr Tyr Ala Lys Ser Val Lys Gly Arg Phe Ala Ile Ser
    50                  55                  60

Arg Asp Asn Ser Lys Asn Thr Leu Ser Leu Gln Met Asn Ser Leu Arg
65                  70                  75                  80

Ala Glu Asp Thr Ala Val Tyr Tyr Cys Val Lys Asp Arg Asp Asn Gly
                85                  90                  95

Trp Ser Ser Ile Val Asp Trp Gly Gln Gly Thr Leu Val Thr Val Ser
            100                 105                 110

Ser


<210> SEQ ID NO 406
<211> LENGTH: 113
<212> TYPE: PRT
<213> ORGANISM: Homo sapiens

<400> SEQUENCE: 406

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Leu Tyr Asn Gly Asp
        35                  40                  45

Asp Ser Thr Tyr Tyr Ala Lys Ser Val Lys Gly Arg Phe Thr Ile Ser
    50                  55                  60

Arg Asp Asn Ser Gln Asn Thr Leu Ser Leu Gln Met Asn Ser Leu Arg
65                  70                  75                  80

Ala Glu Asp Thr Ala Val Tyr Tyr Cys Val Arg Asp Arg Asp Asn Gly
                85                  90                  95

Trp Ser Ser Ile Val Asp Trp Gly Gln Gly Thr Leu Val Thr Val Ser
            100                 105                 110

Ser
```

<210> SEQ ID NO 407
<211> LENGTH: 113
<212> TYPE: PRT
<213> ORGANISM: Homo sapiens

<400> SEQUENCE: 407

Gly Gly Gly Leu Val Arg Pro Gly Gly Ser Leu Arg Leu Ser Cys Thr
1 5 10 15

Ala Ser Gly Phe Thr Phe Arg Arg Phe Ala Met Ala Trp Val Arg Gln
20 25 30

Ala Pro Gly Lys Gly Leu Glu Trp Val Ser Leu Ile Tyr Asn Gly Asp
35 40 45

Asp Ser Thr Tyr Tyr Ala Gln Ser Val Lys Gly Arg Phe Thr Ile Ser
50 55 60

Arg Asp Asn Ser Gln Asn Thr Leu Ser Leu Gln Met Asn Ser Leu Arg
65 70 75 80

Val Glu Asp Thr Ala Val Tyr Tyr Cys Val Lys Asp Arg Asp Thr Gly
85 90 95

Trp Ser Ser Ile Val Asp Trp Gly Gln Gly Thr Leu Val Thr Val Ser
100 105 110

Ser

<210> SEQ ID NO 408
<211> LENGTH: 113
<212> TYPE: PRT
<213> ORGANISM: Homo sapiens

<400> SEQUENCE: 408

Gly Gly Gly Leu Val Arg Pro Gly Gly Ser Leu Arg Leu Ser Cys Thr
1 5 10 15

Ala Ser Gly Phe Thr Phe Arg Arg Phe Ala Met Ala Trp Val Arg Gln
20 25 30

Ala Pro Gly Lys Gly Leu Glu Trp Val Ser Leu Ile Trp Asn Gly Asp
35 40 45

Asp Ser Thr Tyr Tyr Ala Glu Ser Val Arg Gly Arg Phe Thr Ile Ser
50 55 60

Arg Asp Asn Ser His Asn Thr Leu Ser Leu Gln Met Arg Ser Leu Arg
65 70 75 80

Ala Glu Asp Thr Ala Ile Tyr Tyr Cys Val Lys Asp Arg Asp Asn Gly
85 90 95

Trp Ser Ser Ile Val Asp Trp Gly Gln Gly Thr Leu Val Thr Val Ser
100 105 110

Ser

<210> SEQ ID NO 409
<211> LENGTH: 113
<212> TYPE: PRT
<213> ORGANISM: Homo sapiens

<400> SEQUENCE: 409

Gly Gly Gly Leu Val Arg Pro Gly Gly Ser Leu Arg Leu Ser Cys Thr
1 5 10 15

Ala Ser Gly Phe Thr Phe Arg Arg Tyr Ala Met Ala Trp Val Arg Gln
20 25 30

Ala Pro Gly Lys Gly Leu Glu Trp Val Ser Leu Ile Tyr Asn Gly Asp
35 40 45

Asp Ser Thr Tyr Tyr Ala Glu Ser Val Lys Gly Arg Phe Thr Val Ser
    50                  55                  60

Arg Asp Asn Ser Gln Asn Thr Leu Ser Leu Gln Met Asn Ser Leu Arg
65                  70                  75                  80

Ala Glu Asp Thr Ala Ile Tyr Tyr Cys Val Arg Asp Arg Asp Asn Gly
                85                  90                  95

Trp Ser Ser Ile Val Asp Trp Gly Gln Gly Thr Leu Val Thr Val Ser
            100                 105                 110

Ser

<210> SEQ ID NO 410
<211> LENGTH: 113
<212> TYPE: PRT
<213> ORGANISM: Homo sapiens

<400> SEQUENCE: 410

Gly Gly Gly Leu Ala Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Ile Trp Asn Gly Asp
        35                  40                  45

Asp Ser Thr Tyr Tyr Ala Glu Ser Val Lys Gly Arg Phe Thr Ile Ser
    50                  55                  60

Arg Asp Asn Ser Gln Asn Thr Leu Ser Leu Gln Met Asn Ser Leu Arg
65                  70                  75                  80

Ala Glu Asp Thr Ala Val Tyr Tyr Cys Val Lys Asp Arg Asp Thr Gly
                85                  90                  95

Trp Ser Ser Ile Val Asp Trp Gly Gln Gly Thr Leu Val Thr Val Ser
            100                 105                 110

Ser

<210> SEQ ID NO 411
<211> LENGTH: 113
<212> TYPE: PRT
<213> ORGANISM: Homo sapiens

<400> SEQUENCE: 411

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Ile Tyr Asn Ala Tyr
        35                  40                  45

Asp Ser Thr Tyr Tyr Ala Glu Ser Val Lys Gly Arg Phe Thr Ile Ser
    50                  55                  60

Arg Asp Asn Ser Gln Asn Thr Leu Ser Leu Gln Met Ser Ser Leu Arg
65                  70                  75                  80

Ala Glu Asp Thr Ala Val Tyr Tyr Cys Val Lys Asp Arg Asp Thr Gly
                85                  90                  95

Trp Ser Ser Ile Val Asp Trp Gly Gln Gly Thr Leu Val Thr Val Ser
            100                 105                 110

Pro

<210> SEQ ID NO 412
<211> LENGTH: 113

<212> TYPE: PRT
<213> ORGANISM: Homo sapiens

<400> SEQUENCE: 412

Gly Gly Gly Leu Val Arg Pro Gly Gly Ser Leu Arg Leu Ser Cys Thr
1               5                   10                  15

Ala Ser Gly Phe Thr Phe Arg Arg Tyr Ala Met Ala Trp Val Arg Gln
            20                  25                  30

Ala Pro Gly Lys Gly Leu Glu Trp Val Ser Leu Ile Tyr Asn Gly Asp
        35                  40                  45

Asp Ser Thr Tyr Tyr Ala Glu Ser Val Arg Gly Arg Phe Thr Ile Ser
    50                  55                  60

Arg Asp Asn Ser Gln Asn Thr Leu Ser Leu Gln Met Asn Ser Leu Arg
65                  70                  75                  80

Ala Glu Asp Thr Ala Val Tyr Tyr Cys Val Lys Asp Arg Asp Thr Gly
                85                  90                  95

Trp Ser Ser Ile Val Asp Trp Gly Gln Gly Thr Leu Val Thr Val Ser
            100                 105                 110

Ser

<210> SEQ ID NO 413
<211> LENGTH: 113
<212> TYPE: PRT
<213> ORGANISM: Homo sapiens

<400> SEQUENCE: 413

Gly Gly Gly Leu Val Gln Pro Gly Gly Ser Leu Arg Leu Ser Cys Ala
1               5                   10                  15

Ala Ser Gly Phe Thr Phe Ser Asn Tyr Ala Met Ala Trp Val Arg Gln
            20                  25                  30

Ala Pro Gly Lys Gly Leu Glu Trp Val Ser Leu Ile Tyr Ser Gly Asp
        35                  40                  45

Asp Ser Thr Tyr Tyr Ala Asp Phe Val Lys Gly Arg Phe Thr Ile Ser
    50                  55                  60

Arg His Asn Ser Lys Asn Thr Leu Ser Leu Gln Met Asn Ser Leu Arg
65                  70                  75                  80

Ala Glu Asp Thr Ala Ile Tyr Tyr Cys Val Lys Asp Arg Gly Thr Gly
                85                  90                  95

Trp Ser Ser Ile Val His Trp Gly Gln Gly Thr Leu Val Thr Val Ser
            100                 105                 110

Ser

<210> SEQ ID NO 414
<211> LENGTH: 121
<212> TYPE: PRT
<213> ORGANISM: Homo sapiens

<400> SEQUENCE: 414

Gly Ala Glu Val Lys Arg Pro Gly Ala Ser Val Lys Val Ser Cys Lys
1               5                   10                  15

Ala Ser Gly Tyr Thr Phe Thr Ser Tyr Tyr Met His Trp Val Arg Gln
            20                  25                  30

Ala Pro Gly Gln Gly Leu Glu Trp Met Gly Ile Ile Asn Pro Arg Gly
        35                  40                  45

Gly Ser Thr Thr Tyr Ala Gln Lys Phe Gln Gly Arg Val Ala Leu Thr
    50                  55                  60

```
Gly Asp Thr Ser Thr Ser Thr Val Tyr Met Glu Leu Thr Ser Leu Arg
65                  70                  75                  80

Ser Asp Asp Thr Ala Val Tyr Tyr Cys Ala Arg Gly Lys Ala His Gln
                85                  90                  95

Thr Thr Val Val Ile Leu Ser Trp Tyr Tyr Gly Met Asp Val Trp Gly
            100                 105                 110

Gln Gly Thr Thr Val Thr Val Ser Ser
        115                 120


<210> SEQ ID NO 415
<211> LENGTH: 121
<212> TYPE: PRT
<213> ORGANISM: Homo sapiens

<400> SEQUENCE: 415

Gly Ala Glu Val Lys Lys Ser Gly Ala Ser Val Lys Val Ser Cys Lys
1               5                   10                  15

Ala Ser Gly Tyr Ser Phe Thr Thr Asn Tyr Ile His Trp Val Arg Gln
            20                  25                  30

Ala Pro Gly Gln Gly Pro Glu Trp Met Gly Ile Ile Asn Pro Arg Gly
        35                  40                  45

Gly Ser Thr Thr Tyr Ala Gln Lys Phe Gln Gly Arg Val Leu Met Thr
    50                  55                  60

Ser Asp Thr Ser Thr Ser Thr Val Tyr Met Glu Leu Ser Ser Leu Arg
65                  70                  75                  80

Ser Glu Asp Arg Ala Val Tyr Tyr Cys Ala Arg Gly Lys Asn His Gln
                85                  90                  95

Thr Thr Val Ala Val Leu Ser Trp Tyr Tyr Gly Met Asp Val Trp Gly
            100                 105                 110

Gln Gly Thr Thr Val Thr Val Ser Ser
        115                 120


<210> SEQ ID NO 416
<211> LENGTH: 13
<212> TYPE: PRT
<213> ORGANISM: Homo sapiens

<400> SEQUENCE: 416

Val Lys Asp Arg Asp Thr Gly Trp Ser Ser Ile Val Asp
1               5                   10


<210> SEQ ID NO 417
<211> LENGTH: 13
<212> TYPE: PRT
<213> ORGANISM: Homo sapiens

<400> SEQUENCE: 417

Val Lys Asp Arg Asp Asn Gly Trp Ser Ser Ile Val Asp
1               5                   10


<210> SEQ ID NO 418
<211> LENGTH: 13
<212> TYPE: PRT
<213> ORGANISM: Homo sapiens

<400> SEQUENCE: 418

Val Lys Asp Arg Asp Asn Gly Trp Ser Ser Ile Val Asp
1               5                   10


<210> SEQ ID NO 419
```

<211> LENGTH: 13
<212> TYPE: PRT
<213> ORGANISM: Homo sapiens

<400> SEQUENCE: 419

Val Lys Asp Arg Asp Asn Gly Trp Ser Ser Ile Val Asp
1 5 10

<210> SEQ ID NO 420
<211> LENGTH: 13
<212> TYPE: PRT
<213> ORGANISM: Homo sapiens

<400> SEQUENCE: 420

Val Lys Asp Arg Asp Thr Gly Trp Ser Ser Ile Val Asp
1 5 10

<210> SEQ ID NO 421
<211> LENGTH: 13
<212> TYPE: PRT
<213> ORGANISM: Homo sapiens

<400> SEQUENCE: 421

Val Lys Asp Arg Asp Asn Gly Trp Ser Ser Ile Val Asp
1 5 10

<210> SEQ ID NO 422
<211> LENGTH: 12
<212> TYPE: PRT
<213> ORGANISM: Homo sapiens

<400> SEQUENCE: 422

Ala Lys Asp Arg Leu Met Phe Asp Gly Phe His Met
1 5 10

<210> SEQ ID NO 423
<211> LENGTH: 15
<212> TYPE: PRT
<213> ORGANISM: Homo sapiens

<400> SEQUENCE: 423

Ala Lys Asp Arg Leu Gln Leu Gly Val Gly Glu Leu Tyr Glu Ser
1 5 10 15

<210> SEQ ID NO 424
<211> LENGTH: 13
<212> TYPE: PRT
<213> ORGANISM: Homo sapiens

<400> SEQUENCE: 424

Val Lys Asp Arg Asp Thr Gly Trp Ser Ser Ile Val Asp
1 5 10

<210> SEQ ID NO 425
<211> LENGTH: 13
<212> TYPE: PRT
<213> ORGANISM: Homo sapiens

<400> SEQUENCE: 425

Val Lys Asp Arg Asp Thr Gly Trp Ser Ser Ile Val Asp
1 5 10

<210> SEQ ID NO 426
<211> LENGTH: 13
<212> TYPE: PRT

<213> ORGANISM: Homo sapiens

<400> SEQUENCE: 426

Val Lys Asp Arg Asp Asn Gly Trp Ser Ser Ile Val Asp
1               5                   10

<210> SEQ ID NO 427
<211> LENGTH: 13
<212> TYPE: PRT
<213> ORGANISM: Homo sapiens

<400> SEQUENCE: 427

Val Lys Asp Arg Asp Asn Gly Trp Ser Ser Ile Val Asp
1               5                   10

<210> SEQ ID NO 428
<211> LENGTH: 13
<212> TYPE: PRT
<213> ORGANISM: Homo sapiens

<400> SEQUENCE: 428

Val Lys Asp Arg Asp Asn Gly Trp Ser Ser Ile Val Asp
1               5                   10

<210> SEQ ID NO 429
<211> LENGTH: 13
<212> TYPE: PRT
<213> ORGANISM: Homo sapiens

<400> SEQUENCE: 429

Val Lys Asp Arg Asp Thr Gly Arg Ser Ser Ile Val Glu
1               5                   10

<210> SEQ ID NO 430
<211> LENGTH: 15
<212> TYPE: PRT
<213> ORGANISM: Homo sapiens

<400> SEQUENCE: 430

Ala Lys Asp Arg Leu Glu Leu Gly Val Gly Glu Leu Tyr Glu Phe
1               5                   10                  15

<210> SEQ ID NO 431
<211> LENGTH: 13
<212> TYPE: PRT
<213> ORGANISM: Homo sapiens

<400> SEQUENCE: 431

Val Arg Asp Arg Ser Asn Gly Trp Ser Ser Ile Asn Leu
1               5                   10

<210> SEQ ID NO 432
<211> LENGTH: 13
<212> TYPE: PRT
<213> ORGANISM: Homo sapiens

<400> SEQUENCE: 432

Val Lys Asp Arg Asp Asn Gly Trp Ser Ser Ile Val Asp
1               5                   10

<210> SEQ ID NO 433
<211> LENGTH: 13
<212> TYPE: PRT
<213> ORGANISM: Homo sapiens

<400> SEQUENCE: 433

Val Lys Asp Arg Asp Asn Gly Trp Ser Ser Ile Val Asp
1 5 10

<210> SEQ ID NO 434
<211> LENGTH: 13
<212> TYPE: PRT
<213> ORGANISM: Homo sapiens

<400> SEQUENCE: 434

Val Lys Asp Arg Asp Asn Gly Trp Ser Ser Ile Val Asp
1 5 10

<210> SEQ ID NO 435
<211> LENGTH: 13
<212> TYPE: PRT
<213> ORGANISM: Homo sapiens

<400> SEQUENCE: 435

Val Arg Asp Arg Asp Asn Gly Trp Ser Ser Ile Val Asp
1 5 10

<210> SEQ ID NO 436
<211> LENGTH: 13
<212> TYPE: PRT
<213> ORGANISM: Homo sapiens

<400> SEQUENCE: 436

Val Lys Asp Arg Asp Thr Gly Trp Ser Ser Ile Val Asp
1 5 10

<210> SEQ ID NO 437
<211> LENGTH: 13
<212> TYPE: PRT
<213> ORGANISM: Homo sapiens

<400> SEQUENCE: 437

Val Lys Asp Arg Asp Asn Gly Trp Ser Ser Ile Val Asp
1 5 10

<210> SEQ ID NO 438
<211> LENGTH: 13
<212> TYPE: PRT
<213> ORGANISM: Homo sapiens

<400> SEQUENCE: 438

Val Arg Asp Arg Asp Asn Gly Trp Ser Ser Ile Val Asp
1 5 10

<210> SEQ ID NO 439
<211> LENGTH: 13
<212> TYPE: PRT
<213> ORGANISM: Homo sapiens

<400> SEQUENCE: 439

Val Lys Asp Arg Asp Thr Gly Trp Ser Ser Ile Val Asp
1 5 10

<210> SEQ ID NO 440
<211> LENGTH: 13
<212> TYPE: PRT
<213> ORGANISM: Homo sapiens

<400> SEQUENCE: 440

Val Lys Asp Arg Asp Thr Gly Trp Ser Ser Ile Val Asp
1               5                   10

<210> SEQ ID NO 441
<211> LENGTH: 13
<212> TYPE: PRT
<213> ORGANISM: Homo sapiens

<400> SEQUENCE: 441

Val Lys Asp Arg Asp Thr Gly Trp Ser Ser Ile Val Asp
1               5                   10

<210> SEQ ID NO 442
<211> LENGTH: 13
<212> TYPE: PRT
<213> ORGANISM: Homo sapiens

<400> SEQUENCE: 442

Val Lys Asp Arg Gly Thr Gly Trp Ser Ser Ile Val His
1               5                   10

<210> SEQ ID NO 443
<211> LENGTH: 21
<212> TYPE: PRT
<213> ORGANISM: Homo sapiens

<400> SEQUENCE: 443

Ala Arg Gly Lys Ala His Gln Thr Thr Val Val Ile Leu Ser Trp Tyr
1               5                   10                  15

Tyr Gly Met Asp Val
            20

<210> SEQ ID NO 444
<211> LENGTH: 21
<212> TYPE: PRT
<213> ORGANISM: Homo sapiens

<400> SEQUENCE: 444

Ala Arg Gly Lys Asn His Gln Thr Thr Val Ala Val Leu Ser Trp Tyr
1               5                   10                  15

Tyr Gly Met Asp Val
            20

<210> SEQ ID NO 445
<211> LENGTH: 95
<212> TYPE: PRT
<213> ORGANISM: Homo sapiens

<400> SEQUENCE: 445

Ser Ala Ser Val Gly Asp Arg Val Thr Ile Thr Cys Arg Thr Ser Gln
1               5                   10                  15

Thr Ile Ala Asn Trp Leu Ala Trp Tyr Gln Gln Lys Pro Gly Lys Ala
            20                  25                  30

Pro Lys Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Tyr Trp Thr Phe Gly Gln Gly Thr Lys Val Gly Ile Lys
                85                  90                  95

<210> SEQ ID NO 446
<211> LENGTH: 95
<212> TYPE: PRT
<213> ORGANISM: Homo sapiens

<400> SEQUENCE: 446

```
Ser Ala Ser Val Gly Asp Thr Val Thr Ile Thr Cys Arg Ala Ser Gln
1               5                   10                  15

Thr Leu Gly Asn Trp Leu Ala Trp Tyr Gln Gln Lys Pro Gly Lys Ala
            20                  25                  30

Pro Lys Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Phe Trp Thr Phe Gly Gln Gly Thr Lys Val Gly Ile Lys
                85                  90                  95
```

<210> SEQ ID NO 447
<211> LENGTH: 95
<212> TYPE: PRT
<213> ORGANISM: Homo sapiens

<400> SEQUENCE: 447

```
Ser Ala Ser Val Gly Asp Arg Val Thr Ile Thr Cys Arg Ala Ser Gln
1               5                   10                  15

Thr Ile Gly Ser Trp Leu Ala Trp Tyr Gln Gln Lys Pro Gly Lys Ala
            20                  25                  30

Pro Lys Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys His Gln Tyr
65                  70                  75                  80

Ser Thr Tyr Trp Thr Phe Gly Gln Gly Thr Lys Val Gly Met Lys
                85                  90                  95
```

<210> SEQ ID NO 448
<211> LENGTH: 95
<212> TYPE: PRT
<213> ORGANISM: Homo sapiens

<400> SEQUENCE: 448

```
Ser Ala Ser Val Gly Asp Arg Val Thr Ile Thr Cys Arg Ala Ser His
1               5                   10                  15

Asn Ile Gly Gly Leu Leu Ala Trp Tyr Gln Gln Lys Pro Gly Lys Ala
            20                  25                  30

Pro Lys Leu Leu Ile Tyr Gln Ala Ser Arg Leu Glu Ser Gly Val Pro
        35                  40                  45

Ser Arg Phe Ser Gly Ser Gly Ser Gly Thr Glu Phe Thr Leu Thr Ile
    50                  55                  60

Arg Gly Leu Gln Pro Glu Asp Phe Ala Thr Tyr Phe Cys Gln Gln Tyr
65                  70                  75                  80

Ser Thr Tyr Trp Thr Phe Gly Gln Gly Thr Lys Val Ala Ile Lys
                85                  90                  95
```

<210> SEQ ID NO 449
<211> LENGTH: 95
<212> TYPE: PRT
<213> ORGANISM: Homo sapiens

<400> SEQUENCE: 449

Ser Ala Ser Val Gly Asp Arg Val Thr Ile Thr Cys Arg Thr Ser His
1 5 10 15

Thr Ile Gly Asn Trp Leu Ala Trp Tyr Gln Gln Lys Pro Gly Arg Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Arg Ser Leu Gln Pro Glu Asp Phe Ala Thr Tyr Phe Cys Gln Gln Tyr
65 70 75 80

Ser Thr Phe Trp Thr Phe Gly Gln Gly Thr Lys Val Gly Ile Lys
85 90 95

<210> SEQ ID NO 450
<211> LENGTH: 95
<212> TYPE: PRT
<213> ORGANISM: Homo sapiens

<400> SEQUENCE: 450

Ser Ala Ser Val Gly Asp Arg Val Thr Ile Thr Cys Arg Ala Ser Gln
1 5 10 15

Thr Ile Gly Ser Trp Leu Ala Trp Tyr Gln Gln Lys Pro Gly Lys Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Lys Ser Leu Gln Pro Glu Asp Phe Ala Thr Tyr Phe Cys His Gln Tyr
65 70 75 80

Ser Thr Tyr Trp Thr Phe Gly Gln Gly Thr Lys Val Gly Ile Lys
85 90 95

<210> SEQ ID NO 451
<211> LENGTH: 96
<212> TYPE: PRT
<213> ORGANISM: Homo sapiens

<400> SEQUENCE: 451

Ser Ala Ser Val Gly Asp Ser Val Thr Ile Ser Cys Arg Ala Ser Arg
1 5 10 15

Ser Ile Ser Ser Trp Leu Ala Trp Tyr Gln Gln Lys Pro Gly Lys Ala
20 25 30

Pro Lys Leu Leu Ile Tyr Thr Ala Ser Thr Leu Glu Thr Gly Val Pro
35 40 45

Ser Arg Phe Ser Gly Ser Gly Ser Gly Ala Glu Phe Thr Leu Thr Ile
50 55 60

Ser Ser Leu Gln Pro Asp Asp Phe Ala Thr Tyr Tyr Cys Gln Gln Tyr
65 70 75 80

Asn Asn Tyr Pro Trp Thr Phe Gly Gln Gly Thr Thr Val Glu Ile Lys
85 90 95

<210> SEQ ID NO 452

```
<211> LENGTH: 96
<212> TYPE: PRT
<213> ORGANISM: Homo sapiens

<400> SEQUENCE: 452

Ser Ala Ser Val Gly Asp Arg Val Thr Ile Thr Cys Arg Ala Ser Gln
1               5                   10                  15

Asn Ile Asn Ser Trp Leu Ala Trp Tyr Gln Gln Lys Pro Gly Lys Ala
            20                  25                  30

Pro Lys Leu Leu Ile Tyr Met Ala Ser Ser Leu Gln Ser Gly Val Pro
        35                  40                  45

Ser Arg Phe Ser Gly Ser Gly Ser Gly Thr Glu Phe Thr Leu Thr Val
    50                  55                  60

Ser Ser Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Leu Glu Ile Lys
                85                  90                  95


<210> SEQ ID NO 453
<211> LENGTH: 95
<212> TYPE: PRT
<213> ORGANISM: Homo sapiens

<400> SEQUENCE: 453

Ser Ala Ser Val Gly Asp Arg Val Thr Ile Thr Cys Arg Ala Ser Gln
1               5                   10                  15

Asn Val Asp Asn Trp Leu Ala Trp Tyr Gln Gln Lys Pro Gly Lys Ala
            20                  25                  30

Pro Lys Leu Leu Ile Tyr Gln Ala Ser Ile Leu Glu Asn Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Val Ala Thr Tyr Phe Cys Gln Gln Tyr
65                  70                  75                  80

Ser Thr Phe Trp Thr Phe Gly Gln Gly Thr Lys Val Gly Ile Lys
                85                  90                  95


<210> SEQ ID NO 454
<211> LENGTH: 95
<212> TYPE: PRT
<213> ORGANISM: Homo sapiens

<400> SEQUENCE: 454

Ser Ala Ser Val Gly Asp Arg Val Thr Ile Thr Cys Arg Ala Ser Gln
1               5                   10                  15

Thr Ile Ser His Trp Leu Ala Trp Tyr Gln Gln Lys Pro Gly Lys Ala
            20                  25                  30

Pro Lys Leu Leu Ile Tyr Gln Ala Ser Val Leu Glu Thr Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Gly Thr Tyr Phe Cys Gln Gln Tyr
65                  70                  75                  80

Ser Thr Phe Trp Thr Phe Gly Gln Gly Thr Lys Val Glu Ile Lys
                85                  90                  95


<210> SEQ ID NO 455
<211> LENGTH: 95
```

<212> TYPE: PRT
<213> ORGANISM: Homo sapiens

<400> SEQUENCE: 455

Ser Ala Ser Val Gly Asp Thr Val Thr Ile Thr Cys Arg Ala Ser Arg
1 5 10 15

Thr Ile Gly Ser Trp Leu Ala Trp Tyr Gln Gln Lys Pro Gly Lys Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Arg Ser Leu Gln Pro Glu Asp Phe Ala Thr Tyr Phe Cys Gln Gln Tyr
65 70 75 80

Ser Thr Tyr Trp Thr Phe Gly Gln Gly Thr Thr Val Gly Val Lys
85 90 95

<210> SEQ ID NO 456
<211> LENGTH: 95
<212> TYPE: PRT
<213> ORGANISM: Homo sapiens

<400> SEQUENCE: 456

Ser Ala Phe Val Gly Asp Arg Val Thr Ile Thr Cys Arg Ala Ser Gln
1 5 10 15

Thr Ile Gly Asn Trp Leu Ala Trp Tyr Gln Gln Lys Pro Gly Lys Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Arg Ser Leu Gln Pro Glu Asp Phe Ala Thr Tyr Phe Cys Gln Gln Tyr
65 70 75 80

Ser Thr Phe Trp Thr Phe Gly Gln Gly Thr Lys Val Glu Ile Lys
85 90 95

<210> SEQ ID NO 457
<211> LENGTH: 95
<212> TYPE: PRT
<213> ORGANISM: Homo sapiens

<400> SEQUENCE: 457

Ser Ala Ser Val Gly Asp Arg Val Thr Ile Thr Cys Arg Ala Ser Gln
1 5 10 15

Thr Ile Gly Asn Trp Leu Ala Trp Tyr Gln Gln Lys Pro Gly Lys Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Arg Gly Leu Gln Pro Glu Asp Phe Ala Thr Tyr Phe Cys Gln Gln Tyr
65 70 75 80

Ser Thr Tyr Trp Thr Phe Gly Gln Gly Thr Lys Val Gly Ile Lys
85 90 95

<210> SEQ ID NO 458
<211> LENGTH: 95
<212> TYPE: PRT

<213> ORGANISM: Homo sapiens

<400> SEQUENCE: 458

```
Ser Ala Ser Val Gly Asp Arg Val Thr Ile Thr Cys Arg Ala Ser Gln
1               5                   10                  15

Thr Ile Gly Asn Trp Leu Ala Trp Tyr Gln Gln Lys Pro Gly Lys Ala
            20                  25                  30

Pro Lys Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Tyr Trp Thr Phe Gly Gln Gly Thr Lys Val Glu Ile Lys
                85                  90                  95
```

<210> SEQ ID NO 459
<211> LENGTH: 96
<212> TYPE: PRT
<213> ORGANISM: Homo sapiens

<400> SEQUENCE: 459

```
Ser Ala Ser Val Gly Asp Arg Val Thr Ile Thr Cys Arg Ala Ser Gln
1               5                   10                  15

Asn Ile Asn Ser Trp Leu Ala Trp Tyr Gln Gln Lys Pro Gly Lys Ala
            20                  25                  30

Pro Lys Leu Leu Ile Tyr Lys Ala Ser Ser Leu Gln Ser Gly Val Pro
        35                  40                  45

Ser Arg Phe Ser Gly Ser Gly Ser Gly Thr Glu Phe Thr Leu Thr Val
    50                  55                  60

Ser Ser Leu Gln Pro Asp Asp Phe Ala Thr Tyr Tyr Cys Gln His Tyr
65                  70                  75                  80

Tyr Ser Tyr Pro Trp Thr Phe Gly Gln Gly Thr Lys Val Glu Ile Lys
                85                  90                  95
```

<210> SEQ ID NO 460
<211> LENGTH: 95
<212> TYPE: PRT
<213> ORGANISM: Homo sapiens

<400> SEQUENCE: 460

```
Ser Ala Ser Val Gly Asp Arg Val Thr Met Thr Cys Arg Ala Ser Gln
1               5                   10                  15

Thr Ile Ser Gly Trp Leu Ala Trp Tyr Gln Gln Lys Pro Gly Lys Ala
            20                  25                  30

Pro Lys Leu Leu Ile Tyr Gln Ala Ser Arg Leu Glu Ser Gly Ile Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Val Ala Thr Tyr Tyr Cys Gln Gln Tyr
65                  70                  75                  80

Ser Thr Phe Trp Thr Phe Gly Leu Gly Thr Arg Val Glu Ile Lys
                85                  90                  95
```

<210> SEQ ID NO 461
<211> LENGTH: 95
<212> TYPE: PRT
<213> ORGANISM: Homo sapiens

<400> SEQUENCE: 461

Ser Ala Ser Val Gly Asp Arg Val Thr Ile Thr Cys Arg Ala Ser Gln
1 5 10 15

Thr Ile Gly Ser Trp Leu Ala Trp Tyr Gln Gln Lys Pro Gly Lys Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Arg Ser Leu Gln Pro Glu Asp Phe Ala Thr Tyr Phe Cys Gln Gln Tyr
65 70 75 80

Ser Thr Tyr Trp Thr Phe Gly Gln Gly Thr Lys Val Gly Ile Lys
85 90 95

<210> SEQ ID NO 462
<211> LENGTH: 96
<212> TYPE: PRT
<213> ORGANISM: Homo sapiens

<400> SEQUENCE: 462

Ser Ala Ser Val Gly Asp Arg Val Thr Ile Thr Cys Arg Ala Ser Gln
1 5 10 15

Thr Leu Asn Val Trp Leu Ala Trp Tyr Gln Gln Gln Pro Gly Lys Ala
20 25 30

Pro Lys Leu Leu Ile Tyr Lys Ala Ser Thr Leu Gln Ser Gly Val Pro
35 40 45

Ser Arg Phe Ser Gly Ser Gly Ser Gly Thr Glu Phe Thr Leu Thr Ile
50 55 60

Asn Ser Leu Gln Pro Glu Asp Phe Ala Thr Tyr Tyr Cys Gln His Tyr
65 70 75 80

His Ser Tyr Pro Trp Thr Phe Gly Gln Gly Thr Lys Val Glu Ile Lys
85 90 95

<210> SEQ ID NO 463
<211> LENGTH: 95
<212> TYPE: PRT
<213> ORGANISM: Homo sapiens

<400> SEQUENCE: 463

Ser Ala Ser Val Gly Asp Arg Val Thr Ile Thr Cys Arg Ala Ser His
1 5 10 15

Ser Ile Ser Gly Trp Leu Ala Trp Tyr Gln Gln Lys Pro Gly Lys Ala
20 25 30

Pro Lys Leu Leu Ile Tyr Gln Ala Ser Ile Leu Glu Ser Gly Val Pro
35 40 45

Ser Arg Phe Ser Gly Ser Gly Ser Gly Thr Glu Phe Thr Leu Thr Ile
50 55 60

Gly Ser Leu Gln Pro Glu Asp Phe Ala Thr Tyr Phe Cys Gln Gln Tyr
65 70 75 80

Ser Thr Phe Trp Thr Phe Gly Gln Gly Thr Lys Val Glu Ile Lys
85 90 95

<210> SEQ ID NO 464
<211> LENGTH: 95
<212> TYPE: PRT
<213> ORGANISM: Homo sapiens

<400> SEQUENCE: 464

Ser Ala Ser Val Gly Asp Arg Val Thr Ile Thr Cys Arg Ala Ser Gln
1               5                   10                  15

Thr Ile Gly Ser Trp Leu Ala Trp Tyr Gln Gln Lys Pro Gly Lys Ala
            20                  25                  30

Pro Arg Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Phe Trp Thr Phe Gly Gln Gly Thr Lys Val Gly Ile Lys
                85                  90                  95

<210> SEQ ID NO 465
<211> LENGTH: 95
<212> TYPE: PRT
<213> ORGANISM: Homo sapiens

<400> SEQUENCE: 465

Ser Ala Ser Val Gly Asp Arg Val Thr Ile Thr Cys Arg Ala Ser Arg
1               5                   10                  15

Thr Ile Gly Asn Trp Leu Ala Trp Tyr Gln Gln Lys Pro Gly Lys Ala
            20                  25                  30

Pro Lys Leu Leu Ile Tyr Gln Ala Ser Ile Leu Glu Ser Gly Ile Pro
        35                  40                  45

Ser Arg Phe Ser Gly Ser Gly Ser Gly Thr Glu Phe Thr Leu Thr Ile
    50                  55                  60

Arg Gly Leu Gln Pro Glu Asp Phe Gly Thr Tyr Phe Cys Gln Gln Tyr
65                  70                  75                  80

Ser Thr Tyr Trp Thr Phe Gly Gln Gly Thr Lys Val Gly Ile Lys
                85                  90                  95

<210> SEQ ID NO 466
<211> LENGTH: 93
<212> TYPE: PRT
<213> ORGANISM: Homo sapiens

<400> SEQUENCE: 466

Ser Val Gly Asp Arg Val Thr Ile Thr Cys Arg Ala Ser Gln Thr Ile
1               5                   10                  15

Gly Asn Trp Leu Ala Trp Tyr Gln Gln Lys Pro Gly Lys Ala Pro Lys
            20                  25                  30

Leu Leu Ile Tyr Gln Ala Ser Val Leu Glu Ser Gly Val Pro Ser Arg
        35                  40                  45

Phe Ser Gly Ser Gly Ser Gly Thr Glu Phe Thr Leu Thr Ile Ser Ser
    50                  55                  60

Leu Gln Pro Glu Asp Phe Ala Thr Tyr Phe Cys Gln Gln Tyr Ser Thr
65                  70                  75                  80

Phe Trp Thr Phe Gly Gln Gly Thr Lys Val Gly Ile Lys
                85                  90

<210> SEQ ID NO 467
<211> LENGTH: 95
<212> TYPE: PRT
<213> ORGANISM: Homo sapiens

<400> SEQUENCE: 467

```
Ser Ala Ser Val Gly Asp Arg Val Thr Ile Thr Cys Arg Ala Ser Arg
1               5                   10                  15

Thr Ile Gly Ser Trp Leu Ala Trp Tyr Gln Gln Lys Pro Gly Lys Ala
            20                  25                  30

Pro Lys Leu Leu Ile Tyr Gln Ala Ser Ile Leu Glu Gly Gly Val Pro
        35                  40                  45

Ser Arg Phe Ser Gly Ser Val Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Phe Trp Thr Phe Gly Gln Gly Thr Lys Val Glu Ile Lys
                85                  90                  95


<210> SEQ ID NO 468
<211> LENGTH: 95
<212> TYPE: PRT
<213> ORGANISM: Homo sapiens

<400> SEQUENCE: 468

Ser Ala Ser Val Gly Asp Arg Val Thr Ile Thr Cys Arg Ala Ser Gln
1               5                   10                  15

Thr Ile Ala Asn Trp Leu Ala Trp Tyr Gln Gln Lys Pro Gly Gln Pro
            20                  25                  30

Pro Lys Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Phe Trp Thr Phe Gly Gln Gly Thr Lys Val Gly Ile Lys
                85                  90                  95


<210> SEQ ID NO 469
<211> LENGTH: 95
<212> TYPE: PRT
<213> ORGANISM: Homo sapiens

<400> SEQUENCE: 469

Ser Ala Ser Val Gly Asp Arg Val Thr Ile Thr Cys Arg Ala Ser His
1               5                   10                  15

Thr Ile Gly Asn Trp Leu Ala Trp Tyr Gln Gln Lys Pro Gly Lys Ala
            20                  25                  30

Pro Lys Leu Leu Ile Tyr Gln Ala Ser Ile Leu Glu Ser Gly Val Pro
        35                  40                  45

Ser Arg Phe Ser Gly Ser Gly Ser Gly Thr Glu Phe Thr Leu Thr Ile
    50                  55                  60

Arg Ser Leu Gln Pro Glu Asp Phe Ala Thr Tyr Phe Cys Gln Gln Tyr
65                  70                  75                  80

Ser Thr Tyr Trp Thr Phe Gly Gln Gly Thr Lys Val Gly Ile Lys
                85                  90                  95


<210> SEQ ID NO 470
<211> LENGTH: 95
<212> TYPE: PRT
<213> ORGANISM: Homo sapiens

<400> SEQUENCE: 470
```

Ser Ala Ser Val Gly Asp Arg Val Thr Ile Thr Cys Arg Ala Ser His
1 5 10 15

Thr Ile Ser Asn Trp Leu Ala Trp Tyr Gln Gln Lys Pro Gly Lys Ala
20 25 30

Pro Lys Leu Leu Val Tyr Gln Ala Ser Ile Leu Glu Thr Gly Val Pro
35 40 45

Ser Arg Phe Ser Gly Ser Gly Ser Gly Thr Glu Phe Thr Leu Thr Ile
50 55 60

Arg Ser Leu Gln Pro Glu Asp Phe Gly Thr Tyr Phe Cys Gln Gln Tyr
65 70 75 80

Ser Thr Phe Trp Thr Phe Gly Gln Gly Thr Lys Val Glu Ile Lys
85 90 95

<210> SEQ ID NO 471
<211> LENGTH: 95
<212> TYPE: PRT
<213> ORGANISM: Homo sapiens

<400> SEQUENCE: 471

Ser Ala Ser Val Gly Asp Arg Val Thr Ile Thr Cys Arg Ala Ser Gln
1 5 10 15

Thr Ile Ser Asn Trp Leu Ala Trp Tyr Gln Gln Lys Pro Gly Lys Ala
20 25 30

Pro Lys Leu Leu Ile Tyr Gln Ala Ser Ser Leu Glu Ser Gly Val Pro
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Tyr Cys Gln Gln Tyr
65 70 75 80

Ser Thr Tyr Trp Thr Phe Gly Gln Gly Thr Lys Val Glu Ile Lys
85 90 95

<210> SEQ ID NO 472
<211> LENGTH: 96
<212> TYPE: PRT
<213> ORGANISM: Homo sapiens

<400> SEQUENCE: 472

Ser Ala Ser Val Gly Asp Arg Val Thr Ile Thr Cys Arg Ala Ser Gln
1 5 10 15

Gly Ile Ser Ser Trp Leu Ala Trp Tyr Gln Gln Lys Pro Gly Lys Ala
20 25 30

Pro Lys Leu Leu Ile Ser Ala Ala Ser Ser Leu Gln Ser Gly Val Pro
35 40 45

Ser Arg Phe Ser Gly Ser Gly Ser Gly Thr Asp Phe Thr Leu Thr Ile
50 55 60

Ser Ser Leu Gln Pro Glu Asp Phe Ala Thr Tyr Tyr Cys Gln Gln Ala
65 70 75 80

Asn Ser Phe Pro Tyr Thr Phe Gly Gln Gly Thr Lys Leu Glu Ile Lys
85 90 95

<210> SEQ ID NO 473
<211> LENGTH: 96
<212> TYPE: PRT
<213> ORGANISM: Homo sapiens

<400> SEQUENCE: 473

Ser Ala Ser Val Gly Asp Arg Val Thr Ile Thr Cys Arg Ala Ser Gln

```
1               5                   10                  15

Gly Ile Ser Ser Trp Leu Ala Trp Tyr Gln Gln Lys Pro Gly Lys Ala
            20                  25                  30

Pro Lys Leu Leu Ile Ser Ala Ala Ser Ser Leu Gln Ser Gly Val Pro
        35                  40                  45

Ser Arg Phe Ser Gly Ser Gly Ser Gly Thr Asp Phe Thr Leu Thr Ile
    50                  55                  60

Ser Asn Leu Gln Pro Glu Asp Phe Ala Thr Tyr Phe Cys Gln Gln Ala
65                  70                  75                  80

Asn Ser Phe Pro Tyr Thr Phe Gly Gln Gly Thr Lys Leu Glu Ile Lys
                85                  90                  95


<210> SEQ ID NO 474
<211> LENGTH: 8
<212> TYPE: PRT
<213> ORGANISM: Homo sapiens

<400> SEQUENCE: 474

Gln Gln Tyr Ser Thr Tyr Trp Thr
1               5


<210> SEQ ID NO 475
<211> LENGTH: 8
<212> TYPE: PRT
<213> ORGANISM: Homo sapiens

<400> SEQUENCE: 475

Gln Gln Tyr Ser Thr Phe Trp Thr
1               5


<210> SEQ ID NO 476
<211> LENGTH: 8
<212> TYPE: PRT
<213> ORGANISM: Homo sapiens

<400> SEQUENCE: 476

His Gln Tyr Ser Thr Tyr Trp Thr
1               5


<210> SEQ ID NO 477
<211> LENGTH: 8
<212> TYPE: PRT
<213> ORGANISM: Homo sapiens

<400> SEQUENCE: 477

Gln Gln Tyr Ser Thr Tyr Trp Thr
1               5


<210> SEQ ID NO 478
<211> LENGTH: 8
<212> TYPE: PRT
<213> ORGANISM: Homo sapiens

<400> SEQUENCE: 478

Gln Gln Tyr Ser Thr Phe Trp Thr
1               5


<210> SEQ ID NO 479
<211> LENGTH: 8
<212> TYPE: PRT
<213> ORGANISM: Homo sapiens

<400> SEQUENCE: 479
```

His Gln Tyr Ser Thr Tyr Trp Thr
1               5

<210> SEQ ID NO 480
<211> LENGTH: 9
<212> TYPE: PRT
<213> ORGANISM: Homo sapiens

<400> SEQUENCE: 480

Gln Gln Tyr Asn Asn Tyr Pro Trp Thr
1               5

<210> SEQ ID NO 481
<211> LENGTH: 9
<212> TYPE: PRT
<213> ORGANISM: Homo sapiens

<400> SEQUENCE: 481

Gln His Tyr His Ser Tyr Pro Trp Thr
1               5

<210> SEQ ID NO 482
<211> LENGTH: 8
<212> TYPE: PRT
<213> ORGANISM: Homo sapiens

<400> SEQUENCE: 482

Gln Gln Tyr Ser Thr Phe Trp Thr
1               5

<210> SEQ ID NO 483
<211> LENGTH: 8
<212> TYPE: PRT
<213> ORGANISM: Homo sapiens

<400> SEQUENCE: 483

Gln Gln Tyr Ser Thr Phe Trp Thr
1               5

<210> SEQ ID NO 484
<211> LENGTH: 8
<212> TYPE: PRT
<213> ORGANISM: Homo sapiens

<400> SEQUENCE: 484

Gln Gln Tyr Ser Thr Tyr Trp Thr
1               5

<210> SEQ ID NO 485
<211> LENGTH: 8
<212> TYPE: PRT
<213> ORGANISM: Homo sapiens

<400> SEQUENCE: 485

Gln Gln Tyr Ser Thr Phe Trp Thr
1               5

<210> SEQ ID NO 486
<211> LENGTH: 8
<212> TYPE: PRT
<213> ORGANISM: Homo sapiens

<400> SEQUENCE: 486

Gln Gln Tyr Ser Thr Tyr Trp Thr 1 5

<210> SEQ ID NO 487
<211> LENGTH: 8
<212> TYPE: PRT
<213> ORGANISM: Homo sapiens

<400> SEQUENCE: 487

Gln Gln Tyr Ser Thr Tyr Trp Thr
1 5

<210> SEQ ID NO 488
<211> LENGTH: 9
<212> TYPE: PRT
<213> ORGANISM: Homo sapiens

<400> SEQUENCE: 488

Gln His Tyr Tyr Ser Tyr Pro Trp Thr
1 5

<210> SEQ ID NO 489
<211> LENGTH: 8
<212> TYPE: PRT
<213> ORGANISM: Homo sapiens

<400> SEQUENCE: 489

Gln Gln Tyr Ser Thr Phe Trp Thr
1 5

<210> SEQ ID NO 490
<211> LENGTH: 8
<212> TYPE: PRT
<213> ORGANISM: Homo sapiens

<400> SEQUENCE: 490

Gln Gln Tyr Ser Thr Tyr Trp Thr
1 5

<210> SEQ ID NO 491
<211> LENGTH: 9
<212> TYPE: PRT
<213> ORGANISM: Homo sapiens

<400> SEQUENCE: 491

Gln His Tyr His Ser Tyr Pro Trp Thr
1 5

<210> SEQ ID NO 492
<211> LENGTH: 8
<212> TYPE: PRT
<213> ORGANISM: Homo sapiens

<400> SEQUENCE: 492

Gln Gln Tyr Ser Thr Phe Trp Thr
1 5

<210> SEQ ID NO 493
<211> LENGTH: 8
<212> TYPE: PRT
<213> ORGANISM: Homo sapiens

<400> SEQUENCE: 493

Gln Gln Tyr Ser Thr Phe Trp Thr
1 5

<210> SEQ ID NO 494
<211> LENGTH: 8
<212> TYPE: PRT
<213> ORGANISM: Homo sapiens

<400> SEQUENCE: 494

Gln Gln Tyr Ser Thr Tyr Trp Thr
1 5

<210> SEQ ID NO 495
<211> LENGTH: 8
<212> TYPE: PRT
<213> ORGANISM: Homo sapiens

<400> SEQUENCE: 495

Gln Gln Tyr Ser Thr Phe Trp Thr
1 5

<210> SEQ ID NO 496
<211> LENGTH: 8
<212> TYPE: PRT
<213> ORGANISM: Homo sapiens

<400> SEQUENCE: 496

Gln Gln Tyr Ser Thr Phe Trp Thr
1 5

<210> SEQ ID NO 497
<211> LENGTH: 8
<212> TYPE: PRT
<213> ORGANISM: Homo sapiens

<400> SEQUENCE: 497

Gln Gln Tyr Ser Thr Phe Trp Thr
1 5

<210> SEQ ID NO 498
<211> LENGTH: 8
<212> TYPE: PRT
<213> ORGANISM: Homo sapiens

<400> SEQUENCE: 498

Gln Gln Tyr Ser Thr Tyr Trp Thr
1 5

<210> SEQ ID NO 499
<211> LENGTH: 8
<212> TYPE: PRT
<213> ORGANISM: Homo sapiens

<400> SEQUENCE: 499

Gln Gln Tyr Ser Thr Phe Trp Thr
1 5

<210> SEQ ID NO 500
<211> LENGTH: 8
<212> TYPE: PRT
<213> ORGANISM: Homo sapiens

<400> SEQUENCE: 500

Gln Gln Tyr Ser Thr Tyr Trp Thr
1 5

<210> SEQ ID NO 501

<211> LENGTH: 9
<212> TYPE: PRT
<213> ORGANISM: Homo sapiens

<400> SEQUENCE: 501

Gln Gln Ala Asn Ser Phe Pro Tyr Thr
1               5

<210> SEQ ID NO 502
<211> LENGTH: 9
<212> TYPE: PRT
<213> ORGANISM: Homo sapiens

<400> SEQUENCE: 502

Gln Gln Ala Asn Ser Phe Pro Tyr Thr
1               5

<210> SEQ ID NO 503
<211> LENGTH: 116
<212> TYPE: PRT
<213> ORGANISM: Homo sapiens

<400> SEQUENCE: 503

Gly Gly Gly Leu Val Gln Pro Gly Gly Ser Leu Lys Leu Ser Cys Ser
1               5                   10                  15

Ala Ala Gly Phe Asn Phe Arg Ser Tyr Ala Met Ser Trp Ile Arg Gln
            20                  25                  30

Ala Pro Gly Lys Gly Leu Glu Trp Val Ser Ser Leu Gly Thr Arg Gly
        35                  40                  45

Thr Glu Thr Thr Tyr Tyr Ala Ala Ser Val Lys Gly Arg Phe Thr Ile
    50                  55                  60

Ser Arg Asp Asn Ser Lys Asn Ile Leu Tyr Leu Gln Met Asn Ile Leu
65                  70                  75                  80

Gly Ala Glu Asp Thr Ala Val Tyr Tyr Cys Ala Arg Asp Arg Gly Ile
                85                  90                  95

Glu Gly Leu Gly Glu Leu Tyr Ser His Trp Gly Gln Gly Thr Leu Val
            100                 105                 110

Thr Val Ser Ser
        115

<210> SEQ ID NO 504
<211> LENGTH: 115
<212> TYPE: PRT
<213> ORGANISM: Homo sapiens

<400> SEQUENCE: 504

Gly Gly Gly Leu Ala Gln Pro Gly Gly Ser Leu Arg Leu Ser Cys Glu
1               5                   10                  15

Thr Ser Gly Phe Thr Phe Arg Ser Tyr Gly Met Gly Trp Val Arg Gln
            20                  25                  30

Ala Pro Gly Lys Gly Leu Glu Trp Val Ser Ser Ile Tyr Ile Ser Gly
        35                  40                  45

Asp Ser Thr Tyr Tyr Ala Ala Ser Val Lys Gly Arg Phe Thr Ile Ser
    50                  55                  60

Arg Asp Asn Ser Lys Ser Thr Leu Tyr Leu Gln Met Asp Arg Leu Thr
65                  70                  75                  80

Ala Glu Asp Thr Ala Val Tyr Tyr Cys Val Arg Asp Arg Ile Gln Gly
                85                  90                  95

Gly Phe Gly Glu Leu Tyr Arg Tyr Trp Gly Gln Gly Thr Leu Val Thr

```
            100                 105                 110

Val Ser Ser
        115


<210> SEQ ID NO 505
<211> LENGTH: 112
<212> TYPE: PRT
<213> ORGANISM: Homo sapiens

<400> SEQUENCE: 505

Gly Gly Gly Leu Ala Gln Pro Gly Gly Ser Leu Arg Leu Ser Cys Ala
1               5                   10                  15

Ala Ser Gly Phe Thr Phe Ser Ser Tyr Ala Met Thr Trp Val Arg Gln
            20                  25                  30

Ala Pro Gly Lys Gly Leu Glu Trp Val Ser Thr Ile Thr Gly Arg Asp
        35                  40                  45

Gly Ser Thr Tyr Tyr Ala Asp Ser Val Lys Gly Arg Phe Thr Ile Ser
    50                  55                  60

Arg Ala Asn Ser Lys Asn Thr Leu Tyr Leu Gln Met Asn Gly Leu Arg
65                  70                  75                  80

Ala Glu Asp Thr Ala Val Tyr Phe Cys Ala Lys Asp Arg Asp His Phe
                85                  90                  95

Asp Gly His Asp Phe Trp Gly Gln Gly Ala Leu Val Thr Val Ser Ser
            100                 105                 110


<210> SEQ ID NO 506
<211> LENGTH: 115
<212> TYPE: PRT
<213> ORGANISM: Homo sapiens

<400> SEQUENCE: 506

Gly Gly Arg Leu Val Gln Pro Gly Gly Ser Leu Thr Leu Ser Cys Ala
1               5                   10                  15

Ala Ser Gly Phe Pro Phe Ser Thr Tyr Ala Met Ser Trp Leu Arg Gln
            20                  25                  30

Ala Pro Gly Lys Gly Leu Glu Trp Val Ser Gly Ile Thr Gly Asp Ser
        35                  40                  45

Gly Ser Thr Tyr Tyr Ala Ala Ser Val Lys Gly Arg Phe Thr Ile Ser
    50                  55                  60

Arg Asp Asn Ser Lys Asn Thr Leu Tyr Leu Gln Met Asn Ser Leu Thr
65                  70                  75                  80

Ala Asp Asp Thr Ala Val Tyr Tyr Cys Ala Lys Asp Arg Leu His Ser
                85                  90                  95

Gly Leu Gly Glu Leu Phe Ser Tyr Trp Gly Gln Gly Thr Leu Val Thr
            100                 105                 110

Val Ser Ser
        115


<210> SEQ ID NO 507
<211> LENGTH: 115
<212> TYPE: PRT
<213> ORGANISM: Homo sapiens

<400> SEQUENCE: 507

Gly Gly Gly Leu Val Gln Pro Gly Gly Ser Leu Arg Leu Ser Cys Ala
1               5                   10                  15

Ala Ser Gly Phe Ser Phe Arg Thr Tyr Gly Met Ser Trp Val Arg Gln
            20                  25                  30
```

```
Ala Pro Gly Lys Gly Leu Glu Trp Val Ser Ser Ile Ser Ser Val Asp
        35                  40                  45

Asp Ser Thr Tyr Tyr Ala Asp Ser Val Lys Gly Arg Phe Thr Ile Ser
    50                  55                  60

Arg Asp Asn Ser Lys Asn Thr Leu Tyr Leu Gln Met His Asn Leu Ser
65                  70                  75                  80

Ala Lys Asp Thr Ala Leu Tyr Tyr Cys Ala Lys Asp Arg Leu Ala Ser
                85                  90                  95

Gly Ile Gly Glu Leu Phe Ser Ser Trp Gly Gln Gly Thr Leu Val Thr
            100                 105                 110

Val Ala Ser
        115


<210> SEQ ID NO 508
<211> LENGTH: 115
<212> TYPE: PRT
<213> ORGANISM: Homo sapiens

<400> SEQUENCE: 508

Gly Gly Gly Leu Val Gln Pro Gly Gly Ser Leu Arg Leu Ser Cys Ala
1               5                   10                  15

Ala Ser Gly Phe Thr Phe Arg Thr Tyr Gly Met Asn Trp Val Arg Gln
            20                  25                  30

Ala Pro Gly Lys Gly Leu Glu Trp Val Ala Gly Ile Ser Ser Val Asp
        35                  40                  45

Pro Ser Thr Tyr Tyr Ala Gly Ser Val Lys Gly Arg Phe Thr Ile Ser
    50                  55                  60

Arg Asp Asn Ser Lys Asn Met Leu Tyr Leu Gln Met Asn Ser Leu Thr
65                  70                  75                  80

Ala Asp Asp Ser Ala Val Tyr Tyr Cys Ala Lys Asp Arg Met Ser Gly
                85                  90                  95

Gly Phe Gly Glu Leu Asn Glu Ser Trp Gly Gln Gly Thr Arg Val Thr
            100                 105                 110

Val Ser Ser
        115


<210> SEQ ID NO 509
<211> LENGTH: 115
<212> TYPE: PRT
<213> ORGANISM: Homo sapiens

<400> SEQUENCE: 509

Gly Gly Gly Leu Val Gln Pro Gly Gly Ser Leu Arg Leu Ser Cys Val
1               5                   10                  15

Ala Ser Gly Phe Thr Phe Gly Ser Tyr Gly Met Ala Trp Val Arg Gln
            20                  25                  30

Ala Pro Gly Lys Gly Leu Glu Trp Ile Ser Ser Ile Ser Ser Ile Asp
        35                  40                  45

Pro Ser Thr Tyr Tyr Ala Asp Ser Val Lys Gly Arg Phe Thr Val Ser
    50                  55                  60

Arg Asp Asn Ser Glu Asn Thr Leu Tyr Leu His Met Ser Ser Leu Lys
65                  70                  75                  80

Val Glu Asp Thr Ala Val Tyr Phe Cys Ala Lys Asp Arg Leu Asn Gly
                85                  90                  95

Gly Phe Gly Glu Leu Phe Ala Ser Trp Gly Gln Gly Thr Leu Val Thr
            100                 105                 110
```

```
Val Ser Ser
        115


<210> SEQ ID NO 510
<211> LENGTH: 115
<212> TYPE: PRT
<213> ORGANISM: Homo sapiens

<400> SEQUENCE: 510

Gly Gly Gly Leu Gly Gln Pro Gly Gly Ser Leu Arg Leu Ser Cys Ala
1               5                   10                  15

Ala Ser Gly Phe Pro Phe Ser Asp Phe Gly Met Ser Trp Val Arg Gln
            20                  25                  30

Ala Pro Gly Lys Gly Leu Glu Trp Val Ser Ser Ile Ser Gly Pro Gly
        35                  40                  45

Phe Asp Thr Tyr Tyr Ala Asp Ser Val Lys Gly Arg Phe Thr Ile Ser
    50                  55                  60

Arg Asp Asn Ser Lys Asp Thr Leu Phe Leu Gln Met Ser Arg Leu Arg
65                  70                  75                  80

Val Glu Asp Thr Ala Val Tyr Tyr Cys Ala Arg Asp Arg Ile Lys Gly
                85                  90                  95

Gly Leu Gly Glu Leu Phe His Leu Trp Gly Gln Gly Ala Leu Val Thr
            100                 105                 110

Val Ser Ser
        115


<210> SEQ ID NO 511
<211> LENGTH: 115
<212> TYPE: PRT
<213> ORGANISM: Homo sapiens

<400> SEQUENCE: 511

Gly Gly Gly Leu Val Gln Pro Gly Gly Ser Leu Arg Leu Ser Cys Ala
1               5                   10                  15

Ala Ser Gly Phe Thr Phe Asn Thr His Ala Met Ala Trp Leu Arg Gln
            20                  25                  30

Ala Pro Gly Lys Gly Leu Glu Trp Val Ser Ser Val Thr Ala Asn Gly
        35                  40                  45

Gly Asp Ser Trp Tyr Ala Asp Ser Val Lys Gly Arg Phe Thr Ile Ser
    50                  55                  60

Arg Asp Asn Ser Arg Asn Ile Leu Tyr Leu Gln Met Ser Ser Leu Arg
65                  70                  75                  80

Val Glu Asp Thr Ala Val Tyr Tyr Cys Ala Lys Asp Arg Leu Ala Ala
                85                  90                  95

Gly Leu Gly Glu Leu Phe Ser His Trp Gly Gln Gly Thr Leu Val Ser
            100                 105                 110

Val Ser Ser
        115


<210> SEQ ID NO 512
<211> LENGTH: 115
<212> TYPE: PRT
<213> ORGANISM: Homo sapiens

<400> SEQUENCE: 512

Gly Gly Gly Leu Val Gln Pro Gly Gly Ser Leu Arg Leu Ser Cys Ala
1               5                   10                  15
```

-continued

```
Ala Ser Gly Phe Thr Phe Ser Thr Tyr Ala Met Ser Trp Val Arg Gln
            20                  25                  30

Ala Pro Gly Lys Gly Leu Lys Trp Val Ser Gly Ile Thr Gly Asp Ser
        35                  40                  45

Gly Ser Thr Tyr Tyr Ala Arg Ser Val Lys Gly Arg Phe Thr Ile Ser
    50                  55                  60

Arg Asp Asn Ser Lys Asn Thr Leu Tyr Leu Glu Ile Ser Ser Leu Arg
65                  70                  75                  80

Ala Glu Asp Thr Ala Phe Tyr Phe Cys Thr Arg Asp Arg Leu Pro Asn
                85                  90                  95

Gly Ile Gly Glu Leu His Asp His Trp Gly Gln Gly Thr Leu Val Thr
            100                 105                 110

Val Ser Ser
        115


<210> SEQ ID NO 513
<211> LENGTH: 115
<212> TYPE: PRT
<213> ORGANISM: Homo sapiens

<400> SEQUENCE: 513

Gly Gly Gly Leu Val Gln Pro Gly Gly Ser Leu Arg Leu Ser Cys Ala
1               5                   10                  15

Ala Ser Gly Phe Thr Phe Arg Thr Tyr Gly Met Asn Trp Val Arg Gln
            20                  25                  30

Ala Pro Gly Lys Gly Leu Glu Trp Val Ser Gly Ile Ser Gly Ile Asp
        35                  40                  45

Pro Ser Thr Tyr Tyr Ala Asp Ser Val Lys Gly Arg Phe Thr Ile Ser
    50                  55                  60

Arg Asp Asn Ser Lys Asn Ile Leu Phe Leu Gln Met Asn Ser Leu Thr
65                  70                  75                  80

Ala Asp Asp Thr Ala Val Tyr Tyr Cys Thr Lys Asp Arg Leu Ser Gly
                85                  90                  95

Ala Phe Gly Glu Leu Asn Glu Ser Trp Gly Gln Gly Thr Met Val Ile
            100                 105                 110

Val Ser Ser
        115


<210> SEQ ID NO 514
<211> LENGTH: 115
<212> TYPE: PRT
<213> ORGANISM: Homo sapiens

<400> SEQUENCE: 514

Gly Gly Ala Leu Val Gln Pro Gly Gly Ser Leu Arg Leu Ser Cys Ala
1               5                   10                  15

Ala Ser Gly Phe Thr Phe Arg Asn Tyr Gly Val Ser Trp Val Arg Gln
            20                  25                  30

Ala Pro Gly Lys Gly Leu Glu Trp Val Ser Ser Ile Asn Thr Asp Gly
        35                  40                  45

Gly Ser Thr Tyr Tyr Ala Ala Ser Val Lys Gly Arg Phe Thr Ile Ser
    50                  55                  60

Arg Asp Asn Ser Arg Asn Thr Leu Tyr Leu Gln Met Asp Gly Leu Thr
65                  70                  75                  80

Val Ala Asp Thr Ala Met Tyr Phe Cys Thr Lys Asp Arg Val Gln Gly
                85                  90                  95
```

```
Gly Phe Gly Glu Leu Phe His Ser Trp Gly Gln Gly Thr Leu Val Thr
            100                 105                 110

Val Ser Pro
        115


<210> SEQ ID NO 515
<211> LENGTH: 121
<212> TYPE: PRT
<213> ORGANISM: Homo sapiens

<400> SEQUENCE: 515

Gly Gly Gly Leu Ile Gln Pro Gly Gly Ser Leu Arg Leu Ser Cys Ala
1               5                   10                  15

Ala Ser Gly Phe Thr Phe Ser Ser Tyr Ala Met Ser Trp Val Arg Gln
            20                  25                  30

Ala Pro Gly Lys Gly Leu Glu Trp Val Ser Gly Ile Ser Gly Ser Gly
        35                  40                  45

Gly Ala Ser Asp Asn Gly Ala Ser Arg Tyr Tyr Ala Asp Ser Val Lys
    50                  55                  60

Gly Arg Phe Ser Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Lys Asp Arg Leu Ser Gly Gly Phe Gly Glu Leu Phe Gln Lys Trp Gly
            100                 105                 110

Gln Gly Thr Leu Val Thr Val Ser Ser
        115                 120


<210> SEQ ID NO 516
<211> LENGTH: 115
<212> TYPE: PRT
<213> ORGANISM: Homo sapiens

<400> SEQUENCE: 516

Gly Gly Asp Leu Val Gln Pro Gly Gly Ser Leu Arg Leu Ser Cys Ala
1               5                   10                  15

Ala Ser Gly Phe Thr Phe Ser Thr Tyr Gly Met Ala Trp Val Arg Gln
            20                  25                  30

Ala Pro Gly Lys Gly Leu Glu Trp Leu Ser Ser Ile Ser Ser Val Asp
        35                  40                  45

Asp Ser Lys Tyr Tyr Ala Ala Ser Val Lys Gly Arg Phe Thr Ile Ser
    50                  55                  60

Arg Asp Asn Ser Arg Asn Thr Leu Tyr Leu His Met Asn Ser Leu Arg
65                  70                  75                  80

Val Asp Asp Thr Ala Val Tyr Tyr Cys Ala Lys Asp Arg Ile Pro His
                85                  90                  95

Gly Leu Gly Glu Leu Tyr Ala Asn Trp Gly Gln Gly Thr Leu Val Ala
            100                 105                 110

Val Ser Ser
        115


<210> SEQ ID NO 517
<211> LENGTH: 115
<212> TYPE: PRT
<213> ORGANISM: Homo sapiens

<400> SEQUENCE: 517

Gly Gly Asp Leu Val Gln Pro Gly Gly Ser Leu Arg Leu Ser Cys Ala
```

-continued

```
1               5                   10                  15

Ala Ser Gly Phe Thr Phe Arg Thr Tyr Gly Met Thr Trp Val Arg Gln
            20                  25                  30

Ala Pro Gly Lys Gly Leu Glu Trp Val Ser Ser Ile Ser Ser Val Asp
        35                  40                  45

Asp Ser Thr Tyr Tyr Ala Lys Ser Val Lys Gly Arg Phe Thr Ile Ser
    50                  55                  60

Arg Asp Asn Ser Lys Asn Thr Leu Tyr Leu His Ile Thr Asn Leu Arg
65                  70                  75                  80

Val Asp Asp Thr Ala Met Tyr Tyr Cys Ala Lys Asp Arg Ser Pro His
                85                  90                  95

Gly Leu Gly Glu Leu Tyr Gly Asp Trp Gly Gln Gly Thr Leu Val Thr
            100                 105                 110

Val Ser Ser
        115


<210> SEQ ID NO 518
<211> LENGTH: 113
<212> TYPE: PRT
<213> ORGANISM: Homo sapiens

<400> SEQUENCE: 518

Gly Gly Gly Leu Val Lys Pro Gly Gly Ser Leu Arg Leu Ser Cys Ala
1               5                   10                  15

Ala Ser Gly Leu Thr Phe Ser Thr Tyr Ala Met Ser Trp Val Arg Gln
            20                  25                  30

Ala Pro Gly Lys Gly Leu Glu Trp Val Ser Ala Ile Ser Pro Gly Ser
        35                  40                  45

Gly Asp Asn Ile Tyr Tyr Gly Asp Ser Val Lys Gly Arg Phe Thr Ile
    50                  55                  60

Ser Arg Asp Asn Ser Lys Asn Thr Leu Tyr Leu Gln Met Asn Ser Leu
65                  70                  75                  80

Arg Ala Glu Asp Thr Ala Val Tyr Tyr Cys Val Asn Gly Gly Phe Ser
                85                  90                  95

Gly Tyr Tyr Ser Asp Tyr Trp Gly Gln Gly Thr Leu Val Ala Val Ser
            100                 105                 110

Ser


<210> SEQ ID NO 519
<211> LENGTH: 117
<212> TYPE: PRT
<213> ORGANISM: Homo sapiens

<400> SEQUENCE: 519

Gly Gly Gly Leu Gly Gln Pro Gly Gly Ser Leu Arg Leu Ser Cys Gly
1               5                   10                  15

Ala Ser Gly Phe Thr Phe Ser Thr Tyr Ala Met Thr Trp Val Arg Gln
            20                  25                  30

Ala Pro Gly Lys Gly Leu Glu Trp Val Ser Asp Ile Ser Ala Asp Ser
        35                  40                  45

Asp Thr Thr Ser Tyr Ala Asp Ser Val Lys Gly Arg Phe Thr Ile Ser
    50                  55                  60

Arg Asp Asn Ser Lys Asn Thr Leu Tyr Leu Gln Met Asn Ser Leu Arg
65                  70                  75                  80

Ala Glu Asp Ser Ala Val Tyr Tyr Cys Ala Lys Val Lys Asp Ser Ser
                85                  90                  95
```

```
Gly Tyr Met Tyr Tyr Tyr Tyr Met Asp Val Trp Gly Lys Gly Thr Thr
            100                 105                 110

Val Thr Val Ser Ser
        115
```

<210> SEQ ID NO 520
<211> LENGTH: 111
<212> TYPE: PRT
<213> ORGANISM: Homo sapiens

<400> SEQUENCE: 520

```
Gly Gly Gly Leu Val Leu Pro Gly Gly Ser Leu Arg Leu Ser Cys Ala
1               5                   10                  15

Ala Ser Gly Phe Thr Phe Ser Thr His Ala Met Thr Trp Val Arg Gln
            20                  25                  30

Ala Pro Gly Lys Gly Leu Glu Trp Val Ser Val Ile Ser His Ser Gly
        35                  40                  45

Thr Thr Thr Tyr Tyr Ala Asp Ser Phe Arg Gly Arg Phe Thr Ile Ser
    50                  55                  60

Arg Asp Asn Ser Lys Asn Thr Val Tyr Leu Gln Met Asn Arg Leu Arg
65                  70                  75                  80

Val Glu Asp Thr Ala Val Tyr Tyr Cys Ala Lys Asp Leu Tyr Asn Gly
                85                  90                  95

Tyr Phe Asp Tyr Trp Gly Gln Gly Thr Leu Val Thr Val Ser Ser
            100                 105                 110
```

<210> SEQ ID NO 521
<211> LENGTH: 110
<212> TYPE: PRT
<213> ORGANISM: Homo sapiens

<400> SEQUENCE: 521

```
Gly Gly Gly Val Val Gln Pro Gly Arg Ser Leu Arg Leu Ser Cys Ala
1               5                   10                  15

Ala Ser Gly Phe Thr Phe Ser Ile Ser Thr Ile His Trp Val Arg Gln
            20                  25                  30

Ala Pro Gly Lys Gly Leu Glu Tyr Val Val Val Ile Ser His Asp Gly
        35                  40                  45

Asn Thr Lys Tyr Tyr Ala Asp Ser Val Lys Gly Arg Phe Ile Ile Ser
    50                  55                  60

Arg Asp Asn Ser Lys Asn Thr Val Phe Leu Gln Met Asn Ser Leu Arg
65                  70                  75                  80

Pro Val Asp Thr Ala Val Tyr Tyr Cys Ala Arg Gly Glu Val Gly Tyr
                85                  90                  95

Phe Asp Leu Trp Gly Arg Gly Thr Leu Val Thr Val Ser Ser
            100                 105                 110
```

<210> SEQ ID NO 522
<211> LENGTH: 113
<212> TYPE: PRT
<213> ORGANISM: Homo sapiens

<400> SEQUENCE: 522

```
Gly Gly Gly Val Val Gln Pro Gly Arg Ser Leu Arg Leu Ser Cys Ala
1               5                   10                  15

Ala Ser Gly Phe Ser Phe Ser Ser His Ala Met Tyr Trp Val Arg Gln
            20                  25                  30
```

```
Ala Pro Gly Lys Gly Leu Glu Trp Val Ala Ile Val Ser Tyr Asp Gly
        35                  40                  45

Ser Thr Lys Asn Tyr Ala Asp Ser Val Lys Gly Arg Phe Thr Ile Ser
    50                  55                  60

Arg Asp Asn Ser Lys Asn Thr Ile Tyr Leu His Leu Asn Ser Leu Arg
65                  70                  75                  80

Ala Glu Asp Thr Ala Val Tyr Phe Cys Ala Arg Glu Val Asp Gly Ile
                85                  90                  95

Tyr Gly Tyr Leu His Tyr Trp Gly Gln Gly Thr Leu Val Thr Val Ser
            100                 105                 110

Ser


<210> SEQ ID NO 523
<211> LENGTH: 114
<212> TYPE: PRT
<213> ORGANISM: Homo sapiens

<400> SEQUENCE: 523

Gly Gly Gly Val Val Gln Pro Gly Arg Ser Leu Arg Leu Ser Cys Ala
1               5                   10                  15

Ala Ser Gly Phe Thr Phe Ser Asn Tyr Gly Met His Trp Val Arg Gln
            20                  25                  30

Ala Pro Gly Lys Gly Leu Glu Trp Val Ala Ile Ile Ser Tyr Asp Gly
        35                  40                  45

Asn Thr Lys Tyr Tyr Ala Asp Ser Val Lys Gly Arg Phe Thr Ile Ser
    50                  55                  60

Arg Asp Asn Ser Lys Asn Thr Leu Tyr Leu Gln Leu Asn Ser Leu Arg
65                  70                  75                  80

Ala Glu Asp Thr Ala Ile Tyr Tyr Cys Ala Arg Asp Gly Thr Thr Val
                85                  90                  95

Thr Asn Phe Tyr Leu Asp Val Trp Gly Lys Gly Ser Thr Val Thr Val
            100                 105                 110

Ser Ser


<210> SEQ ID NO 524
<211> LENGTH: 110
<212> TYPE: PRT
<213> ORGANISM: Homo sapiens

<400> SEQUENCE: 524

Gly Gly Gly Val Val Gln Pro Gly Arg Ser Leu Arg Leu Ser Cys Ala
1               5                   10                  15

Ala Ser Gly Phe Thr Phe Asn Thr Tyr Ala Val His Trp Val Arg Gln
            20                  25                  30

Ala Pro Gly Lys Gly Leu Asp Trp Val Thr Val Leu Ser His Asp Gly
        35                  40                  45

Asn Ser Lys Tyr Tyr Thr Asp Ser Val Arg Gly Arg Phe Thr Ile Ser
    50                  55                  60

Arg Asp Ser Ser Lys Lys Thr Val Phe Leu Gln Met Asp Asn Leu Arg
65                  70                  75                  80

Thr Glu Asp Thr Ala Val Tyr Tyr Cys Ala Arg Asp Phe His Gly Tyr
                85                  90                  95

Leu Asp Ser Trp Gly Gln Gly Thr Leu Val Thr Val Ser Ser
            100                 105                 110


<210> SEQ ID NO 525
```

<211> LENGTH: 116
<212> TYPE: PRT
<213> ORGANISM: Homo sapiens

<400> SEQUENCE: 525

Gly Pro Gly Leu Val Lys Pro Ser Glu Thr Leu Ser Leu Thr Cys Gly
1 5 10 15

Val Ser Gly Tyr Ser Leu Thr Ser Gly Tyr Tyr Trp Ser Trp Ile Arg
20 25 30

Gln Pro Pro Gly Lys Gly Leu Glu Trp Ile Gly Ser Ile Tyr His Thr
35 40 45

Gly Asn Thr Tyr Tyr Asn Pro Ser Leu Lys Ser Arg Val Thr Ile Leu
50 55 60

Val Asp Thr Ser Lys Asn His Phe Ser Leu Lys Leu Thr Ser Val Thr
65 70 75 80

Ala Ala Asp Thr Ala Met Tyr Tyr Cys Ala Arg Thr Glu Thr Ile Thr
85 90 95

Ile Arg Gly Ala Val Ser Phe Asp Ile Trp Gly Gln Gly Arg Met Val
100 105 110

Thr Val Ser Ser
115

<210> SEQ ID NO 526
<211> LENGTH: 123
<212> TYPE: PRT
<213> ORGANISM: Homo sapiens

<400> SEQUENCE: 526

Gly Pro Gly Leu Val Lys Pro Ser Glu Thr Leu Ser Leu Thr Cys Ser
1 5 10 15

Val Ser Gly Tyr Phe Ile Ser Ser Gly His Tyr Trp Gly Trp Ile Arg
20 25 30

Gln Ser Pro Gly Lys Gly Leu Glu Trp Ile Ala Ser Ile Tyr Gln Ser
35 40 45

Gly Ser Lys Phe Gln Thr Gly Asn Thr Tyr Tyr Asn Pro Ser Leu Glu
50 55 60

Ser Arg Val Thr Ile Ser Met Asp Thr Ser Lys Asn Gln Phe Ser Leu
65 70 75 80

Lys Leu Ser Ser Val Thr Ala Ala Asp Thr Ala Val Tyr Phe Cys Ala
85 90 95

Arg Asp Ala Arg Ser Arg Ser Trp Asp Arg Thr Gly Phe Phe Gly Pro
100 105 110

Trp Gly Gln Gly Ile Leu Val Thr Ile Ser Ser
115 120

<210> SEQ ID NO 527
<211> LENGTH: 15
<212> TYPE: PRT
<213> ORGANISM: Homo sapiens

<400> SEQUENCE: 527

Ala Arg Asp Arg Gly Ile Glu Gly Leu Gly Glu Leu Tyr Ser His
1 5 10 15

<210> SEQ ID NO 528
<211> LENGTH: 15
<212> TYPE: PRT
<213> ORGANISM: Homo sapiens

<400> SEQUENCE: 528

Val Arg Asp Arg Ile Gln Gly Gly Phe Gly Glu Leu Tyr Arg Tyr
1 5 10 15

<210> SEQ ID NO 529
<211> LENGTH: 12
<212> TYPE: PRT
<213> ORGANISM: Homo sapiens

<400> SEQUENCE: 529

Ala Lys Asp Arg Asp His Phe Asp Gly His Asp Phe
1 5 10

<210> SEQ ID NO 530
<211> LENGTH: 15
<212> TYPE: PRT
<213> ORGANISM: Homo sapiens

<400> SEQUENCE: 530

Ala Lys Asp Arg Leu His Ser Gly Leu Gly Glu Leu Phe Ser Tyr
1 5 10 15

<210> SEQ ID NO 531
<211> LENGTH: 15
<212> TYPE: PRT
<213> ORGANISM: Homo sapiens

<400> SEQUENCE: 531

Ala Lys Asp Arg Leu Ala Ser Gly Ile Gly Glu Leu Phe Ser Ser
1 5 10 15

<210> SEQ ID NO 532
<211> LENGTH: 15
<212> TYPE: PRT
<213> ORGANISM: Homo sapiens

<400> SEQUENCE: 532

Ala Lys Asp Arg Met Ser Gly Gly Phe Gly Glu Leu Asn Glu Ser
1 5 10 15

<210> SEQ ID NO 533
<211> LENGTH: 15
<212> TYPE: PRT
<213> ORGANISM: Homo sapiens

<400> SEQUENCE: 533

Ala Lys Asp Arg Leu Asn Gly Gly Phe Gly Glu Leu Phe Ala Ser
1 5 10 15

<210> SEQ ID NO 534
<211> LENGTH: 15
<212> TYPE: PRT
<213> ORGANISM: Homo sapiens

<400> SEQUENCE: 534

Ala Arg Asp Arg Ile Lys Gly Gly Leu Gly Glu Leu Phe His Leu
1 5 10 15

<210> SEQ ID NO 535
<211> LENGTH: 15
<212> TYPE: PRT
<213> ORGANISM: Homo sapiens

<400> SEQUENCE: 535

Ala Lys Asp Arg Leu Ala Ala Gly Leu Gly Glu Leu Phe Ser His
1 5 10 15

<210> SEQ ID NO 536
<211> LENGTH: 15
<212> TYPE: PRT
<213> ORGANISM: Homo sapiens

<400> SEQUENCE: 536

Thr Arg Asp Arg Leu Pro Asn Gly Ile Gly Glu Leu His Asp His
1 5 10 15

<210> SEQ ID NO 537
<211> LENGTH: 15
<212> TYPE: PRT
<213> ORGANISM: Homo sapiens

<400> SEQUENCE: 537

Thr Lys Asp Arg Leu Ser Gly Ala Phe Gly Glu Leu Asn Glu Ser
1 5 10 15

<210> SEQ ID NO 538
<211> LENGTH: 15
<212> TYPE: PRT
<213> ORGANISM: Homo sapiens

<400> SEQUENCE: 538

Thr Lys Asp Arg Val Gln Gly Gly Phe Gly Glu Leu Phe His Ser
1 5 10 15

<210> SEQ ID NO 539
<211> LENGTH: 15
<212> TYPE: PRT
<213> ORGANISM: Homo sapiens

<400> SEQUENCE: 539

Ala Lys Asp Arg Leu Ser Gly Gly Phe Gly Glu Leu Phe Gln Lys
1 5 10 15

<210> SEQ ID NO 540
<211> LENGTH: 15
<212> TYPE: PRT
<213> ORGANISM: Homo sapiens

<400> SEQUENCE: 540

Ala Lys Asp Arg Ile Pro His Gly Leu Gly Glu Leu Tyr Ala Asn
1 5 10 15

<210> SEQ ID NO 541
<211> LENGTH: 15
<212> TYPE: PRT
<213> ORGANISM: Homo sapiens

<400> SEQUENCE: 541

Ala Lys Asp Arg Ser Pro His Gly Leu Gly Glu Leu Tyr Gly Asp
1 5 10 15

<210> SEQ ID NO 542
<211> LENGTH: 12
<212> TYPE: PRT
<213> ORGANISM: Homo sapiens

<400> SEQUENCE: 542

Val Asn Gly Gly Phe Ser Gly Tyr Tyr Ser Asp Tyr
1 5 10

<210> SEQ ID NO 543
<211> LENGTH: 17
<212> TYPE: PRT
<213> ORGANISM: Homo sapiens

<400> SEQUENCE: 543

```
Ala Lys Val Lys Asp Ser Ser Gly Tyr Met Tyr Tyr Tyr Tyr Met Asp
1               5                   10                  15

Val
```

<210> SEQ ID NO 544
<211> LENGTH: 11
<212> TYPE: PRT
<213> ORGANISM: Homo sapiens

<400> SEQUENCE: 544

```
Ala Lys Asp Leu Tyr Asn Gly Tyr Phe Asp Tyr
1               5                   10
```

<210> SEQ ID NO 545
<211> LENGTH: 10
<212> TYPE: PRT
<213> ORGANISM: Homo sapiens

<400> SEQUENCE: 545

```
Ala Arg Gly Glu Val Gly Tyr Phe Asp Leu
1               5                   10
```

<210> SEQ ID NO 546
<211> LENGTH: 13
<212> TYPE: PRT
<213> ORGANISM: Homo sapiens

<400> SEQUENCE: 546

```
Ala Arg Glu Val Asp Gly Ile Tyr Gly Tyr Leu His Tyr
1               5                   10
```

<210> SEQ ID NO 547
<211> LENGTH: 14
<212> TYPE: PRT
<213> ORGANISM: Homo sapiens

<400> SEQUENCE: 547

```
Ala Arg Asp Gly Thr Thr Val Thr Asn Phe Tyr Leu Asp Val
1               5                   10
```

<210> SEQ ID NO 548
<211> LENGTH: 10
<212> TYPE: PRT
<213> ORGANISM: Homo sapiens

<400> SEQUENCE: 548

```
Ala Arg Asp Phe His Gly Tyr Leu Asp Ser
1               5                   10
```

<210> SEQ ID NO 549
<211> LENGTH: 16
<212> TYPE: PRT
<213> ORGANISM: Homo sapiens

<400> SEQUENCE: 549

```
Ala Arg Thr Glu Thr Ile Thr Ile Arg Gly Ala Val Ser Phe Asp Ile
1               5                   10                  15
```

<210> SEQ ID NO 550
<211> LENGTH: 17
<212> TYPE: PRT
<213> ORGANISM: Homo sapiens

<400> SEQUENCE: 550

Ala Arg Asp Ala Arg Ser Arg Ser Trp Asp Arg Thr Gly Phe Phe Gly
1 5 10 15

Pro

<210> SEQ ID NO 551
<211> LENGTH: 96
<212> TYPE: PRT
<213> ORGANISM: Homo sapiens

<400> SEQUENCE: 551

Ser Ala Ser Val Gly Asp Arg Val Thr Ile Thr Cys Arg Ala Ser Gln
1 5 10 15

Ser Ile Asn Ser Trp Val Ala Trp Tyr Gln Gln Lys Pro Gly Lys Ala
20 25 30

Pro Lys Phe Leu Ile Tyr Lys Ala Ser Thr Leu Glu Ser Gly Val Pro
35 40 45

Ser Arg Phe Ser Gly Ser Gly Ser Gly Thr Glu Phe Thr Leu Thr Ile
50 55 60

Thr Ser Leu Gln Pro Asp Asp Phe Ala Thr Tyr Tyr Cys Gln His Tyr
65 70 75 80

Tyr Ser Tyr Pro Trp Thr Phe Gly Gln Gly Thr Lys Val Glu Ile Lys
85 90 95

<210> SEQ ID NO 552
<211> LENGTH: 96
<212> TYPE: PRT
<213> ORGANISM: Homo sapiens

<400> SEQUENCE: 552

Ser Ala Ser Val Gly Asp Arg Val Thr Met Thr Cys Arg Ala Ser Gln
1 5 10 15

Ser Val Asn Lys Trp Leu Ala Trp Tyr Gln Gln Lys Pro Gly Lys Ala
20 25 30

Pro Lys Leu Leu Ile Tyr Glu Thr Ser Ile Leu Glu Ser Gly Val Ser
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Tyr Cys Gln His Tyr
65 70 75 80

His Gly Tyr Pro Trp Thr Phe Gly Gln Gly Thr Lys Val Glu Ile Arg
85 90 95

<210> SEQ ID NO 553
<211> LENGTH: 96
<212> TYPE: PRT
<213> ORGANISM: Homo sapiens

<400> SEQUENCE: 553

Ser Ala Ala Val Gly Asp Ser Val Thr Ile Thr Cys Arg Ala Ser Gln
1 5 10 15

Ser Ile Ser Ser Trp Leu Ala Trp Tyr Gln Gln Lys Pro Gly Arg Ala
20 25 30

```
Pro Lys Leu Leu Ile Ser Lys Ala Ser Asn Val Glu Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln Lys Tyr
65                  70                  75                  80

Asn Ser Tyr Pro Phe Thr Phe Gly Pro Gly Thr Lys Leu Asp Ile Lys
                85                  90                  95
```

<210> SEQ ID NO 554
<211> LENGTH: 96
<212> TYPE: PRT
<213> ORGANISM: Homo sapiens

<400> SEQUENCE: 554

```
Ser Ala Ser Val Gly Asp Arg Val Asn Ile Thr Cys Arg Ala Ser Gln
1               5                   10                  15

Ser Ile Asn Gln Trp Leu Ala Trp Tyr Gln Gln Lys Pro Gly Lys Ala
            20                  25                  30

Pro Lys Phe Leu Met Tyr Lys Ala Ser Thr Leu Glu Thr Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

Phe Ser Tyr Pro Trp Thr Phe Gly Gln Gly Thr Lys Val Glu Ile Lys
                85                  90                  95
```

<210> SEQ ID NO 555
<211> LENGTH: 96
<212> TYPE: PRT
<213> ORGANISM: Homo sapiens

<400> SEQUENCE: 555

```
Ser Ala Ser Val Gly Asp Arg Val Thr Ile Thr Cys Arg Ala Ser Gln
1               5                   10                  15

Asn Ile Asp Met Trp Leu Ala Trp Tyr Gln Gln Lys Pro Gly Arg Ala
            20                  25                  30

Pro Lys Phe Leu Ile His Lys Ala Ser Thr Leu Glu Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Asp Ile Lys
                85                  90                  95
```

<210> SEQ ID NO 556
<211> LENGTH: 96
<212> TYPE: PRT
<213> ORGANISM: Homo sapiens

<400> SEQUENCE: 556

```
Ser Ala Ser Val Gly Asp Arg Val Thr Ile Thr Cys Arg Ala Ser Gln
1               5                   10                  15

Ser Ile Ser Gly Trp Leu Ala Trp Tyr Gln Gln Lys Pro Gly Arg Ala
            20                  25                  30
```

Pro Asn Leu Leu Ile Tyr Gln Ala Ser Ala Leu His Ser Gly Val Pro
35 40 45

Ser Arg Phe Ser Gly Ser Gly Ser Gly Thr Glu Phe Ser Leu Thr Ile
50 55 60

Ser Ser Leu Gln Pro Asp Asp Phe Ala Thr Tyr Tyr Cys Gln His Tyr
65 70 75 80

Phe Ser Tyr Pro Trp Thr Phe Gly Gln Gly Thr Lys Val Glu Ile Lys
85 90 95

<210> SEQ ID NO 557
<211> LENGTH: 96
<212> TYPE: PRT
<213> ORGANISM: Homo sapiens

<400> SEQUENCE: 557

Ser Ala Ser Val Gly Asp Ser Val Thr Ile Thr Cys Arg Ala Ser Gln
1 5 10 15

Ser Ile Ser Ser Trp Leu Ala Trp Tyr Gln Gln Lys Pro Gly Lys Ala
20 25 30

Pro Lys Phe Leu Ile His Lys Ala Ser Ser Leu Glu Ser Gly Ile Pro
35 40 45

Ser Arg Phe Ser Gly Ser Gly Ser Gly Thr Glu Phe Thr Leu Thr Ile
50 55 60

Asn Asn Leu Gln Pro Asp Asp Phe Ala Thr Tyr Tyr Cys Gln His Tyr
65 70 75 80

His Ser Tyr Pro Trp Thr Phe Gly Gln Gly Thr Lys Val Glu Ile Lys
85 90 95

<210> SEQ ID NO 558
<211> LENGTH: 96
<212> TYPE: PRT
<213> ORGANISM: Homo sapiens

<400> SEQUENCE: 558

Ser Ala Ser Val Gly Asp Arg Val Thr Ile Ile Cys Arg Ala Ser Arg
1 5 10 15

Ser Ile Asp Ser Trp Leu Ala Trp Tyr Gln Gln Lys Pro Gly Lys Ala
20 25 30

Pro Arg Leu Leu Ile His Lys Ala Ser Thr Leu His Ser Gly Val Pro
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Phe Cys Gln His Tyr
65 70 75 80

Phe Ser Ser Pro Tyr Ser Phe Gly Gln Gly Thr Lys Leu Glu Ile Lys
85 90 95

<210> SEQ ID NO 559
<211> LENGTH: 96
<212> TYPE: PRT
<213> ORGANISM: Homo sapiens

<400> SEQUENCE: 559

Ser Ala Ser Val Gly Asp Arg Val Thr Ile Thr Cys Arg Ala Gly Gln
1 5 10 15

Asn Ile Asn Ser Trp Leu Ala Trp Tyr Gln Gln Lys Pro Gly Lys Ala
20 25 30

Pro Lys Phe Leu Ile His Lys Ala Ser Thr Leu Glu Ser Gly Val Ser

```
        35                  40                  45

Ser Arg Phe Ser Gly Ser Gly Ser Gly Thr Glu Phe Thr Leu Thr Ile
    50                  55                  60

Asn Asn Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 560
<211> LENGTH: 96
<212> TYPE: PRT
<213> ORGANISM: Homo sapiens

<400> SEQUENCE: 560

Ser Ala Ser Val Gly Asp Arg Val Ser Ile Thr Cys Arg Ala Ser Gln
1               5                   10                  15

Asn Ile Asp Met Trp Leu Ala Trp Tyr Gln Gln Lys Pro Gly Lys Ala
            20                  25                  30

Pro Lys Phe Leu Ile Tyr Lys Ala Ser Asn Leu Lys Ser Gly Val Pro
        35                  40                  45

Ser Arg Phe Ser Gly Ser Gly Ser Gly Thr Glu Phe Thr Leu Thr Ile
    50                  55                  60

Ser Ser Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 561
<211> LENGTH: 96
<212> TYPE: PRT
<213> ORGANISM: Homo sapiens

<400> SEQUENCE: 561

Ser Ala Ser Ile Gly Ala Arg Val Thr Ile Thr Cys Arg Ala Ser Gln
1               5                   10                  15

Asp Ile Ser Gly Trp Leu Ala Trp Tyr Gln Gln Lys Pro Gly Arg Ala
            20                  25                  30

Pro Lys Leu Leu Ile Tyr Gln Ala Ser Thr Leu Tyr Asn Gly Val Pro
        35                  40                  45

Pro Arg Phe Ser Gly Ser Gly Ser Gly Thr Glu Phe Thr Leu Thr Ile
    50                  55                  60

Ser Gly Leu Gln Pro Asp Asp Phe Ala Thr Tyr Tyr Cys Gln His Tyr
65                  70                  75                  80

His Ser Tyr Pro Trp Thr Phe Gly Gln Gly Thr Lys Val Glu Ile Lys
                85                  90                  95


<210> SEQ ID NO 562
<211> LENGTH: 96
<212> TYPE: PRT
<213> ORGANISM: Homo sapiens

<400> SEQUENCE: 562

Ser Ala Ser Val Gly Asp Arg Val Thr Ile Thr Cys Arg Ala Ser Gln
1               5                   10                  15

Asn Ile Asn Ser Trp Leu Ala Trp Tyr Gln Gln Lys Pro Gly Gln Ala
            20                  25                  30

Pro Lys Phe Leu Met His Lys Ala Ser Ile Leu Glu Ser Gly Val Pro
        35                  40                  45
```

Ser Arg Phe Ser Gly Ser Gly Ser Gly Thr Glu Phe Thr Leu Thr Ile
50 55 60

Ser Ser Leu Gln Pro Asp Asp Phe Ala Ser Tyr Phe Cys Gln Gln Tyr
65 70 75 80

His Ser Tyr Pro Trp Thr Phe Gly Pro Gly Thr Lys Val Glu Ile Lys
85 90 95

<210> SEQ ID NO 563
<211> LENGTH: 96
<212> TYPE: PRT
<213> ORGANISM: Homo sapiens

<400> SEQUENCE: 563

Ala Ala Ser Val Gly Asp Arg Val Thr Ile Thr Cys Arg Ala Ser Gln
1 5 10 15

Asn Ile Asn Ser Trp Leu Ala Trp Tyr Gln Gln Lys Pro Gly Lys Ala
20 25 30

Pro Lys Phe Leu Ile Tyr Lys Ala Ser Thr Leu Glu Ser Gly Ala Pro
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Tyr Cys Gln His Tyr
65 70 75 80

Tyr Ser Tyr Pro Tyr Thr Phe Gly Gln Gly Thr Lys Leu Glu Ile Lys
85 90 95

<210> SEQ ID NO 564
<211> LENGTH: 96
<212> TYPE: PRT
<213> ORGANISM: Homo sapiens

<400> SEQUENCE: 564

Ser Ala Ser Val Gly Asp Arg Val Thr Ile Thr Cys Arg Ala Ser Gln
1 5 10 15

Ser Ile Ser Gly Trp Leu Ala Trp Tyr Gln Gln Lys Pro Gly Lys Ala
20 25 30

Pro Arg Leu Leu Met His Lys Ala Ser Ile Leu Tyr Arg Gly Val Pro
35 40 45

Ser Arg Phe Ser Gly Ser Gly Ser Gly Thr Glu Phe Thr Leu Thr Ile
50 55 60

Ser Ser Leu Gln Pro Asp Asp Phe Ala Thr Tyr Tyr Cys Gln His Tyr
65 70 75 80

His Ser Tyr Pro Tyr Thr Phe Gly Gln Gly Thr Lys Leu Glu Ile Lys
85 90 95

<210> SEQ ID NO 565
<211> LENGTH: 96
<212> TYPE: PRT
<213> ORGANISM: Homo sapiens

<400> SEQUENCE: 565

Ser Ala Ser Val Gly Asp Arg Val Thr Ile Thr Cys Arg Ala Ser Gln
1 5 10 15

Ser Ile Ser Ser Trp Leu Ala Trp Tyr Gln Gln Lys Pro Gly Lys Ala
20 25 30

Pro Lys Leu Leu Met His Lys Ala Ser Asn Leu His Val Gly Val Pro
35 40 45

Ser Arg Phe Ser Gly Ser Gly Ser Gly Thr Glu Phe Thr Leu Thr Ile
    50                  55                  60

Thr Ser Leu Gln Pro Asp Asp Phe Ala Thr Tyr Tyr Cys Gln His Tyr
65                  70                  75                  80

Phe Ser Tyr Pro Tyr Thr Phe Gly Gln Gly Thr Lys Val Glu Ile Lys
                85                  90                  95

<210> SEQ ID NO 566
<211> LENGTH: 95
<212> TYPE: PRT
<213> ORGANISM: Homo sapiens

<400> SEQUENCE: 566

Ser Leu Ser Pro Gly Glu Arg Ala Thr Leu Ser Cys Arg Ala Ser Gln
1               5                   10                  15

Ser Val Ser Asn Tyr Leu Ala Trp Tyr Gln Gln Lys Pro Gly Gln Ala
            20                  25                  30

Pro Arg Leu Leu Ile Tyr Asp Ala Ser Asn Met Ala Pro Gly Ile Pro
        35                  40                  45

Ala Arg Phe Ser Gly Ser Gly Ser Gly Thr Asp Phe Thr Leu Thr Ile
    50                  55                  60

Ser Ser Leu Glu Pro Glu Asp Phe Ala Val Tyr Tyr Cys Gln Gln Arg
65                  70                  75                  80

Ser Asn Trp Leu Thr Phe Gly Gly Gly Thr Lys Ile Glu Ile Lys
                85                  90                  95

<210> SEQ ID NO 567
<211> LENGTH: 96
<212> TYPE: PRT
<213> ORGANISM: Homo sapiens

<400> SEQUENCE: 567

Ser Leu Ser Pro Gly Glu Arg Thr Thr Leu Ser Cys Arg Ala Ser Gln
1               5                   10                  15

Ser Ile Ser Asn Tyr Leu Ala Trp Tyr Gln Gln Lys Pro Gly Gln Ala
            20                  25                  30

Pro Arg Leu Leu Ile Tyr Asp Ala Ser Asn Arg Ala Ala Gly Ile Pro
        35                  40                  45

Ala Arg Phe Ser Gly Ser Gly Ser Gly Ile Asp Phe Thr Leu Thr Ile
    50                  55                  60

Ser Ser Leu Glu Pro Glu Asp Phe Gly Val Tyr Tyr Cys Gln Gln Arg
65                  70                  75                  80

Gly Lys Trp Pro Pro Ser Phe Gly Gly Gly Thr Lys Val Glu Ile Lys
                85                  90                  95

<210> SEQ ID NO 568
<211> LENGTH: 97
<212> TYPE: PRT
<213> ORGANISM: Homo sapiens

<400> SEQUENCE: 568

Ser Leu Ser Pro Gly Glu Arg Ala Thr Leu Ser Cys Arg Ala Ser Gln
1               5                   10                  15

Ser Val Arg Asn Phe Leu Ala Trp Tyr Gln Gln Lys Pro Gly Gln Ala
            20                  25                  30

Pro Arg Leu Leu Ile Tyr Asp Ala Ser Asn Arg Ala Thr Gly Ile Pro
        35                  40                  45

Ala Arg Phe Ser Gly Ser Gly Ser Gly Thr Asp Phe Thr Leu Thr Ile 50 55 60

Ser Ser Leu Glu Pro Glu Asp Phe Ala Val Tyr Tyr Cys Gln Gln Arg
65 70 75 80

Gly Asn Trp Pro Pro Ala Thr Phe Gly Gly Gly Thr Lys Val Glu Ile
85 90 95

Lys

<210> SEQ ID NO 569
<211> LENGTH: 97
<212> TYPE: PRT
<213> ORGANISM: Homo sapiens

<400> SEQUENCE: 569

Ser Leu Ser Pro Gly Glu Arg Ala Thr Leu Ser Cys Arg Ala Ser Gln
1 5 10 15

Ser Val Ser Ser Phe Leu Ala Trp Tyr Gln Gln Lys Pro Gly Gln Pro
20 25 30

Pro Arg Leu Leu Ile Tyr Asp Ala Ser Thr Arg Ala Thr Gly Ile Pro
35 40 45

Ala Arg Phe Ser Gly Ser Gly Ser Gly Thr Asp Phe Thr Leu Thr Ile
50 55 60

Ser Ser Leu Glu Pro Glu Asp Phe Ala Val Tyr Tyr Cys Gln Gln Arg
65 70 75 80

Ser Asn Trp Pro Pro Ile Thr Phe Gly Gln Gly Thr Arg Leu Glu Ile
85 90 95

Lys

<210> SEQ ID NO 570
<211> LENGTH: 95
<212> TYPE: PRT
<213> ORGANISM: Homo sapiens

<400> SEQUENCE: 570

Ser Leu Ser Pro Gly Glu Arg Ala Thr Leu Ser Cys Arg Ala Arg Gln
1 5 10 15

Asn Val Arg Asn Phe Leu Ala Trp Tyr Gln Gln Lys Pro Gly Gln Ala
20 25 30

Pro Arg Leu Leu Ile Tyr Asp Ala Ser Asn Arg Ala Thr Asp Ile Pro
35 40 45

Ala Arg Phe Ser Gly Ser Gly Ser Gly Thr Asp Phe Thr Leu Thr Ile
50 55 60

Ser Ser Leu Glu Pro Glu Asp Phe Ala Val Tyr Tyr Cys Gln Gln Arg
65 70 75 80

Ser Tyr Ser Ile Thr Phe Gly Gln Gly Thr Arg Leu Glu Met Lys
85 90 95

<210> SEQ ID NO 571
<211> LENGTH: 96
<212> TYPE: PRT
<213> ORGANISM: Homo sapiens

<400> SEQUENCE: 571

Ser Leu Ser Pro Gly Glu Arg Ala Thr Leu Ser Cys Arg Ala Ser Gln
1 5 10 15

Ser Val Ser Asn Tyr Leu Ala Trp Tyr Gln Gln Lys Pro Gly Gln Ala
20 25 30

Pro Arg Leu Leu Ile Tyr Asp Ala Ser Ser Arg Ala Thr Gly Ile Pro

```
        35                  40                  45

Ala Arg Phe Ser Gly Ser Gly Ser Gly Thr Asp Phe Ser Leu Thr Ile
    50                  55                  60

Ser Ser Leu Glu Pro Glu Asp Phe Ala Val Tyr Tyr Cys Gln Gln Arg
65                  70                  75                  80

Ser Asn Gly Pro Leu Thr Phe Gly Gly Gly Thr Lys Val Glu Ile Lys
                85                  90                  95


<210> SEQ ID NO 572
<211> LENGTH: 97
<212> TYPE: PRT
<213> ORGANISM: Homo sapiens

<400> SEQUENCE: 572

Ser Leu Ser Pro Gly Glu Arg Ala Thr Leu Ser Cys Arg Ala Ser Gln
1               5                   10                  15

Ser Val Ser Asn Phe Phe Ala Trp Tyr Gln Gln Lys Pro Gly Gln Ala
            20                  25                  30

Pro Arg Leu Leu Ile Tyr Asp Ala Ser Lys Arg Ala Thr Gly Ile Pro
        35                  40                  45

Ala Arg Phe Ser Gly Ser Gly Ser Gly Thr Asp Phe Thr Leu Thr Ile
    50                  55                  60

Ser Ser Leu Glu Pro Glu Asp Phe Ala Val Tyr Tyr Cys Gln Gln Arg
65                  70                  75                  80

Ser Asn Trp Pro Pro Leu Thr Phe Gly Gly Gly Thr Lys Val Glu Ile
                85                  90                  95

Lys


<210> SEQ ID NO 573
<211> LENGTH: 99
<212> TYPE: PRT
<213> ORGANISM: Homo sapiens

<400> SEQUENCE: 573

Ser Leu Ser Pro Gly Glu Arg Ala Thr Leu Ser Cys Arg Ala Ser Gln
1               5                   10                  15

Ser Val Ser Ser Ser Tyr Leu Ala Trp Tyr Gln Gln Lys Pro Gly Gln
            20                  25                  30

Ala Pro Arg Leu Leu Ile Tyr Gly Ala Tyr Asn Arg Ala Thr Gly Ile
        35                  40                  45

Pro Asp Arg Phe Ser Gly Ser Gly Ser Gly Thr Asp Phe Thr Leu Thr
    50                  55                  60

Ile Asn Arg Leu Glu Pro Glu Asp Phe Ala Val Tyr Tyr Cys Gln Gln
65                  70                  75                  80

Tyr Gly Thr Ser Pro Pro Glu Phe Thr Phe Gly Arg Gly Thr Lys Val
                85                  90                  95

Glu Ile Lys


<210> SEQ ID NO 574
<211> LENGTH: 97
<212> TYPE: PRT
<213> ORGANISM: Homo sapiens

<400> SEQUENCE: 574

Ser Leu Ser Pro Gly Glu Arg Ala Thr Leu Ser Cys Arg Ala Ser Gln
1               5                   10                  15

Ser Leu Ser Ser Ser Phe Leu Ala Trp Tyr Gln Gln Lys Pro Gly Gln
```

20 25 30

Ser Pro Arg Leu Leu Ile Tyr Gly Thr Ser Ser Arg Asp Thr Gly Ile
35 40 45

Pro Asp Arg Phe Ser Gly Ser Gly Ser Gly Thr Asp Phe Thr Leu Thr
50 55 60

Ile Ser Arg Leu Glu Pro Glu Asp Ser Ala Val Tyr Tyr Cys Gln Gln
65 70 75 80

Tyr Gly Ser Ser Trp Gly Thr Phe Gly Gln Gly Thr Lys Leu Glu Ile
85 90 95

Lys

<210> SEQ ID NO 575
<211> LENGTH: 9
<212> TYPE: PRT
<213> ORGANISM: Homo sapiens

<400> SEQUENCE: 575

Gln His Tyr Tyr Ser Tyr Pro Trp Thr
1 5

<210> SEQ ID NO 576
<211> LENGTH: 9
<212> TYPE: PRT
<213> ORGANISM: Homo sapiens

<400> SEQUENCE: 576

Gln His Tyr His Gly Tyr Pro Trp Thr
1 5

<210> SEQ ID NO 577
<211> LENGTH: 9
<212> TYPE: PRT
<213> ORGANISM: Homo sapiens

<400> SEQUENCE: 577

Gln Lys Tyr Asn Ser Tyr Pro Phe Thr
1 5

<210> SEQ ID NO 578
<211> LENGTH: 9
<212> TYPE: PRT
<213> ORGANISM: Homo sapiens

<400> SEQUENCE: 578

Gln His Tyr Phe Ser Tyr Pro Trp Thr
1 5

<210> SEQ ID NO 579
<211> LENGTH: 9
<212> TYPE: PRT
<213> ORGANISM: Homo sapiens

<400> SEQUENCE: 579

Gln His Tyr His Ser Tyr Pro Trp Thr
1 5

<210> SEQ ID NO 580
<211> LENGTH: 9
<212> TYPE: PRT
<213> ORGANISM: Homo sapiens

<400> SEQUENCE: 580

Gln His Tyr Phe Ser Tyr Pro Trp Thr
1               5

<210> SEQ ID NO 581
<211> LENGTH: 9
<212> TYPE: PRT
<213> ORGANISM: Homo sapiens

<400> SEQUENCE: 581

Gln His Tyr His Ser Tyr Pro Trp Thr
1               5

<210> SEQ ID NO 582
<211> LENGTH: 9
<212> TYPE: PRT
<213> ORGANISM: Homo sapiens

<400> SEQUENCE: 582

Gln His Tyr Phe Ser Ser Pro Tyr Ser
1               5

<210> SEQ ID NO 583
<211> LENGTH: 9
<212> TYPE: PRT
<213> ORGANISM: Homo sapiens

<400> SEQUENCE: 583

Gln His Tyr His Ser Tyr Pro Trp Thr
1               5

<210> SEQ ID NO 584
<211> LENGTH: 9
<212> TYPE: PRT
<213> ORGANISM: Homo sapiens

<400> SEQUENCE: 584

Gln His Tyr His Ser Tyr Pro Trp Thr
1               5

<210> SEQ ID NO 585
<211> LENGTH: 9
<212> TYPE: PRT
<213> ORGANISM: Homo sapiens

<400> SEQUENCE: 585

Gln His Tyr His Ser Tyr Pro Trp Thr
1               5

<210> SEQ ID NO 586
<211> LENGTH: 9
<212> TYPE: PRT
<213> ORGANISM: Homo sapiens

<400> SEQUENCE: 586

Gln Gln Tyr His Ser Tyr Pro Trp Thr
1               5

<210> SEQ ID NO 587
<211> LENGTH: 9
<212> TYPE: PRT
<213> ORGANISM: Homo sapiens

<400> SEQUENCE: 587

Gln His Tyr Tyr Ser Tyr Pro Tyr Thr
1               5

<210> SEQ ID NO 588
<211> LENGTH: 9
<212> TYPE: PRT
<213> ORGANISM: Homo sapiens

<400> SEQUENCE: 588

Gln His Tyr His Ser Tyr Pro Tyr Thr
1               5

<210> SEQ ID NO 589
<211> LENGTH: 9
<212> TYPE: PRT
<213> ORGANISM: Homo sapiens

<400> SEQUENCE: 589

Gln His Tyr Phe Ser Tyr Pro Tyr Thr
1               5

<210> SEQ ID NO 590
<211> LENGTH: 8
<212> TYPE: PRT
<213> ORGANISM: Homo sapiens

<400> SEQUENCE: 590

Gln Gln Arg Ser Asn Trp Leu Thr
1               5

<210> SEQ ID NO 591
<211> LENGTH: 9
<212> TYPE: PRT
<213> ORGANISM: Homo sapiens

<400> SEQUENCE: 591

Gln Gln Arg Gly Lys Trp Pro Pro Ser
1               5

<210> SEQ ID NO 592
<211> LENGTH: 10
<212> TYPE: PRT
<213> ORGANISM: Homo sapiens

<400> SEQUENCE: 592

Gln Gln Arg Gly Asn Trp Pro Pro Ala Thr
1               5                   10

<210> SEQ ID NO 593
<211> LENGTH: 10
<212> TYPE: PRT
<213> ORGANISM: Homo sapiens

<400> SEQUENCE: 593

Gln Gln Arg Ser Asn Trp Pro Pro Ile Thr
1               5                   10

<210> SEQ ID NO 594
<211> LENGTH: 8
<212> TYPE: PRT
<213> ORGANISM: Homo sapiens

<400> SEQUENCE: 594

Gln Gln Arg Ser Tyr Ser Ile Thr
1               5

<210> SEQ ID NO 595
<211> LENGTH: 9
<212> TYPE: PRT
<213> ORGANISM: Homo sapiens

<400> SEQUENCE: 595

Gln Gln Arg Ser Asn Gly Pro Leu Thr
1 5

<210> SEQ ID NO 596
<211> LENGTH: 10
<212> TYPE: PRT
<213> ORGANISM: Homo sapiens

<400> SEQUENCE: 596

Gln Gln Arg Ser Asn Trp Pro Pro Leu Thr
1 5 10

<210> SEQ ID NO 597
<211> LENGTH: 11
<212> TYPE: PRT
<213> ORGANISM: Homo sapiens

<400> SEQUENCE: 597

Gln Gln Tyr Gly Thr Ser Pro Pro Glu Phe Thr
1 5 10

<210> SEQ ID NO 598
<211> LENGTH: 9
<212> TYPE: PRT
<213> ORGANISM: Homo sapiens

<400> SEQUENCE: 598

Gln Gln Tyr Gly Ser Ser Trp Gly Thr
1 5

<210> SEQ ID NO 599
<211> LENGTH: 112
<212> TYPE: PRT
<213> ORGANISM: Homo sapiens

<400> SEQUENCE: 599

Gly Gly Ala Leu Val Gln Pro Gly Gly Ser Leu Arg Leu Ser Cys Ala
1 5 10 15

Ala Ser Gly Phe Thr Phe Asn Tyr Tyr Ala Met Thr Trp Val Arg Gln
20 25 30

Ala Pro Gly Arg Gly Leu Glu Trp Val Ser Thr Ile Thr Asp Asn Gly
35 40 45

Gly Thr Thr Tyr Leu Ala Asp Ser Val Lys Gly Arg Phe Thr Ile Ser
50 55 60

Arg Asp Asn Ser Gln Asn Thr Gln Ser Leu Gln Met Asn Asn Leu Arg
65 70 75 80

Ala Asp Asp Thr Ala Val Tyr Phe Cys Val Lys His Leu Arg Gly Trp
85 90 95

Tyr Thr Phe Glu Ile Trp Gly Gln Gly Thr Leu Val Thr Val Ser Ser
100 105 110

<210> SEQ ID NO 600
<211> LENGTH: 115
<212> TYPE: PRT
<213> ORGANISM: Homo sapiens

<400> SEQUENCE: 600

```
Gly Gly Gly Leu Val Gln Pro Gly Gly Ser Leu Arg Leu Ser Cys Ala
1               5                   10                  15

Ala Ser Gly Tyr Ile Phe Asp Asn Tyr Ala Met Ser Trp Val Arg Gln
            20                  25                  30

Ala Pro Gly Lys Gly Leu Glu Trp Val Ser Tyr Ile Asn Gly Gly Gly
        35                  40                  45

Tyr Gly Thr Asp Tyr Ala Asp Ser Val Lys Gly Arg Phe Thr Ile Ser
    50                  55                  60

Arg Asp Asn Ser Lys Arg Ile Leu Tyr Leu Gln Met Asn Ser Leu Arg
65                  70                  75                  80

Val Gly Asp Thr Ala Val Tyr Tyr Cys Ala Lys Ser Pro Tyr Val Gly
                85                  90                  95

Gly Tyr Gly Leu Pro Gly Asp Ser Trp Gly Gln Gly Thr Leu Val Thr
            100                 105                 110

Val Ser Ser
        115
```

<210> SEQ ID NO 601
<211> LENGTH: 119
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (80)..(80)
<223> OTHER INFORMATION: Any amino acid

<400> SEQUENCE: 601

```
Gly Pro Gly Leu Val Lys Pro Ser Glu Thr Leu Ser Leu Thr Cys Thr
1               5                   10                  15

Val Xaa Gly Gly Ser Ile Ser Arg Tyr Phe Xaa Ser Trp Ile Arg Gln
            20                  25                  30

Pro Pro Gly Lys Gly Leu Glu Trp Ile Gly Tyr Ile Tyr Tyr Thr Gly
        35                  40                  45

Ser Thr Asn Tyr Asn Pro Ser Leu Lys Ser Arg Val Ile Ile Leu Val
    50                  55                  60

Asp Thr Ser Lys Asn Gln Phe Ser Xaa Lys Leu Ser Ser Val Thr Xaa
65                  70                  75                  80

Ala Asp Thr Ala Val Tyr Tyr Cys Ala Arg Gly Pro His Tyr Tyr Asp
                85                  90                  95

Ser Ser Ala Tyr Phe Thr Tyr Asn Gly Met Asp Val Trp Gly Gln Gly
            100                 105                 110

Thr Thr Val Thr Val Ser Ser
        115
```

<210> SEQ ID NO 602
<211> LENGTH: 117
<212> TYPE: PRT
<213> ORGANISM: Homo sapiens

<400> SEQUENCE: 602

Gly Pro Gly Leu Val Lys Pro Ser Glu Thr Leu Ser Leu Thr Cys Thr
1 5 10 15

Val Ser Gly Gly Ser Ile Ser Ser Tyr Tyr Trp Ser Trp Ile Arg Gln
20 25 30

Pro Pro Gly Lys Gly Leu Glu Trp Ile Gly Phe Ile Tyr Tyr Ser Gly
35 40 45

Ser Thr Asn Tyr Asn Pro Ser Leu Lys Ser Arg Val Thr Ile Ser Val
50 55 60

Asp Thr Ser Lys Asn Gln Phe Ser Leu Lys Leu Ser Ser Val Thr Ala
65 70 75 80

Ala Asp Thr Ala Val Tyr Tyr Cys Ala Arg Gly Asp Tyr Tyr Tyr Asp
85 90 95

Ser Ser Gly Tyr Leu Tyr Tyr Phe Asp Tyr Trp Gly Gln Gly Thr Leu
100 105 110

Val Thr Val Ser Ser
115

<210> SEQ ID NO 603
<211> LENGTH: 12
<212> TYPE: PRT
<213> ORGANISM: Homo sapiens

<400> SEQUENCE: 603

Val Lys His Leu Arg Gly Trp Tyr Thr Phe Glu Ile
1 5 10

<210> SEQ ID NO 604
<211> LENGTH: 15
<212> TYPE: PRT
<213> ORGANISM: Homo sapiens

<400> SEQUENCE: 604

Ala Lys Ser Pro Tyr Val Gly Gly Tyr Gly Leu Pro Gly Asp Ser
1 5 10 15

<210> SEQ ID NO 605
<211> LENGTH: 20
<212> TYPE: PRT
<213> ORGANISM: Homo sapiens

<400> SEQUENCE: 605

Ala Arg Gly Pro His Tyr Tyr Asp Ser Ser Ala Tyr Phe Thr Tyr Asn
1 5 10 15

Gly Met Asp Val
20

<210> SEQ ID NO 606
<211> LENGTH: 18
<212> TYPE: PRT
<213> ORGANISM: Homo sapiens

<400> SEQUENCE: 606

Ala Arg Gly Asp Tyr Tyr Tyr Asp Ser Ser Gly Tyr Leu Tyr Tyr Phe
1 5 10 15

Asp Tyr

<210> SEQ ID NO 607
<211> LENGTH: 98
<212> TYPE: PRT

<213> ORGANISM: Homo sapiens

<400> SEQUENCE: 607

Ser Leu Ser Pro Gly Glu Arg Ala Thr Leu Ser Cys Arg Ala Ser Gln
1               5                   10                  15

Ser Val Ser Gly Ser Tyr Leu Ala Trp Tyr Gln Gln Lys Pro Gly Gln
            20                  25                  30

Ala Pro Arg Leu Leu Ile Tyr Gly Ala Ser Arg Arg Ala Thr Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Phe Ala Val Tyr Tyr Cys Gln Gln
65                  70                  75                  80

Phe Gly Ser Ser Pro Arg Tyr Thr Phe Gly Gln Gly Thr Lys Leu Glu
                85                  90                  95

Ile Lys

<210> SEQ ID NO 608
<211> LENGTH: 97
<212> TYPE: PRT
<213> ORGANISM: Homo sapiens

<400> SEQUENCE: 608

Ser Leu Ser Pro Gly Glu Arg Ala Thr Leu Ser Cys Arg Ala Ser Gln
1               5                   10                  15

Thr Ile Phe Phe Asn Tyr Leu Ala Trp Tyr Gln Lys Lys Pro Gly Gln
            20                  25                  30

Ala Pro Arg Leu Leu Val His Gly Ala Ser Thr Arg Ala Thr Gly Ile
        35                  40                  45

Pro Asp Arg Phe Ser Gly Ser Gly Ser Gly Thr Asp Phe Thr Leu Thr
    50                  55                  60

Ile Asn Ser Leu Asp Pro Glu Asp Phe Ala Val Tyr Tyr Cys Gln Gln
65                  70                  75                  80

Tyr Gly Asp Ser Pro Pro Thr Phe Gly Gly Gly Thr Lys Val Asp Ile
                85                  90                  95

Lys

<210> SEQ ID NO 609
<211> LENGTH: 98
<212> TYPE: PRT
<213> ORGANISM: Homo sapiens

<400> SEQUENCE: 609

Ser Leu Ser Pro Gly Glu Arg Ala Thr Leu Ser Cys Arg Val Ser Gln
1               5                   10                  15

Ser Val Ser Ser Asn Ser Leu Ala Trp Tyr Gln Gln Lys Pro Gly Gln
            20                  25                  30

Ala Pro Arg Leu Leu Ile Tyr Gly Ala Ser Ser Arg Ala Thr Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Phe Ala Val Tyr Tyr Cys Gln Gln
65                  70                  75                  80

Tyr Gly Ser Ser Pro Pro Val Thr Phe Gly Gln Gly Thr Arg Leu Glu
                85                  90                  95

Ile Lys

<210> SEQ ID NO 610
<211> LENGTH: 96
<212> TYPE: PRT
<213> ORGANISM: Homo sapiens

<400> SEQUENCE: 610

Ser Leu Ser Pro Gly Glu Arg Ala Thr Leu Ser Cys Arg Ala Ser Gln
1 5 10 15

Ser Val Ser Ser Ser Ser Leu Ala Trp Tyr Gln Gln Lys Pro Gly Gln
20 25 30

Ala Pro Arg Leu Leu Ile Tyr Gly Ala Ser Asn Arg Ala Thr Gly Ile
35 40 45

Pro Asp Arg Phe Ser Gly Ser Gly Ser Gly Thr Asp Phe Thr Leu Thr
50 55 60

Ile Ser Arg Leu Glu Pro Glu Asp Phe Ala Val Tyr Tyr Cys Gln Gln
65 70 75 80

Tyr Gly Thr Ser Val Thr Phe Gly Gly Gly Thr Lys Val Glu Ile Lys
85 90 95

<210> SEQ ID NO 611
<211> LENGTH: 10
<212> TYPE: PRT
<213> ORGANISM: Homo sapiens

<400> SEQUENCE: 611

Gln Gln Phe Gly Ser Ser Pro Arg Tyr Thr
1 5 10

<210> SEQ ID NO 612
<211> LENGTH: 9
<212> TYPE: PRT
<213> ORGANISM: Homo sapiens

<400> SEQUENCE: 612

Gln Gln Tyr Gly Asp Ser Pro Pro Thr
1 5

<210> SEQ ID NO 613
<211> LENGTH: 10
<212> TYPE: PRT
<213> ORGANISM: Homo sapiens

<400> SEQUENCE: 613

Gln Gln Tyr Gly Ser Ser Pro Pro Val Thr
1 5 10

<210> SEQ ID NO 614
<211> LENGTH: 8
<212> TYPE: PRT
<213> ORGANISM: Homo sapiens

<400> SEQUENCE: 614

Gln Gln Tyr Gly Thr Ser Val Thr
1 5

<210> SEQ ID NO 615
<211> LENGTH: 117
<212> TYPE: PRT
<213> ORGANISM: Homo sapiens

<400> SEQUENCE: 615

-continued

Gly Ala Glu Val Lys Lys Pro Gly Ser Ser Val Arg Val Ser Cys Lys
1               5                   10                  15

Ala Ser Gly Asp Thr Phe Ser Asn Tyr Ala Ile Ser Trp Val Arg Gln
            20                  25                  30

Ala Pro Gly Gln Gly Leu Glu Trp Met Gly Gly Ile Ile Pro Ile Phe
        35                  40                  45

Gly Thr Ala Ser Tyr Ala Gln Arg Phe Gln Asp Arg Val Thr Ile Thr
    50                  55                  60

Ala Asp Lys Ser Thr Gly Thr Val Tyr Met Glu Leu Ser Ser Leu Arg
65                  70                  75                  80

Ser Glu Asp Thr Ala Val Phe Tyr Cys Ala Arg Gln Lys Cys Thr Gly
                85                  90                  95

Gly Ser Cys Tyr Ser Gly Asn Phe Asp Pro Trp Gly Gln Gly Thr Leu
            100                 105                 110

Val Thr Val Ser Ser
        115

<210> SEQ ID NO 616
<211> LENGTH: 122
<212> TYPE: PRT
<213> ORGANISM: Homo sapiens

<400> SEQUENCE: 616

Gly Ala Glu Val Lys Lys Pro Gly Ser Ser Val Lys Val Ser Cys Lys
1               5                   10                  15

Ala Pro Gly Gly Thr Phe Ser Arg Tyr Ser Ile Ala Trp Val Arg Gln
            20                  25                  30

Ala Pro Gly Gln Gly Leu Glu Trp Met Gly Gly Ile Asn Pro Thr Phe
        35                  40                  45

Thr Thr Pro Asn Tyr Ala Gln Lys Phe Gln Gly Arg Val Thr Ile Thr
    50                  55                  60

Ala Asp Glu Ser Thr Asn Thr Ala Tyr Leu Asp Leu Ser Ser Leu Arg
65                  70                  75                  80

Ser Glu Asp Thr Ala Val Tyr Tyr Cys Ala Arg Phe Arg Tyr Tyr Tyr
                85                  90                  95

Glu Ser Gly Gly Tyr Ser Asp Ala Ser Pro Tyr Tyr Leu Asp Tyr Trp
            100                 105                 110

Gly Gln Gly Thr Leu Val Thr Val Ser Ser
        115                 120

<210> SEQ ID NO 617
<211> LENGTH: 116
<212> TYPE: PRT
<213> ORGANISM: Homo sapiens

<400> SEQUENCE: 617

Gly Pro Gly Leu Val Lys Pro Ser Gln Thr Leu Ser Leu Thr Cys Thr
1               5                   10                  15

Val Ser Gly Val Ser Ile Ser Ser Gly Gly Tyr Tyr Tyr Ser Trp Phe
            20                  25                  30

Arg Gln Leu Pro Gly Lys Gly Leu Glu Trp Ile Gly His Ile Tyr Tyr
        35                  40                  45

Thr Gly Asn Thr His Tyr Asn Pro Ser Leu Arg Ser Arg Leu Thr Ile
    50                  55                  60

Ser Val Asp Thr Ser Lys Asn Gln Phe Ser Leu Lys Leu Ser Ser Val
65                  70                  75                  80

```
Thr Ala Ala Asp Thr Ala Arg Tyr Tyr Cys Ala Arg Ala Trp Cys Glu
                85                  90                  95

Tyr Ala Ala Tyr Cys Trp Phe Asp Pro Trp Gly Arg Gly Thr Leu Val
            100                 105                 110

Thr Val Ser Ser
        115


<210> SEQ ID NO 618
<211> LENGTH: 117
<212> TYPE: PRT
<213> ORGANISM: Homo sapiens

<400> SEQUENCE: 618

Gly Pro Gly Leu Val Lys Pro Ser Gln Thr Leu Ser Leu Thr Cys Thr
1               5                   10                  15

Val Ser Gly Gly Ser Ile Thr Gly Gly Val Tyr Tyr Trp Asn Trp Ile
            20                  25                  30

Arg His His Pro Gly Lys Gly Leu Glu Trp Ile Gly Tyr Met Phe Tyr
        35                  40                  45

Ser Gly Asp Thr Asp Tyr Asn Pro Ser Leu Arg Ser Arg Val Thr Ile
    50                  55                  60

Ser Gly Asp Thr Ser Lys Asn Lys Phe Ser Leu Asn Leu Asn Ser Val
65                  70                  75                  80

Thr Ala Ala Asp Thr Ala Val Tyr Tyr Cys Ala Arg Ala Gly Phe Asp
                85                  90                  95

Tyr Gly Ser Pro Val Ser Ala Phe Asp Ile Trp Gly Gln Gly Thr Met
            100                 105                 110

Val Thr Val Ser Ser
        115


<210> SEQ ID NO 619
<211> LENGTH: 116
<212> TYPE: PRT
<213> ORGANISM: Homo sapiens

<400> SEQUENCE: 619

Gly Pro Gly Leu Val Lys Pro Ser Glu Thr Leu Ser Leu Thr Cys Thr
1               5                   10                  15

Val Ser Gly Gly Ser Ile Ser Ser Tyr Asn Tyr Tyr Trp Gly Trp Ile
            20                  25                  30

Arg Gln Pro Pro Gly Lys Gly Leu Glu Phe Ile Gly Ser Ile Tyr Tyr
        35                  40                  45

Thr Gly Ser Thr Tyr Tyr Asn Pro Ser Leu Arg Ser Arg Val Thr Ile
    50                  55                  60

Ser Val Asp Thr Ser Lys Asn Gln Phe Ser Leu Lys Leu Thr Ser Val
65                  70                  75                  80

Thr Ala Ala Asp Thr Ala Val Tyr Tyr Cys Ala Arg His Gly Pro Gly
                85                  90                  95

Met Gly His Asn Trp Tyr Phe Asp Leu Trp Gly Arg Gly Thr Leu Val
            100                 105                 110

Thr Val Ser Ser
        115


<210> SEQ ID NO 620
<211> LENGTH: 118
<212> TYPE: PRT
<213> ORGANISM: Homo sapiens
```

<400> SEQUENCE: 620

```
Gly Pro Arg Leu Val Lys Pro Ser Glu Thr Leu Phe Leu Thr Cys Thr
1               5                   10                  15

Val Ser Gly Asp Ser Ile Ser Ser Ser Ser Tyr Phe Trp Gly Trp Ile
            20                  25                  30

Arg Gln Pro Pro Gly Lys Gly Leu Glu Trp Ile Gly Ser Ile Ser Tyr
        35                  40                  45

Ser Gly Ser Thr Tyr Tyr Asn Pro Ser Leu Lys Ser Arg Val Thr Ile
    50                  55                  60

Ser Val Asp Thr Ser Lys Asn Gln Phe Ser Leu Lys Leu Ser Ser Val
65                  70                  75                  80

Thr Ala Ala Asp Thr Val Val Tyr Tyr Cys Ala Lys His Leu Tyr Ser
                85                  90                  95

Ser Ser Trp Asn Ile Gly Ser Ser Phe Asp Ser Trp Gly Pro Gly Thr
            100                 105                 110

Leu Val Thr Val Ser Ser
        115
```

<210> SEQ ID NO 621
<211> LENGTH: 107
<212> TYPE: PRT
<213> ORGANISM: Homo sapiens

<400> SEQUENCE: 621

```
Gly Pro Gly Leu Val Lys Pro Ser Glu Thr Leu Ser Leu Ser Cys Thr
1               5                   10                  15

Val Ser Ser Gly Ser Ile Ser Asn Tyr Tyr Trp Asn Trp Ile Arg Gln
            20                  25                  30

Pro Pro Gly Lys Gly Leu Glu Trp Ile Gly Tyr Ile Tyr Tyr Ser Gly
        35                  40                  45

Ser Ile Ser Tyr Asn Pro Ser Leu Lys Ser Arg Val Thr Ile Ser Val
    50                  55                  60

Asp Thr Ser Lys Asn Gln Leu Ser Leu Lys Leu Asn Ser Val Thr Ala
65                  70                  75                  80

Ala Asp Thr Ala Val Tyr Tyr Cys Ala Arg Gly Pro Asp Asn Arg Tyr
                85                  90                  95

Trp Gly Gln Gly Thr Leu Val Thr Val Ser Ser
            100                 105
```

<210> SEQ ID NO 622
<211> LENGTH: 107
<212> TYPE: PRT
<213> ORGANISM: Homo sapiens

<400> SEQUENCE: 622

```
Gly Pro Gly Leu Val Lys Pro Ser Glu Thr Leu Ser Leu Thr Cys Thr
1               5                   10                  15

Val Ser Gly Gly Ser Ile Ser Asn Tyr Tyr Trp Asn Trp Ile Arg Gln
            20                  25                  30

Pro Pro Gly Lys Gly Leu Glu Trp Ile Gly Tyr Ile Tyr Tyr Ser Gly
        35                  40                  45

Ser Ile Ser Tyr Asn Pro Ser Leu Lys Ser Arg Val Thr Ile Ser Val
    50                  55                  60

Asp Thr Ser Lys Asn Gln Leu Ser Leu Lys Leu Asn Ser Val Thr Ala
65                  70                  75                  80

Ala Asp Thr Ala Val Tyr Tyr Cys Ala Arg Gly Pro Asp Asn Arg Tyr
```

85 90 95

Trp Gly Gln Gly Thr Leu Val Thr Val Ser Ser
100 105

<210> SEQ ID NO 623
<211> LENGTH: 115
<212> TYPE: PRT
<213> ORGANISM: Homo sapiens

<400> SEQUENCE: 623

Gly Ala Glu Val Lys Lys Pro Gly Ser Ser Val Arg Leu Ser Cys Lys
1 5 10 15

Ala Ser Gly Gly Ser Tyr Ser Thr Tyr Ala Ile Ser Trp Val Arg Gln
20 25 30

Ala Pro Gly Gln Gly Leu Glu Trp Met Gly Arg Ile Ile Pro Ser Leu
35 40 45

Gly Lys Thr His Leu Ala Gln Lys Phe Gln Gly Arg Val Thr Phe Thr
50 55 60

Ala Asp Glu Ser Thr Thr Thr Val Tyr Met Val Leu Ser Ser Leu Lys
65 70 75 80

Ser Asp Asp Thr Ala Leu Tyr Tyr Cys Ala Thr Pro Asp Trp Gln Tyr
85 90 95

Ser Ser Ala Tyr Ser Leu Asp His Trp Gly Gln Gly Thr Leu Val Thr
100 105 110

Val Ser Ser
115

<210> SEQ ID NO 624
<211> LENGTH: 115
<212> TYPE: PRT
<213> ORGANISM: Homo sapiens

<400> SEQUENCE: 624

Gly Ala Glu Val Lys Lys Pro Gly Ser Ser Val Arg Leu Ser Cys Lys
1 5 10 15

Ala Ser Gly Gly Ser Tyr Ser Thr Tyr Ala Ile Ser Trp Val Arg Gln
20 25 30

Ala Pro Gly Gln Gly Leu Glu Trp Met Gly Arg Ile Ile Pro Ser Leu
35 40 45

Gly Lys Thr His Leu Ala Gln Lys Phe Gln Gly Arg Val Thr Phe Thr
50 55 60

Ala Asp Glu Ser Thr Thr Thr Val Tyr Met Ile Leu Ser Ser Leu Lys
65 70 75 80

Ser Glu Asp Thr Ala Leu Tyr Tyr Cys Ala Thr Pro Asp Trp Gln Tyr
85 90 95

Ser Ser Ala Tyr Ser Leu Asp His Trp Gly Gln Gly Thr Leu Val Thr
100 105 110

Val Ser Ser
115

<210> SEQ ID NO 625
<211> LENGTH: 116
<212> TYPE: PRT
<213> ORGANISM: Homo sapiens

<400> SEQUENCE: 625

Gly Ala Glu Val Lys Lys Pro Gly Ala Ser Val Lys Val Ser Cys Lys
1 5 10 15

Thr Ser Gly Tyr Thr Phe Thr Ser Tyr Tyr Met Asn Trp Val Arg Gln
20 25 30

Ala Pro Gly Gln Gly Leu Glu Trp Met Gly Ile Ile Lys Pro Ser Asp
35 40 45

Gly Ser Thr Asn Tyr Ala Gln Lys Phe Gln Gly Arg Val Thr Met Thr
50 55 60

Arg Asp Thr Ser Thr Ser Thr Val Tyr Met Glu Leu Arg Ser Leu Arg
65 70 75 80

Ser Glu Asp Thr Ala Val Tyr Tyr Cys Gly Arg Asp Ser Lys Gly Trp
85 90 95

Leu Gln Leu Arg Gly Asp Ile Asp Tyr Trp Gly Gln Gly Thr Leu Val
100 105 110

Thr Val Ser Ser
115

<210> SEQ ID NO 626
<211> LENGTH: 118
<212> TYPE: PRT
<213> ORGANISM: Homo sapiens

<400> SEQUENCE: 626

Gly Ala Glu Val Lys Lys Pro Gly Ala Ser Val Lys Val Ser Cys Lys
1 5 10 15

Ala Ser Gly Tyr Thr Phe Thr Ser Thr Tyr Ile His Trp Val Arg Gln
20 25 30

Ala Pro Gly Gln Gly Leu Glu Trp Met Gly Ile Ile Asn Pro Ser Ser
35 40 45

Ser Asn Thr Asn Tyr Ala Gln Lys Phe Gln Gly Arg Val Thr Met Thr
50 55 60

Arg Asp Thr Ser Thr Ser Thr Val Tyr Met Glu Leu Ser Ser Leu Arg
65 70 75 80

Ser Glu Asp Thr Ala Val Tyr Tyr Cys Ala Arg Asp Phe Gly Gly Tyr
85 90 95

Ser Ser Ser Ser Val Ser Asp Ala Phe Asp Ile Trp Gly Gln Gly Thr
100 105 110

Met Val Thr Val Ser Ser
115

<210> SEQ ID NO 627
<211> LENGTH: 17
<212> TYPE: PRT
<213> ORGANISM: Homo sapiens

<400> SEQUENCE: 627

Ala Arg Gln Lys Cys Thr Gly Gly Ser Cys Tyr Ser Gly Asn Phe Asp
1 5 10 15

Pro

<210> SEQ ID NO 628
<211> LENGTH: 22
<212> TYPE: PRT
<213> ORGANISM: Homo sapiens

<400> SEQUENCE: 628

Ala Arg Phe Arg Tyr Tyr Tyr Glu Ser Gly Gly Tyr Ser Asp Ala Ser
1 5 10 15

Pro Tyr Tyr Leu Asp Tyr

20

<210> SEQ ID NO 629
<211> LENGTH: 15
<212> TYPE: PRT
<213> ORGANISM: Homo sapiens

<400> SEQUENCE: 629

Ala Arg Ala Trp Cys Glu Tyr Ala Ala Tyr Cys Trp Phe Asp Pro
1 5 10 15

<210> SEQ ID NO 630
<211> LENGTH: 16
<212> TYPE: PRT
<213> ORGANISM: Homo sapiens

<400> SEQUENCE: 630

Ala Arg Ala Gly Phe Asp Tyr Gly Ser Pro Val Ser Ala Phe Asp Ile
1 5 10 15

<210> SEQ ID NO 631
<211> LENGTH: 15
<212> TYPE: PRT
<213> ORGANISM: Homo sapiens

<400> SEQUENCE: 631

Ala Arg His Gly Pro Gly Met Gly His Asn Trp Tyr Phe Asp Leu
1 5 10 15

<210> SEQ ID NO 632
<211> LENGTH: 17
<212> TYPE: PRT
<213> ORGANISM: Homo sapiens

<400> SEQUENCE: 632

Ala Lys His Leu Tyr Ser Ser Ser Trp Asn Ile Gly Ser Ser Phe Asp
1 5 10 15

Ser

<210> SEQ ID NO 633
<211> LENGTH: 8
<212> TYPE: PRT
<213> ORGANISM: Homo sapiens

<400> SEQUENCE: 633

Ala Arg Gly Pro Asp Asn Arg Tyr
1 5

<210> SEQ ID NO 634
<211> LENGTH: 8
<212> TYPE: PRT
<213> ORGANISM: Homo sapiens

<400> SEQUENCE: 634

Ala Arg Gly Pro Asp Asn Arg Tyr
1 5

<210> SEQ ID NO 635
<211> LENGTH: 15
<212> TYPE: PRT
<213> ORGANISM: Homo sapiens

<400> SEQUENCE: 635

Ala Thr Pro Asp Trp Gln Tyr Ser Ser Ala Tyr Ser Leu Asp His 1 5 10 15

<210> SEQ ID NO 636
<211> LENGTH: 15
<212> TYPE: PRT
<213> ORGANISM: Homo sapiens

<400> SEQUENCE: 636

Ala Thr Pro Asp Trp Gln Tyr Ser Ser Ala Tyr Ser Leu Asp His
1 5 10 15

<210> SEQ ID NO 637
<211> LENGTH: 16
<212> TYPE: PRT
<213> ORGANISM: Homo sapiens

<400> SEQUENCE: 637

Gly Arg Asp Ser Lys Gly Trp Leu Gln Leu Arg Gly Asp Ile Asp Tyr
1 5 10 15

<210> SEQ ID NO 638
<211> LENGTH: 18
<212> TYPE: PRT
<213> ORGANISM: Homo sapiens

<400> SEQUENCE: 638

Ala Arg Asp Phe Gly Gly Tyr Ser Ser Ser Ser Val Ser Asp Ala Phe
1 5 10 15

Asp Ile

<210> SEQ ID NO 639
<211> LENGTH: 86
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (46)..(46)
<223> OTHER INFORMATION: Any amino acid

<400> SEQUENCE: 639

Ser Gly Arg Ala Ile Glu Ser Val Ser Gly Xaa Leu Ala Trp Tyr Gln
1 5 10 15

Gln Lys Pro Gly Gln Ala Pro Arg Leu Leu Ile Tyr Asp Ala Ser Asn
20 25 30

Arg Ala Thr Gly Ile Pro Pro Arg Phe Ser Gly Ser Gly Xaa Gly Thr
35 40 45

Glu Phe Thr Leu Thr Ile Ser Ser Ala Glu Pro Glu Asp Phe Ala Val
50 55 60

Tyr Tyr Cys His Gln Ser Ile Lys Trp Pro Pro Thr Phe Gly Gly Gly
65 70 75 80

Ser Lys Val Glu Ile Lys
85

<210> SEQ ID NO 640
<211> LENGTH: 91
<212> TYPE: PRT
<213> ORGANISM: Homo sapiens

<400> SEQUENCE: 640

```
Glu Arg Val Thr Leu Ser Cys Arg Ala Ser Gln Ser Val Ser Ser Tyr
1               5                   10                  15

Leu Ala Trp Tyr Gln Gln Lys Pro Gly Gln Ala Pro Arg Leu Leu Ile
            20                  25                  30

Tyr Asp Ala Ser Asn Arg Ala Thr Gly Ile Pro Ala Arg Phe Thr Gly
        35                  40                  45

Ser Gly Ser Gly Thr Asp Phe Thr Leu Thr Ile Ser Ser Leu Glu Pro
    50                  55                  60

Glu Asp Phe Ala Val Tyr Tyr Cys Gln Gln Arg Ser Asn Trp Pro Leu
65                  70                  75                  80

Thr Phe Gly Gly Gly Thr Lys Val Glu Ile Lys
                85                  90


<210> SEQ ID NO 641
<211> LENGTH: 97
<212> TYPE: PRT
<213> ORGANISM: Homo sapiens

<400> SEQUENCE: 641

Ser Leu Ser Pro Gly Glu Arg Ala Thr Leu Ser Cys Arg Ala Ser Gln
1               5                   10                  15

Ser Val Thr Ser Ser Tyr Leu Ala Trp Tyr Gln His Lys Pro Gly Gln
            20                  25                  30

Ala Pro Arg Leu Leu Ile Tyr Gly Ala Ser Ser Arg Ala Pro Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Phe Ala Val Tyr Trp Cys Gln Gln
65                  70                  75                  80

Tyr Gly Arg Ser Pro Phe Thr Phe Gly Gln Gly Thr Asn Leu Glu Ile
                85                  90                  95

Lys


<210> SEQ ID NO 642
<211> LENGTH: 99
<212> TYPE: PRT
<213> ORGANISM: Homo sapiens

<400> SEQUENCE: 642

Ser Leu Ser Pro Gly Glu Arg Ala Thr Leu Ser Cys Arg Ala Ser Gln
1               5                   10                  15

Ser Val Ser Ser Thr Tyr Leu Val Trp Tyr Gln Gln Lys Pro Gly Gln
            20                  25                  30

Ala Pro Arg Leu Leu Ile Tyr Gly Ala Ser Ser Arg Ala Thr Gly Ile
        35                  40                  45

Pro Asp Arg Phe Ser Gly Ser Gly Ser Gly Thr Asp Phe Thr Leu Thr
    50                  55                  60

Ile Ser Arg Leu Glu Pro Glu Asp Phe Ala Val Tyr Phe Cys Gln Gln
65                  70                  75                  80

Tyr Ala His Ser Pro Arg Gly Tyr Thr Phe Gly Gln Gly Thr Lys Leu
                85                  90                  95

Glu Ile Lys


<210> SEQ ID NO 643
<211> LENGTH: 95
<212> TYPE: PRT
<213> ORGANISM: Homo sapiens
```

<400> SEQUENCE: 643

Ser Leu Ser Pro Gly Glu Arg Ala Thr Leu Ser Cys Arg Ala Ser Gln
1 5 10 15

Ser Ile Ser Ser Tyr Leu Ala Trp Tyr Gln Gln Lys Pro Gly Gln Ala
20 25 30

Pro Arg Leu Leu Ile Tyr Asp Ala Ser Asn Arg Ala Pro Gly Ile Pro
35 40 45

Ala Arg Phe Ser Gly Ser Gly Ser Gly Thr Asp Phe Thr Leu Thr Ile
50 55 60

Ser Ser Leu Glu Pro Glu Asp Phe Ala Val Tyr Tyr Cys Gln Gln Arg
65 70 75 80

Ser Thr Trp Leu Thr Phe Gly Gly Gly Thr Lys Val Glu Ile Lys
85 90 95

<210> SEQ ID NO 644
<211> LENGTH: 97
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (37)..(37)
<223> OTHER INFORMATION: Any amino acid

<400> SEQUENCE: 644

Ser Leu Ser Pro Gly Glu Arg Ala Thr Leu Ser Cys Arg Ala Ser Gln
1 5 10 15

Ser Val Ser Xaa Tyr Leu Ala Trp Tyr Gln Gln Lys Pro Gly Gln Ala
20 25 30

Pro Arg Leu Leu Xaa Tyr Asp Ala Ser Ser Arg Ala Thr Gly Ile Pro
35 40 45

Ala Arg Phe Ser Gly Ser Gly Ser Gly Thr Asp Phe Thr Leu Thr Ile
50 55 60

Ser Ser Leu Glu Pro Glu Asp Phe Ala Val Tyr Tyr Cys Gln Gln Gly
65 70 75 80

Ser Lys Trp Pro Val Tyr Thr Phe Gly Gln Gly Thr Lys Leu Glu Ile
85 90 95

Lys

<210> SEQ ID NO 645
<211> LENGTH: 98
<212> TYPE: PRT
<213> ORGANISM: Homo sapiens

<400> SEQUENCE: 645

Ser Val Ser Pro Gly Glu Arg Val Thr Leu Ser Cys Arg Ala Ser Gln
1 5 10 15

Ser Val Ser Tyr Asn Leu Ala Trp His Gln Gln Lys Pro Gly Gln Ala
20 25 30

Pro Arg Leu Leu Ile Tyr Gly Ala Ser Thr Arg Ala Thr Gly Ile Pro
35 40 45

Ala Arg Phe Ser Gly Ser Gly Ser Gly Thr Glu Phe Thr Leu Thr Ile
50 55 60

Ser Asn Met Gln Ser Glu Asp Phe Ala Val Tyr Tyr Cys Gln Gln Tyr
65 70 75 80

Asn Asn Trp Pro Pro Val Phe Thr Phe Gly Pro Gly Thr Lys Val Asp
85 90 95

Ile Lys

<210> SEQ ID NO 646
<211> LENGTH: 98
<212> TYPE: PRT
<213> ORGANISM: Homo sapiens

<400> SEQUENCE: 646

Ser Val Ser Pro Gly Glu Arg Val Thr Leu Ser Cys Arg Ala Ser Gln
1 5 10 15

Ser Val Ser Tyr Asn Leu Ala Trp His Gln Gln Lys Pro Gly Gln Ala
20 25 30

Pro Arg Leu Leu Ile Tyr Ser Ala Ser Thr Arg Ala Thr Gly Ile Pro
35 40 45

Ala Arg Phe Ser Gly Ser Gly Ser Gly Thr Glu Phe Thr Leu Thr Ile
50 55 60

Ser Asn Met Gln Ser Glu Asp Phe Ala Val Tyr Tyr Cys Gln Gln Tyr
65 70 75 80

Asn Asn Trp Pro Pro Val Phe Thr Phe Gly Pro Gly Thr Lys Val Asp
85 90 95

Ile Lys

<210> SEQ ID NO 647
<211> LENGTH: 101
<212> TYPE: PRT
<213> ORGANISM: Homo sapiens

<400> SEQUENCE: 647

Pro Val Thr Pro Gly Glu Pro Ala Ser Ile Ser Cys Arg Ser Ser Gln
1 5 10 15

Ser Leu Leu His Ser Thr Gly Tyr Asn Tyr Leu Asp Trp Tyr Leu Gln
20 25 30

Lys Pro Gly Gln Ser Pro Gln Leu Leu Ile Tyr Leu Gly Ser Asn Arg
35 40 45

Ala Ser Gly Val Pro Asp Arg Phe Ser Gly Ser Gly Ser Gly Thr Asp
50 55 60

Phe Thr Leu Lys Ile Ser Arg Val Glu Ala Glu Asp Val Gly Val Tyr
65 70 75 80

Tyr Cys Met Gln Ala Leu Gln Thr Pro Phe Thr Phe Gly Pro Gly Thr
85 90 95

Lys Val Asp Ile Lys
100

<210> SEQ ID NO 648
<211> LENGTH: 101
<212> TYPE: PRT
<213> ORGANISM: Homo sapiens

<400> SEQUENCE: 648

Pro Val Thr Pro Gly Glu Pro Ala Ser Ile Ser Cys Arg Ser Ser Gln
1 5 10 15

Ser Leu Leu His Ser Thr Gly Tyr Asn Tyr Leu Asp Trp Tyr Leu Gln
20 25 30

Lys Pro Gly Gln Ser Pro Gln Leu Leu Ile Tyr Leu Gly Ser Asn Arg
35 40 45

```
Ala Ser Gly Val Pro Asp Arg Phe Ser Gly Ser Gly Ser Gly Thr Asp
    50                  55                  60

Phe Thr Leu Lys Ile Ser Arg Val Glu Ala Glu Asp Val Gly Val Tyr
65                  70                  75                  80

Tyr Cys Met Gln Ala Leu Gln Thr Pro Phe Thr Phe Gly Pro Gly Thr
                85                  90                  95

Lys Val Asp Ile Lys
            100


<210> SEQ ID NO 649
<211> LENGTH: 103
<212> TYPE: PRT
<213> ORGANISM: Homo sapiens

<400> SEQUENCE: 649

Pro Ala Ser Val Ser Gly Ser Pro Gly Gln Ser Ile Thr Ile Ser Cys
1               5                   10                  15

Ala Gly Thr Ser Ser Asp Val Gly Asn Tyr Asn Leu Val Ser Trp Tyr
            20                  25                  30

Gln Gln His Pro Gly Lys Ala Pro Lys Leu Leu Ile Tyr Glu Val Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Cys Ser Tyr Ala Gly Ser Ser Thr Tyr Val Phe Gly
                85                  90                  95

Thr Gly Thr Glu Val Thr Val
            100


<210> SEQ ID NO 650
<211> LENGTH: 103
<212> TYPE: PRT
<213> ORGANISM: Homo sapiens

<400> SEQUENCE: 650

Pro Ala Ser Val Ser Gly Ser Pro Gly Gln Ser Ile Thr Ile Ser Cys
1               5                   10                  15

Thr Gly Thr Ser Ser Asp Val Gly Ser Phe Asn Leu Val Ser Trp Tyr
            20                  25                  30

Gln Gln His Pro Gly Lys Ala Pro Lys Leu Ile Ile Tyr Glu Val Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Val
65                  70                  75                  80

His Tyr Tyr Cys Cys Ser Tyr Ala Gly Ser Ser Arg Phe Val Phe Gly
                85                  90                  95

Thr Gly Thr Lys Val Thr Val
            100


<210> SEQ ID NO 651
<211> LENGTH: 9
<212> TYPE: PRT
<213> ORGANISM: Homo sapiens

<400> SEQUENCE: 651
```

His Gln Ser Ile Lys Trp Pro Pro Thr
1 5

<210> SEQ ID NO 652
<211> LENGTH: 9
<212> TYPE: PRT
<213> ORGANISM: Homo sapiens

<400> SEQUENCE: 652

Gln Gln Arg Ser Asn Trp Pro Leu Thr
1 5

<210> SEQ ID NO 653
<211> LENGTH: 9
<212> TYPE: PRT
<213> ORGANISM: Homo sapiens

<400> SEQUENCE: 653

Gln Gln Tyr Gly Arg Ser Pro Phe Thr
1 5

<210> SEQ ID NO 654
<211> LENGTH: 11
<212> TYPE: PRT
<213> ORGANISM: Homo sapiens

<400> SEQUENCE: 654

Gln Gln Tyr Ala His Ser Pro Arg Gly Tyr Thr
1 5 10

<210> SEQ ID NO 655
<211> LENGTH: 8
<212> TYPE: PRT
<213> ORGANISM: Homo sapiens

<400> SEQUENCE: 655

Gln Gln Arg Ser Thr Trp Leu Thr
1 5

<210> SEQ ID NO 656
<211> LENGTH: 10
<212> TYPE: PRT
<213> ORGANISM: Homo sapiens

<400> SEQUENCE: 656

Gln Gln Gly Ser Lys Trp Pro Val Tyr Thr
1 5 10

<210> SEQ ID NO 657
<211> LENGTH: 11
<212> TYPE: PRT
<213> ORGANISM: Homo sapiens

<400> SEQUENCE: 657

Gln Gln Tyr Asn Asn Trp Pro Pro Val Phe Thr
1 5 10

<210> SEQ ID NO 658
<211> LENGTH: 11
<212> TYPE: PRT
<213> ORGANISM: Homo sapiens

<400> SEQUENCE: 658

Gln Gln Tyr Asn Asn Trp Pro Pro Val Phe Thr
1 5 10

<210> SEQ ID NO 659
<211> LENGTH: 9
<212> TYPE: PRT
<213> ORGANISM: Homo sapiens

<400> SEQUENCE: 659

Met Gln Ala Leu Gln Thr Pro Phe Thr
1               5

<210> SEQ ID NO 660
<211> LENGTH: 9
<212> TYPE: PRT
<213> ORGANISM: Homo sapiens

<400> SEQUENCE: 660

Met Gln Ala Leu Gln Thr Pro Phe Thr
1               5

<210> SEQ ID NO 661
<211> LENGTH: 10
<212> TYPE: PRT
<213> ORGANISM: Homo sapiens

<400> SEQUENCE: 661

Cys Ser Tyr Ala Gly Ser Ser Thr Tyr Val
1               5                   10

<210> SEQ ID NO 662
<211> LENGTH: 10
<212> TYPE: PRT
<213> ORGANISM: Homo sapiens

<400> SEQUENCE: 662

Cys Ser Tyr Ala Gly Ser Ser Arg Phe Val
1               5                   10

<210> SEQ ID NO 663
<211> LENGTH: 11
<212> TYPE: PRT
<213> ORGANISM: Homo sapiens

<400> SEQUENCE: 663

Ala Arg Thr Ala Gly Asp Tyr Gly Met Asp Val
1               5                   10

<210> SEQ ID NO 664
<211> LENGTH: 12
<212> TYPE: PRT
<213> ORGANISM: Homo sapiens

<400> SEQUENCE: 664

Tyr Arg Val Val Ala Phe Asp Asp Pro Val Asn Ile
1               5                   10

<210> SEQ ID NO 665
<211> LENGTH: 21
<212> TYPE: PRT
<213> ORGANISM: Homo sapiens

<400> SEQUENCE: 665

Ala Arg Leu Pro Ala Tyr Tyr Asp Ile Leu Thr Gly His Ile Lys Gly
1               5                   10                  15

Gly Tyr Phe Asp Tyr

20

<210> SEQ ID NO 666
<211> LENGTH: 18
<212> TYPE: PRT
<213> ORGANISM: Homo sapiens

<400> SEQUENCE: 666

Ala Arg Leu Gly Gly Phe Ser Arg Thr Leu Tyr Ser Tyr Tyr Ser Met
1 5 10 15

Asn Val

<210> SEQ ID NO 667
<211> LENGTH: 18
<212> TYPE: PRT
<213> ORGANISM: Homo sapiens

<400> SEQUENCE: 667

Ala Arg Gly Asp Tyr Arg Ser Ser Tyr Gly Tyr Arg Tyr Tyr Gly Phe
1 5 10 15

Asp Val

<210> SEQ ID NO 668
<211> LENGTH: 15
<212> TYPE: PRT
<213> ORGANISM: Homo sapiens

<400> SEQUENCE: 668

Ala Lys Asp Leu Tyr Ser Ser Gly Trp Tyr Met Gly Pro Asp Tyr
1 5 10 15

<210> SEQ ID NO 669
<211> LENGTH: 17
<212> TYPE: PRT
<213> ORGANISM: Homo sapiens

<400> SEQUENCE: 669

Ala Arg Asp Leu Trp Asp Lys Tyr Ser Ser Ser Leu Gly Ala Phe His
1 5 10 15

Ile

<210> SEQ ID NO 670
<211> LENGTH: 12
<212> TYPE: PRT
<213> ORGANISM: Homo sapiens

<400> SEQUENCE: 670

Ala Arg Asn Gln Pro Gly Gly Arg Ala Phe Asp Phe
1 5 10

<210> SEQ ID NO 671
<211> LENGTH: 17
<212> TYPE: PRT
<213> ORGANISM: Homo sapiens

<400> SEQUENCE: 671

Ala Arg Lys Lys Gly Gly Tyr Gly Ser His Tyr Tyr Tyr Gly Met Asp
1 5 10 15

Val

<210> SEQ ID NO 672
<211> LENGTH: 12

<212> TYPE: PRT
<213> ORGANISM: Homo sapiens

<400> SEQUENCE: 672

Gly Arg Thr Phe Thr Ser Ala Pro Phe Val Asp Gln
1 5 10

<210> SEQ ID NO 673
<211> LENGTH: 12
<212> TYPE: PRT
<213> ORGANISM: Homo sapiens

<400> SEQUENCE: 673

Ala Arg His Leu Pro Tyr Tyr Tyr Gly Met Asp Val
1 5 10

<210> SEQ ID NO 674
<211> LENGTH: 18
<212> TYPE: PRT
<213> ORGANISM: Homo sapiens

<400> SEQUENCE: 674

Ala Arg Gly Arg Arg Arg Ile Gln Gly Val Gly Glu Tyr Ser Gly Met
1 5 10 15

Asp Val

<210> SEQ ID NO 675
<211> LENGTH: 11
<212> TYPE: PRT
<213> ORGANISM: Homo sapiens

<400> SEQUENCE: 675

Ala Ser His Asp Tyr Gly Gly Asn Phe Arg Val
1 5 10

<210> SEQ ID NO 676
<211> LENGTH: 12
<212> TYPE: PRT
<213> ORGANISM: Homo sapiens

<400> SEQUENCE: 676

Ala Arg Val Gly Gly Arg Val Trp Trp Phe Asp Pro
1 5 10

<210> SEQ ID NO 677
<211> LENGTH: 15
<212> TYPE: PRT
<213> ORGANISM: Homo sapiens

<400> SEQUENCE: 677

Ala Lys Tyr Arg Asp Leu Trp Ser Gly Tyr Asp Ala Phe Asp Ile
1 5 10 15

<210> SEQ ID NO 678
<211> LENGTH: 9
<212> TYPE: PRT
<213> ORGANISM: Homo sapiens

<400> SEQUENCE: 678

Ala Thr Val Ile Arg His Phe Asp Asn
1 5

<210> SEQ ID NO 679
<211> LENGTH: 12

<212> TYPE: PRT
<213> ORGANISM: Homo sapiens

<400> SEQUENCE: 679

Ala Lys Val Gln Thr Phe Val Gly Ala Phe Asp Leu
1               5                   10

<210> SEQ ID NO 680
<211> LENGTH: 13
<212> TYPE: PRT
<213> ORGANISM: Homo sapiens

<400> SEQUENCE: 680

Ala Arg Asp Tyr Gly Asn Met Arg Tyr Gly Met Asp Gly
1               5                   10

<210> SEQ ID NO 681
<211> LENGTH: 12
<212> TYPE: PRT
<213> ORGANISM: Homo sapiens

<400> SEQUENCE: 681

Ala Arg Gly Leu Arg Phe Leu Tyr Gly Met Asp Val
1               5                   10

<210> SEQ ID NO 682
<211> LENGTH: 24
<212> TYPE: PRT
<213> ORGANISM: Homo sapiens

<400> SEQUENCE: 682

Ala Ser Glu Asn Leu Ile Ser Gln Gly His Cys Thr Gly Ala Ile Cys
1               5                   10                  15

Tyr Ser Thr Tyr Gly Met Asp Val
            20

<210> SEQ ID NO 683
<211> LENGTH: 26
<212> TYPE: PRT
<213> ORGANISM: Homo sapiens

<400> SEQUENCE: 683

Ala Arg Asp Ser Pro Tyr Tyr Tyr Asp Ala Thr Gly Ser Pro Leu Leu
1               5                   10                  15

Gly Pro Gly Thr Leu Val Thr Val Ser Ser
            20                  25

<210> SEQ ID NO 684
<211> LENGTH: 16
<212> TYPE: PRT
<213> ORGANISM: Homo sapiens

<400> SEQUENCE: 684

Ala Asn His Trp Gly Ser Ala Val Met Val Thr Gly Tyr Phe Asp Tyr
1               5                   10                  15

<210> SEQ ID NO 685
<211> LENGTH: 16
<212> TYPE: PRT
<213> ORGANISM: Homo sapiens

<400> SEQUENCE: 685

Thr Arg Val Arg Trp Asp Gly Ile Glu Ser Thr Met Phe Phe Asp Ser
1               5                   10                  15

<210> SEQ ID NO 686
<211> LENGTH: 16
<212> TYPE: PRT
<213> ORGANISM: Homo sapiens

<400> SEQUENCE: 686

Ala Arg Val Lys Met Ala Asn Gly Ala Ile Pro Pro Tyr Phe Asp His
1 5 10 15

<210> SEQ ID NO 687
<211> LENGTH: 16
<212> TYPE: PRT
<213> ORGANISM: Homo sapiens

<400> SEQUENCE: 687

Val Arg Val Asn Arg Leu His Ser Gly Ser Tyr Phe Ser Phe Asp Tyr
1 5 10 15

<210> SEQ ID NO 688
<211> LENGTH: 18
<212> TYPE: PRT
<213> ORGANISM: Homo sapiens

<400> SEQUENCE: 688

Ala Arg Leu Gly Leu Ile Gln Ser Leu Arg Asn Tyr Tyr Tyr Gly Leu
1 5 10 15

Asp Val

<210> SEQ ID NO 689
<211> LENGTH: 11
<212> TYPE: PRT
<213> ORGANISM: Homo sapiens

<400> SEQUENCE: 689

Thr Thr Ala Ile Arg Val Thr Gly Met Asp Val
1 5 10

<210> SEQ ID NO 690
<211> LENGTH: 11
<212> TYPE: PRT
<213> ORGANISM: Homo sapiens

<400> SEQUENCE: 690

Ala Arg Gly Trp Ser Asp Asn Ser Met Asp Val
1 5 10

<210> SEQ ID NO 691
<211> LENGTH: 14
<212> TYPE: PRT
<213> ORGANISM: Homo sapiens

<400> SEQUENCE: 691

Val Thr Leu Leu His Asp Tyr Gly Asp Tyr Ser Phe Asp Tyr
1 5 10

<210> SEQ ID NO 692
<211> LENGTH: 15
<212> TYPE: PRT
<213> ORGANISM: Homo sapiens

<400> SEQUENCE: 692

Ala Arg Gly Asn Ile Thr His Tyr Asp Leu Leu Pro Cys Asp Ser
1 5 10 15

<210> SEQ ID NO 693
<211> LENGTH: 11
<212> TYPE: PRT
<213> ORGANISM: Homo sapiens

<400> SEQUENCE: 693

```
Ser Leu Gly Arg Ile Asn Tyr Phe Phe Asp Tyr
1               5                   10
```

<210> SEQ ID NO 694
<211> LENGTH: 10
<212> TYPE: PRT
<213> ORGANISM: Homo sapiens

<400> SEQUENCE: 694

```
Ala Arg Ala Ser Gln Leu Val Pro Asp Tyr
1               5                   10
```

<210> SEQ ID NO 695
<211> LENGTH: 14
<212> TYPE: PRT
<213> ORGANISM: Homo sapiens

<400> SEQUENCE: 695

```
Ala Arg Gly Gly Pro Ile Asn Val Pro Leu Gly Phe Asp Pro
1               5                   10
```

<210> SEQ ID NO 696
<211> LENGTH: 22
<212> TYPE: PRT
<213> ORGANISM: Homo sapiens

<400> SEQUENCE: 696

```
Ala Arg Asp Glu Gly Gly Pro Asn Cys Ser Gly Gly Asn Cys Tyr Tyr
1               5                   10                  15

Tyr Tyr Gly Met Asp Val
            20
```

<210> SEQ ID NO 697
<211> LENGTH: 13
<212> TYPE: PRT
<213> ORGANISM: Homo sapiens

<400> SEQUENCE: 697

```
Ala Asn Gly Gly Trp Gln Val Pro His Trp Phe Asp Pro
1               5                   10
```

<210> SEQ ID NO 698
<211> LENGTH: 15
<212> TYPE: PRT
<213> ORGANISM: Homo sapiens

<400> SEQUENCE: 698

```
Ala Arg Ala Arg Ser Gly Tyr Ser Leu Gly Tyr Tyr Phe Asp Tyr
1               5                   10                  15
```

<210> SEQ ID NO 699
<211> LENGTH: 15
<212> TYPE: PRT
<213> ORGANISM: Homo sapiens

<400> SEQUENCE: 699

```
Ala Lys Val Ser Arg Pro Lys Gly Ala Gln Ala Ser Phe Asp Pro
```

1 5 10 15

<210> SEQ ID NO 700
<211> LENGTH: 15
<212> TYPE: PRT
<213> ORGANISM: Homo sapiens

<400> SEQUENCE: 700

Ala Thr Pro Lys Gly Gly Tyr Ser Gly Tyr Asp Gln Leu Asp Tyr
1 5 10 15

<210> SEQ ID NO 701
<211> LENGTH: 18
<212> TYPE: PRT
<213> ORGANISM: Homo sapiens

<400> SEQUENCE: 701

Ala Arg Pro Gly Tyr Thr Phe Gly Tyr His Ser Tyr Tyr Tyr Ala Met
1 5 10 15

Asp Val

<210> SEQ ID NO 702
<211> LENGTH: 6
<212> TYPE: PRT
<213> ORGANISM: Homo sapiens

<400> SEQUENCE: 702

Ala Arg Gly Ile Asp Tyr
1 5

<210> SEQ ID NO 703
<211> LENGTH: 22
<212> TYPE: PRT
<213> ORGANISM: Homo sapiens

<400> SEQUENCE: 703

Ala Arg Gly Ser Leu Arg Gly Thr Asn Gly Trp His Ser His Leu Gly
1 5 10 15

Tyr Tyr Gly Met Asp Val
20

<210> SEQ ID NO 704
<211> LENGTH: 15
<212> TYPE: PRT
<213> ORGANISM: Homo sapiens

<400> SEQUENCE: 704

Ala Arg Ser Arg Leu Arg Tyr Ser Ser Ser Trp Tyr Phe Asp Tyr
1 5 10 15

<210> SEQ ID NO 705
<211> LENGTH: 16
<212> TYPE: PRT
<213> ORGANISM: Homo sapiens

<400> SEQUENCE: 705

Ala Arg Asp Ile Leu Pro His Gly Thr His Gly Trp Tyr Phe Asp Val
1 5 10 15

<210> SEQ ID NO 706
<211> LENGTH: 12
<212> TYPE: PRT
<213> ORGANISM: Homo sapiens

<400> SEQUENCE: 706

Ala Arg Ala Lys Gly Met Ile Ala Glu Leu Asp Tyr
1 5 10

<210> SEQ ID NO 707
<211> LENGTH: 10
<212> TYPE: PRT
<213> ORGANISM: Homo sapiens

<400> SEQUENCE: 707

Gln Ala Trp Asp Ser Ser Thr Ala Val Val
1 5 10

<210> SEQ ID NO 708
<211> LENGTH: 11
<212> TYPE: PRT
<213> ORGANISM: Homo sapiens

<400> SEQUENCE: 708

Gln Ser Ala Asp Thr Asn Gly Ser Ser Trp Ile
1 5 10

<210> SEQ ID NO 709
<211> LENGTH: 9
<212> TYPE: PRT
<213> ORGANISM: Homo sapiens

<400> SEQUENCE: 709

Gln Gln Tyr Tyr Thr Thr Pro Gln Thr
1 5

<210> SEQ ID NO 710
<211> LENGTH: 9
<212> TYPE: PRT
<213> ORGANISM: Homo sapiens

<400> SEQUENCE: 710

Gln Gln Ser Gly Ser Leu Pro Trp Thr
1 5

<210> SEQ ID NO 711
<211> LENGTH: 11
<212> TYPE: PRT
<213> ORGANISM: Homo sapiens

<400> SEQUENCE: 711

Gln Ser Ala Asp Thr Asn Gly Ser Ser Trp Ile
1 5 10

<210> SEQ ID NO 712
<211> LENGTH: 11
<212> TYPE: PRT
<213> ORGANISM: Homo sapiens

<400> SEQUENCE: 712

Gln Ser Tyr Asp Ser Ser Leu Ser Gly Tyr Val
1 5 10

<210> SEQ ID NO 713
<211> LENGTH: 9
<212> TYPE: PRT
<213> ORGANISM: Homo sapiens

<400> SEQUENCE: 713

-continued

Gln Gln Tyr Asn Asn Trp Pro Leu His
1 5

<210> SEQ ID NO 714
<211> LENGTH: 11
<212> TYPE: PRT
<213> ORGANISM: Homo sapiens

<400> SEQUENCE: 714

Gln Glu Arg Asp Asn Trp Pro Leu Thr Trp Pro
1 5 10

<210> SEQ ID NO 715
<211> LENGTH: 9
<212> TYPE: PRT
<213> ORGANISM: Homo sapiens

<400> SEQUENCE: 715

Gln Gln Asp Tyr Ser Leu Pro Thr Thr
1 5

<210> SEQ ID NO 716
<211> LENGTH: 9
<212> TYPE: PRT
<213> ORGANISM: Homo sapiens

<400> SEQUENCE: 716

Gln Gln Tyr Tyr Ser Thr Pro Tyr Thr
1 5

<210> SEQ ID NO 717
<211> LENGTH: 9
<212> TYPE: PRT
<213> ORGANISM: Homo sapiens

<400> SEQUENCE: 717

Gln Gln Tyr Asn Asn Trp Pro Pro Thr
1 5

<210> SEQ ID NO 718
<211> LENGTH: 11
<212> TYPE: PRT
<213> ORGANISM: Homo sapiens

<400> SEQUENCE: 718

Met Gln Ser Leu Gln Thr Pro Arg Ala Leu Thr
1 5 10

<210> SEQ ID NO 719
<211> LENGTH: 9
<212> TYPE: PRT
<213> ORGANISM: Homo sapiens

<400> SEQUENCE: 719

Gln Gln Tyr Gly Ser Ser Pro Arg Thr
1 5

<210> SEQ ID NO 720
<211> LENGTH: 9
<212> TYPE: PRT
<213> ORGANISM: Homo sapiens

<400> SEQUENCE: 720

Gln Gln Thr Tyr Ser Thr Pro Trp Thr
1 5

<210> SEQ ID NO 721
<211> LENGTH: 8
<212> TYPE: PRT
<213> ORGANISM: Homo sapiens

<400> SEQUENCE: 721

Gln Gln Tyr Gly Ser Ser Leu Thr
1 5

<210> SEQ ID NO 722
<211> LENGTH: 10
<212> TYPE: PRT
<213> ORGANISM: Homo sapiens

<400> SEQUENCE: 722

Gln Gln Tyr Asp Asn Leu Pro Gly Phe Thr
1 5 10

<210> SEQ ID NO 723
<211> LENGTH: 11
<212> TYPE: PRT
<213> ORGANISM: Homo sapiens

<400> SEQUENCE: 723

Gln His Tyr Asp Ser Leu Pro Leu Leu Ile Ser
1 5 10

<210> SEQ ID NO 724
<211> LENGTH: 10
<212> TYPE: PRT
<213> ORGANISM: Homo sapiens

<400> SEQUENCE: 724

Gln Gln Asn Asp Asp Ala Arg Ala Leu Thr
1 5 10

<210> SEQ ID NO 725
<211> LENGTH: 8
<212> TYPE: PRT
<213> ORGANISM: Homo sapiens

<400> SEQUENCE: 725

Gln His Tyr Asp Ser Ser Ile Thr
1 5

<210> SEQ ID NO 726
<211> LENGTH: 9
<212> TYPE: PRT
<213> ORGANISM: Homo sapiens

<400> SEQUENCE: 726

Gln Gln Ser Tyr Thr Val Pro Arg Thr
1 5

<210> SEQ ID NO 727
<211> LENGTH: 9
<212> TYPE: PRT
<213> ORGANISM: Homo sapiens

<400> SEQUENCE: 727

Gln Gln Tyr Asn Ser Tyr Pro Arg Thr
1 5

<210> SEQ ID NO 728
<211> LENGTH: 9
<212> TYPE: PRT
<213> ORGANISM: Homo sapiens

<400> SEQUENCE: 728

Gln Gln Tyr Tyr Ser Tyr Pro Arg Thr
1               5

<210> SEQ ID NO 729
<211> LENGTH: 12
<212> TYPE: PRT
<213> ORGANISM: Homo sapiens

<400> SEQUENCE: 729

Ser Ser Tyr Ala Gly Ser Asn Asn Phe Glu Val Val
1               5                   10

<210> SEQ ID NO 730
<211> LENGTH: 9
<212> TYPE: PRT
<213> ORGANISM: Homo sapiens

<400> SEQUENCE: 730

Gln Gln Leu Ile Ser Tyr Pro Pro Thr
1               5

<210> SEQ ID NO 731
<211> LENGTH: 10
<212> TYPE: PRT
<213> ORGANISM: Homo sapiens

<400> SEQUENCE: 731

Cys Ser Tyr Ala Ala Gly Ser Thr Phe Val
1               5                   10

<210> SEQ ID NO 732
<211> LENGTH: 9
<212> TYPE: PRT
<213> ORGANISM: Homo sapiens

<400> SEQUENCE: 732

Gln Ala Trp Asp Ser Arg Ser Val Val
1               5

<210> SEQ ID NO 733
<211> LENGTH: 9
<212> TYPE: PRT
<213> ORGANISM: Homo sapiens

<400> SEQUENCE: 733

Gln Ser Tyr Asp Ser Ser His Tyr Val
1               5

<210> SEQ ID NO 734
<211> LENGTH: 9
<212> TYPE: PRT
<213> ORGANISM: Homo sapiens

<400> SEQUENCE: 734

Gln Gln Tyr Gly Ser Ser Pro Ile Thr
1               5

<210> SEQ ID NO 735
<211> LENGTH: 9

<212> TYPE: PRT
<213> ORGANISM: Homo sapiens

<400> SEQUENCE: 735

Gln Gln Ser Ser Ser Ile Pro Tyr Thr
1 5

<210> SEQ ID NO 736
<211> LENGTH: 9
<212> TYPE: PRT
<213> ORGANISM: Homo sapiens

<400> SEQUENCE: 736

Gln Gln Tyr Tyr Ser Thr Pro His Thr
1 5

<210> SEQ ID NO 737
<211> LENGTH: 9
<212> TYPE: PRT
<213> ORGANISM: Homo sapiens

<400> SEQUENCE: 737

Gln Gln Leu Asn Ser Tyr Pro Leu Thr
1 5

<210> SEQ ID NO 738
<211> LENGTH: 8
<212> TYPE: PRT
<213> ORGANISM: Homo sapiens

<400> SEQUENCE: 738

Gln Gln Arg Ser Asn Trp Leu Thr
1 5

<210> SEQ ID NO 739
<211> LENGTH: 9
<212> TYPE: PRT
<213> ORGANISM: Homo sapiens

<400> SEQUENCE: 739

His Gln Tyr Val Ser Ser Pro Leu Thr
1 5

<210> SEQ ID NO 740
<211> LENGTH: 9
<212> TYPE: PRT
<213> ORGANISM: Homo sapiens

<400> SEQUENCE: 740

Asn Asn Met Ile Leu Ser Leu Gln Leu
1 5

<210> SEQ ID NO 741
<211> LENGTH: 9
<212> TYPE: PRT
<213> ORGANISM: Homo sapiens

<400> SEQUENCE: 741

Gln Gln Ser Tyr Ser Ile Pro Leu Thr
1 5

<210> SEQ ID NO 742
<211> LENGTH: 8
<212> TYPE: PRT
<213> ORGANISM: Homo sapiens

<400> SEQUENCE: 742

Gln Gln Tyr Asp Asp Leu Leu Thr
1 5

<210> SEQ ID NO 743
<211> LENGTH: 9
<212> TYPE: PRT
<213> ORGANISM: Homo sapiens

<400> SEQUENCE: 743

Leu Gln Asp Tyr Asp Tyr Pro Leu Ser
1 5

<210> SEQ ID NO 744
<211> LENGTH: 9
<212> TYPE: PRT
<213> ORGANISM: Homo sapiens

<400> SEQUENCE: 744

Gln Gln Ser Tyr Asn Phe Pro Arg Thr
1 5

<210> SEQ ID NO 745
<211> LENGTH: 6
<212> TYPE: PRT
<213> ORGANISM: Homo sapiens

<400> SEQUENCE: 745

Gln Gln Arg Ala Gly Thr
1 5

<210> SEQ ID NO 746
<211> LENGTH: 9
<212> TYPE: PRT
<213> ORGANISM: Homo sapiens

<400> SEQUENCE: 746

Thr Gln Ala Thr Gln Phe Pro Trp Thr
1 5

<210> SEQ ID NO 747
<211> LENGTH: 9
<212> TYPE: PRT
<213> ORGANISM: Homo sapiens

<400> SEQUENCE: 747

His Gln Ser Phe Ser Ser Pro Asp Thr
1 5

<210> SEQ ID NO 748
<211> LENGTH: 10
<212> TYPE: PRT
<213> ORGANISM: Homo sapiens

<400> SEQUENCE: 748

Gln Gln Tyr Tyr Ser Thr Pro Arg Ile Thr
1 5 10

<210> SEQ ID NO 749
<211> LENGTH: 10
<212> TYPE: PRT
<213> ORGANISM: Homo sapiens

<400> SEQUENCE: 749

Gln His Arg Arg Asp Trp Pro Arg Tyr Thr
1 5 10

<210> SEQ ID NO 750
<211> LENGTH: 10
<212> TYPE: PRT
<213> ORGANISM: Homo sapiens

<400> SEQUENCE: 750

Gln Gln Tyr Arg Asp Thr Pro Ser Tyr Thr
1 5 10

<210> SEQ ID NO 751
<211> LENGTH: 23
<212> TYPE: PRT
<213> ORGANISM: Homo sapiens

<400> SEQUENCE: 751

Thr Thr Glu Ile Gly Leu Gly Gly Pro Asn Thr Pro Ser Ala Gln Leu
1 5 10 15

Tyr Tyr Tyr Gly Ile Asp Val
20

<210> SEQ ID NO 752
<211> LENGTH: 10
<212> TYPE: PRT
<213> ORGANISM: Homo sapiens

<400> SEQUENCE: 752

Ala Ser Phe Arg Ser Gly Ala Phe Glu Ile
1 5 10

<210> SEQ ID NO 753
<211> LENGTH: 20
<212> TYPE: PRT
<213> ORGANISM: Homo sapiens

<400> SEQUENCE: 753

Ala Arg Val Arg Tyr Glu Tyr Asp Ser Gly Gly Tyr Tyr Tyr Val Tyr
1 5 10 15

Asp Phe Glu Tyr
20

<210> SEQ ID NO 754
<211> LENGTH: 19
<212> TYPE: PRT
<213> ORGANISM: Homo sapiens

<400> SEQUENCE: 754

Ala Arg Val Ala Leu Ser Ser Ser Ser Phe Gly Glu His Tyr Tyr Gly
1 5 10 15

Val Asp Val

<210> SEQ ID NO 755
<211> LENGTH: 15
<212> TYPE: PRT
<213> ORGANISM: Homo sapiens

<400> SEQUENCE: 755

Ala Arg Ala Gly Thr Val Phe Ala Gly His Tyr Gly Met Asp Val
1 5 10 15

<210> SEQ ID NO 756
<211> LENGTH: 24
<212> TYPE: PRT
<213> ORGANISM: Homo sapiens

<400> SEQUENCE: 756

Ala Lys Asp Pro Arg Arg Asp Tyr Tyr Asp Ser Ser Gly Tyr Tyr Tyr
1 5 10 15

Pro Ser Arg Gly His Phe Asp Tyr
20

<210> SEQ ID NO 757
<211> LENGTH: 13
<212> TYPE: PRT
<213> ORGANISM: Homo sapiens

<400> SEQUENCE: 757

Ala Arg Ile Ile Thr Arg Asn Gly Asp Ala Phe Asp Ile
1 5 10

<210> SEQ ID NO 758
<211> LENGTH: 13
<212> TYPE: PRT
<213> ORGANISM: Homo sapiens

<400> SEQUENCE: 758

Ala Lys Phe Gln Ser Ser Asn Trp Ser Pro Phe Asp Ser
1 5 10

<210> SEQ ID NO 759
<211> LENGTH: 13
<212> TYPE: PRT
<213> ORGANISM: Homo sapiens

<400> SEQUENCE: 759

Ala Arg Gly Val Trp Phe Gly Glu Phe Ala Val Gly Tyr
1 5 10

<210> SEQ ID NO 760
<211> LENGTH: 13
<212> TYPE: PRT
<213> ORGANISM: Homo sapiens

<400> SEQUENCE: 760

Ile Thr Gly Ile Phe Lys Ser Thr Trp Lys Thr Asp Tyr
1 5 10

<210> SEQ ID NO 761
<211> LENGTH: 13
<212> TYPE: PRT
<213> ORGANISM: Homo sapiens

<400> SEQUENCE: 761

Ala Arg Glu Ser Asp Phe Asn Tyr Gly Ala Val Asp His
1 5 10

<210> SEQ ID NO 762
<211> LENGTH: 14
<212> TYPE: PRT
<213> ORGANISM: Homo sapiens

<400> SEQUENCE: 762

Ala Lys Thr Gln Gly Tyr Asn Pro Asn Trp Pro His Asp Phe
1 5 10

<210> SEQ ID NO 763
<211> LENGTH: 10
<212> TYPE: PRT
<213> ORGANISM: Homo sapiens

<400> SEQUENCE: 763

Ala Lys Asp Gly Arg Gly Ser Ile Asp Tyr
1 5 10

<210> SEQ ID NO 764
<211> LENGTH: 13
<212> TYPE: PRT
<213> ORGANISM: Homo sapiens

<400> SEQUENCE: 764

Glu Arg Asp Ile Val Trp Gly Val Ala Gly Thr Asp Tyr
1 5 10

<210> SEQ ID NO 765
<211> LENGTH: 11
<212> TYPE: PRT
<213> ORGANISM: Homo sapiens

<400> SEQUENCE: 765

Ala Arg Glu Asn Ile Ala Val Phe Phe Asp Ile
1 5 10

<210> SEQ ID NO 766
<211> LENGTH: 15
<212> TYPE: PRT
<213> ORGANISM: Homo sapiens

<400> SEQUENCE: 766

Ala Arg Asp Lys Arg Tyr Ser Ser Gly Trp Tyr Tyr Phe Glu Ser
1 5 10 15

<210> SEQ ID NO 767
<211> LENGTH: 12
<212> TYPE: PRT
<213> ORGANISM: Homo sapiens

<400> SEQUENCE: 767

Val Lys Pro Ser Val Thr Thr His Tyr Phe Asp Tyr
1 5 10

<210> SEQ ID NO 768
<211> LENGTH: 19
<212> TYPE: PRT
<213> ORGANISM: Homo sapiens

<400> SEQUENCE: 768

Ala Arg Asp His Ser Pro Gly Thr Thr Trp Gly Asn Tyr Asn Tyr Gly
1 5 10 15

Met Asp Val

<210> SEQ ID NO 769
<211> LENGTH: 20
<212> TYPE: PRT
<213> ORGANISM: Homo sapiens

<400> SEQUENCE: 769

Ala Arg Asp Ser Arg Tyr Tyr Asp Ser Arg Ser Ser Tyr Tyr Tyr Tyr
1 5 10 15

```
Gly Met Asp Val
            20


<210> SEQ ID NO 770
<211> LENGTH: 15
<212> TYPE: PRT
<213> ORGANISM: Homo sapiens

<400> SEQUENCE: 770

Ala Arg Val Ala Arg Pro Gly Gly Tyr Gly Arg Thr Phe Asp Glu
1               5                   10                  15


<210> SEQ ID NO 771
<211> LENGTH: 15
<212> TYPE: PRT
<213> ORGANISM: Homo sapiens

<400> SEQUENCE: 771

Ala Arg Val Arg Glu Arg Tyr Tyr Tyr Phe Tyr Gly Leu Asp Val
1               5                   10                  15


<210> SEQ ID NO 772
<211> LENGTH: 12
<212> TYPE: PRT
<213> ORGANISM: Homo sapiens

<400> SEQUENCE: 772

Ala Lys Gly Val Ala Ala Pro Gly Tyr Phe Glu Tyr
1               5                   10


<210> SEQ ID NO 773
<211> LENGTH: 11
<212> TYPE: PRT
<213> ORGANISM: Homo sapiens

<400> SEQUENCE: 773

Val Ala Trp Asp Asp Ser Leu Ser Gly Arg Val
1               5                   10


<210> SEQ ID NO 774
<211> LENGTH: 9
<212> TYPE: PRT
<213> ORGANISM: Homo sapiens

<400> SEQUENCE: 774

Gln Gln Tyr Gly Ser Ser Ala Val Ser
1               5


<210> SEQ ID NO 775
<211> LENGTH: 8
<212> TYPE: PRT
<213> ORGANISM: Homo sapiens

<400> SEQUENCE: 775

Cys Ser Tyr Ala Gly Ser Tyr Val
1               5


<210> SEQ ID NO 776
<211> LENGTH: 10
<212> TYPE: PRT
<213> ORGANISM: Homo sapiens

<400> SEQUENCE: 776

Gln Gln Tyr Gly Gly Ser Pro Leu Phe Thr
1               5                   10
```

<210> SEQ ID NO 777
<211> LENGTH: 9
<212> TYPE: PRT
<213> ORGANISM: Homo sapiens

<400> SEQUENCE: 777

Gln Gln Tyr Lys Ser Tyr Pro Leu Thr
1               5

<210> SEQ ID NO 778
<211> LENGTH: 10
<212> TYPE: PRT
<213> ORGANISM: Homo sapiens

<400> SEQUENCE: 778

Ser Ser Tyr Ala Gly Ser Arg Thr Trp Val
1               5                   10

<210> SEQ ID NO 779
<211> LENGTH: 8
<212> TYPE: PRT
<213> ORGANISM: Homo sapiens

<400> SEQUENCE: 779

Cys Ser Tyr Ala Gly Ser Tyr Thr
1               5

<210> SEQ ID NO 780
<211> LENGTH: 9
<212> TYPE: PRT
<213> ORGANISM: Homo sapiens

<400> SEQUENCE: 780

Gln Gln Tyr Gly Asn Leu Pro Arg Thr
1               5

<210> SEQ ID NO 781
<211> LENGTH: 12
<212> TYPE: PRT
<213> ORGANISM: Homo sapiens

<400> SEQUENCE: 781

Gln Gln Tyr Asn Asn Trp Pro Pro Arg Gly Ala Thr
1               5                   10

<210> SEQ ID NO 782
<211> LENGTH: 8
<212> TYPE: PRT
<213> ORGANISM: Homo sapiens

<400> SEQUENCE: 782

Gln Gln Arg Ser Asn Gly Trp Thr
1               5

<210> SEQ ID NO 783
<211> LENGTH: 9
<212> TYPE: PRT
<213> ORGANISM: Homo sapiens

<400> SEQUENCE: 783

Gln Gln Tyr Asn Asn Trp Pro Tyr Thr
1               5

<210> SEQ ID NO 784
<211> LENGTH: 9
<212> TYPE: PRT
<213> ORGANISM: Homo sapiens

<400> SEQUENCE: 784

Gln Gln Leu Asn Gly His Pro Arg Thr
1 5

<210> SEQ ID NO 785
<211> LENGTH: 10
<212> TYPE: PRT
<213> ORGANISM: Homo sapiens

<400> SEQUENCE: 785

Met Gln Ser Ile Gln Leu Pro Pro Ile Thr
1 5 10

<210> SEQ ID NO 786
<211> LENGTH: 9
<212> TYPE: PRT
<213> ORGANISM: Homo sapiens

<400> SEQUENCE: 786

Gln Tyr Tyr Gly Asp Ser Pro Arg Pro
1 5

<210> SEQ ID NO 787
<211> LENGTH: 9
<212> TYPE: PRT
<213> ORGANISM: Homo sapiens

<400> SEQUENCE: 787

Gln Gln His Asp Asn Leu Gln Val Ile
1 5

<210> SEQ ID NO 788
<211> LENGTH: 8
<212> TYPE: PRT
<213> ORGANISM: Homo sapiens

<400> SEQUENCE: 788

Gln His Arg Ala Asn Trp Pro Thr
1 5

<210> SEQ ID NO 789
<211> LENGTH: 10
<212> TYPE: PRT
<213> ORGANISM: Homo sapiens

<400> SEQUENCE: 789

Gln Gln Arg Ser Asn Trp Pro Pro Phe Thr
1 5 10

<210> SEQ ID NO 790
<211> LENGTH: 9
<212> TYPE: PRT
<213> ORGANISM: Homo sapiens

<400> SEQUENCE: 790

Gln Gln Ser Tyr Ser Thr Pro Gln Thr
1 5

<210> SEQ ID NO 791
<211> LENGTH: 9

<212> TYPE: PRT
<213> ORGANISM: Homo sapiens

<400> SEQUENCE: 791

Met Gln Ala Leu Gln Thr Pro Lys Thr
1               5

<210> SEQ ID NO 792
<211> LENGTH: 8
<212> TYPE: PRT
<213> ORGANISM: Homo sapiens

<400> SEQUENCE: 792

Gln Gln Ser Tyr Ser Asp Phe Ser
1               5

<210> SEQ ID NO 793
<211> LENGTH: 8
<212> TYPE: PRT
<213> ORGANISM: Homo sapiens

<400> SEQUENCE: 793

Met Gln Ala Leu Gln Thr Phe Thr
1               5

<210> SEQ ID NO 794
<211> LENGTH: 10
<212> TYPE: PRT
<213> ORGANISM: Homo sapiens

<400> SEQUENCE: 794

Gln Gln Arg Ser Asn Trp Pro Pro Ile Thr
1               5                   10

<210> SEQ ID NO 795
<211> LENGTH: 17
<212> TYPE: PRT
<213> ORGANISM: Homo sapiens

<400> SEQUENCE: 795

Ala Arg Gly Asn Ser Tyr Gly Ser Gly Asn Leu Gly Tyr Tyr Leu Asp
1               5                   10                  15

Phe

<210> SEQ ID NO 796
<211> LENGTH: 16
<212> TYPE: PRT
<213> ORGANISM: Homo sapiens

<400> SEQUENCE: 796

Ala Arg Gly Pro Asp Tyr Asn Asp Thr Pro Gly Tyr Tyr Gly Asn Tyr
1               5                   10                  15

<210> SEQ ID NO 797
<211> LENGTH: 20
<212> TYPE: PRT
<213> ORGANISM: Homo sapiens

<400> SEQUENCE: 797

Ala Arg Gly Ala His Tyr Tyr Asp Ser Ser Gly Tyr Arg Gln Leu Tyr
1               5                   10                  15

Gly Leu Asp Val
            20

<210> SEQ ID NO 798
<211> LENGTH: 12
<212> TYPE: PRT
<213> ORGANISM: Homo sapiens

<400> SEQUENCE: 798

Ala Arg Ala Asn Val Ala Thr Arg Tyr Phe Asp Tyr
1 5 10

<210> SEQ ID NO 799
<211> LENGTH: 14
<212> TYPE: PRT
<213> ORGANISM: Homo sapiens

<400> SEQUENCE: 799

Ala Arg Leu Arg Val Arg Gly Ala Gly Trp Ala Phe Asp Leu
1 5 10

<210> SEQ ID NO 800
<211> LENGTH: 20
<212> TYPE: PRT
<213> ORGANISM: Homo sapiens

<400> SEQUENCE: 800

Ala Lys Ser Asp Tyr Tyr Gly Ser Gly His Tyr Thr Thr Ile Pro Ser
1 5 10 15

Ser Phe Glu Asp
20

<210> SEQ ID NO 801
<211> LENGTH: 15
<212> TYPE: PRT
<213> ORGANISM: Homo sapiens

<400> SEQUENCE: 801

Ala Arg His Pro Thr Gln Asn Tyr Ala Ser Gly Asp Tyr Tyr Thr
1 5 10 15

<210> SEQ ID NO 802
<211> LENGTH: 14
<212> TYPE: PRT
<213> ORGANISM: Homo sapiens

<400> SEQUENCE: 802

Ala Lys Gly Ala Arg Ile Thr Val Phe Gly Gly Leu Asp Val
1 5 10

<210> SEQ ID NO 803
<211> LENGTH: 18
<212> TYPE: PRT
<213> ORGANISM: Homo sapiens

<400> SEQUENCE: 803

Ala Arg Pro Tyr Phe Asp Gly Arg Ser Asn Ser Asn Leu Ile Phe Phe
1 5 10 15

Asp Tyr

<210> SEQ ID NO 804
<211> LENGTH: 20
<212> TYPE: PRT
<213> ORGANISM: Homo sapiens

<400> SEQUENCE: 804

-continued

Ala Arg Val Ile Val Val Val Val Ala Ala Thr Ser Asp Leu Pro Val
1 5 10 15

Gly Phe Asp Pro
20

<210> SEQ ID NO 805
<211> LENGTH: 14
<212> TYPE: PRT
<213> ORGANISM: Homo sapiens

<400> SEQUENCE: 805

Ala Arg Trp Leu Asp Asn Gly Ile Gln Gly Lys Tyr Asp Tyr
1 5 10

<210> SEQ ID NO 806
<211> LENGTH: 16
<212> TYPE: PRT
<213> ORGANISM: Homo sapiens

<400> SEQUENCE: 806

Ala Arg Gly Pro Val Trp Phe Gly Glu Tyr Gly Gly Ala Phe Asp Pro
1 5 10 15

<210> SEQ ID NO 807
<211> LENGTH: 14
<212> TYPE: PRT
<213> ORGANISM: Homo sapiens

<400> SEQUENCE: 807

Ala Arg Ala Lys Gly Arg Gly Leu Gln Asn Trp Phe Asp Pro
1 5 10

<210> SEQ ID NO 808
<211> LENGTH: 25
<212> TYPE: PRT
<213> ORGANISM: Homo sapiens

<400> SEQUENCE: 808

Ala Arg Val Ser Pro Leu Trp Asp Tyr Tyr Asp Ser Gly Pro Tyr Tyr
1 5 10 15

Asn Asp Phe Tyr Tyr Gly Met Asp Val
20 25

<210> SEQ ID NO 809
<211> LENGTH: 11
<212> TYPE: PRT
<213> ORGANISM: Homo sapiens

<400> SEQUENCE: 809

Ser Thr Trp Asp Asp Ser Leu Asn Gly Pro Val
1 5 10

<210> SEQ ID NO 810
<211> LENGTH: 6
<212> TYPE: PRT
<213> ORGANISM: Homo sapiens

<400> SEQUENCE: 810

His His Tyr Gly Arg Thr
1 5

<210> SEQ ID NO 811
<211> LENGTH: 10
<212> TYPE: PRT

<213> ORGANISM: Homo sapiens

<400> SEQUENCE: 811

Gln Gln Arg Ala Asn Trp Pro Ala Leu Thr
1 5 10

<210> SEQ ID NO 812
<211> LENGTH: 9
<212> TYPE: PRT
<213> ORGANISM: Homo sapiens

<400> SEQUENCE: 812

Gln His Leu Ser Thr Tyr Pro Ile Thr
1 5

<210> SEQ ID NO 813
<211> LENGTH: 11
<212> TYPE: PRT
<213> ORGANISM: Homo sapiens

<400> SEQUENCE: 813

Gln Gln Arg Ser Asn Trp Pro Pro Ala Ile Thr
1 5 10

<210> SEQ ID NO 814
<211> LENGTH: 9
<212> TYPE: PRT
<213> ORGANISM: Homo sapiens

<400> SEQUENCE: 814

Gln Gln Tyr Asn Asn Trp Pro Leu Thr
1 5

<210> SEQ ID NO 815
<211> LENGTH: 9
<212> TYPE: PRT
<213> ORGANISM: Homo sapiens

<400> SEQUENCE: 815

Gln Gln Leu Thr Thr Tyr Pro Gly Thr
1 5

<210> SEQ ID NO 816
<211> LENGTH: 9
<212> TYPE: PRT
<213> ORGANISM: Homo sapiens

<400> SEQUENCE: 816

Gln Gln Tyr Met Ser Leu Pro Tyr Ser
1 5

<210> SEQ ID NO 817
<211> LENGTH: 11
<212> TYPE: PRT
<213> ORGANISM: Homo sapiens

<400> SEQUENCE: 817

Gln Gln Tyr Asn Thr Trp Pro Pro Ala Leu Thr
1 5 10

<210> SEQ ID NO 818
<211> LENGTH: 9
<212> TYPE: PRT
<213> ORGANISM: Homo sapiens

<400> SEQUENCE: 818

Gln His Tyr His Ser Tyr Pro Trp Thr
1 5

<210> SEQ ID NO 819
<211> LENGTH: 8
<212> TYPE: PRT
<213> ORGANISM: Homo sapiens

<400> SEQUENCE: 819

Gln Gln Arg His Glu Trp Pro Val
1 5

<210> SEQ ID NO 820
<211> LENGTH: 9
<212> TYPE: PRT
<213> ORGANISM: Homo sapiens

<400> SEQUENCE: 820

Ser Asn Met Leu Gly His Arg Ser Pro
1 5

<210> SEQ ID NO 821
<211> LENGTH: 10
<212> TYPE: PRT
<213> ORGANISM: Homo sapiens

<400> SEQUENCE: 821

Gln Gln Tyr Gly Ser Ser Pro Pro Ile Thr
1 5 10

<210> SEQ ID NO 822
<211> LENGTH: 6
<212> TYPE: PRT
<213> ORGANISM: Homo sapiens

<400> SEQUENCE: 822

Gln Gln His Met Tyr Thr
1 5

<210> SEQ ID NO 823
<211> LENGTH: 16
<212> TYPE: PRT
<213> ORGANISM: Homo sapiens

<400> SEQUENCE: 823

Ala Arg Gly Gly Asp Gly Tyr Thr Thr Arg Trp Phe Tyr Phe Asn His
1 5 10 15

<210> SEQ ID NO 824
<211> LENGTH: 19
<212> TYPE: PRT
<213> ORGANISM: Homo sapiens

<400> SEQUENCE: 824

Ala Arg Leu Gly Ala Glu Tyr Tyr Val Asp Ser Ser Gly Tyr Arg Gly
1 5 10 15

Ile Asp His

<210> SEQ ID NO 825
<211> LENGTH: 21
<212> TYPE: PRT
<213> ORGANISM: Homo sapiens

<400> SEQUENCE: 825

Ala Arg Val Glu Arg Gly His Thr Tyr Gly Leu Asn Tyr Tyr Tyr Tyr
1 5 10 15

Tyr Gly Met Asp Val
20

<210> SEQ ID NO 826
<211> LENGTH: 18
<212> TYPE: PRT
<213> ORGANISM: Homo sapiens

<400> SEQUENCE: 826

Ala Arg Asp Ser Ser Asn Thr Phe His His Asp Ser Ser Gly Tyr Phe
1 5 10 15

Asp Asn

<210> SEQ ID NO 827
<211> LENGTH: 16
<212> TYPE: PRT
<213> ORGANISM: Homo sapiens

<400> SEQUENCE: 827

Ala Arg Leu Ile Pro Gly Ser Gly Trp Arg Lys Gly Gly Phe Asp Tyr
1 5 10 15

<210> SEQ ID NO 828
<211> LENGTH: 19
<212> TYPE: PRT
<213> ORGANISM: Homo sapiens

<400> SEQUENCE: 828

Ala Arg Asp Ser Gly Trp Ser Gly Ile Thr Thr Val Arg Gly Val Pro
1 5 10 15

Pro Asp Phe

<210> SEQ ID NO 829
<211> LENGTH: 16
<212> TYPE: PRT
<213> ORGANISM: Homo sapiens

<400> SEQUENCE: 829

Ala Arg Gly Tyr Phe Tyr Thr Ser Ser Asn Tyr Tyr Asn Thr Asp His
1 5 10 15

<210> SEQ ID NO 830
<211> LENGTH: 20
<212> TYPE: PRT
<213> ORGANISM: Homo sapiens

<400> SEQUENCE: 830

Ala Arg Asp Arg Phe Ser Arg His Tyr Gly Ser Gly Ser Leu His Tyr
1 5 10 15

Ala Met Asp Val
20

<210> SEQ ID NO 831
<211> LENGTH: 12
<212> TYPE: PRT
<213> ORGANISM: Homo sapiens

<400> SEQUENCE: 831

Ala Thr Gly Tyr Gly Gly Asn Phe Ala Phe Asp Met 1 5 10

<210> SEQ ID NO 832
<211> LENGTH: 12
<212> TYPE: PRT
<213> ORGANISM: Homo sapiens

<400> SEQUENCE: 832

Ala Ser Gly Gly Tyr Gly Val Tyr Gly Phe Asp Tyr
1 5 10

<210> SEQ ID NO 833
<211> LENGTH: 14
<212> TYPE: PRT
<213> ORGANISM: Homo sapiens

<400> SEQUENCE: 833

Ala Arg Ala His Ser Tyr Tyr Val Tyr Tyr Tyr Met Asp Val
1 5 10

<210> SEQ ID NO 834
<211> LENGTH: 21
<212> TYPE: PRT
<213> ORGANISM: Homo sapiens

<400> SEQUENCE: 834

Val Arg His Gly Pro His Pro Gly Val Leu Val Trp Phe Gly Glu Gln
1 5 10 15

Ser Lys Ile Asp Tyr
20

<210> SEQ ID NO 835
<211> LENGTH: 22
<212> TYPE: PRT
<213> ORGANISM: Homo sapiens

<400> SEQUENCE: 835

Ala Lys Asp Ile Gly Asn Ile Ala Gly Val Ala Gln Gly Ile Tyr Phe
1 5 10 15

Tyr Phe Gly Met Asp Val
20

<210> SEQ ID NO 836
<211> LENGTH: 12
<212> TYPE: PRT
<213> ORGANISM: Homo sapiens

<400> SEQUENCE: 836

Ala Arg Lys Ser Tyr Gly Asp Pro Phe Phe Asp Tyr
1 5 10

<210> SEQ ID NO 837
<211> LENGTH: 12
<212> TYPE: PRT
<213> ORGANISM: Homo sapiens

<400> SEQUENCE: 837

Ala Ser Ser Val Met Val Val Ala Gln Phe Asp Ser
1 5 10

<210> SEQ ID NO 838
<211> LENGTH: 14
<212> TYPE: PRT
<213> ORGANISM: Homo sapiens

<400> SEQUENCE: 838

Ala Thr Gly Ala Gly Tyr Ser Tyr Pro Val Ala Met Asp Val
1 5 10

<210> SEQ ID NO 839
<211> LENGTH: 13
<212> TYPE: PRT
<213> ORGANISM: Homo sapiens

<400> SEQUENCE: 839

Ala Arg Ile Ile Ile Asn Arg Gly Gln Ser Phe Asp Tyr
1 5 10

<210> SEQ ID NO 840
<211> LENGTH: 20
<212> TYPE: PRT
<213> ORGANISM: Homo sapiens

<400> SEQUENCE: 840

Ala Arg Asn Ala Pro Lys Val Phe Gly Ser Gly Ser Tyr Tyr Ser Asn
1 5 10 15

Trp Phe Asp Pro
20

<210> SEQ ID NO 841
<211> LENGTH: 12
<212> TYPE: PRT
<213> ORGANISM: Homo sapiens

<400> SEQUENCE: 841

Ala Arg Ser Tyr Ser Glu Val Leu Val Gly Tyr Asp
1 5 10

<210> SEQ ID NO 842
<211> LENGTH: 9
<212> TYPE: PRT
<213> ORGANISM: Homo sapiens

<400> SEQUENCE: 842

Gln Gln Tyr Tyr Ser Ala Pro Leu Thr
1 5

<210> SEQ ID NO 843
<211> LENGTH: 10
<212> TYPE: PRT
<213> ORGANISM: Homo sapiens

<400> SEQUENCE: 843

Met Gln Ala Leu Gln Thr Leu Ser Leu Thr
1 5 10

<210> SEQ ID NO 844
<211> LENGTH: 12
<212> TYPE: PRT
<213> ORGANISM: Homo sapiens

<400> SEQUENCE: 844

Ala Ala Trp Asp Asp Ser Leu Arg Gly His Trp Val
1 5 10

<210> SEQ ID NO 845
<211> LENGTH: 9
<212> TYPE: PRT

<213> ORGANISM: Homo sapiens

<400> SEQUENCE: 845

Gln Thr Trp Gly Thr Gly Ile Arg Val
1 5

<210> SEQ ID NO 846
<211> LENGTH: 9
<212> TYPE: PRT
<213> ORGANISM: Homo sapiens

<400> SEQUENCE: 846

Gln His Tyr Lys Asn Trp Pro Gly Thr
1 5

<210> SEQ ID NO 847
<211> LENGTH: 11
<212> TYPE: PRT
<213> ORGANISM: Homo sapiens

<400> SEQUENCE: 847

Leu His Tyr Asn Asn Trp Pro Pro Arg Tyr Thr
1 5 10

<210> SEQ ID NO 848
<211> LENGTH: 9
<212> TYPE: PRT
<213> ORGANISM: Homo sapiens

<400> SEQUENCE: 848

Gln Gln Tyr Lys Ser Tyr Pro Phe Thr
1 5

<210> SEQ ID NO 849
<211> LENGTH: 10
<212> TYPE: PRT
<213> ORGANISM: Homo sapiens

<400> SEQUENCE: 849

Gly Ser Tyr Thr Ser Thr Ser Thr Cys Val
1 5 10

<210> SEQ ID NO 850
<211> LENGTH: 9
<212> TYPE: PRT
<213> ORGANISM: Homo sapiens

<400> SEQUENCE: 850

Met Gln Ala Leu Gln Thr Pro Pro Thr
1 5

<210> SEQ ID NO 851
<211> LENGTH: 9
<212> TYPE: PRT
<213> ORGANISM: Homo sapiens

<400> SEQUENCE: 851

His Gln Tyr Asn Ala Tyr Pro Trp Thr
1 5

<210> SEQ ID NO 852
<211> LENGTH: 10
<212> TYPE: PRT
<213> ORGANISM: Homo sapiens

<400> SEQUENCE: 852

Gln Gln Tyr Asn Asn Trp Leu Pro Ile Thr
1 5 10

<210> SEQ ID NO 853
<211> LENGTH: 9
<212> TYPE: PRT
<213> ORGANISM: Homo sapiens

<400> SEQUENCE: 853

Gln Gln Tyr Tyr Thr Thr Pro Leu Thr
1 5

<210> SEQ ID NO 854
<211> LENGTH: 10
<212> TYPE: PRT
<213> ORGANISM: Homo sapiens

<400> SEQUENCE: 854

Gln Arg Leu Asn Ser Tyr Pro Arg Val Thr
1 5 10

<210> SEQ ID NO 855
<211> LENGTH: 10
<212> TYPE: PRT
<213> ORGANISM: Homo sapiens

<400> SEQUENCE: 855

Ser Ser Tyr Thr Ser Arg Ser Thr Trp Val
1 5 10

<210> SEQ ID NO 856
<211> LENGTH: 9
<212> TYPE: PRT
<213> ORGANISM: Homo sapiens

<400> SEQUENCE: 856

Gln Gln Tyr Gly Asn Ser Pro Trp Thr
1 5

<210> SEQ ID NO 857
<211> LENGTH: 9
<212> TYPE: PRT
<213> ORGANISM: Homo sapiens

<400> SEQUENCE: 857

Met Gln Ala Leu Gln Thr Pro Tyr Thr
1 5

<210> SEQ ID NO 858
<211> LENGTH: 8
<212> TYPE: PRT
<213> ORGANISM: Homo sapiens

<400> SEQUENCE: 858

Cys Ser Tyr Ala Gly Lys Tyr Val
1 5

<210> SEQ ID NO 859
<211> LENGTH: 9
<212> TYPE: PRT
<213> ORGANISM: Homo sapiens

<400> SEQUENCE: 859

Gln Gln Arg Leu Tyr Trp Pro Val Thr
1 5

<210> SEQ ID NO 860
<211> LENGTH: 8
<212> TYPE: PRT
<213> ORGANISM: Homo sapiens

<400> SEQUENCE: 860

Gln Gln Arg Ser Asn Trp Leu Thr
1 5

<210> SEQ ID NO 861
<211> LENGTH: 17
<212> TYPE: PRT
<213> ORGANISM: Homo sapiens

<400> SEQUENCE: 861

Ala Lys Asp Arg Thr Gly Asn Ile Gly Ala Gly Thr Gly Tyr Phe Asp
1 5 10 15

Lys

<210> SEQ ID NO 862
<211> LENGTH: 14
<212> TYPE: PRT
<213> ORGANISM: Homo sapiens

<400> SEQUENCE: 862

Ala Arg Thr Pro Arg Glu Tyr Ile Ala Glu Tyr Phe Gln His
1 5 10

<210> SEQ ID NO 863
<211> LENGTH: 17
<212> TYPE: PRT
<213> ORGANISM: Homo sapiens

<400> SEQUENCE: 863

Ala Arg Val Lys Leu Arg Asp Gly Ser Ser Trp Tyr His Ala Phe Asp
1 5 10 15

Ile

<210> SEQ ID NO 864
<211> LENGTH: 17
<212> TYPE: PRT
<213> ORGANISM: Homo sapiens

<400> SEQUENCE: 864

Ala Arg Trp Gly Leu Ser Ser Ala Trp Val Ala Pro Leu Gly Phe Asp
1 5 10 15

Tyr

<210> SEQ ID NO 865
<211> LENGTH: 21
<212> TYPE: PRT
<213> ORGANISM: Homo sapiens

<400> SEQUENCE: 865

Ala Arg Glu Leu Leu Tyr Ser Gly Arg Gln Thr Tyr Tyr Tyr Ser Tyr
1 5 10 15

Tyr Gly Met Asp Val
20

<210> SEQ ID NO 866
<211> LENGTH: 19
<212> TYPE: PRT
<213> ORGANISM: Homo sapiens

<400> SEQUENCE: 866

Ala Arg Arg Gln Gly Ala His Gly Arg Asp Leu Gly Phe His Tyr Ala
1 5 10 15

Met Asp Val

<210> SEQ ID NO 867
<211> LENGTH: 10
<212> TYPE: PRT
<213> ORGANISM: Homo sapiens

<400> SEQUENCE: 867

Ala Arg Asp Gly Ala Ala Ala Gly Asp Tyr
1 5 10

<210> SEQ ID NO 868
<211> LENGTH: 20
<212> TYPE: PRT
<213> ORGANISM: Homo sapiens

<400> SEQUENCE: 868

Gly Asn Leu Ala Thr Val Gly Ala Thr Ala Pro Tyr Tyr Asn Tyr Tyr
1 5 10 15

Gly Met Tyr Val
20

<210> SEQ ID NO 869
<211> LENGTH: 11
<212> TYPE: PRT
<213> ORGANISM: Homo sapiens

<400> SEQUENCE: 869

Ala Arg Gly Met Ala Thr Pro Ala Leu Leu Asn
1 5 10

<210> SEQ ID NO 870
<211> LENGTH: 17
<212> TYPE: PRT
<213> ORGANISM: Homo sapiens

<400> SEQUENCE: 870

Ala Arg Gly His Asn Lys Trp Leu Gln Leu Asn Phe Tyr Ala Met Asp
1 5 10 15

Val

<210> SEQ ID NO 871
<211> LENGTH: 18
<212> TYPE: PRT
<213> ORGANISM: Homo sapiens

<400> SEQUENCE: 871

Leu Val Gln Leu Gln Gln Trp Gly Ala Gly Leu Leu Lys Pro Ser Glu
1 5 10 15

Thr Leu

<210> SEQ ID NO 872
<211> LENGTH: 17
<212> TYPE: PRT
<213> ORGANISM: Homo sapiens

<400> SEQUENCE: 872

Val Lys Gly Gly Tyr Asn Ser Val Trp Ser Asn Ser Tyr Gly Met Asp
1 5 10 15

Val

<210> SEQ ID NO 873
<211> LENGTH: 19
<212> TYPE: PRT
<213> ORGANISM: Homo sapiens

<400> SEQUENCE: 873

Ala Arg Ala Leu Tyr Val Arg Gly Tyr Asn Tyr Gly Phe Leu Tyr Gly
1 5 10 15

Met Asp Val

<210> SEQ ID NO 874
<211> LENGTH: 19
<212> TYPE: PRT
<213> ORGANISM: Homo sapiens

<400> SEQUENCE: 874

Ala Lys Gly Gly Pro Thr Ala Arg Val Leu Ser Gly Gln Leu Tyr Tyr
1 5 10 15

Phe Asp Tyr

<210> SEQ ID NO 875
<211> LENGTH: 28
<212> TYPE: PRT
<213> ORGANISM: Homo sapiens

<400> SEQUENCE: 875

Ala Arg Gly Pro Ser Gly Leu Ala Val Ala Gly Thr Val Gly Glu Arg
1 5 10 15

Asp Arg Asn Tyr His Tyr Tyr Tyr Gly Met Asp Val
20 25

<210> SEQ ID NO 876
<211> LENGTH: 17
<212> TYPE: PRT
<213> ORGANISM: Homo sapiens

<400> SEQUENCE: 876

Ala Arg Leu Gly Asp Ile Leu Thr Gly Tyr Val Asp Tyr Gly Met Asp
1 5 10 15

Val

<210> SEQ ID NO 877
<211> LENGTH: 13
<212> TYPE: PRT
<213> ORGANISM: Homo sapiens

<400> SEQUENCE: 877

Ala Arg Ser Pro Ile Tyr Gly Asp Tyr Gly Phe Asp Pro
1 5 10

<210> SEQ ID NO 878
<211> LENGTH: 17
<212> TYPE: PRT
<213> ORGANISM: Homo sapiens

<400> SEQUENCE: 878

Ala Arg Thr His Cys Thr Gly Gly Ser Cys Phe Ser Ser Ser Phe Asp
1 5 10 15

Tyr

<210> SEQ ID NO 879
<211> LENGTH: 21
<212> TYPE: PRT
<213> ORGANISM: Homo sapiens

<400> SEQUENCE: 879

Ala Arg Asp Arg Asp Tyr Gly Ser Gly Ser Gln Pro Leu Tyr Tyr Tyr
1 5 10 15

Tyr Ala Met Asp Val
20

<210> SEQ ID NO 880
<211> LENGTH: 11
<212> TYPE: PRT
<213> ORGANISM: Homo sapiens

<400> SEQUENCE: 880

Ala Arg Val Leu Gly Asn Trp Gly Phe Asp Tyr
1 5 10

<210> SEQ ID NO 881
<211> LENGTH: 20
<212> TYPE: PRT
<213> ORGANISM: Homo sapiens

<400> SEQUENCE: 881

Ala Arg Gly Gly Lys Arg Leu Gly Glu Leu Ser Leu Phe His Tyr Tyr
1 5 10 15

Gly Met Asp Val
20

<210> SEQ ID NO 882
<211> LENGTH: 17
<212> TYPE: PRT
<213> ORGANISM: Homo sapiens

<400> SEQUENCE: 882

Ala Arg His Arg Arg Gly Tyr Tyr Asp Ser Ser Gly Tyr Tyr Tyr Asp
1 5 10 15

Tyr

<210> SEQ ID NO 883
<211> LENGTH: 12
<212> TYPE: PRT
<213> ORGANISM: Homo sapiens

<400> SEQUENCE: 883

Thr Arg Tyr Ser Tyr Gly Phe Ser Tyr Phe Asp Tyr
1 5 10

<210> SEQ ID NO 884
<211> LENGTH: 14
<212> TYPE: PRT
<213> ORGANISM: Homo sapiens

<400> SEQUENCE: 884

Ala Arg Ala Pro Thr Arg Ser Ile Gly His Gly Met Asp Leu
1 5 10

<210> SEQ ID NO 885
<211> LENGTH: 18
<212> TYPE: PRT
<213> ORGANISM: Homo sapiens

<400> SEQUENCE: 885

Ala Arg Glu Asn Asn Asn Ile Ala Leu Pro Tyr Tyr Tyr Tyr Gly Met
1 5 10 15

Asp Val

<210> SEQ ID NO 886
<211> LENGTH: 20
<212> TYPE: PRT
<213> ORGANISM: Homo sapiens

<400> SEQUENCE: 886

Ala Arg Asp Ile Arg Tyr Thr Tyr Gly Pro Met Trp Gly Gly Asp Tyr
1 5 10 15

Gly Met Asp Val
20

<210> SEQ ID NO 887
<211> LENGTH: 19
<212> TYPE: PRT
<213> ORGANISM: Homo sapiens

<400> SEQUENCE: 887

Ala Arg Arg Pro Pro Leu Leu Arg Ser His Asn Tyr Asn Tyr Leu Gly
1 5 10 15

Met Asp Val

<210> SEQ ID NO 888
<211> LENGTH: 20
<212> TYPE: PRT
<213> ORGANISM: Homo sapiens

<400> SEQUENCE: 888

Ala Lys Ser Ser Gly Gly His Asn Trp Asn Tyr Val Asp Tyr Tyr Tyr
1 5 10 15

Gly Met Asp Val
20

<210> SEQ ID NO 889
<211> LENGTH: 10
<212> TYPE: PRT
<213> ORGANISM: Homo sapiens

<400> SEQUENCE: 889

Ala Ser Thr His Leu Gly Gly Leu Asp Val
1 5 10

<210> SEQ ID NO 890
<211> LENGTH: 11
<212> TYPE: PRT
<213> ORGANISM: Homo sapiens

<400> SEQUENCE: 890

Ser Arg Ala Thr Asn Tyr Tyr Ala Leu Gly Tyr
1 5 10

<210> SEQ ID NO 891

<211> LENGTH: 9
<212> TYPE: PRT
<213> ORGANISM: Homo sapiens

<400> SEQUENCE: 891

Ala Arg Asp Trp Pro Val Met Asp Val
1 5

<210> SEQ ID NO 892
<211> LENGTH: 13
<212> TYPE: PRT
<213> ORGANISM: Homo sapiens

<400> SEQUENCE: 892

Ala Arg Val Val Gly Thr Thr Leu Tyr Ser Met Gly Tyr
1 5 10

<210> SEQ ID NO 893
<211> LENGTH: 13
<212> TYPE: PRT
<213> ORGANISM: Homo sapiens

<400> SEQUENCE: 893

Ala Arg Val Ala Ala Trp Tyr Ala Gly Ser Phe Asp Ser
1 5 10

<210> SEQ ID NO 894
<211> LENGTH: 17
<212> TYPE: PRT
<213> ORGANISM: Homo sapiens

<400> SEQUENCE: 894

Ala Lys Ala Gly Ala Tyr Cys Gly Gly Asp Cys Tyr Ser Tyr Leu Gln
1 5 10 15

Tyr

<210> SEQ ID NO 895
<211> LENGTH: 9
<212> TYPE: PRT
<213> ORGANISM: Homo sapiens

<400> SEQUENCE: 895

Gln Gln Tyr Asn Asn Tyr Pro Trp Thr
1 5

<210> SEQ ID NO 896
<211> LENGTH: 9
<212> TYPE: PRT
<213> ORGANISM: Homo sapiens

<400> SEQUENCE: 896

Gln Gln Tyr Asn Asn Trp Leu Ile Thr
1 5

<210> SEQ ID NO 897
<211> LENGTH: 10
<212> TYPE: PRT
<213> ORGANISM: Homo sapiens

<400> SEQUENCE: 897

Gln Gln Tyr Tyr Thr Thr Pro Pro Trp Thr
1 5 10

<210> SEQ ID NO 898

<211> LENGTH: 9
<212> TYPE: PRT
<213> ORGANISM: Homo sapiens

<400> SEQUENCE: 898

Gln Gln Tyr Tyr Thr Thr Pro Phe Thr
1 5

<210> SEQ ID NO 899
<211> LENGTH: 10
<212> TYPE: PRT
<213> ORGANISM: Homo sapiens

<400> SEQUENCE: 899

Ser Ser Tyr Thr Ser Asp Asn Thr Arg Val
1 5 10

<210> SEQ ID NO 900
<211> LENGTH: 10
<212> TYPE: PRT
<213> ORGANISM: Homo sapiens

<400> SEQUENCE: 900

Cys Ser Tyr Ala Gly Ser Tyr Ser Trp Val
1 5 10

<210> SEQ ID NO 901
<211> LENGTH: 9
<212> TYPE: PRT
<213> ORGANISM: Homo sapiens

<400> SEQUENCE: 901

Gln Gln Tyr Tyr Asp Tyr Pro Leu Thr
1 5

<210> SEQ ID NO 902
<211> LENGTH: 11
<212> TYPE: PRT
<213> ORGANISM: Homo sapiens

<400> SEQUENCE: 902

Ala Ala Trp Asp Asp Ser Leu Asn Gly Arg Val
1 5 10

<210> SEQ ID NO 903
<211> LENGTH: 9
<212> TYPE: PRT
<213> ORGANISM: Homo sapiens

<400> SEQUENCE: 903

His Gln Tyr Asn Asn Trp Pro Leu Thr
1 5

<210> SEQ ID NO 904
<211> LENGTH: 9
<212> TYPE: PRT
<213> ORGANISM: Homo sapiens

<400> SEQUENCE: 904

Gln Gln Arg Ile Asn Trp Pro Ile Thr
1 5

<210> SEQ ID NO 905
<211> LENGTH: 9
<212> TYPE: PRT

<213> ORGANISM: Homo sapiens

<400> SEQUENCE: 905

Gln Gln Ser Tyr Ser Arg Pro Tyr Ser
1 5

<210> SEQ ID NO 906
<211> LENGTH: 9
<212> TYPE: PRT
<213> ORGANISM: Homo sapiens

<400> SEQUENCE: 906

Gln Gln Tyr Asp Asn Val Pro Tyr Thr
1 5

<210> SEQ ID NO 907
<211> LENGTH: 9
<212> TYPE: PRT
<213> ORGANISM: Homo sapiens

<400> SEQUENCE: 907

Gln Gln Tyr Asp Asn Ser Arg Phe Thr
1 5

<210> SEQ ID NO 908
<211> LENGTH: 8
<212> TYPE: PRT
<213> ORGANISM: Homo sapiens

<400> SEQUENCE: 908

Met Gln Gly Ile His Leu Trp Thr
1 5

<210> SEQ ID NO 909
<211> LENGTH: 9
<212> TYPE: PRT
<213> ORGANISM: Homo sapiens

<400> SEQUENCE: 909

Ser Ser Tyr Ala Gly Thr Ser Tyr Val
1 5

<210> SEQ ID NO 910
<211> LENGTH: 12
<212> TYPE: PRT
<213> ORGANISM: Homo sapiens

<400> SEQUENCE: 910

Ala Ala Trp Asp Asp Ser Leu Asn Gly Leu Tyr Val
1 5 10

<210> SEQ ID NO 911
<211> LENGTH: 9
<212> TYPE: PRT
<213> ORGANISM: Homo sapiens

<400> SEQUENCE: 911

Met Gln Ala Leu Gln Ile Pro Pro Thr
1 5

<210> SEQ ID NO 912
<211> LENGTH: 9
<212> TYPE: PRT
<213> ORGANISM: Homo sapiens

<400> SEQUENCE: 912

Gln Gln Tyr Asn Ser Tyr Pro Pro Thr
1               5

<210> SEQ ID NO 913
<211> LENGTH: 9
<212> TYPE: PRT
<213> ORGANISM: Homo sapiens

<400> SEQUENCE: 913

Gln Gln Ser Tyr Ser Thr Pro Tyr Ser
1               5

<210> SEQ ID NO 914
<211> LENGTH: 9
<212> TYPE: PRT
<213> ORGANISM: Homo sapiens

<400> SEQUENCE: 914

Gln Gln Leu Asn Ser Tyr Pro Phe Thr
1               5

<210> SEQ ID NO 915
<211> LENGTH: 9
<212> TYPE: PRT
<213> ORGANISM: Homo sapiens

<400> SEQUENCE: 915

Met Gln Ala Leu His Thr Pro Trp Thr
1               5

<210> SEQ ID NO 916
<211> LENGTH: 10
<212> TYPE: PRT
<213> ORGANISM: Homo sapiens

<400> SEQUENCE: 916

Ser Ser Tyr Thr Arg Ser Ser Thr Val Val
1               5                   10

<210> SEQ ID NO 917
<211> LENGTH: 9
<212> TYPE: PRT
<213> ORGANISM: Homo sapiens

<400> SEQUENCE: 917

Gln Gln Arg Ser Asn Trp Pro Leu Thr
1               5

<210> SEQ ID NO 918
<211> LENGTH: 10
<212> TYPE: PRT
<213> ORGANISM: Homo sapiens

<400> SEQUENCE: 918

Val Leu Tyr Val Gly Ala Ala Ile Ser Leu
1               5                   10

<210> SEQ ID NO 919
<211> LENGTH: 9
<212> TYPE: PRT
<213> ORGANISM: Homo sapiens

<400> SEQUENCE: 919

Gln Gln Ser Ser Asn Trp Pro Ile Thr
1 5

<210> SEQ ID NO 920
<211> LENGTH: 9
<212> TYPE: PRT
<213> ORGANISM: Homo sapiens

<400> SEQUENCE: 920

Gln Gln Tyr Gly Gly Ser Pro Tyr Thr
1 5

<210> SEQ ID NO 921
<211> LENGTH: 10
<212> TYPE: PRT
<213> ORGANISM: Homo sapiens

<400> SEQUENCE: 921

Gln Gln Tyr Gly Ser Ser Pro Leu Ile Thr
1 5 10

<210> SEQ ID NO 922
<211> LENGTH: 9
<212> TYPE: PRT
<213> ORGANISM: Homo sapiens

<400> SEQUENCE: 922

Gln Gln Leu Asn Ser Tyr Pro Val Thr
1 5

<210> SEQ ID NO 923
<211> LENGTH: 9
<212> TYPE: PRT
<213> ORGANISM: Homo sapiens

<400> SEQUENCE: 923

Met Gln Gly Thr His Trp Pro Leu Thr
1 5

<210> SEQ ID NO 924
<211> LENGTH: 10
<212> TYPE: PRT
<213> ORGANISM: Homo sapiens

<400> SEQUENCE: 924

Ser Ser Tyr Thr Ser Ser Ala Thr Trp Val
1 5 10

<210> SEQ ID NO 925
<211> LENGTH: 10
<212> TYPE: PRT
<213> ORGANISM: Homo sapiens

<400> SEQUENCE: 925

Met Gln Gly Thr His Trp Pro Pro Trp Thr
1 5 10

<210> SEQ ID NO 926
<211> LENGTH: 8
<212> TYPE: PRT
<213> ORGANISM: Homo sapiens

<400> SEQUENCE: 926

Gln Gln Tyr Tyr Asn Thr Trp Thr
1 5

<210> SEQ ID NO 927
<211> LENGTH: 9
<212> TYPE: PRT
<213> ORGANISM: Homo sapiens

<400> SEQUENCE: 927

Ser Ser Tyr Thr Ser Thr Ser Ala Phe
1 5

<210> SEQ ID NO 928
<211> LENGTH: 9
<212> TYPE: PRT
<213> ORGANISM: Homo sapiens

<400> SEQUENCE: 928

Gln Gln Tyr Gln Ser Asp Leu Phe Thr
1 5

<210> SEQ ID NO 929
<211> LENGTH: 19
<212> TYPE: PRT
<213> ORGANISM: Homo sapiens

<400> SEQUENCE: 929

Ala Arg Leu Leu Ile Asp Tyr Thr Asn Tyr Lys Ser Val Ala Ser Ala
1 5 10 15

Phe Asp Ile

<210> SEQ ID NO 930
<211> LENGTH: 21
<212> TYPE: PRT
<213> ORGANISM: Homo sapiens

<400> SEQUENCE: 930

Ala Ser Ser Pro Gly Tyr Asp Thr Arg Gly Tyr Tyr Ile Ala Gly Gln
1 5 10 15

Tyr Tyr Phe Val Asn
20

<210> SEQ ID NO 931
<211> LENGTH: 12
<212> TYPE: PRT
<213> ORGANISM: Homo sapiens

<400> SEQUENCE: 931

Ala Arg Asp Gly Thr Ile Pro Gly Tyr Gly Asp Tyr
1 5 10

<210> SEQ ID NO 932
<211> LENGTH: 16
<212> TYPE: PRT
<213> ORGANISM: Homo sapiens

<400> SEQUENCE: 932

Ala Arg Met Pro Val Ala Ala His Tyr Phe Tyr Asp Gly Met Asp Val
1 5 10 15

<210> SEQ ID NO 933
<211> LENGTH: 15
<212> TYPE: PRT
<213> ORGANISM: Homo sapiens

<400> SEQUENCE: 933

Ala Lys Phe Pro His Arg Ser Thr Ser Trp Tyr Tyr Phe Asp Ser
1 5 10 15

<210> SEQ ID NO 934
<211> LENGTH: 13
<212> TYPE: PRT
<213> ORGANISM: Homo sapiens

<400> SEQUENCE: 934

Ala Arg Gly Leu Arg Val Glu Ile Pro Ile Phe Ala Tyr
1 5 10

<210> SEQ ID NO 935
<211> LENGTH: 14
<212> TYPE: PRT
<213> ORGANISM: Homo sapiens

<400> SEQUENCE: 935

Thr Arg Asp Thr Ile Val Gly Ala Thr Tyr Ala Phe Asp Ile
1 5 10

<210> SEQ ID NO 936
<211> LENGTH: 19
<212> TYPE: PRT
<213> ORGANISM: Homo sapiens

<400> SEQUENCE: 936

Ala Arg Glu Pro Asp Ser Ser Ser Trp Tyr Gln Asp Tyr Tyr Cys Ala
1 5 10 15

Met Asp Val

<210> SEQ ID NO 937
<211> LENGTH: 13
<212> TYPE: PRT
<213> ORGANISM: Homo sapiens

<400> SEQUENCE: 937

Thr Arg Asp Leu Gly Asn Phe Ile Ala Tyr Met Asp Val
1 5 10

<210> SEQ ID NO 938
<211> LENGTH: 24
<212> TYPE: PRT
<213> ORGANISM: Homo sapiens

<400> SEQUENCE: 938

Ser Arg Gly Ser Tyr Tyr Tyr Asp Ser Arg Gly Tyr Tyr Phe Arg Pro
1 5 10 15

Pro Ser Ala Gly Pro Phe Asp Tyr
20

<210> SEQ ID NO 939
<211> LENGTH: 16
<212> TYPE: PRT
<213> ORGANISM: Homo sapiens

<400> SEQUENCE: 939

Val Lys Ile Ala Val Gly Gly Ser Trp Ser Ser Glu Ala Leu Asp Tyr
1 5 10 15

<210> SEQ ID NO 940
<211> LENGTH: 17
<212> TYPE: PRT

<213> ORGANISM: Homo sapiens

<400> SEQUENCE: 940

Ala Arg Gly His Leu Val Gly Ala Thr Ser Tyr Tyr Tyr Gly Met Asp
1 5 10 15

Val

<210> SEQ ID NO 941
<211> LENGTH: 20
<212> TYPE: PRT
<213> ORGANISM: Homo sapiens

<400> SEQUENCE: 941

Ala Arg Val Ser Leu Leu Trp Phe Gly Glu Leu Gly Ala Val Pro Tyr
1 5 10 15

Tyr Phe Asp Tyr
20

<210> SEQ ID NO 942
<211> LENGTH: 16
<212> TYPE: PRT
<213> ORGANISM: Homo sapiens

<400> SEQUENCE: 942

Ala Arg Asp Arg His Arg Ala Gly Ala Leu Arg Tyr Gly Met Asp Val
1 5 10 15

<210> SEQ ID NO 943
<211> LENGTH: 16
<212> TYPE: PRT
<213> ORGANISM: Homo sapiens

<400> SEQUENCE: 943

Ala Lys Gly Gly Thr Ser Val Ala Ile Gly Trp Asn Trp Phe Asp Pro
1 5 10 15

<210> SEQ ID NO 944
<211> LENGTH: 18
<212> TYPE: PRT
<213> ORGANISM: Homo sapiens

<400> SEQUENCE: 944

Ala Arg Gly Tyr Arg Gly Asn Ile Leu Thr Gly Arg Leu Gly Tyr Phe
1 5 10 15

Asp Tyr

<210> SEQ ID NO 945
<211> LENGTH: 23
<212> TYPE: PRT
<213> ORGANISM: Homo sapiens

<400> SEQUENCE: 945

Thr Thr Ala Gly Asn Tyr Tyr Asp Ser Arg Gly Tyr Tyr Phe Ser Arg
1 5 10 15

Pro Arg His Ser Phe Asp Tyr
20

<210> SEQ ID NO 946
<211> LENGTH: 19
<212> TYPE: PRT
<213> ORGANISM: Homo sapiens

<400> SEQUENCE: 946

Ala Arg Ala Pro Gln Asn Tyr Tyr Gly Ser Gly Arg Tyr Tyr Ser Gly
1 5 10 15

Cys Asp Tyr

<210> SEQ ID NO 947
<211> LENGTH: 23
<212> TYPE: PRT
<213> ORGANISM: Homo sapiens

<400> SEQUENCE: 947

Ala Arg Thr Ala Val Asp Arg Tyr Ser Ser Gly Trp Tyr Gly Glu Tyr
1 5 10 15

Tyr Tyr Tyr Ser Met Asp Val
20

<210> SEQ ID NO 948
<211> LENGTH: 21
<212> TYPE: PRT
<213> ORGANISM: Homo sapiens

<400> SEQUENCE: 948

Ala Arg Arg Pro Leu Thr Ser Tyr Tyr Asp Ser Gly Ala Tyr Tyr Pro
1 5 10 15

Tyr Tyr Phe Asp Tyr
20

<210> SEQ ID NO 949
<211> LENGTH: 25
<212> TYPE: PRT
<213> ORGANISM: Homo sapiens

<400> SEQUENCE: 949

Thr Arg Asp Thr Thr Tyr Phe Tyr Asp Asn Ser Gly Tyr Tyr Gly Trp
1 5 10 15

Ala Ser Lys Gly Gly Tyr Phe Asp Tyr
20 25

<210> SEQ ID NO 950
<211> LENGTH: 23
<212> TYPE: PRT
<213> ORGANISM: Homo sapiens

<400> SEQUENCE: 950

Ala Arg Gln Pro Val Arg Gly Arg His Ser Ser Ser Gly Tyr Arg His
1 5 10 15

Tyr Tyr Tyr Gly Met Asp Val
20

<210> SEQ ID NO 951
<211> LENGTH: 23
<212> TYPE: PRT
<213> ORGANISM: Homo sapiens

<400> SEQUENCE: 951

Ala Arg Val Glu Thr Tyr Asp His Val Trp Gly Ala Phe Arg Phe Gly
1 5 10 15

Glu Gly Gly Tyr Phe Asp His
20

<210> SEQ ID NO 952
<211> LENGTH: 21

<212> TYPE: PRT
<213> ORGANISM: Homo sapiens

<400> SEQUENCE: 952

Ala Arg Gly Gly His Tyr Tyr Asp Ser Arg Gly Tyr Phe Thr Leu Ala
1 5 10 15

Gly Pro Ile Asp Tyr
20

<210> SEQ ID NO 953
<211> LENGTH: 11
<212> TYPE: PRT
<213> ORGANISM: Homo sapiens

<400> SEQUENCE: 953

Gln Gln Tyr His Asn Trp Pro Pro Arg Leu Thr
1 5 10

<210> SEQ ID NO 954
<211> LENGTH: 8
<212> TYPE: PRT
<213> ORGANISM: Homo sapiens

<400> SEQUENCE: 954

Gln Gln Tyr Asn Arg Tyr Val Ser
1 5

<210> SEQ ID NO 955
<211> LENGTH: 10
<212> TYPE: PRT
<213> ORGANISM: Homo sapiens

<400> SEQUENCE: 955

Gln Gln Arg Ser Asn Trp Pro Pro Trp Thr
1 5 10

<210> SEQ ID NO 956
<211> LENGTH: 9
<212> TYPE: PRT
<213> ORGANISM: Homo sapiens

<400> SEQUENCE: 956

Gln Gln Tyr Gly Ser Ser Pro Ile Thr
1 5

<210> SEQ ID NO 957
<211> LENGTH: 13
<212> TYPE: PRT
<213> ORGANISM: Homo sapiens

<400> SEQUENCE: 957

Gln Ser Tyr Asp Ser Ser Leu Ser Gly Ser Phe Tyr Val
1 5 10

<210> SEQ ID NO 958
<211> LENGTH: 11
<212> TYPE: PRT
<213> ORGANISM: Homo sapiens

<400> SEQUENCE: 958

Gln Gln Tyr Gly Gly Ser Pro Pro Arg Phe Thr
1 5 10

<210> SEQ ID NO 959

<211> LENGTH: 9
<212> TYPE: PRT
<213> ORGANISM: Homo sapiens

<400> SEQUENCE: 959

Gln Gln His Tyr Ser Thr Pro Phe Thr
1               5

<210> SEQ ID NO 960
<211> LENGTH: 10
<212> TYPE: PRT
<213> ORGANISM: Homo sapiens

<400> SEQUENCE: 960

Cys Ser Tyr Ala Gly Ser Arg Thr Arg Val
1               5                   10

<210> SEQ ID NO 961
<211> LENGTH: 11
<212> TYPE: PRT
<213> ORGANISM: Homo sapiens

<400> SEQUENCE: 961

Ala Ser Trp Asp Asp Asn Leu Asn Ser Arg Val
1               5                   10

<210> SEQ ID NO 962
<211> LENGTH: 10
<212> TYPE: PRT
<213> ORGANISM: Homo sapiens

<400> SEQUENCE: 962

Met Gln Gly Ile Ile Phe Pro Pro Ile Thr
1               5                   10

<210> SEQ ID NO 963
<211> LENGTH: 10
<212> TYPE: PRT
<213> ORGANISM: Homo sapiens

<400> SEQUENCE: 963

Ser Ser Tyr Thr Ser Ser Ser Thr Leu Val
1               5                   10

<210> SEQ ID NO 964
<211> LENGTH: 9
<212> TYPE: PRT
<213> ORGANISM: Homo sapiens

<400> SEQUENCE: 964

Gln Gln Leu Asn Ser Tyr Pro Glu Thr
1               5

<210> SEQ ID NO 965
<211> LENGTH: 9
<212> TYPE: PRT
<213> ORGANISM: Homo sapiens

<400> SEQUENCE: 965

Leu Gln Val Asn Ser Tyr Pro Leu Thr
1               5

<210> SEQ ID NO 966
<211> LENGTH: 10
<212> TYPE: PRT

<213> ORGANISM: Homo sapiens

<400> SEQUENCE: 966

Ser Ser Tyr Thr Thr Ser Thr Thr Val Ile
1 5 10

<210> SEQ ID NO 967
<211> LENGTH: 11
<212> TYPE: PRT
<213> ORGANISM: Homo sapiens

<400> SEQUENCE: 967

Cys Ser Tyr Gly Gly Thr Tyr Ser Pro Tyr Val
1 5 10

<210> SEQ ID NO 968
<211> LENGTH: 9
<212> TYPE: PRT
<213> ORGANISM: Homo sapiens

<400> SEQUENCE: 968

Gln Gln Tyr Ala Lys Tyr Pro Leu Thr
1 5

<210> SEQ ID NO 969
<211> LENGTH: 9
<212> TYPE: PRT
<213> ORGANISM: Homo sapiens

<400> SEQUENCE: 969

Gln Gln Tyr Ala Thr Ser Ser Leu Thr
1 5

<210> SEQ ID NO 970
<211> LENGTH: 11
<212> TYPE: PRT
<213> ORGANISM: Homo sapiens

<400> SEQUENCE: 970

Gly Thr Trp Asp Ser Ser Leu Ser Ala Tyr Val
1 5 10

<210> SEQ ID NO 971
<211> LENGTH: 11
<212> TYPE: PRT
<213> ORGANISM: Homo sapiens

<400> SEQUENCE: 971

Gly Thr Trp Asp Ser Ser Leu Ser Ala Gly Val
1 5 10

<210> SEQ ID NO 972
<211> LENGTH: 10
<212> TYPE: PRT
<213> ORGANISM: Homo sapiens

<400> SEQUENCE: 972

Gln Ser Phe Asp Ser Ser Asn Gln Glu Val
1 5 10

<210> SEQ ID NO 973
<211> LENGTH: 12
<212> TYPE: PRT
<213> ORGANISM: Homo sapiens

<400> SEQUENCE: 973

Gln Ser Tyr Asp Arg Ser Leu Ser Gly Ser Arg Val
1 5 10

<210> SEQ ID NO 974
<211> LENGTH: 9
<212> TYPE: PRT
<213> ORGANISM: Homo sapiens

<400> SEQUENCE: 974

Gln Gln Phe Asn Ser Tyr Pro Gln Thr
1 5

<210> SEQ ID NO 975
<211> LENGTH: 7
<212> TYPE: PRT
<213> ORGANISM: Homo sapiens

<400> SEQUENCE: 975

His His Tyr Asn Asn Trp Thr
1 5

<210> SEQ ID NO 976
<211> LENGTH: 10
<212> TYPE: PRT
<213> ORGANISM: Homo sapiens

<400> SEQUENCE: 976

Gln Gln Tyr His Asp Trp Pro Leu Trp Thr
1 5 10

<210> SEQ ID NO 977
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 977
ctagtagcaa ctgcaaccgg tgtacattcc caggtgcagc tggtgcag 48

<210> SEQ ID NO 978
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 978
ctagtagcaa ctgcaaccgg tgtacattcc gaggtgcagc tggtgcag 48

<210> SEQ ID NO 979
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 979
ctagtagcaa ctgcaaccgg tgtacattcc caggttcagc tggtgcag 48

<210> SEQ ID NO 980

<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 980
ctagtagcaa ctgcaaccgg tgtacattcc caggtccagc tggtacag 48

<210> SEQ ID NO 981
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 981
ctagtagcaa ctgcaaccgg tgtacattct gaggtgcagc tggtggag 48

<210> SEQ ID NO 982
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 982
ctagtagcaa ctgcaaccgg tgtacattct caggtgcagc tggtggag 48

<210> SEQ ID NO 983
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 983
ctagtagcaa ctgcaaccgg tgtacattct gaggtgcagc tgttggag 48

<210> SEQ ID NO 984
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 984
ctagtagcaa ctgcaaccgg tgtacattct caggtgcagc tggtggag 48

<210> SEQ ID NO 985
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 985
ctagtagcaa ctgcaaccgg tgtacattct gaagtgcagc tggtggag 48

<210> SEQ ID NO 986
<211> LENGTH: 48

<212> TYPE: DNA
<213> ORGANISM: Artificial Sequence
<220> FEATURE:
<223> OTHER INFORMATION: Description of Artificial Sequence: Synthetic
primer

<400> SEQUENCE: 986
ctagtagcaa ctgcaaccgg tgtacattcc caggtgcagc tgcaggag 48

<210> SEQ ID NO 987
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 987
ctagtagcaa ctgcaaccgg tgtacattcc caggtgcagc tacagcagtg 50

<210> SEQ ID NO 988
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 988
ctagtagcaa ctgcaaccgg tgtacattcc cagctgcagc tgcaggag 48

<210> SEQ ID NO 989
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 989
ctagtagcaa ctgcaaccgg tgtacattcc caggtacagc tgcagcag 48

<210> SEQ ID NO 990
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 990
ccgatgggcc cttggtcgac gctgaggaga cggtgaccag 40

<210> SEQ ID NO 991
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 991
ccgatgggcc cttggtcgac gctgaagaga cggtgaccat tg 42

<210> SEQ ID NO 992
<211> LENGTH: 40
<212> TYPE: DNA

<213> ORGANISM: Artificial Sequence
<220> FEATURE:
<223> OTHER INFORMATION: Description of Artificial Sequence: Synthetic
primer

<400> SEQUENCE: 992
ccgatgggcc cttggtcgac gctgaggaga cggtgaccag 40

<210> SEQ ID NO 993
<211> LENGTH: 41
<212> TYPE: DNA
<213> ORGANISM: Artificial Sequence
<220> FEATURE:
<223> OTHER INFORMATION: Description of Artificial Sequence: Synthetic
primer

<400> SEQUENCE: 993
ccgatgggcc cttggtcgac gctgaggaga cggtgaccgt g 41

<210> SEQ ID NO 994
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 994
gtagcaactg caaccggtgt acattctgac atccagatga cccagtc 47

<210> SEQ ID NO 995
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 995
gtagcaactg caaccggtgt acattcagac atccagttga cccagtct 48

<210> SEQ ID NO 996
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 996
gtagcaactg caaccggtgt acattgtgcc atccggatga cccagtc 47

<210> SEQ ID NO 997
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 997
gtagcaactg caaccggtgt acatggggat attgtgatga cccagac 47

<210> SEQ ID NO 998
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 998
gtagcaactg caaccggtgt acatggggat attgtgatga ctcagtc 47

<210> SEQ ID NO 999
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 999
gtagcaactg caaccggtgt acatggggat gttgtgatga ctcagtc 47

<210> SEQ ID NO 1000
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 1000
gtagcaactg caaccggtgt acattcagaa attgtgttga cacagtc 47

<210> SEQ ID NO 1001
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 1001
gtagcaactg caaccggtgt acattcagaa atagtgatga cgcagtc 47

<210> SEQ ID NO 1002
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 1002
gtagcaactg caaccggtgt acattcagaa attgtgttga cgcagtct 48

<210> SEQ ID NO 1003
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 1003
gtagcaactg caaccggtgt acattcggac atcgtgatga cccagtc 47

<210> SEQ ID NO 1004
<211> LENGTH: 46
<212> TYPE: DNA
<213> ORGANISM: Artificial Sequence
<220> FEATURE:

<223> OTHER INFORMATION: Description of Artificial Sequence: Synthetic
primer

<400> SEQUENCE: 1004
gaagacagat ggtgcagcca ccgtacgttt gatytccacc ttggtc 46

<210> SEQ ID NO 1005
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1005
gaagacagat ggtgcagcca ccgtacgttt gatctccagc ttggtc 46

<210> SEQ ID NO 1006
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1006
gaagacagat ggtgcagcca ccgtacgttt gatatccact ttggtc 46

<210> SEQ ID NO 1007
<211> LENGTH: 46
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1007
gaagacagat ggtgcagcca ccgtacgttt aatctccagt cgtgtc 46

<210> SEQ ID NO 1008
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1008
ctagtagcaa ctgcaaccgg ttcctgggcc cagtctgtgc tgackcag 48

<210> SEQ ID NO 1009
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1009
ctagtagcaa ctgcaaccgg ttcctgggcc cagtctgccc tgactcag 48

<210> SEQ ID NO 1010
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 1010
ctagtagcaa ctgcaaccgg ttctgtgacc tcctatgagc tgacwcag 48

<210> SEQ ID NO 1011
<211> LENGTH: 47
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1011
ctagtagcaa ctgcaaccgg ttctctctcs cagcytgtgc tgactca 47

<210> SEQ ID NO 1012
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1012
ctagtagcaa ctgcaaccgg ttcttgggcc aattttatgc tgactcag 48

<210> SEQ ID NO 1013
<211> LENGTH: 48
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1013
ctagtagcaa ctgcaaccgg ttccaattcy cagrctgtgg tgacycag 48

<210> SEQ ID NO 1014
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1014
ggcttgaagc tcctcactcg agggygggaa cagagtg 37

<210> SEQ ID NO 1015
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1015
gttaagggat tttggacatg agattatc 28

<210> SEQ ID NO 1016
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1016
gataatctca tgtccaaaat cccttaac 28

<210> SEQ ID NO 1017
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1017
cttggttgag tactcaccag tca 23

<210> SEQ ID NO 1018
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1018
gaagactaca gcgtcgccag 20

<210> SEQ ID NO 1019
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1019
gttattgtct catgcgcgga tac 23

<210> SEQ ID NO 1020
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1020
gtatccgcgc atgagacaat aac 23

<210> SEQ ID NO 1021
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1021
cttcatgcaa ttgtcggtca agcc 24

<210> SEQ ID NO 1022
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 1022
tgactggtga gtactcaacc aag 23

<210> SEQ ID NO 1023
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1023
aggagtcggg gcgaagaaga tcac 24

<210> SEQ ID NO 1024
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1024
gtgatcttct tcgccccgac tcct 24

<210> SEQ ID NO 1025
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1025
aggagtcggg gaggcgaaga tcac 24

<210> SEQ ID NO 1026
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1026
gtgatcttcg cctccccgac tcct 24

<210> SEQ ID NO 1027
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 1027
acttggtcat gatactgctg attgccccgg catacagcat caggtgcata ggagt 55

<210> SEQ ID NO 1028
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1028
ttcgaaccgc ggctgggtcc tattaagcag agacagctgt ggataagaag atc 53

<210> SEQ ID NO 1029
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 1029
cttgaccgac aattgcatga ag 22

<210> SEQ ID NO 1030
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1030
gtctttttcc gttggttgtt catagcctgc ttttttgtac aaac 44

<210> SEQ ID NO 1031
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 1031
gtttgtacaa aaaagcaggc tatgaacaac caacggaaaa agac 44

<210> SEQ ID NO 1032
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 1032
ttcgaaccgc ggctgggtcc tattacgcct gaaccatgac tcctaggtac 50

<210> SEQ ID NO 1033
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 1033
caaagagtgg ttccatgaca tcccattg 28

<210> SEQ ID NO 1034
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 1034
caatgggatg tcatggaacc actctttg 28

<210> SEQ ID NO 1035
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 1035
acttggtcat gatactgctg attgccccgg catacagcat caggtgcata ggagt 55

<210> SEQ ID NO 1036
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1036
ttcgaaccgc ggctgggtcc tattaagcag agacagctgt ggataagaag atc 53

<210> SEQ ID NO 1037
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1037
tgaactcctg aggggaccgt cagtc 25

<210> SEQ ID NO 1038
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 1038
ggtgctgggc acggtggg 18

<210> SEQ ID NO 1039
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1039
aacaaagccc gcccagcccc c 21

<210> SEQ ID NO 1040
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 1040
ggagaccttg cacttgtact ccttg 25

<210> SEQ ID NO 1041
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1041
atgctccgtg ctgcatgagg c 21

<210> SEQ ID NO 1042
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 1042
gagaagacgt tcccctgc 18

<210> SEQ ID NO 1043
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1043
gctctgcaca gccactacac g 21

<210> SEQ ID NO 1044
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1044
ctcatgcagc acggagcatg 20

<210> SEQ ID NO 1045
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 1045
acttggtcat gatactgctg attgccccgg catacagcat caggtgcata ggagt 55

<210> SEQ ID NO 1046
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 1046
ttcgaaccgc ggctgggtcc tattaagcag agacagctgt ggataagaag atc 53

<210> SEQ ID NO 1047
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1047
aggagtcggg gcggcgaaga tcacccac 28

<210> SEQ ID NO 1048
<211> LENGTH: 28
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1048
gtgggtgatc ttcgccgccc cgactcct 28

<210> SEQ ID NO 1049
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1049
ttgtcatagg agtcggggcg gcgaagatca cccaccactg 40

<210> SEQ ID NO 1050
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1050
cataggagtc ggggacaaga agatcaccca c 31

<210> SEQ ID NO 1051
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1051
gtcataggag tcggggagcg taagatcacc caccactgg 39

<210> SEQ ID NO 1052
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1052
acaaggagtg gttccatgac a 21

<210> SEQ ID NO 1053
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1053
ttttccgatg gtgctgccac 20

<210> SEQ ID NO 1054
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1054
gtatgcaggg acagatggac c 21

<210> SEQ ID NO 1055
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1055
accgcatctc gtttccttct t 21

<210> SEQ ID NO 1056
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1056
ggatgatcgt taatgacaca g 21

<210> SEQ ID NO 1057
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1057
accatcttcc caggcttg 18

<210> SEQ ID NO 1058
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1058
ggatcctgat ttgaaagctg c 21

<210> SEQ ID NO 1059

<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1059
ttccacgaca ttccattacc 20

<210> SEQ ID NO 1060
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 1060
atctacgggg ggagtcagga tg 22

<210> SEQ ID NO 1061
<211> LENGTH: 14
<212> TYPE: PRT
<213> ORGANISM: Zika virus

<400> SEQUENCE: 1061

Ile Val Ile Gly Val Gly Glu Lys Lys Ile Thr His His Trp
1 5 10

<210> SEQ ID NO 1062
<211> LENGTH: 14
<212> TYPE: PRT
<213> ORGANISM: Zika virus

<400> SEQUENCE: 1062

Ile Val Ile Gly Val Gly Asp Lys Lys Ile Thr His His Trp
1 5 10

<210> SEQ ID NO 1063
<211> LENGTH: 14
<212> TYPE: PRT
<213> ORGANISM: Dengue virus 1

<400> SEQUENCE: 1063

Ile Val Val Gly Ala Gly Glu Lys Ala Leu Lys Leu Ser Trp
1 5 10

<210> SEQ ID NO 1064
<211> LENGTH: 14
<212> TYPE: PRT
<213> ORGANISM: Dengue virus 2

<400> SEQUENCE: 1064

Ile Ile Ile Gly Val Glu Pro Gly Gln Leu Lys Leu Asn Trp
1 5 10

-continued

<210> SEQ ID NO 1065
<211> LENGTH: 14
<212> TYPE: PRT
<213> ORGANISM: Dengue virus 3

<400> SEQUENCE: 1065

```
Ile Val Ile Gly Ile Gly Asp Asn Ala Leu Lys Ile Asn Trp
1               5                   10
```

<210> SEQ ID NO 1066
<211> LENGTH: 14
<212> TYPE: PRT
<213> ORGANISM: Dengue virus 4

<400> SEQUENCE: 1066

```
Ile Val Ile Gly Val Gly Asn Ser Ala Leu Thr Leu His Trp
1               5                   10
```

<210> SEQ ID NO 1067
<211> LENGTH: 14
<212> TYPE: PRT
<213> ORGANISM: Yellow fever virus

<400> SEQUENCE: 1067

```
Ile Ile Val Gly Arg Gly Asp Ser Arg Leu Thr Tyr Gln Trp
1               5                   10
```

<210> SEQ ID NO 1068
<211> LENGTH: 14
<212> TYPE: PRT
<213> ORGANISM: Yellow fever virus

<400> SEQUENCE: 1068

```
Ile Ile Val Gly Arg Gly Asp Ser Arg Leu Thr Tyr Gln Trp
1               5                   10
```

<210> SEQ ID NO 1069
<211> LENGTH: 14
<212> TYPE: PRT
<213> ORGANISM: West Nile virus

<400> SEQUENCE: 1069

```
Ile Val Val Gly Arg Gly Glu Gln Gln Lys Asn His His Trp
1               5                   10
```

<210> SEQ ID NO 1070
<211> LENGTH: 14
<212> TYPE: PRT
<213> ORGANISM: Zika virus

<400> SEQUENCE: 1070

```
Ile Val Ile Gly Val Gly Glu Arg Lys Ile Thr His His Trp
1               5                   10
```

NEUTRALIZING ANTIBODIES THAT BIND TO THE ZIKA VIRUS DOMAIN III ENVELOPE REGION

CROSS REFERENCE TO RELATED APPLICATIONS

This application claims priority to U.S. provisional patent application No. 62/483,001, filed Apr. 7, 2017, the disclosure of which is incorporated herein by reference.

GOVERNMENT FUNDING

This invention was made with government support under grant no. UM1AI100663 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 6, 2018, is named 076091_00046_SL.txt and is 507,614 bytes in size.

BACKGROUND

Zika virus (ZIKV) infection typically produces mild symptoms consisting of fever, rash and arthralgia that resolve rapidly, and the infection is also occasionally associated with Guillain-Barré Syndrome (Lessler et al., 2016; Miner and Diamond, 2017). However, when infection occurs during pregnancy, vertical transmission can lead to a spectrum of devastating neurodevelopmental aberrations, collectively referred to as Congenital Zika Syndrome. Although the data are still incomplete, infants born to mothers infected with ZIKV during pregnancy carry an up to 42% risk of developing overt clinical or neuroimaging abnormalities (Brasil et al., 2016; Costa et al., 2016; Franca et al., 2016).

ZIKV belongs to the Flavivirus genus, which includes yellow fever (YFV), West Nile (WNV), and the 4 serotypes of dengue virus (DENV1-4). These positive-stranded RNA viruses are responsible for considerable morbidity and mortality in the equatorial and subequatorial regions populated by their mosquito vectors (Kramer et al., 2007; Murray et al., 2013; Weaver and Reisen, 2010). Unlike most other flaviviruses, ZIKV can also be transmitted sexually, and on occasion persists for months (Barzon et al., 2016; Foy et al., 2011; Murray et al., 2017; Suy et al., 2016).

All flaviviruses display a single envelope protein, E, that is highly conserved between different members of this virus family. The E protein ectodomain consists of three structural domains. Domain I (EDI) contains the N-terminus, domain II (EDIT) is an extended finger-like structure that includes the dimerization domain and also a pH-sensitive fusion loop that mediates viral fusion in the lysosomes. Finally, domain III (EDIII) is an immunoglobulin-like domain that mediates attachment to target cells (Barba-Spaeth et al., 2016; Dai et al., 2016; Kostyuchenko et al., 2016; Modis et al., 2003; Mukhopadhyay et al., 2005; Rey et al., 1995; Sirohi et al., 2016; Zhang et al., 2004). Several human neutralizing antibodies targeting different E protein epitopes have been described. Antibodies against the EDIII of flaviviruses are among the most potent neutralizers in this group (Beasley and Barrett, 2002; Crill and Roehrig, 2001; Screaton et al., 2015).

Due to the conserved structural features of the E protein, antibodies that develop in response to infection by one flavivirus may also recognize others (Heinz and Stiasny, 2017). Cross-reactivity can lead to cross-protection as first documented by Sabin who showed experimentally in humans that exposure to DENV1 could provide short-term protection from subsequent challenge with DENV2. In contrast, immunity to the autologous strain was long lasting (Sabin, 1950). More recently, human monoclonal antibodies to DENV have been shown to cross-neutralize ZIKV, and vice versa (Barba-Spaeth et al., 2016; Stettler et al., 2016; Swanstrom et al., 2016). However, there is concern that cross-reacting antibodies that fail to neutralize the virus may enhance rather than curb subsequent flavivirus infections (Harrison, 2016; Wahala and Silva, 2011). In vitro and in vivo experiments in mice suggest that this phenomenon, commonly referred to as Antibody Dependent Enhancement (ADE), extends to ZIKV (Bardina et al., 2017; Dejnirattisai et al., 2016; Harrison, 2016; Priyamvada et al., 2016). While several human antibodies to ZIKV have been cloned from convalescent individuals by methods utilizing B cell transformation with Epstein-Barr virus (Sapparapu et al., 2016; Stettler et al., 2016), individual donors were not selected for high neutralization titers; whether their antibodies are representative of optimal immune responses, and how these antibodies might relate to previous flavivirus exposure remains unknown.

Since no approved prophylaxis or treatment exists, there is an ongoing need for compositions and methods that provide robust protection against ZIKV and other flaviviruses (such as DENV1). Because of the risk of ADE, it is preferable that such compositions and methods avoid the generation of antibodies that bind to the virus but are non-neutralizing and potentially enhancing. Passive administration of monoclonal antibodies represents an alternative approach to vaccines, and has the advantage that antibodies can be modified to prevent interaction with cellular receptors that mediate ADE. The present disclosure is pertinent to this need.

BRIEF SUMMARY

Antibodies to Zika virus (ZIKV) can be protective. To examine the antibody response in individuals that develop high titers of anti-ZIKV antibodies we screened cohorts in Brazil and Mexico for ZIKV envelope domain III (ZEDIII) binding and neutralization. Sequencing of nearly 300 antibodies showed that donors with high ZIKV neutralizing antibody titers had expanded clones of memory B cells that carried the same immunoglobulin VH3-23/VK1-5 genes. These recurring antibodies cross-reacted with DENV1, but not other flaviviruses. In particular, a VH3-23/VK1-5 antibody described in detail below as Z004 neutralized both DENV1 and ZIKV, and protected mice against ZIKV challenge. Structural analyses revealed the mechanism of recognition of the ZEDIII lateral ridge by VH3-23/VK1-5 antibodies. Serologic testing showed that antibodies to this region correlate with serum neutralizing activity to ZIKV, and that reactivity to dengue 1 virus (DENV1) EDIII before ZIKV exposure was associated with increased ZIKV neutralizing titers after exposure. Thus, high neutralizing responses to ZIKV are associated with pre-existing reactivity to DENV1. Accordingly, mice immunization experiments showed that immunization with the EDIII of DENV1 followed by boosting with ZEDIII resulted in higher neutralizing titers against ZIKV than immunization with either component alone. The disclosure takes advantage of these discoveries to provide novel compositions and methods for approaching ZIKV and DENV1 prophylaxis and/or therapy. Furthermore, the present disclosure demonstrates that a combination of two different antibodies that recognize distinct but overlapping epitopes on the EDIII lateral ridge of ZIKV and DENV1 has unique properties. In particular, the antibody described below as Z021 potently neutralized ZIKV and DENV1 in vitro and prevented disease in mice. In macaques, prophylactic co-administration of Z004 with Z021 was protective and suppressed emergence of ZIKV resistant variants. Thus, the present disclosure demonstrates that a combination of two human monoclonal antibodies that recognize distinct but overlapping epitopes on ZIKV EDIII is sufficient to suppress infection and thwart viral escape in macaques, a natural host for ZIKV. It is considered based on these data that similar effects can be elicited in humans.

In embodiments the disclosure thus provides an isolated or recombinant antibody, or polynucleotides encoding the antibody, comprising a complementarity determining region (CDR) 3 (CDR3) amino acid sequence selected from heavy chain and light chain CDR3 sequences in Table 1 and Table 2. Table 1 also provides variable sequences for numerous antibody heavy and light chain from which CDR1, CDR2 and CDR3 sequences can be determined.

In certain embodiments the disclosure provides a Z004 antibody comprising a heavy chain comprising: a CDR1 comprising GFTFRDYA (SEQ ID NO:1), a CDR2 comprising YSGIDDST (SEQ ID NO:2), and a CDR3 comprising AKDRGPRGVGELFDS (SEQ ID NO:3) (a Z004 heavy chain); and a light chain comprising: a CDR1 comprising QSISKW (SEQ ID NO:4), a CDR2 comprising TTS, and a CDR3 comprising QHFYSVPWT (SEQ ID NO:5) (a Z004 light chain). In an embodiment the disclosure provides a Z021 antibody comprising a heavy chain comprising: a CDR1 comprising GGSIDTYY (SEQ ID NO:6), a CDR2 comprising FYYSVDN (SEQ ID NO:7), and a CDR3 comprising ARNQPGGRAFDY (SEQ ID NO:8) (a Z021 heavy chain); and a light chain comprising: a CDR1 comprising QSVSNY (SEQ ID NO:9), a CDR2 comprising DTS, and a CDR3 comprising QERNNWPLTWT (SEQ ID NO:10) (a Z021 light chain), or iii) a bispecific antibody comprising the Z004 heavy chain CDR1, CDR2, CDR3, and the Z004 light chain CDR1, CDR2, CDR3, and the Z021 heavy chain CDR1, CDR2, CDR3, and the Z021 light chain CDR1, CDR2, CDR3.

Any antibody described herein can comprise at least one modification of its constant region. The modification is of any one or more amino acids. The modification can have any of a number of desirable effects. In certain approaches, the modification increases in vivo half-life of the antibody, or alters the ability of the antibody to bind to Fc receptors, or alters the ability of the antibody to cross placenta or to cross a blood-brain barrier or to cross a blood-testes barrier, or inhibits aggregation of the antibodies, or a combination of said modifications, or wherein the antibody is attached to a label or a substrate. In embodiments, the modification improves the manufacturability of the antibody. In embodiments, any antibody or combination thereof described herein can be present in an immunological assay, such as an enzyme-linked immunosorbent assay (ELISA) assay, or an ELISA assay control. The ELISA assay can be any of a direct ELISA assay, an indirect ELISA assay, a sandwich ELISA assay, or a competition ELISA assay.

In another aspect the disclosure provides a method for prophylaxis or therapy of a viral infection comprising administering to an individual in need thereof an effective amount of at least one antibody or antigen binding fragment thereof. The antibody may comprise at least one modification of the constant region. In embodiments, the composition is administered to an individual who is infected with or is at risk of being infected with a virus selected from the group consisting of Zika virus (ZIKV), dengue 1, 2, 3 or 4 viruses (DENV1-4), yellow fever virus (YFV), West Nile virus (WNV), and combinations thereof. In one approach, at least two antibodies are administered. In an embodiment, administering at least two distinct antibodies suppressed formation of viruses that are resistant to the antibodies. In one embodiment, the Z004 antibody and the Z021 antibody are administered.

In another aspect the disclosure provides vaccine formulations. In an embodiment a vaccine formulation comprises: i) an isolated or recombinant polypeptide or a polynucle- In embodiments, the Z004 antibody (also referred to herein as MEX18_89) comprises a heavy chain having the sequence:

(SEQ ID NO: 11)

EVQLLESGGGLVQPGGSLRLTCATS*GFTFRDYA*MSWVRQAPGKGLEWVSSYSGIDD
STYYADSVKGRFTISRDNSKSTLSLHMNSLRAEDSALYFC*AKDRGPRGVGELFDS*W
GQGTLVTVSS and a light chain having the sequence:

(SEQ ID NO: 12)

DIQMTQSPSTLSASVGDRVTITCRAS*QSISKW*LAWYQQKPGKAPKWYTTSTLKSGV
PSRFSGSGSGTEFTLTISSLQPDDFATYYC*QHFYSVPWT*FGQGTKVEIK

In this Z004 sequence and Z021 sequence below, the CDR1 is italicized, the CDR2 is bolded and the CDR3 is italicized and bolded.

otide encoding the polypeptide, wherein the polypeptide is derived from the ZIKV EDIII protein, wherein the polypeptide comprises a segment of the lateral ridge of ZIKV EDIII In embodiments, the Z021 antibody (also referred to herein as MEX84_p4-23) has a heavy chain having the sequence:

(SEQ ID NO: 13)

QVQLQESGPGLVKPSETLSLTCTVS*GGSIDTYY*WSWIRQTPGKGLEWIGCFYYSVDNH
FNPSLESRVTISVDTSKNQFSLKMTSMTASDTAVYYC*ARNQPGGRAFDY*WGPGTLV
TVSS and a light chain having the sequence:

(SEQ ID NO: 14)

EIVLTQSPATLSLSPGQRATLSCRAS*QSVSNY*FAWYQQKPGQAPRLLIYDTSKRATGT
PARFSGSGSGTDFTLTISSLEPEDFAVYYC*QERNNWPLTWT*FGLGTKVEIK.

(ZEDIII); or ii) an isolated or recombinant polypeptide or a polynucleotide encoding the polypeptide, wherein the polypeptide is derived from the DENV1 EDIII protein, wherein the polypeptide comprises a segment of the lateral ridge of the DENV1 EDIII protein, or a combination of i) and ii).

In certain implementations, a vaccine formulation comprises a ZEDIII polypeptide which comprises at least one contiguous segment of ZEDIII comprising amino acids 305-311, 333-336, or 350-352, and/or wherein the segment comprises one or more of ZEDIII amino acids L307, 5306, T309, K394, A311, E393, T335, G334, A310, and D336, and/or wherein the polypeptide comprises one or more of DENV1 EDIII amino acids M301, V300, T303, E384, T329, K385, 5305, E327, G328, and D330. In certain approaches, a ZIKV EDIII epitope and/or a DENV1 EDIII epitope is duplicated in the polypeptide, and/or the polypeptide comprises both ZIKV EDIII and DENV1 EDIII epitopes. In certain approaches, the polypeptide in the vaccine is modified such that it comprises one or more glycans, and/or by addition of amino acids that comprise Th epitope(s), and/or the polypeptide is stapled, and/or is cyclicized, and/or is multimerized.

In another approach the disclosure provides a method for prophylaxis or therapy of a viral infection comprising administering to an individual in need thereof an effective amount of at least one vaccine formulation described herein. In certain embodiments, a first vaccination is performed with a polypeptide or a polynucleotide encoding the polypeptide, wherein the polypeptide is derived from the DENV1 EDIII protein, and wherein the polypeptide comprises a segment of the lateral ridge of the DENV1 EDIII. This can be followed by performing a second vaccination with a polypeptide or polynucleotide encoding the polypeptide, wherein the polypeptide is derived from the ZIKV EDIII protein, and wherein the polypeptide comprises a segment of the lateral ridge of ZIKV EDIII (ZEDIII). Such vaccination approaches can stimulate production of neutralizing antibodies in the individual that inhibit infectivity of a virus selected from the group of viruses consisting of Zika virus, dengue 1, 2, 3 or 4 viruses (DENV1-4), yellow fever virus (YFV), West Nile virus (WNV), and combinations thereof.

In another aspect, a method for detecting antibodies to Zika virus (ZIKV) and/or dengue 1 virus (DENV1) is provided, and comprises: contacting a biological sample with an isolated or recombinant polypeptide derived from ZIKV EDIII protein, wherein the polypeptide comprises a contiguous segment of the ZIKV EDIII protein that includes an epitope that comprises amino acids E393-K394 of the EDIII protein, and/or with an isolated or recombinant polypeptide derived from DENV1 EDIII protein that comprises a contiguous segment of the DENV1 EDIII protein that includes an epitope that comprises amino acids E384-K385 of the DENV1 EDIII protein, and directly or indirectly detecting a complex comprising the polypeptide and the antibodies if the antibodies are present in the biological sample. In embodiments, the method is performed using an ELISA assay, such as a competition ELISA assay. A suitable assays may further comprise contacting the biological sample with the isolated or recombinant polypeptide with added antibodies, wherein the added antibodies are detectably labeled, and wherein the added antibodies compete with antibodies in the biological sample (if present prior to the adding) for binding to the isolated or recombinant polypeptide, and wherein less binding of the added antibodies relative to a control indicates serologic activity against ZIKV and/or DENV1 in the biological sample.

In another embodiment, a suitable assay further comprises performing a control reaction. The control reaction substitutes a recombinant polypeptide derived from ZIKV EDIII protein with a recombinant polypeptide derived from ZIKV EDIII protein that comprises a mutation of E393 and/or K394, wherein the mutation is optionally a substitution of E and/or K with an alanine, and comparing an antibody binding value from the control reaction with an antibody binding value to characterize serologic activity against ZIKV in the biological sample.

In another aspect the disclosure provides one or more recombinant expression vectors, and kits comprising the expression vectors. The expression vectors encode the heavy chain and the light chain of any of the antibodies of described herein. Cells comprising the recombinant expression vectors are included, as are methods of making antibodies by culturing cells that comprise expression vectors that express the antibodies, and separating antibodies from the cells. Cell culture media containing such cells and/or antibodies is also included.

A—Frequency of ZEDIII-specific, $IgG^+$ memory B cells in peripheral blood of 6 donors. Flow cytometry plots display the percentage of all $IgG^+$ memory B cells that bind to a fluorescently tagged ZEDIII bait. Flavivirus naïve peripheral blood samples are shown alongside as negative controls. B—Pie charts show the distribution of antibody clones that share the same IGHV and IGLV; the width of each colored or shaded slice is proportional to the number of clones sharing a distinct combination of IGHV and IGLV sequences. The total number of antibody clones sequenced from each donor is indicated in the center of the pie chart. VH3-23/VK1-5 clones are in red, while other VH3-23 clones are indicated with different shades of blue. Non VH3-23 clones are shown in shades of grey, and singlets are in white. None of the grey clones are recurrent across individuals. C—V(D)J assignments for the VH3-23/VK1-5 clones. IgBLAST was used to assign the germline (GL) reference sequence for IGHV and IGLV. Red highlights differences in D and J usage in the VH3-23 clones between individuals.

Figure 8:
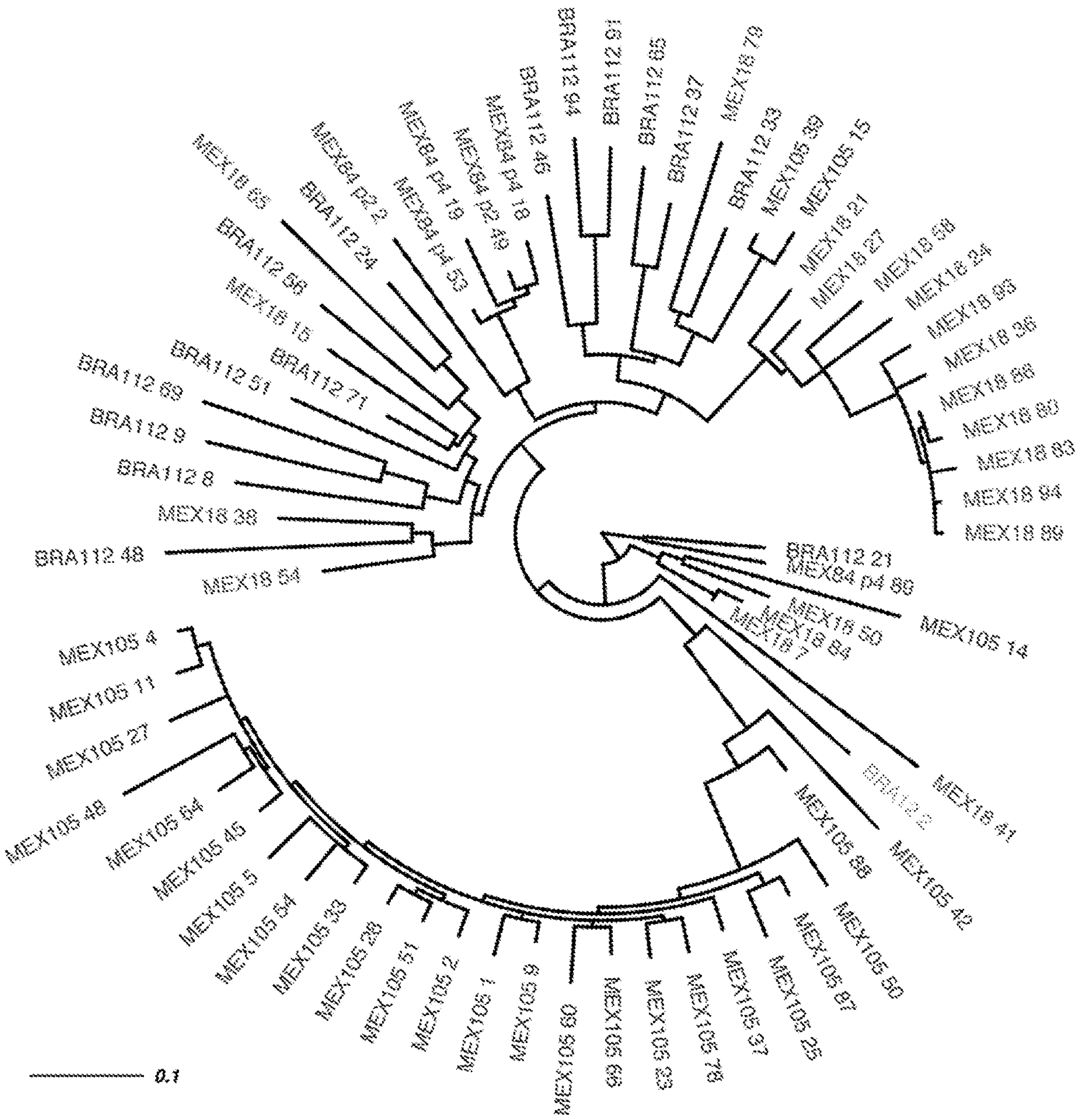

See also FIG. 8, and Tables 1 and 2.

Figure 3:
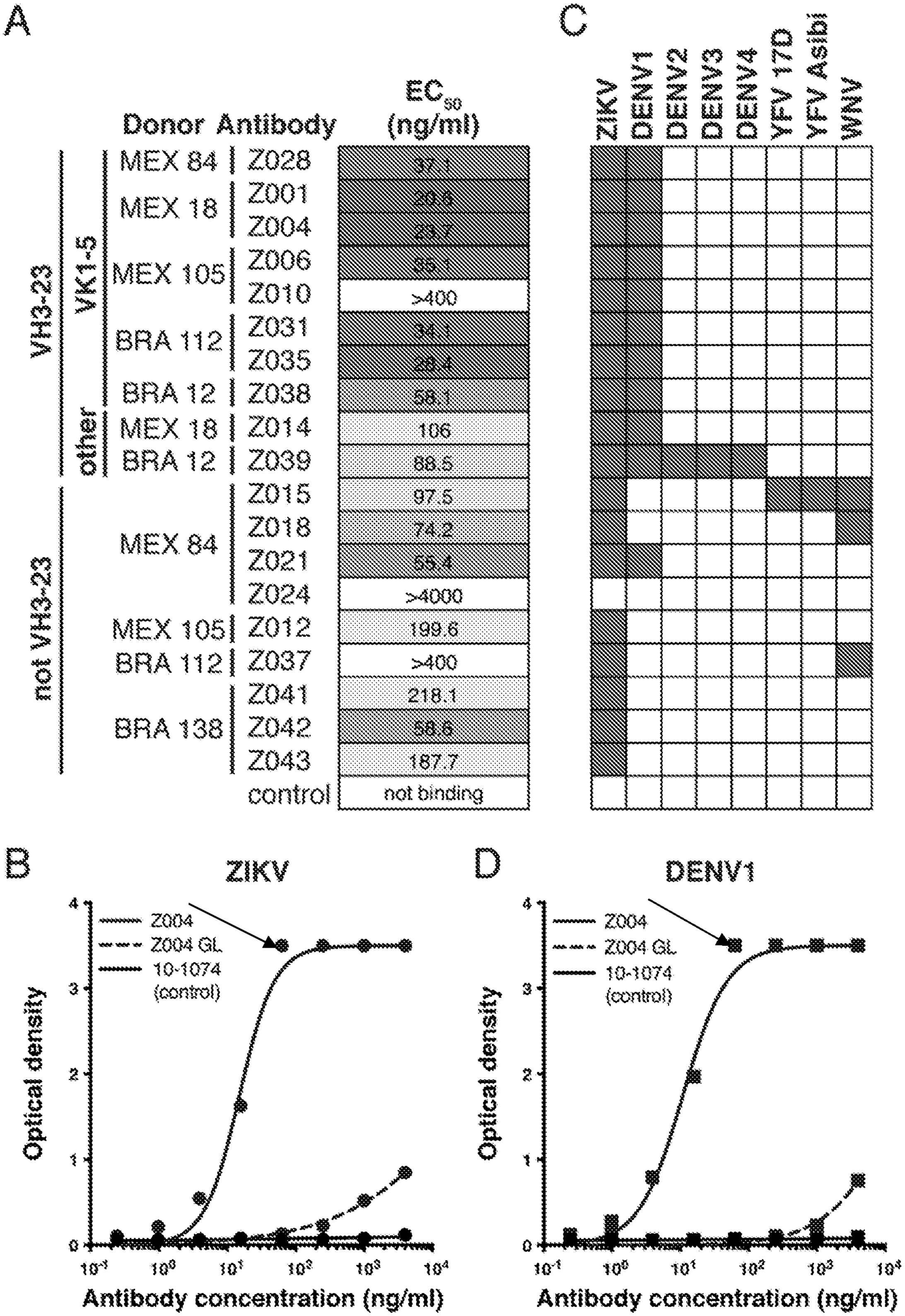

FIG. 3—Binding of cloned antibodies to EDIII from ZIKV and other flaviviruses A—Binding of human monoclonal antibodies to ZEDIII. Human anti-HIV antibody 10-1074 was used as a negative control (Mouquet et al., 2012). The average half effective concentration ($EC_{50}$) from at least two independent experiments is shown. B—Somatic mutations are required for ZEDIII binding. Binding of Z004 (arrow), its predicted germline (GL), and control antibodies to ZEDIII as assessed by ELISA is shown. C—Human monoclonal antibody cross-reactivity by ELISA. Reactivity to the EDIII of the indicated flaviviruses is shown in grey. The list of antibodies is reported on the left of panel A. D—Z004 binds to the EDIII of DENV1. Binding of Z004 (arrow), its predicted germline (GL), and control antibodies to DENV1 EDIII as assessed by ELISA is shown.

Figure 9:
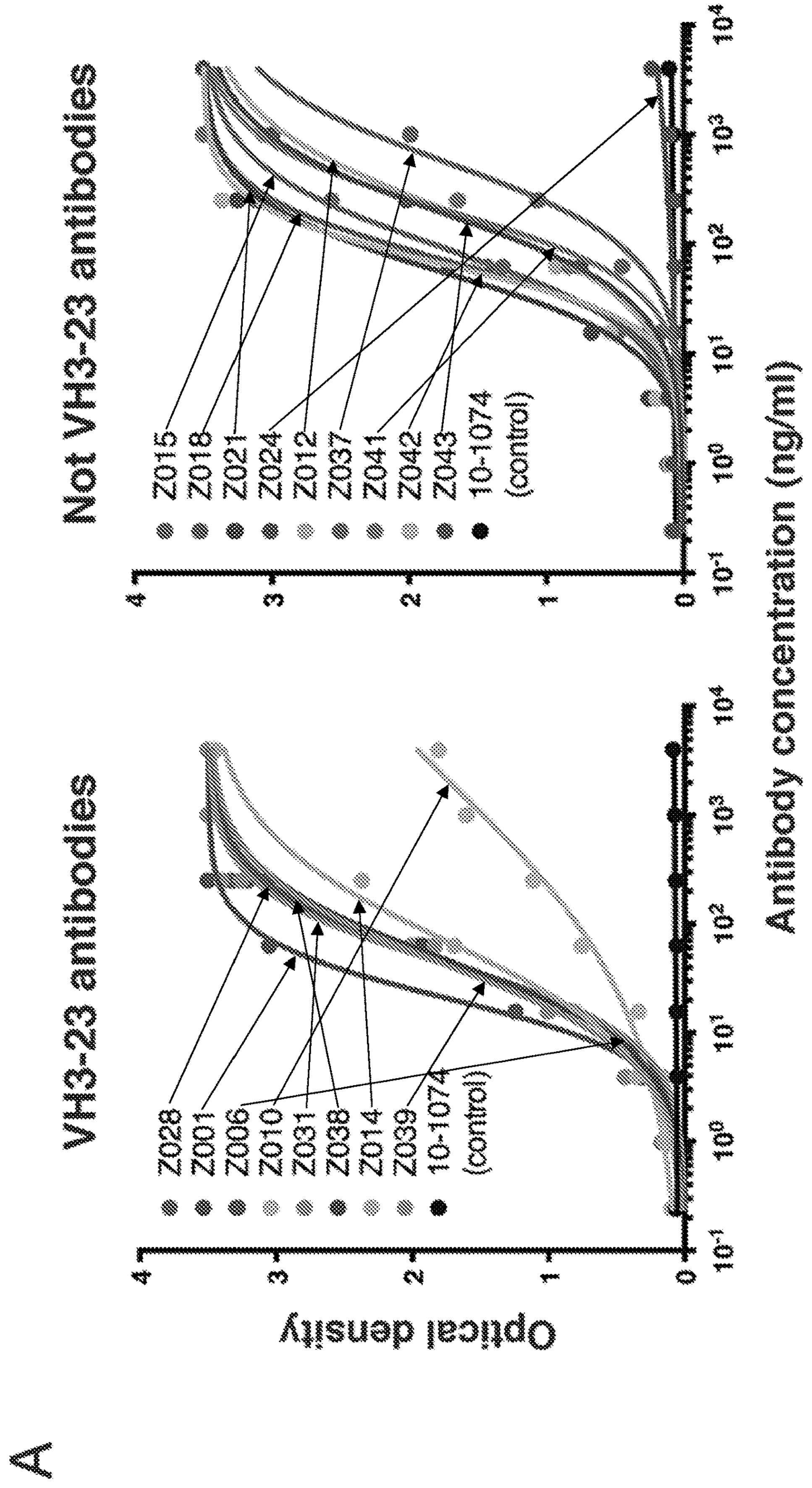
Figure 9:
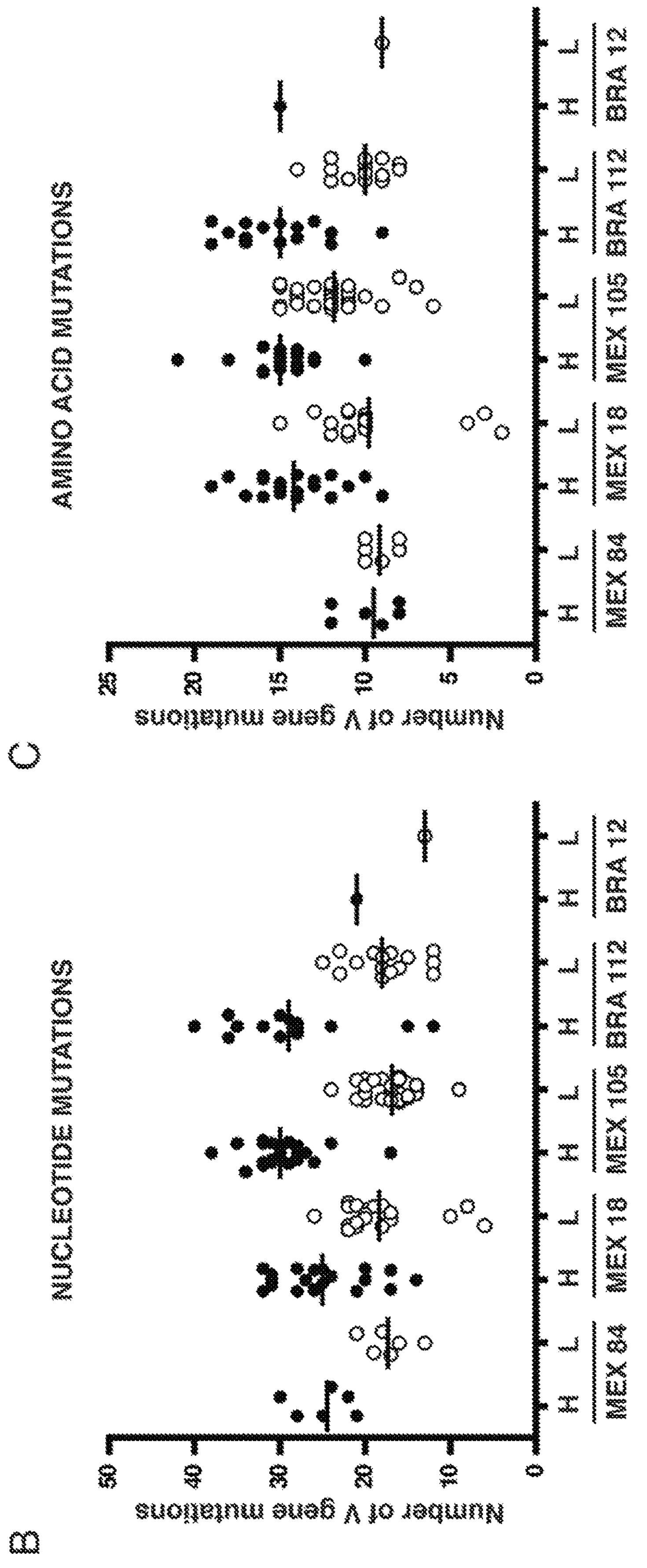

See also FIG. 9.

Figure 4:
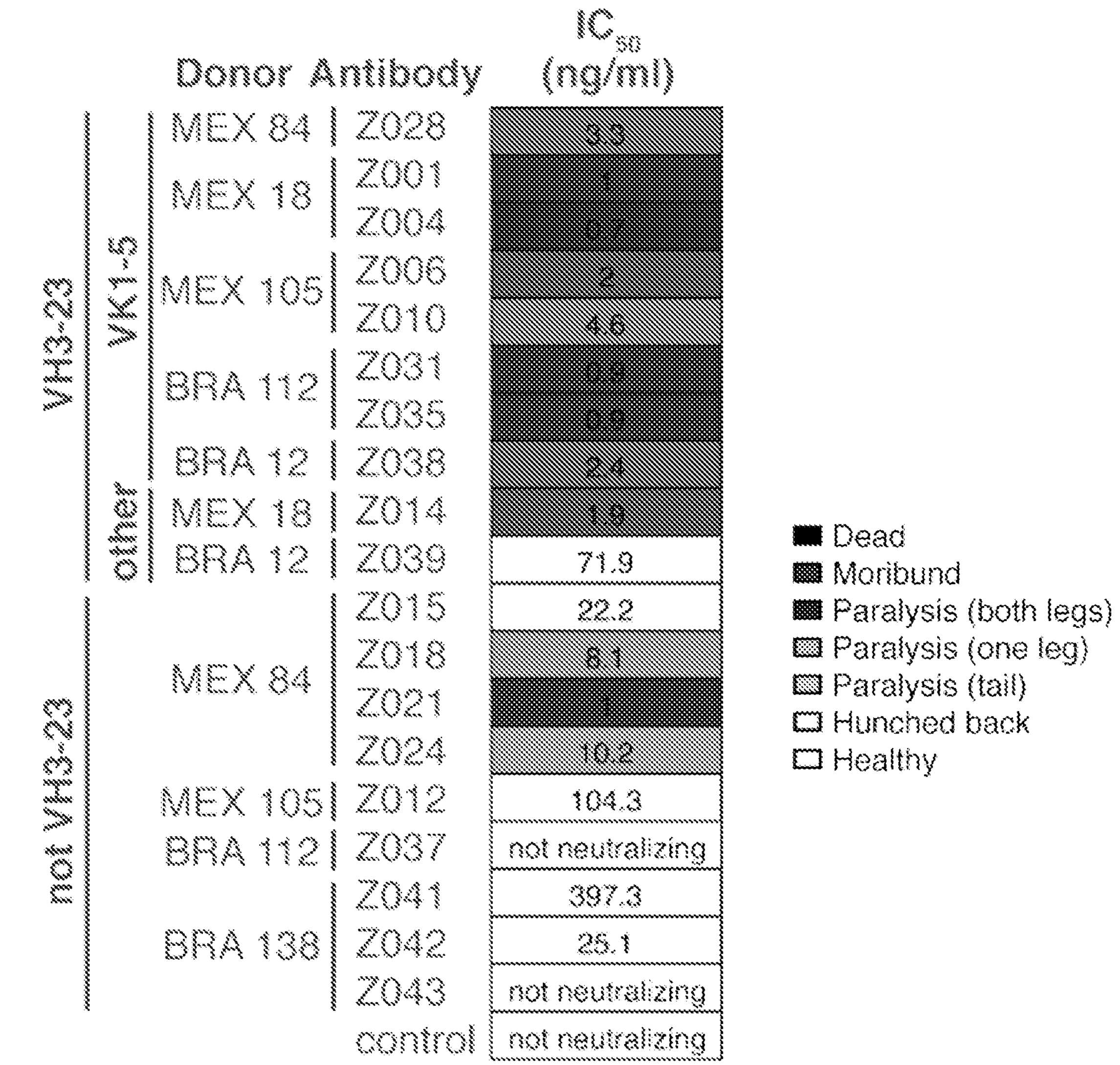
Figure 4:
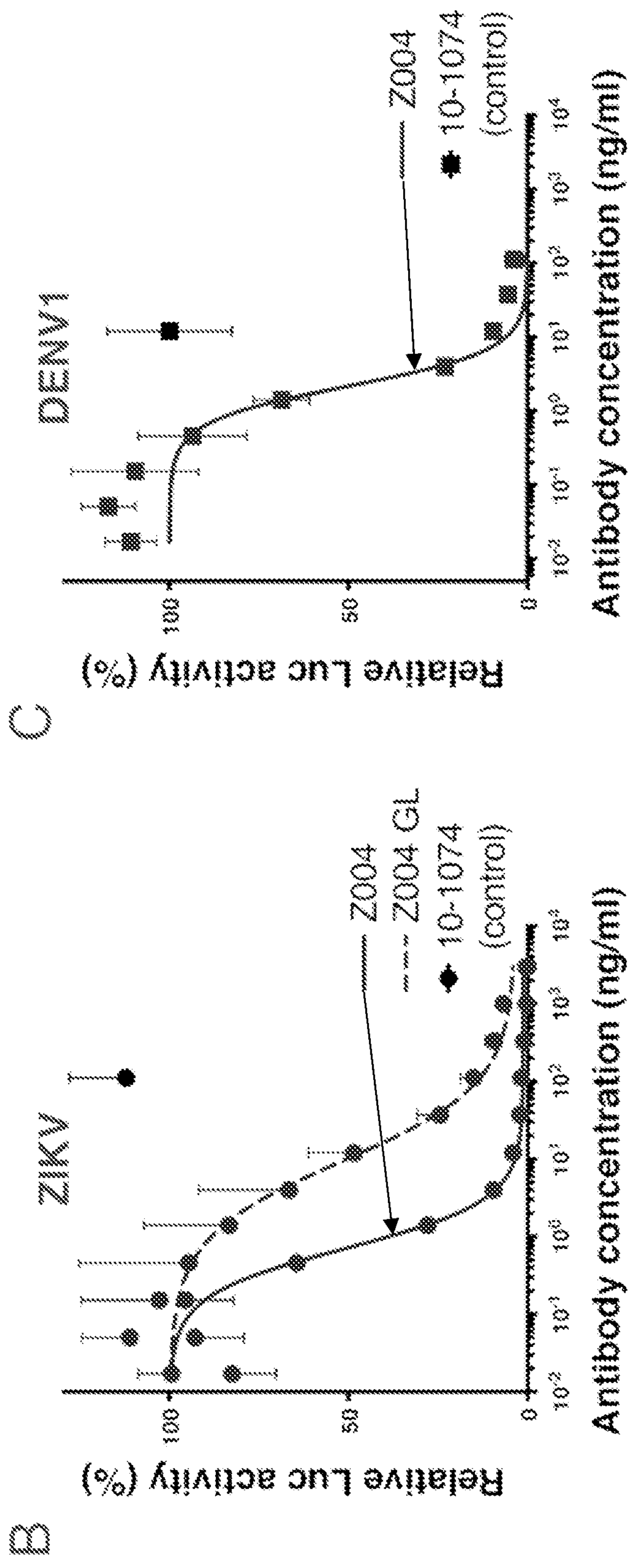
Figure 4:
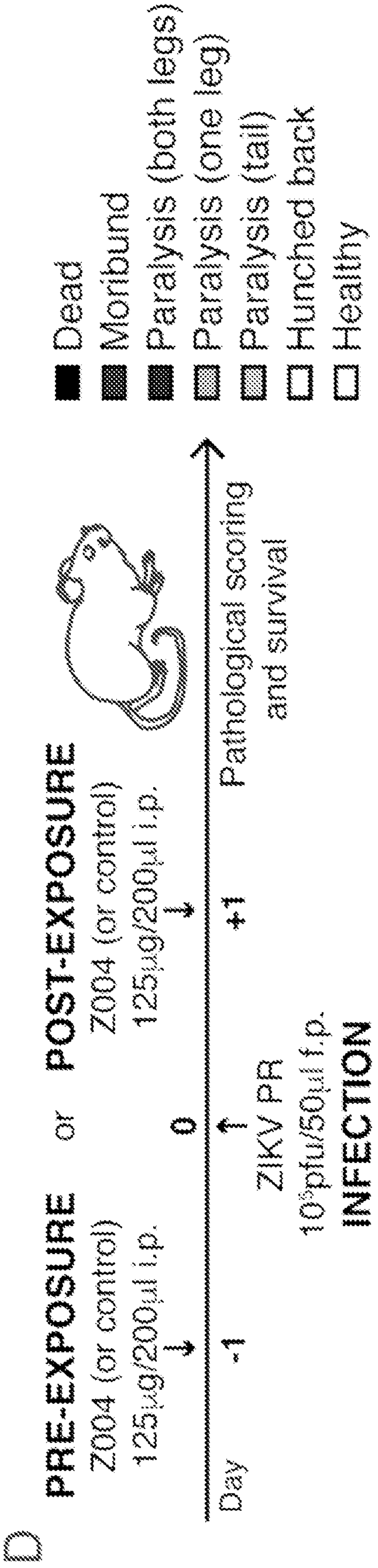
Figure 4:
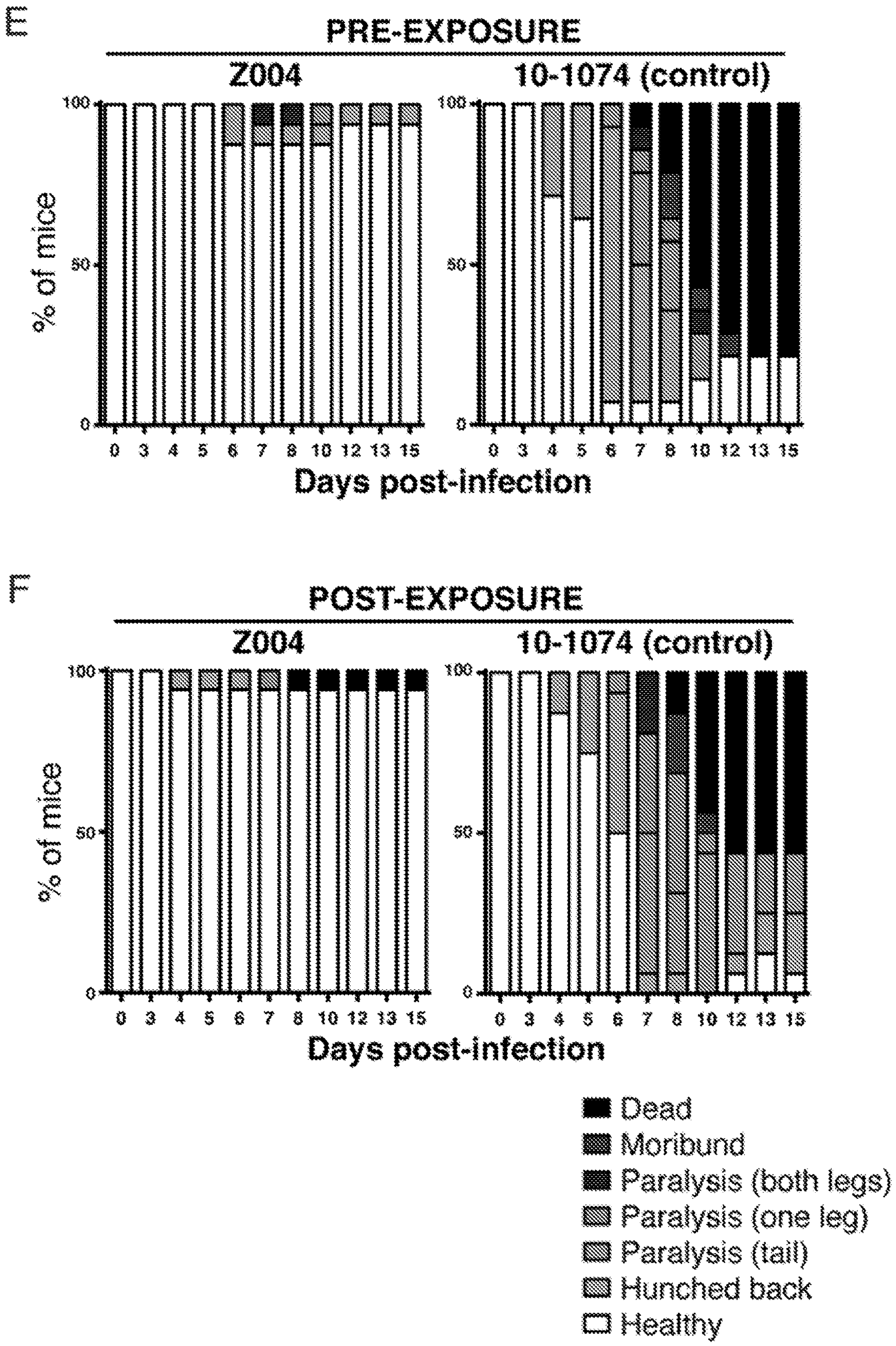
Figure 4:
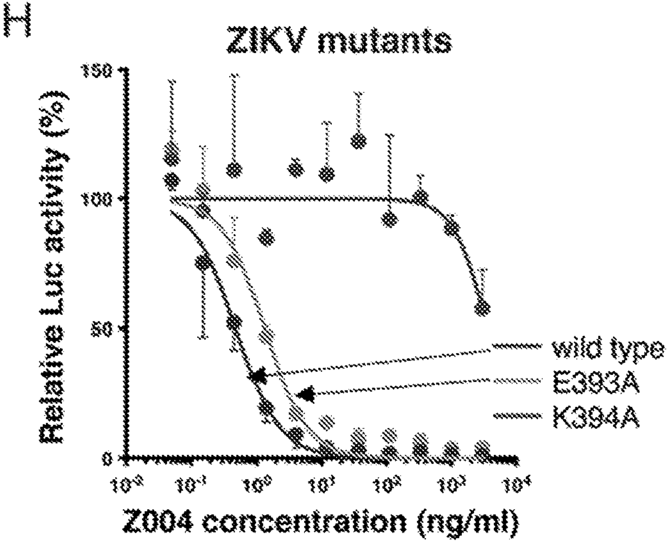
Figure 4:
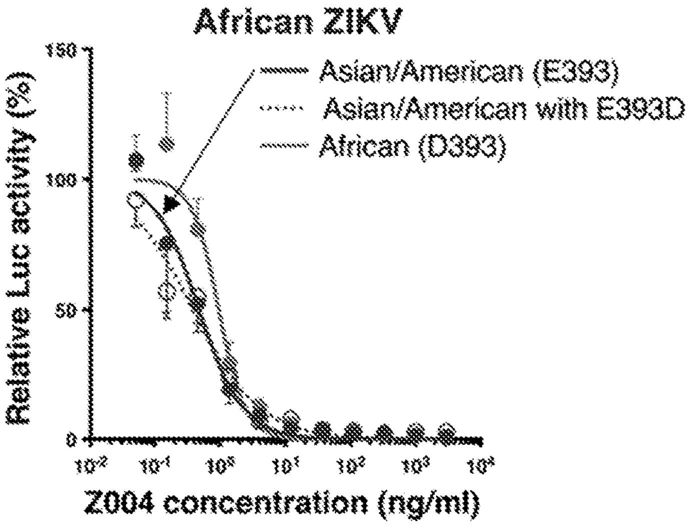

FIG. 4—VH3-23/VK1-5 antibodies neutralize ZIKV and DENV1

A—Neutralization potency of human monoclonal antibodies by ZIKV luciferase RVP assay. The human anti-HIV antibody 10-1074 serves as a negative control. Average values of the half maximal inhibitory concentration ($IC_{50}$) from at least two independent experiments are shown. B and C—Z004 neutralizes ZIKV (B) and DENV1 (C) RVPs. Luciferase activity relative to the no antibody control was determined in the presence of increasing concentrations of Z004 (arrow) or of its predicted germline antibody as indicated. Control antibody was tested at a single concentration. Data are represented as mean±SD. D, E, and F—Z004 protects IFNAR1$^{-/-}$ mice from ZIKV disease. Mice were infected by footpad (f.p.) injection with the Puerto Rican PRVABC59 ZIKV strain and treated intraperitoneally (i.p.) with Z004 (or 10-1074 control) either before (E) or 1 day after (F) infection. Mice were monitored for symptoms and survival. Survival: $p<0.0001$ (pre-exposure) and $p=0.0027$ (post-exposure). Symptoms: $p<0.0001$ (both pre- and post-exposure, Mantel-Cox test). Three independent experiments, of 4 to 7 mice per group, were combined and displayed. G—Amino acid alignment of a portion of the EDIII lateral ridge region for a panel of flaviviruses (SEQ ID NOS 1061-1069, respectively, in order of appearance). The corresponding accession numbers are indicated in parenthesis. H—The K394 residue in the ZEDIII lateral ridge is required for ZIKV neutralization by Z004. Luciferase activity relative to no antibody control was determined for ZIKV wild type or mutant E393A and K394A RVPs. I—Z004 neutralizes both Asian/American and African strains. RVPs bearing Asian/American ZIKV wild type (E393), mutant (Asian/American with E393D) and African strain (D393) E proteins were neutralized by Z004. In H and I data are represented as mean±SD.

Figure 10:
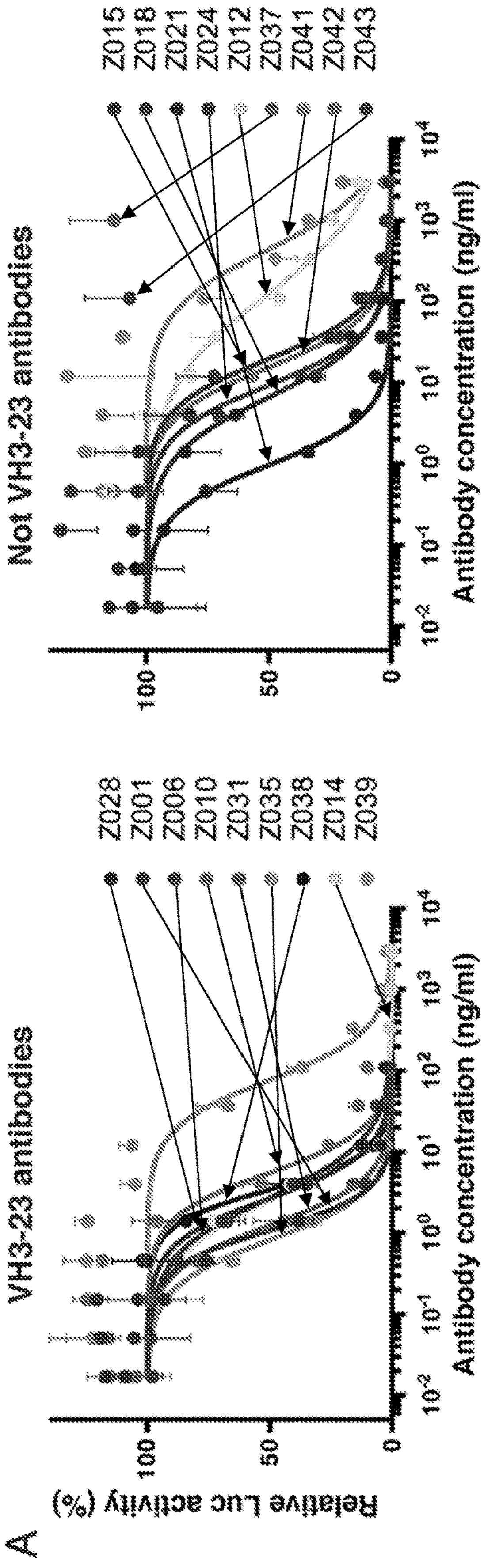
Figure 10:
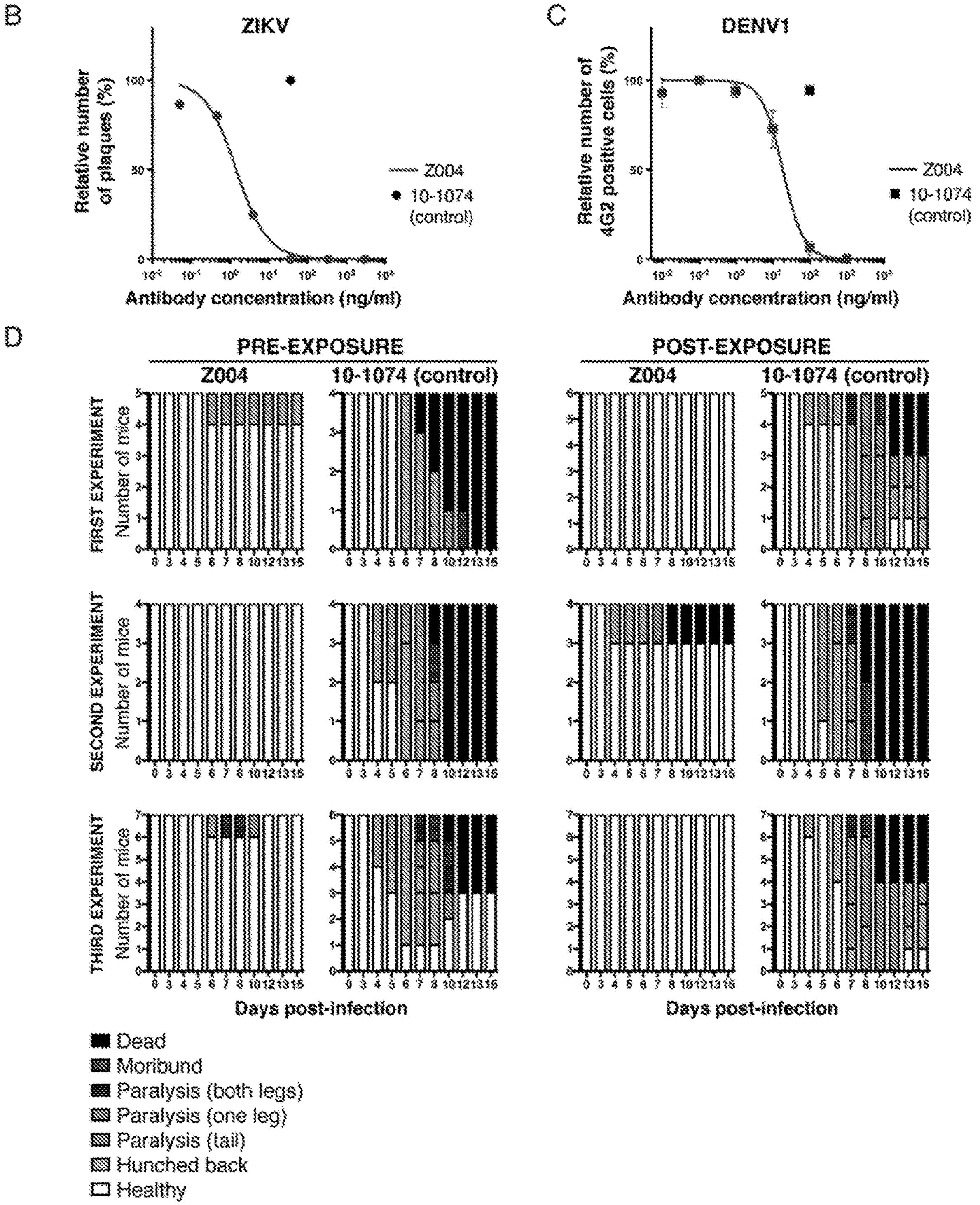
Figure 10:
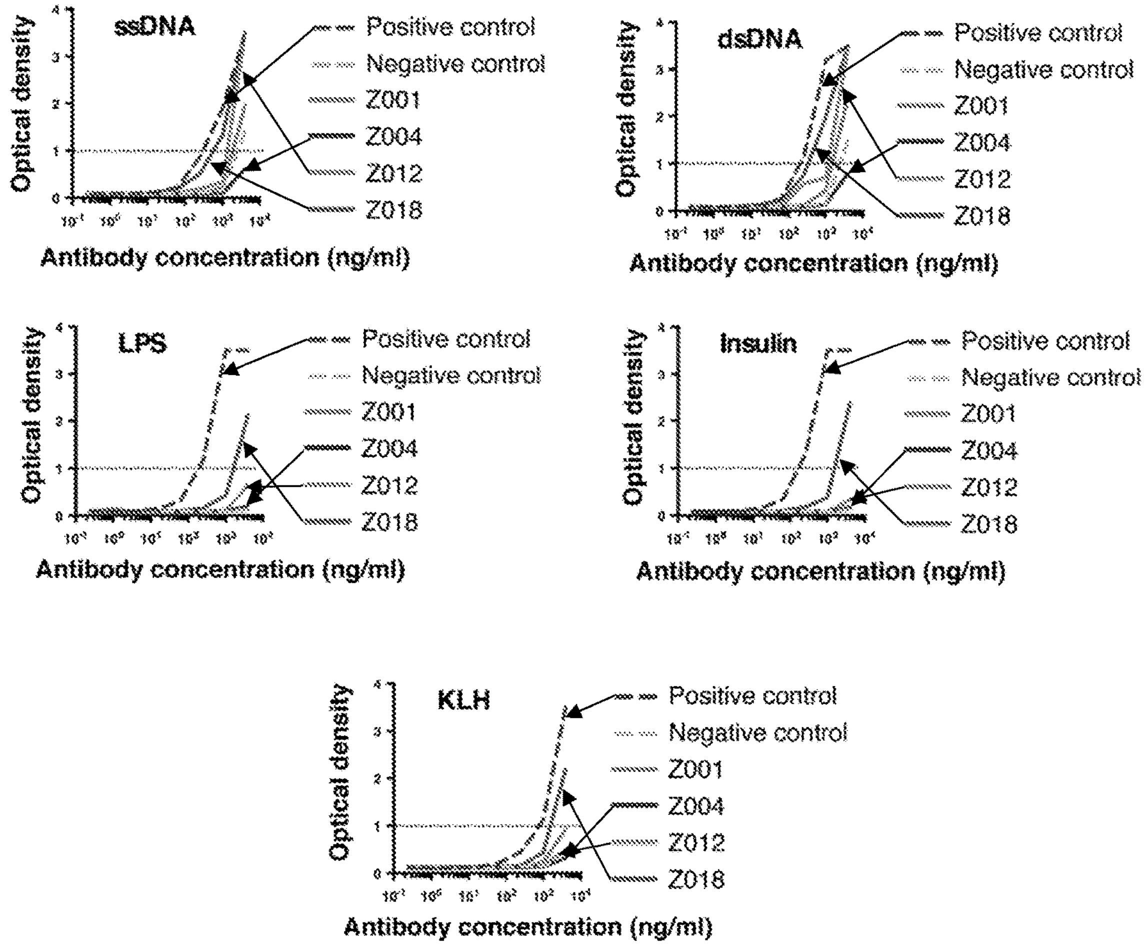

See also FIG. 10.

Figure 5:
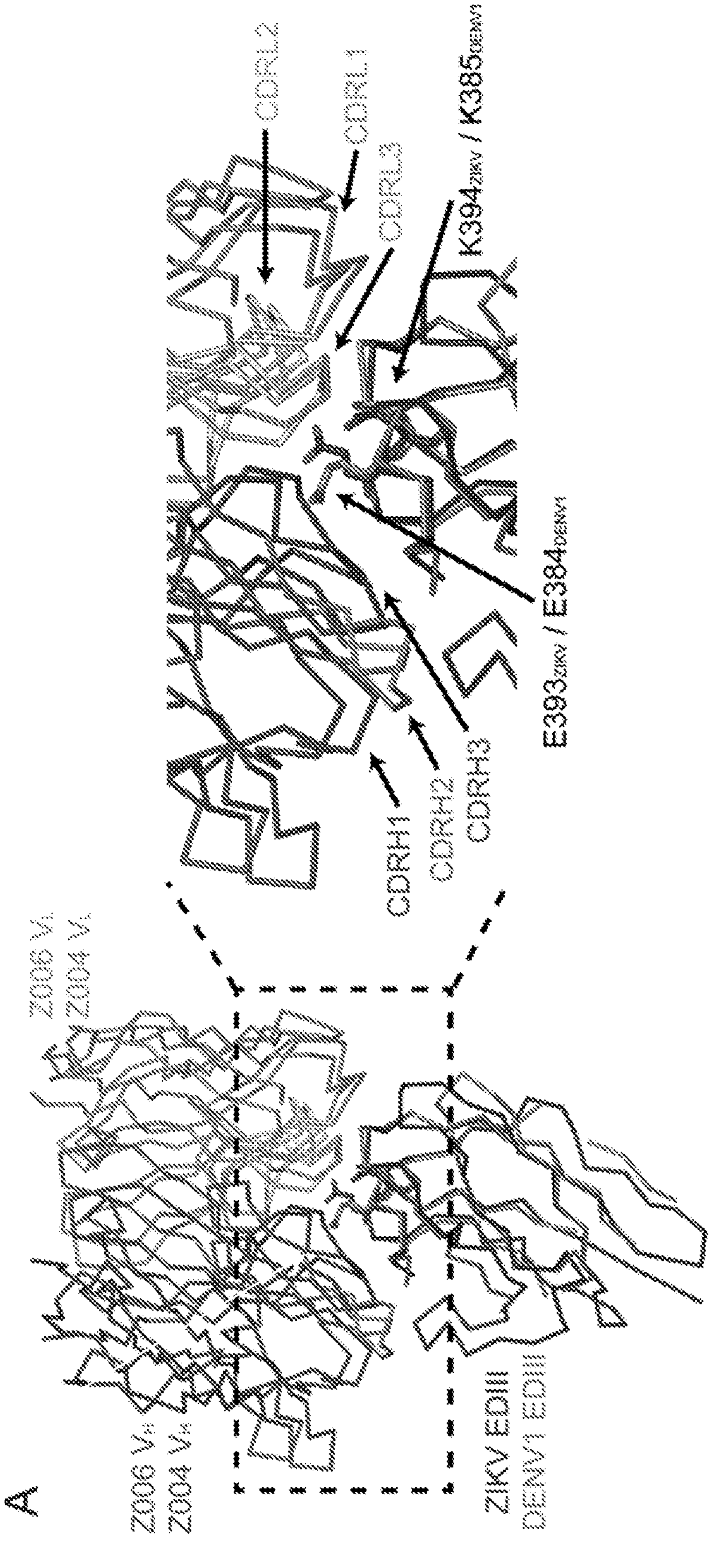
Figure 5:
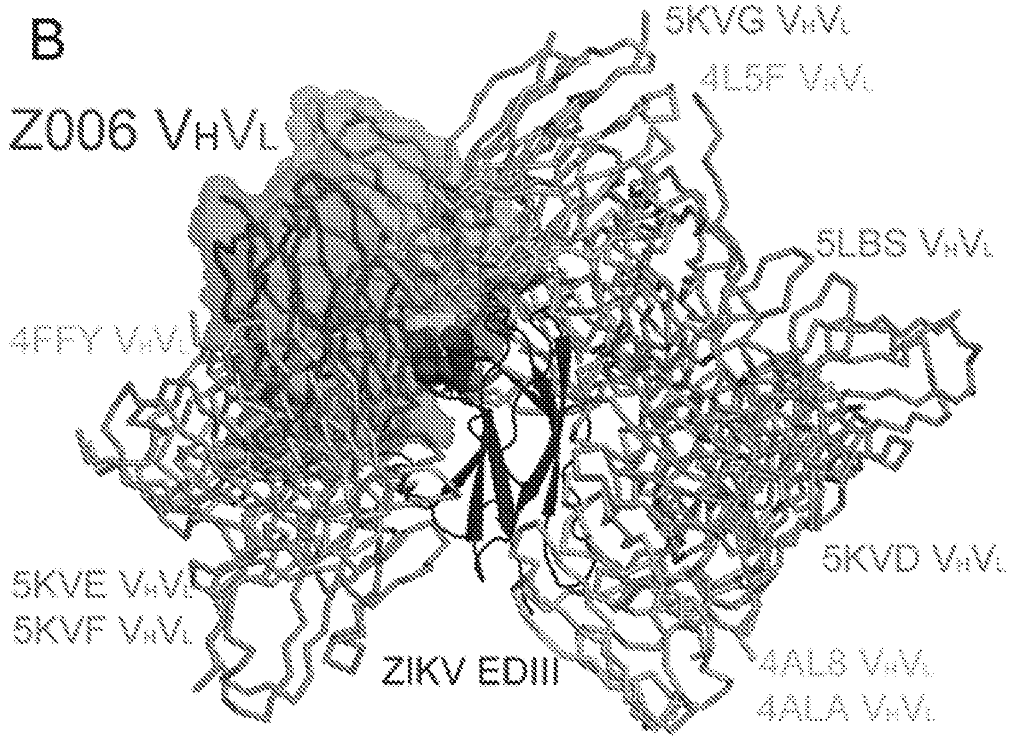
Figure 5:
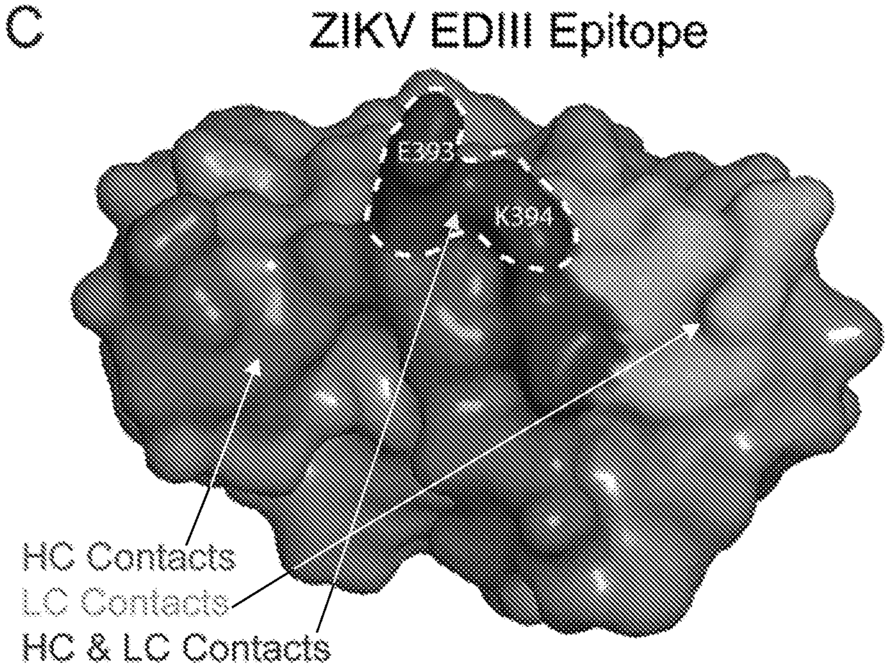
Figure 5:
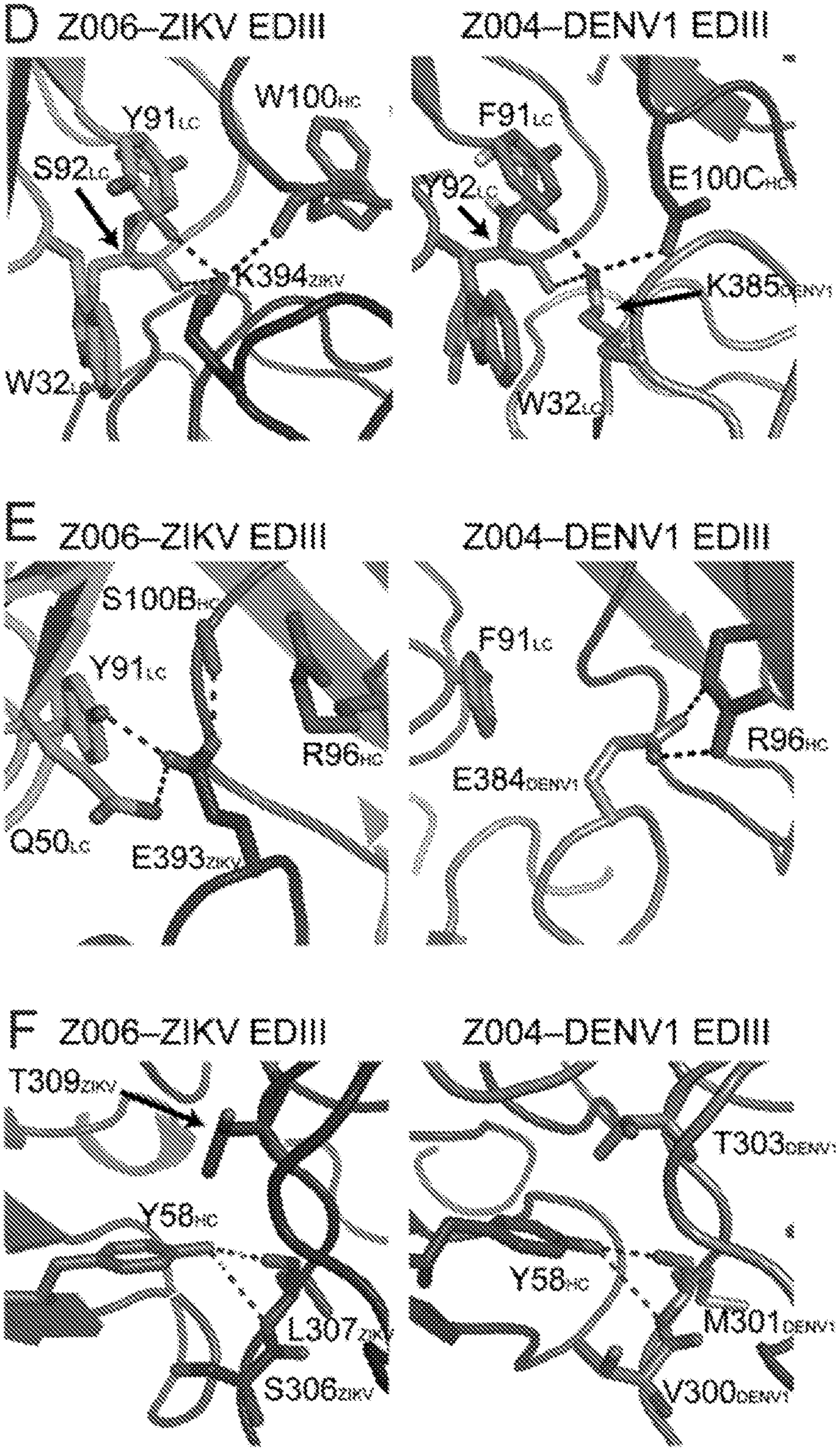

FIG. 5—Structures of Fab complexes with ZIKV and DENV1 EDIII domains

A—Superimposition of Z006 Fab-ZEDIII and Z004 Fab-DENV1 EDIII crystal structures after alignment of the EDIII domains. The $V_H$ domain positions differ by a 14° rotation about an axis passing through the center of the interface. Inset: close-up of interactions between the $E393_{ZIKV}$-$K394_{ZIKV}$/$E384_{DENV1}$-$K385_{DENV1}$ motif (shown as sticks) within the EDIII lateral ridge and the two Fabs. Fab CDRs are highlighted. B—Overlay of the Z006-ZEDIII complex structure (EDIII in black) with previously solved structures of antibodies in complex with ZIKV and DENV1 EDIII domains. The $E393_{ZIKV}$-$K394_{ZIKV}$ side chains in ZEDIII are shown as spheres. Structures were aligned on the EDIII domains; only ZEDIII is shown for clarity. C-ZEDIII epitope: EDIII residues contacted by Z006 Fab are highlighted on a surface representation of the EDIII structure. Residues making interactions with both $V_H$ and $V_L$ are dark grey. The $E393_{ZIKV}$-$K394_{ZIKV}$ motif is outlined. Contacts between the Z004 Fab and DENV1 EDIII were less extensive than Z006-ZEDIII contacts, in part because of disorder of the CC' loop in DENV1 EDIII (residues 343-349). D to F—Comparison of key antibody-antigen interactions for Z006 Fab-ZEDIII and Z004 Fab-DENV1 EDIII structures. Hydrogen bonds are shown as dotted lines. D—Fab interactions with $K394_{ZIKV}$/$K385_{DENV1}$. E—Fab interactions with $E393_{ZIKV}$/$E384_{DENV1}$. F—$Y58_{HC}$ (germline-encoded in VH3-23) interactions with antigen.

See also Tables 5 and 6.

Figure 6:
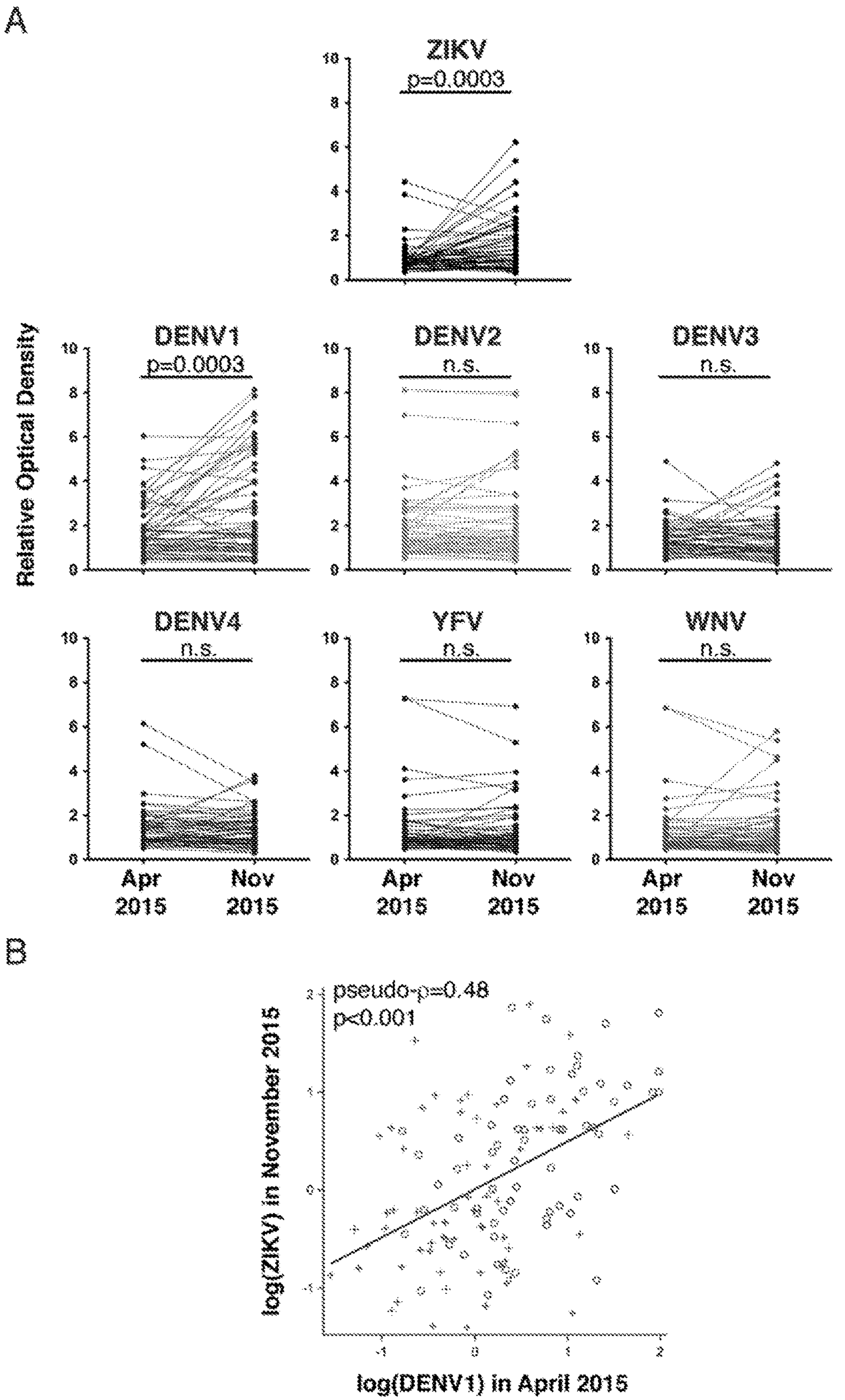

FIG. 6—EDIII reactivity over time

A—A set (n=63) of paired sera from the Brazilian cohort participants were collected in April and November 2015 and assayed for binding to flavivirus EDIII. Optical densities are normalized as described in FIG. 1A. Paired sera from the same individual are connected by a line. Each value represents the average of two independent measurements. P values were determined with the two-tailed paired t test (n.s., not significant). B—Correlation between DENV1 EDIII reactivity in April and ZEDIII reactivity in November 2015. Circles and plus signs distinguish data from two independent experiments. Pseudo-$\rho=0.48$, $p<0.001$ by univariate analysis.

Figure 7:
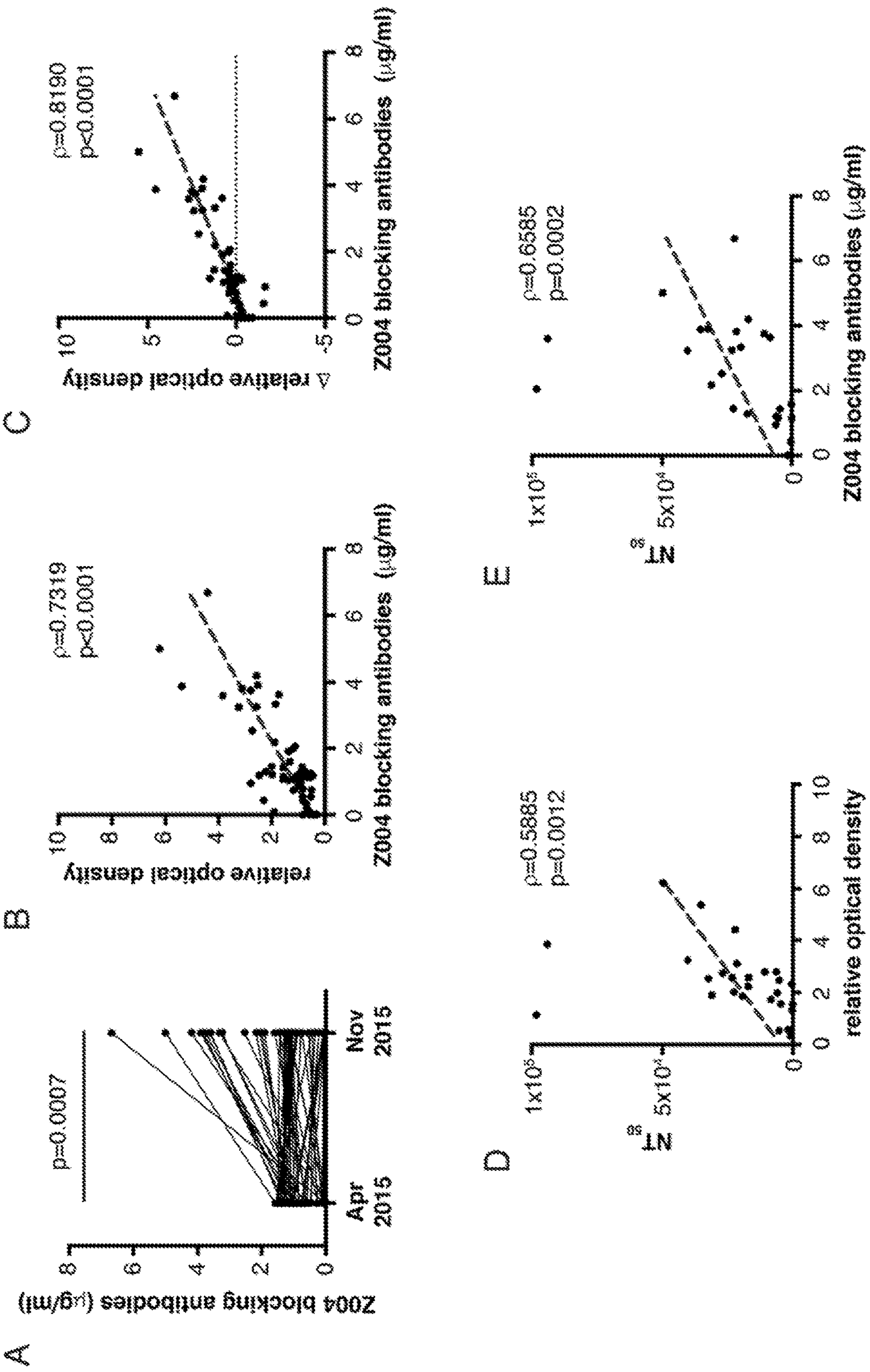

FIG. 7—EDIII antibodies contribute to the serologic response and ZIKV neutralization capacity A—Competition ELISA shows the increase within individuals of serum antibodies that block biotin-Z004 ZEDIII binding after ZIKV exposure. Each dot represents a serum sample (n=62 at each of the indicated time points). A line connects sera from the same individual obtained at different time points. The p value was determined with the two-tailed paired t test. B and C—The estimated quantity (μg/ml) of Z004 blocking antibodies in the serum obtained after ZIKV introduction (X axes) was plotted with the overall serum binding activity to ZEDIII (Y axis, B), and the change in that individual's serum ZEDIII binding from before to after ZIKV (Y axis, C). Binding activity change was determined by subtracting the pre-from the post-ZIKV ELISA relative optical density value (average of two independent measurements). Each dot represents an individual (n=62, two-tailed Spearman r test). D and E—Serum neutralization potency expressed as $NT_{50}$ versus the overall serum binding activity to ZEDIII (D), or Z004 blocking antibody concentrations in sera (E) obtained after ZIKV introduction are plotted. Each dot represents a serum sample from a single donor (n=27, two-tailed Spearman r test). Representative of two independent experiments is shown.

Figure 2:
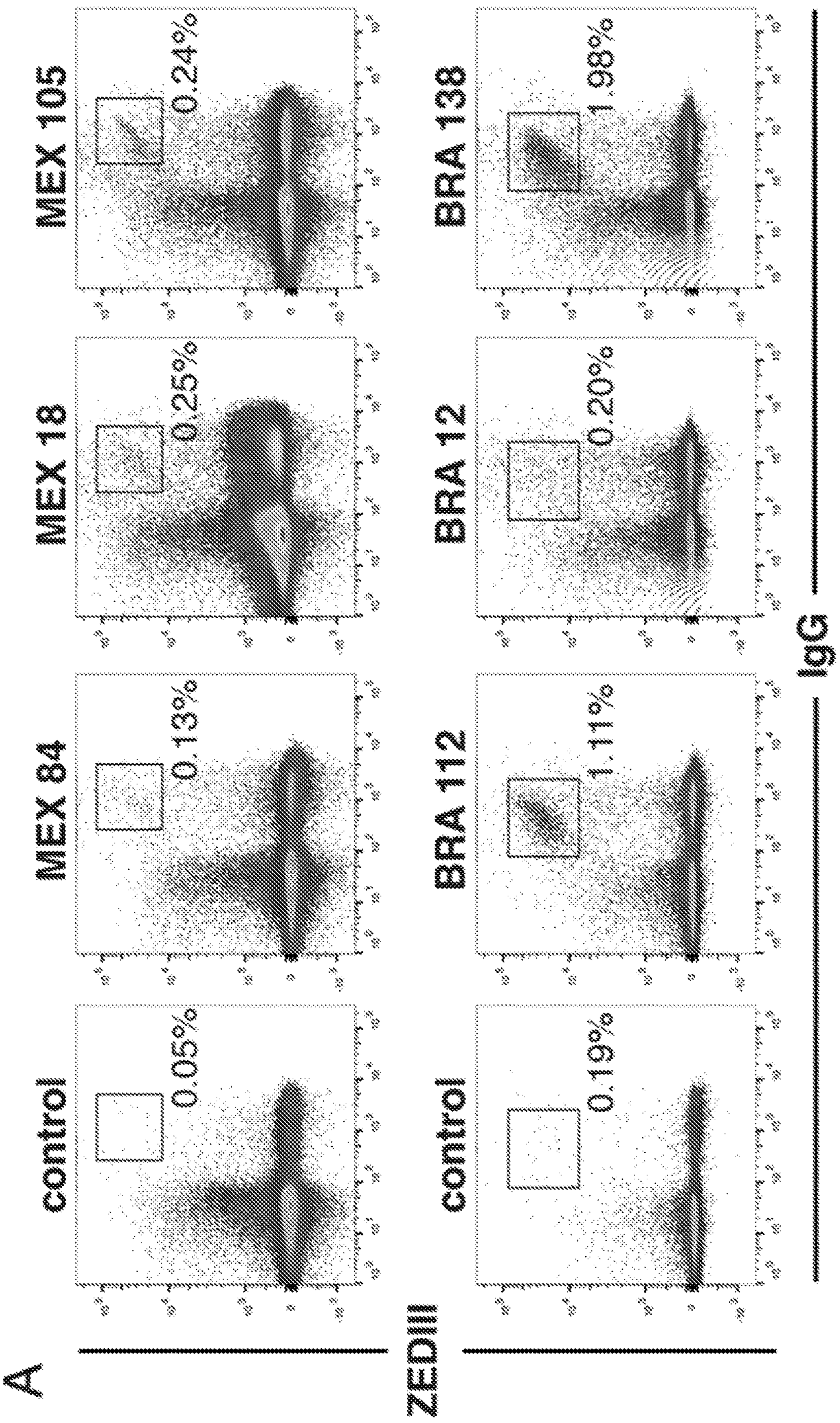
FIG. 2—Discovery of ZEDIII-specific antibodies
Figure 2:
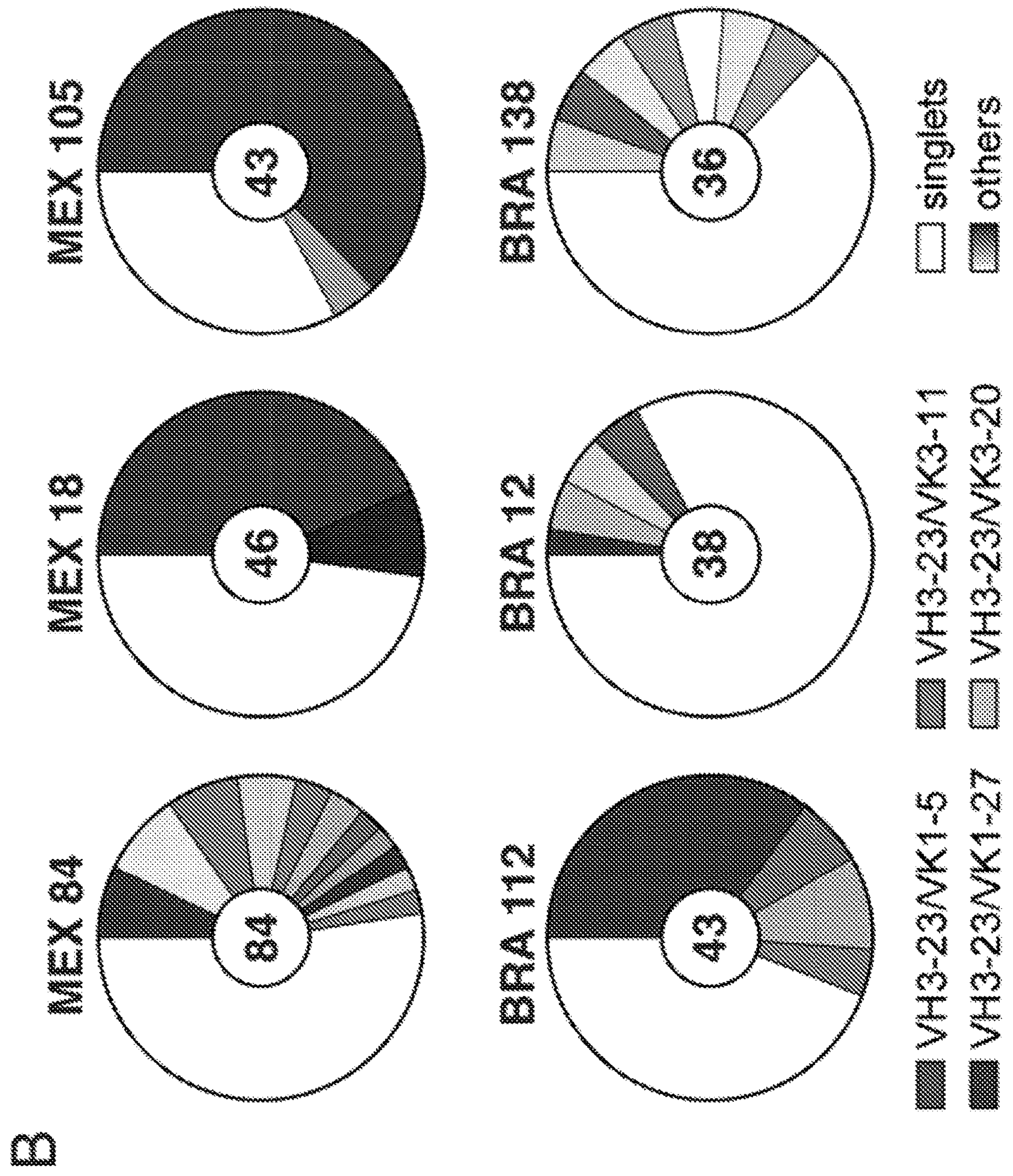

FIG. 8—Maximum likelihood tree of VH3-23/VK1-5 antibodies. Related to FIG. 2 and Table 1.

Antibody amino acid sequences (heavy and light chain combined) are clustered and labeled according to the donor ID (MEX18, MEX105, MEX84, BRA112, BRA12) followed by the clone's unique sequence ID.

FIG. 9—Features of anti-ZIKV antibodies. Related to FIG. 3 and Table 1.

A—Dose-dependent binding of recombinant human monoclonal antibodies to ZEDIII as measured by ELISA. Representative non-linear regression curves are shown. B and C—VH3-23/VK1-5 antibodies have low levels of somatic mutation. The number of V gene nucleotide (B) or amino acid (C) mutations at Heavy (H) and Light (L) chain genes are shown for each donor. Each dot represents one individual antibody V gene (n=69). The average number of nucleotide mutations overall is 27.7 within VH3-23 and 17.5 within VK1-5. The average number of amino acid mutations overall is 14.3 at VH3-23 and 10.6 at VK1-5.

FIG. 10—Neutralization and polyreactivity of anti-ZIKV antibodies. Related to FIG. 4.

A—Dose-dependent neutralization of ZIKV RVPs by recombinant human monoclonal antibodies. Luciferase activity relative to no antibody control is determined in the presence of increasing antibody concentrations. Data are represented as mean±SD. B—ZIKV neutralization by Z004 antibody assessed by PRNT assay. C—DENV1 neutralization by Z004 antibody measured by a flow cytometry-based assay. The number of infected cells was determined using the pan-flavivirus monoclonal antibody 4G2. Data are represented as mean±SD. D—Z004 protects IFNAR1$^{-/-}$ mice from ZIKV infection. Three independent experiments were performed as described in FIG. 4D-F; results were pooled and presented in FIG. 4. E—Low auto- and polyreactivity profile of Z004. ELISA measures Z004 binding over a range of concentrations against the following antigens: single-stranded DNA (ssDNA), double-stranded DNA (dsDNA), lipopolysaccharides (LPS), insulin, and keyhole limpet hemocyanin (KLH).

Figure 11:
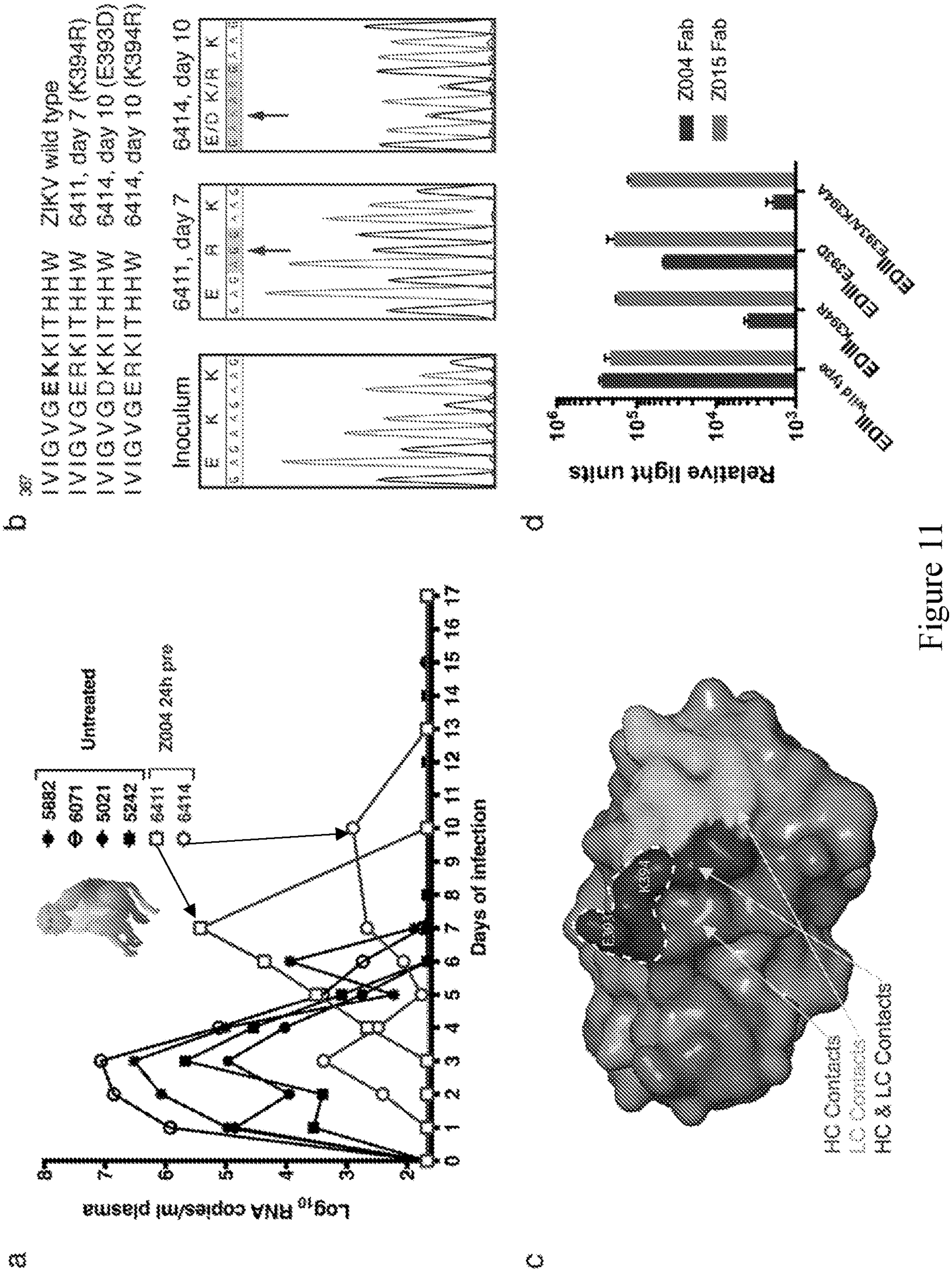

FIG. 11—Treatment with Z004 antibody alone leads to the emergence of resistant ZIKV in rhesus macaques (*Macaca mulatta*).

(a) Macaques were administered Z004 (arrows) or remained untreated (black) one day before intravenous inoculation with $10^5$ PFU of ZIKV. Graph shows plasma viral RNA levels of ZIKV over time as determined by RT-qPCR. (b) Mutations emerging in macaques treated with Z004 alone. An alignment in the region of residues E393/K394 (in bold) is shown at the top (SEQ ID NOS 1061, 1070, 1062, and 1070, respectively, in order of appearance) and chromatograms of the PCR amplicons showing the mutations (indicated by arrows) are shown at the bottom. In macaque 6414, E393D and K394R are on separate viruses, as determined by sequencing of the cloned amplicon. (c) Footprint of the Z004-related antibody Z006 onto the EDIII of ZIKV. The E393/K394 residues are highlighted. (d) Impaired binding of Z004 to the EDIII escape mutants. ELISA demonstrates impaired binding of Z004 Fab to $EDIII_{E393D}$ and $EDIII_{K394R}$. The positive control antibody Z015 recognizes an epitope that is independent of Z004. Data are represented as mean±SD of triplicates and a representative of two experiments is shown.

See also FIG. 5.

Figure 12:
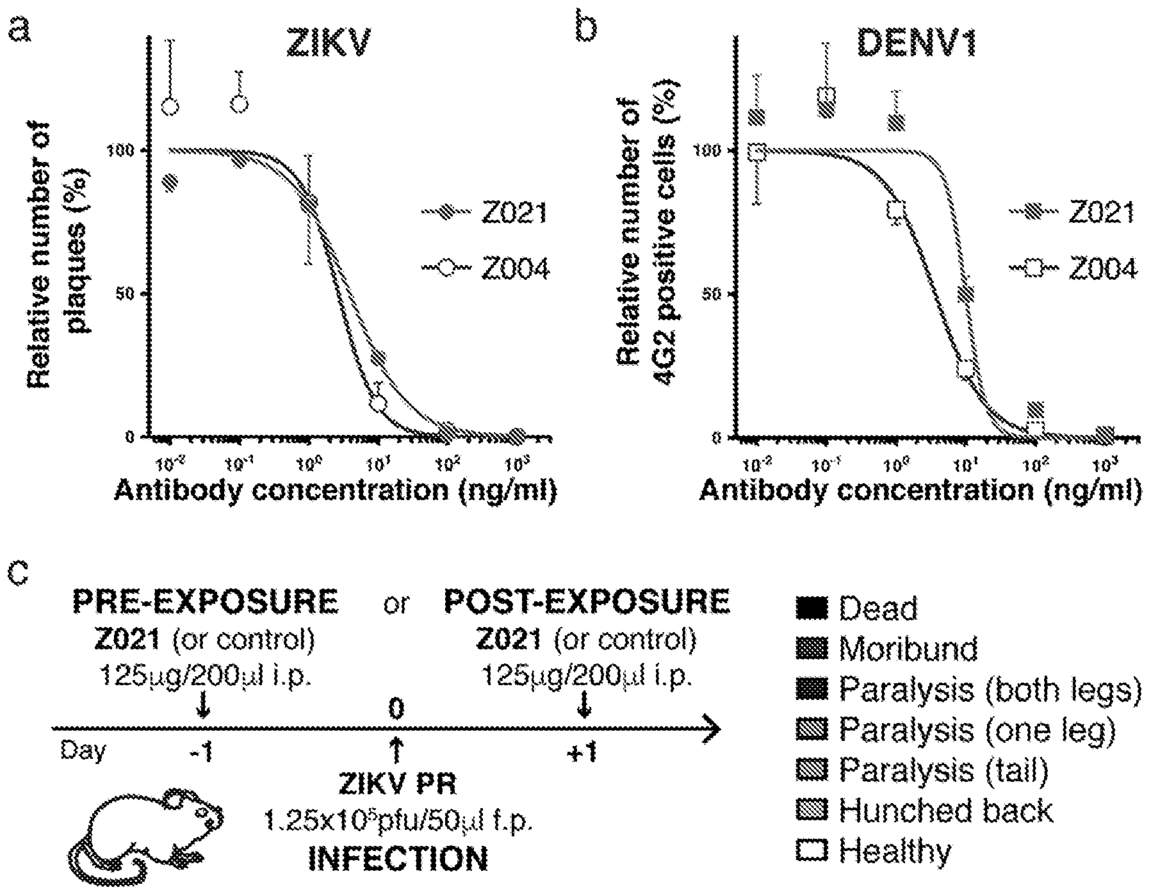
Figure 12:
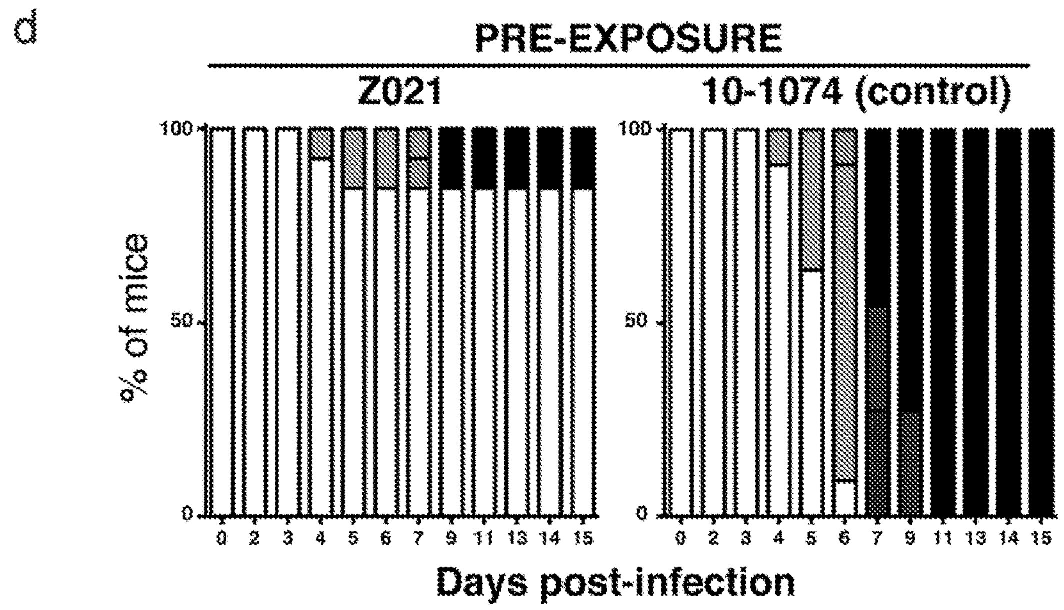
Figure 12:
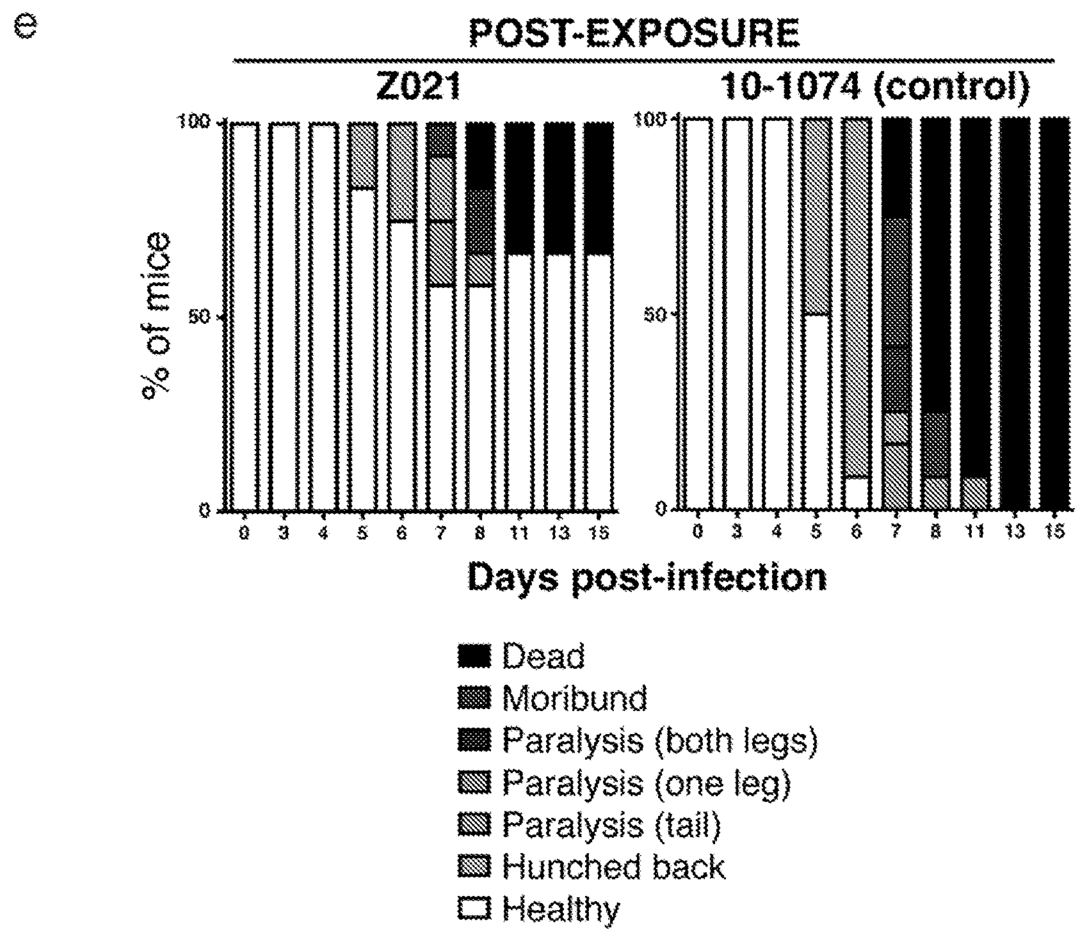

FIG. 12—Antibody Z021 neutralizes ZIKV in vitro and in mice.

(a) Z021 is effective against ZIKV. ZIKV neutralization was determined by measuring the ability of increasing concentrations of Z021 to reduce the number of plaques in a PRNT assay. Data are represented as mean±SD of two independent experiments. (b) Z021 is effective against DENV1. DENV1 neutralization was assessed by measuring the number of 4G2 positive infected cells by flow cytometry. Data are represented as mean±SD of triplicates and a representative of two experiments is shown. In (a) and (b) values are relative to control antibody 10-1074 and antibody Z004 is shown alongside for comparison[5]. (c-e) Z021 protects mice from ZIKV disease. (c) Ifnar 1$^{-/-}$ mice were treated with Z021 or control 10-1074 antibody 1 day before (d) or 1 day after (e) challenge with ZIKV in the footpad (f.p.). Mice were monitored for symptoms and survival. The graph indicates death or symptoms. Survival: $p<0.0001$ (pre-exposure) and $p=0.0002$ (post-exposure). Symptoms: $p=0.0002$ (pre-exposure) and $p=0.0006$ (post-exposure; Mantel-Cox test). Data represent two combined experiments.

Figure 13:
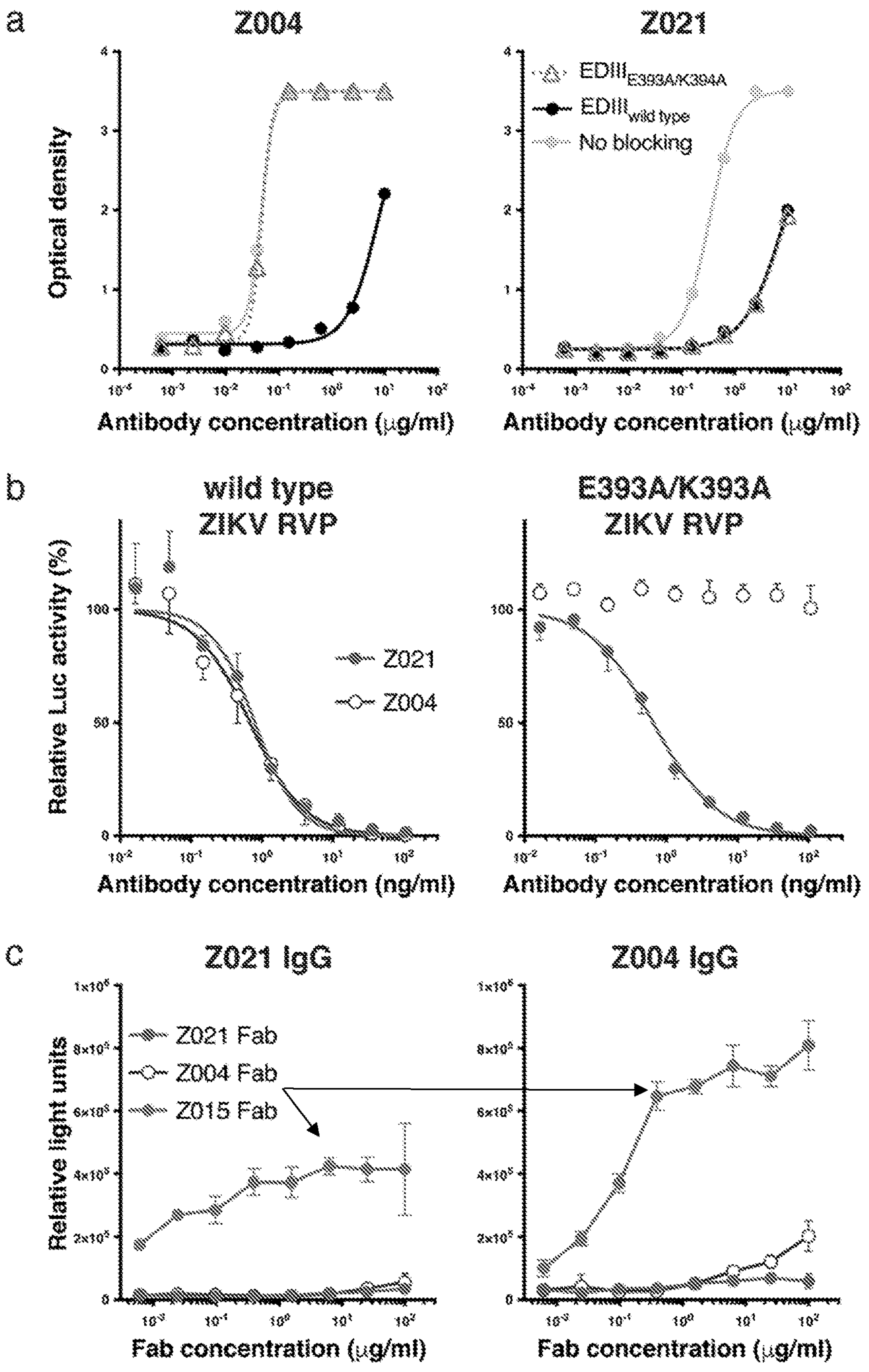

FIG. 13—Antibodies Z021 and Z004 recognize distinct epitopes.

(a) Residues E393/K394 of ZIKV EDIII are dispensable for Z021 binding. Graphs show ELISA binding to ZIKV EDIII by increasing concentrations of antibody Z004 (left) or Z021 (right) after blocking with wild type EDIII or $EDIII_{E393A/K394A}$. (b) Residues E393/K394 are dispensable for ZIKV neutralization by Z021. Graphs show neutralization of ZIKV luciferase RVPs by Z021 and Z004 using wild type RVPs (left) or RVPs mutated at the Z004 binding site (E393A/K394A; right). Data are represented as mean±SD of triplicates and a representative of two experiments is plotted. Values are relative to no antibody control. (c) The epitopes of Z004 and Z021 are overlapping. ZIKV EDIII antigen was immobilized with either Z021 IgG (left) or Z004 IgG (right) before detection by ELISA with Fragments antigen binding (Fab) of Z021 and Z004. The positive control Z015 Fab recognizes an epitope that is independent of both Z021 and Z004[5]. Data are represented as mean±SD from one experiment done in quadruplicate.

Figure 14:
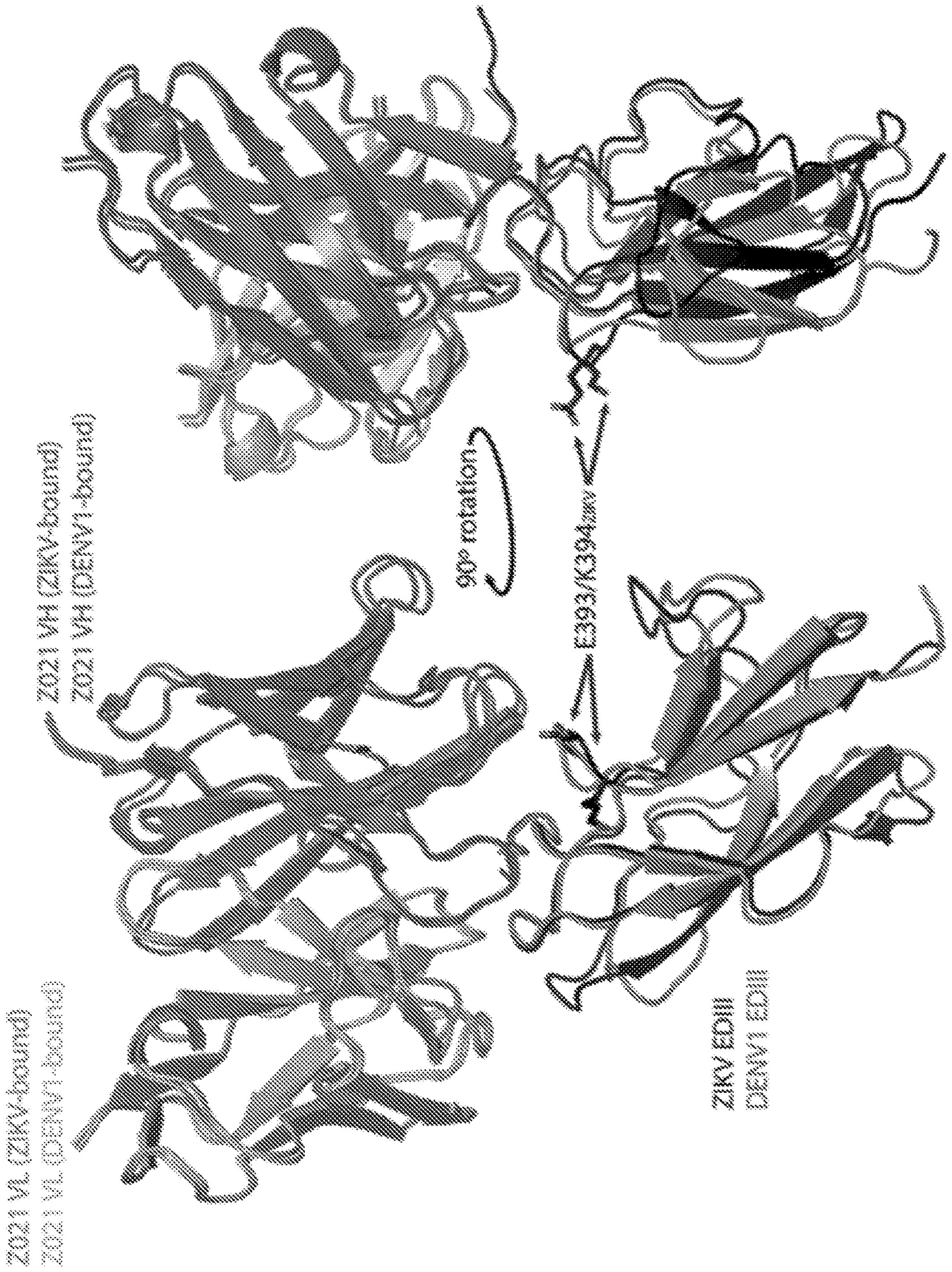
Figure 14:
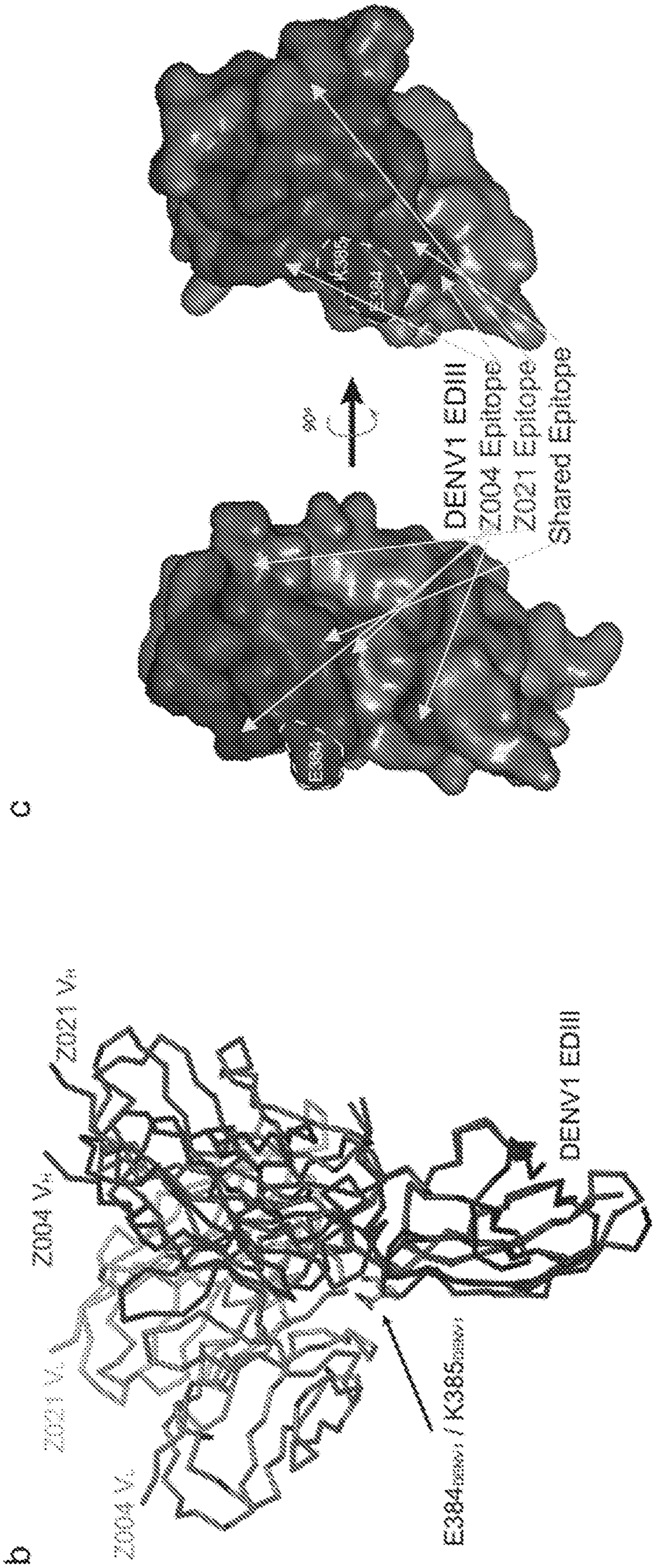

FIG. 14—Comparison of Z021 and Z004 Fab binding to the ZIKV and DENV1 EDIII domain.

(a) Superimposition of Z021 Fab-ZIKV and Z021 Fab-DENV1. The E394 and K395 residues of ZIKV are highlighted. (b) Superimposition of Z021 Fab-DENV1 EDIII with Z004 Fab-DENV1 (PDB ID: 5 VIC). The $V_HV_L$ of Z021 Fab is rotated ~48° around an axis near CDRH2 compared to the Z004 $V_HV_L$ bound to the same antigen. (c) DENV1 EDIII residues within 4 Å of Z021 Fab, Z004 Fab, or both are highlighted on surface representations of the DENV1 EDIII structure. The $E384/K385_{DENV1}$ motif is outlined. The two panels are related by a 90° rotation.

Figure 15:
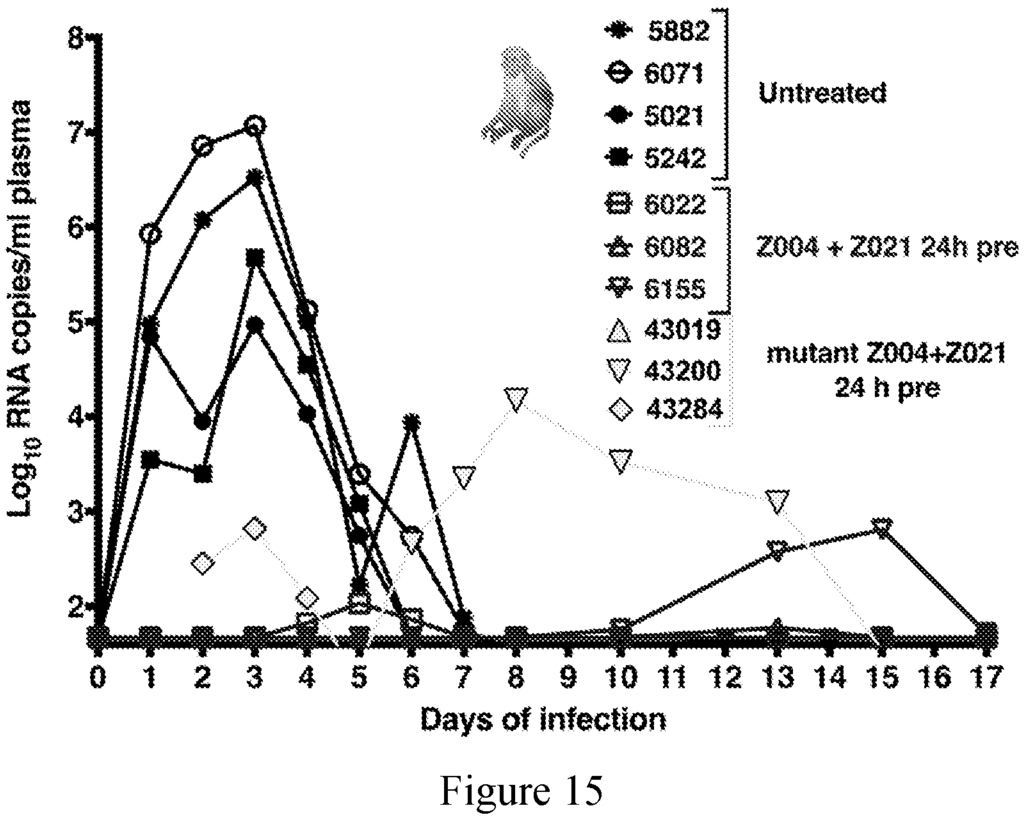

FIG. 15—The combination of Z004 and Z021 protects ZIKV challenged macaques from viral escape.

Macaques were administered the combination of Z004 and Z021 or their Fc mutant version (Z004-GRLR and Z021-GRLR) one day before intravenous inoculation with high-dose ($10^5$ PFU) of ZIKV. Graph shows plasma viral RNA levels of ZIKV over time as determined by RT-qPCR. No mutations were detected in the EDIII region of the emerging virus in the combination treated macaques.

Figure 16:
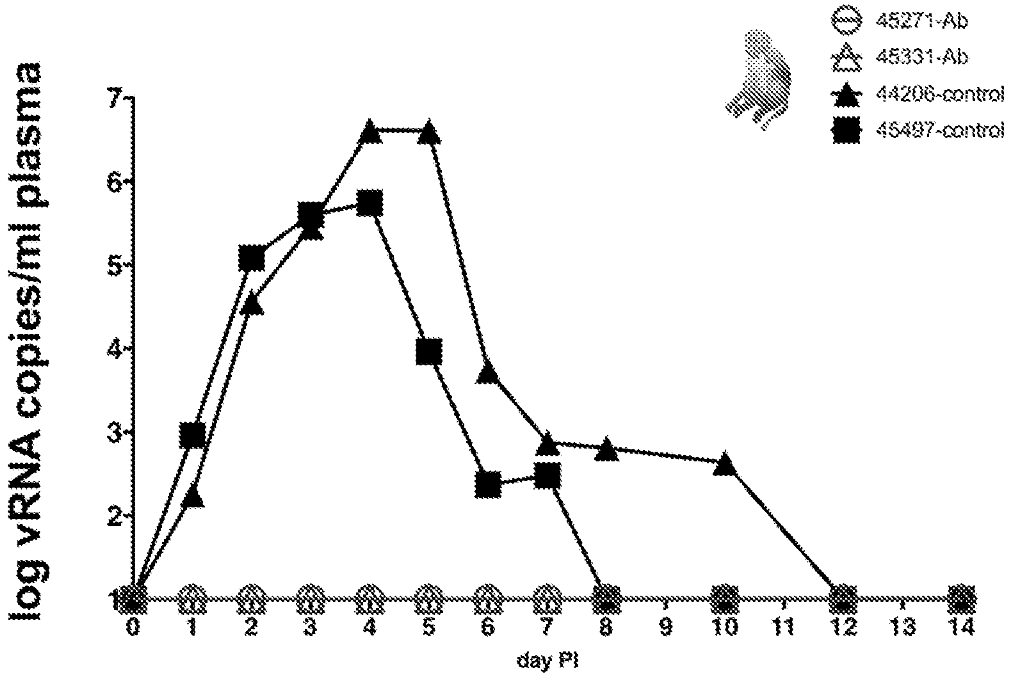

FIG. 16—The combination of Z004-GRLR and Z021-GRLR antibodies fully protects from subcutaneous challenge with $10^3$ PFU of ZIKV.

Macaques were co-administered Z004-GRLR and Z021-GRLR one day before infection. Graph shows plasma viral RNA levels of ZIKV over time, as determined by RT-qPCR.

Figures 17, 18:
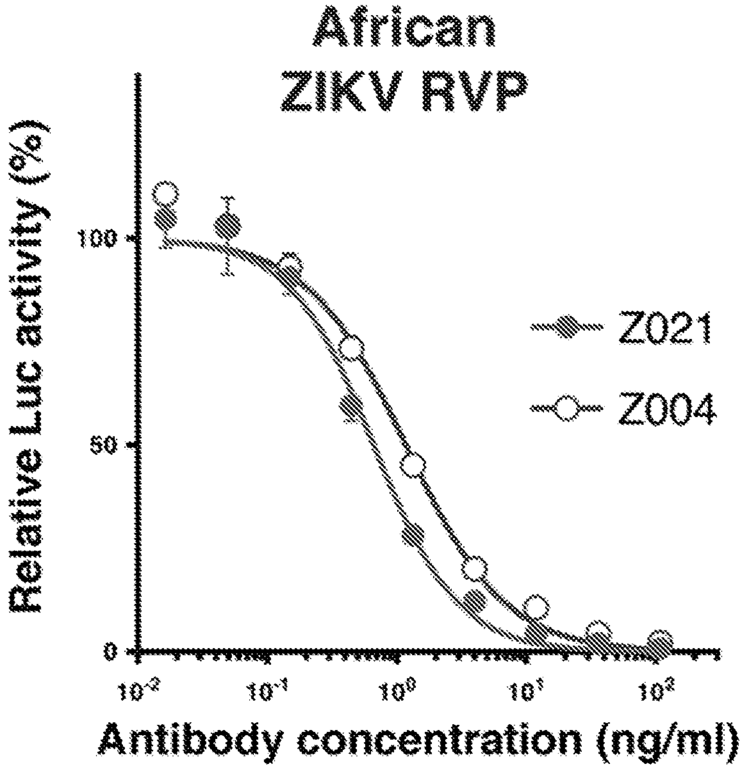

FIG. 17—ZIKV mutations in Ifnar1$^{-/-}$ mice. Related to FIG. 11.

Summary of the analysis of ZIKV EDIII sequences from infected mouse blood at the indicated time points. Empty cell is sequence not determined, grey cell is symptomatic mouse, wt is wild type EDIII sequence. The only identified mutation (K394R) was in a mouse treated with Z004.

FIGS. 18—Z021 neutralizes ZIKV RVPs corresponding to both the Asian/American and the African strain. Related to FIG. 12, Neutralization by Z004 is shown alongside for comparison. Data are represented as mean±SD of triplicates.

Figure 19:
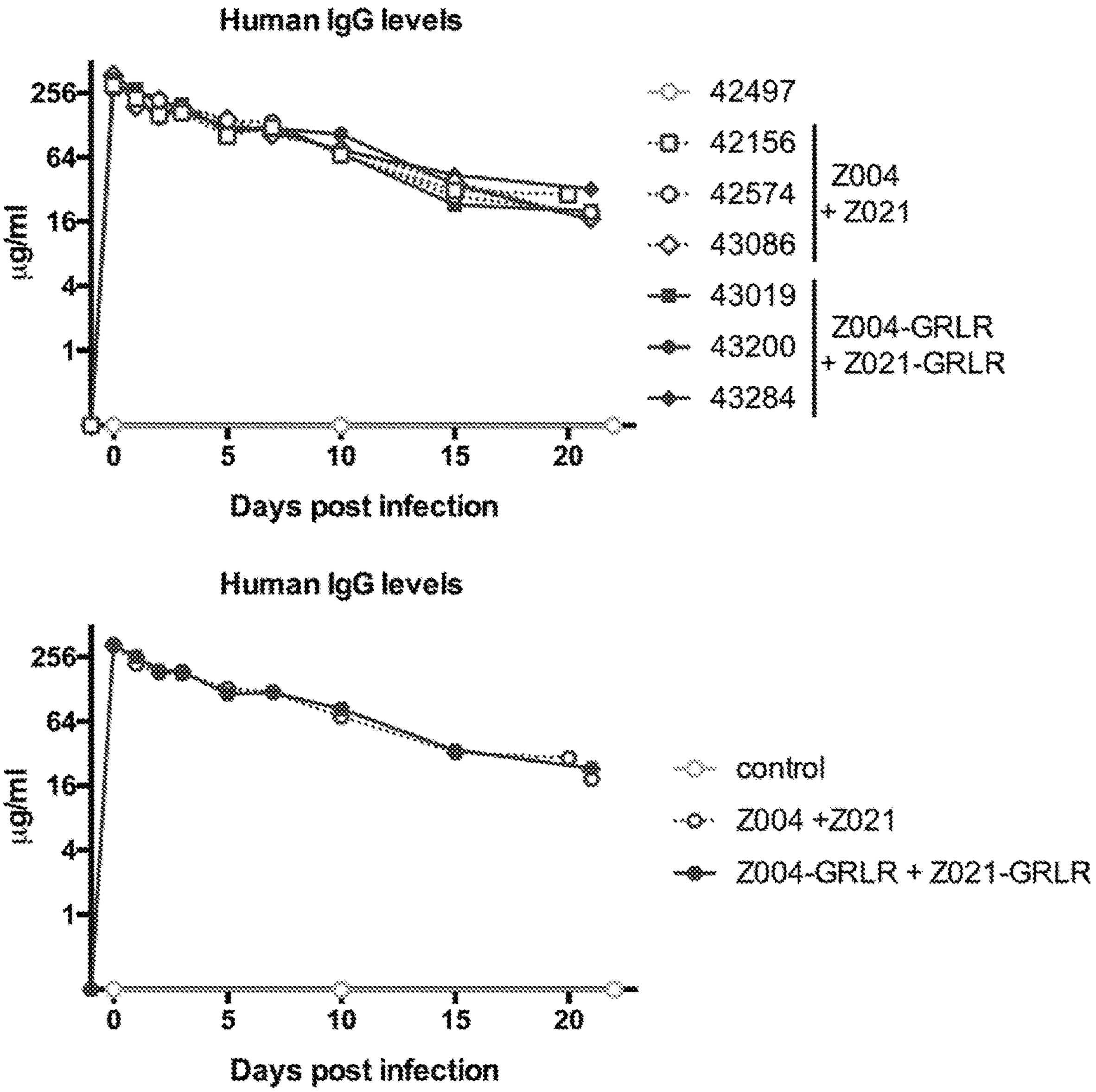

FIG. 19—Human IgG levels in macaque plasma over time. Related to FIG. 15.

The levels of human IgG antibodies were determined by ELISA. The top panel displays human IgGs in individual macaques, the bottom panel shows the mean for each group. Macaques were administered 15 mg/kg of each of the antibodies on day −1. The mean peak antibody levels on the day of infection (day 0) were 334 μg/ml in the Z004+Z021 group and 326 μg/ml in the Z004-GRLR+Z021-GRLR group. The antibody levels on day 15 were 32 μg/ml in the Z004+Z021 group and 34 μg/ml in the Z004-GRLR+Z021-GRLR group, resulting in plasma half-lives of 4.4 days and 4.6 days, respectively.

Figure 20:
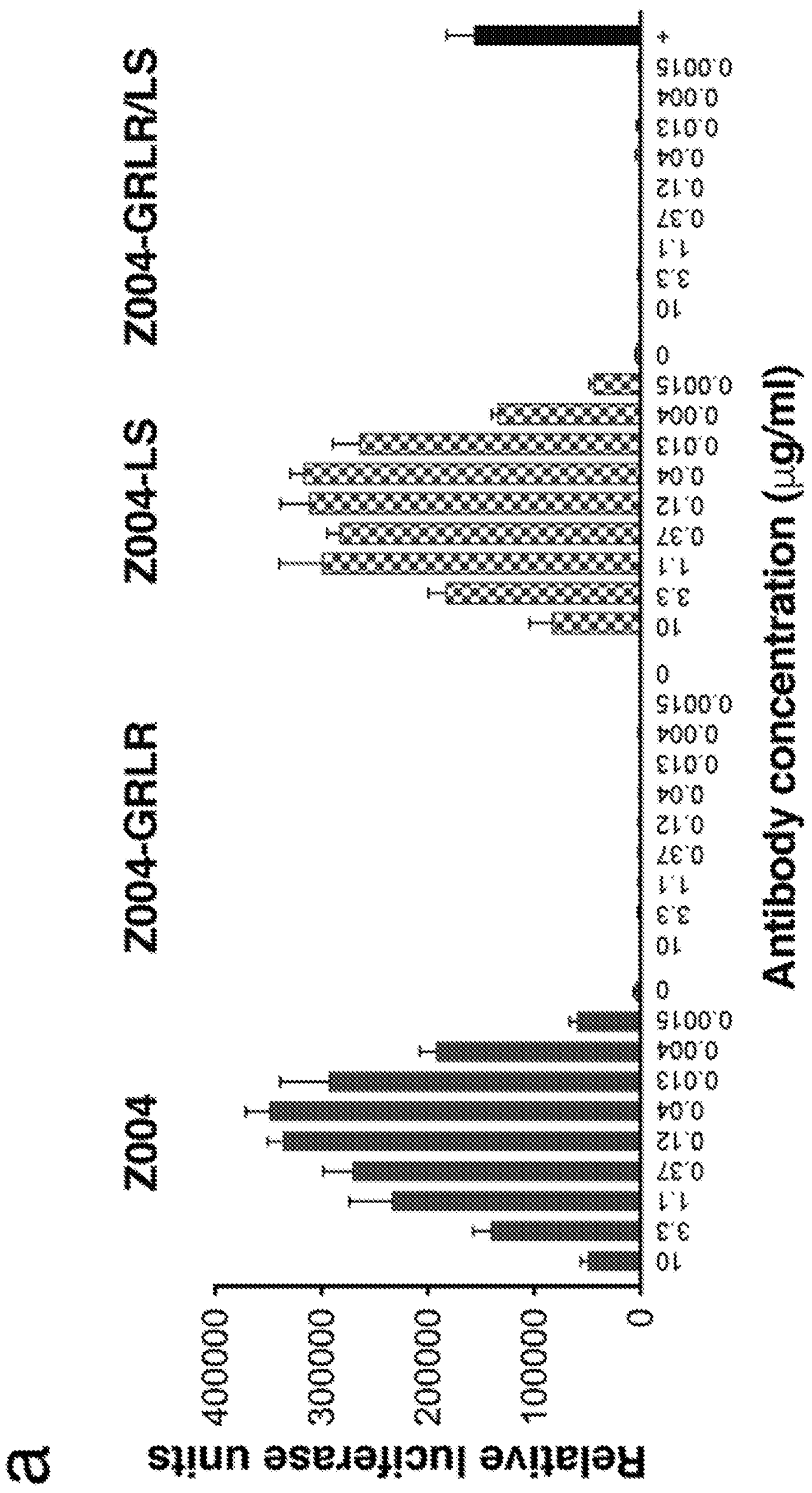
Figure 20:
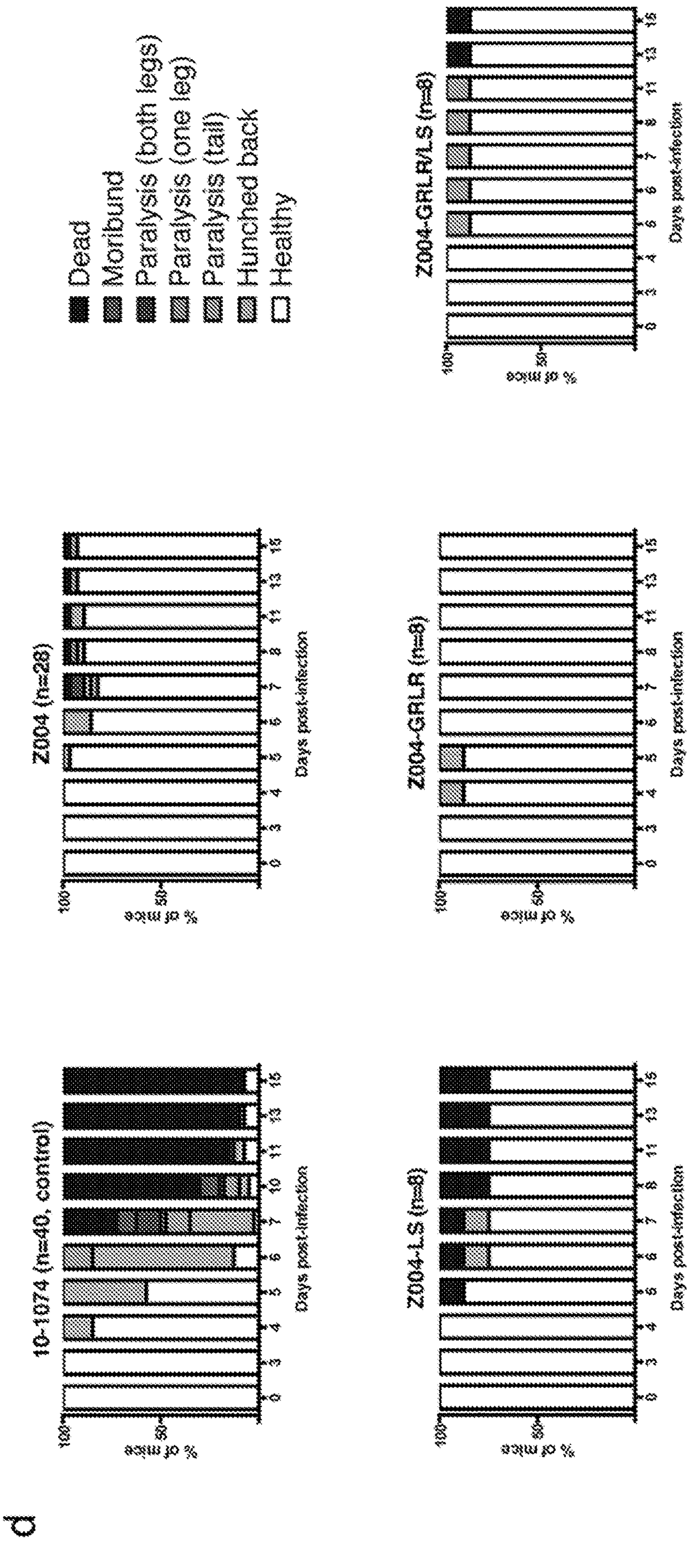

FIGS. 20—Z004 with engineered modifications at the antibody Fc portion that prevent Fc-gamma receptor binding (GRLR mutation;[25,26]) and extend the half-life (LS mutation;[27,28]) prevents ADE and remains effective against ZIKV. Related to FIG. 15.

(a) ADE of Fc-gamma receptor bearing K562 cells is abrogated with Z004 antibodies bearing GRLR and GRLR/LS substitutions. Data are represented as mean±SD of triplicates. Positive control (+) is wild type Z004 antibody (10 ng/ml). (b) Surface plasmon resonance (SPR) binding profile of Z004 bearing the LS and GRLR mutations alone or in combination. (c-d) Z004 antibodies bearing the LS and GRLR substitutions alone or in combination remain effective against ZIKV RVPs in vitro (c) or ZIKV in vivo (d).

Figure 21:
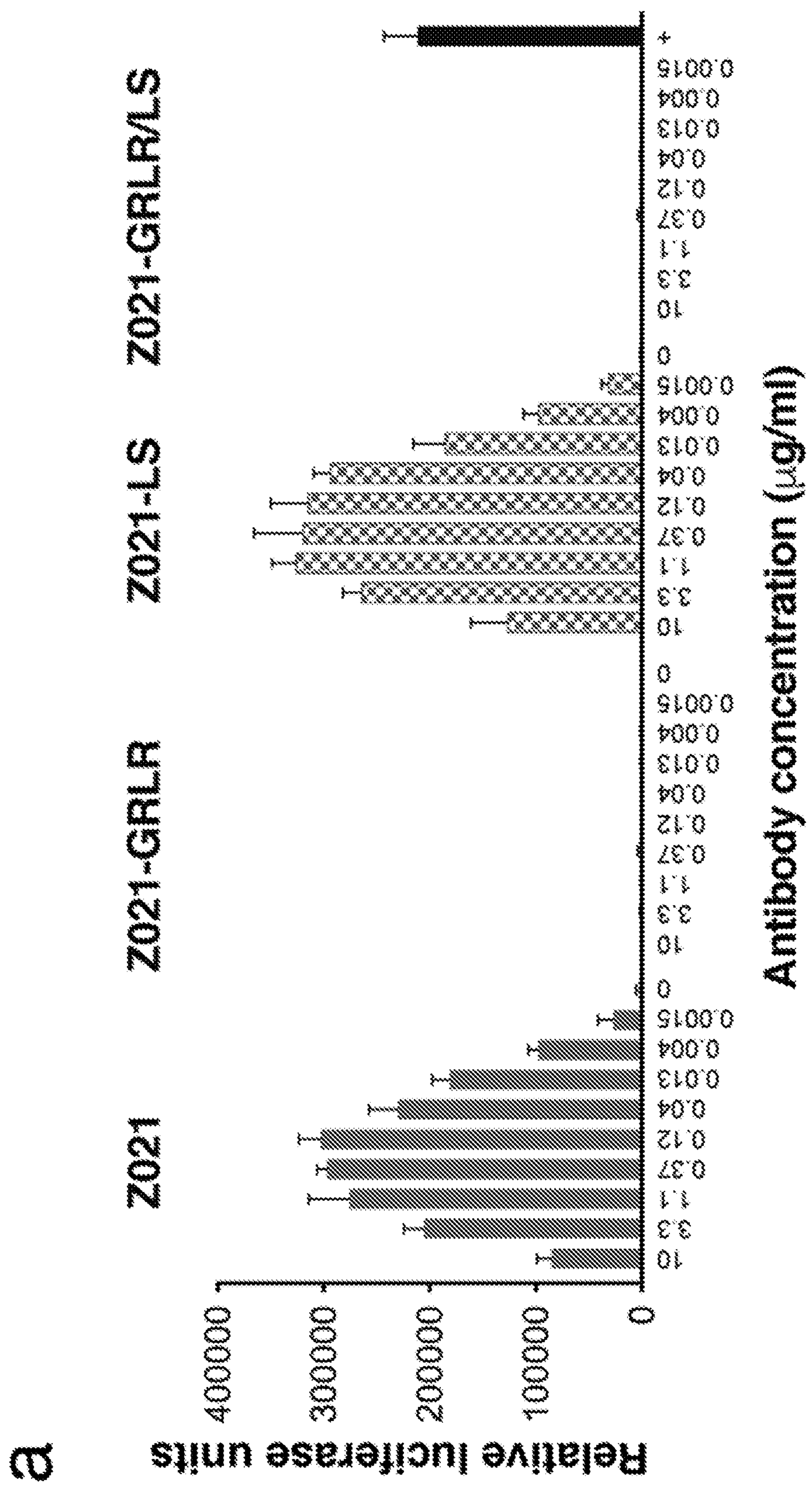
Figure 21:
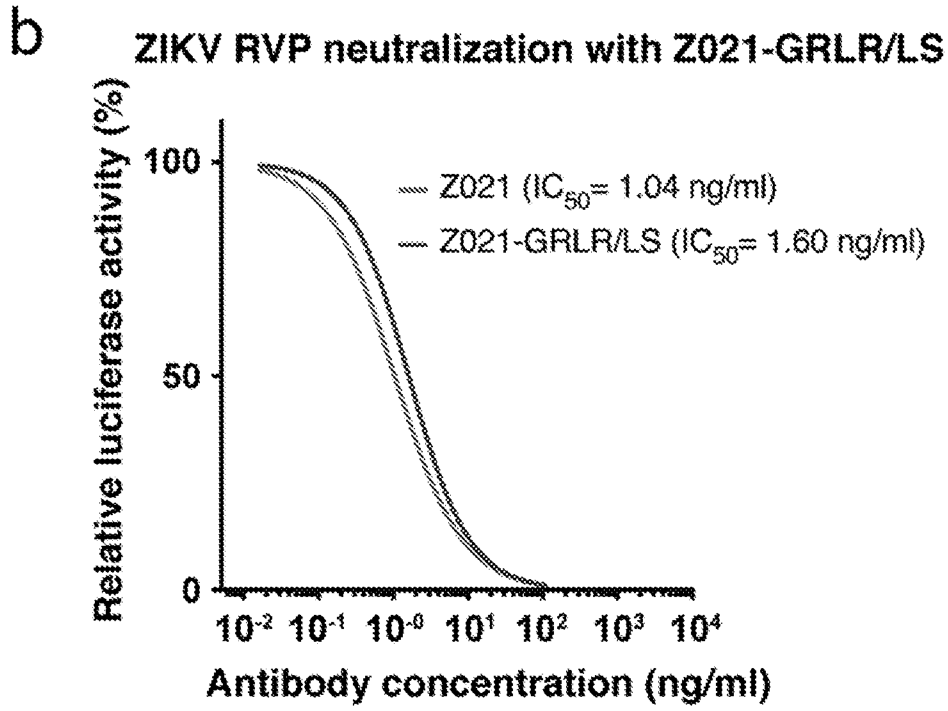
Figure 21:
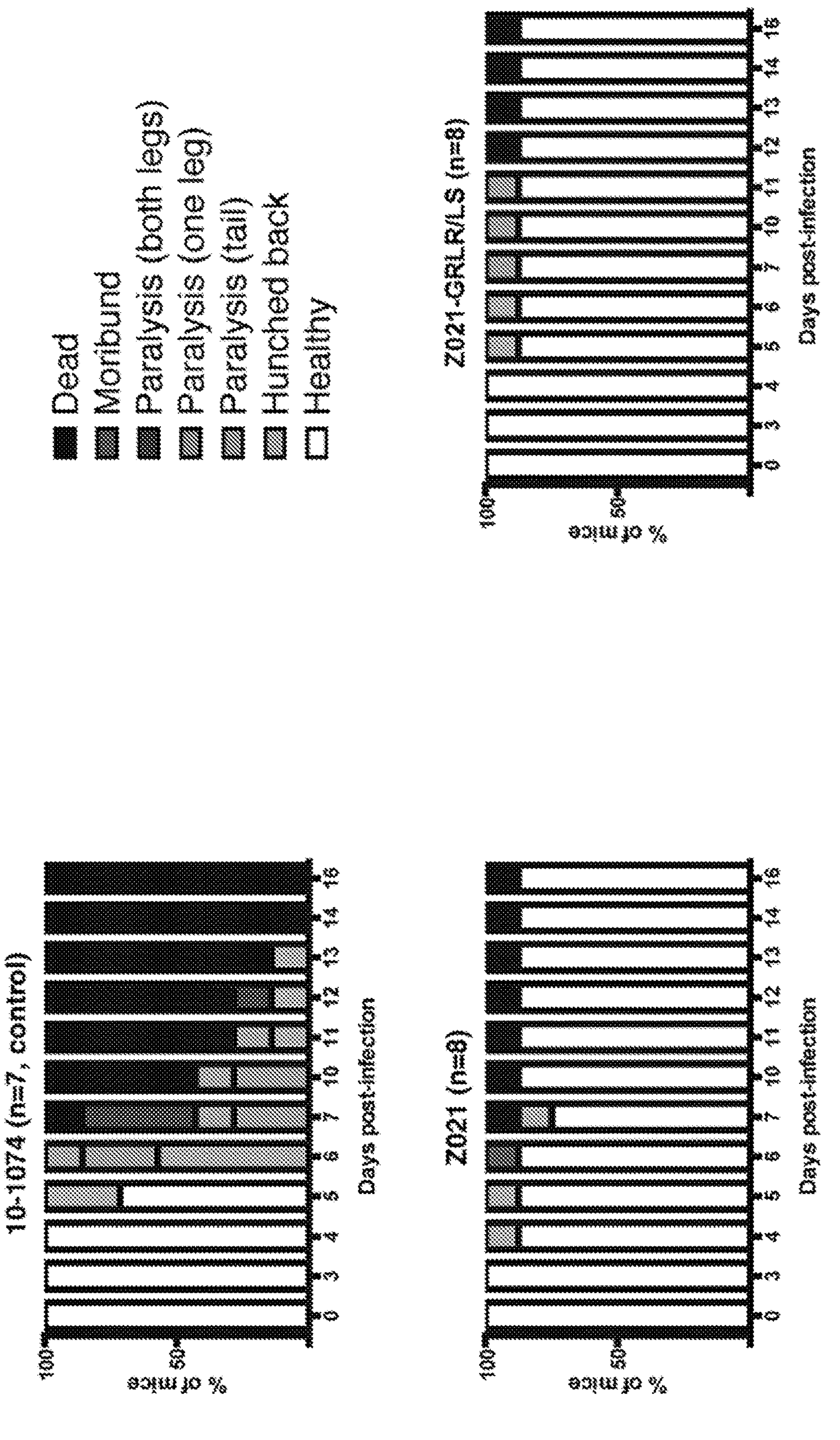

FIGS. 21—Z021 with substitutions that prevent Fc-gamma receptor binding (GRLR) and extend the half-life (LS) prevents ADE and remains effective against ZIKV. Related to FIG. 15.

(a) ADE is abrogated with Z021 antibodies bearing GRLR and GRLR/LS substitutions. Data are represented as mean±SD of triplicates. Positive control (+) is wild type Z004 antibody (10 ng/ml). (b-c) Z021 antibodies bearing the LS and GRLR substitutions remain effective against ZIKV RVPs in vitro (b) or ZIKV in vivo (c).

Figure 22:
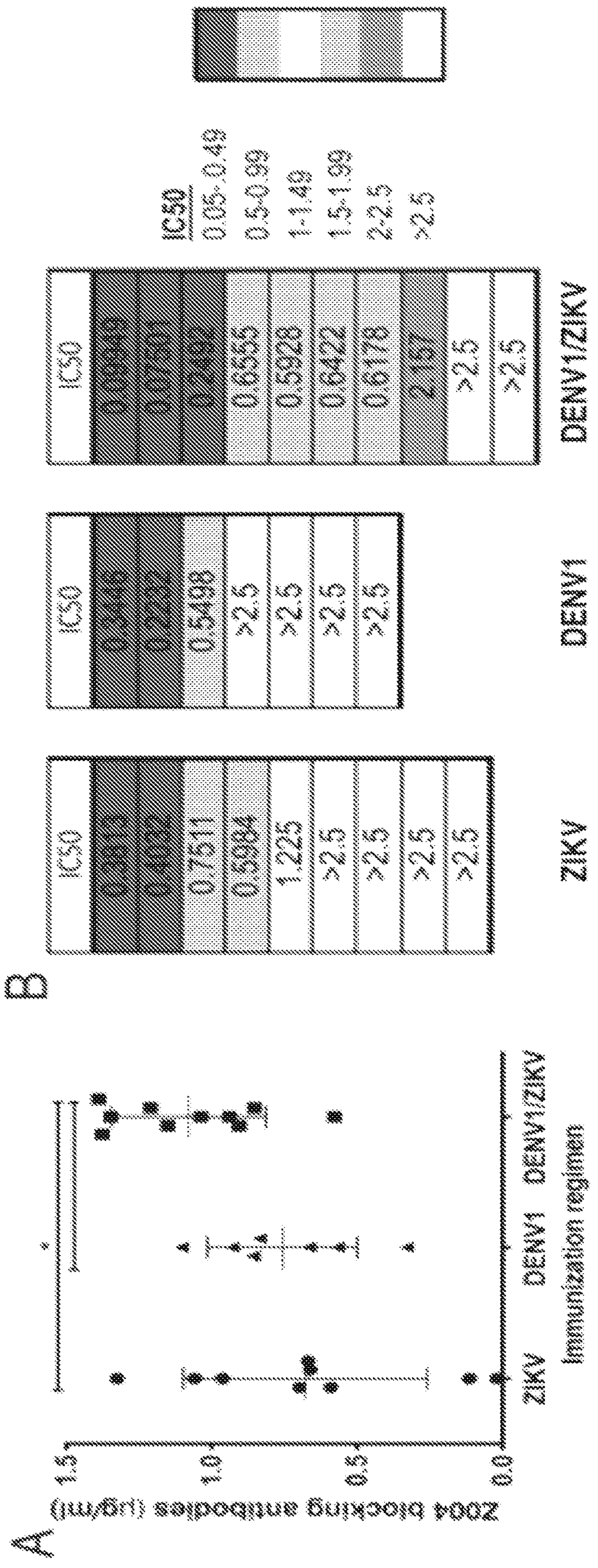

FIG. 22—Immunizing wild type mice with DENV1 EDIII before ZIKV EDIII enhances the mice neutralizing antibody response against ZIKV.

A—Sequential immunization with DENV1 followed by ZIKV EDIII proteins improves antibody titers to the ZEDIII lateral ridge. Competition ELISA with the biotinylated antibody Z004 was used to estimate the concentration of antibodies to the lateral ridge of ZIKV. * is $p<0.05$. B—Sequential immunization with DENV1 followed by ZIKV EDIII proteins induces higher neutralization in more mice. IgG was purified from mouse serum and assayed for neutralization using ZIKV RVPs. IC50 is in μg/ml.

DESCRIPTION OF INVENTION

Unless defined otherwise, all technical and scientific terms used herein have the same meaning as commonly understood by one of ordinary skill in the art to which this invention belongs.

Every numerical range given throughout this specification includes its upper and lower values, as well as every narrower numerical range that falls within it, as if such narrower numerical ranges were all expressly written herein.

This disclosure includes every nucleotide sequence described herein, and in the tables and figures, and all sequences that are complementary to them, RNA equivalents of DNA sequences, all amino acid sequences described herein, and all polynucleotide sequences encoding the amino acid sequences. Every antibody sequence and functional fragments of them are included. Polynucleotide and amino acid sequences having from 80-99% similarity, inclusive, and including ranges of numbers there between, with the sequences provided here are included in the invention. All of the amino acid sequences described herein can include amino acid substitutions, such as conservative substitutions, that do not adversely affect the function of the protein or polypeptide that comprises the amino acid sequences. It will be recognized that when reference herein is made to an "antibody" it does not necessarily mean a single antibody molecule. For example, "administering an antibody" includes administering a plurality of the same antibodies. Likewise, a composition comprising an "antibody" can comprise a plurality of the same antibodies.

Those skilled in the art will recognize that representative sequences from specific ZIKV and DENV1 viruses are presented for use in vaccine formulations and diagnostic approaches, but other sequences from different strains of these viruses are encompassed by this disclosure. The disclosure includes polynucleotides encoding antigens and antibodies from which introns present in the genomic DNA have been removed, i.e., cDNA sequences and DNA sequences complementary thereto.

For amino acid and polynucleotide sequences of this disclosure contiguous segments of the sequences are included, and can range from 2 amino acids, up to full-length viral protein sequences. Polynucleotide sequences encoding such segments are also included.

The disclosure includes DNA and RNA sequences encoding the antibodies and virus peptides described herein for use in prophylactic and therapeutic approaches as protein or DNA and/or RNA vaccines, which may be formulated and/or delivered according to known approaches, given the benefit of this disclosure.

From DNA sequences and amino acid sequences presented in the tables of this disclosure antibody complementarity determining region (CDR) sequences can be identified by using publicly available databases, such as IGBLAST (www.ncbi.nlm.nih.gov/igblast) using the germline database.

The disclosure includes antibodies described herein, which are present in an in vitro complex with a ZIKV or a DENV1 protein.

In certain approaches compositions and methods of this disclosure may be adapted for use in non-human animals that may be determined to be an actual or potential reservoir or vector for the Zika and/or dengue viruses. Thus, veterinary compositions and methods of administering them are included.

From the examples and descriptions of this disclosure it will be apparent to those skilled in the art that the instant disclosure can be distinguished from studies that have examined anti-ZIKV antibodies developing in a small number of available individuals (Sapparapu et al., 2016; Stettler et al., 2016; Wang et al., 2016). In contrast, we screened sera from more than 400 donors from ZIKV epidemic areas of Mexico and Brazil to select high responders. Serologic reactivity to ZIKV varied greatly among individuals, with neutralization potencies spanning over more than 2 logs. To better understand this activity we isolated 290 memory B cell antibodies from 6 individuals with high serum neutralizing activity. The sequencing experiments revealed the existence of expanded clones of memory B cells expressing E protein lateral ridge-specific ZIKV and DENV1 neutralizing VH3-23/VK1-5 antibodies in 4 of the 6 individuals.

Three separate groups have cloned human anti-ZIKV E protein reactive antibodies before the present disclosure (Sapparapu et al., 2016; Stettler et al., 2016; Wang et al., 2016). In all they studied 8 individuals and documented 92 antibodies to the E protein. The great majority of these antibodies (79) were obtained by screening supernatants of Epstein-Barr virus transformed B lymphocytes for binding to ZIKV, and only a minority (15) were directed to the ZEDIII. Among all of these antibodies there was only a single expanded clone containing 3 related VH1-46/VK1-39 antibodies specific for a yet to be determined E epitope.

These 3 antibodies were relatively poor neutralizers (3-257 μg/ml) (Wang et al., 2016). There was also a single VH3-23/VK1-5 antibody that targeted the ZEDIII and neutralized ZIKV (ZIKV-116), but this antibody is believed to be different than those of this disclosure because it failed to neutralize the African ZIKV strain (Sapparapu et al., 2016). Thus, there was no prior indication of a potent recurrent neutralizing response to ZIKV.

We found a total of 69 individual VH3-23/VK1-5 memory B cells antibodies in 5 out of 6 individuals. In addition to recurring V gene segments, VH3-23/VK1-5 antibodies bear the same IGL J gene, and a limited set of IGH D and J genes. These antibodies are closely related and they are potent neutralizers with $IC_{50}$ values ranging from 0.7-4.6 ng/ml. This variation in activity is likely due to somatic mutations, since predicted germline versions of the VH3-23/VK1-5 antibodies bind to ZEDIII and neutralize the virus only weakly. Thus, and without intending to be constrained by any particular theory, it is considered that somatic mutations are required for optimal VH3-23/VK1-5 antibody neutralizing activity.

Recurring antibodies that share the same IGV genes and the same molecular interactions with antigen have not been reported for ZIKV or other flaviviruses before the present disclosure, but they have been described in other viral infections including HIV-1 and influenza. Broadly neutralizing antibodies targeting the CD4 binding site of HIV-1 frequently utilize VH1-2 or VH1-46 genes (Scheid et al., 2011; West et al., 2012), and broadly neutralizing antibodies to Influenza utilize VH1-69 (Laursen and Wilson, 2013; Pappas et al., 2014; Sui et al., 2009; Throsby et al., 2008; Wrammert et al., 2011). However, in both HIV-1 and influenza, the $V_H$ genes can be paired with a collection of different $V_L$ genes, a finding that was explained by structural analysis showing that many of the essential contacts made by influenza and HIV-1 antibodies involve variable portions of the IGHV (Ekiert et al., 2009; Pappas et al., 2014; Scheid et al., 2011; Wrammert et al., 2011; Zhou et al., 2010).

Although the Z004 and the related Z006 antibodies have CDRH3s and CDRL3s of different lengths they share a common mode of EDIII binding. Several shared sequence features may be important for this binding mode. The most suggestive of these is $R96_{HC}$. This CDRH3 residue appears to derive from N region addition, thus the different VH3-23/VK1-5 clones do not share this residue due to shared germline genes. Examination of a large collection (n=44, 270) of VH3-23-derived antibody sequences indicates that only 13% have R at position 100 (Rubelt et al., 2012). However, 68 of 69 of the sequenced VH3-23/VK1-5 clones contain R96. The clones also tend to conserve the germline residues forming the Z004/Z006/EDIII common interactions: $Y58_{HC}$, $W32_{LC}$, $Y91_{LC}$, and $S93_{LC}$.

Without intending to be bound by any particular interpretation, the requirement for conserved IGHV and IGLV genes in VH3-23/VK1-5 antibodies appears to be explained in part by interactions using germline residues. For the light chain, CDRL1 germline residue $W32_{LC}$ interacts with $K394_{ZIKV}$. Few IGLV genes contain W32; the most common of these is VK1-5 (followed by VK1-12, but this gene is several-fold less common than VK1-5). For the heavy chain, residue $Y58_{HC}$ (present in the VH3-23 germline) makes a contact with EDIII residue $307_{ZIKV}$. $Y58_{HC}$ is present in ~50% of VH germlines, potentially explaining a portion of the restriction. Finally, VH3-23 is among the most frequently used VH genes as is VK1-5 (Arnaout et al., 2011; DeKosky et al., 2015). Therefore it is likely that naïve B cell precursors carrying DENV1 and ZIKV reactive VH3-23/VK1-5 antibodies would also be common in the pre-immune repertoire making this epitope a particularly attractive vaccine candidate.

VH3-23/VK1-5 antibodies recognize and neutralize both DENV1 and ZIKV, suggesting that clones of VH3-23/VK1-5 producing B cells originally elicited in response to DENV1 were further expanded in response to ZIKV. This prime-boost, or original antigenic sin hypothesis, is supported by two observations. First, pre-existing antibodies to DENV1 EDIII are associated with a higher antibody response to ZEDIII. Second, at the population level, the introduction of ZIKV correlates with an increase in DENV1 EDIII-reactive antibodies at a time when DENV1 was not circulating. Although DENV1 and ZIKV only share 50% amino acid identity in EDIII, they are structurally very similar, particularly in the lateral ridge region that is recognized by VH3-23/VK1-5 (FIG. 5). Thus, DENV1 EDIII reactive memory B cells have a significant probability of being cross-reactive to ZEDIII. A primary response to DENV1 would increase the frequency of these ZIKV cross-reactive memory B cells and thereby increase their likelihood of undergoing clonal expansion in response to ZIKV. Consistent with this, memory B cells with VH3-23/VK1-5 antibodies represent close to half of all ZEDIII-specific B cell clones in 3 of the 6 individuals examined.

Infection by DENV1 confers transient protection to infection by DENV2 (Sabin, 1950, 1952). Whether prior DENV1 infection also protects from ZIKV by cross-priming or in other cases enhances infection is unclear (Castanha et al., 2016; Dejnirattisai et al., 2016; Priyamvada et al., 2016; Swanstrom et al., 2016; Wahala and Silva, 2011). However, the existence of human antibodies to DENV that cross-neutralize or enhance ZIKV in vitro indicates that protection by cross-priming is possible (Barba-Spaeth et al., 2016; Dejnirattisai et al., 2016; Harrison, 2016; Pierson and Graham, 2016; Priyamvada et al., 2016; Stettler et al., 2016; Swanstrom et al., 2016).

ZIKV infection is asymptomatic in most people. Only 20% of ZIKV infected individuals develop symptoms, and in those cases the severity of the disease varies broadly (Miner and Diamond, 2017). Similarly, the spectrum and incidence of developmental sequelae in infants born to women infected with ZIKV during pregnancy differs within and across geographic areas with risk estimates that range from 6-42% (Brasil et al., 2016; Honein et al., 2017). Examples of this disclosure indicate a cellular and molecular explanation for how a history of DENV1 exposure could alter host responses and susceptibility to ZIKV.

In embodiments, the disclosure provides an isolated or recombinant antibody that binds with specificity to a neutralizing epitope in the lateral ridge of Zika virus (ZIKV) envelope domain III (ZEDIII) protein, wherein the epitope comprises E393-K394 of the ZEDIII protein, and wherein the antibody optionally comprises a modification of the amino acid sequence, including but not limited to a modification of its constant region. Such antibodies can also bind with specificity to a neutralizing epitope of dengue 1 virus (DENV1) EDIII protein. Specific and non-limiting examples of antibodies are provided herein, along with amino acid sequences of pertinent parts of the antibodies, including heavy (H) and light (L) chain sequences.

All combinations of H and L chains are included. In embodiments, a single antibody of this disclosure may comprise an H+L chain from one antibody, and an H+L chain from another antibody that is described below. In embodiments, the modifications are not coded for in any B cells obtained from an individual, and/or the antibodies are not produced by immune cells in an individual from which a biological sample from the individual is used at least in part to identify and/or generate and/or characterize the antibodies of this disclosure. In embodiments, antibodies provided by this disclosure can be made recombinantly, and can be expressed with a constant region of choice, which may be different from a constant region that was coded for in any sample from which the amino acid sequences of the antibodies were deduced.

In certain approaches the disclosure provides one or more isolated or recombinant antibodies comprising a complementarity determining region 3 (CDR3) amino acid sequence selected from heavy chain and light chain CDR3 sequences in Table 1 and Table 2, and combinations of said heavy and light chain CDR3 amino acid sequences. In non-limiting embodiments the disclosure includes amino acid sequences encoded by VH3-23/VK1-5 human immunoglobulin genes, but all of the H and L gene segments described herein and the proteins they encode are included in the invention.

In certain embodiments, the antibodies contain one or more modifications, such as non-naturally occurring mutations, non-limiting examples of which are further described herein. In non-limiting examples, antibodies described herein can be modified according to various approaches that will be apparent to those skilled in the art, given the benefit of this disclosure. In certain approaches the Fc region of the antibodies can be changed, and may be of any isotype, including but not limited to any IgG type, or an IgA type, etc. Antibodies of this disclosure can be modified to improve certain biological properties of the antibody, e.g., to improve stability, to modify effector functions, to improve or prevent interaction with cell-mediated immunity and transfer across tissues (placenta, blood-brain barrier, blood-testes barrier), and for improved recycling, half-life and other effects, such as manufacturability and delivery.

In embodiments, an antibody of this disclosure can be modified by using techniques known in the art, such as those described in Buchanan, et al., Engineering a therapeutic IgG molecule to address cysteinylation, aggregation and enhance thermal stability and expression mAbs 5:2, 255-262; March/April 2013, and in Zalevsky J. et al., (2010) Nature Biotechnology, Vol. 28, No. 2, p 157-159, and Ko, S-Y, et al., (2014) Nature, Vol. 514, p 642-647, and Horton, H. et al., Cancer Res 2008; 68: (19), Oct. 1, 2008, from which the descriptions are incorporated herein by reference. In certain embodiments an antibody modification increases in vivo half-life of the antibody (e.g. LS mutations), or alters the ability of the antibody to bind to Fc receptors (e.g. GRLR mutations), or alters the ability to cross the placenta or to cross the blood-brain barrier or to cross the blood-testes barrier. In embodiments bi-specific antibodies are provided by modifying and combining segments of antibodies as described herein, such as by combining heavy and light chain pairs from distinct antibodies into a single antibody. Suitable methods of making bispecific antibodies are known in the art, such as in Kontermann, E. et al., Bispecific antibodies, Drug Discovery Today, Volume 20, Issue 7, July 2015, Pages 838-847, the description of which is incorporated herein by reference.

In embodiments, any antibody described herein comprises a modified heavy chain, a modified light chain, a modified constant region, or a combination thereof, thus rendering them distinct from antibodies produced by humans. In embodiments, the modification is made in a hypervariable region, and/or in a framework region (FR). In certain embodiments an antibody modification increases in vivo half-life of the antibody and/or alters the ability of the antibody to bind to Fc receptors. In embodiments, the mutations comprise LS or GRLR mutations. In certain embodiments an antibody modification increases in vivo half-life of the antibody by way of LS mutations, or alters the ability of the antibody to bind to Fc receptors by way of GRLR mutations. In embodiments, the mutation(s) can thus comprise a change of G to R, L to R, M to L, or N to S, or any combination thereof.

In embodiments, mutations to an antibody described herein, including but not limited to the antibodies described below as Z004 and Z021, comprise modifications relative to the antibodies originally produced in humans. Such modifications include but are not necessarily limited to the heavy chain of Z004, which can comprise G241R and/or L333R mutations to prevent binding to Fc gamma receptors, and/or M433L/N439S mutations to increase the antibody half-life.

In an embodiment, a Z004 IgG1 heavy chain comprises or consists of a contiguous segment or the entire sequence:

EVQLLESGGGLVQPGGSLRLTCATSGFTFRDYAM-
SWVRQAPGKGLEWVSSYSG IDDSTYY-
ADSVKGRFTISRDNSKSTLSLHMNSLRAED-
SALYFCAKDRGPRGVGEL
FDSWGQGTLVTVSSASTKGPSVFPLAPSSKST-
SGGTAALGCLVKDYFPEPVTVSWN SGALT-
SGVHTFPAVLQSSGLYS-
LSSVVTVPSSSLGTQTYICNVNHKPSNTKVDKRVEP
KSCDKTHTCPPCPAPELL *R* GPSVFLFPPKPKDTLMIS-
RTPEVTCVVVDVSHEDPEVKF
NWYVDGVEVHNAKTKPREEQYN-
STYRVVSVLTVLHQDWLNGKEYKCKVSNKA *R* P
APIEKTISKAKGQPREPQVYTLPPSREEMTKNQVSLT-
CLVKGFYPSDIAVEWESNGQP
ENNYKTTPPVLDSDGSFFLYSK-
LTVDKSRWQQGNVFSCSV *L* HEALHSHYTQKSLSLS
PG (SEQ ID NO: 15). In this SEQ ID NO: 15 the variable sequence is bolded, and the remaining sequence comprises Fc sequence which is shown with the G241R and/or L333R mutations to prevent binding to Fc gamma receptors and M433L/N439S mutations to increase the antibody half-life in bold and italics. A C-terminal lysine was removed to reduce micro-heterogeneity (removed lysine not shown).

In an embodiment, a Z004 light chain comprises or consists of a contiguous segment or the entire sequence:

DIQMTQSPSTLSASVGDRVTITCRASQ-
SISKWLAWYQQKPGKAPKLLIYTTSTLK
SGVPSRFSGSGSGTEFTLTISSLQPDDFA-
TYYCQHFYSVPWTFGQGTKVEIKRTV
AAPSVFIFPPSDEQLKSGTASVVCLLNNFY-
PREAKVQWKVDNALQSGNSQESVTEQD SKDSTYS-
LSSTLTLSKADYEKHKVYACE-
VTHQGLSSPVTKSFNRGEC (SEQ ID NO: 16). In this sequence the variable region is shown in bold.

In an embodiment, a Z021 heavy chain includes an IgG1, with modifications that can include G237R/L329R mutations to prevent binding to Fc gamma receptors, M429L/N435S mutations to increase the antibody half-life, and a C-terminal lysine removed to reduce micro-heterogeneity.

In an embodiment, a Z021 heavy chain comprises or consists of a contiguous segment or the entire sequence:

QVQLQESGPGLVKP-
SETLSLTCTVSGGSIDTYYWSWIRQTPGK-
GLEWIGCFYYS
VDNHFNPSLESRVTISVDTSKNQFSLKMTSMTASD-
TAVYYCARNQPGGRAFDY WGPGTLVTVSSAS-
TKGPSVFPLAPSSKSTSGGTAALGCLVKDYF-
PEPVTVSWNSGA

LTSGVHTFPAVLQSSGLYS-LSSVVTVPSSSLGTQTYICNVNHKPSNTKVDKRVE-PKSC DKTHTCPPCPAPELL *R* GPSVFLFPPKPKDTLMISRTPE-VTCVVVDVSHEDPEVKFNWY VDGVEVHNAKTKPREEQYN-STYRVVSVLTVLHQDWLNGKEYKCKVSNKA *R* PAPIE KTISKAKGQPREPQVYTLPPSREEMT-KNQVSLTCLVKGFYPSDIAVEWESNGQPENN YKTTPPVLDSDGSFFLYSK-LTVDKSRWQQGNVFSCSV *L* HEALHSHYTQKSLSL-SPG (SEQ ID NO: 17). In this SEQ ID NO: 17, the variable sequence is bolded, and the remaining sequence comprises Fc sequence which is shown with the G237R/L329R mutations to prevent binding to Fc gamma receptors and M429L/N435S mutations to increase the antibody half-life in bold and italics. A C-terminal lysine was removed to reduce micro-heterogeneity (removed lysine not shown). In an embodiment, the Z021 heavy chain sequence comprises a C50 modification, which may reduce unwanted disulfide bond formation. Thus, in one embodiment, the disclosure comprises a Z021 heavy chain of SEQ ID NO: 17, wherein the C50 is changed, such as to a V, but other amino acid substitutions can also be made provided they do not adversely affect affinity of the antibody for its epitope and/or the antibody's ability to neutralize ZIKV and/or DENV1.

In an embodiment, a Z021 light chain comprises or consists of a contiguous segment or the entire sequence:

EIVLTQSPATLSL-SPGQRATLSCRASQSVSNYFAWYQQKPGQAPRLLI-YDTSKRA TGTPARFSGSGSGTDFTLTISSLEPED-FAVYYCQERNNWPLTWTFGLGTKVEIKR TVAAPSVFIFPPSDEQLKSGTASVVCLLNNFY-PREAKVQWKVDNALQSGNSQESVTE QDSKDSTYS-LSSTLTLSKADYEKHKVYACE-VTHQGLSSPVTKSFNRGEC (SEQ ID NO: 18). In this sequence the variable region is shown in bold.

Similar mutations can be made in any antibody of this disclosure.

In embodiments, antibodies of this disclosure have variable regions that are described herein, and may comprise or consist of any of these sequences, and may include sequences that have from 80-99% similarity, inclusive, and including ranges of numbers there between, with the sequences expressly disclosed herein, provided antibodies that have differing sequences retain the same or similar binding affinity as an antibody with an unmodified sequence. In embodiments, the sequences are at least 95%, 96%, 97%, 98% or 99% similar to an expressly disclosed sequence herein.

Those skilled in the art will recognize that antibodies of this disclosure are from time to time described using nomenclature that includes a "Z" and a number, and that these are correlated with nomenclature in the tables of this disclosure, such as "MEX" or "BRA" followed by an alphanumeric designation. Those skilled in the art will be able to readily attribute the particular Z number with the MEX and BRA numbers in view of the description and tables presented herein. For example, Z004 is also referred to herein as MEX18_89 and Z021 is referred to as MEX84_p4-23.

In non-limiting embodiments the disclosure provides antibodies with a CDR3 heavy chain sequence and a CDR3 light chain sequence selected from amino acid sequences in Table 1 or Table 2 having one of the following designations:

Z001 (MEX18_21), Z006 (MEX105_42), Z010 (MEX105_88), Z012 (MEX105_57), Z014 (MEX18_91), Z015 (MEX84_p2-44), Z018 (MEX84_p2-45), Z024 (MEX84_p4-12), Z028 (MEX84_p4-53), Z031 (BRA112_46), Z035 (BRA112_71), Z037 (BRA112_57), Z038 (BRA12_2), Z039 (BRA12_21), Z041 (BRA138_57), Z042 (BRA138_17), Z043 (BRA138_15), Z002 (MEX18_27), Z003 (MEX18_58), Z005 (MEX18_13), Z007 (MEX105_50), Z008 (MEX105_60), Z009 (MEX105_64), Z011 (MEX105_15), Z013 (MEX18_84), Z016 (MEX84_p2-55), Z017 (MEX84_p2-58), Z019 (MEX84_p4-16), Z020 (MEX84_p4-30), Z032 (BRA112_24), Z034 (BRA112_09), Z036 (BRA112_91), Z040 (BRA12_81), Z044 (BRA138_46), Z045 (BRA12_08), Z048 (BRA112_23), Z050 (BRA138_28), Z051 (BRA138_59), Z052 (BRA138_62), Z053 (BRA138_65), Z054 (BRA138_94), Z055 (MEX84_p4-61), Z056 (MEX84_p2-94), Z057 (MEX84_p4-54), Z058 (MEX84_p2-53), Z059 (MEX84_p4-34), Z060 (BRA12_58), Z061 (BRA112_36), and Z062 (BRA112_70).

In embodiments an antibody of this disclosure comprises a CDR1 and/or a CDR2 amino acid sequence comprised by IgH and/or IgL amino acid sequences of Table 1.

Antibodies comprising the following list of variable sequences have been expressed and characterized for at least binding affinity, and as otherwise described herein. Bispecific antibodies comprising distinct heavy and light chain pairs from distinct antibodies listed below are included in the disclosure. In the following sequences, the CDR1 is italicized, the CDR2 is bolded and the CDR3 is italicized and bolded. All of these CDR1, CDR2 and CDR3 sequences are included in this disclosure as separate sequences, apart from the remainder of the disclosed variable/framework sequences that are also disclosed in this list:

Z004 (MEX18_89)
Heavy Chain (HC)

(SEQ ID NO: 11)

EVQLLESGGGLVQPGGSLRLTCATS*GFTFRDY*AMSWVRQAPGKGLEWVSSYSGIDD
STYYADSVKGRFTISRDNSKSTLSLHMNSLRAEDSALYFC*AKDRGPRGVGELFDS*W
GQGTLVTVSS

Light Chain (LC)

(SEQ ID NO: 12)

DIQMTQSPSTLSASVGDRVTITCRAS*QSISKW*LAWYQQKPGKAPKLLIYTTSTLKSGV
PSRFSGSGSGTEFTLTISSLQPDDFATYYC*QHFYSVPWT*FGQGTKVEIK

Z021 (MEX84_p4-23)
Heavy Chain (HC)

(SEQ ID NO: 13)

QVQLQESGPGLVKPSETLSLTCTVS*GGSIDTYY*WSWIRQTPGKGLEWIGCFYYSVDNH
FNPSLESRVTISVDTSKNQFSLKMTSMTASDTAVYYC*ARNQPGGRAFDY*WGPGTLV
TVSS

-continued

Light Chain (LC)

(SEQ ID NO: 14)

EIVLTQSPATLSLSPGQRATLSCRAS*QSVSNY*FAWYQQKPGQAPRLLIYDTSKRATGT
PARFSGSGSGTDFTLTISSLEPEDFAVYYC*QERNNWPLTWT*FGLGTKVEIK

Z001 (MEX18_21)
Heavy Chain (HC)

(SEQ ID NO: 19)

EVQLLESGGGLVQPGGSRRLSCATS*GFSFDTY*AMSWLRQAPGKGLEWVSSFSGLDD
STYYADSVKGRFTISRDNSKNTLYLQMNSLRAEDTAIYYC*AKDRGPRGIGELFDF*W
GQGTLVTVSS

Light Chain (LC)

(SEQ ID NO: 20)

DIQMTQSPSTLSASVGDRVTITCRAS*QSISRW*LAWYQQKPGKAPKWYKTSTLKSEV
PSRFSGSGSGTEFTLTISSLQPDDFATYYC*QHFHSVPWT*FGQGTKVEIK

Z006 (MEX105_42)
Heavy Chain (HC)

(SEQ ID NO: 21)

EVQLLESGGGLVQPGGSLRLSCAAS*GFTFKNY*AMAWVRQAPGKGLEWVSLLYNSEE
STYYADSVKGRFTISRDNSKNTLFLQMNRLRVEDTAVYFC*VRDRSNGWSSINL*WGR
GTLVTVSS

Light Chain (LC)

(SEQ ID NO: 22)

DIQMTQSPSTLSASVGDRVTMTCRAS*QTISGW*LAWYQQKPGKAPKLLIYQASRLESG
IPSRFSGSGSGTEFTLTISSLQPDDVATYYC*QQYSTFWT*FGLGTKVEIK

Z010 (MEX105_88)
Heavy Chain (HC)

(SEQ ID NO: 23)

EVQLLESGGGLVQPGGSLRLSCAAS*GFTFSNY*AMAWVRQAPGKGLEWVSLIYSGDD
STYYADFVKGRFTISRHNSKNTLSLQMNSLRAEDTAIYYC*VKDRGTGWSSIVH*WGQ
GTLVTVSS

Light Chain (LC)

(SEQ ID NO: 24)

DIQMTQSPSTLSASVGDRVTITCRAS*QTISNW*LAWYQQKPGKAPKLLIYQASSLESGV
PSRFSGSGSGTEFTLTISSLQPDDFATYYC*QQYSTYWT*FGQGTKVEIK

Z012 (MEX105_57)
Heavy Chain (HC)

(SEQ ID NO: 25)

QVQLVQSGAEVKKSGASVKVSCKAS*GYSFTTNY*IHWVRQAPGQGPEWMGIINPRGG
STTYAQKFQGRVLMTSDTSTSTVYMELSSLRSEDRAVYYCA*ARGKNHQTTVAVLSWY*
*YGMDV*WGQGTTVTVSS

Light Chain (LC)

(SEQ ID NO: 26)

DIQMTQSPSSVSASVGDRVTITCRAS*QGISSW*LAWYQQKPGKAPKLLISAASSLQSGV
PSRFSGSGSGTDFTLTISNLQPEDFATYFC*QQANSFPYT*FGQGTKLEIK

Z014 (MEX18_91)
Heavy Chain (HC)

(SEQ ID NO: 27)

EVQLLESGGDLVQPGGSLRLSCAAS*GFTFSSYG*MSWVRQAPGKGLEWVSSISGFDPS
TYYADSVRGRFTIARDNSKNTLYLQMKSLRVEDTAIYYC*AKDRLVRGFGEVLDS*WG
QGTLVTVSS

Light Chain (LC)

(SEQ ID NO: 28)

DIQMTQSPSSLSASVGDRVTITCRAS*QGISNY*LAWYQQKPREVPKLLIYAASTLHSGV
PSRFSGSGSGTDFTLTISGLQPEDVATYYC*QKYNSVPWT*FGQGTKVEIK

Z015 (MEX84_p2-44)
Heavy Chain (HC)

(SEQ ID NO: 29)

QVQLVQSGAEVKKPGASVKLSCKSS*GYSFTSY*YMHWVRQAPGQGLEWMGIINPSGV
FTSYAQRFQGRVTMTSDTATSTVYMELSSLRSGDTAVYYC*TRSLVTPAAQSVQYFDS*
WGQGTLVTVSS

-continued

Light Chain (LC)

(SEQ ID NO: 30)

EIVLTQSPGTLSLSPGERATLSCRAS*QSVSLSF*LAWYQQKPGQAPRLLIYGASNRATGI
PDRFSGSGSGTDFTLTISRLEPGDFAVYYC*QQYGSSPLT*FGPGTKVDIK

Z018 (MEX84_p2-45)
Heavy Chain (HC)

(SEQ ID NO: 31)

QVQLVQSGPGVKKPGASVKVSCKAS*GYIFSDYY*ILWVRQAPGQGLEYMGWMNPISG
FTHYAQNFQGRVTMTRDTSISTAYMELTRLASDDTAVYYC*ARGGRINSPLGFDP*WG
QGTLVTVSS

Light Chain (LC)

(SEQ ID NO: 32)

EIVLTQSPATLSLSPGERATLSCRAS*QSISTFS*LAWYQQKFGQAPRLLIYGASSRATGIP
DRFSGSGSGTDFTLTISRLEPEDFAVYYC*QQYVSSPLT*FGGGTKVEIK

Z024 (MEX84_p4-12)
Heavy Chain (HC)

(SEQ ID NO: 33)

EVQLVQSGAEVRKPGESLRISCKTS*GYTFTSHW*VAWVRQMPGKGLEWMGIIYPGDS
DTRYSPSFQGQISISADKSINTAYLQWSSLKASDTGIYYC*ARHDGRGYCSPTRCFFSG*
*MDV*WGQGTTVTVSS

Light Chain (LC)

(SEQ ID NO: 34)

DIQLTQSPSSLSASVGDRVTITCRAS*QSISNY*LNWYQQKPGKAPNLLIYAASSLQSGVP
SRFSGSGSGTDFTLTISSLQPEDYAIYYC*QQTDRTPLT*FGQGTKVEIK

Z028 (MEX84_p4-53)
Heavy Chain (HC)

(SEQ ID NO: 35)

EVQLLESGGGLVQPGGSLRLSCAAS*GFTFSAY*AMSWVRQAPGKGLEWVSSINGHSDS
TYFADSVKGRFTISRDNSKNTLYLQMNSLRAEDTALYYC*AKDRLREGIGELFHS*WG
QGTLVTVSS

Light Chain (LC)

(SEQ ID NO: 36)

DIQMTQSPSTLSASIGDRVTITCRAS*QSITPW*LAWYQQKPGKAPKFLIYQTSILESGVP
SRFSGSGSGTEFTLTISSLQPDDFATYYC*QHYHSYPWT*FGQGTKVEIK

Z031 (BRA112_46)
Heavy Chain (HC)

(SEQ ID NO: 37)

EVQLLESGGGLVQPGGSLRLSCVAS*GFTFGSYG*MAWVRQAPGKGLEWISSISSIDPST
YYADSVKGRFTVSRDNSENTLYLHMSSLKVEDTAVYFC*AKDRLNGGFGELFAS*WG
QGTLVTVSS

Light Chain (LC)

(SEQ ID NO: 38)

DIQMTQSPSTLSASVGDSVTITCRAS*QSISSW*LAWYQQKPGKAPKFLIHKASSLESGIP
SRFSGSGSGTEFTLTINNLQPDDFATYYC*QHYHSYPWT*FGQGTKVEIK

Z035 (BRA112_71)
Heavy Chain (HC)

(SEQ ID NO: 39)

EVQLLESGGGLIQPGGSLRLSCAAS*GFTFSSY*AMSWVRQAPGKGLEWVSGISGSGGA
SDNGASRYYADSVKGRFSISRDNSKNTVYLQMNSLRAEDTAVYYC*AKDRLSGGFG*
*ELFQK*WGQGTLVTVSS

Light Chain (LC)

(SEQ ID NO: 40)

DIQMTQSPSTLAASVGDRVTITCRAS*QNINSW*LAWYQQKPGKAPKFLIYKASTLESG
APSRFSGSGSGTEFTLTISSLQPDDFATYYC*QHYYSYPYT*FGQGTKVEIK

Z037 (BRA112_57)
Heavy Chain (HC)

(SEQ ID NO: 41)

QVQLQESGPGLVKPSETLSLTCSVS*GYFISSGHY*WGWIRQSPGKGLEWIASIYQSGSK
FQTGNTYYNPSLESRVTISMDTSKNQFSLKLSSVTAADTAVYFCARD*ARDARSRSWDRTG*
*FFGP*WGQGILVTVSS

Light Chain (LC)

(SEQ ID NO: 42)

EIVLTQSPGTLSLSPGERATLSCRAS*QSLSSSF*LAWYQQKPGQSPRLLIYGTSSRDTGIP
DRFSGSGSGTDFTLTISRLEPEDSAVYYC*QQYGSSWGT*FGQGTKLEIK

-continued

Z038 (BRA12_2)
Heavy Chain (HC)

(SEQ ID NO: 43)
EVQLLESGGGLVQPGGSLRLSCEAS*GFTFSNYA*MNWVRQAPGKGLEWVSTLGATDN
SGDSTYYVESAKGRFTISRDNSKNTLYLQMNSLRVEDTAVYFC*AKDRTGNIGAGTG*
*YFDK*WGQGTLVTVSS

Light Chain (LC)

(SEQ ID NO: 44)
DIQMTQSPSTLSASVGDRVTITCRAS*HRISGW*LAWYQQKPGKAPKLLIYQASGLESGV
PSRFSGSGYGTEFTLTISSLQADDFATYYC*QQYNNYPWT*FGQGTKVEIK

Z039 (BRA12_21)
Heavy Chain (HC)

(SEQ ID NO: 45)
EVQLLESGGGLVQPGGSLRLSCAAS*GYIFDNYA*MSWVRQAPGKGLEWVSYINGGGY
GTDYADSVKGRFTISRDNSKRILYLQMNSLRVGDTAVYYC*AKSPYVGGYGLPGDS*W
GQGTLVTVSS

Light Chain (LC)

(SEQ ID NO: 46)
EIVLTQSPGTLSLSPGERATLSCRAS*QTIFFNY*LAWYQKKPGQAPRLLVHGASTRATG
IPDRFSGSGSGTDFTLTINSLDPEDFAVYYC*QQYGDSPPT*FGGGTKVEIK

Z041 (BRA138_57)
Heavy Chain (HC)

(SEQ ID NO: 47)
QVQLVQSGAEVKKPGSSVRLSCKAS*GGSYSTYA*ISWVRQAPGQGLEWMGRIIPSLGK
THLAQKFQGRVTFTADESTTTVYMILSSLKSEDTALYYC*ATPDWQYSSAYSLDH*WG
QGTLVTVSS

Light Chain (LC)

(SEQ ID NO: 48)
DIVMTQSPLSLPVTPGEPASISCRS*SQSLLHSTGYNY*LDWYLQKPGQSPQLLIYLGSNR
ASGVPDRFSGSGSGTDFTLKISRVEAEDVGVYYC*MQALQTPFT*FGPGTKVDIK

Z042 (BRA138_17)
Heavy Chain (HC)

(SEQ ID NO: 49)
QVQLQESGPGLVKPSETLSLSCTVS*SGSISNYY*WNWIRQPPGKGLEWIGYIYYSGSISY
NPSLKSRVTISVDTSKNQLSLKLNSVTAADTAVYYC*ARGPDNRY*WGQGTLVTVSS

Light Chain (LC)

(SEQ ID NO: 50)
EIVMTQSPATLSVSPGERVTLSCRAS*QSVSYN*LAWHQQKPGQAPRLLIYGASTRATGI
PARFSGSGSGTEFTLTISNMQSEDFAVYYC*QQYNNWPPVFT*FGPGTKVDIK

Z043 (BRA138_15)
Heavy Chain (HC)

(SEQ ID NO: 51)
QVQLVQSGAEVKKPGASVKVSCKTS*GYTFTSYY*MNWVRQAPGQGLEWMGIIKPSDG
STNYAQKFQGRVTMTRDTSTSTVYMELRSLRSEDTAVYYC*GRDSKGWLQLRGDIDY*
WGQGTLVTVSS

Light Chain (LC)

(SEQ ID NO: 52)
QSALTQPASVSGSPGQSITISCAGT*SSDVGNYNL*VSWYQQHPGKAPKLLIYEVSKRPSG
VSNRFSGSKSGNTASLTISGLQAEDEADYYC*CSYAGSSTYV*FGTGTEVTVL

Z002 (MEX18_27)
Heavy Chain (HC)

(SEQ ID NO: 53)
EVQLLESGGGLVQPGGSLRLSCATS*GFTFSTYA*MSWVRQAPGKGLEWVSSFSGVDDS
TYYAESVKGRFTISRDNSKNTVYLQMTRLRAEDTAVYYC*AKDRGPRGVGELFDS*W
GQGTLVTVSS

Light Chain (LC)

(SEQ ID NO: 54)
DIQMTQSPSTLSASVGDRVTMTCRAS*QSINRW*LAWYQQKPGKAPKLLIYTTSTLKSG
VPSRFSGSGSGTEFTLTISSLQPDDFATYYC*QHFHSVPWT*FGQGTKVEIK

Z003 (MEX18_58)
Heavy Chain (HC)

(SEQ ID NO: 55)
EVQLLESGGGLVQPGGSLRLSCATS*GFTFTTFA*MSWVRQAPGKGLEWVSSISGADDS
TYYAASVKGRFTISRDNSRSTLFLQMNSLRAEDTAVYYC*AKDRGPRGVGELFDS*WG
QGTLVTVSS

-continued

Light Chain (LC)

(SEQ ID NO: 56)

DIQMTQSPSTLSASVGDRVTITCRAS*QSISKW*LAWYQQKPGKAPRLLIYTTSTLKSGV
PSRFSGSGSGTEFTLTISSLQPDDFATYYC*QHFFSVPWT*FGQGTKVEIK

Z005 (MEX18_13)
Heavy Chain (HC)

(SEQ ID NO: 57)

EVQLLESGGGLVQPGGSLRLSCAAS*GFTFSSY*AMSWVRQAPGKGLEWVSSFSGIDDS
TWYADSVKGRFTISRDNSKSTLYLQMNSLRAEDTAVYYC*AKDRLVRGFAEVLDY*W
GRGTLVTVSS

Light Chain (LC)

(SEQ ID NO: 58)

DIQMTQSPSSLSASVGDRVTITCRAS*QDISKY*LAWYQQRPGKVPNLLIYTASTLQSGV
PSRFSGSGSGTHFTLTISSLQPEDVATYYC*QKYNSVPWT*FGQGTKVEIK

Z007 (MEX105_50)
Heavy Chain (HC)

(SEQ ID NO: 59)

EVQLLESGGGLVRPGGSLRLSCTAS*GFTFRRY*AMAWVRQAPGKGLEWVSLIYDGDD
STYYAKSVKGRFAISRDNSKNTLSLQMNSLRAEDTAVYYC*VKDRDNGWSSIVD*WG
QGTLVTVSS

Light Chain (LC)

(SEQ ID NO: 60)

DIQMTQSPSTLSASVGDRVTITCRAS*HSISGW*LAWYQQKPGKAPKLLIYQASILESGV
PSRFSGSGSGTEFTLTIGSLQPEDFATYFC*QQYSTFWT*FGQGTKVEIK

Z008 (MEX105_60)
Heavy Chain (HC)

(SEQ ID NO: 61)

EVQLLESGGGLVRPGGSLRLSCTAS*GFTFRRF*AMAWVRQAPGKGLEWVSLIWNGDD
STYYAESVRGRFTISRDNSHNTLSLQMRSLRAEDTAIYYC*VKDRDNGWSSIVD*WGQ
GTLVTVSS

Light Chain (LC)

(SEQ ID NO: 62)

DIQMTQSPSTLSASVGDRVTITCRAS*QTIGNW*LAWYQQKPGKAPKLLIYQASVLESG
VPSRFSGSGSGTEFTLTISSLQPEDFATYFC*QQYSTFWT*FGQGTKVEIK

Z009 (MEX105_64)
Heavy Chain (HC)

(SEQ ID NO: 63)

EVQLLESGGGLVRPGGSLRLSCTAS*GFTFRRY*AMAWVRQAPGKGLEWVSLIYNGDD
STYYAESVKGRFTVSRDNSQNTLSLQMNSLRAEDTAIYYC*VRDRDNGWSSIVD*WGQ
GTLVTVSS

Light Chain (LC)

(SEQ ID NO: 64)

DIQMTQSPSTLSASVGDRVTITCRAS*RTIGSW*LAWYQQKPGKAPKLLIYQASILEGGV
PSRFSGSVSGTEFTLTIRSLQPEDFATYFC*QQYSTFWT*FGQGTKVEIK

Z011 (MEX105_15)
Heavy Chain (HC)

(SEQ ID NO: 65)

EVQLLESGGGLVQPGGSLRLSCAAS*GFTFRTY*AMSWVRQPPGKGLEWVSSISAREDS
TYFAASVRGRFTISRDNSKNTLYLQMNNLRAEDTALYYC*AKDRLQLGVGELYES* WG
QGTLVTVSS

Light Chain (LC)

(SEQ ID NO: 66)

DIQMTQSPSTLSASVGDRVTITCRAS*QNINSW*LAWYQQKPGKAPKLLIYMASSLQSG
VPSRFSGSGSGTEFTLTVSSLQPDDFATYYC*QHYHSYPWT*FGQGTKVEIK

Z013 (MEX18_84)
Heavy Chain (HC)

(SEQ ID NO: 67)

EVQLLESGGGLVQPGGSLRLSCAAS*GFTFTSY*AMNWVRQAPGKGLEWVSGIGGRGA
IAGDGSIYYADSVKGRFTISRDNSKNIVYLQMNGLRVEDTAVYYC*AKDRVAFDGFH*
*V*WGQGTLVTVSS

Light Chain (LC)

(SEQ ID NO: 68)

DIQMTQSPPTLSASVGDRVTITCRAS*QSISSW*LAWYQQKPGKAPKLLIYKASSLESGV
PSRFSGSGSGTEFSLTISSLQPEDFATYYC*QQYNSYPWT*FGQGTKVEIK

Z016 (MEX84_p2-55)
Heavy Chain (HC)

(SEQ ID NO: 69)

QVQLVQSGAEVKKPGASVKLSCKAS*GYTFTSY*YVHWVRQAPGQGLEWMGIINPGNN
FVSFAQNFYDRATMTRDTSTNTVYMELTNLQSEDTAVYYC*ARTLVAPSAQSMYYFD*
*F*WGQGTLVTVSS

-continued

Light Chain (LC)

(SEQ ID NO: 70)

EIVLTQSPGTLSLSPGERGTLSCRAS*QYITTGH*FAWYQQKPGRAPRLLIYGASVRATG
VPDRFSGSGAETDFTLTISRLDPEDVGVYYC*QQYGSSPVT*FGPGTKVDIK

Z017 (MEX84_p2-58)
Heavy Chain (HC)

(SEQ ID NO: 71)

QVQLVQSGAGMRKPGASVKVSCKAS*GYSFNDYY*IHWVRQAPGQGLEWMGWINPKS
GFTNYAQRFQGRVTMTGDTSNSVAYMELTRLTSDDTAVYYC*ARGGRINAPLGFDP*
WGQGTLVTVSS

Light Chain (LC)

(SEQ ID NO: 72)

EIVLTQSPDTLSLSPGETATLSCRAS*QSIGSIS*LGWYQQKFGQAPRLLIYGASTRATGTP
DRFSGSGSETDFTLTISRLEPEDSAVYYC*QQYVSSPLR*FGGGTKVEIK

Z019 (MEX84_p4-16)
Heavy Chain (HC)

(SEQ ID NO: 73)

QVQLVQSGAEVKKPGASVKVSCKAS*GYTFTTYF*IHWVRQAPGQGLEWMGIINPNSG
STNYAQKIQGRVTMTTDTSASTVYMELSGLRSEDTAVYYC*ARGGSYPVAIRGVTFGI*
WGQGTMVTVSS

Light Chain (LC)

(SEQ ID NO: 74)

DIQLTQSPSSLSASVGDRVTITCRAS*QSISNY*LNWYQQKPGKAPNLLIFATSSLQSGVP
SRFSGSGSGTDFTLTISSLQPEDFATYYC*QQSFSTPLT*FGGGTKVEIK

Z020 (MEX84_p4-30)
Heavy Chain (HC)

(SEQ ID NO: 75)

QVQLQQWGARPLKPSETLSLTCGVN*GGSFSGYHWS*WIRQPPGKGLEWIGEIDHNGRI
NYNPSLKSRVTISIDTFKSQFSLRLTSIIAADTAVYYC*ARDVVTMVEGLRFHYYYNYY*
*GMDV* WGQGTTVTVSS

Light Chain (LC)

(SEQ ID NO: 76)

EIVLTQSPGTLSLSPGDRATLSCGAS*QSVSSNY*LAWYQQKLGQAPRLLIYAASTRATGI
PDRFSGGGSGTDFTLTINKLEAEDFAMYYC*QIYDSSVRT*FGQGTKVEIK

Z032 (BRA112_24)
Heavy Chain (HC)

(SEQ ID NO: 77)

EVQLLESGGRLVQPGGSLTLSCAAS*GFPFSTY*AMSWLRQAPGKGLEWVSGITGDSGS
TYYAASVKGRFTISRDNSKNTLYLQMNSLTADDTAVYYC*AKDRLHSGLGELFSY* W
GQGTLVTVSS

Light Chain (LC)

(SEQ ID NO: 78)

DIQMTQSPSTLSASVGDRVNITCRAS*QSINQW*LAWYQQKPGKAPKFLMYKASTLETG
VPSRFSGSGSGTEFTLTISSLQPDDFATYYC*QHYFSYPWT*FGQGTKVEIK

Z034 (BRA112_09)
Heavy Chain (HC)

(SEQ ID NO: 79)

EVQLLESGGGLAQPGGSLRLSCETS*GFTFRSYG*MGWVRQAPGKGLEWVSSIYISGDS
TYYAASVKGRFTISRDNSKSTLYLQMDRLTAEDTAVYYC*VRDRIQGGFGELYRY*WG
QGTLVTVSS

Light Chain (LC)

(SEQ ID NO: 80)

DIQMTQSPSTLSASVGDRVTMTCRAS*QSVNKW*LAWYQQKPGKAPKLLIYETSILESG
VSSRFSGSGSGTEFTLTISSLQPDDFATYYC*QHYHGYPWT*FGQGTKVEIK

Z036 (BRA112_91)
Heavy Chain (HC)

(SEQ ID NO: 81)

EVQLLESGGDLVQPGGSLRLSCAAS*GFTFSTYG*MAWVRQAPGKGLEWLSSISSVDDS
KYYAASVKGRFTISRDNSRNTLYLHMNSLRVDDTAVYYC*AKDRIPHGLGELYAN*W
GQGTLVTVSS

Light Chain (LC)

(SEQ ID NO: 82)

DIQMTQSPSTLSASVGDRVTITCRAS*QSISGW*LAWYQQKPGKAPRLLMHKASNLYSG
VPSRFSGSGSGTEFTLTISSLQPDDFATYYC*QHYHSYPYT*FGQGTKVEIK

-continued

Z040 (BRA12_81)
Heavy Chain (HC)
(SEQ ID NO: 83)
EVQLLESGGGLVQPGGSLRLSCAAS*GFTFSTY*AMSWVRQAPGKGLEWVSA***ISGSGRS
TY*YADSVKGRFTISRDNSKNTLYLQMNSLRGEDTAVYYC*AKSSGGHNWNYVDYYY
GMDV***WGQGTTVTVSS Light Chain (LC)
(SEQ ID NO: 84)
DIQLTQSPSFLSASVGDRVTITCRAS*QGISS*YLAWYQQKPGKAPKLLIY*AAS*TLQSGVP
SRFSGSGSGTEFTLTISSLQPEDFATYYC*QQLNSYPVT*FGPGTKVDIK Z044 (BRA138_46)
Heavy Chain (HC)
(SEQ ID NO: 85)
QVQLVQSGAEVKKPGASVKVSCKA*SGYTFTSTY*IHWVRQAPGQGLEWMGI***INPSSSN
T*NYAQKFQGRVTMTRDTSTSTVYMELSSLRSEDTAVYYC*ARDFGGYSSSSVSDAFDI***
WGQGTMVTVSS Light Chain (LC)
(SEQ ID NO: 86)
QSALTQPASVSGSPGQSITISCTGT*SSDVGSFNL*VSWYQQHPGKAPKLIIY*EVS*KRPSG
VSNRFSGSKSGNTASLTISGLQAEDEVHYY*CCSYAGSSRFV*FGTGTKVTVL Z045 (BRA12_08)
Heavy Chain (HC)
(SEQ ID NO: 87)
EVQLLESGGALVQPGGSLRLSCAAS*GFTFNYY*AMTWVRQAPGRGLEWVST***ITDNGG
TT*YLADSVKGRFTISRDNSQNTQSLQMNNLRADDTAVYFC*VKHLRGWYTFE***WGQ
GTLVTVSS Light Chain (LC)
(SEQ ID NO: 88)
EIVLTQSPGTLSLSPGERATLSCRAS*QSVSGS*YLAWYQQKPGQAPRLLIY*GAS*RRATGI
PDRFSGSGSGTDFTLTISRLEPEDFAVYYC*QQFGSSPRYT*FGQGTKLEIK Z048 (BRA112_23)
Heavy Chain (HC)
(SEQ ID NO: 89)
EVQLLESGGGLVKPGGSLRLSCAAS*GLTFSTY*AMSWVRQAPGKGLEWVSA***ISPGSGD
NI*YYGDSVKGRFTISRDNSKNTLYLQMNSLRAEDTAVYYC*VNGGFSGYYSDY***WGQG
TLVTVSS Light Chain (LC)
(SEQ ID NO: 90)
EIVLTQSPATLSLSPGERATLSCRAS*QSVSN*YLAWYQQKPGQAPRLLIY*DAS*NMAPGIP
ARFSGSGSGTDFTLTISSLEPEDFAVYYC*QQRSNWLT*FGGGTKVDIK Z050 (BRA138_28)
Heavy Chain (HC)
(SEQ ID NO: 91)
QVQLVQSGAEVKKPGSSVKVSCKAP*GGTFSRYS*IAWVRQAPGQGLEWMGG***INPTFT
TP*NYAQKFQGRVTITADESTNTAYLDLSSLRSEDTAVYYC*ARFRYYYESGGYSDASP
YYLDY***WGQGTLVTVSS Light Chain (LC)
(SEQ ID NO: 92)
EIVLTQSPATLSLSPGERVTLSCRAS*QSVSS*YLAWYQQKPGQAPRLLIY*DAS*NRATGIP
ARFTGSGSGTDFTLTISSLEPEDFAVYYC*QQRSNWPLT*FGGGTKVEIK Z051 (BRA138_59)
Heavy Chain (HC)
(SEQ ID NO: 93)
QVQLQESGPGLVKPSQTLSLTCTVS*GVSISSGGYYYS*WFRQLPGKGLEWIGH***IYYTGN
T*HYNPSLRSRLTISVDTSKNQFSLKLSSVTAADTARYYC*QQRSNWPLT***WG
RGTLVTVSS Light Chain (LC)
(SEQ ID NO: 94)
EIVLTQSPGTLSLSPGERATLSCRAS*QSVTSS*YLAWYQHKPGQAPRLLIY*GAS*SRAPGIP
DRFSGSGSGTDFTLTISRLEPEDFAVYWC*QQYGRSPFT*FGQGTKLEIK Z052 (BRA138_62)
Heavy Chain (HC)
(SEQ ID NO: 95)
QVQLQESGPGLVKPSQTLSLTCTVS*GGSITGGVYY*WNWIRHHPGKGLEWIGY***MFYSG
DT*DYNPSLRSRVTISGDTSKNKFSLNLNSVTAADTAVYYC*ARAGFDYGSPVSAFDI***W
GQGTLVTVSS -continued Light Chain (LC)

(SEQ ID NO: 96)

EIVLTQSPATLSLSPGERATLSCRAS*QSVSSTY*LVWYQQKPGQAPRLLIYGASSRATGI
PDRFSGSGSGTDFTLTISRLEPEDFAVYFC*QQYAHSPRGYT*FGQGTKLEIK

Z053 (BRA138_65)
Heavy Chain (HC)

(SEQ ID NO: 97)

QLQLQESGPGLVKPSETLSLTCTVS*GGSISSYNYY*WGWIRQPPGKGLEFIGSIYYTGST
YYNPSLRSRVTISVDTSKNQFSLKLTSVTAADTAVYYC*ARHGPGMGHNWYFDL*WG
RGTLVTVSS

Light Chain (LC)

(SEQ ID NO: 98)

EIVLTQSPATLSLSPGERATLSCRAS*QSISSY*LAWYQQKPGQAPRLLIYDASNRAPGIPA
RFSGSGSGTDFTLTISSLEPEDFAVYYC*QQRSTWLT*FGGGTKVEIK

Z054 (BRA138_94)
Heavy Chain (HC)

(SEQ ID NO: 99)

QLQLQESGPRLVKPSETLFLTCTVS*GDSISSSSYF*WGWIRQPPGKGLEWIGSISYSGST
YYNPSLKSRVTISVDTSKNQFSLKLSSVTAADTVVYYC*AKHLYSSSWNIGSSFDS*WG
PGTLVTVSS

Light Chain (LC)

(SEQ ID NO: 100)

EIVLTQSPATLSLSPGERATLSCRAS*QSVSIY*LAWYQQKPGQAPRLLIYDASSRATGIPA
RFSGSGSGTDFTLTISSLEPEDFAVYYC*QQRSNWPVYT*FGQGTKVEIK
Z055 (MEX84_p4-61)
Heavy Chain (HC)

(SEQ ID NO: 101)

EVQLVQSGAEVKKPGASVKVSCKAS*GYTFSGYY*IHWLRQAPGQGLEWMGWINSNSG
GADSGPRFHGRVTMTRDTSINTAYLELTNLRSDDTAVYYC*ARRTYYDTRFPYWYFD*
*L*WGRGTLVTVSS

Light Chain (LC)

(SEQ ID NO: 102)

AIRMTQSPSSLSASVGDRVTITCRAS*QDIGSY*LNWYQQKPGKAPNVLISAASTLQSGV
PSRISGIGSGTDFTLTISSLQPEDFATYYC*QQSLSAPYT*FGQGTKLEIK

Z056 (MEX84_p2-94)
Heavy Chain (HC)

(SEQ ID NO: 103)

EVQLVQSGAEVKKPGASVKVSCKAS*GNTFMGYY*FHWVRQAPGQGLEWMGWINPNS
GHANIAQTFQGRVTMTRDPSITTAYMELSRLRSDDTAVFYC*ARGGMLGQLWALDN*
WGQGTLVTVSS

Light Chain (LC)

(SEQ ID NO: 104)

DIQMTQSPSTLSASVGDRVTITCRAS*QSISHW*LAWYQQRPGEAPKLLIYQASTLESGV
PSRFSGSGSGTEFTLSISSLQPDDFATYYC*QQYQSSPYT*FGQGTKLEIK

Z057 (MEX84_p4-54)
Heavy Chain (HC)

(SEQ ID NO: 105)

EVQLVQSGAEVKRPGASVKVSCKAS*GYTFADYY*IHWVRQAPGLGLEWMGWINPKT
GFSHYEQTFQGRVTMARDTSIPAAYMELSSLKSDDTAIYYC*ARGGRINVAEALRYW*
GQGSLVTVSS

Light Chain (LC)

(SEQ ID NO: 106)

DIQMTQSPSTLSTFVGDRVTITCRAS*QTIGDW*LAWYQQKPGKAPKLLISKATRLESGV
PSRFSGSGSETEFSLTINSLQPDDVAAYYC*QQYMSYPYT*FGQGTKLEIK

Z058 (MEX84_p2-53)
Heavy Chain (HC)

(SEQ ID NO: 107)

EVQLVQSGAEVKKPGSSVKVSCKAS*GGTFSSYA*IIWVRQAPGQGLEWMGGIIPIFGT
TNYAQKFRGRVTIATDASKSAAYMDLSSLKSEDTAIYYC*ARSWGTAATGGSFVQ*WG
QGTLVTVSS

Light Chain (LC)

(SEQ ID NO: 108)

EIVMTQSPATLSVSPGERATLSCRAS*HSVTSN*LAWYQQKPGQAPRLLIYGASTRATGI
PARFSGSGSGTEFTLTISSLQSEDSAVYYC*QYYTNWPPHVA*FGQGTKLEIK

-continued

Z059 (MEX84_p4-34)
Heavy Chain (HC)
(SEQ ID NO: 109)
EVQLVQSGAEVKTPGSSVKVSCKTS*GGTFSNFA*ITWVRQAPGQGLEWMGGIIPLFGI
TNYTQKFQGRVTITTDESKTTAYMDLSGLRSEDTAVYFCA*RGRDSSGRLLDH*WGQG
TLVTVSS Light Chain (LC)
(SEQ ID NO: 110)
EIVMTQSPATLSVSPGERATLSCRAS*QTVNRN*LAWYQQKPGQAPRLLIYAASARATG
VPARFSGSGSGTEFTLTISSLQSEDFVVYYC*QQYNNWPPLT*FGGGTKLEIK Z060 (BRA12_58)
Heavy Chain (HC)
(SEQ ID NO: 111)
QVQLQESGPGLVKPSETLSLTCTVS*GGSISSYY*WSWIRQPPGKGLEWIGFIYYSGSTNY
NPSLKSRVTISVDTSKNQFSLKLSSVTAADTAVYYC*ARGDYYYDSSGYLYYFDY*WGQ
GTLVTVSS Light Chain (LC)
(SEQ ID NO: 112)
EIVLTQSPGTLSLSPGERATLSCRAS*QSVSSSS*LAWYQQKPGQAPRLLIYGASNRATGI
PDRFSGSGSGTDFTLTISRLEPEDFAVYYC*QQYGTSVT*FGGGTKVEIK Z061 (BRA112_36)
Heavy Chain (HC)
(SEQ ID NO: 113)
EVQLVESGGGVVQPGRSLRLSCAAS*GFTFSIST*IHWVRQAPGKGLEYVVVISHDGNT
KYYADSVKGRFIISRDNSKNTVFLQMNSLRPVDTAVYYC*ARGEVGYFDL*WGRGTLV
TVSS Light Chain (LC)
(SEQ ID NO: 114)
EIVLTQSPATLSLSPGERATLSCRASQ*SVSSF*LAWYQQKPGQPPRLLIYDASTRATGIP
ARFSGSGSGTDFTLTISSLEPEDFAVYYC*QQRSNWPPIT*FGQGTRLEIK Z062 (BRA112_70)
Heavy Chain (HC)
(SEQ ID NO: 115)
EVQLVESGGGVVQPGRSLRLSCAAS*GFSFSSHA*MYWVRQAPGKGLEWVAIVSYDGS
TKNYADSVKGRFTISRDNSKNTIYLHLNSLRAEDTAVYFC*AREVDGIYGYLHY*WGQ
GTLVTVSS Light Chain (LC)
(SEQ ID NO: 116)
EIVLTQSPATLSLSPGERATLSCRAR*QNVRNF*LAWYQQKPGQAPRLLIYDASNRATDI
PARFSGSGSGTDFTLTISSLEPEDFAVYYC*QQRSYSIT*FGQGTRLEIK The following Table A table provides a summary of neutralizing and binding properties that pertain to the immediately forgoing 32 antibodies.

TABLE A

| Antibody | ZIKV neutralization $IC_{50}$ (ng/ml) | ZIKV EDIII binding $EC_{50}$ (ng/ml) | DENV1 binding | DENV2binding | DENV3 binding | DENV4 binding | YFV binding | WNV binding |
|---|---|---|---|---|---|---|---|---|
| Z002 | 1.5 | 25.2 | + | − | − | − | − | − |
| Z003 | 1 | 25.5 | + | − | − | − | − | − |
| Z005 | 1.3 | 216.3 | + | − | − | − | − | − |
| Z007 | 1.5 | 34.6 | + | − | − | − | − | − |
| Z008 | 1.7 | 32.6 | + | − | − | − | − | − |
| Z009 | 1.4 | 28.4 | + | − | − | − | − | − |
| Z011 | 1 | 38.0 | + | − | − | − | − | − |
| Z013 | 4.1 | >10000 | + | − | − | − | − | − |
| Z016 | 68.9 | 72.4 | − | − | − | − | + | + |
| Z017 | n.d. | >10000 | − | − | − | − | − | + |
| Z019 | n.d. | >10000 | n.d. | n.d. | n.d. | n.d. | n.d. | n.d. |
| Z020 | n.d. | >10000 | n.d. | n.d. | n.d. | n.d. | n.d. | n.d. |
| Z032 | 0.9 | 19.5 | n.d. | n.d. | n.d. | n.d. | n.d. | n.d. |
| Z034 | 1.3 | 23.5 | + | − | − | − | − | − |
| Z036 | 0.7 | 17.2 | + | − | − | − | − | − |
| Z040 | n.d. | >10000 | − | − | − | − | − | − |
| Z044 | n.d. | >10000 | − | − | − | − | − | − |
| Z045 | n.d. | >10000 | n.d. | n.d. | n.d. | n.d. | n.d. | n.d. |
| Z048 | n.d. | >10000 | n.d. | n.d. | n.d. | n.d. | n.d. | n.d. |
| Z050 | 36.7 | 30.3 | − | − | − | − | − | + |

TABLE A-continued

| Antibody | ZIKV neutralization $IC_{50}$ (ng/ml) | ZIKV EDIII binding $EC_{50}$ (ng/ml) | DENV1 binding | DENV2binding | DENV3 binding | DENV4 binding | YFV binding | WNV binding |
|---|---|---|---|---|---|---|---|---|
| Z051 | n.n. | 1864.5 | − | − | − | − | − | − |
| Z052 | 10.9 | 13.1 | − | − | − | − | − | + |
| Z053 | n.n. | 1683 | − | − | − | − | − | − |
| Z054 | n.n. | >10000 | − | − | − | − | − | − |
| Z055 | 54.4 | 1878 | − | − | − | − | + | + |
| Z056 | 36.7 | 982 | − | − | − | − | + | + |
| Z057 | 28.8 | 82.8 | − | − | − | − | + | + |
| Z058 | n.n. | >10000 | n.d. | n.d. | n.d. | n.d. | n.d. | n.d. |
| Z059 | 96.0 | 610.4 | − | − | − | − | + | + |
| Z060 | n.d. | >10000 | n.d. | n.d. | n.d. | n.d. | n.d. | n.d. |
| Z061 | n.d. | 311.3 | − | − | − | − | − | − |
| Z062 | n.d. | 208.2 | − | − | − | − | − | − |

n.d. = not determined
n.n. = non-neutralizing

In embodiments the disclosure provides neutralizing antibodies. The term "neutralizing antibody" refers to an antibody or a plurality of antibodies that inhibits, reduces or completely prevents viral infection. Whether any particular antibody is a neutralizing antibody can be determined by in vitro assays described in the examples below, and as is otherwise known in the art.

Antibodies of this disclosure can be provided as intact immunoglobulins, or as fragments of immunoglobulins, including but not necessarily limited to antigen-binding (Fab) fragments, Fab' fragments, $(Fab')_2$ fragments, Fd (N-terminal part of the heavy chain) fragments, Fv fragments (the two variable domains), dAb fragments, single domain fragments or single monomeric variable antibody domains, isolated CDR regions, single-chain variable fragment (scFv), and other antibody fragments that retain virus-binding capability and preferably virus neutralizing activity as further described below.

Antibodies and peptides or mRNA or DNA vaccines of this disclosure can be provided in pharmaceutical formulations. It is considered that administering a DNA or RNA vaccine encoding any protein (including peptides and polypeptides) antigen described herein is also a method of delivering such peptide antigens to an individual, provided the DNA and RNA are expressed in the individual. Methods of delivering DNA and RNAs encoding proteins are known in the art and can be adapted to deliver the protein antigens, given the benefit of the present disclosure. Similarly, the antibodies of this disclosure can be administered as DNA molecules encoding for such antibodies using any suitable expression vector(s), or as RNA molecules encoding the antibodies.

Pharmaceutical formulations containing antibodies or viral antigens can be prepared by mixing them with pharmaceutically acceptable carriers. Pharmaceutically acceptable carriers include solvents, dispersion media, isotonic agents and the like. The carrier can be liquid, semi-solid, e.g. pastes, or solid carriers. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, resins, porous matrices, binders, fillers, coatings, stabilizers, preservatives, liposomes, antioxidants, chelating agents such as EDTA; salt forming counter-ions such as sodium; non-ionic surfactants such as TWEEN, PLURONICS or polyethylene glycol (PEG), or combinations thereof. In embodiments, a pharmaceutical/vaccine formulation exhibits an improved activity relative to a control, such as antibodies that are delivered without adding additional agents, or a particular added agent improves the activity of the antibodies.

The formulation can contain more than one antibody type or antigen, and thus mixtures of antibodies, and mixtures of antigens, and combinations thereof as described herein can be included. These components can be combined with a carrier in any suitable manner, e.g., by admixture, solution, suspension, emulsification, encapsulation, absorption and the like, and can be made in formulations such as tablets, capsules, powder (including lyophilized powder), syrup, suspensions that are suitable for injections, ingestions, infusion, or the like. Sustained-release preparations can also be prepared.

The antibodies and vaccine components of this disclosure are employed for the treatment and/or prevention of ZIKV and/or DENV1 infection in a subject, as well as for inhibition and/or prevention of their transmission from one individual to another, and in particular in the case of transmission of Zika virus from a mother to a fetus, or from one partner to another during sexual intercourse wherein transmission between the individuals can take place. Accordingly, while embodiments of the disclosure are appropriate for use with any individual who is at risk of, is suspected of having, or has been diagnosed with a Zika virus infection, or a dengue 1 virus infection (or other related viruses), in particular embodiments of the disclosure comprise administering a composition of this invention to a female who is known to be pregnant, intending to become pregnant, suspected of being pregnant, or is engaging in sexual activity which raises a likelihood of pregnancy. Administration soon after delivery is also included, and direct administration to a fetus or to a newborn is also included.

The term "treatment" of viral infection refers to effective inhibition of the viral infection so as to delay the onset, slow down the progression, reduce viral load, and/or ameliorate the symptoms caused by the infection.

The term "prevention" of viral infection means the onset of the infection is delayed, and/or the incidence or likelihood of contracting the infection is reduced or eliminated.

The term "prevention" of viral transmission means the incidence or likelihood of a viral infection being transmitted from one individual to another (e.g., from a ZIKV-positive woman to her child during pregnancy, labor or delivery, or breastfeeding; or between sexual partners) is reduced or eliminated.

In embodiments, to treat and/or prevent viral infection, a therapeutic amount of an antibody or antigen vaccine disclosed herein is administered to a subject in need. The term "therapeutically effective amount" means the dose required to effect an inhibition of infection so as to treat and/or prevent the infection.

In embodiments, the disclosure comprises co-administration of a combination of antibodies. In an embodiment, administration of a combination of distinct antibodies suppresses formation of viruses that are resistant to the effects of either one of the antibodies alone. In embodiments, a combination of at least two antibodies includes at least two antibodies that each recognize distinct epitopes on Zika Envelope Domain III (EDIII), non-limiting examples of which are described below. In one non-limiting example, a combination of antibodies described herein as Z004 and Z021 is protective and suppresses emergence of resistant variants and/or fully suppresses virus emergence altogether. Thus, in embodiments, such a co-administration of a combination of at least two distinct antibodies described herein suppresses formation of variant Zika viruses that are resistant to treatment and/or prevents infection. In embodiments, the Z004 and Z021 antibodies can be administered concurrently or sequentially.

The dosage of an antibody or antigen vaccine depends on the disease state and other clinical factors, such as weight and condition of the subject, the subject's response to the therapy, the type of formulations and the route of administration. The precise dosage to be therapeutically effective and non-detrimental can be determined by those skilled in the art. As a general rule, a suitable dose of an antibody for the administration to adult humans parenterally is in the range of about 0.1 to 20 mg/kg of patient body weight per day, once a week, or even once a month, with the typical initial range used being in the range of about 2 to 10 mg/kg. Since the antibodies will eventually be cleared from the bloodstream, re-administration may be required. Alternatively, implantation or injection of the antibodies provided in a controlled release matrix can be employed.

The antibodies and/or antigen vaccines (as proteins or polynucleotides encoding the proteins) can be administered to the subject by standard routes, including oral, transdermal, and parenteral (e.g., intravenous, intraperitoneal, intradermal, subcutaneous or intramuscular). In addition, the antibodies and/or the antigen vaccines can be introduced into the body, by injection or by surgical implantation or attachment such that a significant amount of an antibody or the vaccine is able to enter blood stream in a controlled release fashion. In certain embodiments antibodies described herein are incorporated into one or more prophylactic compositions or devices to, for instance, neutralize a virus before it enters cells of the recipient's body. For example, in certain embodiments a composition and/or device comprises a polymeric matrix that may be formed as a gel, and comprises at least one of hydrophilic polymers, hydrophobic polymers, poly(acrylic acids) (PAA), poly(lactic acids) (PLA), carageenans, polystyrene sulfonate, polyamides, polyethylene oxides, cellulose, poly(vinylpyrrolidone) (PVP), poly(vinyl alcohol) (PVA), chitosan, poly (ethylacrylate), methylmethacrylate, chlorotrimethyl ammonium methylmethacrylate, hydroxyapatite, pectin, porcine gastric mucin, poly(sebacic acid) (PSA), hydroxypropyl methylcellulose (HPMC), cellulose acetate phthalate (CAP), magnesium stearate (MS), polyethylene glycol, gum-based polymers and variants thereof, poly (D,L)-lactide (PDLL), polyvinyl acetate and povidone, carboxypolymethylene, and derivatives thereof. In certain aspects the disclosure comprises including antibodies in micro- or nano-particles formed from any suitable biocompatible material, including but not necessarily limited to poly(lactic-co-glycolic acid) (PLGA). Liposomal and microsomal compositions are also included. In certain aspects a gel of this disclosure comprises a carbomer, methylparaben, propylparaben, propylene glycol, sodium carboxymethylcellulose, sorbic acid, dimethicone, a sorbitol solution, or a combination thereof. In embodiments a gel of this disclosure comprises one or a combination of benzoic acid, BHA, mineral oil, peglicol 5 oleate, pegoxol 7 stearate, and purified water, and can include any combination of these compositions.

The disclosure includes devices and kits that relate to inserting into vagina an intravaginal medicated device comprising antibodies of the disclosure. In certain embodiments the disclosure provides a vaginal tampon, vaginal ring, vaginal cup, vaginal tablet, vaginal sponge, a vaginal bioadhesive tablet, a vaginal lubricant, a condom, or a modified female hygiene or other vaginal health care product, such as prescription and over-the-counter antifungal products that treat and/or cure vaginal yeast infections, or bacterial vaginosis, but that have been adapted to include antibodies of this disclosure. Applicators that are provided with female hygiene or vaginal health care products can be adapted for intravaginal administration of the antibodies. In certain aspects a method of the invention comprises intravaginal insertion of a medicated device antibodies of this disclosure. The delivery composition can be formulated to adhere to and act directly on the vaginal epithelium and/or mucosa. In certain aspects a composition and/or device of this may comprise one or more additional agents known to be suitable for treatment of viral, or other bacterial or parasitic infections. Such compositions include but are not limited to antibiotics and previously known anti-viral agents, and chemical compounds that act as biocides or antiseptic agents, such as benzalkonium chloride. Additional agents include but are not limited to soothing compositions that contain, for example anti-irritant and/or anti-inflammatory agents, such as hydrocortisone or related compounds, or emollients, or anti-hemorrhagic or hemostatic or anti-allergic agents. In embodiments a composition and/or device of this disclosure comprises a contraceptive agent, such as a spermicide or a hormonal or non-hormonal contraceptive drug that is combined with one or more antibodies of this disclosure.

Antibodies of this disclosure can be produced by utilizing techniques available to those skilled in the art. For example, one or distinct DNA molecules encoding one or both of the H and L chains of the antibodies can be constructed based on the coding sequence using standard molecular cloning techniques. The resulting DNAs can be placed into a variety of suitable expression vectors known in the art, which are then transfected into host cells, which are preferably human cells cultured in vitro, but may include *E. coli* or yeast cells, simian COS cells, Chinese Hamster Ovary (CHO) cells, and human embryonic kidney 293 cells, etc.

In certain approaches the invention includes neutralizing antibodies as discussed above, and methods of stimulating the production of such antibodies. Antibodies can be produced from a single, or separate expression vectors, including but not limited to separate vectors for heavy and light chains, and may include separate vectors for kappa and lambda light chains as appropriate.

The antibodies may be neutralizing with respect to infectivity by ZIKV, DENV1, and combinations thereof. Neutralization may extend beyond ZIKV and DENV1 to include other viruses of the same genus (such as but not limited to DENV2, DENV3, DENV4, YFV, WNV), given that the EDIII of these viruses shares structural similarities. In this regard, the present disclosure demonstrates that at least some of the antibodies described herein bind to DENV2-4, yellow fever virus (YFV) and West Nile virus (WNV) (see e.g. FIG. 3C). In embodiments antibodies are neutralizing with respect to Asian/American strains of ZIKV, and also to African ZIKV, wherein the African ZIKV comprises an amino acid difference in its EDIII protein relative to the ZIKV Asian/American EDIII protein, and wherein the difference is optionally at position 393 in the African ZIKV EDIII protein, and wherein the difference at position 393 is optionally D393 instead of E393.

In certain approaches the disclosure includes methods for prophylaxis and/or therapy for a viral infection(s) comprising administering to an individual a vaccine formulation comprising antibodies and/or viral antigens described herein. The compositions can be administered to any individual in need thereof, wherein the individual is infected with or is at risk of being infected with Zika virus and/or dengue 1 virus. In one approach, administration of a vaccine comprising and/or encoding Zika polypeptides described herein is preceded by administering to the individual a composition comprising a DENV1 antigen, which without intending to be bound by any particular theory is believed to be able at least in some instances to enhance protection against Zika virus.

In certain embodiments the disclosure provides for consecutive or concurrent administration of ZIKV and DENV1 antigens, as well as other EDIII-derived antigens from other structurally similar viruses, including but not limited to DENV2-4, YFV, and WNV. In connection with this, it is contemplated that administering an antigen described herein, or a structurally similar antigen, may provide for stimulating production and/or proliferation of B lymphocytes that express a VH3-23/VK1-5 gene combination, which without intending to be bound by any particular theory, may provide for enhanced neutralizing antibodies against ZIKV, DENV1 and other related viruses.

An aspect of the disclosure is illustrated in FIG. 22. Data summarized in FIG. 22 show results of immunizing mice using the EDIII of flaviviruses as the immunogen. The antibody response to the EDIII lateral ridge region, which as discussed above is the neutralizing epitope recognized by antibody Z004, is enhanced if the immunization with the ZIKV EDIII is preceded by priming with the EDIII of DENV1 (Panel A). Moreover, this regimen results in antibodies with higher neutralization capacity (Panel B). This result is consistent with the observation that the lateral ridge represents a shared neutralizing epitope for both ZIKV and DENV1, and that individuals exposed to DENV1 are more likely to become high responders to ZIKV.

In certain implementations the invention includes antigens and segments thereof for use in vaccine formulations and diagnostic approaches. In non-limiting examples the ZEDIII polypeptide for use as antigen in vaccination comprises or consists of all or a contiguous or non-contiguous segment of the ZIKV EDIII sequence:

```
i)
                                        (SEQ ID NO: 117)
VSYSLCTAAFTFTKIPAETLHGTVTVEVQYAGTDGPCKVPAQMAVDMQTL
TPVGRLITANPVITESTENSKMMLELDPPFGDSYIVIGVGEKKITMWHRS
(ZIKV E protein residues 303-403);
```

and/or comprises or consists of all or a contiguous or non-contiguous segments of the DENV1 EDIII sequence:

```
ii)
                                        (SEQ ID NO: 118)
MSYVMCTGSFKLEKEVAETQHGTVLVQVKYEGTDAPCKIPFSSQDEKGVT
QNGRLITANPIVTDKEKPVNIEAEPPFGESYIVVGAGEKALKLSWFKK
(DENV1 E protein residues 297-394),
```

or sequences having from 80-99% identity with the sequence of i) and/or ii).

In embodiments a ZEDIII polypeptide of this disclosure optionally comprises at least one contiguous segment of ZEDIII comprising amino acids 305-311, 333-336, or 350-352 (and combinations thereof), and/or the segment optionally comprises one or more of ZEDIII amino acids L307, S306, T309, K394, A311, E393, T335, G334, A310, and D336, and/or the polypeptide comprises a segment of the DENV1 EDIII that includes an epitope that comprises amino acids M301, V300, T303, E384, T329, K385, S305, E327, G328, D330 DENV1 EDIII protein.

In certain approaches the disclosure includes vaccinating an individual using a composition described herein, and determining the presence, absence, and/or an amount of neutralizing antibodies produced in response to the vaccination. Thus, methods of determining and monitoring efficacy of a vaccination at least in terms of neutralizing antibody production are included. Determination of the neutralizing antibodies can be performed using any suitable approach, one of which includes a competitive ELISA assay as described herein. In an embodiment, subsequent to determining an absence of neutralizing antibodies, and/or an amount of neutralizing antibodies below a suitable reference value, the invention includes administering a composition disclosed herein to the individual. Subsequent administrations and measurements can be made to track the treatment efficacy and make further adjustments to treatment accordingly. In one embodiment the presence, absence and/or amount of ZIKV and/or DENV1 neutralizing antibodies is determined using a biological sample from a pregnant human female, and the determination of the antibodies is used in estimating risk of fetal complications, including but not necessarily a risk of the fetus developing microcephaly. In one approach, determining an absence of neutralizing antibodies, and/or an amount of neutralizing antibodies below a suitable reference value for a pregnant female is followed by administering a composition described herein for the purpose of inhibiting development of the fetal complications.

Antibodies and proteins of this disclosure can be detectably labeled and/or attached to a substrate. Any substrate and detectable label conventionally used in immunological assays and/or devices is included. In embodiments the substrate comprises biotin, or a similar agent that binds specifically with another binding partner to facilitate immobilization and/or detection and/or quantification of antibodies and/or viral proteins.

In embodiments the disclosure comprises immunological assays to, for example, characterize serologic activity against ZIKV or DENV1.

In embodiments any type of enzyme-linked immunosorbent (ELISA) assay can be used, and can be performed using polypeptides and/or antibodies of this disclosure for diagnostic purposes, and can include direct, indirect, and competitive ELISA assays, and adaptations thereof that will be apparent to those skilled in the art given the benefit of this disclosure.

In embodiments the disclosure provides for a competition ELISA using, for example, assay plates coated with any ZEDII protein described herein. Upon exposure of a patient sample, such as a blood or serum sample, patient antibodies to the lateral ridge (LR) epitope present on the ZEDII protein (if such patient antibodies are present) will bind to the ZEDII protein. Taking a labeled Z004 antibody as a non-limiting example of a detecting antibody, the presence in serum of antibodies to the LR-epitope will block binding of labeled Z004, whereas absence of (or less) patient antibodies to the LR-epitope will allow binding of labeled Z004, enabling detection. The concentration of Z004 blocking antibodies can then extrapolated from a standard curve.

In another embodiment an ELISA is conducted after serum blocking is performed. To perform such an assay, patient serum dilutions are incubated ('blocked') with saturating amounts of either wild type ZEDIII protein or with ZEDIII protein mutated as described herein, such as by alanine at the E393 and K394 residues. (Alternatively, DENV1 proteins can be adapted for similar use, and can include, for example, using DENV1 EDIII protein mutated at the E384 and/or K385 residues). Next, the remaining IgG binding to wild type ZEDIII is measured by ELISA and the $BT_{50}$ values (=50% of maximal binding titer, binding titer 50) for the samples blocked with ZEDIII wild type or with ZEDIII mutant proteins are determined. The shift in binding activity between the two blocking can be represented graphically as the $\Delta BT_{50}$ and is a measure of the amount of LR-epitope specific antibodies in the patient sample.

Any diagnostic result described herein can be compared to any suitable control. Further, any diagnostic result can be fixed in a tangible medium of expression and communicated to a health care provider, or any other recipient. In one aspect the disclosure comprises diagnosing an individual as infected with ZIKV and/or DENV1 and administering a composition of this invention to the individual.

In certain embodiments the disclosure includes one or more recombinant expression vectors encoding H and L chains of an antibody of this disclosure, cells and cell cultures comprising the expression vectors, methods comprising culturing such cells and separating antibodies from the cell culture, the cell culture media that comprises the antibodies, antibodies that are separated from the cell culture, and kits comprising the expression vectors encoding an antibody and/or a polypeptide of this disclosure. Products containing the antibodies and/or the polypeptides are provided, wherein the antibodies and/or the polypeptides are provided as a pharmaceutical formulation contained in one or more sealed containers, which may be sterile and arranged in any manner by which such agents would be suitable for administration to a human or non-human subject. The products/kits may further comprise one or more articles for use in administering the compositions.

The following Examples are intended to illustrate but not limit the invention.

Example 1

Serologic Responses to ZIKV in Brazil and Mexico

Individuals infected with pathogens display a spectrum of antibody responses ranging from low levels of non-neutralizing antibodies to high titers of neutralizing antibodies. To determine whether a population infected with ZIKV also displays a range of antibody responses we screened 405 individuals living in ZIKV epidemic areas for serum IgG capable of binding to ZIKV E Domain III (ZEDIII, FIG. 1A).

Nearly three hundred sera were obtained in November 2015, shortly after ZIKV was introduced in Salvador, Brazil, from participants who were enrolled in a prospective study in 2013 from Pau da Lima, an urban slum community within the city (Cardoso et al., 2015; Felzemburgh et al., 2014; Hagan et al., 2016). An additional 108 sera were from Santa Maria Mixtequilla, a rural town in Oaxaca, Mexico. ZIKV infections were documented by PCR in Santa Maria Mixtequilla at the time of sample collection in April of 2016. Dengue virus (DENV) is endemic at both sites. Sera obtained from the Pau da Lima cohort in 2010 following a DENV outbreak, but before the introduction of ZIKV into Brazil, served as non-ZIKV flavivirus-exposed control for background reactivity against ZIKV (Silva et al., 2016). ZIKV introduction was associated with a broad distribution of serologic reactivity against ZEDIII in both Brazilian and Mexican samples by ELISA (FIG. 1A).

To determine whether serologic reactivity to ZEDIII is associated with ZIKV neutralizing activity, we assessed the top 31 sera (black symbols in FIG. 1A) for neutralization of luciferase-expressing reporter viral particles (RVP) bearing ZIKV structural proteins (see Methods; FIG. 1B). Neutralizing titers, expressed as the reciprocal of the dilution resulting in a 50% reduction of the luciferase signal achieved in the absence of serum ($NT_{50}$), varied by over 2 logs indicating a broad range of humoral immune responses to ZIKV (FIG. 1B).

Human Monoclonal Antibodies to ZIKV

Figure 1:
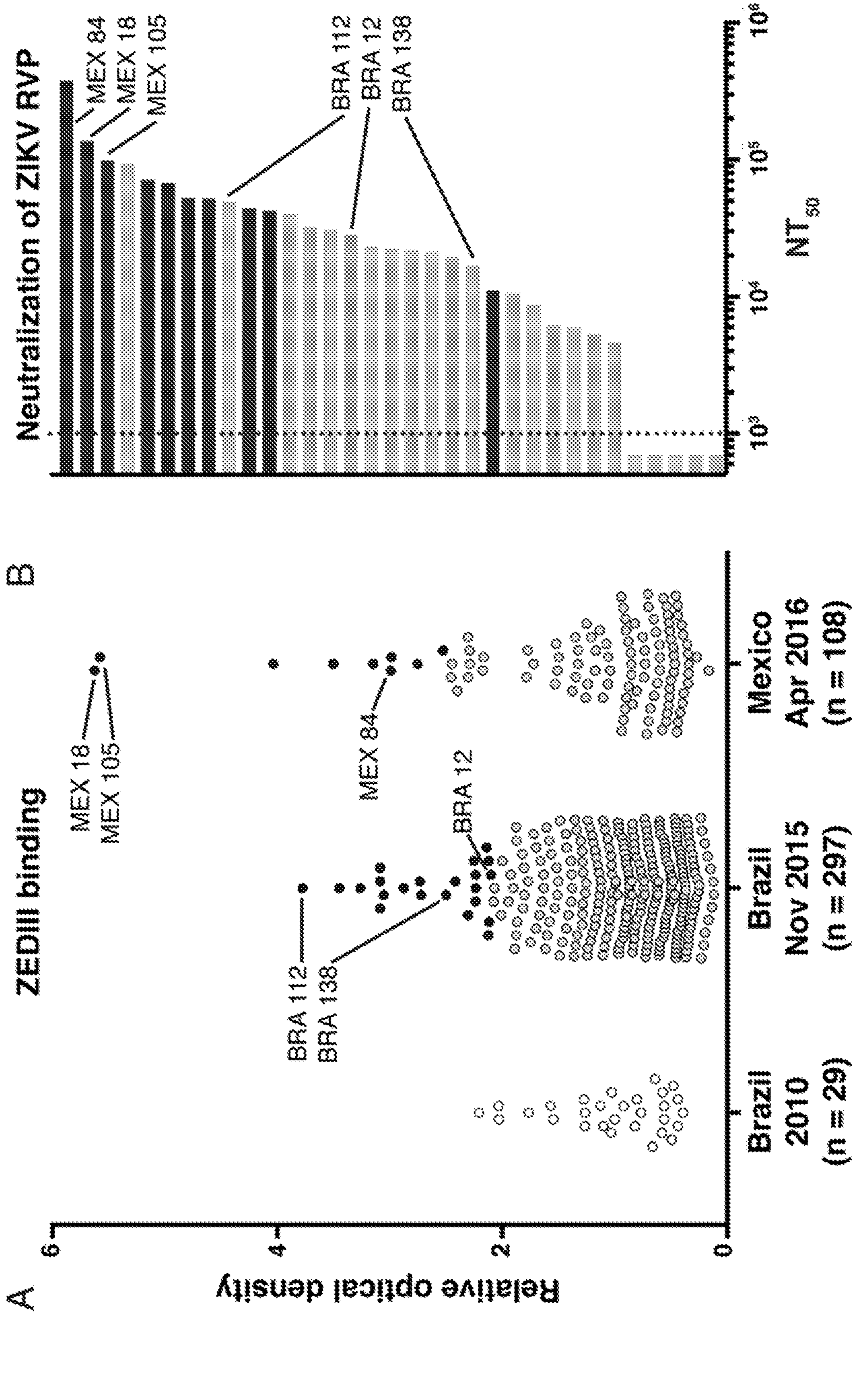
FIG. 1—Identification of individuals with high ZEDIII binding and neutralization capacity A—Sera from the Brazilian and Mexican cohorts were screened by ELISA for IgG antibodies binding to ZEDIII. Each dot represents an individual donor. Optical densities are normalized to control serum from a flavivirus naïve individual vaccinated for YFV. In black are sera selected for neutralization analysis. B—The neutralization capacity of selected sera from Mexico (dark grey) and Brazil (light grey) was determined by a ZIKV luciferase reporter viral particle (RVP) neutralization assay. The reciprocal of the serum dilution that resulted in 50% inhibition compared to RVP alone is reported as the 50% neutralization titer ($NT_{50}$). The dotted line indicates the lower limit of dilutions that were examined. The five samples below the dotted line have $NT_{50}$ values lower than $10^3$. Individuals from whom antibodies were sequenced and cloned are indicated.

To further characterize the antibody response in 6 individuals with high neutralizing titers, 3 from each cohort, we used fluorescently-labeled ZEDIII to identify and purify single memory B cells in the peripheral blood (FIG. 2A). ZEDIII-specific memory B cells were found at frequencies ranging from 0.13-1.98% of all circulating $IgG^+$ memory B cells (FIG. 2A, see Methods). Although the sample size is limited, the frequency of ZEDIII-specific memory B cells did not appear to correlate with either ZEDIII binding or neutralizing activity (FIG. 1). We conclude that there is significant variability in the frequency of ZEDIII-specific memory B cells in individuals that show serum ZIKV neutralizing activity.

Antibody heavy (IGH) and light (IGL) chain genes were amplified from single purified ZEDIII binding B cells by RT-PCR and sequenced (Scheid et al., 2009; von Boehmer et al., 2016). Overall, 290 antibodies were identified from the 6 individuals. Nearly one half of all of the antibodies (133) were found in expanded clones that shared the same IGH and IGL variable (IGVH and IGVL) gene segments, and the remaining half were unique (FIG. 2B and Tables 1 and 2).

Memory B cells expressing antibodies composed of VH3-23 paired with VK1-5 were found in 5 out of the 6 individuals assayed (FIG. 2B, and FIG. 8). Moreover, VH3-23/VK1-5 was present as an expanded clone in 4 individuals, and was the largest expanded clone in 3 out of the 6 individuals. The sequence of the VH3-23/VK1-5 antibodies in the expanded clones was further limited in that the VK1-5 gene segment was always recombined with JK1 (FIG. 2C). In addition to VH3-23/VK1-5 clones we also found expanded clones of memory B cells expressing antibodies composed of VH3-23 paired with other IGL genes (VH3-23/VK1-27, VH3-23/VK3-11 and VH3-23/VK3-20; FIG. 2B). Of the 6 individuals examined, only BRA 138, who exhibited the lowest level of neutralizing activity, did not have any detectable memory B cells expressing VH3-23/VK1-5 antibodies. We conclude that individuals with high serologic neutralizing titers to ZIKV in geographically distinct outbreak areas frequently show clonally expanded ZEDIII-specific memory B cells that express VH3-23/VK1-5 antibodies.

Cross-Reactivity with Other Flaviviruses

Nineteen representative antibodies obtained from expanded memory B cell clones from the 6 individuals were expressed for further testing. This antibody panel included 8 different VH3-23/VK1-5 antibodies from 5 separate volunteers. Antibody binding activity to ZEDIII was measured by ELISA, and found to vary broadly even among the closely related VH3-23/VK1-5 antibodies, with $EC_{50}$ values ranging from 20 to >4000 ng/ml (FIGS. 3A, 3B, and 9A). Like other human antibodies derived from memory B cells, anti-ZEDIII antibodies showed somatic mutations. For example, the number of IGH V gene mutations in the VH3-23/VK1-5 clones ranged from 12-40 nucleotides (average=27.7, FIG. 9B), which is far lower than that seen in antibodies during chronic HIV-1 infection (Escolano et al., 2017). Nevertheless, the mutations in anti-ZEDIII antibodies are essential to the binding activity of the antibodies since reversion of the mutations to the predicted germline sequence impaired binding to the antigen (FIG. 3B).

To determine whether the antibodies cloned from our cohorts cross-react to the EDIII proteins of other flaviviruses, we screened for binding to the four DENV serotypes (DENV1-4), YFV (Asibi and 17D strains), and WNV. We observed 5 different patterns of cross-reactivity with other flaviviruses (FIG. 3C). All 8 of the VH3-23/VK1-5 antibodies tested cross-reacted with DENV1, but not with the other flaviviruses in our panel (FIGS. 3C and 3D). Other antibodies showed singular cross-reactivity to WNV, or broader reactivity to DENV1-4, or YF and WNV, and some antibodies were uniquely specific for ZIKV (FIG. 3C). Similar to ZIKV, mutations in the VH3-23/VK1-5 antibodies were required for optimal binding to DENV1 EDIII since reversion to the predicted germline sequence impaired binding to the DENV1 antigen (FIG. 3D). We conclude that anti-ZEDIII VH3-23/VK1-5 antibodies cross-react with DENV1 but not with other flaviviruses.

Neutralizing Activity In Vitro and In Vivo

To determine whether the anti-ZEDIII antibodies neutralize ZIKV in vitro we measured their neutralizing activity in the ZIKV luciferase RVP assay described above. Neutralizing activity varied among the different antibodies ranging from sub-nanogram 50% inhibitory concentrations ($IC_{50}$) to non-neutralizing (FIGS. 4A, 4B and 10A). The most potent antibody, Z004, a member of one of the VH3-23/VK1-5 clones, displayed an $IC_{50}$ of 0.7 ng/ml (FIGS. 4A, 4B). Similar results were obtained by plaque reduction neutralization test (PRNT) using a Puerto Rican strain of ZIKV ($IC_{50}$ of 2.2 ng/ml, FIG. 10B). All of the other VH3-23/VK1-5 antibodies tested were also potent neutralizers of ZIKV with $IC_{50}$ values ranging from 0.7-4.6 ng/ml (FIG. 4A).

Z004 is a member of the VH3-23/VK1-5 family that cross-reacts with DENV1. To determine whether Z004 also neutralizes DENV1, we measured its neutralizing activity against DENV1 luciferase RVPs and by flow cytometry using authentic DENV1. We found that Z004 is a potent neutralizer of DENV1 in both assays ($IC_{50}$=1.6 ng/ml by luciferase assay, and $IC_{50}$=16.4 ng/ml by flow cytometry; FIGS. 4C and 10C). Thus, the VH3-23/VK1-5 antibody Z004 binds and neutralizes both ZIKV and DENV1.

To determine whether VH3-23/VK1-5 antibodies also neutralize ZIKV in vivo, we passively transferred Z004 to IFNAR1$^{-/-}$ mice one day before or one day after ZIKV infection (FIG. 4D). In 3 independent pre-exposure experiments, with a total of 14 mice infected with ZIKV in the presence of control antibody, we found that 93% developed clinical symptoms and 79% succumbed to infection. In contrast, pre-exposure prophylaxis with Z004 resulted in a significant reduction in disease symptoms and mortality. Only 12.5% of the Z004 group developed clinical symptoms and none died ($p<0.0001$ for both disease and survival; FIGS. 4E and 10D). Similar results were also obtained when the antibody was administered one day after infection ($p<0.0001$ for symptoms, $p=0.0027$ for survival; FIGS. 4F and 10D). We conclude that Z004 was protective and significantly reduced both symptoms and mortality when administered either before or after infection. Z004 also displayed a suitable profile of low poly- and auto-reactivity (FIG. 10E). Thus, VH3-23/VK1-5 antibodies have the potential for further pre-clinical evaluation.

VH3-23/VK1-5 Antibodies Recognize the Lateral Ridge of ZEDIII

There are only 2 contiguous amino acids that are uniquely shared between the EDIIIs of ZIKV and DENV1, and not by DENV2, DENV3, DENV4, WNV or YFV (E393 and K394 in ZIKV, E384 and K385 in DENV1; FIG. 4G). These 2 amino acids are found in the lateral ridge region of the ZEDIII, which is a region that is associated with virus interaction with cellular receptors (Mukhopadhyay et al., 2005). To determine whether these 2 amino acids are essential for interaction between VH3-23/VK1-5 antibodies and ZIKV, we made alanine substitutions in the context of the ZIKV RVPs and tested the recombinant RVPs for sensitivity to Z004-mediated neutralization. Although ZIKV RVPs bearing the E393A substitution remained sensitive to Z004, K394A mutant RVPs were resistant to the antibody (FIG. 4H). African ZIKV strains differ from others at position 393 carrying aspartic acid at this position. Similar to wild type Asian/American ZIKV RVPs, African ZIKV RVPs carrying D393 instead of E393 were sensitive to Z004, and Asian/American ZIKV RVPs with an E393D substitution were also efficiently neutralized (FIGS. 4G and I). Thus a shared epitope in the lateral ridge region could account for the finding that Z004 neutralizes ZIKV and DENV1, but not other flaviviruses.

Structures of ZIKV Antibodies/EDIII Complexes Reveal a Shared Binding Mode

To gain additional insights into the molecular basis of ZEDIII recognition by VH3-23/VK1-5 antibodies, we solved crystal structures of complexes of the antigen-binding fragment (Fab) of two antibodies isolated from different donors, Z006 and Z004, with ZIKV and DENV1 EDIII domains, respectively (FIG. 5). The Z006 Fab-ZEDIII and Z004 Fab-DENV1 EDIII structures showed a common mode of antigen recognition, as revealed by similar orientations of Fab $V_H$ and $V_L$ domains when the EDIII domains were superimposed (FIG. 5A). The Z006/Z004 Fab orientation is distinct from orientations in other crystallographically-characterized Fab/ZIKV and Fab/DENV1 EDIII complexes (FIG. 5B). The Z006 epitope extends over much of the EDIII lateral ridge (FIG. 5C): beyond the E393-$K394_{ZIKV}$ region, the next largest parts of the interface consist of the N-terminal region of EDIII (residues 305-$311_{ZIKV}$), CC' loop residues 350-$352_{ZIKV}$, and BC loop residues 333-$336_{ZIKV}$. The E393-$K394_{ZIKV}$ (E384-$K385_{DENV1}$) motif is central to the interface (FIG. 5C) and contacts residues within the Fab CDRH3, CDRL3, and CDRL1 loops in both structures (FIG. 5A, D-F). Despite the antibodies originating from different donors and binding to two different flavivirus EDIIIs, a number of contact interactions occur in both complexes (Table 6). Specifically, the side chain of residue $K394_{ZIKV}$ ($K385_{DENV1}$) occupies a hydrophobic pocket formed by $W32_{LC}$ and $Y91_{LC}$(Z006)/$F91_{LC}$(Z004) and forms an H-bond with the latter residue's backbone oxygen atom (FIG. 5D). The side chain of residue $E393_{ZIKV}$ ($E384_{DENV1}$) interacts with $R96_{HC}$, although this interaction differs somewhat in the two structures: in the Z006 structure, $E393_{ZIKV}$ forms an H-bond with the $Y91_{LC}$ hydroxyl and an electrostatic interaction with $R96_{HC}$, while for Z004, the side chain of residue $F91_{LC}$ lacks a hydroxyl group to form an H-bond, and instead the side chain of $E384_{DENV1}$ forms a salt bridge with $R96_{HC}$ (FIG. 5E). Other common interactions include the side chain of $Y58_{HC}$ forming an H-bond to the backbone oxygen of $L307_{ZIKV}$ ($M301_{DENV1}$) (FIG. 5F), and the side chain of $T93_{LC}$ (Z006)/$S93_{LC}$ (Z004) forming an H-bond to the backbone N of $T335_{ZIKV}$ ($T329_{DENV1}$). Hence the common mode of recognition involves using equivalent pairwise interactions as well as binding with a similar orientation.

Pre-Existing DENV1 Reactivity is Associated with Enhanced ZEDIII Antibody Responses The existence of VH3-23/VK1-5 antibodies that neutralize both DENV1 and ZIKV and are recurrently found in expanded clones suggests that prior exposure to DENV1 primes the development of protective ZIKV immunity. To examine this possibility, we tested sera obtained at time points before and after introduction of ZIKV in the Pau da Lima community in Salvador, Brazil. Anti-ZEDIII serum IgG reactivity increased significantly between April and November of 2015 (FIG. 6A). Interestingly, a similar increase was seen for DENV1, although there was no documented DENV1 outbreak in this area at this time, with only 5 DENV1 cases reported between September 2014 and July 2016 (FIG. 6A). In contrast, no significant increase in reactivity was observed for DENV2, DENV3, DENV4, YFV, or WNV EDIIIs (FIG. 6A). Consistent with the hypothesis that DENV1 primes the subsequent response to ZIKV, we observed a significant positive correlation between DENV1 EDIII-reactive IgG levels pre-ZIKV, and ZEDIII-reactive IgG levels post-ZIKV (Pseudo-$\rho$=0.48, $p<0.001$, FIG. 6B). Together, these data indicate that the exposure to ZIKV boosted the pre-existing DENV1 antibody response, and that individuals with pre-existing antibodies targeting the DENV1 EDIII are more likely to develop high levels of EDIII antibodies upon ZIKV infection.

Lateral Ridge Antibodies are Associated with ZIKV Neutralization

To determine whether antibodies to the lateral ridge region recognized by Z004 contribute to serologic activity against ZIKV in the Pau da Lima cohort, we developed a competition ELISA assay. In this assay we measure inhibition of biotin-Z004 binding to ZEDIII in order to quantify lateral ridge-binding antibodies present in serum (see Methods). Paired samples from April 2015 (before ZIKV) and November 2015 (after ZIKV) showed an increase in lateral ridge reactivity after ZIKV introduction (p=0.0007, FIG. 7A). Levels of antibodies present in the post-ZIKV serum that are capable of blocking Z004 binding to ZEDIII were directly correlated with the overall reactivity of antibodies to ZEDIII (Spearman coefficient, $\rho$=0.7319, $p<0.0001$ FIG. 7B), as well as with the increase in reactivity to ZEDIII from prior to after ZIKV ($\rho$=0.8190, $p<0.0001$, FIG. 7C). Finally, there was also a significant correlation between ZIKV neutralizing activity and total ZEDIII reactivity ($\rho$=0.5885, p=0.0012, FIG. 7D), as well as Z004 blocking activity ($\rho$=0.6585, p=0.0002, FIG. 7E). We conclude that antibodies that block Z004 binding to the lateral ridge make a measurable contribution to the overall serum neutralizing activity to ZIKV in exposed individuals.

Example 2

This Example provides a description of materials and methods used to obtain the results discussed above.

Experimental Model and Subjects Details

Human Subjects

Samples of peripheral blood were obtained upon consent from community participants of cohort studies in Pau da Lima (Brazil) and Santa Maria Mixtequilla (Mexico) under protocols approved by the ethical committees of the Rockefeller University (IRB DRO-0898), Yale University (IRB HIC 1603017508), FIOCRUZ (CAAE 63343516.1.0000.5028), Hospital Geral Roberto Santos (1.998.103), and National Institute of Respiratory Diseases (C16-16). Information regarding sex and age of study participants can be obtained upon request. Details on the size of the cohorts and time when samples were obtained is listed in the Results section of the manuscript.

Mice $IFNAR1^{-/-}$ mice were obtained from The Jackson Laboratory and bred and maintained in the AAALAC-certified facility of the Rockefeller University. Mice were specific pathogen free and maintained under a 12 hr light/dark cycle with standard chow diet. Both male and female mice (3-4 week old) were used for all experiments and were equally distributed within experimental and control groups. Animal protocols were in agreement with NIH guidelines and approved by the Rockefeller University Institutional Animal Care and Use Committee (16855-H).

Cell Lines

Human embryonic kidney HEK-293-6E suspension cells were cultured at 37'C in 8% $CO_2$, shaking at 120 rpm. All other cell lines described below were cultured at 37° C. in 5% $CO_2$, without shaking. Green monkey VERO cells and human hepatocytes Huh-7.5 cells (Blight et al., 2002) were cultured in Dulbecco's Modified Eagle Medium (DMEM) supplemented with 1% nonessential amino acids (NEAA) and 5% FBS. Human Lenti-X 293T cells (Clontech) and $STAT1^{-/-}$, an SV40 large T antigen immortalized skin fibroblast line (Chapgier et al., 2006), were grown in DMEM 10% FBS.

Bacteria

*E. coli* BL21(DE3) were cultured at 37° C., shaking at 250 rpm. MC1061 cells were cultured in LB medium, with 250 rpm shaking, at 30-37° C. depending on the plasmid.

Viruses

Zika virus (ZIKV), 2015 Puerto Rican PRVABC59 strain (Lanciotti et al., 2016), was obtained from the CDC and passaged once in $STAT1^{-/-}$ fibroblasts ($STAT1^{-/-}$-ZIKV stock, used in mouse experiments) or twice in Huh-7.5 cells (Huh-7.5-ZIKV stock, used in all other experiments). The Thai human isolate of DENV1 PUO-359 (TVP-1140) was obtained from Robert Tesh and amplified by three passages in C6/36 insect cells.

Method Details

Collection of Human Samples

Samples of peripheral blood for serum or mononuclear cells (PBMCs) isolation were obtained from community participants and donors and frozen at the cohorts' sites. PBMCs were purified using the gradient centrifugation method with Ficoll and cryopreserved in 90% heat-inactivated fetal bovine serum (FBS) supplemented with 10% dimethylsulfoxide (DMSO), prior to shipment to Rockefeller University in liquid nitrogen. Serum aliquots were heat-inactivated at 56° C. for 1 h and stored at 4° C. thereafter.

Production and Biotinylation of Flavivirus Protein

The coding sequences for the EDIII portion of flaviviruses were preceded by sequences encoding the human CD5 signal peptide (MPMGSLQPLATLYLLGMLVASCLG (SEQ ID NO: 119)) and followed by a polyhistidine-AviTag (SIH-GLNDIFEAQKIEWHE (SEQ ID NO: 120)). The following flavivirus sequences were used.

```
ZIKV (KJ776791):
                                        (SEQ ID NO: 121)
5'GTGTCATACTCCTTGTGTACCGCAGCGTTCACATTCACCAAGATCCCG

GCTGAAACACTGCACGGGACAGTCACAGTGGAGGTACAGTACGCAGGGAC

AGATGGACCTTGCAAGGTTCCAGCTCAGATGGCGGTGGACATGCAAACTC

TGACCCCAGTTGGGAGGTTGATAACCGCTAACCCCGTAATCACTGAAAGC

ACTGAGAACTCTAAGATGATGCTGGAACTTGATCCACCATTTGGGGACTC

TTACATTGTCATAGGAGTCGGGGAGAAGAAGATCACCCACCACTGGCACA

GGAGT.

DENV1 (codon-optimized based on NC_001477):
                                        (SEQ ID NO: 122)
5'ATGTCATATGTGATGTGTACGGGGTCCTTTAAACTTGAAAAGGAGGTG

GCAGAAACACAGCACGGAACAGTACTTGTGCAGGTTAAATATGAGGGAAC

CGATGCTCCTTGTAAAATACCGTTTTCAAGCCAGGACGAAAAGGGTGTAA

CACAAAATGGTCGCCTGATTACAGCCAACCCAATAGTCACTGATAAGGAG

AAACCTGTGAATATCGAGGCAGAGCCACCATTCGGCGAAAGTTATATCGT

AGTTGGTGCTGGAGAAAAGGCCCTGAAACTCTCTTGGTTTAAGAAG.

DENV2 (NC_001474):
                                        (SEQ ID NO: 123)
5'ATGTCATACTCTATGTGCACAGGAAAGTTTAAAGTTGTGAAGGAAATA

GCAGAAACACAACATGGAACAATAGTTATCAGAGTGCAATATGAAGGGGA

CGGCTCTCCATGCAAGATCCCTTTTGAGATAATGGATTTGGAAAAAAGAC

ATGTCTTAGGTCGCCTGATTACAGTCAACCCAATTGTGACAGAAAAAGAT

AGCCCAGTCAACATAGAAGCAGAACCTCCATTCGGAGACAGCTACATCAT

CATAGGAGTAGAGCCGGGACAACTGAAGCTCAACTGGTTTAAGAAA.

DENV3 (codon-optimized based on NC_001475.2):
                                        (SEQ ID NO: 124)
5'ATGTCATACGCAATGTGTACGAACACATTCGTTCTTAAAAAAGAGGTA

AGTGAAACCCAACATGGTACTATCCTTATAAAAGTTGAGTACAAGGGCGA

GGACGCTCCCTGCAAAATACCGTTTTCCACAGAGGACGGGCAAGGTAAGG

CACACAATGGGAGACTTATAACCGCCAATCCAGTAGTGACCAAGAAAGAG

GAACCAGTCAACATTGAAGCGGAGCCCCCTTTCGGAGAATCCAACATAGT

GATAGGCATTGGGGACAACGCTCTGAAGATCAACTGGTATAAGAAG.

DENV4 (codon-optimized based on NC_002640.1):
                                        (SEQ ID NO: 125)
5'ATGTCATATACAATGTGTAGCGGTAAATTCAGCATTGATAAAGAAATG

GCCGAGACACAGCACGGCACCACCGTGGTAAAAGTGAAATACGAAGGAGC
```

-continued

```
GGGAGCCCCGTGCAAGGTCCCCATCGAAATCAGGGATGTAAACAAAGAGA

AGGTCGTTGGTAGAATAATTTCTTCTACACCACTGGCCGAGAACACTAAT

ACTCAGTTACGAATATAGATTGAGCCCCCCTTTGGTGACAGCTATATAGT

CTATTGGCGTGGGAAATTCTGCATGACTCTGCATTGGTTCCGAAAA.

YFV (Asibi strain, KF769016):
                                        (SEQ ID NO: 126)
5'ACATCCTACAAAATGTGCACTGACAAAATGTCTTTTGTCAAGAACCCA

ACTGACACTGGCCATGGCACTGTTGTGATGCAGGTGAAAGTGCCAAAAGG

AGCCCCCTGCAAGATTCCAGTGATAGTAGCTGATGATCTTACAGCGGCAA

TCAATAAAGGCATTTTGGTTACAGTTAACCCCATCGCCTCAACCAATGAT

GATGAAGTGCTGATTGAGGTGAACCCACCTTTTGGAGACAGCTACATTAT

CGTTGGGACAGGAGATTCACGTCTCACTTACCAGTGGCACAAAGAG

YFV (17D strain, KF769015):
                                        (SEQ ID NO: 127)
5'ACATCCTACAAAATATGCACTGACAAAATGTTTTTTGTCAAGAACCCA

AACCTGACTGGCCATGGCACTGTTGTGATGCAGGTGAAAGTGTCAAAAGG

AGCCCCCTGCAGGATTCCAGTGATAGTAGCTGATGATCTTACAGCGGCAA

TCAATAAAGGCATTTTGGTTACAGTTAACCCCATCGCCTCAACCAATGAT

GATGAAGTGCTGATTGAGGTGAACCCACCTTTTGGAGACAGCTACATTAT

CGTTGGGAGAGGAGATTCACGTCTCACTTACCAGTGGCACAAAGAG.

WNV (KX547539.1):
                                        (SEQ ID NO: 128)
5'ACAACCTATGGCGTCTGTTCAAAGGCTTTCAAGTTTCTTGGGACTCCC

GCAGACACAGGTCACGGCACTGTGGTGTTGGAATTGCAGTACACTGGCAC

GGATGGACCTTGCAAAGTTCCTATCTCGTCAGTGGCTTCATTGAACGACC

TAACGCCAGTGGGCAGATTGGTCACTGTCAACCCTTTTGTTTCAGTGGCC

ACGGCCAACGCTAAGGTCCTGATTGAATTGGAACCACCCTTTGGAGACTC

ATACATAGTGGTGGGCAGAGGAGAACAACAGATCAATCACCACTGGCACA

AGTCT.
```

Gene synthesis was by Genscript. The proteins were produced by transient transfection into HEK-293-6E cells using PEI (polyethylenimine, branched). After 7 days of incubation, cell supernatants were cleared by centrifugation and histidine-tagged proteins were purified with Ni Sepharose 6 Fast Flow. Purified ZEDIII was biotinylated using the Biotin-Protein Ligase-BIRA kit according to manufacturer's instructions.

ELISA Assays

Serum and Recombinant Antibody

The binding of serum IgG or recombinant IgG antibodies to the EDIII proteins was measured by standard ELBA. ELISA plates were coated with 250 ng of EDIII protein in PBS per well and stored overnight at room temperature, Plates were then blocked with 1% BSA, 0.1 mM EDTA in PBS-T (PBS with 0.05% Tween20) for 1 h at 37° C. Plates were washed with PBS-T in between each step above. Serum samples were diluted 1:500 with PBS-T and added for 1 h at 37° C. Secondary HRP-conjugated goat anti-human IgG (0.16 μg/ml) was added for 1 h at 37° C. Plates were then developed using ABTS substrate and read at 405 nm. The relative binding affinity of recombinant monoclonal antibodies was determined similarly, using serially diluted samples. The half effective concentration ($EC_{50}$) needed for maximal binding was determined by non-linear regression analysis.

Cross-Reactivity ELISA

The binding of monoclonal antibodies to the panel of flavivirus EDIII proteins was determined using the standard ELISA setup described above. Antibodies were tested at 10 μg/ml alongside a control serum weakly cross-reactive to all flaviviruses. Samples with a relative optical density ratio of >1 compared to control were deemed reactive.

Auto- and Poly-Reactivity ELISA

To determine the auto- and poly-reactivity of recombinant antibodies, ELISA plates were coated with 500 PBS containing dsDNA ssDNA (10 μg/ml, obtained by denaturing dsDNA at 95° C. for 30 minutes), LPS (10 μg/ml), Insulin (5 μg/ml), or keyhole limpet hemocyanin (KLH; 10 μg/ml). After washing with PBS-T, plates were blocked with 1% BSA and 0.5 mM EDTA in 0.05% PBS-T for 2 h at room temperature. Serial dilutions of antibody samples were then incubated for 2 h, also at room temperature. Incubation with secondary antibody and ELISA development were performed as described above. Previously reported antibodies ED38 (Wardemann et al., 2003) and mG053 (Yurasov et al., 2005) were used as positive and negative control, respectively.

Competition ELISA

Competition ELISA was performed as described above for serum EDIII, binding, with the following modifications. After 1 h of incubation with serum (diluted 1:10 in PBS-T) at room temperature, biotinylated antibody 2004 (biotin-Z004) was added at a final concentration of 0.16 μg/ml to compete for an additional 15 min at room temperature. After washing, streptavidin-HRP was used for detection of bound biotin-Z004. The optimal concentration of biotin-Z004 (0.16 μg/ml) was determined by measuring its binding to ZEDIII over a range of concentrations, and corresponds to 50% of the observed maximal binding. The concentration of Z004 blocking antibodies in serum was estimated by interpolation with a standard curve generated by competing biotin-Z004 (0.16 μg/ml) with a range of non-biotinylated. Z004 concentrations, and using the stats package nls( ) function in R 3.3.2.

Antibody Discovery and Production

Isolation of $ZEDIII^+$ Memory B Cells

B cell purification, labeling and antibody discovery were performed as previously described in detail (Tiller et al., 2008; von Boehmer et al., 2016), with the following modifications. PBMCs were resuscitated and washed in 37° C. RPMI. To enrich for B cells, PBMCs were incubated with CD19 microbeads according to the manufacturer's instructions. Upon washing, B cells were positively selected using LS magnetic columns, washed with PBS 3% FBS, and incubated with anti-CD20-PECy7, anti IgG-APC, and fluorescently-labeled ZEDIII bait at 4° C. for 20 min. The fluorescently-labeled ZEDIII bait was previously prepared by incubating 2-3 μg of biotin-ZEDIII with streptavidin-PE for at least 1 h at 4° C. in the dark. After wash, single $CD20^+ZEDIII^+gG^+$ memory B cells were sorted into 96-well plates using a FACSAriaII (Becton Dickinson).

Antibody Sequencing and Production

RNA from single cells was reverse-transcribed using random primers (von Boehmer et al., 2016), followed by nested PCR amplifications and sequencing using the primers listed in (Tiller et al., 2008). V(D)J gene segment assignment and determination of the CDR3 sequences were with IgBlast (Ye et al., 2013). Sequences that were non-productive, out of frame, or with premature stop codons were excluded. Similarly, sequences for which a matching light or heavy chain sequence was not identifiable were omitted. Cloning for recombinant antibody production was by the Sequence and Ligation-Independent Cloning (SLIC; (Li and Elledge, 2007)) method as detailed in (von Boehmer et al., 2016). Amplicons from the first sequencing PCR reaction were used as template for amplification with the SLIC-adapted primers listed in Table 3, and cloned into IGγ1-, IGκ or IGλ-expression vectors as detailed in (von Boehmer et al., 2016). The recombinantly expressed antibodies correspond to the following antibody sequence IDs (see Tables 1 and 2): Z028 (MEX84_p4-53), Z001 (MEX18_21), Z004 (MEX18_89), Z006 (MEX105_42), Z010 (MEX105_88), Z031 (BRA112_46), Z035 (BRA112_71), Z038 (BRA12_2), Z014 (MEX18_91), Z039 (BRA12_21), Z015 (MEX84_p2-44), Z018 (MEX84_p2-45), Z021 (MEX84_p4-23), Z024 (MEX84_p4-12), Z012 (MEX105_57), Z037 (BRA112_57), Z041 (BRA138_57), Z042 (BRA138_17), Z043 (BRA138_15). The variable portion of the predicted germline antibody Z004-GL was codon-optimized, synthesized by Genscript, and cloned as described above (IGH 5'GAGGTGCAGCTGTTG-GAGTCTGGGGGAGGTCTTGTTCAGCCGGGTGGAT-CATT GAGACTTTCTTGTGCTGCAAGTGGATT-TACTTTCTCTTCCTACGCCATGTCTTGGG TTCGACAAGCTCCAGGGAAAGGACTCGAATGGGT-TAGTGCGATATCTGGGTCTG GAGGATCTACTTAC-TACGCAGATTCAGTAAAAGGGCGCTTCACAATAT-CACGCG ATAATTCCAAGAATACGCTCTACCTTCAGAT-GAACAGTCTTCGGGCAGAGGACAC AGCGGTTTAT-TATTGTGCGAAA-GATCGCGGTCCCAGAGGCGTGGGCGAACTGTTC GACTATTGGGGACAAGGCACCCTGGT-CACCGTCTCCTCAG (SEQ ID NO: 129) and IGK 5'GACATCCAGATGACCCAGTCACCGTC-TACCTTGTCAGCGTCAGTTGGTGACCGG GTAAC-CATTACTTGCCGCGCTAGTCAGAGTAT-TTCCTCCTGGCTCGCCTGGTATCA ACAAAAACCAGGTAAAGCCCCCAAATTGCTGATC-TATAAGGCAAGTAGCTTGGA ATCAG-GAGTTCCCAGCCGCTTCTCTGGCTCAGGGTCCG-GTACTGAATTTACATTG ACCATCTCTTCTCTCCAGCCAGATGACTTCGC-CACGTACTATTGTCAACAGTATA ACT-CATATCCCTGGACTTTTGGACAGGGGACCAAGGTG-GAAATCAAAC (SEQ ID NO: 130)). Recombinant antibodies were produced as previously described (Klein et al., 2014). Briefly, HEK-293-6E cells were transiently transfected with equal amounts of immunoglobulin heavy and light chain expression vectors. After 7 days, the supernatant was harvested and antibodies were purified with Protein G Sepharose 4 Fast Flow. For antibody biotinylation, 1.5 mg/ml of Z004 were used with FluoReporter Mini-biotin-XX Protein Labeling Kit as instructed by the manufacturer.

Mouse Experiments

All experiments involving mice were performed under protocols approved by the Rockefeller University Institutional Animal Care and Use Committee. 123 μg of monoclonal antibodies in 200 μl of PBS were administered intraperitoneally to 3-4 week old $IFNAR1^{-/-}$ mice one day prior or after infection with $1.25\times10^5$ PFU ZIKV Puerto Rican strain in 50 μl into the footpad. Mice were monitored for symptoms and survival over time.

Virus Titration

Viral titers were measured on VERO cells by plaque assay (PA) for ZIKV virus and focus forming assay (FFA) for DENV-1 strains. For PA, 200 μl of serial 10-fold virus dilutions in OPTI-MEM were used to infect 400,000 cells seeded the day prior in a 6-well format. After 90 minutes adsorption, the cells were overlayed with DMEM containing 2% FBS with 1.2% Avicel and Pen/Strep. Four days later the cells were fixed with 3.5% formaldehyde and stained with crystal violet for plaque enumeration. For FFA, 100 μl of serial 10-fold virus dilutions in OPTI-MEM were used to infect 250,000 cells seeded the day prior in a 12-well format. After 90 minutes, the cells were overlayed as described above for PA. Six to 7 days later the cells were fixed and incubated with 2 μg/ml of antibody Z004 in PBS/5% FBS/0.25% Triton X-100 for 1 h at room temperature. Foci were enumerated after reaction with goat anti-human IgG HRP-conjugated antibodies and TrueBlue HRP substrate, followed by addition of a few drops of DAB buffer solution (DAKO). Experiments with infectious ZIKV and DENV strains were performed in a biosafety level 2 laboratory.

Plaque Reduction Neutralization Test

Antibody neutralization activity was measured using a standard plaque reduction neutralization test (PRNT) on VERO cells. Diluent medium consisted of medium 199 (Lonza) supplemented with 1% BSA and Pen/Strep (BA-1 diluent). Briefly, 3- to 10-fold serial human antibody dilutions were added to a constant amount of Huh-7.5-ZIKV stock diluted in BA-1 diluent and incubated for 1 h at 37° C. prior to application to VERO cells seeded at 400,000 cells per 6-well the day prior. After 90 min adsorption at 37° C. the cells were overlayed as per PA protocol above. After 4 days at 37° C., the wells were fixed and stained to enumerate plaques. $PRNT_{50}$ values were determined as the antibody concentration that resulted in 50% of the number of plaques obtained with the no antibody control.

RVP Plasmid Construction

West Nile virus (WNV) subgenomic replicon-expressing plasmid pWNVII-Rep-REN-IB (Pierson et al., 2006) and a ZIKV C-prM-E expression plasmid (pZIKV/HPF/CprME) were obtained from Ted Pierson (NIH). Plasmid pWNVII-Rep-REN-IB encodes a *Renilla* luciferase-expressing WNV replicon RNA while pZIKV/HPF/CprME encodes the structural proteins (C-prM-E) of the ZIKV French Polynesian strain H/PF/2013, both under the control of a CMV promoter. Co-transfection of the two plasmids into permissive cells allows the WNV replicon RNA to replicate, express luciferase and be packaged by the ZIKV H/PF/2013 structural proteins to generate RVPs that can be used for single round infection studies (Mukherjee et al., 2014; Pierson et al., 2006). To facilitate expression of the envelopes of a wide range of ZIKV strains, plasmid pZIKV/HPF/CprME was engineered to have a unique BspHI restriction enzyme site immediately upstream of the envelope region by PCR-based site-directed mutagenesis of two other BspHI restriction sites located in the plasmid backbone. The resulting plasmid, pZIKV/HPF/CprM*E*, has unique BspHI and SacII restriction sites flanking the envelope region, allowing facile manipulation. PCR-based site-directed mutagenesis was used to introduce E393A or K394A mutations into the envelope of H/PF/2013 in pZIKV/HPF/CprM*E*, resulting in plasmids pZIKV/HPF/CprME(E393A) and pZIKV/HPF/CprME(K394A). We generated pZIKV/HPF-CprM/MR766-E by replacing the H/PF/2013 envelope in pZIKV/HPF/CprM*E* with that of the ZIKV African strain, MR766. Because the African strains contain a BspHI site within the E protein coding region, this site was mutated using assembly PCR prior to swapping in the MR766-based BspHI and SacII fragment. To generate pDENV1/PUO-359/CprME, DENV1 (strain PUO-359) virion RNA was isolated by TRIzol extraction (Thermo Fisher Scientific), cDNA generated using Superscript II reverse transcriptase (Thermo Fisher Scientific), and the C-prM-E region amplified by PCR. After PCR assembly with the upstream promoter and vector sequences, the corresponding region of pZIKV/HPF/CprME was replaced using SnaBI/SacII enzymes. PCR reactions utilized either PfuUltra Hotstart DNA Polymerase (Agilent technologies), Phusion High Fidelity DNA polymerase (NEB) or KOD DNA polymerase (Toyobo). All PCR-derived plasmid regions were verified by sequencing. Primer sequences used for assembly PCR and mutagenesis are listed in Table 4.

RVP Production

Reporter viral particles (RVPs) were produced in Lenti-X 293T cells, seeded the day before DNA transfection at $1\times10^6$ cells/well in collagen coated 6-well plates. One μg of pWNVII-Rep-REN-IB (WNV replicon expression construct) and 3 μg of the appropriate flavivirus CprME expression construct were co-transfected using Lipofectamine 2000 (Invitrogen) according to the manufacturer's instructions. Lipid—DNA complexes were removed after 4-5 h incubation at 37° C. and replaced with DMEM containing 20 mM HEPES and 10% FBS. After incubation for 48-72 h at 34° C., RVP-containing supernatants were harvested, filtered through a 0.45 micron filter and frozen at −80° C. RVPs were titrated on Huh-7.5 cells to determine the dilution to use in the RVP-based neutralization assay to achieve ~$2\text{-}5\times10^6$ RLU in the absence of serum/antibody.

RVP Neutralization Assay

The day before infection, 96-well plates were seeded with 15,000 Huh-7.5 cells/well in a volume of 100 μl. RVPs were diluted in BA-diluent (ranging from 1:4 to 1:32 depending on the RVP stock) and 100 μl were added to 100 μl of triplicate samples of 3- or 10-fold serially diluted human serum/antibody. After incubation for 1 h at 37° C., 100 μl of the RVP/antibody mixture was added to the cells. After 24 h incubation at 37° C., the medium was removed and cells were lysed in 75 μl lysis buffer and 20 μl used for *Renilla* luciferase measurement using the *Renilla* Luciferase Assay System (Promega) according to the manufacturer's instructions using a FLUOstar Omega luminometer (BMG LabTech). Neutralization capacity of the serum/antibody was determined by the percentage of luciferase activity obtained relative to activity from RVPs incubated with BA-diluent alone (no serum/antibody). $NT_{50}$ values represented the reciprocal of the serum dilution or the antibody concentration that resulted in 50% inhibition compared to RVP alone.

Flow Cytometry-Based Neutralization Assay

The day prior to infection 5,000 VERO cells/well were seeded in 96-well plates. Serial dilutions of antibody were mixed with ZIKV or DENV-1 virus for 1 h at 37° C. and then applied to infect cells, using an MOI of 0.02 for ZIKV and DENV-1. After 3 days, cells were fixed with 2% formaldehyde and permeabilized in PBS containing 1% FBS and 0.5% saponin. Cells were stained with 2 □g/ml of the pan flavivirus anti-E protein 4G2 monoclonal antibody (Henchal et al., 1982). After incubation with Alexa Fluor 488-conjugated anti-mouse IgG antibody (Invitrogen) at 1:1,000 dilution, the number of infected cells was determined by flow cytometry. The percentage of infected cells relative to cells infected with virus in the absence of antibody was calculated for each antibody dilution to estimate the 50% reduction.

Protein Production and Crystallization

His-tagged Fabs were transiently expressed in HEK-293-6E cells by co-transfecting with appropriate heavy and light chain plasmids. Fabs were purified from the supernatant using Ni-NTA affinity chromatography (GE Healthcare) and size exclusion chromatography (Superdex 200; GE Healthcare) in 20 mM Tris pH 8.0, 150 mM NaCl, 0.02% $NaN_3$. The Fabs were concentrated to 10-20 mg/mL for crystallography. Untagged constructs of ZEDIII and DENV1 EDIII were expressed in *E. coli* and refolded from inclusion bodies as previously described (Sapparapu et al., 2016). Briefly, BL21(DE3) *E. coli* were transformed with an appropriate expression vector encoding ZIKV E protein residues 299-407 (ZIKV EDIII, strain H/PF/2013) or DENV1 E protein residues 297-396 (DENV1 EDIII, strain clone 45AZ5). Cells were grown to mid-log phase and induced with isopropyl β-D-1-thiogalactopyranoside (IPTG) for 4 hours. The cells were lysed and the insoluble fraction containing inclusion bodies was solubilized in buffer containing 6M guanidine hydrochloride and 20 mM β-mercaptoethanol, and then clarified by centrifugation. The solubilized inclusion bodies were refolded using rapid dilution into 400 mM L-arginine, 100 mM Tris-base (pH 8.0), 2 mM EDTA, 0.2 mM phenylmethylsulfonyl fluoride, and 5 and 0.5 mM reduced and oxidized glutathione at 4° C. The refolded protein was filtered and concentrated, and then purified by size exclusion chromatography (Superdex 75; GE Healthcare) in 20 mM Tris pH 8.0, 150 mM NaCl, 0.02% $NaN_3$. Antigens were concentrated to 2-15 mg/mL for crystallography. Complexes for crystallization were produced by mixing Fab and antigen at a 1:1 molar ratio and incubating at room temperature for 1-2 hours. Crystals of Z006 Fab-ZEDIII complex (space group H32; a=385.08 Å, b=385.08 Å, c=56.64 Å, α=90°, β=90°, γ=120°; two molecules per asymmetric unit) were obtained by combining 0.2 μL of crystallization sample with 0.2 μL of 10% isopropanol, 0.1M sodium citrate tribasic dihydrate pH 5.0, 26% PEG 400 in sitting drops at 22° C. Crystals of Z004 Fab-DENV1 EDIII complex (space group $P4_32_12$; α=74.23 Å, b=74.23 Å, c=190.76 Å; one molecule per asymmetric unit) were obtained by combining 0.2 μL of crystallization sample with 0.2 μL of 0.1M sodium acetate trihydrate pH 4.5, 30% w/v PEG 1500 in sitting drops at 22° C.

Structure Determination and Refinement

X-ray diffraction data were collected at Stanford Synchrotron Radiation Lightsource (SSRL) beamline 12-2 using a Dectris Pilatus 6M detector. The data were integrated using Mosflm (Battye et al., 2011) and scaled using CCP4 (Winn et al., 2011) (Table 5). The Z006-ZEDIII complex structure (PDB ID 5VIG) was solved by molecular replacement with a Z006 unbound Fab structure (data not shown) and Zika EDIII (PDB ID 5KVG) as the search models using Phaser and Molrep (CCP4) and refined to 3.0 Å using an iterative approach involving (i) refinement in CNS and Phenix applying NCS constraints and (ii) manual rebuilding into electron density maps using O and AntibodyDatabase (Jones, 2004; West et al., 2013). The final model ($R_{work}$=21.2%; $R_{free}$=25.7%) contains 7,892 protein atoms and one citrate ion (12 atoms). 90.8, 7.6, and 1.6% of the residues were in the favored, allowed, and disallowed regions, respectively, of the Ramachandran plot (Table 5). Residues 1, 128-133, 214-219, and the 6×-His tag of the Z006 heavy chain; residue 214 of the LC; and residues 299-304 and 405-407 were disordered and are not included in the model. The Z004-DENV1 EDIII complex structure (PDB ID 5VIC) was solved by molecular replacement using the $V_HV_L$ (CDR residues removed) and $C_HC_L$ domains from PDB 3 SKJ and DENV1 EDIII from PDB 4L5F as search models in Phenix (Adams et al., 2010). The model was refined to 3.0 Å resolution using an iterative approach involving (i) refinement in Phenix and (ii) manual rebuilding into a simulated annealing composite omit map using Coot (Emsley and Cowtan, 2004). The final model ($R_{work}$=23.6%; $R_{free}$=28.1%) contains 3,904 protein atoms. 93.0%, 6.8%, and 0.2% of the residues were in the favored, allowed, and disallowed regions, respectively, of the Ramachandran plot (Table 5). Residues that were disordered and not included in the model were Fab HC residues 129-132, 215-219, and the 6×-His tag; LC residues 212-214; and DENV1 EDIII domain residues 315-317, 341-347, 373-374, and 393-396. Structures were superimposed, rmsd calculations done, and figures were generated using PyMOL. Hydrogen bonds were assigned using the following criteria: a distance of <3.5 Å, and an A-D-H angle of >90°.

Statistical Analysis Details

Unless otherwise noted, statistical analysis was with Prism software. The half effective concentration ($EC_{50}$) needed for maximal binding by ELISA was determined by non-linear regression analysis (FIG. 3A). Data are the average of at least two independent experiments. Similarly, luciferase- and flow cytometry-based neutralization assays were performed in triplicate wells, and the serum dilution ($NT_{50}$) or antibody concentration ($IC_{50}$) that neutralized 50% of the virus or RVP inoculum was calculated by nonlinear, dose-response regression analysis (FIG. 4A). The Mantel-Cox test was applied to analyze disease and survival in mice infection experiments (FIG. 4D-F). The Paired t test was used to analyze changes in sero-reactivity over time (FIGS. 6A and 7A). Univariate associations were assessed between log-relative optical densities of anti-ZEDIII antibodies at t=2 (November 2015) with log-relative optical densities of anti-DENV1 EDIII antibodies at t=1 (April 2015) using proc mixed in SAS v 9.4 (FIG. 6B). An individual-level random intercept was included to account for non-independence of the two replicated measurements. The two-tailed Spearman r test was used for the correlations in FIG. 7B-E.

References cited for the foregoing description and FIGS. 1-10. This reference listing is not an indication that any of the references are material to patentability of any invention encompassed by this disclosure Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta crystallographica Section D, Biological crystallography 66, 213-221.

Arnaout, R., Lee, W., Cahill, P., Honan, T., Sparrow, T., Weiand, M., Nusbaum, C., Rajewsky, K., and Koralov, S. B. (2011). High-resolution description of antibody heavy-chain repertoires in humans. PloS one 6, e22365.

Barba-Spaeth, G., Dejnirattisai, W., Rouvinski, A., Vaney, M. C., Medits, I., Sharma, A., Simon-Loriere, E., Sakuntabhai, A., Cao-Lormeau, V. M., Haouz, A., et al. (2016). Structural basis of potent Zika-dengue virus antibody cross-neutralization. Nature 536, 48-53.

Bardina, S. V., Bunduc, P., Tripathi, S., Duehr, J., Frere, J. J., Brown, J. A., Nachbagauer, R., Foster, G. A., Krysztof, D., Tortorella, D., et al. (2017) Enhancement of Zika virus pathogenesis by preexisting antiflavivirus immunity. Science.

Barzon, L., Pacenti, M., Franchin, E., Lavezzo, E., Trevisan, M., Sgarabotto, D., and Palu, G. (2016). Infection dynamics in a traveller with persistent shedding of Zika virus RNA in semen for six months after returning from Haiti to Italy, January 2016. Euro surveillance: bulletin Europeen sur les maladies transmissibles=European communicable disease bulletin 21.

Battye, T. G., Kontogiannis, L., Johnson, O., Powell, H. R., and Leslie, A. G. (2011). iMOSFLM: a new graphical interface for diffraction-image processing with MOSFLM. Acta crystallographica Section D, Biological crystallography 67, 271-281.
Beasley, D. W., and Barrett, A. D. (2002). Identification of neutralizing epitopes within structural domain III of the West Nile virus envelope protein. Journal of virology 76, 13097-13100.
Blight, K. J., McKeating, J. A., and Rice, C. M. (2002). Highly permissive cell lines for subgenomic and genomic hepatitis C virus RNA replication. Journal of virology 76, 13001-13014.
Brasil, P., Pereira, J. P., Jr., Moreira, M. E., Ribeiro Nogueira, R. M., Damasceno, L., Wakimoto, M., Rabello, R. S., Valderramos, S. G., Halai, U. A., Salles, T. S., et al. (2016). Zika Virus Infection in Pregnant Women in Rio de Janeiro. The New England journal of medicine 375, 2321-2334.
Cardoso, C. W., Paploski, I. A., Kikuti, M., Rodrigues, M. S., Silva, M. M., Campos, G. S., Sardi, S. I., Kitron, U., Reis, M. G., and Ribeiro, G. S. (2015). Outbreak of Exanthematous Illness Associated with Zika, Chikungunya, and Dengue Viruses, Salvador, Brazil. Emerging infectious diseases 21, 2274-2276.
Castanha, P. M., Nascimento, E. J., Cynthia, B., Cordeiro, M. T., de Carvalho, O. V., de Mendonca, L. R., Azevedo, E. A., Franca, R. F., Rafael, D., and Marques, E. T., Jr. (2016). Dengue virus (DENV)-specific antibodies enhance Brazilian Zika virus (ZIKV) infection. The Journal of infectious diseases.
Chapgier, A., Boisson-Dupuis, S., Jouanguy, E., Vogt, G., Feinberg, J., Prochnicka-Chalufour, A., Casrouge, A., Yang, K., Soudais, C., Fieschi, C., et al. (2006). Novel STAT1 alleles in otherwise healthy patients with mycobacterial disease. PLoS genetics 2, e131.
Costa, F., Sarno, M., Khouri, R., de Paula Freitas, B., Siqueira, I., Ribeiro, G. S., Ribeiro, H. C., Campos, G. S., Alcantara, L. C., Reis, M. G., et al. (2016). Emergence of Congenital Zika Syndrome: Viewpoint From the Front Lines. Annals of internal medicine 164, 689-691.
Crill, W. D., and Roehrig, J. T. (2001). Monoclonal antibodies that bind to domain III of dengue virus E glycoprotein are the most efficient blockers of virus adsorption to Vero cells. Journal of virology 75, 7769-7773.
Dai, L., Song, J., Lu, X., Deng, Y. Q., Musyoki, A. M., Cheng, H., Zhang, Y., Yuan, Y., Song, H., Haywood, J., et al. (2016). Structures of the Zika Virus Envelope Protein and Its Complex with a Flavivirus Broadly Protective Antibody. Cell host & microbe 19, 696-704.
Dejnirattisai, W., Supasa, P., Wongwiwat, W., Rouvinski, A., Barba-Spaeth, G., Duangchinda, T., Sakuntabhai, A., Cao-Lormeau, V. M., Malasit, P., Rey, F. A., et al. (2016). Dengue virus sero-cross-reactivity drives antibody-dependent enhancement of infection with zika virus. Nature immunology 17, 1102-1108.
DeKosky, B. J., Kojima, T., Rodin, A., Charab, W., Ippolito, G. C., Ellington, A. D., and Georgiou, G. (2015). In-depth determination and analysis of the human paired heavy- and light-chain antibody repertoire. Nature medicine 21, 86-91.
Ekiert, D. C., Bhabha, G., Elsliger, M. A., Friesen, R. H., Jongeneelen, M., Throsby, M., Goudsmit, J., and Wilson, I. A. (2009). Antibody recognition of a highly conserved influenza virus epitope. Science 324, 246-251.
Emsley, P., and Cowtan, K. (2004). Coot: model-building tools for molecular graphics. Acta crystallographica Section D, Biological crystallography 60, 2126-2132.
Escolano, A., Dosenovic, P., and Nussenzweig, M. C. (2017). Progress toward active or passive HIV-1 vaccination. The Journal of experimental medicine 214, 3-16.
Felzemburgh, R. D., Ribeiro, G. S., Costa, F., Reis, R. B., Hagan, J. E., Melendez, A. X., Fraga, D., Santana, F. S., Mohr, S., dos Santos, B. L., et al. (2014). Prospective study of leptospirosis transmission in an urban slum community: role of poor environment in repeated exposures to the Leptospira agent. PLoS neglected tropical diseases 8, e2927.
Foy, B. D., Kobylinski, K. C., Chilson Foy, J. L., Blitvich, B. J., Travassos da Rosa, A., Haddow, A. D., Lanciotti, R. S., and Tesh, R. B. (2011). Probable non-vector-borne transmission of Zika virus, Colorado, USA. Emerging infectious diseases 17, 880-882.
Franca, G. V., Schuler-Faccini, L., Oliveira, W. K., Henriques, C. M., Carmo, E. H., Pedi, V. D., Nunes, M. L., Castro, M. C., Serruya, S., Silveira, M. F., et al. (2016). Congenital Zika virus syndrome in Brazil: a case series of the first 1501 livebirths with complete investigation. Lancet 388, 891-897.
Hagan, J. E., Moraga, P., Costa, F., Capian, N., Ribeiro, G. S., Wunder, E. A., Jr., Felzemburgh, R. D., Reis, R. B., Nery, N., Santana, F. S., et al. (2016). Spatiotemporal Determinants of Urban Leptospirosis Transmission: Four-Year Prospective Cohort Study of Slum Residents in Brazil. PLoS neglected tropical diseases 10, e0004275.
Harrison, S. C. (2016). Immunogenic cross-talk between dengue and Zika viruses. Nature immunology 17, 1010-1012.
Heinz, F. X., and Stiasny, K. (2017). The Antigenic Structure of Zika Virus and Its Relation to Other Flaviviruses: Implications for Infection and Immunoprophylaxis. Microbiology and molecular biology reviews: MMBR 81.
Henchal, E. A., Gentry, M. K., McCown, J. M., and Brandt, W. E. (1982). Dengue virus-specific and flavivirus group determinants identified with monoclonal antibodies by indirect immunofluorescence. The American journal of tropical medicine and hygiene 31, 830-836.
Honein, M. A., Dawson, A. L., Petersen, E. E., Jones, A. M., Lee, E. H., Yazdy, M. M., Ahmad, N., Macdonald, J., Evert, N., Bingham, A., et al. (2017). Birth Defects Among Fetuses and Infants of US Women With Evidence of Possible Zika Virus Infection During Pregnancy. Jama 317, 59-68.
Jones, T. A. (2004). Interactive electron-density map interpretation: from INTER to O. Acta crystallographica Section D, Biological crystallography 60, 2115-2125.
Klein, F., Nogueira, L., Nishimura, Y., Phad, G., West, A. P., Jr., Halper-Stromberg, A., Horwitz, J. A., Gazumyan, A., Liu, C., Eisenreich, T. R., et al. (2014) Enhanced HIV-1 immunotherapy by commonly arising antibodies that target virus escape variants. The Journal of experimental medicine 211, 2361-2372.
Kostyuchenko, V. A., Lim, E. X., Zhang, S., Fibriansah, G., Ng, T. S., Ooi, J. S., Shi, J., and Lok, S. M. (2016). Structure of the thermally stable Zika virus. Nature 533, 425-428.
Kramer, L. D., Li, J., and Shi, P. Y. (2007). West Nile virus. The Lancet Neurology 6, 171-181. Lanciotti, R. S., Lambert, A. J., Holodniy, M., Saavedra, S., and Signor Ldel, C. (2016). Phylogeny of Zika Virus in Western Hemisphere, 2015. Emerging infectious diseases 22, 933-935.

Laursen, N. S., and Wilson, I. A. (2013). Broadly neutralizing antibodies against influenza viruses. Antiviral research 98, 476-483.

Lessler, J., Chaisson, L. H., Kucirka, L. M., Bi, Q., Grantz, K., Salje, H., Carcelen, A. C., Ott, C. T., Sheffield, J. S., Ferguson, N. M., et al. (2016). Assessing the global threat from Zika virus. Science 353, aaf8160.

Li, M. Z., and Elledge, S. J. (2007). Harnessing homologous recombination in vitro to generate recombinant DNA via SLIC. Nature methods 4, 251-256.

Miner, J. J., and Diamond, M. S. (2017). Zika Virus Pathogenesis and Tissue Tropism. Cell host & microbe 21, 134-142.

Modis, Y., Ogata, S., Clements, D., and Harrison, S. C. (2003). A ligand-binding pocket in the dengue virus envelope glycoprotein. Proceedings of the National Academy of Sciences of the United States of America 100, 6986-6991.

Mouquet, H., Scharf, L., Euler, Z., Liu, Y., Eden, C., Scheid, J. F., Halper-Stromberg, A., Gnanapragasam, P. N., Spencer, D. I., Seaman, M. S., et al. (2012). Complex-type N-glycan recognition by potent broadly neutralizing HIV antibodies. Proceedings of the National Academy of Sciences of the United States of America 109, E3268-3277.

Mukherjee, S., Pierson, T. C., and Dowd, K. A. (2014). Pseudo-infectious reporter virus particles for measuring antibody-mediated neutralization and enhancement of dengue virus infection. Methods in molecular biology 1138, 75-97.

Mukhopadhyay, S., Kuhn, R. J., and Rossmann, M. G. (2005). A structural perspective of the flavivirus life cycle. Nature reviews Microbiology 3, 13-22.

Murray, K. O., Gorchakov, R., Carlson, A. R., Berry, R., Lai, L., Natrajan, M., Garcia, M. N., Correa, A., Patel, S. M., Aagaard, K., et al. (2017). Prolonged Detection of Zika Virus in Vaginal Secretions and Whole Blood. Emerging infectious diseases 23, 99-101.

Murray, N. E., Quam, M. B., and Wilder-Smith, A. (2013). Epidemiology of dengue: past, present and future prospects. Clinical epidemiology 5, 299-309.

Pappas, L., Foglierini, M., Piccoli, L., Kallewaard, N. L., Turrini, F., Silacci, C., Fernandez-Rodriguez, B., Agatic, G., Giacchetto-Sasselli, I., Pellicciotta, G., et al. (2014). Rapid development of broadly influenza neutralizing antibodies through redundant mutations. Nature 516, 418-422. Pierson, T. C., and Graham, B. S. (2016). Zika Virus: Immunity and Vaccine Development. Cell 167, 625-631.

Pierson, T. C., Sanchez, M. D., Puffer, B. A., Ahmed, A. A., Geiss, B. J., Valentine, L. E., Altamura, L. A., Diamond, M. S., and Doms, R. W. (2006). A rapid and quantitative assay for measuring antibody-mediated neutralization of West Nile virus infection. Virology 346, 53-65.

Priyamvada, L., Quicke, K. M., Hudson, W. H., Onlamoon, N., Sewatanon, J., Edupuganti, S., Pattanapanyasat, K., Chokephaibulkit, K., Mulligan, M. J., Wilson, P. C., et al. (2016). Human antibody responses after dengue virus infection are highly cross-reactive to Zika virus. Proceedings of the National Academy of Sciences of the United States of America 113, 7852-7857.

Rey, F. A., Heinz, F. X., Mandl, C., Kunz, C., and Harrison, S. C. (1995). The envelope glycoprotein from tick-borne encephalitis virus at 2 A resolution. Nature 375, 291-298.

Rubelt, F., Sievert, V., Knaust, F., Diener, C., Lim, T. S., Skriner, K., Klipp, E., Reinhardt, R., Lehrach, H., and Konthur, Z. (2012). Onset of immune senescence defined by unbiased pyrosequencing of human immunoglobulin mRNA repertoires. PloS one 7, e49774.

Sabin, A. B. (1950). The dengue group of viruses and its family relationships. Bacteriological reviews 14, 225-232.

Sabin, A. B. (1952). Research on dengue during World War II. The American journal of tropical medicine and hygiene 1, 30-50.

Sapparapu, G., Fernandez, E., Kose, N., Bin, C., Fox, J. M., Bombardi, R. G., Zhao, H., Nelson, C. A., Bryan, A. L., Barnes, T., et al. (2016). Neutralizing human antibodies prevent Zika virus replication and fetal disease in mice. Nature 540, 443-447.

Scheid, J. F., Mouquet, H., Feldhahn, N., Walker, B. D., Pereyra, F., Cutrell, E., Seaman, M. S., Mascola, J. R., Wyatt, R. T., Wardemann, H., et al. (2009). A method for identification of HIV gp140 binding memory B cells in human blood. Journal of immunological methods 343, 65-67.

Scheid, J. F., Mouquet, H., Ueberheide, B., Diskin, R., Klein, F., Oliveira, T. Y., Pietzsch, J., Fenyo, D., Abadir, A., Velinzon, K., et al. (2011). Sequence and structural convergence of broad and potent HIV antibodies that mimic CD4 binding Science 333, 1633-1637.

Screaton, G., Mongkolsapaya, J., Yacoub, S., and Roberts, C. (2015). New insights into the immunopathology and control of dengue virus infection. Nature reviews Immunology 15, 745-759.

Silva, M. M., Rodrigues, M. S., Paploski, I. A., Kikuti, M., Kasper, A. M., Cruz, J. S., Queiroz, T. L., Tavares, A. S., Santana, P. M., Araujo, J. M., et al. (2016). Accuracy of Dengue Reporting by National Surveillance System, Brazil. Emerging infectious diseases 22, 336-339.

Sirohi, D., Chen, Z., Sun, L., Klose, T., Pierson, T. C., Rossmann, M. G., and Kuhn, R. J. (2016). The 3.8 A resolution cryo-EM structure of Zika virus. Science 352, 467-470.

Stettler, K., Beltramello, M., Espinosa, D. A., Graham, V., Cassotta, A., Bianchi, S., Vanzetta, F., Minola, A., Jaconi, S., Mele, F., et al. (2016). Specificity, cross-reactivity, and function of antibodies elicited by Zika virus infection. Science 353, 823-826.

Sui, J., Hwang, W. C., Perez, S., Wei, G., Aird, D., Chen, L. M., Santelli, E., Stec, B., Cadwell, G., Ali, M., et al. (2009). Structural and functional bases for broad-spectrum neutralization of avian and human influenza A viruses. Nature structural & molecular biology 16, 265-273.

Suy, A., Sulleiro, E., Rodo, C., Vazquez, E., Bocanegra, C., Molina, I., Esperalba, J., Sanchez-Seco, M. P., Boix, H., Pumarola, T., et al. (2016). Prolonged Zika Virus Viremia during Pregnancy. The New England journal of medicine 375, 2611-2613.

Swanstrom, J. A., Plante, J. A., Plante, K. S., Young, E. F., McGowan, E., Gallichotte, E. N., Widman, D. G., Heise, M. T., de Silva, A. M., and Baric, R. S. (2016). Dengue Virus Envelope Dimer Epitope Monoclonal Antibodies Isolated from Dengue Patients Are Protective against Zika Virus. mBio 7.

Throsby, M., van den Brink, E., Jongeneelen, M., Poon, L. L., Alard, P., Cornelissen, L., Bakker, A., Cox, F., van Deventer, E., Guan, Y., et al. (2008). Heterosubtypic neutralizing monoclonal antibodies cross-protective against H5N1 and H1N1 recovered from human IgM+ memory B cells. PloS one 3, e3942.

Tiller, T., Meffre, E., Yurasov, S., Tsuiji, M., Nussenzweig, M. C., and Wardemann, H. (2008). Efficient generation of monoclonal antibodies from single human B cells by single cell RT-PCR and expression vector cloning. Journal of immunological methods 329, 112-124.
von Boehmer, L., Liu, C., Ackerman, S., Gitlin, A. D., Wang, Q., Gazumyan, A., and Nussenzweig, M. C. (2016). Sequencing and cloning of antigen-specific antibodies from mouse memory B cells. Nature protocols 11, 1908-1923.
Wahala, W. M., and Silva, A. M. (2011). The human antibody response to dengue virus infection. Viruses 3, 2374-2395.
Wang, Q., Yang, H., Liu, X., Dai, L., Ma, T., Qi, J., Wong, G., Peng, R., Liu, S., Li, J., et al. (2016). Molecular determinants of human neutralizing antibodies isolated from a patient infected with Zika virus. Science translational medicine 8, 369ra179.
Wardemann, H., Yurasov, S., Schaefer, A., Young, J. W., Meffre, E., and Nussenzweig, M. C. (2003). Predominant autoantibody production by early human B cell precursors. Science 301, 1374-1377.
Weaver, S. C., Costa, F., Garcia-Blanco, M. A., Ko, A. I., Ribeiro, G. S., Saade, G., Shi, P. Y., and Vasilakis, N. (2016). Zika virus: History, emergence, biology, and prospects for control. Antiviral research 130, 69-80.
Weaver, S. C., and Reisen, W. K. (2010). Present and future arboviral threats. Antiviral research 85, 328-345.
West, A. P., Jr., Diskin, R., Nussenzweig, M. C., and Bjorkman, P. J. (2012). Structural basis for germ-line gene usage of a potent class of antibodies targeting the CD4-binding site of HIV-1 gp120. Proceedings of the National Academy of Sciences of the United States of America 109, E2083-2090.
West, A. P., Jr., Scharf, L., Horwitz, J., Klein, F., Nussenzweig, M. C., and Bjorkman, P. J. (2013). Computational analysis of anti-HIV-1 antibody neutralization panel data to identify potential functional epitope residues. Proceedings of the National Academy of Sciences of the United States of America 110, 10598-10603.
Winn, M. D., Ballard, C. C., Cowtan, K. D., Dodson, E. J., Emsley, P., Evans, P. R., Keegan, R. M., Krissinel, E. B., Leslie, A. G., McCoy, A., et al. (2011). Overview of the CCP4 suite and current developments. Acta crystallographica Section D, Biological crystallography 67, 235-242.
Wrammert, J., Koutsonanos, D., Li, G. M., Edupuganti, S., Sui, J., Morrissey, M., McCausland, M., Skountzou, I., Hornig, M., Lipkin, W. I., et al. (2011). Broadly cross-reactive antibodies dominate the human B cell response against 2009 pandemic H1N1 influenza virus infection. The Journal of experimental medicine 208, 181-193.
Ye, J., Ma, N., Madden, T. L., and Ostell, J. M. (2013). IgBLAST: an immunoglobulin variable domain sequence analysis tool. Nucleic acids research 41, W34-40.
Yurasov, S., Wardemann, H., Hammersen, J., Tsuiji, M., Meffre, E., Pascual, V., and Nussenzweig, M. C. (2005). Defective B cell tolerance checkpoints in systemic lupus erythematosus. The Journal of experimental medicine 201, 703-711.
Zhang, Y., Zhang, W., Ogata, S., Clements, D., Strauss, J. H., Baker, T. S., Kuhn, R. J., and Rossmann, M. G. (2004). Conformational changes of the flavivirus E glycoprotein. Structure 12, 1607-1618.
Zhou, T., Georgiev, I., Wu, X., Yang, Z. Y., Dai, K., Finzi, A., Kwon, Y. D., Scheid, J. F., Shi, W., Xu, L., et al. (2010). Structural basis for broad and potent neutralization of HIV-1 by antibody VRC01. Science 329, 811-81.

TABLE 1

MEX 84-refers to an individual donor. Sequences were analyzed with IgBlast

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| VH3-23/VK1-5 | MEX84_p2-02 | GGGLIQPGGTLRLSCAASGFSFTNYAMSWVRQAPGKGLEWVSAITGDGESTYYSDSVKGRFTISRDNSKNTLYLQMNSLTADDTALYYCAKDRPRQGVGELYDSWGQGTLVTVSS | 131 | IGHV3-23*01 | IGHD3-10*01 | IGHJ5*01 | AKDRPRQGVGELYDS | 171 | SASVGDRVTITCRASQSIGSWLAWYQQKPGKAPKLLIYTASILESGVPSRFSGSGSGTEFTLTINSLQPDDFATYYCQKFNSVPWTFGPGTKVEVK | 211 | IGKV1-5*03 | IGKJ1*01 | QKFNSVPWT | 251 |
| | MEX84_p2-49 | GGGLVQPGGSLRLSCAASGFTFSAYAMSWVRQAPGKGLEWVSSISVQSDSTYFADSVKGRFTISRDNSKNTLYLQMNSLRAEDTALYYCAKDRLEKGIGELFHSWGQGTLVTVSS | 132 | IGHV3-23*01 | IGHD3-10*01 | IGHJ5*01 | AKDRLEKGIGELFHS | 172 | SASLGDRVTITCRASQSISPWLAWYQQKPGKAPKFLIYQTSILESGVPSRFSGSGSGTEFTLTISSLQPDDFATYYCQHYHSYPWTFGQGTKVEIK | 212 | IGKV1- | IGKJ1*5*03 | QHYHSY01 | 252PWT |
| | MEX84_p4-18 | GGGLVQPGGSLRLSCAASGFTFSAYAMSWVRQAPGKGLEWVSGISVQSDSTYLADSVKGRFTTSRDNSKNTLYLQMNSLRVEDTALYYCAKDRLRQGVGELFHSWGQGTLVTVSS | 133 | IGHV3-23*01 | IGHD3-10*01 | IGHJ502 | AKDRLRQGVGELFHS | 173 | SASIGDRVTITCRASQSISPWLAWYQQKPGKAPKFLIYQTSILESGVPSRFSGSGSGTEFTLTISSLQPDDLATYYCQHYHSYPWTFGQGTKVEIK | 213 | IGKV1-5*03 | IGKJ1*01 | QHYHSYPWT | 253 |
| | MEX84_p4-19 | GGGLVQPGGSLRLSCAASGFTFGAYAMSWVRQAPGKGLEWVSSISVHSDSTYYADSVRGRFTISRDNSKNTLYLQMN | 134 | IGHV3-23*01 | IGHD3-10*01 | IGHJ4*01 | AKDRLREGVGELYQY | 174 | SASVGDRVTITCRASQNISPWLAWYQQKPGKAPKFLIYQTSILESGVPSRFSGSGSGTDFTLTISSLQPDDFATY | 214 | IGKV1-5*03 | IGKJ1*01 | QHYHSYPWT | 254 |

TABLE 1-continued

| | | | | | | | | | | | | | |
|---|---|---|---|---|---|---|---|---|---|---|---|---|---|
| | | SLRAEDTALYYCAKDRLREGVGELYQYWGHGTLVTVSS | | | | | | | YCQHYHSYPWTFGQGTKVEIK | | | | | |
| | MEX84_p4-53? | GGGLVQPGGSLRLSCAASGFTFSAYAMSWVRQAPGKGLEWVSSINGHSDSTYFADSVKGRFTISRDNSKNTLYLQMNSLRAEDTALYYCAKDRLREGIGELFHSWGQGTLVTVSS | 135 | IGHV3-23*01 | IGHD3-10*01 | IGHJ5*02 | AKDRLREGIGELFHS | 175 | SASIGDRVTITCRASQSITPWLAWYQQKPGKAPKFLIYQTSILESGVPSRFSGSGSGTEFTLTISSLQPDDFATYYCQHYHSYPWTFGQGTKVEIK | 215 | IGKV1-5*03 | IGKJ1*01 | QHYHSYPWT | 255 |
| | MEX84_p4-89 | GGGLVQPGGSLRLSCAGSGFTFSSFAMSWVRQAPGKGLEWVSTITGIGGDTYYTDSVKGRFTVSRDNSKKTVFLHMNSLRAEDTAVYYCAKDRDHFDGHDVWGQGTMVTVSS | 136 | IGHV3-23*01 | IGHD1-14*01 | IGHJ3*01 | AKDRDHFDGHDV | 176 | SASVGGRVTITCRASQSISSWLAWYQQKPGKAPKLLISKASNLESGVPSRFSGGGSETEFTLTISSLQPDDFATYYCQRYDSYPFTFGPGTKVTIK | 216 | IGKV1-5*03 | IGKJ3*01 | QRYDSYPFT | 256 |
| VH1-2/VK3-20 | MEX84_p2-13 | GAGVKKPGASVKVSCKASGYIFSDYYMQWVRQAPGQGLQWMGWINPKSGFTNYAQKFQGRVTMTRDTSISTAYMELTGLTSDDTAIYYCARGGPVNAPRGFDPWGQGTLVTVSS | 137 | IGHV1-2*02 | IGHD3-22*01 | IGHJ5*02 | ARGGPVNAPRGFDP | 177 | SLSPGERATLSCRASQEIGSFSLGWYQQKFGQPPRLLIYGASSRATGIPDRFSGSGSGTDFTLTISRLEPEDVAVYYCQQYVSSPLTFGGGTKVEIK | 217 | IGKV3-20*01 | IGKJ4*01 | QQYVSSPLT | 257 |
| | MEX84_p2-15 | GAGVKIPGASVKVSCKASGYIFSDYYMQWVRQAPGQGLEWMGWINPKSGFSDYAQKFQGRVSMTRDTAISTAYMELTRLTSDDTA | 138 | IGHV1-2*02 | IGHD1-26*01 | IGHJ5*02 | ARGGPVNSPLGFDP | 178 | SLSPGDRATLSCRASQSIGSFSLAWYQQKFGHAPRLLIYGASSRATGIPDRFSGSGSDTDYTLTISRLEPEDFAVYYCQQYVSS | 218 | IGKV3-20*01 | IGKJ4*01 | QQYVSSPLT | 258 |

TABLE 1-continued

| | | | | | | | | | | | | | |
|---|---|---|---|---|---|---|---|---|---|---|---|---|---|
| | VYYCARGGPV<br>NSPLGFDPW<br>GQGTLVTVSS | | | | | | | PLTFGGGTK<br>VEIK | | | | | |
| MEX84_p2-<br>45 | GPGVKKPGAS<br>VKVSCKASGY<br>IFSDYYILWV<br>RQAPGQGLE<br>YMGWMNPIS<br>GFTHYAQNF<br>QGRVTMTRD<br>TSISTAYMEL<br>TRLASDDTA<br>VYYCARGGRI<br>NSPLGFDPW<br>GQGTLVTVSS | 139 | IGHV1-<br>2*02 | IGHD1-<br>26*01 | IGHJ5*<br>02 | ARGGR<br>INSPLG<br>FDP | 179 | SLSPGERAT<br>SCRASQSIS<br>TFSLAWYQQ<br>KFGQAPRLL<br>IYGASSRATG<br>IPDRFSGSGS<br>GTDFTLTISR<br>LEPEDFAVY<br>YCQQYVSSP<br>LTFGGGTKV<br>EIR | 219 | IGKV3-<br>20*01 | IGKJ4*<br>01 | QQYVSS<br>PLT | 259 |
| MEX84_p2-<br>51 | GAEVKKPGAS<br>VKVSCKVSGY<br>TFTGYYMQW<br>VRQAPGQGL<br>EWMGWINP<br>KTGHTNFAQ<br>KFQGRVTMT<br>RDTSISTAYM<br>ELARLTSDDT<br>AVYFCARGG<br>QISAPHGFDP<br>WGQGTLVTV<br>SS | 140 | IGHV1-<br>2*02 | IGHD5-<br>24*01 | IGHJ5*<br>02 | ARGGQ<br>ISAPHG<br>FDP | 180 | SLSPGERAT<br>LSCRASQSVS<br>SIHLGWYQQ<br>KPGQAPRLL<br>IYGASSRATG<br>IPDRFSGSGS<br>GTDFTLTISR<br>LEPEDFAVY<br>YCQQYGSSP<br>LTFGGGTKV<br>EIK | 220 | IGKV3-<br>20*01 | IGKJ4*<br>01 | QQYGSS<br>PLT | 260 |
| MEX84_p2-<br>58 | GAGMRKPGA<br>SVKVSCKASG<br>YSFNDYYIH<br>WVRQAPGQG<br>LEWMGWINP<br>KSGFTNYAQ<br>RFQGRVTMT<br>GDTSNSVAY<br>MELTRLTSD<br>DTAVYYCAR<br>GGRINAPLGF<br>DPWGQGTLV<br>TVSS | 141 | IGHV1-<br>2*02 | IGHD2-<br>8*01 | IGHJ5*<br>02 | ARGGR<br>INAPLG<br>FDP | 181 | SLSPGETAT<br>LSCRASQSIG<br>SISLGWYQQ<br>KFGQAPRLL<br>IYGASTRAT<br>GTPDRFSGS<br>GSETDFTLTI<br>SRLEPEDSA<br>VYYCQQYVS<br>SPLRFGGGT<br>KVEIK | 221 | IGKV3-<br>20*01 | IGKJ4*<br>01 | QQYVSS<br>PLR | 261 |
| MEX84_p4-<br>65 | GAEVKKPGAS<br>VKVSCKVSGY<br>TFSDYYMQW<br>VRQAPGQGL<br>EWMGWINP<br>KTGHTNFAQ<br>KFQGRVTVT<br>RDTSITTAYM<br>ELRTLTSDDT<br>AVYFCARGGP<br>ISAPLGFDPW<br>GQGTLVTVSS | 142 | IGHV1-<br>2*02 | IGHD6-<br>6*01 | IGHJ5*<br>02 | ARGGPI<br>SAPLGF<br>DP | 182 | SLSPGERAT<br>LSCRASQSVS<br>SIHLAWYQQ<br>RPGQAPRLL<br>INGASSRAT<br>GIPDRFSGSG<br>SGTDFTLTIS<br>RLEPEDFAV<br>YYCQQYGSS<br>PLTFGGGTK<br>VEIK | 222 | IGKV3-<br>20*01 | IGKJ4*<br>01 | QQYGSS<br>PLT | 262 |

TABLE 1-continued

| | | | | | | | | | | | | | | |
|---|---|---|---|---|---|---|---|---|---|---|---|---|---|---|
| | MEX84_p4-91 | GAEVKKPGASVKVSCKASAYSFTDYYIHWVRQAPGQGLQWMGWINPDSGEVNYVQKFQDRVTMTRGTSISTAYMELRRLRSDDTAVYYCARAAMNRISGVVPPGDAFDLWGQGTLVTVSS | 143 | IGHV1-2*02 | IGHD1-14*01 | IGHJ3*01 | ARAAMNRISGVVPPGDAFDL | 183 | SLSPGERATLSCRASQSLSSNYLAWYQQKPGQAPRLLIYGASSRATGIPDRFSGSGSGTDFTLTISRLEPEDFAVYYCQQYGSSRGTFGQGTKVEIK | 223 | IGKV3-20*01 | IGKJ1*01 | QQYGSSRGT | 263 |
| VH1-46/VK3-20 | MEX84_p2-44 | GAEVKKPGASVKLSCKSSGYSFTSYYMHWVRQAPGQGLEWMGIINPSGVFTSYAQRFQGRVTMTSDTATSTVYMELSSLRSGDTAVYYCTRSLVTPAAQSVQYFDSWGQGTLITVSS | 144 | IGHV1-46*01 | IGHD2-2*01 | IGHJ4*02 | TRSLVTPAAQSVQYFDS | 184 | SLSPGERATLSCRASQSVSLSFLAWYQQKPGQAPRLLIYGASNRATGIPDRFSGSGSGTDFTLTISRLEPGDFAVYYCQQYGSSPLTFGPGTKVDIK | 224 | IGKV3-20*01 | IGKJ3*01 | QQYGSSPLT | 264 |
| | MEX84_p2-55 | GAEVKKPGASVKLSCKASGYTFTSYYVHWVRQAPGQGLEWMGIINPGNNFVSFAQNFYDRATMTRDTSTNTVYMELTNLQSEDTAVYYCARTLVAPSAQSMYYFDFWGQGTLVTVSS | 145 | IGHV1-46*01 | IGHD2-8*02 | IGHJ4*02 | ARTLVAPSAQSMYYFDF | 185 | SLSPGERGTLSCRASQYITTGHFAWYQQKPGRAPRLLIYGASVRATGVPDRFSGSGAETDFTLTISRLDPEDVGVYYCQQYGSSPVTFGPGTKVEIK | 225 | IGKV3-20*01 | IGKJ3*01 | QQYGSSPVT | 265 |
| | MEX84_p4-33 | GSEVKKPGASVKLSCKASGYTFTSYYIHWVRQAPGQGLEWVGVINPGNVFTSYAQRFHDRVTMTRDTSTSTVYMEMSSLRSEDTAVYYCTRTQVVPSAQSVYYFDFWGQGTLVTVSS | 146 | IGHV1-46*01 | IGHD2-15*01 | IGHJ4*02 | TRTQVVPSAQSVYYFDF | 186 | SLSPGERATLSCRASQNIGLDYFAWYQQKPGQAPRLLIYGASIRATGIPDRFSGSGSGTDFTLTISRLVPEDIAVYYCQQYGSSPVTFGPGTKVEVK | 226 | IGKV3-20*01 | IGKJ3*01 | QQYGSSPVT | 266 |

TABLE 1-continued

| | | | | | | | | | | | | | | |
|---|---|---|---|---|---|---|---|---|---|---|---|---|---|---|
| | MEX84_p4-68 | GAEVKKPGTSVKVSCKASGYTFTSYYIHWVREAPGQGLEWVGIINPGNTFTSYAPRFHGRVSMTRDTSTSTVYMELSSLRSEDTAVYYCTRTRVVPSAQSVYYFDFWGQGTLVTVSS | 147 | IGHV1-46*01 | IGHD3-3*01 | IGHJ4*02 | TRTRVVPSAQSVYYFDF | 187 | SLSPGERATLSCRASQSVTSGYFAWYQHKPGQAPRLLIYGASIRATGIPDRFSGSESGTDFTLTISRLEPEDVAVYYCQQYGSSPVTFGPGTKVDIK | 227 | IGKV3-20*01 | IGKJ3*01 | QQYGSSPVT | 267 |
| | MEX84_p4-85 | GAEVKKPGASVKVSCKTSGFTFTSYYIHWVRQAPGQGLEWMGFINPTSGFTSYTQNLHGRVTMTRDTSTRTVFMELRSLASGDTAVYYCTRTQIIPAAQSVYFFDYWGPGTLVTVSS | 148 | IGHV1-46*01 | IGHD2-2*01 | IGHJ4*02 | TRTQIIPAAQSVYFFDY | 188 | SLSPGERATLSCRASQFVISGHFAWYQQKPGQAPRLLIYGTSNRATGIPDRFSGSESGADFTLTISRLEPEDFAVYFCQQYGSSPPTFGPGTKVDIK | 228 | IGKV3-20*01 | IGKJ3*01 | QQYGSSPPT | 268 |
| | MEX84_p4-92 | GAEVAKPGTSVKVSCKASGYTFTSYYIHWVRQAPGQGLEWVGIINPGGAFTSYAQRFHGRVRMTRDTSASTVYVELSSLRSDDTAVYYCTRTRIIAAAQSVYHYDLWGQGTLVTVSS | 149 | IGHV1-46*01 | IGHD6-6*01 | IGHJ5*02 | TRTRIIAAAQSVYHYDL | 189 | SLSPGDRATLSCRASQHITTGHFAWYQQKPGQAPRLLIYGASIRASGIPDRFSGSGSGTDFSLTISRLEPEDCAVYYCQQYGSSPVTFGPGTKVDIK | 229 | IGKV3-20*01 | IGKJ3*01 | QQYGSSPVT | 269 |
| VH1-46/VK1-39 | MEX84_p2-21 | GAEVKKPGASVKVSCKASGYTFSSYYIHWVRQAPGQGLEWMGIIKPSSGSTNYAHKFQDRVTMTTDTSTSTVYMELSSLRYQDTAVYYCARAQDPATAIRGLRWEYWGQGSLVTVSS | 150 | IGHV1-46*01 | IGHD2-21*02 | IGHJ4*02 | ARAQDPATAIRGLRWEY | 190 | SASVGDRVTITCRASQSIDTYLNWYQQKPGKVPAILIYAASSLQSGVPSRFSGSGSGTDFTLTINSLQPEDFATYYCQQSYITPLTFGGGTKVEIK | 230 | IGKV1-39*01 | IGKJ4*01 | QQSYITPLT | 270 |

TABLE 1-continued

| | | | | | | | | | | | | | |
|---|---|---|---|---|---|---|---|---|---|---|---|---|---|
| MEX84_p4-16 | GAEVKKPGASVKVSCKASGYTFTTYFIHWVRQAPGQGLEWMGIINPNSGSTNYAQKIQGRVTMTTDTSASTVYMELSGLRSEDTAVYYCARGGSYPVAIRGVTFGIWGQGTMVTVSS | 151 | IGHV1-46*01 | IGHD2-2*02 | IGHJ3*02 | ARGGSYPVAIRGVTFGI | 191 | SASVGDRVTITCRASQSISNYLNWYQQKPGKAPNLLIFATSSLQSGVPSRFSGSGSGTDFTLTISSLQPEDFATYYCQQSFSTPLTFGGGTKVEIR | 231 | IGKV1-39*01 | IGKJ4*01 | QQSFSTPLT | 271 |
| MEX84_p4-41 | GAEVKKPGASVRVSCKASGYTFTSYYMHWVRQAPGQGLEWMGIINPSSGSTSYAQKLHDRVTMTRDTSTSTVYMEMSSLRSEDTAVYYCARGAAYPTAIRGVIYGFWGQGTMVTVSS | 152 | IGHV1-46*01 | IGHD2-2*02 | IGHJ3*01 | ARGAAYPTAIRGVIYGF | 192 | SASVGDRVTITCRASQSISTYLNWYQQKPGKAPKLLIFAASTLQSGVPSRFSGSGSGTEFTLTITSLQPADFAIYYCQQSYISPLTFGGGTKVEIN | 232 | IGKV1-39*01 | IGKJ4*01 | QQSYISPLT | 272 |
| MEX84_p4-80 | GAEVKKPGASVKISCKASADTFTKNYVHWVRQAPGQGLEWMGIINPSSGWTSNPQKFQGRVTMTRDTSTSTVYMELSSLRSDDTALYYCATSPAAAGSGHPSGWFDPWGPGTLVTVSS | 153 | IGHV1-46*01 | IGHD6-13*01 | IGHJ5*02 | ATSPAAAGSGHPSGWFDP | 193 | SASVGDRVTITCRASQSIINYLNWYQQKPGKAPKLLIYTASSLQSGVPSRFSGSGSGTSFTLTIISLQPEDFAIYYCHQSFSAPYTFGQGTKLEIK | 233 | IGKV1-39*01 | IGKJ2*01 | HQSFSAPYT | 273 |
| MEX84_p4-82 | GAEMKKPGASVKVSCQASGYSFTNHFIHWVRQAPGQGLEWMGTINPSGGSTTFAQKFQGRVTMTRDTSTSTVYMELSSLRSEDTAVYYCARPPGRSFLDGMDVWGQGTTVTVSS | 154 | IGHV1-46*01 | IGHD2-21*01 | IGHJ6*02 | ARPPGRSFLDGMDV | 194 | SASVGHRVTITCRASQSISSYLNWYQQKPGKAPKLLIFAASSLQSGVPSRFSGSGSGTDFTLTINSLQPGDFATYYCQQSYSTPLSFGQGTRVEIK | 234 | IGKV1-39*01 | IGKJ1*01 | QQSYSTPLS | 274 |

TABLE 1-continued

| | | | | | | | | | | | | | |
|---|---|---|---|---|---|---|---|---|---|---|---|---|---|
| VH4-34/VL2-32 | MEX84_p2-68 | GAGLLKTSETLYLTCTVYGDSFNHYYWGWIRQPPGKGLEWLGEINHRGTTNYNPSLKSRVSILVDTSQKQFSLRVTSVTAADTSVYYCTRVRWDGIEFTMFFDSWGQGSLVTVSP | 155 | IGHV4-34*01 | IGHD3-3*01 | IGHJ4*02 | TRVRWDGIEFTMFFDS | 195 | PASVSGSPGQSITIYCSGSSSDVGSYNLVSWYQQHPGKAPKLIIYGVTRRPSGVSSRFSGSKSGNTASLTFSGLQVEDDADYYCCSYANSGTFVFGTGTKVTV | 235 | IGLV2-23*02 | IGLJ1*01 | CSYANSGTFV | 275 |
| | MEX84_p2-76 | GAGLLKTSETLYLTCTVYGDSFNHYYWGWIRQPPGKGLEWLGEINHRGTTNYNPSLKSRVSILVDTSHKQFSLRVTSVTAADTSVYYCARVRWDGIESTMFFDSWGQGSLVTVSP | 156 | IGHV4-34*01 | IGHD5-12*01 | IGHJ4*02 | ARVRWDGIESTMFFDS | 196 | PASVSGSPGQSITIYCSGSSSDVGSYNLVSWYQQHPGKAPKLIIYGVTRRPSGVSSRFSGSKSGNTASLTFSGLQVEDDADYYCCSYANSGTFVFGTGTKVTV | 236 | IGLV2-23*02 | IGLJ1*01 | CSYANSGTFV | 276 |
| | MEX84_p2-83 | GAGLLKTSETLYLTCTVYGDSFNHYYWGWIRQPPGKGLEWLGEINHRGTTNYNPSLKSRVSILVDTSQKQFSLRVTSVTAADTSVYYCTRVRWDGIESTMFFDSWGQGSLVTVSP | 157 | IGHV4-34*01 | IGHD5-12*01 | IGHJ4*02 | TRVRWDGIESTMFFDS | 197 | PASVSGSPGQSITIYCSGSSSDVGSYNLVSWYQQHPGKAPKLIIYGVTRRPSGVSSRFSGSKSGNTASLTFSGLQVEDDADYYCCSYANSGTFVFGTGTKVTV | 237 | IGLV2-23*02 | IGLJ1*01 | CSYANSGTFV | 277 |
| VH4-34/VK-3-20 | MEX84_p4-30 | GARPLKPSETLSLTCGVNGGSFSGYHWSWIRQPPGKGLEWIGEIDHNGRINYNPSLKSRVTISIDTFKSQFSLRLTSIIAADTAVYYCARDVVTMVEGLRFHYYYNYYGMDVWGQGTPVTVSS | 158 | IGHV4-34*01 | IGHD3-10*01 | IGHJ6*02 | ARDVVTMVEGLRFHYYYNYYGMDV | 198 | SLSPGDRATLSCGASQSVSSNYLAWYQQKLGQAPRLLIYAASTRATGIPDRFSGGGSGTDFTLTINKLEAEDFAMYYCQIYDSSVRTFGQGTKVEIK | 238 | IGKV3-20*01 | IGKJ1*01 | QIYDSSVRT | 278 |
| | MEX84_p4-37 | GARPLKPSETLSLTCGVNGGSFSGYHWTW | 159 | IGHV4-34*01 | IGHD3-10*01 | IGHJ6*02 | ARDVVTMVEGLRFHY | 199 | SLSPGDRATLSCRASQSVSSNYLAWYQ | 239 | IGKV3-20*01 | IGKJ1*01 | QIYDSSVRT | 279 |

TABLE 1-continued

| | | | | | | | | | | | | | | |
|---|---|---|---|---|---|---|---|---|---|---|---|---|---|---|
| | | IRQPPGKGLEWIGEIDHNGRINYNPSLKSRVTISIDTFKSQFSLRLTSITAADTAIYYCARDVVTMVEGLRFHYYYNYYGMDVWGQGTPVTVSS | | | | | YYNYYGMDV | | QKLGQAPRLLIYGASTRATGIPDRFSGGGSGTDFTLTINKLEAEDFAVYYCQIYDSSVRTFGQGTKVEIK | | | | | |
| | MEX84_p4-57 | GARPLKPSETLSLTCGVNGGSFSGYHWSWIRQPPGKGLEWIGEIDHNGRINYNPSLKSRVTMSIDTFKSQFSLRLTSITAADTAVYYCARDVVTMVEGLRFHYYYNYYGMDVWGQGTPVTVSS | 160 | IGHV4-34*01 | IGHD3-10*01 | IGHJ6*02 | ARDVVTMVEGLRFHYYYNYGMDV | 200 | SLSPGDRATLSCGASQSVSSNYLAWYQQKLGQAPRLLIYGASTRATGIPDRFSGGGSGTDFTLTINKLEAEDFAMYYCQIYDSSLRTFGQGTKVEIK | 240 | IGKV3-20*01 | IGKJ1*01 | QIYDSSLRT | 280 |
| VH4-59/VK 3-11 | MEX84_p4-10 | GPGLVKPSETLSLTCTVSGGSISTYYWSWIRQTPGKGLEWIGCIYYSVDTHFNPSLESRVTISVDTSKNQFSLKMTSMTAADTAVYYCARNQPGGRAFDYWGPGTLVTVSS | 161 | IGHV4-59*01 | IGHD3-16*01 | IGHJ4*02 | 201 | ARNQPGGRAFDY | SLSPGQRATLSCRASQSVSNYFAWYQQKPGQAPRLLIYDTSKRATGTPARFSGSGSGTDFTLTISSLEPEDFAVYYCQERNNWPLTWTFGLGTKVEIK | 241 | IGKV3-11*01 | IGKJ1*01 | QERNNWPLTWT | 281 |
| | MEX84_p4-23 | GPGLVKPSETLSLTCTVSGGSIDTYYWSWIRQTPGKGLEWIGCFYYSVDNHFNPSLESRVTISVDTSKNQFSLKMTSMTASDTAVYYCARNQPGGRAFDYWGPGTLVTVSS | 162 | IGHV4-59*01 | IGHD3-16*01 | IGHJ4*02 | ARNQPGGRAFDY | 202 | SLSPGQRATLSCRASQSVSNYFAWYQQKPGQAPRLLIYDTSKRATGTPARFSGSGSGTDFTLTISSLEPEDFAVYYCQERNNWPLTWTFGLGTKVEIK | 242 | IGKV3-11*01 | IGKJ1*01 | QERNNWPLTWT | 282 |
| VH5-51/VK 1-39 | MEX84_p2-11 | GAEVKKPGESLRISCKTSGYTFTSHWLAWVRQMPGKGL | 163 | IGHV5-51*03 | IGHD2-15*01 | IGHJ6*02 | ARHDGRGYCSPTRCFFSGMD | 203 | SASVGDRVTITCRASQSISNYLNWYQQKPGKAPNLL | 243 | IGKV1-39*01 | IGKJ1*01 | QQTDRTPLT | 283 |

TABLE 1-continued

| | | | | | | | | | | | | | | |
|---|---|---|---|---|---|---|---|---|---|---|---|---|---|---|
| | | EWMGIIYPGDSDTRYSPSFQGQISISADKSINTAYLQWSSLKASDTAIYYCARHDGRGYCSPTRCFFSGMDVWGQGTTVIVSP | | | | | V | | IYAASSLQSGVPSRFSGSGSGTDFTLTISSLQPEDYAIYYCQQTDRTPLTFGQGTKVEIK | | | | | |
| | MEX84_p4-12 | GAEVRKPGESLRISCKTSGYTFTSHWVAWVRQMPGKGLEWMGIIYPGDSDTRYSPSFQGQISISADKSINTAYLQWSSLKASDTGIYYCARHDGRGYCSPTRCFFSGMDVWGQGTTVIVSP | 164 | IGHV5-51*03 | IGHD2-15*01 | IGHJ6*02 | ARHDGRGYCSPTRCFFSGMDV | 204 | SASVGDRVTITCRASQSISNYLNWYQQKPGKAPNLLIYAASSLQSGVPSRFSGSGSGTDFTLTISSLQPEDYAIYYCQQTDRTPLTFGQGTKVEIK | 244 | IGKV1-39*01 | IGKJ1*01 | QQTDRTPLT | 284 |
| VH1-2/VK1-39 | MEX84_p2-38 | GAEVKKPGASVRVSCKASGYTFSDYYVHWLRQAPGQRLEWMGWINANTGGSDSGPKFYGRVTLTRDTSVNTAYMELSRLRSDDTAVYFCARRTYYDNRFPYWYFDLWGRGTLVTVSS | 165 | IGHV1-2*02 | IGHD3-16*01 | IGHJ2*01 | ARRTYYDNRFPYWYFDL | 205 | SASVGDRVTITCRASQSIGKYLNWYQQKPGLAPEVLISGATTLQSGVPSRFSGSGSETDFTLTINSLQPEDLATYVCQQSISAPYTFGPGTKLEIK | 245 | IGKV1-39*01 | IGKJ2*01 | QQSISAPYT | 285 |
| | MEX84_p4-61 | GAEVKKPGASVKVSCKASGYTFSGYYIHWLRQAPGQGLEWMGWINSNSGGADSGPRFHGRVTMTRDTSINTAYLELTNLRSDDTAVYYCARRTYYDTRFPYWYFDLWGRGTLVTVSS | 165 | IGHV1-2*02 | IGHD3-22*01 | IGHJ2*01 | ARRTYYDTRFPYWYFDL | 206 | SASVGDRVTITCRASQDIGSYLNWYQQKPGKAPNVLISAASTLQSGVPSRISGIGSGTDFTLTISSLQPEDFATYYCQQSLSAPYTFGQGTKLEIK | 246 | IGKV1-39*01 | IGKJ2*01 | QQSLSAPYT | 286 |
| VH1-69/VK3-15 | MEX84_p2-53 | GAEVKKPGSSVKVSCKASGGTFSSYAIIWV | 167 | IGHV1-69*05 | IGHD2-8*02 | IGHJ4*02 | ARSWGTAATGGSFVQ | 207 | SVSPGERATLSCRASHSVTSNLAWYQ | 247 | IGKV3-15*01 | IGKJ2*01 | QYYTNWPPHVA | 287 |

TABLE 1-continued

| | | | | | | | | | | | | | | |
|---|---|---|---|---|---|---|---|---|---|---|---|---|---|---|
| | | RQAPGQGLEWMGGIIPIFGTTNYAQKFRGRVTIATDASKSAAYMDLSSLKSEDTAIYYCARSWGTAATGGSFVQWGQGTLVTVSS | | | | | | | QKPGQAPRLLIYGASTRATGIPARFSGSGSGTEFTLTISSLQSEDSAVYYCQYYTNWPPHVAFGQGTKLEIK | | | | | |
| | MEX84_p4-34 | GAEVKTPGSSVKVSCKTSGGTFSNFAITWVRQAPGQGLEWMGGIIPLFGITNYTQKFQGRVTITTDESKTTAYMDLSGLRSEDTAVYFCARGRDSSGRLLDHWGQGTLVTVSS | 168 | IGHV1-69*13 | IGHD2-21*02 | IGHJ5*02 | ARGRDSSGRLLDH | 208 | SVSPGERATLSCRASQTVNRNLAWYQQKPGQAPRLLIYAASARATGVPARFSGSGSGTEFTLTISSLQSEDFAVYYCQQYNNWPPLTFGGGTKVEIK | 248 | IGKV3-15*01 | IGKJ4*01 | QQYNNWPPLT | 288 |
| VH1-2/VK1-5 | MEX84_p2-94 | GAEVKKPGASVKVSCKASGNTFMGYYFHWVRQAPGQGLEWMGWINPNSGHANIAQTFQGRVTMTRDPSITTAYMELSRLRSDDTAVFYCARGGMLGQLWALDNWGQGTLVTVSS | 169 | IGHV1-2*02 | IGHD6-13*01 | IGHJ4*02 | ARGGMLGQLWALDN | 209 | SASVGDRVTITCRASQSISHWLAWYQQRPGEAPKLLIYQASTLESGVPSRFSGSGSGTEFTLSISSLQPDDFATYYCQQYQSSPYTFGQGTKLEIK | 249 | IGKV1-5*03 | IGKJ2*01 | QQYQSSPYT | 289 |
| | MEX84_p4-54 | GAEVKRPGASVKVSCKASGYTFADYYIHWVRQAPGLGLEWMGWINPKTGFSHYEQTFQGRVTMARDTSIPAAYMELSSLKSDDTAIYYCARGGRINVAEALRYWGQGSLVIVSS | 170 | IGHV1-2*02 | IGHD2-21*01 | IGHJ4*02 | ARGGRINVAEALRY | 210 | STFVGDRVTITCRASQTIGDWLAWYQQKPGKAPKLLISKATRLESGVPSRFSGSGSETEFSLTINSLQPDDVAAYYCQQYMSYPWTFGQGTKVEIK | 250 | IGKV1-5*03 | IGKJ1*01 | QQYMSYPWT | 290 |

TABLE 1-continued

MEX 18-refers to an individual donor. Sequences were analyzed with IgBlast

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| VH3-23/VK 1-5 | MEX18_07 | GGGLVQPGGSLRLSCAASGFTFSSYAMNWVRQAPGKGLEWVSGIGGRGAIAGDGSIYYADSVKGRFTISRDNSKNTLYLQMNGLRVEDTAVYYCAKDRVAFDGFHVWGQGTTVTVSS | 291 | IGHV3-23*01 | none | IGHJ3*01 | AKDRVAFDGFHV | 315 | SASVGDRVTITCRASQSISSWLAWYQQKPGKAPKLLIYKASSLESGVPSRFSGSGSGTEFSLTISSLQPDDFATYYCQQYNSYPWTFGQGTKVEIK | 339 | IGKV1-5*03 | IGKJ1*01 | QQYNSYPWT | 363 |
| | MEX18_15 | GGGLIQPGGSLRLSCSASGFTFSSYAMSWVRQAPGKGLEWVSGISPLDGSTYYAASVKGRFTISRDNSKNTLFLQMNSLRVEDTAIYYCAKDRLTMGVGELFVDWGPGTLVSVSS | 292 | IGHV3-23*01 | IGHD3-10*01 | IGHJ1*01 | AKDRLTMGVGELFVD | 316 | SASVGDRVTITCRASQNINSWLAWYQQKPGKAPKFLIYQASTLQNGVPSRFSGSGSGTEFTLTISSLQPDDFATYYCQHYYSYPWTFGQGTKVEIK | 340 | IGKV1-5*03 | IGKJ1*01 | QHYYSYPWT | 364 |
| | MEX18_21 | GGGLVQPGGSRRLSCATSGFSFDTYAMSWLRQAPGKGLEWVSSFSGLDDSTYYADSVKGRFTISRDNSKNTLYLQMNSLRAEDTAIYYCAKDRGPRGIGELFDFWGQGTLVSVSS | 293 | IGHV3-23*01 | IGHD3-10*01 | IGHJ4*02 | AKDRGPRGIGELFDF | 317 | SASVGDRVTITCRASQSISRWLAWYQQKPGKAPKLLIYKTSTLKSEVPSRFSGSGSGTEFTLTISSLQPDDFATYYCQHFHSVPWTFGQGTKVEIK | 341 | IGKV1-5*03 | IGKJ1*01 | QHFHSVPWT | 365 |
| | MEX18_24 | GGGLVQPGGSLRLSCVTSGFSFDTYALSWVRQAPGKGLEWVSSFSGIDDSTYYTESVKGRFTMSRDNSKSTLFLQMN | 294 | IGHV3-23*01 | IGHD5-24*01 | IGHJ4*02 | SKDRGPRGVGELFDS | 318 | SASVGDRVTITCRASQSISKWLAWYQQKPGKAPKLLIYTTSTLKSGVPSRFSGSGSGTEFTLTISSLQPDDFATY | 342 | IGKV1-5*03 | IGKJ1*01 | QHFYSVPWT | 366 |

TABLE 1-continued

| | | | | | | | | | | | | | |
|---|---|---|---|---|---|---|---|---|---|---|---|---|---|
| | GLRAEDTAMYYCSKDRGPRGVGELFDSWGQGTLVIFSS | | | | | | | YCQHFYSVPWTFGQGTKVEIK | | | | | |
| MEX18_27 | GGGLVQPGGSLRLSCATSGFTFSTYAMSWVRQAPGKGLEWVSSFSGVDDSTYYAESVKGRFTISRDNSKNTVYLQMTRLRAEDTAVYYCAKDRGPRGVGELFDSWGQGTLVTVSS | 295 | IGHV3-23*01 | IGHD3-10*01 | IGHJ4*02 | AKDRGPRGVGELFDS | 319 | SASVGDRVTMTCRASQSINRWLAWYQQKPGKAPKLLIYTTSTLKSGVPSRFSGSGSGTEFTLTISSLQPDDFATYYCQHFHSVPWTFGQGTKVEIK | 343 | IGKV1-5*03 | IGKJ1*01 | QHFHSVPWT | 367 |
| MEX18_36 | GGGLVRPGGSLTLTCATSGFTFSDYAMSWVRQAPGKGLEWVSSYSGIDDSTYYADSVKGRFTISRDNSKRTLSLHMNSLRAGDSALYYCAKDRGPRGVGELFDSWGPGTLVTVSS | 296 | IGHV3-23*01 | IGHD3-10*01 | IGHJ4*02 | AKDRGPRGVGELFDS | 320 | SASVGDRVTITCRASQSISKWLAWYQQKPGKAPKLLIYTTSTLKSGVPSRFSGSGSGTEFTLTISSLQPDDFATYYCQHFYSVPWTFGQGTKVEIK | 344 | IGKV1-5*03 | IGKJ1*01 | QHFYSVPWT | 368 |
| MEX18_38 | GGGLVQPGGSLRLSCAASGFTFSDYAMGWVRQAPGKGLEWLSSMTRTGDNLYYADSVKGRFTISRDNSKNTLYLQMSSLRVEDTAIYFCAKDRLPEGFGKLFDYWGQGTLVTVST | 297 | IGHV3-23*01 | IGHD3-10*01 | IGHJ4*02 | AKDRLPEGFGKLFDY | 321 | SAAIGDRVTFTCRASQSINTWLAWYQQKPGKAPKLLMHKASTLHSGVPSRFSGSGSGTEFTLTISSLQPDDFATYYCQHYYSYPWTFGQGTKVEIK | 345 | IGKV1-5*03 | IGKJ1*01 | QHYYSYPWT | 369 |
| MEX18_41 | GGGLVQPGGSLRLSCAASGFSFSDFAMSWVRQAPNQGLDWVSCVSGGGDTTYYADSVKGRFTISRDNSKNTVFLEM | 298 | IGHV3-23*01 | IGHD1-26*01 | IGHJ5*02 | ARDQEVIGHYPSDH | 322 | SVSVGDRVTITCRASQNINSWLAWYQQKPGKAPKLLIYKASRLERGVPSRFSGRGSGTEFALTISGLQPDDFAT | 346 | IGKV1-5*03 | IGKJ4* | QQYSSFFT | 370 |

TABLE 1-continued

| | | | | | | | | | | | | | |
|---|---|---|---|---|---|---|---|---|---|---|---|---|---|
| | NNLRPEDTAVYYCARDQEVIGHYPSDHWGQGTLVIVSS | | | | | | | YYCQQYSSFFTFGGGTKVEIK | | | | | |
| MEX18_50 | GGGLVQPGGSLRLSCVASGFTFSNYGMNWVRQAPGKGLEWVSGITGSGDDTYYADSVKGRFTISRDNSRNTLYVQMNNLRAEDTAIYYCTKDRILFDAFHVWGQGTMVTVSS | 299 | IGHV3-23*01 | IGHD3-9*01 | IGHJ3*01 | TKDRILFDAFHV | 323 | SASVGDRVTITCRASQSISSWLAWYQQKPGKAPNLLIYKASTLESGVPSRFSGSGSGTEFTLTISSLQPDDFATYYCQQYNNYPWTFGQGTKVEIK | 347 | IGKV1-5*03 | IGKJ1*01 | QQYNNYPWT | 371 |
| MEX18_54 | GGDLVQPGGSLRLSCVASGFTFSAYGMSWVRQAPGKGLEWVSAMTGSGDSTYYADSVKGRFTISRDNSKNTLYLQMNSLRVEDTAIYYCAKDRVSGGFGELQDYWGQGTLVTVSS | 300 | IGHV3-23*01 | IGHD3-10*01 | IGHJ4*02 | AKDRVSGGFGELQDY | 324 | SASVGDRVTITCRASQNINSWLAWFQQKPGKAPELLIYKTSTLHTGVPSRFRGRGSGTEFTLTISSLQPDDFATYYCQHYYSYPWTFGQGTKVEIK | 348 | IGKV1-5*03 | IGKJ1*01 | QHYYSYPWT | 372 |
| MEX18_58 | GGGLVQPGGSLRLSCATSGFTFTTFAMSWVRQAPGKGLEWVSSISGADDSTYYAASVKGRFTISRDNSRSTLFLQMNSLRAEDTAVYYCAKDRGPRGVGELFDSWGQGTVVSVSS | 301 | IGHV3-23*01 | IGHD3-10*01 | IGHJ5*02 | AKDRGPRGVGELFDS | 325 | SASVGDRVTITCRASQSISKWLAWYQQKPGKAPRLLIYTTSTLKSGVPSRFSGSGSGTEFTLTISSLQPDDFATYYCQHFFSVPWTFGQGTKVEIK | 349 | IGKV1-5*03 | IGKJ1*01 | QHFFSVPWT | 373 |
| MEX18_65 | GGGLVQPGGSLTLSCAGSGFPFNTYALIWVRQAPGKGLEWVSSISYDSASTYYAESVKGRFTISRDNSQNTLYLEMNFLRADDTAVYFCAKDRVTMGFGELFAHWGQGTLVAVSS | 302 | IGHV3-23*01 | IGHD3-10*01 | IGHJ4*02 | AKDRVTMGFGELFAH | 326 | SASIGDRVTITCRASQSVSGWLAWYQQKPGKAPKLLIHKASTLQSGVPSRFSGSGSGTEFTLTITSLQPDDFATYYCQHYYSYPWTFGQGTKVEVK | 350 | IGKV1-5*03 | IGKJ1*01 | QHYYSYPWT | 374 |

TABLE 1-continued

| | | | | | | | | | | | | | |
|---|---|---|---|---|---|---|---|---|---|---|---|---|---|
| MEX18_79 | GGGLKQPGGSLRLSCAASGFTFRNYGMSWVRQAPGKGLEWVSSISSLDDSTYYADSVKGRSAISRDDSKNTLYLQIHSLRAEDTALYFCAKDRVEKGFGELWASWGQGTLVTVSS | 303 | IGHV3-23*01 | IGHD3-10*01 | IGHJ4*02 | AKDRVEKGFGELWAS | 351 | PASVGDRVTITCRASQNINSWLAWYQQTPGRPPKLLIYKASASLDGVPSRFSGSGSGTEFTLTITSLQPHDFATYYCQHYHSYPWTFGQGTKVEIK | 327 | IGKV1-5*03 | IGKJ1*01 | QHYHSYPWT | 375 |
| MEX18_80 | GGGLVQPGGSLRLTCATSGFTFSDYAMSWVRQAPGKGLEWVSSYSGIDDSTYYADSVKGRFIISRDNSKNTLSLHMNSLRAEDSALYFCAKDRGPRGVGELFDSWGQGTLVTVSS | 304 | IGHV3-23*01 | IGHD3-10*01 | IGHJ4*02 | AKDRGPRGVGELFDS | 328 | SASVGDRVTITCRASQSISKWLAWYQQKPGKAPKLLIYTTSTLKSGVPSRFSGSGSGTEFTLTISSLQPDDFATYYCQHFHSVPWTFGQGTKVEIK | 352 | IGKV1-5*03 | IGKJ1*01 | QHFHSVPWT | 376 |
| MEX18_83 | GGGLVQPGGSLRLTCATSGFTFSDYAMSWVRQAPGKGLEWVSSYSGIDDSTYYADSVKGRFTISRDNSRSTLSLHMNSLRAEDSALYFCAKDRGPRGVGELFDSWGQGTLVTVSS | 305 | IGHV3-23*01 | IGHD3-10*01 | IGHJ4*02 | AKDRGPRGVGELFDS | 329 | SASVGDRVTITCRASQSVSKWLAWYQQKPGKAPKLLIYTTSTLKSGVPSRFSGSGSGTEFTLTISSLQPDDFATYYCQHFHSVPWAFGQGTKVEIK | 353 | IGKV1-5*03 | IGKJ1*01 | QHFHSVPWA | 377 |
| MEX18_84 | GGGLVQPGGSLRLSCAASGFTFTSYAMNWVRQAPGKGLEWVSGIGGRGAIAGDGSIYYADSVKGRFTISRDNSKNIVYLQMNGLRVEDTAVYYCAKDRVAFDGFHVWGQGTITTVSS | 306 | IGHV3-23*01 | none | IGHJ3*01 | AKDRVAFDGFHV | 330 | SASVGDRVTITCRASQSISSWLAWYQQKPGKAPKLLIYKASSLESGVPSRFSGSGSGTEFSLTISSLQPEDFATYYCQQYNSYPWTFGQGTKVEIK | 354 | IGKV1-5*03 | IGKJ1*01 | QQYNSYPWT | 378 |
| MEX18_86 | GGGLVQPGGSLRLTCATSGFTFSDYAMSWVRQAPGKGL | 307 | IGHV3-23*01 | IGHD1-26*01 | IGHJ4*02 | AKDRGPRGVGELFDS | 331 | SASVGDRVTITCRASQSISKWLAWYQQKPGKAPKLL | 355 | IGKV1-5*03 | IGKJ1*01 | QHFYSVPWT | 379 |

TABLE 1-continued

| | | | | | | | | | | | | | | |
|---|---|---|---|---|---|---|---|---|---|---|---|---|---|---|
| | | EWVSSYSGIDDSTYYADSVKGRFIISRDNSKSTLSLHMNSLRAEDSALYFCAKDRGPRGVGELFDSWGQGTLVTVSS | | | | | | | IYTTSTLKSGVPSRFSGSGSGTEFTLTISSLQPDDFATYYCQHFYSVPWTFGQGTKVEIK | | | | | |
| | MEX18_89 | GGGLVQPGGSLRLTCATSGFTFRDYAMSWVRQAPGKGLEWVSSYSGIDDSTYYADSVKGRFTISRDNSKSTLSLHMNSLRAEDSALYFCAKDRGPRGVGELFDSWGQGTLVTVSS | 308 | IGHV3-23*01 | IGHD3-10*01 | IGHJ4*02 | AKDRGPRGVGELFDS | 332 | SASVGDRVTITCRASQSISKWLAWYQQKPGKAPKLLIYTTSTLKSGVPSRFSGSGSGTEFTLTISSLQPDDFATYYCQHFYSVPWTFGQGTKVEIK | 356 | IGKV1-5*03 | IGKJ1*01 | QHFYSVPWT | 380 |
| | MEX18_93 | GGGLVQPGGSLRLTCATSGFTFSDYAMSWVRQAPGKGLEWVSSYSGIDDSTYYADSVKGRFTISRDNSKSTLSLYMKSLRAEDSALYYCAKDRGPRGVGELFDSWGQGTLVTVSS | 309 | IGHV3-23*01 | IGHD3-10*01 | IGHJ4*02 | AKDRGPRGVGELFDS | 333 | SASVGDRVTITCRASQSISKWLAWYQQKPGKAPKLLIYTTSTLKSGVPSRFSGSGSGTEFTLTISGLQPDDFATYYCQHFFSVPWTFGQGTKVESK | 357 | IGKV1-5*03 | IGKJ1*01 | QHFFSVPWT | 381 |
| | MEX18_94 | GGGLVQPGGSLRLTCATSGFTFSDYAMSWVRQAPGKGLEWVSSYSGIDDSTYYADSVKGRFTISRDNSKSTLSLHMNSLRAEDSALYFCAKDRGPRGVGELFDSWGQGTLVTVSS | 310 | IGHV3-23*01 | IGHD3-10*01 | IGHJ4*02 | AKDRGPRGVGELFDS | 334 | SASVGDRVTITCRASQSISKWLAWYQQKPGKAPKLLIYTTSTLKTGVPSRFSGSGSGTEFTLTISSLQPDDFATYYCQHFYSVPWTFGQGTKVEIK | 358 | IGKV1-5*03 | IGKJ1*01 | QHFYSVPWT | 382 |
| VH3-23/VK1-27 | MEX18_09 | GGDLVQPGGSLRLSCAASGFTFSSYGMSWVRQAPGKGLEWVSSISGFDPSTYYADSVRGRFTIARDNSKNTLYLQMK | 311 | IGHV3-23*01 | IGHD3-10*01 | IGHJ5*02 | AKDRLVRGFGEVLAS | 335 | SASVGDRVTITCRASQGISNYLAWYQQKPREVPKLLIYAASTLHSGVPSRFSGSGSGTDFTLTISGLQPEDVATY | 359 | IGKV1-27*01 | IGKJ1*01 | QKYNSVPWT | 383 |

TABLE 1-continued

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| | | SLRVEDTAIY YCAKDRLVR GFGEVLASW GQGTLVTVSS | | | | | | | YCQKYNSVP WTFGQGTK VEMK | | | | | |
| | MEX18_13 | GGGLVQPGGS LRLSCAASGF TFSSYAMSW VRQAPGKGL EWVSSFSGID DSTWYADSV KGRFTISRDN SKSTLYLQMN SLRAEDTAVY YCAKDRLVR GFAEVLDYW GRGTLVTVSS | 312 | IGHV3-23*01 | IGHD6-6*01 | IGHJ4*02 | AKDRLV RGFAEV LDY | 336 | SASVGDRVT ITCRASQDIS KYLAWYQQ RPGKVPNLL IYTASTLQSG VPSRFSGSGS GTHFTLTISS LQPEDVATY YCQKYNSVP WTFGQGTK VEIK | 360 | IGKV1-27*01 | IGKJ1*01 | QKYNSVP WT | 384 |
| | MEX18_52 | GGGLVQPGGS LRLSCAASGF TFSSYAMSW VRQAPGKGL EWVSSFSGID DSTWYADSV KGRFTISRDN SKSTLFLQMN SLRAEDTAVY YCAKDRLVR GFAEVLEHW GRGTLVTVSS | 313 | IGHV3-23*01 | IGHD6-6*01 | IGHJ4*02 | AKDRLV RGFAEV LEH | 337 | SASVGDRVT ITCRASQDIS KYLAWYQQ RPGKVPNLL IYTASTLQSG VPSRFSGSGS GTHFTLTISS LQPEDVATY YCQKYNSVP WTFGQGTK VEIK | 361 | IGKV1-27*01 | IGKJ1*01 | QKYNSVP WT | 385 |
| | MEX18_91 | GGDLVQPGGS LRLSCAASGF TFSSYGMSW VRQAPGKGL EWVSSISGFD PSTYYADSVR GRFTIARDNS KNTLYLQMK SLRVEDTAIY YCAKDRLVR GFGEVLDSW GQGTLVTVSS | 314 | IGHV3-23*01 | IGHD3-10*01 | IGHJ4*02 | AKDRLV RGFGEV LDS | 338 | SASVGDRVT ITCRASQGIS NYLAWYQQ KPREVPKLLI YAASTLHSG VPSRFSGSGS GTDFTLTISG LQPEDVATY YCQKYNSVP WTFGQGTK VEMK | 362 | IGKV1-27*01 | IGKJ1*01 | QKYNSVP WT | 386 |

MEX 105-refers to an individual donor. Sequences were analyzed with IgBlast

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| VH3-23/VK 1-5 | MEX105_01 | GGGLVRPGG SLRLSCKASG FTFRRYAMA WVRQAPGK GLEWVSLIY NGDDSTYYA | 387 | IGHV3-23*03 | IGHD6-19*01 | IGHJ4*02 | VKDRD TGWSS IVD | 416 | SASVGDRVT ITCRTSQTIA NWLAWYQQ KPGKAPKLL IYQASILESG VPSRFSGSGS | 445 | IGKV1-5*03 | IGKJ1*01 | QQYSTYW T | 474 |

TABLE 1-continued

| | | | | | | | | | | | | | |
|---|---|---|---|---|---|---|---|---|---|---|---|---|---|
| | KSVKGRFTISRDDSQSTLSLQMNSLRAEDTAVYYCVKDRDTGWSSIVDWGQGTLVTVSS | | | | | | | GTEFTLTIRSLQPEDFATYFCQQYSTYWTFGQGTKVGIK | | | | | |
| MEX105_02 | GGGLVRPGGSLRLSCTASGFTFRRYAMAWVRQAPGKGLEWVSLIYNGDDSTYYSKSVKGRFTISRDNSQNTLSLQMNSLRVEDTAVYYCVKDRDNGWSSIVDWGQGTLVTVSS | 388 | IGHV3-23*03 | IGHD6-19*01 | IGHJ4*02 | VKDRDNGWSSIVD | 417 | SASVGDTVTITCRASQTLGNWLAWYQQKPGKAPKLLIYQASILESGVPSRFSGSGSGTEFTLTIRSLQPEDFATYFCQQYSTFWTFGQGTKVGIK | 446 | IGKV1-5*03 | IGKJ1*01 | QQYSTFWT | 475 |
| MEX105_04 | GGGLVRPGGSLRLSCTASGFTFRRYAMAWVRQAPGKGLEWVSLIFNGDDSTYYAASVKGRFTISRDNSQNTLSLQMNSLRAEDTAVYYCVKDRDNGWSSIVDWGQGTLVTVSS | 389 | IGHV3-23*03 | IGHD6-19*01 | IGHJ4*02 | VKDRDNGWSSIVD | 418 | SASVGDRVTITCRASQTIGSWLAWYQQKPGKAPKLLIYQASILESGVPSRFSGSGSGTEFTLTIRSLQPEDFATYFCHQYSTYWTFGQGTKVGMK | 447 | IGKV1-5*03 | IGKJ1*01 | HQYSTYWT | 476 |
| MEX105_05 | GGGLVRPGGSLRLSCTASGFTFRRYALAWVRQVPGKGLEWVSLIYNGDDSTYYAESVKGRFTISRDNSQNTLSLQMNSLRAEDTAVYYCVKDRDNGWSSIVDWGQGTLVTVSS | 390 | IGHV3-23*03 | IGHD6-19*01 | IGHJ4*02 | VKDRDNGWSSIVD | 419 | SASVGDRVTITCRASHNIGGLLAWYQQKPGKAPKLLIYQASRLESGVPSRFSGSGSGTEFTLTIRGLQPEDFATYFCQQYSTYWTFGQGTKVAIK | 448 | IGKV1-5*03 | IGKJ1*01 | QQYSTYWT | 477 |
| MEX105_09 | GGGLVRPGGSLRLSCTASGFTFRRYAMAWVRQAPGKGLEWVSLIYNGDDSTYYAESVKGRFTIS | 391 | IGHV3-23*03 | IGHD6-19*01 | IGHJ4*02 | VKDRDTGWSSIVD | 420 | SASVGDRVTITCRTSHTIGNWLAWYQQKPGRAPKLLIYQASILESGVPSRFSGSGSGTEFTLTIRS | 449 | IGKV1-5*03 | IGKJ1*01 | QQYSTFWT | 478 |

TABLE 1-continued

| | | | | | | | | | | | | |
|---|---|---|---|---|---|---|---|---|---|---|---|---|
| | RDNSQNTLSLQMNSLRAEDTAIYYCVKDRDTGWSSIVDWGQGTLVTVSS | | | | | | | LQPEDFATYFCQQYSTFWTFGQGTKVGIK | | | | | |
| MEX105_11 | GGGLVRPGGSLRLSCTASGFTFRRYAMAWVRQAPGKGLEWVSLIYDGEDSTYYAASVKGRFTISRDNSQNTLSLQMNSLRAEDTAIYYCVKDRDNGWSSIVDWGQGTLVTVSS | 392 | IGHV3-23*03 | IGHD6-19*01 | IGHJ4*02 | VKDRDNGWSSIVD | 421 | SASVGDRVTITCRASQTIGSWLAWYQQKPGKAPKLLIYQASILESGVPSRFSGSGSGTEFTLTIKSLQPEDFATYFCHQYSTYWTFGQGTKVGIK | 450 | IGKV1-5*03 | IGKJ1*01 | HQYSTYWT | 479 |
| MEX105_14 | GGDLAQPGGSLRLSCAVSGLSIGRYGMNWIRQAPGKGLEWVSGISDDGGSTYYAASVKGRFTISRDNSKNSVYLQMSSLRAEDTARYYCAKDRLMFDGFHMWGQGTMVTVSS | 393 | IGHV3-23*01 | IGHD2-8*01 | IGHJ3*02 | AKDRLMFDGFHM | 422 | SASVGDSVTISCRASRSISSWLAWYQQKPGKAPKLLIYTASTLETGVPSRFSGSGSGAEFTLTISSLQPDDFATYYCQQYNNYPWTFGQGTTVEIK | 451 | IGKV1-5*03 | IGKJ1*01 | QQYNNYPWT | 480 |
| MEX105_15 | GGGLVQPGGSLRLSCAASGFTFRTYAMSWVRQPPGKGLEWVSSISAREDSTYFAASVRGRFTISRDNSKNTLYLQMNNLRAEDTALYYCAKDRLQLGVGELYESWGQGTLVTVSS | 394 | IGHV3-23*01 | IGHD3-16*01 | IGHJ5*02 | AKDRLQLGVGELYES | 423 | SASVGDRVTITCRASQNINSWLAWYQQKPGKAPKLLIYMASSLQSGVPSRFSGSGSGTEFTLTVSSLQPDDFATYYCQHYHSYPWTFGQGTKLEIK | 452 | IGKV1-5*03 | IGKJ1*01 | QHYHSYPWT | 481 |
| MEX105_23 | GGGLVRPGGSLRLSCTASGFTFRRYAMAWVRQAPGKGLEWVSLIYNADDSTYYAESVKGRFTISRDNSQNTLS | 395 | IGHV3-23*03 | IGHD6-19*01 | IGHJ4*02 | VKDRDTGWSSIVD | 424 | SASVGDRVTITCRASQNVDNWLAWYQQKPGKAPKLLIYQASILENGVPSRFSGSGSGTEFTLTIRSLQPEDVA | 453 | IGKV1-5*03 | IGKJ1*01 | QQYSTFWT | 482 |

TABLE 1-continued

| | | | | | | | | | | | | | |
|---|---|---|---|---|---|---|---|---|---|---|---|---|---|
| | LQMNSLRAEDTAVYYCVKDRDTGWSSIVDWGQGTLVTVSS | | | | | | | TYFCQQYSTFWTFGQGTKVGIK | | | | | |
| MEX105_25 | GGGLVRPGGSLRLSCSASGFTFRRYAMAWVRQAPGKGLEWVSLLYNGDDSTYYAESVKGRFIISRDNSLNTLSLQMNSLRAEDTAVYYCVKDRDTGWSSIVDWGRGTLVTVSS | 396 | IGHV3-23*03 | IGHD6-19*01 | IGHJ4*02 | VKDRDTGWSSIVD | 425 | SASVGDRVTITCRASQTISHWLAWYQQKPGKAPKLLIYQASVLETGVPSRFSGSGSGTEFTLTIRSLQPEDFGTYFCQQYSTFWTFGQGTKVEIK | 454 | IGKV1-5*03 | IGKJ1*01 | QQYSTFWT | 483 |
| MEX105_27 | GGGLVRPGGSLRLSCTASGFTFRRYAMAWVRQAPGKGLEWVSLIYDGHDTTYYADSVKGRFTISRDNSQNTLSLQMNSLRAEDTAVYYCVKDRDNGWSSIVDWGQGTLVAVSS | 397 | IGHV3-23*03 | IGHD6-19*01 | IGHJ4*02 | VKDRDNGWSSIVD | 426 | SASVGDTVTITCRASRTIGSWLAWYQQKPGKAPKLLIYQASILESGVPSRFSGSGSGTEFTLTIRSLQPEDFATYFCQQYSTYWTFGQGTTVGVK | 455 | IGKV1-5*03 | IGKJ1*01 | QQYSTYWT | 484 |
| MEX105_28 | GGGLVRPGGSLRLSCTASGFNFRRYAMAWVRQAPGKGLEWVSLLYNGDDSTYYAKSVKGRFTISRDNSQNTLSLQMNSLRAEDTAVYYCVKDRDNGWSSIVDWGQGTLVTVSS | 398 | IGHV3-23*03 | IGHD6-19*01 | IGHJ4*02 | VKDRDNGWSSIVD | 427 | SAFVGDRVTITCRASQTIGNWLAWYQQKPGKAPKLLIYQASILESGVPSRFSGSGSGTEFTLTIRSLQPEDFATYFCQQYSTFWTFGQGTKVEIK | 456 | IGKV1-5*03 | IGKJ1*01 | QQYSTFWT | 485 |
| MEX105_33 | GGGLVRPGGSLRLSCTASGFTFRRYAMAWVRQAPGKGLEWVSLIWNGDDSTYYASSVKGRFTISRDNSQNTLSLQMNSLRAE | 399 | IGHV3-23*03 | IGHD6-19*01 | IGHJ4*02 | VKDRDNGWSSIVD | 428 | SASVGDRVTITCRASQTIGNWLAWYQQKPGKAPKLLIYQASILESGVPSRFSGSGSGTEFTLTIRGLQPEDFATYFCQQYSTYW | 457 | IGKV1-5*03 | IGKJ1*01 | QQYSTYWT | 486 |

TABLE 1-continued

| | | | | | | | | | | | | | |
|---|---|---|---|---|---|---|---|---|---|---|---|---|---|
| | DTAVYYCVKDRDNGWSSIVDWGQGTLVTVSA | | | | | | | TFGQGTKVGIK | | | | | |
| MEX105_37 | GGGLVRPGGSLRLSCTASGFTFRRYAMAWVRQAPGKGLEWVSLLYNGDDSTYYAESVKGRFTISRDNSQNTLSLQMNSLRAEDTAVYYCVKDRDTGRSSIVEWGQGTWVTVSS | 400 | IGHV3-23*03 | IGHD2-15*01 | IGHJ4*02 | VKDRDTGRSSIVE | 429 | SASVGDRVTITCRASQTIGNWLAWYQQKPGKAPKLLIYQASILESGVPSRFSGSGSGTEFTLTIRSLQPEDFATYFCQQYSTYWTFGQGTKVEIK | 458 | IGKV1-5*03 | IGKJ1*01 | QQYSTYWT | 487 |
| MEX105_39 | GGGLVQPGGSLRLSCAASGFTFRTYAMSWVRQAPGKGLEWVSSISASDDSTYFAASVRGRFTISRDNSKNTLYLQMNNLRAEDTALYYCAKDRLELGVGELYEFWGQGTLVTVSS | 401 | IGHV3-23*01 | IGHD3-02 | IGHJ4*10*01 | AKDRLELGVGELYEF | 430 | SASVGDRVTITCRASQNINSWLAWYQQKPGKAPKLLIYKASSLQSGVPSRFSGSGSGTEFTLTVSSLQPDDFATYYCQHYYSYPWTFGQGTKVEIK | 459 | IGKV1-5*03 | IGKJ1*01 | QHYYSYPWT | 488 |
| MEX105_42 | GGGLVQPGGSLRLSCAASGFTFKNYAMAWVRQAPGKGLEWVSLLYNSEESTYYADSVKGRFTISRDNSKNTLFLQMNRLRVEDTAVYFCVRDRSNGWSSINLWGRGTLVTVSS | 402 | IGHV3-23*03 | IGHD2-02 | IGHJ4*15*01 | VRDRSNGWSSINL | 431 | SASVGDRVTMTCRASQTISGWLAWYQQKPGKAPKLLIYQASRLESGIPSRFSGSGSGTEFTLTISSLQPDDVATYYCQQYSTFWTFGLGTRVEIK | 460 | IGKV1-5*03 | IGKJ1*01 | QQYSTFWT | 489 |
| MEX105_45 | GGGLVRPGGSLRLSCTASGFNFRRYAMAWVRQAPGKGLEWVSQIYNGEDSTYYAESVKGRFTISRDNSQNTLSLQMNGLRAE | 403 | IGHV3-23*03 | IGHD6-19*01 | IGHJ4*02 | VKDRDNGWSSIVD | 432 | SASVGDRVTITCRASQTIGSWLAWYQQKPGKAPKLLIYQASILESGVPSRFSGSGSGTEFTLTIRSLQPEDFATYFCQQYSTYW | 461 | IGKV1-5*03 | IGKJ1*01 | QQYSTYWT | 490 |

TABLE 1-continued

| | | | | | | | | | | | | | |
|---|---|---|---|---|---|---|---|---|---|---|---|---|---|
| | DTAIYYCVKDRDNGWSSIVDWGQGTLVTVSS | | | | | | | TFGQGTKVGIK | | | | | |
| MEX105_48 | GGGLVRPGGSLRLSCTASGFTFRRYAMAWVRQAPGKGLEWVSLIYDGDDSTYYAESVKGRFTISRDNSQNTVSLQMTSLRAEDTALYYCVKDRDNGWSSIVDWGQGTLVTVSS | 404 | IGHV3-23*03 | IGHD6-19*01 | IGHJ4*02 | VKDRDNGWSSIVD | 433 | SASVGDRVTITCRASQTLNVWLAWYQQQPGKAPKLLIYKASTLQSGVPSRFSGSGSGTEFTLTINSLQPEDFATYYCQHYHSYPWTFGQGTKVEIK | 462 | IGKV1-5*03 | IGKJ1*01 | QHYHSYPWT | 491 |
| MEX105_50 | GGGLVRPGGSLRLSCTASGFTFRRYAMAWVRQAPGKGLEWVSLIYDGDDSTYYAKSVKGRFAISRDNSKNTLSLQMNSLRAEDTAVYYCVKDRDNGWSSIVDWGQGTLVTVSS | 405 | IGHV3-23*03 | IGHD6-19*01 | IGHJ4*02 | VKDRDNGWSSIVD | 434 | SASVGDRVTITCRASHSISGWLAWYQQKPGKAPKLLIYQASILESGVPSRFSGSGSGTEFTLTIGSLQPEDFATYFCQQYSTFWTFGQGTKVEIK | 463 | IGKV1-5*03 | IGKJ1*01 | QQYSTFWT | 492 |
| MEX105_51 | GGGLVRPGGSLRLSCTASGFTFRRYAMAWVRQAPGKGLEWVSLLYNGDDSTYYAKSVKGRFTISRDNSQNTLSLQMNSLRAEDTAVYYCVRDRDNGWSSIVDWGQGTLVTVSS | 406 | IGHV3-23*03 | IGHD6-19*01 | IGHJ4*02 | VRDRDNGWSSIVD | 435 | SASVGDRVTITCRASQTIGSWLAWYQQKPGKAPRLLIYQASILESGVPSRFSGSGSGTEFTLTIRSLQPEDFATYFCQQYSTFWTFGQGTKVGIK | 464 | IGKV1-5*03 | IGKJ1*01 | QQYSTFWT | 493 |
| MEX105_54 | GGGLVRPGGSLRLSCTASGFTFRRFAMAWVRQAPGKGLEWVSLIYNGDDSTYYAQSVKGRFTISRDNSQNTLS | 407 | IGHV3-23*03 | IGHD6-19*01 | IGHJ4*02 | VKDRDTGWSSIVD | 436 | SASVGDRVTITCRASRTIGNWLAWYQQKPGKAPKLLIYQASILESGIPSRFSGSGSGTEFTLTIRGLQPEDFGTYF | 465 | IGKV1-5*03 | IGKJ1*01 | QQYSTYWT | 494 |

TABLE 1-continued

| | | | | | | | | | | | | | |
|---|---|---|---|---|---|---|---|---|---|---|---|---|---|
| | LQMNSLRVEDTAVYYCVKDRDTGWSSIVDWGQGTLVTVSS | | | | | | | CQQYSTYWTFGQGTKVGIK | | | | | |
| MEX105_60 | GGGLVRPGGSLRLSCTASGFTFRRFAMAWVRQAPGKGLEWVSLIWNGDDSTYYAESVRGRFTISRDNSHNTLSLQMRSLRAEDTAIYYCVKDRDNGWSSIVDWGQGTLVTVSS | 408 | IGHV3-23*03 | IGHD6-19*01 | IGHJ4*02 | VKDRDNGWSSIVD | 437 | SVGDRVTITCRASQTIGNWLAWYQQKPGKAPKLLIYQASVLESGVPSRFSGSGSGTEFTLTISSLQPEDFATYFCQQYSTFWTFGQGTKVGIK | 466 | IGKV1-5*03 | IGKJ1*01 | QQYSTFWT | 495 |
| MEX105_64 | GGGLVRPGGSLRLSCTASGFTFRRYAMAWVRQAPGKGLEWVSLIYNGDDSTYYAESVKGRFTVSRDNSQNTLSLQMNSLRAEDTAIYYCVRDRDNGWSSIVDWGQGTLVTVSS | 409 | IGHV3-23*03 | IGHD6-19*01 | IGHJ4*02 | VRDRDNGWSSIVD | 438 | SASVGDRVTITCRASRTIGSWLAWYQQKPGKAPKLLIYQASILEGGVPSRFSGSVSGTEFTLTIRSLQPEDFATYFCQQYSTFWTFGQGTKVEIK | 467 | IGKV1-5*03 | IGKJ1*01 | QQYSTFWT | 496 |
| MEX105_66 | GGGLARPGGSLRLSCTASGFTFRRYAMAWVRQAPGKGLEWVSLIWNGDDSTYYAESVKGRFTISRDNSQNTLSLQMNSLRAEDTAVYYCVKDRDTGWSSIVDWGQGTLVTVSS | 410 | IGHV3-23*03 | IGHD6-19*01 | IGHJ4*02 | VKDRDTGWSSIVD | 439 | SASVGDRVTITCRASQTIANWLAWYQQKPGQPPKLLIYQASILESGVPSRFSGSGSGTEFTLTIRSLQPEDFATYFCQQYSTFWTFGQGTKVGIK | 468 | IGKV1-5*03 | IGKJ1*01 | QQYSTFWT | 497 |
| MEX105_78 | GGGLVRPGGSLRLSCTASGFTFRRYAMAWVRQAPGKGLEWVSLIYNAYDSTYYAESVKGRFTISRDNSQNTLSLQMSSLRAE | 411 | IGHV3-23*03 | IGHD6-19*01 | IGHJ4*02 | VKDRDTGWSSIVD | 440 | SASVGDRVTITCRASHTIGNWLAWYQQKPGKAPKLLIYQASILESGVPSRFSGSGSGTEFTLTIRSLQPEDFATYFCQQYSTYW | 469 | IGKV1-5*03 | IGKJ1*01 | QQYSTYWT | 498 |

TABLE 1-continued

| | | | | | | | | | | | | | | |
|---|---|---|---|---|---|---|---|---|---|---|---|---|---|---|
| | | DTAVYYCVKDRDTGWSSIVDWGQGTLVTVSP | | | | | | | TFGQGTKVGIK | | | | | |
| | MEX105_87 | GGGLVRPGGSLRLSCTASGFTFRRYAMAWVRQAPGKGLEWVSLIYNGDDSTYYAESVRGRFTISRDNSQNTLSLQMNSLRAEDTAVYYCVKDRDTGWSSIVDWGQGTLVTVSS | 412 | IGHV3-23*03 | IGHD6-19*01 | IGHJ4*02 | VKDRDTGWSSIVD | 441 | SASVGDRVTITCRASHTISNWLAWYQQKPGKAPKLLVYQASILETGVPSRFSGSGSGTEFTLTIRSLQPEDFGTYFCQQYSTFWTFGQGTKVEIK | 470 | IGKV1-5*03 | IGKJ1*01 | QQYSTFWT | 499 |
| | MEX105_88 | GGGLVQPGGSLRLSCAASGFTFSNYAMAWVRQAPGKGLEWVSLIYSGDDSTYYADFVKGRFTISRHNSKNTLSLQMNSLRAEDTAIYYCVKDRGTGWSSIVHWGQGTLVTVSS | 413 | IGHV3-23*03 | IGHD2-15*01 | IGHJ4*02 | VKDRGTGWSSIVH | 442 | SASVGDRVTITCRASQTISNWLAWYQQKPGKAPKLLIYQASSLESGVPSRFSGSGSGTEFTLTISSLQPDDFATYYCQQYSTYWTFGQGTKVEIK | 471 | IGKV1-5*03 | IGKJ1*01 | QQYSTYWT | 500 |
| VH1-46/VK1-12 | MEX105_40 | GAEVKRPGASVKVSCKASGYTFTSYYMHWVRQAPGQGLEWMGIINPRGGSTTYAQKFQGRVALTGDTSTSTVYMELTSLRSDDTAVYYCARGKAHQTTVVILSWYYGMDVWGQGTTVTVSS | 414 | IGHV1-46*01 | IGHD4-23*01 | IGHJ6*02 | ARGKAHQTTVVILSWYYGMDV | 443 | SASVGDRVTITCRASQGISSWLAWYQQKPGKAPKLLISAASSLQSGVPSRFSGSGSGTDFTLTISSLQPEDFATYYCQQANSFPYTFGQGTKLEIK | 472 | IGKV1-12*01 | IGKJ2*01 | QQANSFPYT | 501 |
| | MEX105_57 | GAEVKKSGASVKVSCKASGYSFTTNYIHWVRQAPGQGPEWMGIINPRGGSTTYAQKFQGRVLMTSDTSTSTV | 415 | IGHV1-46*01 | IGHD4-23*01 | IGHJ6*02 | ARGKNHQTTVAVLSWYYGMDV | 444 | SASVGDRVTITCRASQGISSWLAWYQQKPGKAPKLLISAASSLQSGVPSRFSGSGSGTDFTLTISNLQPEDFAT | 473 | IGKV1-12*01 | IGKJ2*01 | QQANSFPYT | 502 |

TABLE 1-continued

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| | | YMELSSLRSEDRAVYYCARGKNHQTTVAVLSWYYGMDVWGQGTTVTVSS | | | | | | | YFCQQANSFPYTFGQGTKLEIK | | | | | |

BRA 112-refers to an individual donor. Sequences were analyzed with IgBlast

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| VH3-23/VK 1-5 | BRA112_08 | GGGLVQPGGSLKLSCSAAGFNFRSYAMSWIRQAPGKGLEWVSSLGTRGTETTYYAASVKGRFTISRDNSKNILYLQMNILGAEDTAVYYCARDRGIEGLGELYSHWGQGTLVTVSS | 503 | IGHV3-23*03 | IGHD3-10*01 | IGHJ4*02 | ARDRGIEGLGELYSH | 527 | SASVGDRVTITCRASQSINSWVAWYQQKPGKAPKFLIYKASTLESGVPSRFSGSGSGTEFTLTITSLQPDDFATYYCQHYYSYPWTFGQGTKVEIK | 551 | IGKV1-5*03 | IGKJ1*01 | QHYYSYPWT | 575 |
| | BRA112_09 | GGGLAQPGGSLRLSCETSGFTFRSYGMGWVRQAPGKGLEWVSSIYISGDSTYYAASVKGRFTISRDNSKSTLYLQMDRLTAEDTAVYYCVRDRIQGGFGELYRYWGQGTLVTVSS | 504 | IGHV3-23*05 | IGHD5-18*01 | IGHJ4*02 | VRDRIQGGFGELYRY | 528 | SASVGDRVTMTCRASQSVNKWLAWYQQKPGKAPKLLIYETSILESGVSSRFSGSGSGTEFTLTISSLQPDDFATYYCQHYHGYPWTFGQGTKVEIR | 552 | IGKV1-5*03 | IGKJ1*01 | QHYHGYPWT | 576 |
| | BRA112_21 | GGGLAQPGGSLRLSCAASGFTFSSYAMTWVRQAPGKGLEWVSTITGRDGSTYYADSVKGRFTISRANSKNTLYLQMNGLRAEDTAVYFCAKDRDHFDGHDFWGQGALVTVSS | 505 | IGHV3-23*01 | IGHD3-3*01 | IGHJ4*02 | AKDRDHFDGHDF | 529 | SAAVGDSVTITCRASQSISSWLAWYQQKPGRAPKLLISKASNVESGVPSRFSGSGSGTEFTLTISSLQPDDFATYYCQKYNSYPFTFGPGTKLDIK | 553 | IGKV1-5*03 | IGKJ3*01 | QKYNSYPFT | 577 |

TABLE 1-continued

| | | | | | | | | | | | | |
|---|---|---|---|---|---|---|---|---|---|---|---|---|
| BRA112_24 | GGRLVQPGGSLTLSCAASGFPFSTYAMSWLRQAPGKGLEWVSGITGDSGSTYYAASVKGRFTISRDNSKNTLYLQMNSLTADDTAVYYCAKDRLHSGLGELFSYWGQGTLVTVSS | 506 | IGHV3-23*01 | IGHD3-10*01 | IGHJ4*02 | AKDRLHSGLGELFSY | 530 | SASVGDRVNITCRASQSINQWLAWYQQKPGKAPKFLMYKASTLETGVPSRFSGSGSGTEFTLTISSLQPDDFATYYCQHYFSYPWTFGQGTKVEIK | 554 | IGKV1-5*03 | IGKJ1*01 | QHYFSYPWT 578 |
| BRA112_33 | GGGLVQPGGSLRLSCAASGFSFRTYGMSWVRQAPGKGLEWVSSISSVDDSTYYADSVKGRFTISRDNSKNTLYLQMHNLSAKDTALYYCAKDRLASGIGELFSSWGQGTLVTVAS | 507 | IGHV3-23*01 | IGHD3-10*01 | IGHJ5*02 | AKDRLASGIGELFSS | 531 | SASVGDRVTITCRASQNIDMWLAWYQQKPGRAPKFLIHKASTLESGVPSRFSGSGSGTEFTLTISSLQPDDFATYYCQHYHSYPWTFGQGTKVDIK | 555 | IGKV1-5*03 | IGKJ1*01 | QHYHSYPWT 579 |
| BRA112_37 | GGGLVQPGGSLRLSCAASGFTFRTYGMNWVRQAPGKGLEWVAGISVDPSTYYAGSVKGRFTISRDNSKNMLYLQMNSLTADDSAVYYCAKDRMSGGFGELNESWGQGTRVTVSS | 508 | IGHV3-23*01 | IGHD3-10*01 | IGHJ5*02 | AKDRMSGGFGELNES | 532 | SASVGDRVTITCRASQSISGWLAWYQQKPGRAPNLLIYQASALHSGVPSRFSGSGSGTEFSLTISSLQPDDFATYYCQHYFSYPWTFGQGTKVEIK | 556 | IGKV1-5*03 | IGKJ1*01 | QHYFSYPWT 580 |
| BRA112_46 | GGGLVQPGGSLRLSCVASGFTFGSYGMAWVRQAPGKGLEWISSISSIDPSTYYADSVKGRFTVSRDNSENTLYLHMSSLKVEDTAVYFCAKDRLNGGFGELFASWGQGTLVTVSS | 509 | IGHV3-23*01 | IGHD3-10*01 | IGHJ4*02 | AKDRLNGGFGELFAS | 533 | SASVGDSVTITCRASQSISSWLAWYQQKPGKAPKFLIHKASSLESGIPSRFSGSGSGTEFTLTINNLQPDDFATYYCQHYHSYPWTFGQGTKVEIK | 557 | IGKV1-5*03 | IGKJ1*01 | QHYHSYPWT 581 |

TABLE 1-continued

| | | | | | | | | | | | | | |
|---|---|---|---|---|---|---|---|---|---|---|---|---|---|
| BRA112_48 | GGGLGQPGGSLRLSCAASGFPFSDFGMSWVRQAPGKGLEWVSSISGPGFDTYYADSVKGRFTISRDNSKDTLFLTLTISSLQPDQMSRLRVEDTAVYYCARDRIKGGLGELFHLWGQGALVTVSS | 510 | IGHV3-23*01 | IGHD3-10*01 | IGHJ4*02 | ARDRIKGGLGELFHL | 534 | SASVGDRVTIICRASRSIDSWLAWYQQKPGKAPRLLIHKASTLHSGVPSRFSGSGSGTEFDFATYFCQHYFSSPYSFGQGTKLEIK | 558 | IGKV1-5*03 | IGKJ2*03 | QHYFSSPYS | 582 |
| BRA112_51 | GGGLVQPGGSLRLSCAASGFTFNTHAMAWLRQAPGKGLEWVSSVTANGGDSWYADSVKGRFTISRDNSRNILYLQMSSLRVEDTAVYYCAKDRLAAGLGELFSHWGQGTLVSVSS | 511 | IGHV3-23*01 | IGHD3-16*01 | IGHJ4*02 | AKDRLAAGLGELFSH | 535 | SASVGDRVTITCRAGQNINSWLAWYQQKPGKAPKFLIHKASTLESGVSSRFSGSGSGTEFTLTINNLQPDDFATYYCQHYHSYPWTFGQGTKVEIK | 559 | IGKV1-5*03 | IGKJ1*01 | QHYHSYPWT | 583 |
| BRA112_56 | GGGLVQPGGSLRLSCAASGFTFSTYAMSWVRQAPGKGLKWVSGITGDSGSTYYARSVKGRFTISRDNSKNTLYLEISSLRAEDTAFYFCTRDRLPNGIGELHDHWGQGTLVTVSS | 512 | IGHV3-23*01 | IGHD3-10*01 | IGHJ4*02 | TRDRLPNGIGELHDH | 536 | SASVGDRVSITCRASQNIDMWLAWYQQKPGKAPKFLIYKASNLKSGVPSRFSGSGSGTEFTLTISSLQPDDFATYYCQHYHSYPWTFGQGTKVEIK | 560 | IGKV1-5*03 | IGKJ1*01 | QHYHSYPWT | 584 |
| BRA112_65 | GGGLVQPGGSLRLSCAASGFTFRTYGMNWVRQAPGKGLEWVSGISGIDPSTYYADSVKGRFTISRDNSKNILFLQMNSLTADDTAVYYCTKDRLSGAFGELNESWGQGTMVIVSS | 513 | IGHV3-23*01 | IGHD3-10*01 | IGHJ5*02 | TKDRLSGAFGELNES | 537 | SASIGARVTITCRASQDISGWLAWYQQKPGRAPKLLIYQASTLYNGVPPRFSGSGSGTEFTLTISGLQPDDFATYYCQHYHSYPWTFGQGTKVEIK | 561 | IGKV1-5*03 | IGKJ1*01 | QHYHSYPWT | 585 |

TABLE 1-continued

| | | | | | | | | | | | | | |
|---|---|---|---|---|---|---|---|---|---|---|---|---|---|
| BRA112_69 | GGALVQPGGSLRLSCAASGFTFRNYGVSWVRQAPGKGLEWVSSINTDGGSTYYAASVKGRFTISRDNSRNTLYLQMDGLTVADTAMYFCTKDRVQGGFGELFHSWGQGTLVTVSP | 514 | IGHV3-23*01 | IGHD3-10*01 | IGHJ5*02 | TKDRVQGGFGELFHS | 538 | SASVGDRVTITCRASQNINSWLAWYQQKPGQAPKFLMHKASILESGVPSRFSGSGSGTEFTLTISSLQPDDFASYFCQQYHSYPWTFGPGTKVEIK | 562 | IGKV1-5*03 | IGKJ1*01 | QQYHSYPWT | 586 |
| BRA112_71 | GGGLIQPGGSLRLSCAASGFTFSSYAMSWVRQAPGKGLEWVSGISGSGGASDNGASRYYADSVKGRFSISRDNSKNTVYLQMNSLRAEDTAVYYCAKDRLSGGFGELFQKWGQGTLVTVSS | 515 | IGHV3-23*01 | IGHD3-10*01 | IGHJ4*02 | AKDRLSGGFGELFQK | 539 | AASVGDRVTITCRASQNINSWLAWYQQKPGKAPKFLIYKASTLESGAPSRFSGSGSGTEFTLTISSLQPDDFATYYCQHYYSYPYTFGQGTKLEIK | 563 | IGKV1-5*03 | IGKJ2*01 | QHYYSYPYT | 587 |
| BRA112_91 | GGDLVQPGGSLRLSCAASGFTFSTYGMAWVRQAPGKGLEWLSSISSVDDSKYYAASVKGRFTISRDNSRNTLYLHMNSLRVDDTAVYYCAKDRIPHGLGELYANWGQGTLVAVSS | 516 | IGHV3-23*01 | IGHD3-16*01 | IGHJ4*02 | AKDRIPHGLGELYAN | 540 | SASVGDRVTITCRASQSISGWLAWYQQKPGKAPRLLMHKASILYRGVPSRFSGSGSGTEFTLTISSLQPDDFATYYCQHYHSYPYTFGQGTKLEIK | 564 | IGKV1-5*03 | IGKJ2*01 | QHYHSYPYT | 588 |
| BRA112_94 | GGDLVQPGGSLRLSCAASGFTFRTYGMTWVRQAPGKGLEWVSSISSVDDSTYYAKSVKGRFTISRDNSKNTLYLHITNLRVDDTAMYYCAKDRSPHGLGELYGDWGQGTLVTVSS | 517 | IGHV3-23*01 | IGHD3-16*01 | IGHJ4*02 | AKDRSPHGLGELYGD | 541 | SASVGDRVTITCRASQSISSWLAWYQQKPGKAPKLLMHKASNLHVGVPSRFSGSGSGTEFTLTITSLQPDDFATYYCQHYFSYPYTFGQGTKVEIK | 565 | IGKV1-5*03 | IGKJ2*01 | QHYFSYPYT | 589 |

TABLE 1-continued

| | | | | | | | | | | | | | | |
|---|---|---|---|---|---|---|---|---|---|---|---|---|---|---|
| VH3-23/VK 3-11 | BRA112_23 | GGGLVKPGGSLRLSCAASGLTFSTYAMSWVRQAPGKGLEWVSAISPGSGDNIYYGDSVKGRFTISRDNSKNTLYLQMNSLRAEDTAVYYCVNGGFSGYYSDYWGQGTLVAVSS | 518 | IGHV3-23*01 | IGHD3-22*01 | IGHJ4*02 | VNGGFSGYYSDY | 542 | SLSPGERATLSCRASQSVSNYLAWYQQKPGQAPRLLIYDASNMAPGIPARFSGSGSGTDFTLTISSLEPEDFAVYYCQQRSNWLTFGGGTKIEIK | 566 | IGKV3-11*01 | IGKJ4*01 | QQRSNWLT | 590 |
| | BRA112_52 | GGGLGQPGGSLRLSCGASGFTFSTYAMTWVRQAPGKGLEWVSDISADSDTTSYADSVKGRFTISRDNSKNTLYLQMNSLRAEDSAVYYCAKVKDSSGYMYYYYMDVWGKGTTVTVSS | 519 | IGHV3-23*01 | IGHD3-22*01 | IGHJ6*03 | AKVKDSSGYMYYYYMDV | 543 | SLSPGERTTLSCRASQSISNYLAWYQQKPGQAPRLLIYDASNRAAGIPARFSGSGSGIDFTLTISSLEPEDFGVYYCQQRGKWPPSFGGGTKVEIK | 567 | IGKV3-11*01 | IGKJ4*01 | QQRGKWPPS | 591 |
| | BRA112_63 | GGGLVLPGGSLRLSCAASGFTFSTHAMTWVRQAPGKGLEWVSVISHSGTTTYYADSFRGRFTISRDNSKNTVYLQMNRLRVEDTAVYYCAKDLYNGYFDYWGQGTLVTVSS | 520 | IGHV3-23*01 | IGHD1-14*01 | IGHJ4*02 | AKDLYNGYFDY | 544 | SLSPGERATLSCRASQSVRNFLAWYQQKPGQAPRLLIYDASNRATGIPARFSGSGSGTDFTLTISSLEPEDFAVYYCQQRGNWPPATFGGGTKVEIK | 568 | IGKV3-11*01 | IGKJ4*01 | QQRGNWPPAT | 592 |
| VH3-30/VK 3-11 | BRA112_36 | GGGVVQPGRSLRLSCAASGFTFSISTIHWVRQAPGKGLEYVVVISHDGNTKYYADSVKGRFIISRDNSKNTVFLQMNSLRPVDTAVYYCARGEVGYFDLWGRGTLVTVSS | 521 | IGHV3-30*04 | IGHD1-26*01 | IGHJ2*01 | ARGEVGYFDL | 545 | SLSPGERATLSCRASQSVSSFLAWYQQKPGQPPRLLIYDASTRATGIPARFSGSGSGTDFTLTISSLEPEDFAVYYCQQRSNWPPITFGQGTRLEIK | 569 | IGKV3-11*01 | IGKJ5*01 | QQRSNWPPIT | 593 |

TABLE 1-continued

| | | | | | | | | | | | | | | |
|---|---|---|---|---|---|---|---|---|---|---|---|---|---|---|
| | BRA112_70 | GGGVVQPGRSLRLSCAASGFSFSSHAMYWVRQAPGKGLEWVAIVSYDGSTKNYADSVKGRFTISRDNSKNTIYLHLNSLRAEDTAVYFCAREVDGIYGYLHYWGQGTLVTVSS | 522 | IGHV3-30*07 | IGHD5-24*01 | IGHJ1*01 | AREVDGIYGYLHY | 546 | SLSPGERATLSCRARQNVRNFLAWYQQKPGQAPRLLIYDASNRATDIPARFSGSGSGTDFTLTISSLEPEDFAVYYCQQRSYSITFGQGTRLEMK | 570 | IGKV3-11*01 | IGKJ5*01 | QQRSYSIT | 594 |
| | BRA112_75 | GGGVVQPGRSLRLSCAASGFTFSNYGMHWVRQAPGKGLEWVAIISYDGNTKYYADSVKGRFTISRDNSKNTLYLQLNSLRAEDTAIYYCARDGTTVTNFYLDVWGKGSTVTVSS | 523 | IGHV3-30*03 | IGHD4-17*01 | IGHJ6*03 | ARDGTTVTNFYLDV | 547 | SLSPGERATLSCRASQSVSNYLAWYQQKPGQAPRLLIYDASSRATGIPARFSGSGSGTDFSLTISSLEPEDFAVYYCQQRSNGPLTFGGGTKVEIK | 571 | IGKV3-11*01 | IGKJ4*01 | QQRSNGPLT | 595 |
| | BRA112_76 | GGGVVQPGRSLRLSCAASGFTFNTYAVHWVRQAPGKGLDWVTVLSHDGNSKYYTDSVRGRFTISRDSSKKTVFLQMDNLRTEDTAVYYCARDFHGYLDSWGQGTLVTVSS | 524 | IGHV3-30*10 | IGHD5-18*01 | IGHJ4*02 | ARDFHGYLDS | 548 | SLSPGERATLSCRASQSVSNFFAWYQQKPGQAPRLLIYDASKRATGIPARFSGSGSGTDFTLTISSLEPEDFAVYYCQQRSNWPPLTFGGGTKVEIK | 572 | IGKV3-11*01 | IGKJ4*01 | QQRSNWPPLT | 596 |
| VH4-38-2/VK3-20 | BRA112_20 | GPGLVKPSETLSLTCGVSGYSLTSGYYWSWIRQPPGKGLEWIGSIYHTGNTYYNPSLKSRVTILVDTSKNHFSLKLTSVTAADTAMYYCARTETITIRGAVSFDIWGQGRMVTVSS | 525 | IGHV4-38-2*01 | IGHD3-10*01 | IGHJ3*02 | ARTETITIRGAVSFDI | 549 | SLSPGERATLSCRASQSVSSSYLAWYQQKPGQAPRLLIYGAYNRATGIPDRFSGSGSGTDFTLTINRLEPEDFAVYYCQQYGTSPPEFTFGRGTKVEIK | 573 | IGKV3-20*01 | IGKJ4*01 | QQYGTSPPEFT | 597 |

TABLE 1-continued

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| | BRA112_57 | GPGLVKPSETLSLTCSVSGYFISSGHYWGWIRQSPGKGLEWIASIYQSGSKFQTGNTYYNPSLESRVTISMDTSKNQFSLKLSSVTAADTAVYFCARDARSRSWDRTGFFGPWGQGILVTISS | 526 | IGHV4-38-2*02 | IGHD6-13*01 | IGHJ5*02 | ARDARSRSWDRTGFFGP | 550 | SLSPGERATLSCRASQSLSSSFLAWYQQKPGQSPRLLIYGTSSRDTGIPDRFSGSGSGTDFTLTISRLEPEDSAVYYCQQYGSSWGTFGQGTKLEIK | 574 | IGKV3-20*01 | IGKJ2*02 | QQYGSSWGT | 598 |

BRA 12-refers to an individual donor. Sequences were analyzed with IgBlast

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| VH3-23/VK 3-20 | BRA12_08 | GGALVQPGGSLRLSCAASGFTFNYYAMTWVRQAPGRGLEWVSTITDNGGTTYLADSVKGRFTISRDNSQNTQSLQMNNLRADDTAVYFCVKHLRGWYTFEIWGQGTLVTVSS | 599 | IGHV3-23*01 | IGHD6-19*01 | IGHJ4*02 | VKHLRGWYTFEI | 603 | SLSPGERATLSCRASQSVSGSYLAWYQQKPGQAPRLLIYGASRRATGIPDRFSGSGSGTDFTLTISRLEPEDFAVYYCQQFGSSPRYTFGQGTKLEIK | 607 | IGKV3-20*01 | IGKJ2*01 | QQFGSSPRYT | 611 |
| | BRA12_21 | GGGLVQPGGSLRLSCAASGYIFDNYAMSWVRQAPGKGLEWVSYINGGGYGTDYADSVKGRFTISRDNSKRILYLQMNSLRVGDTAVYYCAKSPYVGGYGLPGDSWGQGTLVTVSS | 600 | IGHV3-23*01 | IGHD3-16*01 | IGHJ4*02 | AKSPYVGGYGLPGDS | 604 | SLSPGERATLSCRASQTIFFNYLAWYQKKPGQAPRLLVHGASTRATGIPDRFSGSGSGTDFTLTINSLDPEDFAVYYCQQYGDSPPTFGGGTKVDIK | 608 | IGKV3-20*01 | IGKJ4*01 | QQYGDSPPT | 612 |
| VH4-59/VK 3-20 | BRA12_06 | GPGLVKPSETLSLTCTVXGGSISRYFXSWIRQPPGKGLEWIGYIYYT | 601 | IGHV4-59*01 | IGHD3*22*01 | IGHJ6*02 | ARGPHYYDSSAYFTYNGMDV | 605 | SLSPGERATLSCRVSQSVSSNSLAWYQQKPGQAPRLLIYGASSRAT | 609 | IGKV3-20*01 | IGKJ5*01 | QQYGSSPPVT | 613 |

TABLE 1-continued

| Clone | Antibody ID | amino acids | SEQ ID NO: | VH | DH | JH | CDR3 | SEQ ID NO: | amino acids | SEQ ID NO: | VK/L | JK/L | CDR3 | SEQ ID NO: |
|---|---|---|---|---|---|---|---|---|---|---|---|---|---|---|
| | | GSTNYNPSLKSRVIILVDTSKNQFSXKLSSVTXADTAVYYCARGPHYYDSSAYFTYNGMDVWGQGTTVTVSS | | | | | | | GIPDRFSGSGSGTDFTLTISRLEPEDFAVYYCQQYGSSPPVTFGQGTRLEIK | | | | | |
| | BRA12_58 | GPGLVKPSETLSLTCTVSGGSISSYYWSWIRQPPGKGLEWIGFIYYSGSTNYNPSLKSRVTISVDTSKNQFSLKLSSVTAADTAVYYCARGDYYYDSSGYLYYFDYWGQGTLVTVSS | 602 | IGHV4-59*01 | IGHD3-22*01 | IGHJ4*02 | ARGDYYYDSSGYLYYFDY | 606 | SLSPGERATLSCRASQSVSSSSLAWYQQKPGQAPRLLIYGASNRATGIPDRFSGSGSGTDFTLTISRLEPEDFAVYYCQQYGTSVTFGGGTKVEIK | 610 | IGKV3-20*01 | IGKJ4*01 | QQYGTSVT | 614 |
| BRA 138-refers to an individual donor. Sequences were analyzed with IgBlast | | | | | | | | | | | | | | |
| VH1-69/VK3-11 | BRA138_23 | GAEVKKPGSSVRVSCKASGDTFSNYAISWVRQAPGQGLEWMGGIIPIFGTASYAQRFQDRVTITADKSTGTVYMELSSLRSEDTAVFYCARQKCTGGSCYSGNFDPWGQGTLVTVSS | 615 | IGHV1-69*06 | IGHD2-8*02 | IGHJ5*02 | ARQKCTGGSCYSGNFDP | 627 | SGRAIESVSGXLAWYQQKPGQAPRLLIYDASNRATGIPPRFSGSGXGTEFTLTISSAEPEDFAVYYCHQSIKWPPTFGGGSKVEIK | 639 | IGKV3-11*01 | IGKJ4*01 | HQSIKWPPT | 651 |
| | BRA138_28 | GAEVKKPGSSVKVSCKAPGGTFSRYSIAWVRQAPGQGLEWMGGINPTFTTPNYAQKFQGRVT | 616 | IGHV1-69*01 | IGHD3-22*01 | IGHJ4*02 | ARFRYYYESGGYSDASPYYLDY | 628 | ERVTLSCRASQSVSSYLAWYQQKPGQAPRLLIYDASNRATGIPARFTGSGSGTDFTLTISSLEPEDFAVY | 640 | IGKV3-11*01 | IGKJ4*01 | QQRSNWPLT | 652 |

TABLE 1-continued

| | | | | | | | | | | | | | |
|---|---|---|---|---|---|---|---|---|---|---|---|---|---|
| | | ITADESTNTAYLDLSSLRSEDTAVYYCARFRYYYESGGYSDASPYYLDYWGQGTLVTVSS | | | | | | | YCQQRSNWPLTFGGGTKVEIK | | | | | |
| VH4-31/VK 3-20 | BRA138_59 | GPGLVKPSQTLSLTCTVSGVSISSGGYYYSWFRQLPGKGLEWIGHIYYTGNTHYNPSLRSRLTISVDTSKNQFSLKLSSVTAADTARYYCARAWCEYAAYCWFDPWGRGTLVTVSS | 617 | IGHV4-31*03 | IGHD1-26*01 | IGHJ5*02 | ARAWCEYAAYCWFDP | 629 | SLSPGERATLSCRASQSVTSSYLAWYQHKPGQAPRLLIYGASSRAPGIPDRFSGSGSGTDFTLTISRLEPEDFAVYWCQQYGRSPFTFGQGTNLEIK | 641 | IGKV3-20*01 | IGKJ2*01 | QQYGRSPFT | 653 |
| | BRA138_62 | GPGLVKPSQTLSLTCTVSGGSITGGVYYWNWIRHHPGKGLEWIGYMFYSGDTDYNPSLRSRVTISGDTSKNKFSLNLNSVTAADTAVYYCARAGFDYGSPVSAFDIWGQGTMVTVSS | 618 | IGHV4-31*03 | IGHD4-17*01 | IGHJ3*02 | ARAGFDYGSPVSAFDI | 630 | SLSPGERATLSCRASQSVSSTYLVWYQQKPGQAPRLLIYGASSRATGIPDRFSGSGSGTDFTLTISRLEPEDFAVYFCQQYAHSPRGYTFGQGTKLEIK | 642 | IGKV3-20*01 | IGKJ2*01 | QQYAHSPRGYT | 654 |
| VH4-39/VK 3-11 | BRA138_65 | GPGLVKPSETLSLTCTVSGGSISSYNYYWGWIRQPPGKGLEFIGSIYYTGSTYYNPSLRSRVTISVDTSKNQFSLKLTSVTAADTAVYYCARHGPGMGHNWYFDLWGRGTLVTVSS | 619 | IGHV4-39*01 | IGHD3-16*01 | IGHJ2*01 | ARHGPGMGHNWYFDL | 631 | SLSPGERATLSCRASQSISSYLAWYQQKPGQAPRLLIYDASNRAPGIPARFSGSGSGTDFTLTISSLEPEDFAVYYCQQRSTWLTFGGGTKVEIK | 643 | IGKV3-11*01 | IGKJ4*01 | QQRSTWLT | 655 |
| | BRA138_94 | GPRLVKPSETLFLTCTVSGDSISSSSYFWGWIRQPPGKGLEWIGSISY | 620 | IGHV4-39*01 | IGHD6-13*01 | IGHJ4*02 | AKHLYSSSWNIGSSFDS | 632 | SLSPGERATLSCRASQSVSXYLAWYQQKPGQAPRLLXYDASSRATGIPA | 644 | IGKV3-11*01 | IGKJ2*01 | QQGSKWPVYT | 656 |

TABLE 1-continued

| | | | | | | | | | | | | | | |
|---|---|---|---|---|---|---|---|---|---|---|---|---|---|---|
| | | SGSTYYNPSLKSRVTISVDTSKNQFSLKLSSVTAADTVVYYCAKHLYSSSWNIGSSFDSWGPGTLVTVSS | | | | | | | RFSGSGSGTDFTLTISSLEPEDFAVYYCQQGSKWPVYTFGQGTKLEIK | | | | | |
| VH4-59/VK3-15 | BRA138_17 | GPGLVKPSETLSLSCTVSSGSISNYYWNWIRQPPGKGLEWIGYIYYSGSISYNPSLKSRVTISVDTSKNQLSLKLNSVTAADTAVYYCARGPDNRYWGQGTLVTVSS | 621 | IGHV4-59*1 | IGHD3-16*02 | IGHJ4*02 | ARGPDNRY | 633 | SVSPGERVTLSCRASQSVSYNLAWHQQKPGQAPRLLIYGASTRATGIPARFSGSGSGTEFTLTISNMQSEDFAVYYCQQYNNWPPVFTFGPGTKVDIK | 645 | IGKV3-15*01 | IGKJ3*01 | QQYNNWPPVFT | 657 |
| | BRA138_79 | GPGLVKPSETLSLTCTVSGGSISNYYWNWIRQPPGKGLEWIGYIYYSGSISYNPSLKSRVTISVDTSKNQLSLKLNSVTAADTAVYYCARGPDNRYWGQGTLVTVSS | 622 | IGHV4-59*1 | IGHD3-16*02 | IGHJ4*02 | ARGPDNRY | 634 | SVSPGERVTLSCRASQSVSYNLAWHQQKPGQAPRLLIYSASTRATGIPARFSGSGSGTEFTLTISNMQSEDFAVYYCQQYNNWPPVFTFGPGTKVDIK | 646 | IGKV3-15*01 | IGKJ3*02 | QQYNNWPPVFT | 658 |
| VH1-69/VK2-28 | BRA138_49 | GAEVKKPGSSVRLSCKASGGSYSTYAISWVRQAPGQGLEWMGRIIPSLGKTHLAQKFQGRVTFTADESTTTVYMVLSSLKSDDTALYYCATPDWQYSSAYSLDHWGQGTLVTVSS | 623 | IGHV1-69*11 | IGHD6-25*01 | IGHJ4*02 | ATPDWQYSSAYSLDH | 635 | PVTPGEPASISCRSSQSLLHSTGYNYLDWYLQKPGQSPQLLIYLGSNRASGVPDRFSGSGSGTDFTLKISRVEAEDVGVYYCMQALQTPFTFGPGTKVDIK | 647 | IGKV2-28*01 | IGKJ3*01 | MQALQTPFT | 659 |
| | BRA138_57 | GAEVKKPGSSVRLSCKASGGSYSTYAISWVRQAPGQGLEWMGRIIPSLGKTHLA | 624 | IGHV1-69*11 | IGHD6-25*01 | IGHJ4*02 | ATPDWQYSSAYSLDH | 636 | PVTPGEPASISCRSSQSLLHSTGYNYLDWYLQKPGQSPQLLIYLGSNRASGVPDRFSGSG | 648 | IGKV2-28*01 | IGKJ3*01 | MQALQTPFT | 660 |

TABLE 1-continued

| | | | | | | | | | | | | | | |
|---|---|---|---|---|---|---|---|---|---|---|---|---|---|---|
| | | QKFQGRVTFTADESTTTVYMILSSLKSEDTALYYCATPDWQYSSAYSLDHWGQGTLVTVSS | | | | | | | SGTDFTLKISRVEAEDVGVYYCMQALQTPFTFGPGTKVDIK | | | | | |
| VH1-46/VL2-23 | BRA138_15 | GAEVKKPGASVKVSCKTSGYTFTSYYMNWVRQAPGQGLEWMGIIKPSDGSTNYAQKFQGRVTMTRDTSTSTVYMELRSLRSEDTAVYYCGRDSKGWLQLRGDIDYWGQGTLVTVSS | 625 | IGHV1-46*01 | IGHD5-24*01 | IGHJ4*02 | GRDSKGWLQLRGDIDY | 637 | PASVSGSPGQSITISCAGTSSDVGNYNLVSWYQQHPGKAPKLLIYEVSKRPSGVSNRFSGSKSGNTASLTISGLQAEDEADYYCCSYAGSSTYVFGTGTEVTV | 649 | IGLV2-23*02 | IGLJ1*01 | CSYAGSSTYV | 661 |
| | BRA138_46 | GAEVKKPGASVKVSCKASGYTFTSTYIHWVRQAPGQGLEWMGIINPSSSNTNYAQKFQGRVTMTRDTSTSTVYMELSSLRSEDTAVYYCARDFGGYSSSSVSDAFDIWGQGTMVTVSS | 626 | IGHV1-46*01 | IGHD6-6*01 | IGHJ3*02 | ARDFGGYSSSSVSDAFDI | 638 | PASVSGSPGQSITISCTGTSSDVGSFNLVSWYQQHPGKAPKLIIYEVSKRPSGVSNRFSGSKSGNTASLTISGLQAEDEVHYYCCSYAGSSRFVFGTGTKVTV | 650 | IGLV2-23*02 | IGLJ1*01 | CSYAGSSRFV | 662 |

TABLE 2

MEX 84-refers to an individual donor. Sequences were analyzed with IgBlast

| | IgH | | | | | IgL | | | |
|---|---|---|---|---|---|---|---|---|---|
| Antibody ID | VH | DH | JH | CDR3 | SEQ ID NO: | VK/L | JK/L | CDR3 | SEQ ID NO: |
| MEX84_p2_03 | IGHV4-39*01 | IGHD6-13*01 | IGHJ6*02 | ARTAGDYGMDV | 663 | IGLV3-1*01 | IGLJ2*01 | QAWDSSTAVV | 707 |
| MEX84_p2_04 | IGHV3-30*03 | IGHD2-15*01 | IGHJ3*02 | YRVVAFDDPVNI | 664 | IGLV3-25*02 | IGLJ2*01 | QSADTNGSSWI | 708 |
| MEX84_p2_07 | IGHV5-51*03 | IGHD3-9*01 | IGHJ4*02 | ARLPAYYDILTGHIKGGYFDY | 665 | IGKV4-1*01 | IGKJ1*01 | QQYYTTPQT | 709 |
| MEX84_p2_09 | IGHV4-30-4*01 | IGHD3-10*01 | IGHJ6*02 | ARLGGFSRTLYSYYSMNV | 666 | IGKV3-20*01 | IGKJ1*01 | QQSGSLPWT | 710 |
| MEX84_p2_12 | IGHV3-11*01 | IGHD5-18*01 | IGHJ6*02 | ARGDYRSSYGYRYYGFDV | 667 | IGLV3-25*03 | IGLJ2*01 | QSADTNGSSWI | 711 |
| MEX84_p2_19 | IGHV3-30*02 | IGHD6-19*01 | IGHJ4*02 | AKDLYSSGWYMGPDY | 668 | IGLV1-40*01 | IGLJ1*01 | QSYDSSLSGYV | 712 |
| MEX84_p2_20 | IGHV3-30-3*01 | IGHD6-13*01 | IGHJ3*02 | ARDLWDKYSSSLGAFHI | 669 | IGKV3D-15*01 | IGKJ4*01 | QQYNNWPLH | 713 |
| MEX84_p2_27 | IGHV4-4*07 | IGHD1-14*01 | IGHJ4*02 | ARNQPGGRAFDF | 670 | IGKV3-11*01 | IGKJ1*01 | QERDNWPLTWP | 714 |
| MEX84_2_30p | IGHV4-34*01 | IGHD5-12*01 | IGHJ6*01 | ARKKGGYGSHYYYGMDV | 671 | IGKV3/OR2-268*02 | IGKJ1*01 | QQDYSLPTT | 715 |
| MEX84_p2_32 | IGHV4-30-4*01 | IGHD3-10*01 | IGHJ4*02 | GRTFTSAPFVDQ | 672 | IGKV4-1*01 | IGKJ2*01 | QQYYSTPYT | 716 |
| MEX84_p2_34 | IGHV4-59*08 | None | IGHJ6*02 | ARHLPYYYGMDV | 673 | IGKV3-15*01 | IGKJ2*01 | QQYNNWPPT | 717 |
| MEX84_p2_36 | IGHV3-13*01 | IGHD2/OR15-2a*01 | IGHJ6*02 | ARGRRRIQGVGEYSGMDV | 674 | IGKV2-28*01 | IGKJ4*01 | MQSLQTPRALT | 718 |
| MEX84_p2_46 | IGHV3-7*01 | IGHD4-23*01 | IGHJ4*02 | ASHDYGGNFRV | 675 | IGKV3-20*01 | IGKJ1*01 | QQYGSSPRT | 719 |
| MEX84_p2_48 | IGHV4-59*01 | IGHD2-21*01 | IGHJ5*02 | ARVGGRVWWFDP | 676 | IGKV1-39*01 | IGKJ1*01 | QQTYSTPWT | 720 |
| MEX84_p2_56 | IGHV3-23*01 | IGHD3-10*01 | IGHJ3*02 | AKYRDLWSGYDAFDI | 677 | IGKV3-20*01 | IGKJ4*01 | QQYGSSLT | 721 |

TABLE 2-continued

| | | | | | | | | | |
|---|---|---|---|---|---|---|---|---|---|
| MEX84_p2_59 | IGHV4-39*01 | IGHD3-22*01 | IGHJ4*02 | ATVIRHFDN | 678 | IGKV1-33*01 | IGKJ3*01 | QQYDNLPGFT | 722 |
| MEX84_p2_61 | IGHV3-9*01 | IGHD3-16*01 | IGHJ3*01 | AKVQTFVGAFDL | 679 | IGKV1-33*01 | IGKJ3*01 | QHYDSLPLLIS | 723 |
| MEX84_p2_64 | IGHV3-30*04 | IGHD3-16*01 | IGHJ6*02 | ARDYGNMRYGMDG | 680 | IGKV1-39*01 | IGKJ1*01 | QQNDDARALT | 724 |
| MEX84_p2_66 | IGHV4-61*02 | IGHD3-3*01 | IGHJ6*02 | ARGLRFLYGMDV | 681 | IGKV3-20*01 | IGKJ5*01 | QHYDSSIT | 725 |
| MEX84_p2_71 | IGHV4-4*02 | IGHD2-8*02 | IGHJ6*02 | ASENLISQGHCTGAICYSTYGMDV | 682 | IGKV1-39*01 | IGKJ1*01 | QQSYTVPRT | 726 |
| MEX84_p2_73 | IGHV4-31*03 | IGHD3-22*01 | IGHJ4*02 | ARDSPYYYDATGSPLLGPGTLVTVSS | 683 | IGKV1-5*03 | IGKJ1*01 | QQYNSYPRT | 727 |
| MEX84_p2_88 | IGHV3-23*01 | IGHD5-18*01 | IGHJ4*02 | ANHWGSAVMVTGYFDY | 684 | IGKV1-8*01 | IGKJ1*01 | QQYYSYPRT | 728 |
| MEX84_p2_89 | IGHV4-34*01 | IGHD5-12*01 | IGHJ4*02 | TRVRWDGIESTMFFDS | 685 | IGLV2-8*01 | IGLJ2*01 | SSYAGSNNFEVV | 729 |
| MEX84_p2_92 | IGHV1-2*02 | IGHD5-24*01 | IGHJ4*02 | ARVKMANGAIPPYFDH | 686 | IGKV1-9*01 | IGKJ3*01 | QQLISYPPT | 730 |
| MEX84_p4_01 | IGHV3-64D*06 | IGHD1-26*01 | IGHJ4*02 | VRVNRLHSGSYFSFDY | 687 | IGLV2-23*02 | IGLJ2*01 | CSYAAGSTFV | 731 |
| MEX84_p4_02 | IGHV4-59*08 | IGHD5-18*01 | IGHJ6*02 | ARLGLIQSLRNYYYGLDV | 688 | IGLV3-1*01 | IGLJ2*01 | QAWDSRSVV | 732 |
| MEX84_p4_04 | IGHV3-15*07 | IGHD3-10*01 | IGHJ6*02 | TTAIRVTGMDV | 689 | IGLV1-40*01 | IGLJ1*01 | QSYDSSHYV | 733 |
| MEX84_p4_07 | IGHV3-20*01 | IGHD2-2*01 | IGHJ6*02 | ARGWSDNSMDV | 690 | IGKV3-20*01 | IGKJ5*01 | QQYGSSPIT | 734 |
| MEX84_p4_26 | IGHV4-31*06 | IGHD4-17*01 | IGHJ4*02 | VTLLHDYGDYSFDY | 691 | IGKV1-39*01 | IGKJ2*01 | QQSSSIPYT | 735 |
| MEX84_p4_27 | IGHV4-31*03 | IGHD5-12*01 | IGHJ4*02 | ARGNITHYDLLPCDS | 692 | IGKV4-1*01 | IGKJ2*01 | QQYYSTPHT | 736 |
| MEX84_p4_28 | IGHV3-23*01 | IGHD3-10*01 | IGHJ4*02 | SLGRINYFFDY | 693 | IGKV1-9*01 | IGKJ4*01 | QQLNSYPLT | 737 |
| MEX84_p4_32 | IGHV4-30-4*01 | IGHD6-6*01 | IGHJ4*02 | ARASQLVPDY | 694 | IGKV3-11*01 | IGKJ4*01 | QQRSNWLT | 738 |

TABLE 2-continued

| Antibody ID | VH | DH | JH | CDR3 | SEQ ID NO: | VK/L | JK/L | CDR3 | SEQ ID NO: |
|---|---|---|---|---|---|---|---|---|---|
| MEX84_ p4_35 | IGHV1- 2*02 | IGHD3- 10*02 | IGHJ5* 02 | ARGGPINVPLGFDP | 695 | IGKV3-20*01 | IGKJ4*01 | HQYVSSPLT | 739 |
| MEX84_ p4_43 | IGHV1- 69*06 | IGHD2- 15*01 | IGHJ6* 02 | ARDEGGPNCSGGNC YYYYGMDV | 696 | IGKV1-33*01 | IGKJ4*01 | NNMILSLQL | 740 |
| MEX84_ p4_44 | IGHV3- 23*01 | IGHD2- 15*01 | IGHJ5* 02 | ANGGWQVPHWFDP | 697 | IGKV1-39*01 | IGKJ4*01 | QQSYSIPLT | 741 |
| MEX84_ p4_46 | IGHV4- 61*02 | IGHD5- 18*01 | IGHJ4* 02 | ARARSGYSLGYYFD Y | 698 | IGKV1-33*01 | IGKJ4*01 | QQYDDLLT | 742 |
| MEX84_ p4_47 | IGHV3- 30*18 | IGHD3- 16*01 | IGHJ5* 02 | AKVSRPKGAQASFD P | 699 | IGKV1-6*01 | IGKJ1*01 | LQDYDYPLS | 743 |
| MEX84_ p4_52 | IGHV3- 15*07 | IGHD5- 12*01 | IGHJ4* 02 | ATPKGGYSGYDQLD Y | 700 | IGKV1-39*01 | IGKJ4*01 | QQSYNFPRT | 744 |
| MEX84_ p4_59 | IGHV1- 69*01 | IGHD3- 22*01 | IGHJ6* 02 | ARPGYTFGYHSYYY AMDV | 701 | IGKV3-11*01 | IGKJ5*01 | QQRAGT | 745 |
| MEX84_ p4_66 | IGHV3- 23*01 | IGHD6- 13*01 | IGHJ4* 01 | ARGIDY | 702 | IGKV2-24*01 | IGKJ1*01 | TQATQFPWT | 746 |
| MEX84_ p4_69 | IGHV1- 2*02 | IGHD6- 19*01 | IGHJ6* 02 | ARGSLRGTNGWHS HLGYYGMDV | 703 | IGKV1-39*01 | IGKJ2*01 | HQSFSSPDT | 747 |
| MEX84_ p4_72 | IGHV3- 48*03 | IGHD6-6*01 | IGHJ4* 02 | ARSRLRYSSSWYFD Y | 704 | IGKV4-1*01 | IGKJ5*01 | QQYYSTPRIT | 748 |
| MEX84_ p4_73 | IGHV3- 48*01 | IGHD1-7*01 | IGHJ2* 01 | ARDILPHGTHGWYF DV | 705 | IGKV3-11*01 | IGKJ2*01 | QHRRDWPRYT | 749 |
| MEX84_ p4_75 | IGHV3- 53*01 | IGHD2- 21*01 | IGHJ4* 02 | ARAKGMIAELDY | 706 | IGKV4-1*01 | IGKJ2*01 | QQYRDTPSYT | 750 |

MEX 18-refers to an individual donor. Sequences were analyzed with IgBlast

| | IgH | | | | | IgL | | | |
|---|---|---|---|---|---|---|---|---|---|
| Antibody ID | VH | DH | JH | CDR3 | SEQ ID NO: | VK/L | JK/L | CDR3 | SEQ ID NO: |
| MEX18_01 | IGHV3-15*01 | IGHD5-24*01 | IGHJ6*02 | TTEIGLGGPNTPSAQLY YYGIDV | 751 | IGLV1-47*01 | IGLJ3*02 | VAWDDSLSGRV | 773 |
| MEX18_06 | IGHV3-11*06 | IGHD1-26*01 | IGHJ3*02 | ASFRSGAFEI | 752 | IGKV3-20*01 | IGKJ3*01 | QQYGSSAVS | 774 |
| MEX18_08 | IGHV4-59*01 | IGHD3-22*01 | IGHJ4*02 | ARVRYEYDSGGYYYVYD FEY | 753 | IGLV2-11*01 | IGLJ1*01 | CSYAGSYV | 775 |
| MEX18_12 | IGHV4-31*03 | IGHD6-6*01 | IGHJ6*02 | ARVALSSSSFGEHYYGV DV | 754 | IGKV3-20*01 | IGKJ3*01 | QQYGGSPLFT | 776 |

TABLE 2-continued

| | | | | | | | | | |
|---|---|---|---|---|---|---|---|---|---|
| MEX18_14 | IGHV3-72*01 | IGHD4-17*01 | IGHJ6*02 | ARAGTVFAGHYGMDV | 755 | IGKV1-16*02 | IGKJ4*01 | QQYKSYPLT | 777 |
| MEX18_17 | IGHV3-23*01 | IGHD3-22*01 | IGHJ4*02 | AKDPRRDYYDSSGYYYP SRGHFDY | 756 | IGLV2-8*01 | IGLJ3*02 | SSYAGSRTWV | 778 |
| MEX18_18 | IGHV4-61*01 | IGHD1-14*01 | IGHJ3*02 | ARIITRNGDAFDI | 757 | IGLV2-11*01 | IGLJ2*0 | CSYAGSYT | 779 |
| MEX18_25 | IGHV3-23*01 | IGHD1-20*01 | IGHJ4*02 | AKFQSSNWSPFDS | 758 | IGKV3-20*01 | IGKJ1*01 | QQYGNLPRT | 780 |
| MEX18_26 | IGHV4-30-4*01 | IGHD3-10*01 | IGHJ4*02 | ARGVWFGEFAVGY | 759 | IGKV3-15*01 | IGKJ3*01 | QQYNNWPPRGA T | 781 |
| MEX18_31 | IGHV3-15*01 | IGHD1-1*01 | IGHJ4*02 | ITGIFKSTWKTDY | 760 | IGKV3-11*01 | IGKJ1*01 | QQRSNGWT | 782 |
| MEX18_32 | IGHV4-31*03 | IGHD4/OR15-4a*01 | IGHJ4*02 | ARESDFNYGAVDH | 761 | IGKV3-15*01 | IGKJ2*01 | QQYNNWPYT | 783 |
| MEX18_35 | IGHV5-51*01 | IGHD1-1*01 | IGHJ4*02 | AKTQGYNPNWPHDF | 762 | IGKV1-9*01 | IGKJ2*01 | QQLNGHPRT | 784 |
| MEX18_37 | IGHV3-30*18 | IGHD3-10*01 | IGHJ4*02 | AKDGRGSIDY | 763 | IGKV2D-29*02 | IGKJ5*01 | MQSIQLPPIT | 785 |
| MEX18_43 | IGHV3-7*03 | IGHD2-15*01 | IGHJ4*02 | ERDIVWGVAGTDY | 764 | IGKV3-20*01 | IGKJ1*01 | QYYGDSPRP | 786 |
| MEX18_44 | IGHV4-61*03 | IGHD6-19*01 | IGHJ3*02 | ARENIAVFFDI | 765 | IGKV1-33*01 | IGKJ4*01 | QQHDNLQVI | 787 |
| MEX18_51 | IGHV4-30-4*01 | IGHD6-19*01 | IGHJ4*02 | ARDKRYSSGWYYFES | 766 | IGKV3-11*01 | IGKJ1*01 | QHRANWPT | 788 |
| MEX18_59 | IGHV3-64D*06 | IGHD4-17*01 | IGHJ4*02 | VKPSVTTHYFDY | 767 | IGKV3-11*01 | IGKJ2*01 | QQRSNWPPFT | 789 |
| MEX18_61 | IGHV4-31*03 | IGHD1-1*01 | IGHJ6*02 | ARDHSPGTTWGNYNYG MDV | 768 | IGKV1-39*01 | IGKJ2*01 | QQSYSTPQT | 790 |
| MEX18_74 | IGHV1-18*04 | IGHD3-22*01 | IGHJ6*02 | ARDSRYYDSRSSYYYYG MDV | 769 | IGKV2-28*01 | IGKJ1*01 | MQALQTPKT | 791 |
| MEX18_75 | IGHV3-11*01 | IGHD5-12*01 | IGHJ4*02 | ARVARPGGYGRTFDE | 770 | IGKV1-39*01 | IGKJ4*01 | QQSYSDFS | 792 |
| MEX18_88 | IGHV3-33*05 | None | IGHJ6*02 | ARVRERYYYFYGLDV | 771 | IGKV2-28*01 | IGKJ5*01 | MQALQTFT | 793 |
| MEX18_92 | IGHV3-30*18 | IGHD6-19*01 | IGHJ4*02 | AKGVAAPGYFEY | 772 | IGKV3-11*01 | IGKJ5*01 | QQRSNWPPIT | 794 |

MEX 105-refers to an individual donor. Sequences were analyzed with IgBlast

| | IgH | | | | | IgL | | | |
|---|---|---|---|---|---|---|---|---|---|
| Antibody ID | VH | DH | JH | CDR3 | SEQ ID NO: | VK/L | JK/L | CDR3 | SEQ ID NO: |
| MEX105_10 | IGHV1-46*01 | IGHD3-10*01 | IGHJ4*02 | ARGNSYGSGNLGYYLDF | 795 | IGLV1-44*01 | IGLJ3*02 | STWDDSLNGPV | 809 |
| MEX105_21 | IGHV1-69*01 | IGHD3-22*01 | IGHJ4*02 | ARGPDYNDTPGYYGNY | 796 | IGKV3-20*01 | IGKJ3*01 | HHYGRT | 810 |

TABLE 2-continued

| | | | | | | | | | |
|---|---|---|---|---|---|---|---|---|---|
| MEX105_29 | IGHV1-18*01 | IGHD3-22*01 | IGHJ6*02 | ARGAHYYDSSGYRQLYGLDV | 797 | IGKV3-11*01 | IGKJ4*01 | QQRANWPALT | 811 |
| MEX105_35 | IGHV3-72*01 | IGHD2-21*01 | IGHJ4*02 | ARANVATRYFDY | 798 | IGKV1-9*01 | IGKJ5*01 | QHLSTYPIT | 812 |
| MEX105_44 | IGHV4-39*01 | IGHD3-10*01 | IGHJ3*01 | ARLRVRGAGWAFDL | 799 | IGKV3-11*01 | IGKJ5*01 | QQRSNWPPAIT | 813 |
| MEX105_47 | IGHV3-23*03 | IGHD3-10*01 | IGHJ4*02 | AKSDYYGSGHYTTIPSSFED | 800 | IGKV3D-15*01 | IGKJ3*01 | QQYNNWPLT | 814 |
| MEX105_55 | IGHV5-51*03 | IGHD3-22*01 | IGHJ5*02 | ARHPTQNYASGDYYT | 801 | IGKV1-9*01 | IGKJ4*01 | QQLTTYPGT | 815 |
| MEX105_61 | IGHV1-2*02 | IGHD3-3*01 | IGHJ6*02 | AKGARITVFGGLDV | 802 | IGKV1-5*03 | IGKJ2*03 | QQYMSLPYS | 816 |
| MEX105_69 | IGHV1-46*01 | IGHD4-11*01 | IGHJ4*02 | ARPYFDGRSNSNLIFFDY | 803 | IGKV3-15*01 | IGKJ1*01 | QQYNTWPPALT | 817 |
| MEX105_72 | IGHV1-18*01 | IGHD2-15*01 | IGHJ5*02 | ARVIVVVVAATSDLPVGFDP | 804 | IGKV1-5*03 | IGKJ1*01 | QHYHSYPWT | 818 |
| MEX105_79 | IGHV3-21*01 | IGHD5-18*01 | IGHJ4*02 | ARWLDNGIQGKYDY | 805 | IGKV3-11*01 | IGKJ2*01 | QQRHEWPV | 819 |
| MEX105_84 | IGHV4-59*01 | IGHD3-10*01 | IGHJ5*02 | ARGPVWFGEYGGAFDP | 806 | IGKV3-20*01 | IGKJ5*01 | SNMLGHRSP | 820 |
| MEX105_93 | IGHV5-51*01 | IGHD3-10*02 | IGHJ5*02 | ARAKGRGLQNWFDP | 807 | IGKV3D-20*01 | IGKJ5*01 | QQYGSSPPIT | 821 |
| MEX105_94 | IGHV4-31*03 | IGHD3-10*01 | IGHJ6*02 | ARVSPLWDYYDSGPYYNDFYYG MDV | 808 | IGKV3-15*01 | IGKJ2*01 | QQHMYT | 822 |

BTA 112-refers to an individual donor. Sequences were analyzed with IgBlast

| | IgH | | | | | IgL | | | |
|---|---|---|---|---|---|---|---|---|---|
| Antibody ID | VH | DH | JH | CDR3 | SEQ ID NO: | VK/L | JK/L | CDR3 | SEQ ID NO: |
| BRA112_01 | IGHV4-31*01 | IGHD5-24*01 | IGHJ4*02 | ARGGDGYTTRWFYFNH | 823 | IGKV1-NL1*01 | IGKJ4*01 | QQYYSAPLT | 842 |
| BRA112_04 | IGHV4-31*03 | IGHD3-22*01 | IGHJ4*02 | ARLGAEYYVDSSGYRGIDH | 824 | IGKV2-28*01 | IGKJ4*01 | MQALQTLSLT | 843 |
| BRA112_11 | IGHV1-8*01 | IGHD3-10*01 | IGHJ6*02 | ARVERGHTYGLNYYYYYGMDV | 825 | IGLV1-47*01 | IGLJ3*02 | AAWDDSLRGHWV | 844 |
| BRA112_12 | IGHV4-31*03 | IGHD3-22*01 | IGHJ4*02 | ARDSSNTFHHDSSGYFDN | 826 | IGLV4-69*01 | IGLJ3*02 | QTWGTGIRV | 845 |
| BRA112_15 | IGHV4-31*03 | IGHD6-19*01 | IGHJ4*02 | ARLIPGSGWRKGGFDY | 827 | IGKV3-15*01 | IGKJ1*01 | QHYKNWPGT | 846 |
| BRA112_22 | IGHV1-46*01 | IGHD3-10*01 | IGHJ4*02 | ARDSGWSGITTVRGVPPDF | 828 | IGKV3-15*01 | IGKJ2*01 | LHYNNWPPRYT | 847 |
| BRA112_29 | IGHV1-8*01 | IGHD3-10*01 | IGHJ4*02 | ARGYFYTSSNYYNTDH | 829 | IGKV1-16*02 | IGKJ3*01 | QQYKSYPFT | 848 |
| BRA112_31 | IGHV1-2*04 | IGHD3-10*01 | IGHJ6*02 | ARDRFSRHYGSGSLHYAMDV | 830 | IGLV2-14*01 | IGLJ1*01 | GSYTSTSTCV | 849 |
| BRA112_32 | IGHV3-7*01 | IGHD4-23*01 | IGHJ3*02 | ATGYGGNFAFDM | 831 | IGKV2-28*01 | IGKJ1*01 | MQALQTPPT | 850 |
| BRA112_34 | IGHV3-7*01 | IGHD4-17*01 | IGHJ4*02 | ASGGYGVYGFDY | 832 | IGKV1-5*03 | IGKJ1*01 | HQYNAYPWT | 851 |
| BRA112_39 | IGHV4-39*07 | IGHD3-10*02 | IGHJ6*03 | ARAHSYYVYYYMDV | 833 | IGKV3-15*01 | IGKJ5*01 | QQYNNWLPIT | 852 |

TABLE 2-continued

| | | | | | | | | | |
|---|---|---|---|---|---|---|---|---|---|
| BRA112_42 | IGHV4-39*01 | IGHD3-10*01 | IGHJ4*02 | VRHGPHPGVLVWFGEQSKIDY | 834 | IGKV4-1*01 | IGKJ5*01 | QQYYTTPLT | 853 |
| BRA112_53 | IGHV3-9*01 | IGHD6-13*01 | IGHJ6*02 | AKDIGNIAGVAQGIYFYFGMDV | 835 | IGKV1-9*01 | IGKJ4*01 | QRLNSYPRVT | 854 |
| BRA112_54 | IGHV3-21*01 | IGHD4-17*01 | IGHJ4*02 | ARKSYGDPFFDY | 836 | IGLV2-14*01 | IGLJ3*02 | SSYTSRSTWV | 855 |
| BRA112_58 | IGHV4-31*03 | IGHD2-15*01 | IGHJ4*02 | ASSVMVVAQFDS | 837 | IGKV3-20*01 | IGKJ1*01 | QQYGNSPWT | 856 |
| BRA112_59 | IGHV1-3*01 | IGHD5-18*01 | IGHJ6*02 | ATGAGYSYPVAMDV | 838 | IGKV2-28*01 | IGKJ2*01 | MQALQTPYT | 857 |
| BRA112_68 | IGHV4-59*01 | IGHD3-10*01 | IGHJ4*02 | ARIIINRGQSFDY | 839 | IGLV2-11*01 | IGLJ1*01 | CSYAGKYV | 858 |
| BRA112_87 | IGHV3-20*01 | IGHD3-10*01 | IGHJ5*02 | ARNAPKVFGSGSYYSNWFDP | 840 | IGKV3-11*01 | IGKJ5*01 | QQRLYWPVT | 859 |
| BRA112_89 | IGHV4-31*03 | IGHD3-22*01 | IGHJ4*01 | ARSYSEVLVGYD | 841 | IGKV3-11*01 | IGKJ4*01 | QQRSNWLT | 860 |

BRA 12-refers to an individual donor. Sequences were analyzed with IgBlast

| | IgH | | | | | IgL | | | |
|---|---|---|---|---|---|---|---|---|---|
| Antibody ID | VH | DH | JH | CDR3 | SEQ ID NO: | VK/L | JK/L | CDR3 | SEQ ID NO: |
| BRA12_02 | IGHV3-23*01 | IGHD6-19*01 | IGHJ4*02 | AKDRTGNIGAGTGYFDK | 861 | IGKV1-5*03 | IGKJ1*01 | QQYNNYPWT | 895 |
| BRA12_03 | IGHV1-18*01 | IGHD5-24*01 | IGHJ1*01 | ARTPREYIAEYFQH | 862 | IGKV3-15*01 | IGKJ5*01 | QQYNNWLIT | 896 |
| BRA12_05 | IGHV3-53*01 | IGHD6-13*01 | IGHJ3*02 | ARVKLRDGSSWYHAFDI | 863 | IGKV4-1*01 | IGKJ1*01 | QQYYTTPPWT | 897 |
| BRA12_11 | IGHV1-3*01 | IGHD6-19*01 | IGHJ4*02 | ARWGLSSAWVAPLGFDY | 864 | IGKV4-1*01 | IGKJ3*01 | QQYYTTPFT | 898 |
| BRA12_13 | IGHV1-2*04 | IGHD1-26*01 | IGHJ6*02 | ARELLYSGRQTYYYSYYGMD V | 865 | IGLV2-14*01 | IGLJ3*02 | SSYTSDNTRV | 899 |
| BRA12_14 | IGHV5-51*03 | IGHD1-26*01 | IGHJ6*02 | ARRQGAHGRDLGFHYAMDV | 866 | IGLV2-11*01 | IGLJ3*02 | CSYAGSYSWV | 900 |
| BRA12_16 | IGHV1-18*01 | IGHD6-13*01 | IGHJ4*02 | ARDGAAAGDY | 867 | IGKV1-8*01 | IGKJ3*01 | QQYYDYPLT | 901 |
| BRA12_19 | IGHV4-34*01 | IGHD1-26*01 | IGHJ6*02 | GNLATVGATAPYYNYYGMYV | 868 | IGLV1-47*01 | IGLJ1*01 | AAWDDSLNGRV | 902 |
| BRA12_31 | IGHV1-3*01 | IGHD5-24*01 | IGHJ4*02 | ARGMATPALLN | 869 | IGKV3-15*01 | IGKJ4*01 | HQYNNWPLT | 903 |
| BRA12_36 | IGHV4-34*01 | IGHD5-24*01 | IGHJ6*02 | ARGHNKWLQLNFYAMDV | 870 | IGKV3-11*01 | IGKJ5*01 | QQRINWPIT | 904 |
| BRA12_37 | IGHV4-34*01 | IGHD6-19*01 | IGHJ4*03 | LVQLQQWGAGLLKPSETL | 871 | IGKV1-39*01 | IGKJ2*03 | QQSYSRPYS | 905 |
| BRA12_38 | IGHV3-9*01 | IGHD6-19*01 | IGHJ6*02 | VKGGYNSVWSNSYGMDV | 872 | IGKV1-33*01 | IGKJ2*01 | QQYDNVPYT | 906 |
| BRA12_40 | IGHV1-69*01 | IGHD3-10*01 | IGHJ6*02 | ARALYVRGYNYGFLYGMDV | 873 | IGKV3-20*01 | IGKJ3*01 | QQYDNSRFT | 907 |
| BRA12_42 | IGHV1-2*02 | IGHD1-1*01 | IGHJ4*02 | AKGGPTARVLSGQLYYFDY | 874 | IGKV2-29*03 | IGKJ1*01 | MQGIHLWT | 908 |

TABLE 2-continued

| | | | | | | | | | |
|---|---|---|---|---|---|---|---|---|---|
| BRA12_46 | IGHV4-34*01 | IGHD6-19*01 | IGHJ6*02 | ARGPSGLAVAGTVGERDRNY HYYYGMDV | 875 | IGLV2-8*01 | IGLJ1*01 | SSYAGTSYV | 909 |
| BRA12_51 | IGHV1-8*02 | IGHD3-9*01 | IGHJ6*02 | ARLGDILTGYVDYGMDV | 876 | IGLV1-44*01 | IGLJ1*01 | AAWDDSLNGLYV | 910 |
| BRA12_54 | IGHV1-3*01 | IGHD4-17*01 | IGHJ5*02 | ARSPIYGDYGFDP | 877 | IGKV2-28*01 | IGKJ1*01 | MQALQIPPT | 911 |
| BRA12_55 | IGHV1-69*01 | IGHD2-15*01 | IGHJ4*01 | ARTHCTGGSCFSSSFDY | 878 | IGKV1-16*02 | IGKJ4*01 | QQYNSYPPT | 912 |
| BRA12_56 | IGHV3-21*01 | IGHD3-10*01 | IGHJ6*02 | ARDRDYGSGSQPLYYYYAMD V | 879 | IGKV1-39*01 | IGKJ2*03 | QQSYSTPYS | 913 |
| BRA12_60 | IGHV1-69*06 | IGHD7-27*01 | IGHJ4*02 | ARVLGNWGFDY | 880 | IGKV1-9*01 | IGKJ3*01 | QQLNSYPFT | 914 |
| BRA12_63 | IGHV3-48*03 | IGHD3-16*02 | IGHJ6*02 | ARGGKRLGELSLFHYYGMDV | 881 | IGKV2-28*01 | IGKJ1*01 | MQALHTPWT | 915 |
| BRA12_67 | IGHV5-51*01 | IGHD3-22*01 | IGHJ4*02 | ARHRRGYYDSSGYYYDY | 882 | IGLV2-14*01 | IGLJ2*01 | SSYTRSSTVV | 916 |
| BRA12_70 | IGHV4-39*01 | IGHD5-18*01 | IGHJ4*02 | TRYSYGFSYFDY | 883 | IGKV3-11*01 | IGKJ4*01 | QQRSNWPLT | 917 |
| BRA12_71 | IGHV3-30*04 | IGHD6-6*01 | IGHJ6*02 | ARAPTRSIGHGMDL | 884 | IGLV8-61*01 | IGLJ3*02 | VLYVGAAISL | 918 |
| BRA12_75 | IGHV3-48*03 | IGHD2/OR15-2a*01 | IGHJ6*02 | ARENNNIALPYYYYGMDV | 885 | IGKV3-11*01 | IGKJ4*01 | QQSSNWPIT | 919 |
| BRA12_77 | IGHV4-39*07 | IGHD1-1*01 | IGHJ6*01 | ARDIRYTYGPMWGGDYGMD V | 886 | IGKV3-20*01 | IGKJ2*01 | QQYGGSPYT | 920 |
| BRA12_79 | IGHV4-34*01 | IGHD1-1*01 | IGHJ6*02 | ARRPPLLRSHNYNYLGMDV | 887 | IGKV3-20*01 | IGKJ5*01 | QQYGSSPLIT | 921 |
| BRA12_81 | IGHV3-23*01 | IGHD1-20*01 | IGHJ6*02 | AKSSGGHNWNYVDYYYGMD V | 888 | IGKV1-9*01 | IGKJ3*01 | QQLNSYPVT | 922 |
| BRA12_82 | IGHV1-46*01 | None | IGHJ6*02 | ASTHLGGLDV | 889 | IGKV2-30*01 | IGKJ4*01 | MQGTHWPLT | 923 |
| BRA12_84 | IGHV3-49*04 | IGHD3-10*01 | IGHJ4*02 | SRATNYYALGY | 890 | IGLV2-14*01 | IGLJ3*02 | SSYTSSATWV | 924 |
| BRA12_86 | IGHV4-39*07 | None | IGHJ6*02 | ARDWPVMDV | 891 | IGKV2-30*01 | IGKJ1*01 | MQGTHWPPWT | 925 |
| BRA12_88 | IGHV1-3*01 | IGHD2-15*01 | IGHJ4*02 | ARVVGTTLYSMGY | 892 | IGKV4-1*01 | IGKJ1*01 | QQYYNTWT | 926 |
| BRA12_93 | IGHV3-21*01 | IGHD6-13*01 | IGHJ4*02 | ARVAAWYAGSFDS | 893 | IGLV2-18*02 | IGLJ1*01 | SSYTSTSAF | 927 |
| BRA12_94 | IGHV3-33*06 | IGHD2-21*02 | IGHJ4*02 | AKAGAYCGGDCYSYLQY | 894 | IGKV1-5*03 | IGKJ3*01 | QQYQSDLFT | 928 |

TABLE 2-continued

BRA 138-refers to an individual donor. Sequences were analyzed with IgBlast

| Antibody ID | IgH VH | IgH DH | IgH JH | IgH CDR3 | IgH SEQ ID NO: | IgL VK/L | IgL JK/L | IgL CDR3 | IgL SEQ ID NO: |
|---|---|---|---|---|---|---|---|---|---|
| BRA138_02 | IGHV4-38-2*02 | IGHD4-11*01 | IGHJ3*02 | ARLLIDYTNYKSVASAFDI | 929 | IGKV3-15*01 | IGKJ4*01 | QQYHNWPPRLT | 953 |
| BRA138_05 | IGHV4-30-4*01 | IGHD3-22*01 | IGHJ4*02 | ASSPGYDTRGYYIAGQYYFVN | 930 | IGKV1-5*03 | IGKJ4*01 | QQYNRYVS | 954 |
| BRA138_06 | IGHV3-30-3*01 | IGHD4-17*01 | IGHJ4*02 | ARDGTIPGYGDY | 931 | IGKV3-11*01 | IGKJ1*01 | QQRSNWPPWT | 955 |
| BRA138_09 | IGHV4-61*01 | IGHD6-19*01 | IGHJ6*02 | ARMPVAAHYFYDGMDV | 932 | IGKV3-20*01 | IGKJ5*01 | QQYGSSPIT | 956 |
| BRA138_12 | IGHV3-9*01 | IGHD6-13*01 | IGHJ4*02 | AKFPHRSTSWYYFDS | 933 | IGLV1-40*01 | IGLJ1*01 | QSYDSSLSGSFYV | 957 |
| BRA138_22 | IGHV5-51*01 | IGHD1-1*01 | IGHJ4*01 | ARGLRVEIPIFAY | 934 | IGKV3-20*01 | IGKJ3*01 | QQYGGSPPRFT | 958 |
| BRA138_26 | IGHV1-69*01 | IGHD3-9*01 | IGHJ3*02 | TRDTIVGATYAFDI | 935 | IGKV4-1*01 | IGKJ3*01 | QQHYSTPFT | 959 |
| BRA138_27 | IGHV3-21*01 | IGHD6-13*01 | IGHJ6*02 | AREPDSSSWYQDYYCAMDV | 936 | IGLV2-23*02 | IGLJ1*01 | CSYAGSRTRV | 960 |
| BRA138_34 | IGHV4-61*02 | IGHD3-16*02 | IGHJ6*03 | TRDLGNFIAYMDV | 937 | IGLV1-44*01 | IGLJ2*01 | ASWDDNLNSRV | 961 |
| BRA138_35 | IGHV3-49*05 | IGHD3-22*01 | IGHJ4*02 | SRGSYYYDSRGYYFRPPSAGPFDY | 938 | IGKV2-29*02 | IGKJ5*01 | MQGIIFPPIT | 962 |
| BRA138_51 | IGHV3-64D*06 | IGHD1-26*01 | IGHJ4*02 | VKIAVGGSWSSEALDY | 939 | IGLV2-14*01 | IGLJ2*0 | SSYTSSSTLV | 963 |
| BRA138_54 | IGHV3-7*02 | IGHD1-26*01 | IGHJ6*02 | ARGHLVGATSYYYGMDV | 940 | IGKV1-9*01 | IGKJ1*01 | QQLNSYPET | 964 |
| BRA138_63 | IGHV4-34*01 | IGHD3-10*01 | IGHJ4*02 | ARVSLLWFGELGAVPYYFDY | 941 | IGKV1-9*01 | IGKJ3*01 | LQVNSYPLT | 965 |
| BRA138_66 | IGHV1-69*01 | IGHD6-19*01 | IGHJ6*02 | ARDRHRAGALRYGMDV | 942 | IGLV2-14*01 | IGLJ2*01 | SSYTTSTTVI | 966 |
| BRA138_68 | IGHV3-9*01 | IGHD6-19*01 | IGHJ5*02 | AKGGTSVAIGWNWFDP | 943 | IGLV2-11*01 | IGLJ1*01 | CSYGGTYSPYV | 967 |
| BRA138_70 | IGHV4-30-2*01 | IGHD3-9*01 | IGHJ4*02 | ARGYRGNILTGRLGYFDY | 944 | IGKV1-33*01 | IGKJ1*01 | QQYAKYPLT | 968 |
| BRA138_71 | IGHV3-49*04 | IGHD3-22*01 | IGHJ4*02 | TTAGNYYDSRGYYFSRPRHSFDY | 945 | IGKV3-20*01 | IGKJ4*01 | QQYATSSLT | 969 |
| BRA138_77 | IGHV3-33*01 | IGHD3-10*01 | IGHJ4*02 | ARAPQNYYGSGRYYSGCDY | 946 | IGLV1-51*01 | IGLJ1*01 | GTWDSSLSAYV | 970 |
| BRA138_78 | IGHV4-59*01 | IGHD6-19*01 | IGHJ6*03 | ARTAVDRYSSGWYGEYYYYSMDV | 947 | IGLV1-51*01 | IGLJ2*01 | GTWDSSLSAGV | 971 |
| BRA138_84 | IGHV1-18*01 | IGHD3-22*01 | IGHJ4*02 | ARRPLTSYYDSGAYYPYYFDY | 948 | IGLV6-57*01 | IGLJ1*01 | QSFDSSNQEV | 972 |

TABLE 2-continued

| | | | | | | | | | |
|---|---|---|---|---|---|---|---|---|---|
| BRA138_87 | IGHV3-49*04 | IGHD3-22*01 | IGHJ4*02 | TRDTTYFYDNSGYYGWASKGGYFDY | 949 | IGLV1-40*01 | IGLJ2*01 | QSYDRSLSGSRV | 973 |
| BRA138_89 | IGHV4-39*01 | IGHD6-25*01 | IGHJ6*02 | ARQPVRGRHSSSGYRHYYYGMDV | 950 | IGKV1-13*02 | IGKJ1*01 | QQFNSYPQT | 974 |
| BRA138_90 | IGHV4-31*03 | IGHD3-16*01 | IGHJ4*02 | ARVETYDHVWGAFRFGEGGYFDH | 951 | IGKV3-15*01 | IGKJ1*01 | HHYNNWT | 975 |
| BRA138_91 | IGHV4-30-2*01 | IGHD3-22*01 | IGHJ4*01 | ARGGHYYDSRGYFTLAGPIDY | 952 | IGKV3-15*01 | IGKJ1*01 | QQYHDWPLWT | 976 |

TABLE 3

List of primers for cloning recombinant antibodies by the SLIC method. Related to Methods of this example.

| Primer ID | Primer sequence | Best V or J gene segment match | SEQ ID NO: |
|---|---|---|---|
| Human antibody heavy chain (forward) | | | |
| p1355DFR | 5′CTAGTAGCAACTGCAACCGGTGTACATTCCCAGGTGCAGCTGGTGCAG | VH 1 | 977 |
| p1356DFR | 5′CTAGTAGCAACTGCAACCGGTGTACATTCCGAGGTGCAGCTGGTGCAG | VH 1/5 | 978 |
| p1357DFR | 5′CTAGTAGCAACTGCAACCGGTGTACATTCCCAGGTTCAGCTGGTGCAG | VH 1-18 | 979 |
| p1358DFR | 5′CTAGTAGCAACTGCAACCGGTGTACATTCCCAGGTCCAGCTGGTACAG | VH 1-24 | 980 |
| p1359DFR | 5′CTAGTAGCAACTGCAACCGGTGTACATTCTGAGGTGCAGCTGGTGGAG | VH 3 | 981 |
| p1360DFR | 5′CTAGTAGCAACTGCAACCGGTGTACATTCTCAGGTGCAGCTGGTGGAG | VH 3-11 | 982 |
| p1361DFR | 5′CTAGTAGCAACTGCAACCGGTGTACATTCTGAGGTGCAGCTGTTGGAG | VH 3-23 | 983 |
| p1362DFR | 5′CTAGTAGCAACTGCAACCGGTGTACATTCTCAGGTGCAGCTGGTGGAG | VH 3-33 | 984 |
| p1363DFR | 5′CTAGTAGCAACTGCAACCGGTGTACATTCTGAAGTGCAGCTGGTGGAG | VH 3-9 | 985 |
| p1364DFR | 5′CTAGTAGCAACTGCAACCGGTGTACATTCCCAGGTGCAGCTGCAGGAG | VH 4 | 986 |
| p1365DFR | 5′CTAGTAGCAACTGCAACCGGTGTACATTCCCAGGTGCAGCTACAGCAGTG | VH 4-34 | 987 |
| p1366DFR | 5′CTAGTAGCAACTGCAACCGGTGTACATTCCCAGCTGCAGCTGCAGGAG | VH 4-39 | 988 |
| p1367DFR | 5′CTAGTAGCAACTGCAACCGGTGTACATTCCCAGGTACAGCTGCAGCAG | VH 6-1 | 989 |
| Human antibody heavy chain (reverse) | | | |
| p1370DFR | 5′CCGATGGGCCCTTGGTCGACGCTGAGGAGACGGTGACCAG | JH 1/2 | 990 |
| p1371DFR | 5′CCGATGGGCCCTTGGTCGACGCTGAAGAGACGGTGACCATTG | JH 3 | 991 |
| p1372DFR | 5′CCGATGGGCCCTTGGTCGACGCTGAGGAGACGGTGACCAG | JH 4/5 | 992 |
| p1373DFR | 5′CCGATGGGCCCTTGGTCGACGCTGAGGAGACGGTGACCGTG | JH 6 | 993 |
| Human antibody light chain kappa (forward) | | | |
| p1379DFR | 5′GTAGCAACTGCAACCGGTGTACATTCTGACATCCAGATGACCCAGTC | VK 1-5 | 994 |
| p1380DFR | 5′GTAGCAACTGCAACCGGTGTACATTCAGACATCCAGTTGACCCAGTCT | VK 1-9 | 995 |
| p1381DFR | 5′GTAGCAACTGCAACCGGTGTACATTGTGCCATCCGGATGACCCAGTC | VK 1D-43 | 996 |
| p1382DFR | 5′GTAGCAACTGCAACCGGTGTACATGGGGATATTGTGATGACCCAGAC | VK 2-2 | 997 |
| p1383DFR | 5′GTAGCAACTGCAACCGGTGTACATGGGGATATTGTGATGACTCAGTC | VK 2-28 | 998 |
| p1384DFR | 5′GTAGCAACTGCAACCGGTGTACATGGGGATGTTGTGATGACTCAGTC | VK 2-30 | 999 |
| p1385DFR | 5′GTAGCAACTGCAACCGGTGTACATTCAGAAATTGTGTTGACACAGTC | VK 3-11 | 1000 |
| p1386DFR | 5′GTAGCAACTGCAACCGGTGTACATTCAGAAATAGTGATGACGCAGTC | VK 3-15 | 1001 |
| p1387DFR | 5′GTAGCAACTGCAACCGGTGTACATTCAGAAATTGTGTTGACGCAGTCT | VK 3-20 | 1002 |
| p1388DFR | 5′GTAGCAACTGCAACCGGTGTACATTCGGACATCGTGATGACCCAGTC | VK 4-1 | 1003 |
| Human antibody light chain kappa (reverse) | | | |
| p1390DFR | GAAGACAGATGGTGCAGCCACCGTACGTTTGATYTCCACCTTGGTC | JK 1/4 | 1004 |
| p1391DFR | GAAGACAGATGGTGCAGCCACCGTACGTTTGATCTCCAGCTTGGTC | JK 2 | 1005 |
| p1392DFR | GAAGACAGATGGTGCAGCCACCGTACGTTTGATATCCACTTTGGTC | JK 3 | 1006 |
| p1393DFR | GAAGACAGATGGTGCAGCCACCGTACGTTTAATCTCCAGTCGTGTC | JK 5 | 1007 |

TABLE 3-continued

List of primers for cloning recombinant antibodies by the SLIC method. Related to Methods of this example.

| Primer ID | Primer sequence | Best V or J gene segment match | SEQ ID NO: |
|---|---|---|---|
| Human antibody light chain lambda (forward) | | | |
| p1402DFR | CTAGTAGCAACTGCAACCGGTTCCTGGGCCCAGTCTGTGCTGACKCAG | VL 1 | 1008 |
| p1403DFR | CTAGTAGCAACTGCAACCGGTTCCTGGGCCCAGTCTGCCCTGACTCAG | VL 2 | 1009 |
| p1404DFR | CTAGTAGCAACTGCAACCGGTTCTGTGACCTCCTATGAGCTGACWCAG | VL 3 | 1010 |
| p1405DFR | CTAGTAGCAACTGCAACCGGTTCTCTCTCSCAGCYTGTGCTGACTCA | VL 4/5 | 1011 |
| p1406DFR | CTAGTAGCAACTGCAACCGGTTCTTGGGCCAATTTTATGCTGACTCAG | VL 6 | 1012 |
| p1407DFR | CTAGTAGCAACTGCAACCGGTTCCAATTCYCAGRCTGTGGTGACYCAG | VL 7/8 | 1013 |
| Human antibody light chain lambda (reverse) | | | |
| p1409DFR | GGCTTGAAGCTCCTCACTCGAGGGYGGGAACAGAGTG | Constant L | 1014 |

TABLE 4

List of primers for the generation of RVP expression constructs. Related to Methods of this example.

| Primer ID | Primer sequence | Comments | SEQ ID NO: |
|---|---|---|---|
| Mutation of BspHI sites in pZIKV/HPF/CprME to generate pZIKV/HPF/CprM*E* | | | |
| RU-O-24303 | GTTAAGGGATTTTGGACATGAGATTATC | BspHI at nt 6419 forward | 1015 |
| RU-O-24304 | GATAATCTCATGTCCAAAATCCCTTAAC | BspHI at nt 6419 reverse | 1016 |
| RU-O-24309 | CTTGGTTGAGTACTCACCAGTCA | Reverse outer (for 6419) | 1017 |
| RU-O-24310 | GAAGACTACAGCGTCGCCAG | Forward outer (for 6419) | 1018 |
| RU-O-24305 | GTTATTGTCTCATGCGCGGATAC | BspHI at nt 7427 forward | 1019 |
| RU-O-24306 | GTATCCGCGCATGAGACAATAAC | BspHI at nt 7427 reverse | 1020 |
| RU-O-24307 | CTTCATGCAATTGTCGGTCAAGCC | Reverse outer (for 7427) | 1021 |
| RU-O-24308 | TGACTGGTGAGTACTCAACCAAG | Forward outer (for 7427) | 1015 |
| Generation of E mutations in pZIKV/HPF/CprM*E* | | | |
| RU-O-24998 | AGGAGTCGGGGCGAAGAAGATCAC | E393A forward | 1022 |
| RU-O-24999 | GTGATCTTCTTCGCCCCGACTCCT | E393A reverse | 1023 |
| RU-O-25000 | AGGAGTCGGGGAGGCGAAGATCAC | K394A forward | 1024 |
| RU-O-25001 | GTGATCTTCGCCTCCCCGACTCCT | K394A reverse | 1025 |
| RU-O-24379 | ACTTGGTCATGATACTGCTGATTGCCCCGGCATACAGCATCA GGTGCATAGGAGT | Forward outer | 1026 |
| RU-O-24380 | TTCGAACCGCGGCTGGGTCCTATTAAGCAGAGACAGCTGTG GATAAGAAGATC | Reverse outer | 1027 |
| Generation of pDENV1/PUO-359/CprME | | | |
| RU-O-24611 | CTTGACCGACAATTGCATGAAG | Upstream of SnaBI site forward | 1029 |
| RU-O-24610 | GTCTTTTTCCGTTGGTTGTTCATAGCCTGCTTTTTTGTACAAAC | CMV promoter-Capsid fusion reverse | 1030 |

TABLE 4-continued

List of primers for the generation of RVP expression constructs. Related to Methods of this example.

| Primer ID | Primer sequence | Comments | SEQ ID NO: |
|---|---|---|---|
| RU-O-24608 | GTTTGTACAAAAAAGCAGGCTATGAACAACCAACGGAAAAAGAC | CMV promoter-Capsid fusion forward | 1031 |
| RU-O-24609 | TTCGAACCGCGGCTGGGTCCTATTACGCCTGAACCATGACTC CTAGGTAC | E C-terminus-Sacl I site reverse | 1032 |
| Generation of pZIKV/HPF-CprM/MR766-E | | | |
| RU-O-24994 | CAAAGAGTGGTTCCATGACATCCCATTG | BspHI site mutation forward | 1033 |
| RU-O-24995 | CAATGGGATGTCATGGAACCACTCTTTG | BspHI site mutation reverse | 1034 |
| RU-O-24379 | ACTTGGTCATGATACTGCTGATTGCCCCGGCATACAGCAT CAGGTGCATAGGAGT | Forward outer | 1035 |
| RU-O-24380 | TTCGAACCGCGGCTGGGTCCTATTAAGCAGAGACAGCTG TGGATAAGAAGATC | Reverse outer | 1036 |

TABLE 5

Data collection and refinement statistics. Related to FIG. 5.

| | Z006-ZIKV EDIII | Z004-DENV1 EDIII |
|---|---|---|
| Data Collection | | |
| Resolution Range (Å) | 29.75-3.0 (3.107-3.0) | 37.11-3.0 (3.107-3.0) |
| Space group | R3 2: H | P $4_3$ $2_1$2 |
| Cell dimensions | | |
| α, β, χ (⊕) | 385.08, 385.08, 56.64 | 74.23, 74.23, 190.76 |
| α, β, γ (≡) | 90, 90, 120 | 90, 90, 90 |
| Total reflections | 170795 (25781) | 121867 (20556) |
| Unique reflections | 31520 (3151) | 11154 (1101) |
| Multiplicity | 5.4 (5.6) | 10.9 (11.6) |
| Completeness (%) | 98.71 (99.78) | 98.30 (99.73) |
| Mean I/σ(I) | 8.2 (2.3) | 11.1 (3.3) |
| Wilson B-factor ($Å^2$) | 77.8 | 58.7 |
| $R_{merge}$ | 0.120 (0.598) | 0.179 (0.829) |

TABLE 5-continued

Data collection and refinement statistics. Related to FIG. 5.

| | Z006-ZIKV EDIII | Z004-DENV1 EDIII |
|---|---|---|
| $R_{pim}$ | 0.083 (0.410) | 0.079 (0.358) |
| CC½ | 0.992 (0.779) | 0.994 (0.869) |
| Refinement | | |
| $R_{work}/R_{free}$ | 0.210/0.256 | 0.258/0.315 |
| Number of atoms | 7878 | 3759 |
| Protein residues | 1050 | 492 |
| RMS (bonds) (Å) | 0.013 | 0.005 |
| RMS (angles) (°) | 1.42 | 0.97 |
| Clashscore | 15.93 | 13.28 |
| Average B-factor ($Å^2$) | 103.02 | 56.59 |
| Number of TLS groups | 6 | 17 |

Statistics for the highest-resolution shell are shown in parentheses.

TABLE 6

Antibody-antigen contacts. Related to FIG. 5

| Chain | Z006 Fab | ZIKV EDIII | Closest distance | Z004 Fab | DENV1 EDIII | Closest distance | Description | Origin | Count in clones |
|---|---|---|---|---|---|---|---|---|---|
| HC | N31 | Q350, T351 | | | | | | | |
| | Y52 | T351 | | I53 | P336, A382 | | | | |
| | | | | D54 | M301 | | | | |
| | E55 | K340, S306, L307, Y305 | | | | | | | |
| | S56 | L307 | | S56 | M301, V300 | | | | |
| | T57 | S306 | | | | | | | |
| | Y58 | L307, S306, T309 | 3.07 | Y58 | M301, V300, T303 | 2.54 | Tyr-OH w/antigen backbone oxygen | V Germline | 62 Y, 1 W |
| | R96 | E393 | 3.44 | R96 | E384 | 2.55 | electrostatic/ salt bridge | N addition | 62 R, 1 H |
| | S97 | K395, G392, E393 | | | | | | | |
| | N98 | L352, G392, V391, K395 | | | | | | | |
| | G99 | G392 | | R99 | G383, S338, A382 | | | | |

TABLE 6-continued

Antibody-antigen contacts. Related to FIG. 5

| Chain | Z006 Fab | ZIKV EDIII | Closest distance | Z004 Fab | DENV1 EDIII | Closest distance | Description | Origin | Count in clones |
|---|---|---|---|---|---|---|---|---|---|
| | W100 | T309, K394 | | G100 | G383 | | | | |
| | S100A | G392 | | V100A | T303 | | | | |
| | S100B | E393 | | | | | | | |
| | | E100C | E384, G383, K385, A382 | | | | | | |
| | | L100D | E384 | | | | | | |
| LC | Q27 | T335 | 3.28 | Q27 | T329 | 3.96 | | V Germline | 58 Q, 6 H, 5 R |
| | | | | S30 | E327 | | | | |
| | W32 | K394, A311 | 3.08 | W32 | K385, S305, E327 | 3.37 | hydrophobic (plus cation-pi) | V Germline | 68 W, 1 L |
| | Y49 | E393 | | | | | | | |
| | Q50 | E393 | | | | | | | |
| | Y91 | K394, E393 | 2.45 | F91 | K385 | 2.28 | hydrophobic (plus Tyr-OH/Glu H-bond for ZIKV) | V Germline/ SHM | 57 Y, 12 F |
| | S92 | A310, K394, T309 | 3.03 | Y92 | G328, K385, 327, G304, T303 | | | | |
| | T93 | T335, G334, D336, A310, T309 | 3.22 | S93 | T329, T303, G328 | 2.68 | H-bond to antigen backbone nitrogen antigen sidechain | V Germline/SHM | 42 S, 23 T, 3 N |
| | F94 | T309, D336 | 3.42 | V94 | T303, T329, D330 | 3.1 | H-bond to LC backbone plus vDW for antibody sidechain | | 43 Y, 13 F, 12 V |
| | | | | W96 | T303 | | | | |

Contacts are defined as residues in which any atom is within 4 Å of an atom from a residue on the interacting partner using AntibodyDatabase (West et al., 2013). Table 6 is organized by antibody residue, listing all antigen residues contacted by each antibody residue (ordered by contact distance). Antibody residues are highlighted when corresponding interactions occur in both complexes. For the highlighted interactions additional information is listed including the antibody residue's origin in V(D)J recombination and the residue distribution at that antibody position in the sequenced antibody clones.

Example 3

This Example extends the disclosure of Examples 1 and 2 above. Zika virus (ZIKV) infection causes severe neurologic complications and fetal aberrations[1]. As discussed in Examples 1 and 2, human monoclonal antibody Z004 is a VH3-23/VK1-5 antibody that recognizes the lateral ridge of the Envelope Domain III (EDIII) of ZIKV, is a potent neutralizer in vitro, and prevents disease in mice. In this Example we demonstrate that when Z004 is administered to macaques for prophylaxis, it leads to emergence of resistant ZIKV variants bearing mutations in the antibody target site. As discussed above, Z021 has a structure in complex with the antigen that reveals a distinct although overlapping epitope on EDIII. Z021 potently neutralizes ZIKV in vitro and prevents disease in mice. This Example shows that in a clinically relevant macaque model, prophylactic co-administration of Z004 with Z021 is protective and suppresses emergence of resistant variants. Thus, a combination of two potent human monoclonal antibodies to EDIII is sufficient to suppress infection and thwart viral escape in macaques, a natural host for ZIKV.

In more detail, to determine whether human monoclonal antibodies are efficacious against ZIKV in primates, who are natural hosts for infection, we administered Z004 to rhesus macaques 24 hours before intravenous challenge with high dose ($10^5$ PFU) of a Brazilian strain of ZIKV. Infection was monitored by PCR to detect viral RNA in the plasma (FIG. 11*a*). All four control animals developed viremia, which peaked on day 3 with plasma viral loads ranging between $10^5$-$10^7$ RNA copies/ml (FIG. 11*a*, in black). Similar to previous reports, viremia cleared spontaneously beginning on day 7 (FIG. 11*a*, and [19]). In contrast, viremia was either undetectable or below $10^4$ RNA copies/ml in the Z004-treated macaques on day 3. However, the Z004-treated macaques showed delayed viremia peaking on day 7-10 at $3\times10^2$-$5\times10^5$ RNA copies/ml (FIG. 11*a*, in grey). Thus, Z004 alone alters the course of ZIKV infection and leads to prolonged but lower levels of viremia.

To determine whether the viremia in Z004-treated animals was associated with viral escape mutations, we sequenced the EDIII from the virus found in the plasma of the treated macaques on day 7 and 10. In both animals the circulating viruses carried mutations in the Z004 target site; K394R in one animal and E393D or K394R in the other (FIGS. 11*b* and 11*c*). We were unable to find these mutant viruses at earlier time points in the same animals, in untreated controls, or in the inoculum (data not shown). While D393 is present in ZIKV strains of African origin, no ZIKV sequences with R394 were found out of 704 ZIKV sequences that were analyzed (ViPR database, Oct. 9, 2017). ELISA assays using ZIKV $EDIII_{E393D}$ and $EDIII_{K394R}$ mutant proteins confirmed that these mutations interfere with Z004 binding (FIG. 11*d*). In contrast to the macaque, antibody resistance mutations were rare in Ifnar $1^{-/-}$ mice treated with Z004; nevertheless, the only mouse that developed mutations had the same K394R as observed in macaque (n=8; FIG. 17). Therefore, when administered prophylactically to macaques prior to a high-dose intravenous ZIKV inoculation, Z004 selects for resistant viral mutants.

We tested whether a second antibody could help prevent the development of resistance. Z021 is a human monoclonal antibody that, like Z004, was isolated from an individual with exceptional serum neutralizing activity against ZIKV[5].

Z021 binds to the EDIII of both ZIKV and DENV1, it neutralizes ZIKV reporter viral particles (RVPs) bearing Asian/American or African lineage E proteins with an $IC_{50}$ of 1 ng/ml and 0.7 ng/ml, respectively (FIG. 12 and FIG. 18), and has strong activity in plaque reduction neutralization assays using an infectious Puerto Rican strain of ZIKV (PRNT; $IC_{50}$ of 4 ng/ml, FIG. 12*a*). Z021 is also a potent neutralizer of DENV1 ($IC_{50}$ of 10.1 ng/ml; FIG. 12*b*).

To determine whether Z021 neutralizes ZIKV in vivo, we administered Z021 to Ifnar $1^{-/-}$ mice either 24 hours before or 24 hours after ZIKV challenge (FIG. 12*c*). Whereas 100% of control mice developed symptoms and died (n=11, FIG. 12*d*), only 15% did so when Z021 was administered before infection (n=13; p=0.0002 for disease and p<0.0001 for survival; FIG. 12*d*). Moreover, only 42% developed symptoms and 33% succumbed to disease when the antibody was administered 1 day after infection (n=12; p=0.0006 for disease and p=0.0002 for survival; FIG. 12*e*). Thus, Z021 is efficacious against ZIKV in vitro and in Ifnar $1^{-/-}$ mice.

Z004 binding and neutralization of ZIKV and DENV1 is dependent on ZIKV EDIII residue K394 and also partially dependent on E393 (DENV1 residues K385 and E384, respectively; FIG. 11*d* and [5]). To determine whether Z004 and Z021 recognize distinct neutralizing epitopes on EDIII, we performed ELISA assays (FIG. 13*a* and see Methods of this Example). Each monoclonal antibody was incubated with saturating amounts of either wild type ZIKV EDIII, or an EDIII bearing mutations in the Z004 target site that interfere with its binding and neutralizing activity ($EDIII_{E393A/K394A}$). Residual binding to wild type EDIII was measured by ELISA. Whereas, Z004 binding to ZIKV EDIII was only blocked by wild type ZIKV EDIII, binding of Z021 was blocked by both wild type and ZIKV $EDIII_{E393A/K394A}$, indicating that residues E393 and K394 are critical for Z004 but dispensable for Z021 binding (FIG. 13*a*). In agreement with this finding, Z004 failed to neutralize ZIKV RVPs that were altered to bear the E393A/K394 Å mutations but Z021 remained active against the mutant RVPs in vitro (FIG. 13*b*). To determine whether the Z004 and Z021 epitopes overlap, we performed competition ELISA assays, which showed that Z004 prevented binding by Z021, and vice-versa (FIG. 13*c* and see Methods of this Example). Thus, Z021 binds to a neutralizing epitope on the EDIII that does not require E393/K394 but is close to or overlapping with the epitope recognized by Z004.

Structural analysis of Z004 and of the related VH3-23/VK1-5 antibody Z006 with the EDIII of DENV1 and ZIKV, respectively, revealed that VH3-23/VK1-5 antibodies bind to these two different flaviviruses in a very similar manner, with $E393/K394_{ZIKV}$ and $E384/K385_{DENV1}$ being central to the epitope[5]. To gain structural insights into how Z021 recognizes its epitope, we crystallized Z021 in complex with the EDIII of ZIKV and of DENV1 (FIG. 14). Z021 recognizes the EDIII of both flaviviruses in a similar fashion, and makes no contacts with the $E393/K394_{ZIKV}$ and $E384/K385_{DENV1}$ residues (FIG. 14*a*). Similar to Z004, Z021 recognizes the lateral ridge region of DENV1 EDIII, but its epitope is distinct. Compared to the Z004 Fab, the Z021 Fab is rotated ~48° around an axis near the complementarity determining region 2 (CDRH2), positioning the heavy chains in similar regions, while the light chains exhibit divergent footprints (FIG. 14*b*). Z021 uses both its heavy and light chains to contact the N-terminal region and the BC loop of DENV EDIII, makes light chain contacts to the DE loop, and heavy chain contacts to the FG loop. Notably, when compared to Z004 Fab, Z021 Fab makes unique contacts to the N-terminal region of DENV1 EDIII and shows no ordered contacts with $K385_{DENV1}$ (FIG. 14*c*). Thus, consistent with the ELISA and neutralization results (FIG. 13), Z021 recognizes a distinct but overlapping epitope on EDIII from that of Z004.

Since Z021 binding and neutralizing activity is resistant to mutations in EDIII E393 and K394, and its epitope is distinct from Z004 (FIGS. 13 and 14), we co-administered the two antibodies to macaques 24 hours before challenge with ZIKV. Two out of three macaques developed low viremia, with approximately $10^2$ or lower RNA copies/ml at around day 5 or 13 after infection. The third macaque developed viremia below $10^3$ RNA copies/ml starting on day 13 (FIG. 15). Viremia was not a consequence of rapid clearance of Z004 and Z021, as high levels of human antibodies were detectable in the macaque plasma (FIG. 19). In contrast to macaques treated with Z004 alone (FIG. 11), no mutations in the EDIII region of the circulating virus were detected in animals treated with the combination of Z004 with Z021 (data not shown). We conclude that treatment of non-human primates with the combination of Z004 and Z021, two antibodies that target distinct but overlapping epitopes, suppresses and delays viremia and prevents the emergence of ZIKV escape mutants upon high-dose intravenous ZIKV challenge.

Viremia in the absence of viral escape could result from antibody Z004 and Z021 promoting ZIKV infection through antibody-dependent enhancement (ADE). ADE depends on the ability of antibodies to engage Fc-gamma receptors. We modified the fragment crystallizable (Fc) region of both antibodies to preclude Fc-gamma receptor binding (GRLR or GRLR/LS mutations. These modifications prevented Fc binding and ADE in vitro, while maintaining neutralization potency against ZIKV in vitro and in mice (FIGS. 20 and 21). To determine whether the late-onset low-level plasma viremia of macaques treated with the combination of Z004 and Z021 was dependent on Fc-gamma receptors, we administered to macaques Z004-GRLR and Z021-GRLR antibodies and challenged them with ZIKV. Human antibody levels were comparable in macaques treated with the wild type or GRLR version of Z004 and Z021 (FIG. 19). Low plasma viremia was detected in all three animals (FIG. 15): one macaque had a single viral blip less than $10^2$ RNA copies/ml on day 3, one had viremia below $10^3$ RNA copies/ml between days 2-4, and one was viremic between days 6-13 (peak viremia of $10^4$ RNA copies/ml). No mutations were identified in the EDIII region of the emerging viruses. We conclude that the low-level viremia that develops in the presence of Z004 and Z021 is not dependent on Fc-gamma receptor engagement.

The most common mean of ZIKV transmission is through the bite of an infected mosquito. To determine whether the combination of Z004-GRLR and Z021-GRLR was protective against subcutaneous challenge, we infected macaques with $10^3$ PFU of a Puerto Rican strain of ZIKV by this route. As the size of the inoculum during mosquito feeding is uncertain, we chose this dose of virus because it is similar to recent vaccination experiments in non-human primates[18, 20,21]. None of the challenged macaques developed viremia during the observation period (FIG. 16). Without intending to be bound by any particular viewpoint, we conclude that combining Z004-GRLR with Z021-GRLR prevents viremia altogether after subcutaneous infection with ZIKV.

Those skilled in the art will recognize that although the error rate of the ZIKV polymerase has not been determined, flaviviruses are RNA viruses that are generally assumed to undergo high rates of error prone replication thereby producing mutant forms that can be selected for antibody resistance[29-31]. Antibody evasion by flaviviruses such as DENV[32-34], WNV[35,36], YFV[37], Japanese encephalitis virus[38], tick-borne encephalitis virus[39], and recently ZIKV[40], has been amply documented using cell culture experiments. Resistant virus also emerged upon administration of a single monoclonal antibody to mice challenged with WNV[41] or to Rhesus monkeys challenged with DENV[42,43]. In macaques, a combination of 3 antibodies (including 2 VH3-23/VK1-5 antibodies) is effective against subcutaneous challenge with $10^3$ PFU of ZIKV[18], but whether escape occurs with single antibodies, or whether fewer than 3 antibodies might be sufficient to protect was not determined. The present disclosure demonstrates that in contrast to in Ifnar $1^{-/-}$ mice escape is a significant problem upon challenge with $10^5$ PFU of ZIKV in single-antibody treated primates, which are a natural host for the virus. Moreover, it is demonstrated herein that prophylaxis with 2 antibodies to the EDIII is sufficient to prevent escape.

The Z004 and Z021 antibodies share a number of important features including potent neutralizing activity against both ZIKV and DENV1 but no binding to any of the other flaviviruses tested[5]. The overlapping activity can be attributed to distinct but overlapping target sites. Although the epitopes are similar, Z021 makes unique contacts to the N-terminal region of DENV1 EDIII with both its heavy and light chains, while Z004 makes more extensive contacts to the FG loop, including the E384/K385$_{DENV1}$ motif. Because the E384/K385$_{DENV1}$ motif is peripheral to the Z021 epitope, viruses with mutations at these positions will likely remain sensitive to Z021. These differences account for the efficacy of the combination of the two antibodies despite the similarities in their target sites.

Method for this Example

Reagents.

Antibodies. Z021, Z004, Z015 and 10-1074 were prepared by transient transfection of mammalian HEK-293-6E cells and purified as previously described[5]. LPS was removed with TritonX-114 and the antibodies concentrated to 4.6 to 19 mg/ml in PBS. The GRLR, LS and combined (GRLR/LS) modifications in the Fc portion of Z004 and Z021 human IgG1 expression plasmids were generated with Q5 site-directed mutagenesis kit (New England Biolabs) according to the company's instructions and primers: DFRp1455 5'TGAACTCCTGaGGGGACCGTCAGTC (SEQ ID NO: 1037) and DFRp1456 5' GGTGCTGGGCACGGTGGG (SEQ ID NO: 1038); DFRp1457 5'AACAAAGCCCgCCCAGCCCCC (SEQ ID NO: 1039) and DFRp1458 5'GGA-GACCTTGCACTTGTACTCCTTG (SEQ ID NO: 1040); DFRp1459 5'ATGCTCCGTGcTGCATGAGGC (SEQ ID NO: 1041) and DFRp1460 5'GAGAAGACGTTCCCCTGC (SEQ ID NO: 1042); DFRp1461 5'GCTCTGCACAgC-CACTACACG (SEQ ID NO: 1043) and DFRp1462 5'CTCATGCAGCACGGAGCATG (SEQ ID NO: 1044).

Virus. For in vitro experiments, ZIKV 2015 Puerto Rican PRVABC59[44] was obtained from the CDC and passaged twice in human Huh-7.5 cells, and the Thai isolate of DENV1 PUO-359 (TVP-1140) was obtained from Robert Tesh and amplified by three passages in C6/36 insect cells. For mouse experiments, ZIKV 2015 Puerto Rican PRV-ABC59 was passaged once in STAT$1^{-/-}$ human fibroblasts. For macaque experiments, a 2015 isolate of ZIKV from Brazil (strain Zika virus/*H. sapiens*-tc/BRA/2015/Brazil-_SPH2015; genbank accession number KU321639.1) was used. The strain was isolated from the plasma of a transfusion recipient and was passaged twice in mycoplasma free Vero cells. The Puerto Rican ZIKV strain (PRVABC59; KU501215) was used for subcutaneous challenge. Virus titration was as previously described[5,19].

Reporter viral particles (RVPs). Wild type ZIKV RVPs with E proteins corresponding to Asian/American or African lineage were previously reported[5]. A plasmid for expression of ZIKV CprME with E393A/K394A mutations was generated from plasmid pZIKV/HPF/CprM*E*[5], a derivative of pZIKV/HPF/CprME, a ZIKV C-prM-E expression construct provided by Ted Pierson (NIH), engineered to contain unique BspHI and SacII restriction sites flanking the envelope region, allowing facile manipulation. Assembly PCR-based site-directed mutagenesis was used to introduce the E393A/K394A double mutation into the envelope of ZIKV H/PF/2013 in pZIKV/HPF/CprM*E*, resulting in plasmid pZIKV/HPF/CprME(E393A/K394A). All PCR-derived plasmid regions were verified by sequencing. Primers used for assembly PCR and mutagenesis were: Forward outer (RU-O-24379) 5'ACTTGGTCATGATACTGCTGAT-TGCCCCGGCATACAGCATCAGGTGCATAGGA GT (SEQ ID NO: 1045); Reverse outer (RU-O-24380) 5' TTCGAACCGCGGCTGGGTCCTATTAAGCAGA-GACAGCTGTGGATAAGAAGATC (SEQ ID NO: 1046); E393A/K394A forward (RU-O-25002) 5'AGGAGTCGGGGCGGCGAAGATCACCCAC (SEQ ID NO: 1047); and E393A/K394 Å reverse (RU-O-25003) 5' GTGGGTGATCTTCGCCGCCCCGACTCCT (SEQ ID NO: 1048). RVPs bearing the ZIKV E protein with E393A/K394 Å mutations were generated by cotransfection of Lenti-X-293T cells with plasmids pZIKV/HPF/CprME (E393A/K394A) and pWNVII-Rep-REN-IB[45] as previously described[5].

EDIII proteins. Expression plasmids encoding the ZIKV mutant proteins EDIII$_{E393A/K394A}$, EDIII$_{E393D}$ and EDIII$_{K394R}$ were generated by QuikChange site-directed mutagenesis (Agilent Technologies) and confirmed by DNA sequencing. Primers used for mutagenesis are the following: E393A/K394 Å 5' TTGTCATAGGAGTCGGGGCGGCGAAGATCACC-CACCACTG (SEQ ID NO: 1049); E393D 5' CATAG-GAGTCGGGGACAAGAAGATCACCCAC (SEQ ID NO: 1050); and K394R: 5'GTCATAGGAGTCGGG-GAGCGTAAGATCACCCACCACTGG (SEQ ID NO: 1051).

Mutant ZIKV EDIII proteins were expressed in *E. coli*, refolded from inclusion bodies, and purified as described previously[5,13].

Animal Care and Experiments.

Mice. Interferon-αβ receptor knock-out mice were obtained from The Jackson Laboratory (Ifnar $1^{-/-}$; B6. 129S2-Ifnar $1^{tm1Agt}$/Mmjax) and were bred and maintained in the animal facility at the Rockefeller University. Mice were specific pathogen free and on a standard chow diet. Both male and female mice (3-4 week old) were used for experiments and were equally distributed within experimental and control groups. 125 μg of monoclonal antibodies in 200 μl of PBS were administered intraperitoneally to Ifnar $1^{-/-}$ mice one day before or one day after footpad infection with $1.25\times10^5$ plaque forming units (PFU) of ZIKV Puerto Rican strain in 50 μl. Mice were monitored for symptoms and survival over time. Animal protocols were in agreement with NIH guidelines and approved by the Rockefeller University Institutional Animal Care and Use Committee.

Macaques. Macaques were from the conventional colony at the California National Primate Research Center (CN-PRC), and were type D retrovirus-free, SIV-free and simian lymphocyte tropic virus type 1 antibody negative. Animals were housed in accordance with Association for Assessment and Accreditation of Laboratory Animal Care Standards. We strictly adhered to *Guide for the Care and Use of Laboratory Animals* prepared by the Institute for Laboratory Animal Research. The study was approved by the Institutional Animal Care and Use Committee of the University of California Davis. Z004 and Z021 antibodies were administered to macaques at doses of 15 mg/kg body weight each by slow intravenous (i.v.) infusion (2 ml/minute) 24 hours before saphenous vein i.v. inoculation with ZIKV Brazilian strain ($10^5$ PFU in 1 ml of RPMI-1640 medium). Macaques were evaluated twice daily for clinical signs of disease including poor appetence, stool quality, dehydration, diarrhea, and inactivity. When necessary, macaques were immobilized with 10 mg/kg ketamine hydrochloride (Parke-Davis) injected intramuscularly after overnight fasting. Animals were sedated at time zero (time of virus inoculation), daily for 7 to 8 days, and then every few days for sample collection. EDTA-anti-coagulated blood samples were collected using venipuncture. Complete blood counts and separation of plasma for cryopreservation of aliquots were performed as described earlier[19].

Neutralization and ADE Assays In Vitro.

Plaque reduction neutralization test with ZIKV PRV-ABC59, and flow cytometry-based neutralization assay with DENV1 PUO-359 were used to measure antibody neutralization activity in Vero cells, as described[5]. Neutralization of luciferase-encoding RVPs by antibodies using the ZIKV wild type, E393A/K394A, and African mutant RVPs was performed as previously described[5]. Antibody dependent enhancement (ADE) assays using antibodies or macaque plasma were similar to neutralization assays with RVPs, except that Fc-receptor bearing K562 cells were used, and that the cells were in 96-well plates coated with 0.01% poly-L-lysine (Sigma).

ELISA Assays.

ELISA after antibody blocking, Serial dilutions of Z004 or Z021 antibody were incubated overnight with nutation at 4° C. in V-bottom 96-well plates in the presence of saturating concentrations of either wild type EDIII, $EDIII_{E393A/K394A}$, or no protein control. In preliminary experiments, the saturating concentration of EDIII protein was determined as being approximately 1 μg/ml, and was increased to 10 μg/ml for the actual experiment. After overnight incubation the samples were added to ELISA plates that had been pre-coated with wild type EDIII and the residual antibody binding to EDIII was detected as previously described[5], with the exception that the signal was enhanced by two amplification steps. First, after incubating with goat anti-human IgG-HRP (Jackson ImmunoResearch Cat #109-035-098; 1 hour, room temperature) and washing with PBS containing Tween-20 0.05%, anti-goat IgG-biotin was added (Jackson ImmunoResearch Cat #705-065-147; 1 hour, room temperature). Second, after washing, streptavidin-HRP was added (Jackson ImmunoResearch Cat #016-030-084; 1 hour, room temperature). After the final washes, the reaction was developed with ABTS substrate (Life Technologies).

Competition ELISA. Z004 or Z021 IgG (5 μg/mL) was adsorbed overnight at 4° C. in a Nunc MaxiSorp 384-well ELISA plate. The ELISA plate was blocked with 3% bovine serum albumin (BSA) in TRIS buffered saline with 0.05% Tween-20 (TBS-T), and then 5 μg/mL EDIII (ZIKV EDIII or DENV1 EDIII) was added and incubated for 3 hours at room temperature. The plate was washed with TBS-T to remove excess antigen, and serial dilutions of Fab were then added and incubated for 3 hours at room temperature. Bound His-tagged Fab was detected using THE His Tag Antibody (Genscript Cat #A00186; 1 hour, room temperature), followed by goat-anti mouse IgG-HRP (Jackson ImmunoResearch Cat #115-035-003; 1 hour, room temperature), and developed with SuperSignal ELISA Femto Substrate (Thermo Fisher). Relative light units (RLU) were plotted as a function of Fab concentration for each IgG-antigen pair.

Fab ELISA. 5 μg/mL EDIII antigen (WT ZIKV EDIII, E393A/K394A ZIKV EDIII, E393D ZIKV EDIII, or K394R ZIKV EDIII) was adsorbed to a Nunc MaxiSorp 384-well ELISA plate overnight at 4° C. The ELISA plate was blocked with 3% BSA in TBS-T, washed with TBS-T, and then serial dilutions of Fab were added and incubated for 3 hours at room temperature. After washing the plate with TBS-T, bound Fab was detected using goat-anti-human IgG-HRP (GenScript Cat #A00166; 1 hour, room temperature) and developed with SuperSignal ELISA Femto Substrate (Thermo Fisher).

ELISA for human IgG detection in macaque plasma. Neutravidin (ThermoScientific 31000; 2 μg/ml in PBS) was absorbed to high binding 96-well plates for overnight at 4° C. After washing the plate using PBS with 0.05% Tween-20 (PBS-T), the biotinylated anti-human IgG capture antibody was added (ThermoScientific 7103322100; 2 μg/ml in PBS-T, 1 hour at room temperature). Upon washes, the plates were blocked with 2% BSA in PBS-T (2 hours at room temperature), blotted, and then serial dilutions of the macaque plasma were added to the wells (5 steps of 1:4 dilutions in PBS-T, starting with 1:10). Each plate included two dilution series of the standard (Z004 IgG, 11 steps of 1:3 dilutions in PBS-T, starting with 10 μg/ml). Plates were incubated for 1 hour at room temperature and washed prior to adding the detection reagent anti-human IgG-HRP (Jackson Immunoresearch 109-036-088; 1 hour at room temperature). After the final washes, the reaction was developed with ABTS substrate (Life Technologies).

Surface Plasmon Resonance.

FcγR and FcRn binding affinity of the Z004 Fc domain variants was determined by surface plasmon resonance (SPR), using previously described protocols[46,47]. All experiments were performed on a Biacore T200 SPR system (GE Healthcare) at 25° C. in EMS-$EP^+$ buffer (GE Healthcare; pH 7.4 for FcγRs, pH 6.0 for FcRn). Recombinant protein G (Thermo Fisher) was immobilized to the surface of a CMS sensor chip (GE Healthcare) using amine coupling chemistry at a density of 500 resonance units (RU). Fc variants of the Z004 antibody were captured on the Protein G-coupled surface (250 nM injected for 60 s at 20 μl/min) and recombinant human FcγR ectodomains (7.8125-2000 nM; Sinobiological) or FcRn/β2 microglobulin (1.95-500 nM; Sinobiological) were injected through flow cells at a flow rate of 20 μl/min. Association time was 60 s followed by a 600-s dissociation step. At the end of each cycle, the sensor surface was regenerated with 10 mM glycine, pH 2.0 (50 μl/min; 40 s). Background binding to blank immobilized flow cells was subtracted and affinity constants were calculated using BIAcore T200 evaluation software (GE Healthcare) using the 1:1 Langmuir binding model.

Crystallization and Structure Determination.

Crystallization and structure determination. The complex for crystallization was produced by mixing Z021 Fab and DENV1 EDIII at a 1:1 molar ratio, incubating at room temperature for 1-2 hours, and concentrating to 12.25 mg/mL. Crystals of Z021 Fab-DENV1 EDIII complex (space group $C222_1$; a=60.54 Å, b=91.60 Å, c=187.14 Å; one molecule per asymmetric unit) were obtained by combining 0.2 μL of crystallization sample with 0.2 μL of 0.1M sodium citrate pH 4.8, 28% Jeffamine® ED-2001 pH 7.0 in sitting drops at 22° C. Crystals were cryoprotected with Fomblin Y oil.

X-ray diffraction data were collected at Stanford Synchrotron Radiation Lightsource (SSRL) beamline 12-2 using a Dectris Pilatus 6M detector. The data were integrated using Mosflm[48] and scaled using CCP4[49]. The Z021-DENV1 DIII complex structure was solved by molecular replacement using the $V_HV_L$ and $C_HC_L$ domains from PDB 4YK4 and DENV1 DIII from PDB 4L5F as search models in Phenix[50]. The model was refined to 2.07 Å resolution using an iterative approach involving refinement in Phenix and manual rebuilding into a simulated annealing composite omit map using Coot[51]. The final model ($R_{work}$=18.8%; $R_{free}$=23.0%) contains 532 protein residues and 120 water molecules. 95%, 4%, and 1% of the protein residues were in the favored, allowed, and disallowed regions, respectively, of the Ramachandran plot. Residues that were disordered and not included in the model were: HC residues 215-219 and the 6×His tag; LC residues 1 and 213-214.

Isolation and Quantitation of Viral RNA.

Zika virus RNA was isolated from plasma and measured by qRT-PCR according to methods described previously[52] and modified to increase the initial volume of sample tested from 140 to 300 μl (when available) to increase sensitivity. The limit of detection for plasma viral RNA copies was typically 1.1 $\log_{10}$.

Virus Sequencing

For detection of virus escape mutations in macaques, ZIKV RNA was extracted from plasma using the Qiaamp viral RNA mini kit following the manufacturer's recommendations with elution of RNA in water. Qiagen One-Step RT-PCR was performed using either of 2 primer sets targeting sequences surrounding the ZIKV EDIII region: 1618p 5'ACAAGGAGTGGTTCCATGACA (SEQ ID NO: 1052) and 2204n 5'TTTTCCGATGGTGCTGCCAC (SEQ ID NO: 1053) or 19'70p 5'GTATGCAGGGACAGATGGACC (SEQ ID NO: 1054) and 2537n 5'ACCGCATCTCGTTTCCTTCTT (SEQ ID NO: 1055) with 50° C. for 30 m, 95° C. for 15 m. Next, 40 cycles of each of the 3 steps were performed: 94° C. for 1 m, 58° C. for 1 m, 72° C. for 1 m 15° s, followed by final extension of 72° C. for 10 m. RT-PCR amplicons were visualized on 1% agarose gels stained with ethidium bromide and sequenced after purification using the Qiaquick PCR purification kit. Sequences were called based on clean chromatograms sequenced with the primers used for amplification. Viral sequences in mice were from blood. RNA was extracted from TRIzol-LS (Life Technologies) and reverse transcribed with Superscript III RT (Thermo Fisher Scientific) and random primers according to the company's protocol prior to PCR amplification of the ZIKV EDIII region with primers DFRp1284 5'GGATGATCGTTAATGACACAG (SEQ ID NO: 1056) and DFRp1469 5'ACCATCTTCCCAGGCTTG (SEQ ID NO: 1057) followed by PCR clean-up with Nucleospin (Macherey-Nagel) and direct sequencing with primer DFRp1283 5'GGATCCTGATTTGAAAGCTGC (SEQ ID NO: 1058). Where necessary, a second round of nested PCR was performed with primers DFRp1472 5' TTCCACGACATTCCATTACC (SEQ ID NO: 1059) and DFRp1470 5'ATCTACGGGGGGAGTCAGGATG (SEQ ID NO: 1060).

References cited for this Example. This reference listing is not an indication that any of the references are material to patentability of any invention encompassed by this disclosure 1 Miner, J. J. & Diamond, M. S. Zika Virus Pathogenesis and Tissue Tropism. *Cell host & microbe* 21, 134-142, doi: 10.1016/j.chom.2017.01.004 (2017).

2 Harrison, S. C. Immunogenic cross-talk between dengue and Zika viruses. *Nature immunology* 17, 1010-1012, doi:10.1038/ni.3539 (2016).

3 Screaton, G. & Mongkolsapaya, J. Which Dengue Vaccine Approach Is the Most Promising, and Should We Be Concerned about Enhanced Disease after Vaccination? The Challenges of a Dengue Vaccine. *Cold Spring Harbor perspectives in biology*, doi:10.1101/cshperspect.a029520 (2017).

4 Heinz, F. X. & Stiasny, K. The Antigenic Structure of Zika Virus and Its Relation to Other Flaviviruses: Implications for Infection and Immunoprophylaxis. *Microbiology and molecular biology reviews: MMBR* 81, doi:10.1128/MMBR.00055-16 (2017).

5 Examples 1 and 2 of this disclosure.

6 Weaver, S. C. & Reisen, W. K. Present and future arboviral threats. *Antiviral research* 85, 328-345, doi:10.1016/j.antiviral.2009.10.008 (2010).

7 Munoz, L. S., Barreras, P. & Pardo, C. A. Zika Virus-Associated Neurological Disease in the Adult: Guillain-Barre Syndrome, Encephalitis, and Myelitis. *Seminars in reproductive medicine* 34, 273-279, doi:10.1055/s-0036-1592066 (2016).

8 Brasil, P. et al. Zika Virus Infection in Pregnant Women in Rio de Janeiro. The New England journal of medicine 375, 2321-2334, doi:10.1056/NEJMoa1602412 (2016).

9 Del Campo, M. et al. The phenotypic spectrum of congenital Zika syndrome. *American journal of medical genetics. Part A* 173, 841-857, doi:10.1002/ajmg.a.38170 (2017).

10 George, J. et al. Prior Exposure to Zika Virus Significantly Enhances Peak Dengue-2 Viremia in Rhesus Macaques. *Scientific reports* 7, 10498, doi:10.1038/s41598-017-10901-1 (2017).

11 Katzelnick, L. C. et al. Antibody-dependent enhancement of severe dengue disease in humans. *Science* 358, 929-932, doi:10.1126/science.aan6836 (2017).

12 Stettler, K. et al. Specificity, cross-reactivity, and function of antibodies elicited by Zika virus infection. *Science* 353, 823-826, doi:10.1126/science.aaf8505 (2016).

13 Sapparapu, G. et al. Neutralizing human antibodies prevent Zika virus replication and fetal disease in mice. *Nature* 540, 443-447, doi:10.1038/nature20564 (2016).

14 Fernandez, E. et al. Human antibodies to the dengue virus E-dimer epitope have therapeutic activity against Zika virus infection. *Nature immunology*, doi:10.1038/ni.3849 (2017).

15 Swanstrom, J. A. et al. Dengue Virus Envelope Dimer Epitope Monoclonal Antibodies Isolated from Dengue Patients Are Protective against Zika Virus. *mBio* 7, doi: 10.1128/mBio.01123-16 (2016).

16 Yu, L. et al. Delineating antibody recognition against Zika virus during natural infection. *JCI insight* 2, doi: 10.1172/jci.insight.93042 (2017).

17 Beltramello, M. et al. The human immune response to Dengue virus is dominated by highly cross-reactive antibodies endowed with neutralizing and enhancing activity. *Cell host & microbe* 8, 271-283, doi:10.1016/j.chom.2010.08.007 (2010).

18 Magnani, D. M. et al. Neutralizing human monoclonal antibodies prevent Zika virus infection in macaques. *Science translational medicine* 9, doi:10.1126/scitranslmed.aan8184 (2017).

19 Coffey, L. L. et al. Zika Virus Tissue and Blood Compartmentalization in Acute Infection of Rhesus Macaques. *PloS one* 12, e0171148, doi:10.1371/journal.pone.0171148 (2017).

20 Larocca, R. A. et al. Vaccine protection against Zika virus from Brazil. *Nature* 536, 474-478, doi:10.1038/nature18952 (2016).

21 Dowd, K. A. et al. Rapid development of a DNA vaccine for Zika virus. *Science* 354, 237-240, doi:10.1126/science.aai9137 (2016).

22 Whitehead, S. S. & Subbarao, K. Which Dengue Vaccine Approach Is the Most Promising, and Should We Be Concerned about Enhanced Disease after Vaccination? The Risks of Incomplete Immunity to Dengue Virus Revealed by Vaccination. *Cold Spring Harbor perspectives in biology*, doi:10.1101/cshperspect.a028811 (2017).

23 Halstead, S. B. Which Dengue Vaccine Approach Is the Most Promising, and Should We Be Concerned about Enhanced Disease after Vaccination? There Is Only One True Winner. *Cold Spring Harbor perspectives in biology*, doi:10.1101/cshperspect.a030700 (2017).

24 de Silva, A. M. & Harris, E. Which Dengue Vaccine Approach Is the Most Promising, and Should We Be Concerned about Enhanced Disease after Vaccination? The Path to a Dengue Vaccine: Learning from Human Natural Dengue Infection Studies and Vaccine Trials. *Cold Spring Harbor perspectives in biology*, doi:10.1101/cshperspect.a029371 (2017).

25 Horton, H. M. et al. Potent in vitro and in vivo activity of an Fc-engineered anti-CD19 monoclonal antibody against lymphoma and leukemia. *Cancer research* 68, 8049-8057, doi:10.1158/0008-5472.CAN-08-2268 (2008).

26 Lu, C. L. et al. Enhanced clearance of HIV-1-infected cells by broadly neutralizing antibodies against HIV-1 in vivo. *Science* 352, 1001-1004, doi:10.1126/science.aaf1279 (2016).

27 Zalevsky, J. et al. Enhanced antibody half-life improves in vivo activity. *Nature biotechnology* 28, 157-159, doi:10.1038/nbt.1601 (2010).

28 Ko, S. Y. et al. Enhanced neonatal Fc receptor function improves protection against primate SHIV infection. *Nature* 514, 642-645, doi:10.1038/nature13612 (2014).

29 Elena, S. F., Miralles, R., Cuevas, J. M., Turner, P. E. & Moya, A. The two faces of mutation: extinction and adaptation in RNA viruses. *IUBMB life* 49, 5-9, doi:10.1080/713803585 (2000).

30 Drake, J. W., Charlesworth, B., Charlesworth, D. & Crow, J. F. Rates of spontaneous mutation. *Genetics* 148, 1667-1686 (1998).

31 Diamond, M. S. Evasion of innate and adaptive immunity by flaviviruses. *Immunology and cell biology* 81, 196-206, doi:10.1046/j.1440-1711.2003.01157.x (2003).

32 Lin, B., Parrish, C. R., Murray, J. M. & Wright, P. J. Localization of a neutralizing epitope on the envelope protein of dengue virus type 2. *Virology* 202, 885-890, doi:10.1006/viro.1994.1410 (1994).

33 Lok, S. M., Ng, M. L. & Aaskov, J. Amino acid and phenotypic changes in dengue 2 virus associated with escape from neutralisation by IgM antibody. *Journal of medical virology* 65, 315-323 (2001).

34 Zou, G. et al. Resistance analysis of an antibody that selectively inhibits dengue virus serotype-1. *Antiviral research* 95, 216-223, doi:10.1016/j.antiviral.2012.06.010 (2012).

35 Beasley, D. W. & Barrett, A. D. Identification of neutralizing epitopes within structural domain III of the West Nile virus envelope protein. Journal of virology 76, 13097-13100 (2002).

36 Chambers, T. J Halevy, M., Nestorowicz, A., Rice, C. M. & Lustig, S. West Nile virus envelope proteins: nucleotide sequence analysis of strains differing in mouse neuroinvasiveness. *The Journal of general virology* 79 (Pt 10), 2375-2380, doi:10.1099/0022-1317-79-10-2375 (1998).

37 Daffis, S. et al. Antibody responses against wild-type yellow fever virus and the 17D vaccine strain: characterization with human monoclonal antibody fragments and neutralization escape variants. *Virology* 337, 262-272, doi:10.1016/j.virol.2005.04.031 (2005).

38 Shimoda, H. et al. Production and characterization of monoclonal antibodies to Japanese encephalitis virus. *The Journal of veterinary medical science* 75, 1077-1080 (2013).

39 Holzmann, H., Mandl, C. W., Guirakhoo, F., Heinz, F. X. & Kunz, C. Characterization of antigenic variants of tick-borne encephalitis virus selected with neutralizing monoclonal antibodies. *The Journal of general virology* 70 (Pt 1), 219-222, doi:10.1099/0022-1317-70-1-219 (1989).

40 Wang, J. et al. A Human Bi-specific Antibody against Zika Virus with High Therapeutic Potential. *Cell* 171, 229-241 e215, doi:10.1016/j.cell.2017.09.002 (2017).

41 Sapkal, G. N. et al. Neutralization escape variant of West Nile virus associated with altered peripheral pathogenicity and differential cytokine profile. *Virus research* 158, 130-139, doi:10.1016/j.virusres.2011.03.023 (2011).

42 Lai, C. J. et al. Epitope determinants of a chimpanzee dengue virus type 4 (DENV-4)-neutralizing antibody and protection against DENV-4 challenge in mice and rhesus monkeys by passively transferred humanized antibody. *Journal of virology* 81, 12766-12774, doi:10.1128/JVI.01420-07 (2007).

43 Magnani, D. M. et al. Dengue Virus Evades AAV-Mediated Neutralizing Antibody Prophylaxis in Rhesus Monkeys. *Molecular therapy: the journal of the American Society of Gene Therapy* 25, 2323-2331, doi:10.1016/j.ymthe.2017.06.020 (2017).

44 Lanciotti, R. S., Lambert, A. J., Holodniy, M., Saavedra, S. & Signor Ldel, C. Phylogeny of Zika Virus in Western Hemisphere, 2015. *Emerging infectious diseases* 22, 933-935, doi:10.3201/eid2205.160065 (2016).

45 Pierson, T. C. et al. A rapid and quantitative assay for measuring antibody-mediated neutralization of West Nile virus infection. *Virology* 346, 53-65, doi:10.1016/j.virol.2005.10.030 (2006).

46 Li, T. et al. Modulating IgG effector function by Fc glycan engineering. *Proceedings of the National Academy of Sciences of the United States of America* 114, 3485-3490, doi:10.1073/pnas.1702173114 (2017).

47 Wang, T. T. et al. IgG antibodies to dengue enhanced for FcgammaRIIIA binding determine disease severity. Science 355, 395-398, doi:10.1126/science.aai8128 (2017).

48 Battye, T. G., Kontogiannis, L., Johnson, O., Powell, H. R. & Leslie, A. G. iMOSFLM: a new graphical interface for diffraction-image processing with MOSFLM. *Acta crystallographica. Section D, Biological crystallography* 67, 271-281, doi:10.1107/S0907444910048675 (2011).

49 Winn, M. D. et al. Overview of the CCP4 suite and current developments. *Acta crystallographica. Section D, Biological crystallography* 67, 235-242, doi:10.1107/S0907444910045749 (2011).

50 Adams, P. D. et al. PHENIX: a comprehensive Python-based system for macromolecular structure solution. *Acta crystallographica. Section D, Biological crystallography* 66, 213-221, doi:10.1107/S0907444909052925 (2010).

51 Emsley, P. & Cowtan, K. Coot: model-building tools for molecular graphics. *Acta crystallographica. Section D, Biological crystallography* 60, 2126-2132, doi:10.1107/S0907444904019158 (2004).

52 Lanciotti, R. S. et al. Genetic and serologic properties of Zika virus associated with an epidemic, Yap State, Micronesia, 2007. *Emerging infectious diseases* 14, 1232-1239, doi:10.3201/eid1408.080287 (2008).

While the invention has been described through specific embodiments, routine modifications will be apparent to those skilled in the art and such modifications are intended to be within the scope of the present invention.

---

What is claimed is:

1. A recombinant antibody, said antibody comprising a heavy chain comprising the sequence: EVQLLESGG-GLVQPGGSLRLTCATSGFTFRDYAMSWVRQAPGK-GLEWVSSYSGIDDST YYADSVKGRFTISRDNSK-STLSLHMNSLRAEDSALYFCAKDRGPRGVGELFDSWGQGT-LVTVSS (SEQ ID NO:11), and a light chain comprising the sequence: DIQMTQSPSTLSASVGDRVTITCRASQ-SISKWLAWYQQKPGKAPKLLIYTTSTLKSGVPS RFSGSGSGTEFTLTISSLQPDDFA-TYYCQHFYSVPWTFGQGTKVEIK (SEQ ID NO: 12).

2. The antibody of claim 1 comprising at least one modification of its constant region, wherein the modification increases in vivo half-life of the antibody, or alters the ability of the antibody to bind to Fc receptors, or alters the ability of the antibody to cross placenta or to cross a blood-brain barrier or to cross a blood-testes barrier, or inhibits aggregation of the antibodies, or a combination of said modifications, or wherein the antibody is attached to a label or a substrate.

3. The antibody of claim 2, comprising the modification that increases in vivo half-life of the antibody.

4. The antibody of claim 2, comprising the modification that alters the ability of the antibody to bind to Fc receptors.

5. The antibody of claim 2, comprising the modification that increases in vivo half-life of the antibody and the modification that alters the ability of the antibody to bind to Fc receptors.

6. The antibody of claim 1, wherein the antibody is attached to a label or a substrate.

7. An isolated and non-naturally occurring antibody that is capable of binding with specificity to the lateral ridge of Zika virus envelope Domain III protein, said antibody comprising a heavy chain comprising: a CDR1 comprising the sequence GFTFRDYA (SEQ ID NO:1), a CDR2 comprising the sequence YSGIDDST (SEQ ID NO:2), and a CDR3 comprising the sequence AKDRGPRGVGELFDS (SEQ ID NO:3), and a light chain comprising: a CDR1 comprising the sequence QSISKW (SEQ ID NO:4), a CDR2 comprising the sequence TTS, and a CDR3 comprising the sequence QHFYSVPWT (SEQ ID NO:5).

* * * * *